US010246694B2

(12) United States Patent
Beck et al.

(10) Patent No.: US 10,246,694 B2
(45) Date of Patent: Apr. 2, 2019

(54) PHOSPHOKETOLASES FOR IMPROVED PRODUCTION OF ACETYL COENZYME A-DERIVED METABOLITES, ISOPRENE, ISOPRENOID PRECURSORS, AND ISOPRENOIDS

(71) Applicants: Danisco US Inc., Palo Alto, CA (US); The Goodyear Tire & Rubber Company, Akron, OH (US)

(72) Inventors: Zachary Q. Beck, Palo Alto, CA (US); Jeffrey W. Munos, San Francisco, CA (US); Derek H. Wells, Palo Alto, CA (US); Jian Yao, Sunnyvale, CA (US)

(73) Assignees: DANISCO US INC., Palo Alto, CA (US); THE GOODYEAR TIRE & RUBBER COMPANY, Akron, OH (US)

( * ) Notice: Subject to any disclaimer, the term of this patent is extended or adjusted under 35 U.S.C. 154(b) by 477 days.

(21) Appl. No.: 14/783,391

(22) PCT Filed: Apr. 10, 2014

(86) PCT No.: PCT/US2014/033688

§ 371 (c)(1),
(2) Date: Oct. 8, 2015

(87) PCT Pub. No.: WO2014/169144

PCT Pub. Date: Oct. 16, 2014

(65) Prior Publication Data

US 2016/0068831 A1 Mar. 10, 2016

Related U.S. Application Data

(60) Provisional application No. 61/834,359, filed on Jun. 12, 2013, provisional application No. 61/810,696, filed on Apr. 10, 2013.

(51) Int. Cl.

| | |
|---|---|
| ***C12N 9/88*** | (2006.01) |
| ***C12P 5/02*** | (2006.01) |
| ***C12P 19/32*** | (2006.01) |
| ***C12P 5/00*** | (2006.01) |
| ***C12Q 1/527*** | (2006.01) |

(52) U.S. Cl.

CPC ................ *C12N 9/88* (2013.01); *C12P 5/007* (2013.01); *C12P 5/026* (2013.01); *C12P 19/32* (2013.01); *C12Q 1/527* (2013.01); *C12Y 401/02009* (2013.01)

(58) Field of Classification Search

None

See application file for complete search history.

(56) References Cited

U.S. PATENT DOCUMENTS

| | | | | |
|---|---|---|---|---|
| 7,632,995 | B2 | 12/2009 | Eichelberger et al. | |
| 7,659,097 | B2 | 2/2010 | Renninger et al. | |
| 7,785,858 | B2 | 10/2010 | Kozlov et al. | |
| 7,915,026 | B2 | 3/2011 | Keasling et al. | |
| 8,173,410 | B2 | 5/2012 | Bott et al. | |
| 8,288,148 | B2 | 10/2012 | Cervin et al. | |
| 8,415,136 | B1 † | 4/2013 | Gardner | |
| 2005/0287655 | A1 | 12/2005 | Tabata et al. | |
| 2010/0003716 | A1 | 1/2010 | Cervin et al. | |
| 2010/0048964 | A1 | 2/2010 | Calabria et al. | |
| 2010/0086978 | A1 | 4/2010 | Beck et al. | |
| 2010/0196977 | A1 | 8/2010 | Chotani et al. | |
| 2010/0285549 | A1 | 11/2010 | Muramatsu et al. | |
| 2011/0045563 | A1 | 2/2011 | Melis | |
| 2011/0159557 | A1 | 6/2011 | Beck et al. | |
| 2011/0178261 | A1 | 7/2011 | Feher et al. | |
| 2013/0089906 | A1 * | 4/2013 | Beck ....................... | C12P 5/007 435/167 |
| 2013/0309741 | A1 | 11/2013 | Campbell et al. | |
| 2013/0309742 | A1 | 11/2013 | Campbell et al. | |

FOREIGN PATENT DOCUMENTS

| | | | |
|---|---|---|---|
| JP | 2008/61506 | A | 3/2008 |
| WO | WO 1998/02550 | A2 | 1/1998 |
| WO | WO 1998/02550 | A3 | 1/1998 |
| WO | WO 2004/033646 | A2 | 4/2004 |
| WO | WO 2006/016705 | * | 2/2006 |
| WO | WO 2009/005704 | * | 1/2009 |

(Continued)

OTHER PUBLICATIONS

Genbank Accession No. WP002319371 (Retrieved from the Internet: < https://www.ncbi.nlm.nih.gov/protein/488248163?report=genbank&log$=protalign&blast_rank=1&RID=094U5YW8015>, retrieved on Nov. 9, 2017).*

Genbank Accession No. EA075473.1 (Retrieved from the Internet: https://www.ncbi.nlm.nih.gov/protein/77172321?report=genbank&log$=prottop&blast_rank=1&RID=095E3WZ0015, retrieved on Nov. 9, 2017).*

Ausubel, F. M., et al., "Introduction of DNA into Mammalian Cells" *Current Protocols in Molecular Biology* (eds.) Chapter 9, 1987.

Baldwin, et. al., "Purification and Characterization of the Class-II D-Fructose 1,6-Bisphosphate Aldolase from *Escherichia coli* (Crookes' Strain)," *Biochem J.,* 1978, 169(3):633-41.

Berka & Barnett, "The Development of Gene Expression Systems for Filamentous Fungi," Iotechnology Advances, 1989, 7(2): 127-154.

(Continued)

*Primary Examiner* — Suzanne M Noakes
*Assistant Examiner* — Jae W Lee
(74) *Attorney, Agent, or Firm* — Mintz Levin Cohn Ferris Glovsky and Popeo P.C.

(57) ABSTRACT

This present invention relates to cultured recombinant cells comprising a heterologous phosphoketolase (PKL) polypeptide that are capable of increased production of acetyl coenzyme A-derived metabolites, as well as methods for producing and using the same. In some embodiments, the recombinant cells further comprise one or more mevalonate (MVA) pathway polypeptides for the production of isoprenoid precursors, isoprene and isoprenoids.

20 Claims, 42 Drawing Sheets

Specification includes a Sequence Listing.

(56) References Cited

FOREIGN PATENT DOCUMENTS

| | | | |
|---|---|---|---|
| WO | WO 2009/076676 | A2 | 6/2009 |
| WO | WO 2009/076676 | A3 | 6/2009 |
| WO | WO 2009/132220 | A2 | 10/2009 |
| WO | WO 2009/132220 | A3 | 10/2009 |
| WO | WO 2009/132220 | A9 | 10/2009 |
| WO | WO 2010/003007 | A2 | 1/2010 |
| WO | WO 2010/003007 | A3 | 1/2010 |
| WO | WO 2010/031062 | A1 | 3/2010 |
| WO | WO 2010/031068 | A1 | 3/2010 |
| WO | WO 2010/031076 | A2 | 3/2010 |
| WO | WO 2010/031076 | A3 | 3/2010 |
| WO | WO 2010/031077 | A1 | 3/2010 |
| WO | WO 2010/031079 | A1 | 3/2010 |
| WO | WO 2010/078457 | A2 | 7/2010 |
| WO | WO 2010/078457 | A3 | 7/2010 |
| WO | WO 2010/101855 | A2 | 9/2010 |
| WO | WO 2010/101855 | A3 | 9/2010 |
| WO | WO 2010/124146 | A2 | 10/2010 |
| WO | WO 2010/124146 | A3 | 10/2010 |
| WO | WO 2011/034863 | A1 | 3/2011 |
| WO | 2011159853 | † | 12/2011 |
| WO | WO 2011/159853 | * | 12/2011 |
| WO | WO 2011/159853 | A1 | 12/2011 |
| WO | WO 2012/058494 | A2 | 5/2012 |
| WO | WO 2012/058494 | A3 | 5/2012 |
| WO | 2012149469 | † | 11/2012 |
| WO | WO 2012/149469 | A1 | 11/2012 |
| WO | WO 2012/149491 | A2 | 11/2012 |
| WO | WO 2012/149491 | A3 | 11/2012 |
| WO | 2013007786 | † | 1/2013 |
| WO | WO 2013/007786 | A1 | 1/2013 |
| WO | WO 2013/066568 | A1 | 5/2013 |

OTHER PUBLICATIONS

Bhayana, et al., "Amino Acid Sequence of *Escherichia coli* Citrate Synthase," Biochemistry, 1984, 23: 2900-2905 (Fig. 5).

Bologna, et al., "*Escherichia coli* Malic Enzymes: Two Isoforms with Substantial Differences in Kinetic Properties, Metabolic Regulation, and Structure," Journal of Bacteriology, 2007, 189:5937-5946.

Branlant G. and Branlant C., "Nucleotide Sequence of the *Escherichia coli* Gap Gene," Eur. J. Biochem., 1985. 150:61-66.

Bunch, et al., "The IdhA Gene Encoding the Fermentative Lactate Dehydrogenase of *Escherichia coli*," Microbiology, 1997, 143:187-195.

Campbell, et al., "Improved Transformation Efficiency of Aspergillus niger Using the Homologus niaD Gene for Nitrate Reductase," Current Genetics, 1989, 16:53-56.

Danner, et al., "Four Terpene Synthases Produce Major Compounds of the Gypsy Moth Feeding-Induced Volatile Bend of Populus Trichocarpa," *Pytochemistry,* Jun. 2011, vol. 72, Issue 9, pp. 897-908.

Dawes, et al., "The Route to Ethanol Formation in Zymomonas Mobilies," *Biochem. J.,* 1966, 98:795-803.

Duckworth, et al., "Structural Basis for Regulation in Gram-Negative Bacterial Citrate Synthases," *Biochem Soc Symp.,* 1987, 54:83-92.

Egan, et al., "Molecular Characterization of the Entner-Doudoroff Pathway in *Escherichia coli:* Sequence Analysis and Localization of Promoters for the Edd-Eda Operon," *J. Bact.,* 1992, 174:4638-4646.

Fleige, et al., "Estabilshment of an Alternative Phosphoketolase-Dependent Pathway for Fructose Catabolism in Ralstonia Eutropha H16," *Appl Microbial Biotechnol.,* 2011, 91:3, 769-776.

Frey, Brendan J. and Dueck, Delbert "Clustering by Passing Messages Between Data Points," *University of Toronto Science,* 2007, 315:972-976.

Geer, L.V., al., "CDART: protein homology by domain architecture," Genome Res., 2002, 12(10)1619-23.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

Genbank Accession No. FR669447, last updated on Jan. 19, 2012, located at <https://www.ncbi.nlm.nih.gov/nuccore/FR669447>, last visited on Feb. 6, 2018.

GenBank Accession No. NC_001416, last updated on Mar. 11, 2011, located at <http://www.ncbi.nlm.nih.gov/nuccore/9626243?report=genbank>, last visited on May 13, 2014, 42 pages.

GenBank Accession No. ZP_05675307.1, last updated on Nov. 27, 2012, located at <http://www.ncbi.nlm.nih.gov/protein/257895654?sat=4&satkey=87017062>, last visited Mar. 28, 2018, 1 page.

GenBank Accession No. EFV98011.1, last updated Jan. 20, 2011, located at <http://www.ncbi.nlm.nih.gov/protein/319745714?sat=17&satkey=6270800>, last visited Mar. 28. 2018, 2 page.

UniProt Database Accession No. UPI0001CEBBDB, formerly D4SNE7, last update Nov. 30, 2017, located at <http://www.uniprot.org/uniparc/?query=D4SNE7>, last visited on Feb. 6, 2018.

UnitProt Database Accession No. UPI00005C5A1E, formerly Q3D7KO, last update Nov. 30, 2017. located at <http://www.uniprot.org/uniparc/UPI00005C5A1E.fasta>, last visited on Feb. 6, 2018.

Heath, EC., et al., "Pentose fermentation by Lactobacillus plantarum. I. The cleavage of xylulose 5-phosphate by phosphoketolase," *J Bio Chem,* 1957, 1009-1029.

Hedl, et al. "Enterococcus Faecalis Acetoacetyl-Coenzyme a Thiolase/3-Hydroxy-3-Methyglutaryl-Coenzyme a Reductase, a Dual-Function Protein of Isopentenyl Diphosphate Biosynthesis," *Journal of Bacteriology,* Apr. 2002, 184(8):2116-2122.

Hsieh, et al., "Structure and Mechanism of an *Arabidopsis* Medium/Long-Chain-Length Prenyl Pyrophosphate Synthase," *Plant Physiology,* Mar. 2011, 155(3):1079-1090.

International Search Report and the Written Opinion of the International Searching Authority for International Application No. PCT/US2014/033688, dated Oct. 10, 2014.

Jeong, et al., "Cloning and Characterization of a Gene Encoding Phosphoketolase in a Lactobacillus Paraplantarum Isolated from Kimchi," *J. Microbiol. Biotechnol.,* 2007, 17:5, 822-829.

Jones, et al., *J Biol Chem.* Mar. 24, 2011 ("Sandalwood Fragrance Biosynthesis Involves Sesquiterpene Synthases of Both the Terpene Synthase (TPS)-a and TPS-b Subfamilies, including Santalene Syntheses," J. Biol. Chem. 2011 286: 17445-17454.

Kakuda, et al., "Identification and Characterization of the ackA (Acetate Kinase A)-pta (Phosphotransacetylase) Operon and Complementation Analysis of Acetate Utilization by an ackA-pta Deletion Mutant of *Escherichia coli,". J. Biochem.,* 1994, 11:916-922.

Keeling, et al., "Transcriptome Mining, Functional Characterization, and Phylogeny of a Large Terpene Synthase Gene Family in Spruce (*Picea* spp.)," *BMC Plant Biol.,* Mar. 2011, 7;11:43.

Garms, Köllner, and Boland, "A Multiproduct Terpine Synthase from *Medicago tuncatula* Generates Cadalane Sesquiterpenes via Two Different Mechanisms," *J Org Chem.,* Aug. 2010, 20;75(16):5590-5600.

Kotlarz, et al., "Regulation of the Amount and of the Activity of Phosphofructokinases and Pyruvate Kinases in *Escherichia coli," Biochlm. Biophys. Acta,* 1975, 381:257-268.

Kumeta & Ito, "Characterization of d-Gualene Synthases from Cultured Cells of Aquilaria, Responsible for the Formation of the Sesquiterpenes in Agarwood," *Plant Physiol.,* Dec. 2010;154(4):1998-2007.

Lengeler J., Drews and Schlegel, "Biology of the Prokaryotes," Blackwell Science, New York ,1999, p. 299-301.

Lindberg, et al., "Engineering a Platform for Photosynthetic Isoprene Production in Cyanobacteria, Using Synechocystis as the Model Organism," *Metab. Eng.,* 2010, 12(f):70-79).

(56) References Cited

OTHER PUBLICATIONS

Liu, Siqing, et al., "Lactobacillus buchnerl strain NRRL B-30929 converts a concentrated mixture of xylose and glucose into ethanol and other products," *J Ind Microbial Biotechnol,* 2008, (35), 75-81.
Martin. et al., "Engineering a Mevalonate Pathway in *Escherichia coli* for Production of Terpenoids," *Nature Biotechnology,* 2003, 21(7):796-802.
Martin, et al., "Functional Annotation, Genome Organization and Phylogeny of the Grapevine (*Vitis vinifera*) Terpene Synthase Gene Family Based on Genome Assembly, FLcDNA Cloning, and Enzyme Assays," *BMC Plant Biol.,* Oct. 21, 2010;10:226.
Maurus, et al., "Insights into the Evolution of Allosteric Properties. The NADH Binding Site of Hexameric Type II Citrate Synthases," *Biochemistry,* 2003, 42:5555-5565.
Meile, et al., "Characterization of the D-Xylulose 5-Phosphate/D-Fructose 6-Phosphate Phosphoketolase Gene (xfP) from Bifidobacterium Lactis," *J. Bact.,* 2001, 183:2929-2936.
Miller, et al., "First Isolation of an Isoprene Synthase Gene from Poplar and Successful Expression of the Gene in *Escherichia coli,*" *Planta,* (e-pub. May 10, 2001) 213:483-487.
Ner, et al., "Complete Sequence of the glt A Gene Encoding Citrate Synthase in *Escherichia coli,*" *Biochemistry,* 1983, 22: 5243-5249.
Ogasawara, H. et al., PdhR (Pyruvate Dehydrogenase Complex Regulator) Controls the Respiratory Electron Transport System in *Escherichia coli, J. Bact.,* 2007, 189:5534-5541.
Okamura, et al., "Unprecedented Acetoacetyl-coenzyme a Synthesizing Enzyme of the Thiolase Superfamily Involved in the Mevalonate Pathway," *PNAS,* 2010, vol. 107, No. 25:11265-11270.
Palframan. R. J., et al., "Carbohydrate Preferences of *Bifidobacterium* Species Isolated from the Human Gut," *Curr Issues Intest Microbial,* 2003, (4), 71-75.
Papini, Marta, et al: "Physiological characterization of recombinantexpressing thephosphoketolase pathway: validation of activity throughC-based metabolic flux analysis", *Applied Microbiology and Biotechnology Springer, Berlin,* DE, Feb. 26, 2012, vol. 95, No. 4.
Peekhaus and Conway, "What's for Dinner?: Entner-Doudoroff Metabolism in *Escherichia coli,*" *J. Bact.,* 1998, 180:3495-3502.
Postma, P.W., et al., "Phosphoenolpyruvate:Carbohydrate Phosphotransferase Systems of Bacteria," *Microbiol Rev.,* 1993, 57(3):543-594.
Sharkey, et al., "Evolution of the Isoprene Biosynthetic Pathway in Kudzu," *Plant Physiology,* 2005, 137: 700-712.
Romanos, et al., "Foreign Gene Expression in Yeast: a Review," Yeast, 1992, 8(6):423-488).
Sanchez, et al., "Novel Pathway Engineering Design of the Anaerobic Central Metabolic Pathway In *Escherichia coli* to Increase Succinate Yield and Productivity," *Metab. Eng.,* 2005, 7:229-239.
Sgorbati, B., et al., "Purification and Properties of Two Fructose-6-Phosphate Phosphoketolases in Bifidobacterium," *Antonio van Leeuwenhoek,* 1976 (42), 49-57.
Shimizu, et al., "Phosphotransacetylase of *Escherichia coli* B, Purification and Properties," Biochim. Biophys., Acta, 1969, 191: 550-558.
Silver, G.M. et al., "Enzymatic Synthesis of Isoprene from Dimethylallyl Diphosphate in Aspen Leaf Extracts," *Plant Physiol,* 1991, 97:1588-1591.
Sonderegger, et al. "Metabolic Engineering of a Phosphoketolase Pathway for Pentose Catabolism in *Saccharomyces cerevisiae,*" *Applied and Environmental Microbiology,* 2004, 70:5, 2892-97.
Sprenger, Genetics of Pentose-Phosphate Pathway Enzymes of *Schenthie coli* K-12, *Arch. Microbial.,* 1995, 164:324-330.
Stokell, D. et al., Isoprene Syntahse Genes Form a Monophyletic Clade of Acyclic Terpene Synthase in the TPS-B Terpene Synthase Family, *J. Biol. Chem.,* 2003, 278: 35435-43.
Stulke and Hillen. "Regulation of Carbon Catabolism in *Bacillus* Species," *Annu. Rev. Microbiol.,* 2000, 54, 849-880.
Suzuki, et al., "Overexpression, Crystallization and Preliminary X-Ray Analysis of Xylulose-5-Phosphate/Fructose-6-Phosphate Phosphoketolase from Bifidobacterium Breve." *Acta Cryst.* F66, 2010, 66:8, 941-943.
Tabata, K. and Hashimoto, S. I., "Production of Mevalonate by a Metabolically-Engineered *Escherichia coli,*" *Biotechnology Letters,* 2004, 26: 1487-1491.
Underwood, et al., Flux through Citrate Synthase Limits the Growth of Ethanologenlc *Scherichia coli* KO11 during Xylose Fermentation, *Appl. Environ. Microbiol.,* 2002, 68:1071-1081.
Wiegand, et al., "Citrate Synthase: Structure, Control, and Mechanism," *Annual Rev. Biophysics Biophys. Chem.,* 1986, 15: 97-117.
Wolfe, "The Acetate Switch," *Microb. Mol. Biol. Rev.,* 2005, 69:12-50.
Yevenes, A. Frey, P.A., "Cloning, Expression, Purification, Cofactor Requirements, and Steady State Kinetics of Phosphoketolase-2 From Lactobacillus Plantarum," *Bioorganic Chem.,* 2008, 36: 121-127.
Krutsakorn et al.: Construction of an in vitro bypassed pyruvate decarboxylation pathway using thermostable enzyme modules and its application to N-acetylglutamate production; pp. 1-9; 2013; Microbiol Cell Factories 12:91.†

* cited by examiner
† cited by third party

PHOSPHOKETOLASES FOR IMPROVED PRODUCTION OF ACETYL COENZYME A-DERIVED METABOLITES, ISOPRENE, ISOPRENOID PRECURSORS, AND ISOPRENOIDS

CROSS-REFERENCE TO RELATED APPLICATIONS

This application is a U.S. National Phase patent application, filed under 35 U.S.C. § 371, of International Application No. PCT/US2014/033688, filed on Apr. 10, 2014, which claims priority to U.S. Provisional Patent Application No. 61/810,696, filed Apr. 10, 2013, and U.S. Provisional Patent Application No. 61/834,359, filed Jun. 12, 2013, the disclosures of each of which are incorporated by reference herein in their entirety.

INCORPORATION BY REFERENCE

The content of the following submission on ASCII text file is incorporated herein by reference in its entirety: a computer readable form (CRF) of the Sequence Listing (file name: 48768-510N01USSEQLIST.txt, date recorded: Oct. 6, 2015, size: 508,713 bytes).

FIELD OF THE INVENTION

This present invention relates to cultured recombinant cells comprising a heterologous phosphoketolase (PKL) polypeptide that are capable of increased production of acetyl coenzyme A-derived metabolites, as well as methods for producing and using the same. In some embodiments, the recombinant cells further comprise one or more mevalonate (MVA) pathway polypeptides for the production of isoprenoid precursors, isoprene and isoprenoids.

BACKGROUND OF THE INVENTION

Glycolysis allows the metabolic conversion of a carbon source into intermediate compounds such as acetyl-Coenzyme A (acetyl-CoA) which is an important intermediate in the synthesis of essential biological compounds, including polyketides, fatty acids, amino acids, vitamins, isoprene, isoprenoids, phenolics, and alkaloids. Several of these acetyl-CoA derived metabolites have industrial utility. For example, isoprene (2-methyl-1,3-butadiene) is the critical starting material for a variety of synthetic polymers, most notably synthetic rubbers. Isoprene can be obtained by fractionating petroleum; however, the purification of this material is expensive and time-consuming. Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex. Isoprene can also be naturally produced by a variety of microbial, plant, and animal species. In particular, two pathways have been identified for the natural biosynthesis of isoprene: the mevalonate (MVA) pathway and the non-mevalonate (DXP) pathway.

Isoprenoids are also acetyl-CoA-derived metabolites that demonstrate industrial utility. For example, isoprenoids are used in pharmaceutical products and as biofuels, food additives, and other specialty chemicals. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Recent developments in the production of isoprene, isoprenoid precursor molecules, and isoprenoids disclose methods for the production of isoprene and isoprenoids at rates, titers, and purities that can be sufficient to meet the demands of robust commercial processes (see, for example, International Patent Application Publication No. WO 2009/076676 A2 and U.S. Pat. No. 7,915,026); however, alternate pathways to improve production and yields of the same are still needed.

For example, theoretically, three molecules of acetyl-CoA can be derived from a single molecule of glucose in a balanced reaction. However, organisms typically produce only up to two molecules of acetyl-CoA, with the remainder mass being lost as $CO_2$. The release of $CO_2$ occurs during the formation of acetyl-CoA from pyruvate, a reaction catalyzed by pyruvate dehydrogenase. The loss of one carbon atom results in decreased production yields of acetyl-CoA-derived metabolites, isoprenoid precursors, isoprene, and isoprenoid molecules. An exception to this reaction loss is the Wood-Ljungdahl pathway, which relies on carbon monoxide dehydrogenase and acetyl-CoA synthase enzymes to reduce the carbon dioxide to acetyl-CoA in anaerobic acetogens.

What is needed, therefore, are recombinant cells that utilize alternate metabolic process which can potentially produce three molecules of acetyl-CoA from one molecule of glucose using a pathway which does not rely on the Wood-Ljungdahl pathway enzymes in the production of isoprene, isoprenoid precursor molecules, and isoprenoids.

The invention described herein addresses these problems and provides additional benefits as well.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, cultured recombinant cells, compositions of these cells and methods of using these cells to increase production of metabolic intermediates such as erythrose 4-phosphate (E4P), glyceraldehyde 3-phosphate (GAP), and acetyl-phosphate (Ac-P) as well as to increase production of isoprenoid precursors, isoprene, isoprenoids, and/or molecules derived from Acetyl-CoA such as amino acids.

Accordingly, in one aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:1.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:2.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:3.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:4.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:5.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:6.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:7.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:8.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:9.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:10.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:11.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:12.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:13.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:14.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:15.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:16

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:17.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:18.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:19.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:20.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:21.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:22.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:23.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:24.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:25.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:26.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:27.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:28.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:29.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:30.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:31.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:32.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:33.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:34.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:35.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:36.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:37.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:38.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:39.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:40.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:41.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:42.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:43.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:44.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:45.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:46.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:47.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:48.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:49.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:50.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:51.

In some aspects, in any of the embodiments above and/or herein, culturing of the recombinant cell in a suitable media increases one or more of an intracellular amount of erythrose 4-phosphate, an intracellular amount of glyceraldehyde 3-phosphate, or intracellular amount phosphate. In other aspects, in any of the embodiments above and/or herein, the polypeptide having phosphoketolase activity is capable of synthesizing glyceraldehyde 3-phosphate and acetyl phosphate from xylulose 5-phosphate. In other aspects, in any of the embodiments above and/or herein, the polypeptide having phosphoketolase activity is capable of synthesizing erythrose 4-phosphate and acetyl phosphate from fructose 6-phosphate.

In other aspects, provided herein is a recombinant cell disclosed in any of the embodiments above and/or herein capable of producing isoprene, wherein the recombinant cell further comprises (i) one or more nucleic acids encoding one or more polypeptides of the complete MVA pathway and (ii) a heterologous nucleic acid encoding an isoprene synthase polypeptide, wherein culturing of the recombinant cell in a suitable media provides for the production of isoprene. In another aspect of the cells disclosed in any of the embodiments above and/or herein, the one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate. In another aspect of the cells disclosed in any of the embodiments above and/or herein, the heterologous nucleic acid encoding an isoprene synthase polypeptide is a plant isoprene synthase polypeptide. In another aspect of the cells disclosed in any of the embodiments above and/or herein, the plant isoprene synthase polypeptide is a polypeptide from *Pueraria* or *Populus* or a hybrid, *Populus alba*×*Populus tremula*. In another aspect of the cells disclosed in any of the embodiments above and/or herein, the isoprene synthase polypeptide is selected from the group consisting of *Pueraria montana* or *Pueraria lobata, Populus tremuloides, Populus alba, Populus nigra*, and *Populus trichocarpa*. In another aspect of the cells disclosed in any of the embodiments above and/or herein, the recombinant cells further comprise one or more nucleic acids encoding one or more 1-deoxy-D-xylulose 5-phosphate (DXP) pathway polypeptides.

In other aspects, provided herein is a recombinant cell disclosed in any of the embodiments above and/or herein capable of producing isoprenoid precursors, wherein the recombinant cell further comprises one or more nucleic acids encoding one or more polypeptides of the complete MVA pathway, wherein culturing of the recombinant cell in a suitable media provides for the production of isoprenoid precursors.

In other aspects, provided herein is a recombinant cell disclosed in any of the embodiments above and/or herein capable of producing isoprenoids, wherein the recombinant cell further comprises (i) one or more nucleic acids encoding one or more polypeptides of the complete MVA pathway and (ii) a heterologous nucleic acid encoding an polyprenyl pyrophosphate synthase polypeptide, wherein culturing of the recombinant cell in a suitable media provides for the production of isoprenoids.

In other aspects, provided herein is a recombinant cell capable of producing an acetyl CoA-derived metabolite, wherein culturing of the recombinant cells disclosed in any of the embodiments above and/or herein in a suitable media provides for the production of the acetyl CoA-derived metabolite.

In some aspects, in any of the embodiments above and/or herein, the nucleic acid is placed under an inducible promoter or a constitutive promoter. In other aspects of any of the embodiments above and/or herein, the nucleic acid is cloned into one or more multicopy plasmids. In other aspects of any of the embodiments above and/or herein, the nucleic acid is integrated into a chromosome of the cells.

In other aspects of any of the embodiments above and/or herein, the recombinant cells are gram-positive bacterial cells, gram-negative bacterial cells, fungal cells, filamentous fungal cells, algal cells or yeast cells. In other aspects of any of the embodiments above and/or herein, the recombinant cells are selected from the group consisting of *Corynebacteria* spp. (e.g., *C. glutamicum*), *Bacillus subtilis, Streptomyces lividans, Streptomyces coelicolor, Streptomyces griseus, Escherichia coli, Pantoea citrea, Trichoderma reesei, Aspergillus oryzae* and *Aspergillus niger, Saccharomyces cerevisiae* and *Yarrowia lipolytica.*

In other aspects of any of the embodiments above and/or herein, the isoprenoid is selected from group consisting of monoterpenes, diterpenes, triterpenes, tetraterpenes, sequiterpene, and polyterpene. In other aspects of any of the embodiments above and/or herein, the isoprenoid is a sesquiterpene. In other aspects of any of the embodiments above and/or herein, the isoprenoid is selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In other aspects of any of the embodiments above and/or herein, the acetyl CoA-derived metabolite is selected from the group consisting of polyketides, polyhydroxybutyrate, fatty alcohols, and fatty acids. In other aspects of any of the embodiments above and/or herein, the acetyl CoA-derived metabolite is selected from the group consisting of glutamic acid, glutamine, aspartate, asparagine, proline, arginine, methionine, threonine, cysteine, succinate, lysine, leucine, and isoleucine. In other aspects of any of the embodiments above and/or herein, the acetyl CoA-derived metabolite is selected from the group consisting of acetone, isopropanol, isobutene, and propene.

In other aspects of any of the embodiments above and/or herein, the suitable media comprises a carbon source. In other aspects of any of the embodiments above and/or herein, the carbon source is a carbohydrate selected from the group consisting of monosaccharide, disaccharide, oligosaccharide, polysaccharide, C6 sugar, C5 sugar, and invert sugar.

In other aspects, provided herein is a method of producing isoprene comprising: (a) culturing the recombinant cell disclosed in any of the embodiments above and/or herein under conditions suitable for producing isoprene and (b) producing isoprene.

In other aspects, provided herein is a method of producing an isoprenoid precursor comprising: (a) culturing the recombinant cell disclosed in any of the embodiments above and/or herein under conditions suitable for producing an isoprenoid precursor and (b) producing an isoprenoid precursor.

In other aspects, provided herein is a method of producing an isoprenoid comprising: (a) culturing the recombinant cell disclosed in any of the embodiments above and/or herein under conditions suitable for producing an isoprenoid and (b) producing an isoprenoid.

In other aspects, provided herein are methods of producing an acetyl CoA-derived metabolite comprising: (a) culturing the recombinant cell disclosed in any of the embodiments above and/or herein under conditions suitable for producing an acetyl CoA-derived metabolite and (b) producing an acetyl CoA-derived metabolite.

In other aspects, provided herein are methods for detecting in vivo phosphoketolase activity of a polypeptide in a recombinant cell comprising (a) culturing a recombinant cell comprising a heterologous nucleic acid encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

In other aspects, provided herein is isolated polypeptides with phosphoketolase activity produced by any methods of screening, identifying, and/or detecting disclosed herein.

In other aspects, provided herein are recombinant cells capable of increased carbon flux through the phosphoketolase pathway, wherein the recombinant cells comprise a heterologous nucleic acid sequence encoding a polypeptide having phosphoketolase activity, wherein the polypeptide comprises at least 65% sequence identity to SEQ ID NO:8. In other aspects, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other aspects, provided herein are recombinant cells capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments of any of the aspects described above or herein, the polypeptide comprises at least 90% sequence identity to SEQ ID NO:23. In some embodiments of any of the aspects described above or herein, the polypeptide comprises at least 90% sequence identity to SEQ ID NO:24. In some embodiments of any of the aspects described above or herein, the polypeptide comprises at least 90% sequence identity to SEQ ID NO:25. In some embodiments of any of the aspects described above or herein, the polypeptide comprises at least 90% sequence identity to SEQ ID NO:26. In some embodiments of any of the aspects described above or herein, the polypeptide comprises at least 90% sequence identity to SEQ ID NO:27. In some embodiments of any of the aspects described above or herein, the polypeptide comprises at least 90% sequence identity to SEQ ID NO:28. In some embodiments of any of the aspects described above or herein, the polypeptide comprises at least 90% sequence identity to SEQ ID NO:29. In some embodiments of any of the aspects described above or herein, the polypeptide comprises at least 90% sequence identity to SEQ ID NO:30. In some embodiments of any of the aspects described above or herein, the polypeptide comprises at least 90% sequence identity to SEQ ID NO:31.

In another aspect, provided herein are recombinant cells capable of increased carbon flux through the phosphoketolase pathway, wherein the recombinant cells comprise a heterologous nucleic acid sequence encoding a polypeptide having phosphoketolase activity, wherein the polypeptide comprises at least 65% sequence identity to SEQ ID NO:11. In another aspect, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In another aspect, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments of any of the aspects described above or herein, the polypeptide comprises at least 90% sequence identity to SEQ ID NO:32. In some embodiments of any of the aspects described above or herein, the polypeptide comprises at least 90% sequence identity to SEQ ID NO:33. In some embodiments of any of the aspects described above or herein, the polypeptide comprises at least 90% sequence identity to SEQ ID NO:34. In some embodiments of any of the aspects described above or herein, the polypeptide comprises at least 90% sequence identity to SEQ ID NO:35. In some embodiments of any of the aspects described above or herein, the polypeptide comprises at least 90% sequence identity to SEQ ID NO:36. In some embodiments of any of the aspects described above or herein, the polypeptide comprises at least 90% sequence identity to SEQ ID NO:37. In some embodiments of any of the aspects described above or herein, the polypeptide comprises at least 90% sequence identity to SEQ ID NO:38. In some embodiments of any of the aspects described above or herein, the polypeptide comprises at least 90% sequence identity to SEQ ID NO:39. In some embodiments of any of the aspects described above or herein, the polypeptide comprises at least 90% sequence identity to SEQ ID NO:40. In some embodiments of any of the aspects described above or herein, the polypeptide comprises at least 90% sequence identity to SEQ ID NO:41. In some embodiments of any of the aspects described above or herein, the polypeptide comprises at least 90% sequence identity to SEQ ID NO:42. In some embodiments of any of the aspects described above or herein, the polypeptide comprises at least 90% sequence identity to SEQ ID NO:43. In some embodiments of any of the aspects described above or herein, the polypeptide comprises at least 90% sequence identity to SEQ ID NO:44. In some embodiments of any of the aspects described above or herein, the polypeptide comprises at least 90% sequence identity to SEQ ID NO:45. In some embodiments of any of the aspects described above or herein, the polypeptide comprises at least 90% sequence identity to SEQ ID NO:46.

In some embodiments of any of the aspects described above or herein, culturing of the recombinant cell in a suitable media increases one or more of an intracellular amount of erythrose 4-phosphate, an intracellular amount of glyceraldehyde 3-phosphate, or intracellular amount of acetyl phosphate. In some embodiments of any of the aspects described above or herein, the polypeptide having phosphoketolase activity is capable of synthesizing glyceraldehyde 3-phosphate and acetyl phosphate from xylulose 5-phosphate. In some embodiments of any of the aspects described above or herein, the polypeptide having phosphoketolase activity is capable of synthesizing erythrose 4-phosphate and acetyl phosphate from fructose 6-phosphate.

In other embodiments of any of the aspects described above or herein, the one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

In other aspects, provided herein are recombinant cells capable of producing isoprene, wherein the recombinant cell (such as any recombinant cell provided herein) further comprises a heterologous nucleic acid encoding an isoprene synthase polypeptide, wherein culturing of the recombinant cell in a suitable media provides for the production of isoprene with a Performance Index value of greater than 1.0 in one or more of the following parameters: (a) isoprene yield or (b) isoprene specific productivity. In some embodiments of any of the aspects described above or herein, the heterologous nucleic acid encoding an isoprene synthase polypeptide is a plant isoprene synthase polypeptide. In some embodiments of any of the aspects described above or herein, the plant isoprene synthase polypeptide is a polypeptide from *Pueraria* or *Populus* or a hybrid, *Populus alba*×*Populus tremula*. In some embodiments of any of the aspects described above or herein, the isoprene synthase polypeptide is selected from the group consisting of *Pueraria montana, Pueraria lobata, Populus tremuloides, Populus alba, Populus nigra*, and *Populus trichocarpa*. In some embodiments of any of the aspects described above or herein, the recombinant cells further comprise one or more nucleic acids encoding one or more 1-deoxy-D-xylulose 5-phosphate (DXP) pathway polypeptides.

In other aspects, provided herein are recombinant cells capable of producing isoprenoid precursors, wherein the recombinant cell (such as any recombinant cell provided herein) is cultured in a suitable media and produces said isoprenoid precursors.

In other aspects, provided herein are recombinant cells of producing isoprenoids, wherein the recombinant cell (such as any recombinant cell provided herein) further comprises a heterologous nucleic acid encoding an polyprenyl pyrophosphate synthase polypeptide, wherein culturing of the recombinant cell in a suitable media provides for the production of isoprenoids.

In yet other aspects, provided herein are recombinant cells capable of producing an acetyl CoA-derived metabolite, wherein culturing of the recombinant cell (such as any recombinant cell provided herein) in a suitable media provides for the production of the acetyl CoA-derived metabolite.

In some embodiments of any of the aspects described above or herein, the nucleic acid is placed under an inducible promoter or a constitutive promoter. In some embodiments of any of the aspects described above or herein, the nucleic acid is cloned into one or more multicopy plasmids. In some embodiments of any of the aspects described above or herein, the nucleic acid is integrated into a chromosome of the cells.

In some embodiments of any of the aspects described above or herein, the recombinant cells are gram-positive bacterial cells, gram-negative bacterial cells, fungal cells, filamentous fungal cells, algal cells or yeast cells. In some embodiments of any of the aspects described above or herein, the recombinant cells are selected from the group consisting of *Corynebacteria, Bacillus subtilis, Streptomyces lividans, Streptomyces coelicolor, Streptomyces griseus,*

*Escherichia coli, Pantoea citrea, Trichoderma reesei, Aspergillus oryzae* and *Aspergillus niger, Saccharomyces cerevisiae* and *Yarrowia lipolytica.*

In some embodiments of any of the aspects described above or herein, the isoprenoid is selected from group consisting of monoterpenes, diterpenes, triterpenes, tetraterpenes, sequiterpene, and polyterpene. In some embodiments of any of the aspects described above or herein, the isoprenoid is a sesquiterpene. In some embodiments of any of the aspects described above or herein, the isoprenoid is selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some embodiments of any of the aspects described above or herein, the acetyl CoA-derived metabolite is selected from the group consisting of polyketides, polyhydroxybutyrate, fatty alcohols, and fatty acids. In some embodiments of any of the aspects described above or herein, the acetyl CoA-derived metabolite is selected from the group consisting of glutamic acid, glutamine, aspartate, asparagine, proline, arginine, methionine, threonine, cysteine, succinate, lysine, leucine, and isoleucine. In some embodiments of any of the aspects described above or herein, the acetyl CoA-derived metabolite is selected from the group consisting of acetone, isopropanol, isobutene, and propene.

In some embodiments of any of the aspects described above or herein, the suitable media comprises a carbon source. In some embodiments of any of the aspects described above or herein, the carbon source is a carbohydrate selected from the group consisting of monosaccharide, disaccharide, oligosaccharide, polysaccharide, C6 sugar, C5 sugar, and invert sugar.

In other aspects, also provided herein are methods for producing isoprene comprising: (a) culturing the recombinant cell (such as any recombinant cell provided herein) under conditions suitable for producing isoprene and (b) producing isoprene. In other aspects, also provided herein are methods for producing an isoprenoid precursor comprising: (a) culturing the recombinant cell (such as any recombinant cell provided herein) under conditions suitable for producing an isoprenoid precursor and (b) producing an isoprenoid precursor.

In other aspects, also provided herein are methods for producing an isoprenoid comprising: (a) culturing the recombinant cell (such as any recombinant cell provided herein) under conditions suitable for producing an isoprenoid and (b) producing an isoprenoid.

In other aspects, also provided herein are methods for producing an acetyl CoA-derived metabolite comprising: (a) culturing the recombinant cell (such as any recombinant cell provided herein) under conditions suitable for producing an acetyl CoA-derived metabolite and (b) producing an acetyl CoA-derived metabolite.

In other aspects, also provided herein are methods for detecting in vivo phosphoketolase activity of a polypeptide in a recombinant cell comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

In other aspects, also provided herein are isolated polypeptides with phosphoketolase activity detected by any of the methods described above or herein.

DETAILED DESCRIPTION

Figure 1:
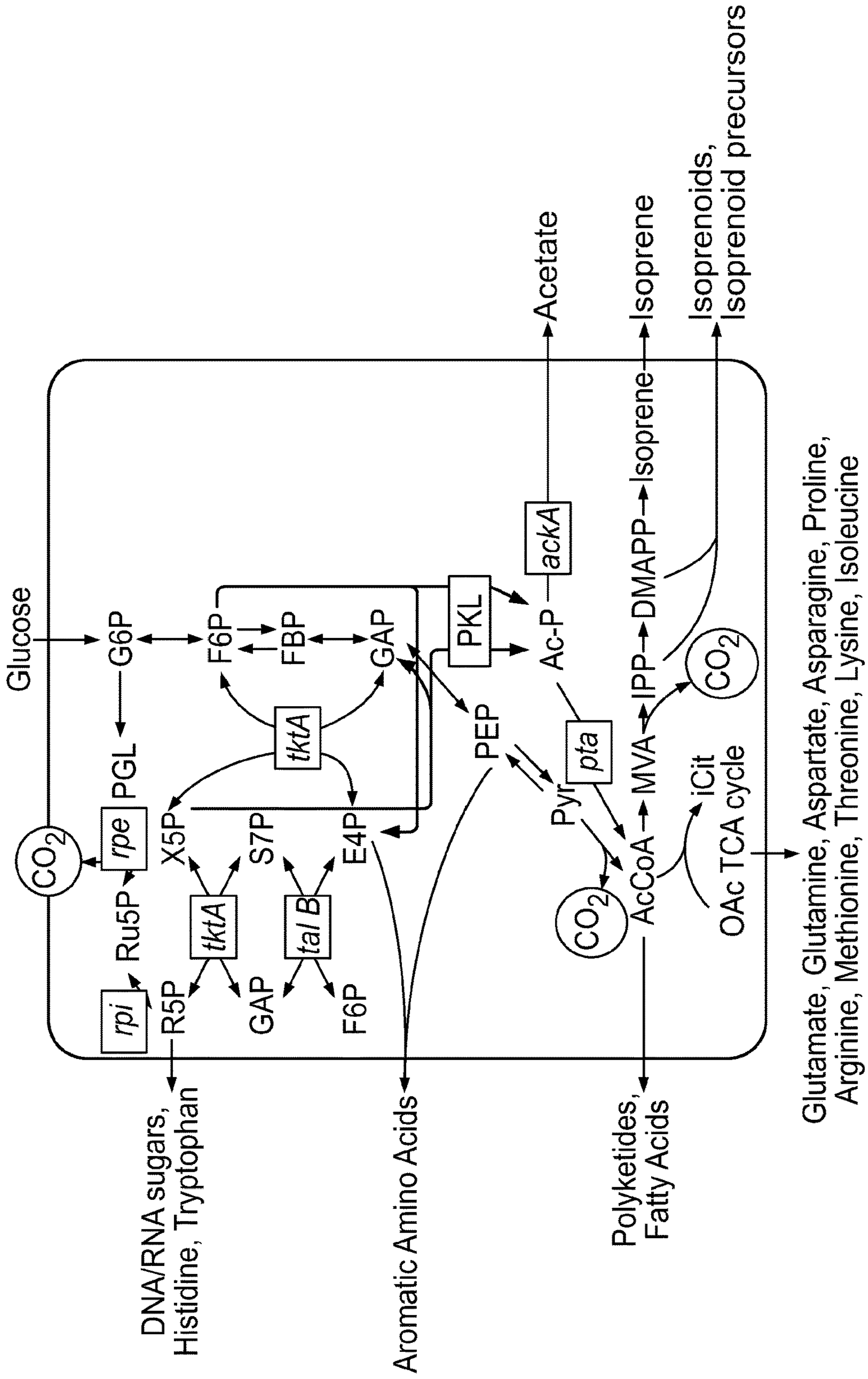
FIG. 1 depicts an engineered metabolic pathway with phosphoketolase (PKL) present. PKLs have been classified into two types based on substrate preference: xylulose-5-phosphate (X5P) phosphoketolases (EC 4.1.2.9), which only act on X5P, and xylulose-5-phosphate/fructose-6-phosphate (F6P) phosphoketolases (EC 4.1.2.22), which act on both X5P and F6P with comparable activities. acetyl phosphate (Ac-P) formed from F6P and/or X5P in PKL-catalyzed reaction(s) is subsequently converted to acetyl-CoA for use in the MVA pathway or can be converted to acetate. Other products of PKL-catalyzed reaction, namely glyceraldehyde 3-phosphate (GAP) and erythrose 4-phosphate (E4P) produced from X5P and F6P, respectively, can be recycled through manipulated metabolic pathways to maximize yield. Acetyl-Coa can be converted to many products such as polyketides, fatty acids and amino acids such as lysine.

The invention provided herein discloses, inter alia, compositions and methods for the production of acetyl coenzyme A-derived metabolites, isoprenoid precursor molecules, isoprene and/or isoprenoids in recombinant cells that have been engineered to express a phosphoketolase polypeptide. The phosphoketolase enzymes of this invention can use various substrates, as described in greater detail infra. In certain embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate. In other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of fructose 6-phosphate to erythrose 4-phosphate and acetyl phosphate. In still other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of sedoheptulose-7-phosphate to ribose-5-phosphate and acetyl phosphate. In still other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Recombinantly expressed phosphoketolase has been used to engineer metabolic pathways in host cells. See U.S. Pat. No. 7,785,858. Sonderegger et al. (*Applied and Environmental Microbiology,* 2004, 70:5, 2892-97) describe the use of phosphoketolase in *Saccharomyces cerevisiae* for the overproduction of ethanol. Fleige et al. (*Appl Microbial Biotechnol.,* 2011, 91:3, 769-76) describe the expression of a *bifidobacterium* phosphoketolase gene (Meile et al., supra) in a modified *Ralstonia eutropha* strain which restored the capability for the organism to utilize fructose as a sole carbon source for growth.

Theoretically, three molecules of acetyl-CoA can be derived from a single molecule of glucose in a balanced reaction. However, organisms typically produce only up to two molecules of acetyl-CoA, with the remainder mass being lost as $CO_2$. The release of $CO_2$ occurs during the formation of acetyl-CoA from pyruvate, a reaction catalyzed by pyruvate dehydrogenase. The loss of one carbon atom results in decreased production yields of acetyl-CoA-derived metabolites, isoprenoid precursors, isoprene, and isoprenoid molecules. An exception to this reaction loss is the Wood-Ljungdahl pathway, which relies on carbon monoxide dehydrogenase and acetyl-CoA synthase enzymes to reduce the carbon dioxide to acetyl-CoA in anaerobic acetogens.

The present invention provides an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms [see, for example, Biology of the Prokaryotes (ed. Lengeler, Drews and Schlegel); Blackwell Science, New York, 1999, p. 299-301; Meile et al., *J. of Bacteriology,* 2001, 183:9, 2929-36; Jeong et al., *J. Microbiol. Biotechnol.,* 2007, 17:5, 822-829]. Phosphoketolase enzymes allow for formation of acetyl-CoA (via acetyl-phosphate) from xylulose 5-phosphate or fructose 6-phosphate rather than through oxidation of pyruvate as in typical metabolism.

Phosphoketolases have been classified into two types based on their substrate preference: xylulose-5-phosphate (X5P) phosphoketolases, which only act on X5P, and X5P/fructose-6-phosphate (F6P) phosphoketolases, which can act on both X5P and F6P (Suzuki et al., *Acta Cryst. F*66, 2010, 66:8, 941-43). Phosphoketolases catalyze the cleavage of X5P or F6P utilizing inorganic phosphate ($P_i$) to produce acetyl phosphate (acetyl-P), $H_2O$ and glyceraldehyde 3-phosphate or erythrose 4-phosphate. The high-energy metabolite acetyl-P is subsequently converted to acetic acid by acetate kinase to produce ATP from ADP in the pathway (FIG. 1). In addition to acetyl-phosphate, the glyceraldehyde 3-phosphate produced from the enzymatic reaction can be recycled through manipulated metabolic pathways so that the maximum yield of 3 acetyl-CoA per glucose can be achieved. Significantly, acetyl-CoA production by phosphoketolase eliminates the loss of carbon (e.g. $CO_2$) as observed from pyruvate dehydrogenase mediated reactions.

Phosphoketolases can also act upon sedoheptulose-7-phosphate to convert it to ribose-5-phosphate and acetyl phosphate. A non-limiting example of such a phosphoketolase is *Bifidobacterium longum* phosphoketolase, which has catalytic activity with sedoheptulose-7-phosphate.

The present invention is directed to the use of phosphoketolase enzymes in the production of acetyl-CoA-derived metabolites, isoprenoid precursors, isoprene and/or isoprenoids to enhance product yield. In particular, the theoretical isoprene product yield is enhanced as represented by the following balanced equations (with the assumption that an organism is capable of producing ATP from the complete oxidation of 1 mol glucose to 6 mol $CO_2$):

MVA Pathway Only 1.5 Glucose+2.00 $O_2$→1.00 Isoprene+4.00 $CO_2$+5.00 $H_2O$

Theoretical yield—0.252 g Isoprene/g Glucose

DXP Pathway 1.25 Glucose+0.50 $O_2$→1.00 Isoprene+2.50 $CO_2$+3.50 $H_2O$

Theoretical yield—0.302 g Isoprene/g Glucose

MVA+Phosphoketolase Pathways 1.22 Glucose+0.33 $O_2$→1.00 Isoprene+2.33 $CO_2$+3.32 $H_2O$ Theoretical yield—0.309 g Isoprene/g Glucose The mevalonate-dependent biosynthetic pathway is particularly important for the production of isoprenoid precursor molecules, e.g., dimethylallyl diphosphate (DMAPP) and isopentenyl pyrophosphate (IPP). The enzymes of the upper mevalonate pathway convert acetyl CoA, produced from glucose, into mevalonate via three enzymatic reactions. Without being bound to theory, it is believed that increased intracellular pools of E4P, GAP, and Ac-P produced by the use of a phosphoketolase polypeptide for the increased biosynthesis of acetyl CoA can result in increased productivity of the upper mevalonate-dependent biosynthetic pathway which will substantially increase biosynthesis of mevalonate and, consequently, of downstream isoprenoid precursor molecules such as DMAPP and IPP (FIG. 1). Furthermore, the increased biosynthesis of acetyl-CoA can result in the increased synthesis of acetyl-CoA-derived metabolites such as fatty acids, amino acids, and acetone (FIG. 1). The increased intracellular amount-CoA production by this alternate PKL pathway is therefore advantageous for commercial applications.

Acetone is produced by certain microorganisms, such as *Clostridium acetobutylicum*. It starts out with condensation of two molecules of acetyl-CoA into acetoacetyl-CoA by acetyl-CoA acetyltransferase (EC 2.3.1.9). Acetoacetyl-CoA is then converted into acetoacetate by a reaction with acetic acid or butyric acid resulting in the production of acetyl-CoA or butyryl-CoA. This reaction is catalyzed by an enzyme such as acetoacetylCoA transferase (EC 2.8.3.8). AcetoacetylCoA transferase is known from various organisms, such as *E. coli* or *C. acetobutylicum*. However, also other enzymes can catalyze this reaction, such as 3-oxoacid CoA transferase (EC 2.8.3.5) or succinate CoA ligase (EC 6.2.1.5). In the last step of the reaction, acetoacetate is converted into acetone by a decarboxylation step catalyzed by acetoacetate decarboxylase (EC 4.1.1.4). Acetone can be subsequently converted to isopropanol, isobutene and/or propene as described in WO 2013/07786, the contents of which are expressly incorporated herein by reference in their entirety with respect to acetone, isoprene and propene.

Accordingly, in certain aspects, the invention provides recombinant cells with an increased intracellular amount of erythrose 4-phosphate, an increased intracellular amount of glyceraldehyde 3-phosphate, and/or an increased intracellular amount phosphate, wherein the cells comprise one or more heterologous nucleic acids encoding a polypeptide having phosphoketolase activity, and wherein the cells produce the increased intracellular amount of erythrose 4-phosphate, increased intracellular amount of glyceraldehyde 3-phosphate, and/or increased intracellular amount phosphate as compared to cells that do not comprise the one or more heterologous nucleic acids encoding a polypeptide having phosphoketolase activity.

In some aspects, the invention provides recombinant cells with an increased intracellular amount of acetyl-CoA, wherein the cells comprise one or more heterologous nucleic acids encoding a polypeptide having phosphoketolase activity, and wherein the cells produce the increased intracellular amount of acetyl-CoA as compared to cells that do not comprise the one or more heterologous nucleic acids encoding a polypeptide having phosphoketolase activity.

In certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In other aspects, the present invention provides recombinant cells capable of enhanced production of isoprenoid precursors, wherein the cells comprise one or more heterologous nucleic acids encoding a polypeptide having phosphoketolase activity and one or more nucleic acids encoding one or more polypeptides of the complete MVA pathway, wherein the cells produce increased amounts of isoprenoid precursors compared to cells that do not comprise the one or more heterologous nucleic acids encoding a polypeptide having phosphoketolase activity.

In still other aspects, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

In yet other aspects, the present invention provides recombinant cells capable of producing isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells are capable of producing recoverable amounts of isoprenoids. In certain embodiments, the present invention provides recombinant cells capable of enhanced production of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity.

In other aspects, the present invention provides recombinant cells capable of producing an acetyl CoA-derived metabolite, wherein the cells comprise one or more heterologous nucleic acids encoding a polypeptide having phosphoketolase activity, wherein the cells are capable of producing recoverable amounts of the acetyl CoA-derived metabolite. In certain embodiments, the present invention provides recombinant cells capable of enhanced production of an acetyl CoA-derived metabolite, wherein the cells comprise one or more heterologous nucleic acids encoding a polypeptide having phosphoketolase activity, wherein the cells produce increased amounts of the acetyl CoA-derived metabolite as compared to acetyl CoA-derived metabolite producing cells that do not comprise the one or more heterologous nucleic acids encoding a polypeptide having phosphoketolase activity.

In any of the aspects herein, the present invention provides recombinant cells, wherein the cells can comprise one or more heterologous nucleic acids encoding a polypeptide having phosphoketolase activity and can be further engineered to modulate the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD), glucose-6-phosphate dehydrogenase (zwf), 6-phosphofructokinase-1 (pfkA and/or pfkB), fructose bisphosphate aldolase (Tha, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH) to improve carbon flux through the phosphoketolase pathway.

In some embodiments, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an isoprene synthase polypeptide, and (iii) is further engineered to modulate the activity of one or more genes to increases carbon flux through the phosphoketolase pathway, wherein the cells produce increased amounts of isoprene compared to isoprene-producing cells that do not comprise the one or more heterologous nucleic acids encoding a polypeptide having phosphoketolase activity.

In some embodiments, the present invention provides recombinant cells capable of producing isoprenoids, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an polyprenyl pyrophosphate synthase polypeptide, and (iii) is further engineered to modulate the activity of one or more genes to increases carbon flux through the phosphoketolase pathway, wherein the cells produce increased amounts of isoprenoids compared to isoprenoid producing cells that do not comprise the one or more heterologous nucleic acids encoding a polypeptide having phosphoketolase activity.

In other embodiments, the present invention provides recombinant cells capable of enhanced production of an acetyl CoA-derived metabolite, wherein the cells comprise one or more heterologous nucleic acids encoding a polypeptide having phosphoketolase activity and is further engineered to modulate the activity of one or more genes to increases carbon flux through the phosphoketolase pathway, wherein the cells produce increased amounts of the acetyl CoA-derived metabolite as compared to acetyl CoA-derived metabolite producing cells that do not comprise the one or more heterologous nucleic acids encoding a polypeptide having phosphoketolase activity.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "Methods in Enzymology" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Definitions

The term "isoprene" refers to 2-methyl-1,3-butadiene (CAS#78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the phosphoketolase gene from *Burkholderia phytofirmans, Lactobacillus buchneri, Bifidobacterium gallicum, Bifidobacterium dentium, Bifidobacterium bifidum*, and/or *Clostridium acetobutylicum* and used to transform an *E. coli* is a heterologous nucleic acid.

As used herein, the terms "phosphoketolase", "phosphoketolase enzyme" or "phosphoketolase polypeptide" are used interchangeably and refer to a polypeptide that converts 5-phosphate to glyceraldehyde 3-phosphate and acetyl phosphate and/or converts fructose 6-phosphate to erythrose 4-phosphate and acetyl phosphate. Generally, phosphoketolases act upon ketoses. In certain embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth media containing the minimum nutrients possible for cell growth, generally without the presence of amino acids. Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., mevalonate (e.g., mevalonic acid (MVA)), isopentenyl pyrophosphate (IPP) and dimethylallyl diphosphate (DMAPP).

As used herein, the term "mass yield" refers to the mass of the product produced by the recombinant cells divided by the mass of the glucose consumed by the recombinant cells expressed as a percentage.

By "specific productivity," it is meant the mass of the product produced by the recombinant cell divided by the product of the time for production, the cell density, and the volume of the culture.

By "titer," it is meant the mass of the product produced by the recombinant cells divided by the volume of the culture.

As used herein, the term "cell productivity index (CPI)" refers to the mass of the product produced by the recombinant cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Cells Expressing a Phosphoketolase Polypeptide

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produce mevalonate, isoprenoid precursor molecules, isoprene and/or isoprenoids or can be utilized to produce acetyl-CoA-derived metabolites.

As used herein, the term "acetyl-CoA-derived metabolite" can refer to a metabolite resulting from the catalytic conversion of acetyl-CoA to said metabolite. The conversion can be a one-step reaction or a multi-step reaction. For example, acetone is an acetyl-CoA derived metabolite that is produced from acetyl-CoA by a three step reaction (e.g., a multi-step reaction): 1) the condensation of two molecules of acetyl-CoA into acetoacetyl-CoA by acetyl-CoA acetyltransferase; 2) conversion of acetoacetyl-CoA into acetoacetate by a reaction with acetic acid or butyric acid resulting in the production of acetyl-CoA or butyryl-CoA; and 3) conversion of acetoacetate into acetone by a decarboxylation step catalyzed by acetoacetate decarboxylase. Acetone can be subsequently converted to isopropanol, isobutene and/or propene which are also expressly contemplated herein to be acetyl-CoA-derived metabolites. In some embodiments, the acetyl CoA-derived metabolite is selected from the group consisting of polyketides, polyhydroxybutyrate, fatty alcohols, and fatty acids. In some embodiments, the acetyl CoA-derived metabolite is selected from the group consisting of glutamic acid, glutamine, aspartate, asparagine, proline, arginine, methionine, threonine, cysteine, succinate, lysine, leucine, and isoleucine. In some embodiments, the acetyl CoA-derived metabolite is selected from the group consisting of acetone, isopropanol, isobutene, and propene. Thus the amount of these compounds (e.g., acetyl-CoA, acetyl-CoA-derived metabolite, acetyl-P, E4P, etc.) produced from a carbohydrate substrate may be increased.

Production of acetyl-P and acetyl-CoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary Phosphoketolase Polypeptides and Nucleic Acids

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein (See for example, FIGS. 2-24 and Example 2). Additionally, Table 1 and Table 2 provides a non-limiting list of certain exemplary phosphoketolases from different species which may be utilized within embodiments of the invention.

Biochemical characteristics of exemplary phosphoketolases include, but are not limited to, protein expression, protein solubility, and activity. Phosphoketolases can also be selected on the basis of other characteristics, including, but not limited to, diversity amongst different types of organisms (e.g., gram positive bacteria, cyanobacteria, *actinomyces*), facultative low temperature aerobe, close relatives to a desired species (e.g., *E. coli*), and thermotolerance.

In some instances, phosphoketolases from certain organisms can be selected if the organisms lack a phosphofructokinase gene in its genome.

In yet another example, phosphoketolases can be selected based on a secondary structure of the amino acid sequence and/or the method described in Example 1.

In still another example, phosphoketolases can be selected based on an in vitro assay as described in Example 6.

In still another example, phosphoketolases can be selected based on an in vivo assay as described in Example 7. In some aspects, provided herein is a method for determining the presence of in vivo phosphoketolase activity of a polypeptide comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) determining the presence of in vivo phosphoketolase activity of said polypeptide based upon the amount of observed cell growth. In some aspects, provided herein is a method of identifying a polypeptide with phosphoketolase activity comprising (a) culturing a recombinant cell comprising a heterologous nucleic acid sequence encoding a polypeptide suspected of having phosphoketolase activity wherein the recombinant cell is defective in transketolase activity (tktAB) under culture conditions with glucose or xylose as a carbon source; (b) assessing cell growth of the recombinant cell and (c) identifying the polypeptide with phosphoketolase activity when cell growth is observed. In some aspects, provided herein is a method for detecting in vivo phosphoketolase activity of a polypeptide in a recombinant cell comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

As provided herein, phosphoketolase activity can improve production of acetyl-CoA-derived metabolites, isoprenoid precursors (e.g., IPP), isoprene, and/or isoprenoids. Provided herein is a recombinant host comprising phosphoketolase wherein the cells display at least one property of interest to improve production of acetyl-CoA-derived metabolites, isoprenoid precursors (e.g., IPP), isoprene, and/or isoprenoids.

In some aspects, at least one property of interest is selected from but not limited to the group consisting of specific productivity, yield, titer and cellular performance index (e.g., growth). As used herein, “performance index” refers to calculated activity per unit relative to a parental molecule. In some aspects of any of the embodiments disclosed herein, the parental molecule used in the calculation of the performance index is a phosphoketolase from *E. gallinarum*. In some embodiments, the parental molecule has a performance index of one, by definition. In other embodiments, a performance index greater than one (PI>1.0) indicates improved activity of a phosphoketolase compared to the parent molecule (e.g., a phosphoketolase from *E. gallinarum*).

In certain embodiments, suitable phosphoketolases for use herein include soluble phosphoketolases. Techniques for measuring protein solubility are well known in the art. Techniques for measuring protein solubility include those disclosed herein in the Examples. In some embodiments, a phosphoketolase for use herein includes those with a solubility of at least 20%. In some embodiments, phosphoketolase solubility is between about any of 5% to about 100%, between about 10% to about 100%, between about 15% to about 100%, between about 20% to about 100%, between about 25% to about 100%, between about 30% to about 100%, between about 35% to about 100%, between about 40% to about 100%, between about 45% to about 100%, between about 50% to about 100%, between about 55% to about 100%, between about 60% to about 100%, between about 65% to about 100%, between about 70% to about 100%, between about 75% to about 100%, between about 80% to about 100%, between about 85% to about 100%, or between about 90% to about 100%, In some embodiments, phosphoketolase solubility is between about 5% to about 100%. In some embodiments, solubility is between 5% and 100%. In some embodiments, phosphoketolase solubility is less than about any of 100, 90, 80, 70, 60, 50, 40, 30, 20, or 10 but no less than about 5%. In some embodiments, solubility is greater than about any of 5, 10, 15, 20, 25, 30, 35, 40, 45, 50, 55, 60, 65, 70, 75, 80, 85, 90, or 95%.

Phosphoketolases with a desired kinetic characteristic increases the production of isoprene. Kinetic characteristics include, but are not limited to, specific activity, $K_{cat}$, $K_i$ and $K_m$. In some aspects, the $k_{cat}$ is at least about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 17.8, 18.0, 18.2, 18.4, 18.6, 18.8, 19.0, 19.2, 19.4, 19.6, 19.8, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 200, 300, 400, 500, 600, 700, or 800. In other aspects, the $k_{cat}$ is at least about 0.2, 0.4, 0.6, 0.8, 1.0, 1.1, 1.2, 1.3, 1.4, 1.5, 1.6, 1.7, 1.8, 1.9 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, or 16.6.

In some aspects, the $K_m$ is at least about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, or 56. In other aspects, the $k_m$ is at least about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, or 22.

Properties of interest include, but are not limited to: increased intracellular activity, specific productivity, yield, and cellular performance index as compared to as compared to a recombinant cell that does not comprise the phosphoketolase polypeptide. In some embodiments, specific productivity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6 7, 8, 9, 10 times or more. In one embodiment, specific productivity is about 40 mg/L/OD/hr. In some embodiments, yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, MVA yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, isoprene yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more.

In other embodiments, the performance index values for properties of interest, including but not limited to, (a) cell growth on glucose, (b) cell growth on xylose, (c) cell growth on glucose-6-phosphate or (d) production of intracellular Acetyl-phosphate for a recombinant cell comprising a polypeptide having phosphoketolase activity as set forth herein and one or more nucleic acids encoding one or more polypeptides of the complete MVA pathway is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, the performance index values for properties of interest, including but not limited to, (a) protein solubility, (b) protein expression, or (c) F6P specific activity for a polypeptide having phosphoketolase activity in a recombinant cell further comprising one or more nucleic acids encoding one or more polypeptides of the complete MVA pathway is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, the performance index values for properties of interest, including but not limited to, (a) isoprene yield protein solubility or (b) isoprene specific productivity for a recombinant cell comprising (i) a polypeptide having phosphoketolase activity, (ii) one or more nucleic acids encoding one or more polypeptides of the complete MVA pathway, and (iii) a heterologous nucleic acid encoding an isoprene synthase polypeptide is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, cell performance index increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein is a phosphoketolase isolated from a microorganism. In some aspects, a phosphoketolase isolated from the group consisting of a gram positive bacterium, a gram negative bacterium, an aerobic bacterium, an anaerobic bacterium, a thermophilic bacterium, a psychrophilic bacterium, a halophilic bacterium or a cyanobacterium. In some aspects, a phosphoketolase isolated from a fungi. In other aspects, exemplary phosphoketolase nucleic acids include, for example, a phosphoketolase isolated from *Burkholderia* phytofirmans, *Lactobacillus buchneri, Bifidobacterium gallicum, Bifidobacterium dentium, Bifidobacterium bifidum*, and/or *Clostridium acetobutylicum*. In other aspects, exemplary phosphoketolase nucleic acids include, for example, a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other aspects, exemplary phosphoketolase nucleic acids include, for example, a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In yet other aspects, exemplary phosphoketolase nucleic acids include, for example, a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

Other phosphoketolases that can be used include, but are not limited to, *B. longum, L. plantarum, C. acetobutylicum, L. reuteri, L. paraplantarum, R. palustris, Nostoc punctiforme, B. animalis, B. breve, G. vaginalis, E. gallinarum, M. paludis, Panteoa* sp., *R. aquatilis, N. punctiforme, S. avennetilis*, and *T. fusca*. Additional phosphoketolases that can be used, include but are not limited to, *Burkholderia phytofirmans, Lactobacillus buchneri, Bifidobacterium gallicum, Bifidobacterium dentium, Bifidobacterium bifidum*, and *Clostridium acetobutylicum*.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity as described herein is suitable for use in the present invention. In some embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In still other embodiments, the phosphoketolase polypeptide capable of catalyzing the conversion of sedoheptulose-7-phosphate to ribose-5-phosphate and acetyl phosphate. In still other embodiments, the phosphoketolase polypeptide catalyzes the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

In any of the embodiments described herein, a phosphoketolase nucleic acid can have at least about 99%, 98%, 97%, 96%, 95%, 95%, 93%, 92%, 91%, 90%, 89%, 88%, 87%, 86%, or 85% sequence identity to any of the phosphoketolase nucleic acid sequences described herein. In some embodiments, the phosphoketolase nucleic acid encoded by the *Mycobacterium gilvum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:52. In some embodiments, the phosphoketolase nucleic acid encoded by the *Shewanella baltica* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:53. In some embodiments, the phosphoketolase nucleic acid encoded by the *Lactobacillus rhamnosus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:54. In some embodiments, the phosphoketolase nucleic acid encoded by the *Lactobacillus crispatus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:55. In some embodiments, the phosphoketolase nucleic acid encoded by the *Leuconostoc citreum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:56. In some embodiments, the phosphoketolase nucleic acid encoded by the *Bradyrhizobium* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:57. In some embodiments, the phosphoketolase nucleic acid encoded by the *Brucella microti* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:58. In some embodiments, the phosphoketolase nucleic acid encoded by the *Lactobacillus salivarius* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:59. In some embodiments, the phosphoketolase nucleic acid encoded by the *Rhodococcus imtechensis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:60. In some embodiments, the phosphoketolase nucleic acid encoded by the *Burkholderia xenovorans* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:61. In some embodiments, the phosphoketolase nucleic acid encoded by the *Mycobacterium intracellulare* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:62. In some embodiments, the phosphoketolase nucleic acid encoded by the *Nitrosomonas* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:63. In some embodiments, the phosphoketolase nucleic acid encoded by the *Schizosaccharomyces pombe* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:64. In some embodiments, the phosphoketolase nucleic acid encoded by the *Lactobacillus buchneri* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:65. In some embodiments, the phosphoketolase nucleic acid encoded by the *Streptomyces ghanaensis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:66. In some embodiments, the phosphoketolase nucleic acid encoded by the *Cyanothece* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:67. In some embodiments, the phosphoketolase nucleic acid encoded by the *Neosartorya fischeri* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:68. In some embodiments, the phosphoketolase nucleic acid encoded by the *Enterococcus faecium* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:69. In some embodiments, the phosphoketolase nucleic acid encoded by the *Listeria grayi* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:70. In some embodiments, the phosphoketolase nucleic acid encoded by the *Enterococcus casseliflavus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:71. In some embodiments, the phosphoketolase nucleic acid encoded by the *Mycoplasma alligatoris* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:72. In some embodiments, the phosphoketolase nucleic acid encoded by the *Carnobacterium* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:73. In some embodiments, the phosphoketolase nucleic acid encoded by the *Melissococcus plutonius* phosphoketolase gene can have at least about 99%, 98%, 97%, 96%, 95%, 95%, 93%, 92%, 91%, 90%, 89%, 88%, 87%, 86%, or 85% sequence identity to any one of SEQ ID NOs:74 and 76. In some embodiments, the phosphoketolase nucleic acid encoded by the *Tetragenococcus halophilus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:75. In some embodiments, the phosphoketolase nucleic acid encoded by the *Mycoplasma arthritidis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:77. In some embodiments, the phosphoketolase nucleic acid encoded by the *Streptococcus agalactiae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:78. In some embodiments, the phosphoketolase nucleic acid encoded by the *Mycoplasma agalactiae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:79. In some embodiments, the phosphoketolase nucleic acid encoded by the *Streptococcus gordonii* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:80. In some embodiments, the phosphoketolase nucleic acid encoded by the *Kingella oralis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:81. In some embodiments, the phosphoketolase nucleic acid encoded by the *Mycoplasma fermentans* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:82. In some embodiments, the phosphoketolase nucleic acid encoded by the *Granulicatella adiacens* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:83. In some embodiments, the phosphoketolase nucleic acid encoded by the *Mycoplasma hominis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:84. In some embodiments, the phosphoketolase nucleic acid encoded by the *Mycoplasma crocodyli* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:85. In some embodiments, the phosphoketolase nucleic acid encoded by the *Neisseria* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:86. In some embodiments, the phosphoketolase nucleic acid encoded by the *Eremococcus coleocola* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:87. In some embodiments, the phosphoketolase nucleic acid encoded by the *Aerococcus urinae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:88. In some embodiments, the phosphoketolase nucleic acid encoded by the *Kingella kingae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:89. In some embodiments, the phosphoketolase nucleic acid encoded by the *Streptococcus criceti* phosphoketolase gene can have at least about 99%, 98%, 97%, 96%, 95%, 95%, 93%, 92%, 91%, 90%, 89%, 88%, 87%, 86%, or 85% sequence identity to any one of SEQ ID NOs:90 and 91. In some embodiments, the phosphoketolase nucleic acid encoded by the *Mycoplasma columbinum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:92.

In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycobacterium gilvum* phosphoketolase amino acid sequence SEQ ID NO:1. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Shewanella baltica* phosphoketolase amino acid sequence SEQ ID NO:2. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus rhamnosus* phosphoketolase amino acid sequence SEQ ID NO:3. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus crispatus* phosphoketolase amino acid sequence SEQ ID NO:4. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Bifidobacterium longum* phosphoketolase amino acid sequence SEQ ID NO:5. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Leuconostoc citreum* phosphoketolase amino acid sequence SEQ ID NO:6. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Bradyrhizobium* sp. phosphoketolase amino acid sequence SEQ ID NO:7. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus faecium* phosphoketolase amino acid sequence SEQ ID NO:8. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Brucella microti* phosphoketolase amino acid sequence SEQ ID NO:9. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Lactobacillus salivarius* phosphoketolase amino acid sequence SEQ ID NO:10. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus agalactiae* phosphoketolase amino acid sequence SEQ ID NO:11. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Rhodococcus imtechensis* phosphoketolase amino acid sequence SEQ ID NO:12. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Burkholderia xenovorans* phosphoketolase amino acid sequence SEQ ID NO:13. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Mycobacterium intracellulare* phosphoketolase amino acid sequence SEQ ID NO:14. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Nitrosomonas* sp. phosphoketolase amino acid sequence SEQ ID NO:15. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Schizosaccharomyces pombe* phosphoketolase amino acid sequence SEQ ID NO:16. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Leuconostoc mesenteroides* phosphoketolase amino acid sequence SEQ ID NO:17. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Streptomyces* sp. phosphoketolase amino acid sequence SEQ ID NO:18. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Lactobacillus buchneri* phosphoketolase amino acid sequence SEQ ID NO:19. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Streptomyces ghanaensis* phosphoketolase amino acid sequence SEQ ID NO:20. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Cyanothece* sp. phosphoketolase amino acid sequence SEQ ID NO:21. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Neosartorya fischeri* phosphoketolase amino acid sequence SEQ ID NO:22. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus faecium* phosphoketolase amino acid sequence SEQ ID NO:23. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Listeria grayi* phosphoketolase amino acid sequence SEQ ID NO:24. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus casseliflavus* phosphoketolase amino acid sequence SEQ ID NO:25. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma* alligatoris phosphoketolase amino acid sequence SEQ ID NO:26. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Carnobacterium* sp. phosphoketolase amino acid sequence SEQ ID NO:27. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Melissococcus plutonius* phosphoketolase amino acid sequence SEQ ID NO:28. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Tetragenococcus halophilus* phosphoketolase amino acid sequence SEQ ID NO:29. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Melissococcus plutonius* phosphoketolase amino acid sequence SEQ ID NO:30. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma arthritidis* phosphoketolase amino acid sequence SEQ ID NO:31. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus agalactiae* phosphoketolase amino acid sequence SEQ ID NO:32. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma agalactiae* phosphoketolase amino acid sequence SEQ ID NO:33. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus gordonii* phosphoketolase amino acid sequence SEQ ID NO:34. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Kingella oralis* phosphoketolase amino acid sequence SEQ ID NO:35. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma fermentans* phosphoketolase amino acid sequence SEQ ID NO:36. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Granulicatella adiacens* phosphoketolase amino acid sequence SEQ ID NO:37. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma hominis* phosphoketolase amino acid sequence SEQ ID NO:38. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma crocodyli* phosphoketolase amino acid sequence SEQ ID NO:39. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Neisseria* sp. phosphoketolase amino acid sequence SEQ ID NO:40. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Eremococcus coleocola* phosphoketolase amino acid sequence SEQ ID NO:41. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Aerococcus urinae* phosphoketolase amino acid sequence SEQ ID NO:42. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Kingella kingae* phosphoketolase amino acid sequence SEQ ID NO:43. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus criceti* phosphoketolase amino acid sequence SEQ ID NO:44. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus criceti* phosphoketolase amino acid sequence SEQ ID NO:45. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma columbinum* phosphoketolase amino acid sequence SEQ ID NO:46. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Burkholderia phytofirmans* phosphoketolase amino acid sequence SEQ ID NO:47. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus buchneri* phosphoketolase amino acid sequence SEQ ID NO:48. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium gallicum* phosphoketolase amino acid sequence SEQ ID NO:49. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium dentium* phosphoketolase amino acid sequence SEQ ID NO:50. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium bifidum* phosphoketolase amino acid sequence SEQ ID NO:51.

Additional examples of phosphoketolase enzymes which can be used herein are described in U.S. Pat. No. 7,785,858 and WO 2011/159853, which are incorporated by reference herein, especially with respect to all disclosure about phosphoketolase enzymes.

In some aspects, provided herein is a recombinant cell capable of increased carbon flux through the phosphoketolase pathway, wherein the recombinant cell comprises a heterologous nucleic acid sequence encoding a polypeptide having phosphoketolase activity as described herein. In some embodiments, the polypeptide having phosphoketolase activity is isolated from *Burkholderia phytofirmans, Lactobacillus buchneri, Bifidobacterium gallicum, Bifidobacterium dentium, Bifidobacterium bifidum*, and/or *Clostridium acetobutylicum*. In other aspects, the polypeptide having phosphoketolase activity isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other aspects, the polypeptide having phosphoketolase activity isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In yet other aspects, the polypeptide having phosphoketolase activity isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In any of the embodiments herein, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Methods of Using Recombinant Cells to Produce Increased Amounts of Acetyl-CoA and Acetyl-Derived Metabolites Also provided herein are methods for the production of acetyl-CoA. In some aspects, the method for producing acetyl-CoA comprises: (a) culturing a composition comprising recombinant cells which have been engineered to increase carbon flux through the phosphoketolase pathway as described herein (including any of the recombinant cells described above), or progeny thereof, capable of producing acetyl-CoA; and (b) producing mevalonate. In some aspects, the method of producing acetyl-CoA comprises the steps of culturing any of the recombinant cells described herein under conditions suitable for the production of acetyl-CoA and allowing the recombinant cells to produce acetyl-CoA. In some aspects, the method of producing acetyl-CoA further comprises a step of recovering the acetyl-CoA.

As described herein, the methods of producing acetyl-CoA comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide; and (b) producing acetyl-CoA. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. In some embodiments, the recombinant cells comprise one or more copies of a heterologous nucleic acid encoding a phosphoketolase identified from an in vivo screening assay as described in Example 7. Additionally, the recombinant cells can produce acetyl-CoA in concentrations greater than that of the same cells lacking one or more heterologous copies of a gene encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, when the cells are cultured in minimal medium. In certain embodiments, the one or more copies of a heterologous nucleic acid encoding an phosphoketolase polypeptide described herein is a heterologous nucleic acid that is integrated into the host cell's chromosome.

Also provided herein are methods for the production of acetyl-CoA-derived metabolites. In some aspects, the method for producing acetyl-CoA-derived metabolites comprises: (a) culturing a composition comprising recombinant cells which have been engineered to increase carbon flux through the phosphoketolase pathway as described herein (including any of the recombinant cells described above), or progeny thereof, capable of producing acetyl-CoA-derived metabolites; and (b) producing mevalonate. In some aspects, the method of producing acetyl-CoA-derived metabolites comprises the steps of culturing any of the recombinant cells described herein under conditions suitable for the production of acetyl-CoA-derived metabolites and allowing the recombinant cells to produce acetyl-CoA-derived metabolites. In some aspects, the method of producing acetyl-CoA further comprises a step of recovering the acetyl-CoA-derived metabolites.

As described herein, the methods of producing acetyl-CoA-derived metabolites comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide; and (b) producing acetyl-CoA-derived metabolites. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. In some embodiments, the recombinant cells comprise one or more copies of a heterologous nucleic acid encoding a phosphoketolase identified from an in vivo screening assay as described in Example 7. Additionally, the recombinant cells can produce acetyl-CoA-derived metabolites in concentrations greater than that of the same cells lacking one or more heterologous copies of a gene encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, when the cells are cultured in minimal medium. In certain embodiments, the one or more copies of a heterologous nucleic acid encoding an phosphoketolase polypeptide described herein is a heterologous nucleic acid that is integrated into the host cell's chromosome.

In any of the embodiments herein, the acetyl-CoA-derived metabolite can be one or more of polyketides, polyhydroxybutyrate, fatty alcohols, or fatty acids. In any of the embodiments herein, the acetyl-CoA-derived metabolite can be one or more of an amino acid selected from the group consisting of: glutamic acid, glutamine, aspartate, asparagine, proline, arginine, methionine, threonine, cysteine, lysine, leucine, and isoleucine. In some embodiments, the acetyl-CoA-derived metabolite is succinate. In any of the embodiments herein, the acetyl-CoA-derived metabolite can be one or more of acetone, isopropanol, isobutene, or propene.

Also provided herein are methods for producing acetyl-CoA-derived metabolites comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said acetyl-CoA-derived metabolites. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said acetyl-CoA-derived metabolites. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said acetyl-CoA-derived metabolites. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said acetyl-CoA-derived metabolites. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Expressing a Phosphoketolase Polypeptide and One or More Polypeptides of the MVA Pathway The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules DMAPP and IPP, which serve as the basis for the biosynthesis of terpenes, terpenoids, isoprenoids, and isoprene.

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase.

Thus, in certain embodiments, the recombinant cells of the present invention are recombinant cells having the ability to produce mevalonate, isoprenoid precursors, isoprene or isoprenoids via the MVA pathway wherein the recombinant cells comprise: (i) a heterologous gene encoding a phosphoketolase capable of synthesizing glyceraldehyde 3-phosphate and acetyl phosphate from xylulose 5-phosphate, (ii) one or more heterologous genes encoding one or more MVA polypeptides, and (iii) one or more heterologous genes involved in mevalonate, isoprenoid precursor, or isoprene or isoprenoid biosynthesis that enables the synthesis of mevalonate, isoprenoid precursors, isoprene or isoprenoids from acetoacetyl-CoA in the host cell. In other embodiments, recombinant cells of the present invention are recombinant cells having the ability to produce mevalonate, isoprenoid precursors, isoprene or isoprenoids wherein the recombinant cells comprise: (i) a heterologous gene encoding a phosphoketolase capable of synthesizing erythrose 4-phosphate and acetyl phosphate from fructose 6-phosphate, (ii) one or more heterologous genes encoding one or more MVA polypeptides, and (iii) one or more heterologous genes involved in mevalonate, isoprenoid precursors, isoprene or isoprenoid biosynthesis that enables the synthesis of produce mevalonate, isoprenoid precursors, isoprene or isoprenoids from acetoacetyl-CoA in the host cell.

Upper MVA Pathway Polypeptides

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated in can be expressed in recombinant cells in any of the ways described herein.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In *L. grayi, E. faecium, E. gallinarum, E. casseliflavus*, and *E. faecalis*, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol.* 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis*, to produce mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of mevalonate, isoprenoid precursors, isoprene, and/or isoprenoids. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 μl. For the assay, 1 enzyme unit (eu) represents the synthesis or thiolysis in 1 min of 1 μmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 μl. Reactions are initiated by adding the enzyme. For the assay, 1 eu represents the turnover, in 1 min, of 1 μmol of NADP(H). This corresponds to the turnover of 0.5 μmol of HMG-CoA or mevalonate.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium, Enterococcus gallinarum* EG2, *Enterococcus faecalis*, and/or *Enterococcus casseliflavus*. The mvaE nucleic acid encoded by the *Listeria grayi*_DSM 20601 mvaE gene can have at least about 99%, 98%, 97%, 96%, 95%, 95%, 93%, 92%, 91%, 90%, 89%, 88%, 87%, 86%, or 85% sequence identity to SEQ ID NO:95. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:96. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:97. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:98. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.,* 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10,M-acetoacetyl-CoA and 5 μl samples of extracts can be added, followed by simultaneous addition of acetyl-CoA (100 μM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-$MgCl_2$), is $12.2\times10^3$ $M^{-1}$ $cm^{-1}$. By definition, 1 unit of enzyme activity causes 1 μmol of acetoacetyl-CoA to be transformed per minute.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium, Enterococcus gallinarum* EG2, *Enterococcus faecalis*, and/or *Enterococcus casseliflavus*. The mvaS nucleic acid encoded by the *Listeria grayi*_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:99. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:100. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:101. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:102. The mvaS nucleic acid encoded by the *Enterococcus faecalis* mvaS gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Acetoacetyl-CoA Synthase Gene

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used. An example of such an acetoacetyl-CoA synthase gene is the gene encoding a protein having the amino. Such a protein having the amino acid sequence of SEQ ID NO:103 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO:103 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506 A.

As described herein, an acetoacetyl-CoA synthase gene for use in the present invention is not limited to a gene encoding a protein having the amino acid sequence of SEQ ID NO:103 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO:103 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO:103, which is calculated by performing alignment of the amino acid sequence of SEQ ID NO:103 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO:103 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO:103 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. two times SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO:103 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO:103 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO:103 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Recombinant Cells Capable of Increased Production of Mevalonate

The recombinant cells (e.g., recombinant bacterial cells) described herein can produce mevalonate at an amount and/or concentration greater than that of the same cells without any manipulation to the various enzymatic pathways described herein. Thus, the recombinant cells (e.g., bacterial cells) that have been engineered for modulation in the various pathways described herein are useful in the enhance production of mevalonate.

Accordingly, in certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In certain aspects, the recombinant cells described herein comprise one or more copies of a heterologous nucleic acid encoding a phosphoketolase isolated from isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In another embodiment, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In still another embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24.

In one embodiment, the recombinant cells further comprise one or more copies of a heterologous nucleic acid encoding mvaE and mvaS polypeptides from *L. grayi, E. faecium, E. gallinarum, E. casseliflavus*, and/or *E. faecalis*. In another embodiment, the recombinant cells further comprise an acetoacetyl-CoA synthase and one or more nucleic acids encoding one or more polypeptides of the upper MVA pathway.

In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (OA), EI (ptsf), $EIICB^{Glc}$ (ptsG), $EIIA^{Glc}$ (crr), and/or HPr (ptsH).

In one aspect, the recombinant cells described herein can produce mevalonate at a higher volumetric productivity than that of the same cells lacking one or more copies of a heterologous nucleic acid encoding a polypeptide having phosphoketolase activity. In certain embodiments, the recombinant cell can produce greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr. 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers.

In one aspect, the recombinant cells described herein can produce mevalonate at a higher titer than that of the same cells lacking one or more copies of a heterologous nucleic acid encoding a polypeptide having phosphoketolase activity. These recombinant cells can produce greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers.

In other embodiments, the recombinant cells described herein further comprise one or more mutations which increase carbon flux towards the MVA pathway and can thus produce higher titers of mevalonate in comparison to cells which have not been similarly engineered. In such embodiments, the recombinant cells described herein produce mevalonate at a higher peak titer than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), $EIICB^{Glc}$ (ptsG), $EIIA^{Glc}$ (crr), and/or HPr (ptsH).

In one aspect, the recombinant cells described herein can produce mevalonate at a higher cell productivity index (CPI) for mevalonate than that of the same cells lacking one or more copies of a heterologous nucleic acid encoding a polypeptide having phosphoketolase activity. The recombinant cells can have a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers.

In certain embodiments, the recombinant cells described herein further comprise one or more mutations which increase carbon flux towards the MVA pathway which results in a higher cell productivity index (CPI) for mevalonate in comparison to cells which have not been similarly engineered. Additionally, the recombinant cells described herein have a higher CPI than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), $EIICB^{Glc}$ (ptsG), $EIIA^{Glc}$ (crr), and/or HPr (ptsH).

Additionally, the cells described herein have a higher mass yield of mevalonate from glucose than that of the same cells lacking one or more copies of a heterologous nucleic acid encoding phosphoketolase polypeptide having phosphoketolase activity. The recombinant cells can produce a mass yield of mevalonate from glucose of at least about 28%. Alternatively, the recombinant cells can produce a mass yield of mevalonate from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers.

In certain embodiments, the recombinant cells described herein further comprise one or more mutations which increase carbon flux towards the MVA pathway which results in a higher mass yield of mevalonate in comparison to cells which have not been similarly engineered. Additionally, the recombinant cells described herein have a higher mass yield of mevalonate than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), $EIICB^{Glc}$ (ptsG), $EIIA^{Glc}$ (crr), and/or HPr (ptsH).

In one aspect, the recombinant cells described herein produce mevalonate while accumulating less acetate in the fermentation broth as compared to the same cells lacking one or more copies of a heterologous nucleic acid encoding a polypeptide having phosphoketolase activity. The recombinant cells can produce increased levels of mevalonate while accumulating less than 4.5 g/L of acetate in the fermentation broth over a 48 hr fermentation. Alternatively, the recombinant cells can produce increased levels of mevalonate while accumulating less than about 8.0 g/L, 7.5 g/L, 7.0 g/L, 6.5 g/L, 6.0 g/L, 5.5 g/L, 5.0 g/L, 4.5 g/L, 4.0 g/L, 3.5 g/L, 3.0 g/L, 2.5 g/L, 2.0 g/L, or 1.5 g/L, of acetate in the fermentation broth over a 48 hr fermentation inclusive, as well as any numerical value in between these numbers. In certain embodiments, the decreased accumulation of acetate in the fermentation broth can improve cell viability during the fermentation run.

In certain embodiments, the recombinant cells described herein further comprise one or more mutations which increase carbon flux towards the MVA pathway which results increased levels of mevalonate while accumulating less acetate in the fermentation broth in comparison to cells which have not been similarly engineered. In certain embodiments, the decreased accumulation of acetate in the fermentation broth can improve cell viability during the fermentation run.

Also provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using Recombinant Cells to Produce Increased Amounts of Mevalonate

Also provided herein are methods for the production of mevalonate. In some aspects, the method for producing mevalonate comprises: (a) culturing a composition comprising recombinant cells which have been engineered to increase carbon flux through the phosphoketolase pathway as described herein (including any of the recombinant cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

As described herein, the methods of producing mevalonate comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. Additionally, the recombinant cells can produce mevalonate in concentrations greater than that of the same cells lacking one or more heterologous copies of a gene encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum* along with one or more heterologous nucleic acids expressing one or more MVA pathway peptides, when the cells are cultured in minimal medium. In certain embodiments, the one or more copies of a heterologous nucleic acid encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum* is a heterologous nucleic acid that is integrated into the host cell's chromosome.

The instant methods for the production of mevalonate produce can produce mevalonate using cells having a volumetric productivity of greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr. 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells produce mevalonate with a higher peak titer after 48 hours of fermentation than that of the same cells lacking one or more heterologous copies of a gene encoding an phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

The instant methods for the production of mevalonate can produce mevalonate using cells that can produce a peak titer of greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells have a CPI for mevalonate higher than that of the same cells lacking one or more heterologous copies of a gene encoding an phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

The instant methods for the production of mevalonate can produce mevalonate using cells with a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

In certain embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Provided herein are methods of using any of the cells described above for enhanced mevalonate production. The production of mevalonate by the cells can be enhanced by the expression of one or more heterologous nucleic acids encoding a phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, and/or Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

In other aspects, the methods described herein can provide for the enhanced production of mevalonate can by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production.

In addition, more specific cell culture conditions can be used to culture the cells in the methods described herein. For example, in some aspects, the method for the production of mevalonate comprises the steps of (a) culturing recombinant cells (including, but not limited to, *E. coli* cells) that do not endogenously have a phosphoketolase gene in minimal medium at 34° C., wherein the recombinant cells heterologously express one or more copies of a heterologous gene encoding a phosphoketolase polypeptide on a low to medium copy plasmid and under the control of a strong promoter; and (b) producing mevalonate. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24. In some aspects, the method of producing mevalonate further comprises a step of recovering the mevalonate.

Also provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said mevalonate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said mevalonate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said mevalonate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing mevalonate comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said mevalonate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Capable of Producing Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of E4P, GAP, Ac-P, and/or acetyl-CoA in recombinant cells comprising the mevalonate pathway by any of the compositions and methods described above will likewise result in the production of higher amounts of isoprene. Increasing the molar yield of mevalonate production from glucose translates into higher molar yields of isoprenoid precursors, isoprene and/or isoprenoids produced from glucose when combined with appropriate enzymatic activity levels of mevalonate kinase, phosphomevalonate kinase, diphosphomevalonate decarboxylase, isopentenyl diphosphate isomerase (e.g., the lower MVA pathway) and other appropriate enzymes for isoprene and isoprenoid production.

As described herein, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway (i.e., the upper MVA pathway and the lower MVA pathway) and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

Production of isoprene can also be made by using any of the recombinant host cells described herein further comprising one or more of the enzymatic pathways manipulations wherein enzyme activity is modulated to increase carbon flow towards mevalonate production and subsequent isoprenoid precursor, isoprenoid, and/or isoprene production. The recombinant cells described herein that have various enzymatic pathways manipulated for increased carbon flux through the phosphoketolase pathway for production of acetyl-CoA that can be used for mevalonate production and subsequent isoprenoid precursor, isoprenoid, and/or isoprene production. In one embodiment, the recombinant cells can be further engineered to increase the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), $EIICB^{Glc}$ (ptsG), $EIIA^{Glc}$ (crr), and/or HPr (ptsH).

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *M. Burtonii* mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis*, or *Methanosarcina mazei.*

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. In some embodiments, the lower MVK polypeptide can be from *M. burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variant.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus* sakei mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, *Methanosarcina mazei* mevalonate kinase polypeptide, and *M. Burtonii* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Nucleic Acids Encoding Isoprene Synthase Polypeptides

In some aspects of the invention, the cells described in any of the compositions or methods described herein (including host cells that have been engineered for increased carbon flux through the phosphoketolase pathway as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba*×*Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) can be added to 25 μL of cell extract in a 20 ml Headspace vial with a metal screw cap and teflon coated silicon septum (Agilent Technologies) and cultured at 37° C. for 15 minutes with shaking. The reaction can be quenched by adding 200 μL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba*×*tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making cells encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, WO2010/148256, WO 2012/058494, and U.S. Pat. No. 8,173,410.

Isoprene Biosynthetic Pathway

Isoprene can be produced from two different alcohols, 3-methyl-2-buten-1-ol and 2-methyl-3-buten-2-ol. For example, in a two-step isoprene biosynthetic pathway, dimethylallyl diphosphate is converted to 2-methyl-3-buten-2-ol by an enzyme such as a synthase (e.g., a 2-methyl-3-buten-2-ol synthase), followed by conversion of 2-methyl-3-buten-2-ol to isoprene by a 2-methyl-3-buten-2-ol dehydratase. As another example, in a three-step isoprene biosynthetic pathway, dimethylallyl diphosphate is converted to 3-methyl-2-buten-1-ol by either a phosphatase or a synthase (e.g., a geraniol synthase or farnesol synthase) capable of converting dimethylallyl diphosphate to 3-methyl-2-buten-1-ol, 3-methyl-2-buten-1-ol is converted to 2-methyl-3-buten-2-ol by a 2-methyl-3-buten-2-ol isomerase, and 2-methyl-3-buten-2-ol is converted to isoprene by a 2-methyl-3-buten-2-ol dehydratase. See for example, U.S. Patent Application Publication No.: US 20130309742 A1 and U.S. Patent Application Publication No.: US 20130309741 A1.

In some aspects of the invention, the cells described in any of the compositions or methods described herein (including host cells that have been modified as described herein) further comprise one or more nucleic acids encoding a polypeptide of an isoprene biosynthetic pathway selected from the group consisting of 2-methyl-3-buten-2-ol dehydratase, 2-methyl-3-butene-2-ol isomerase, and 3-methyl-2-buten-1-ol synthase. In some aspects, the polypeptide of an isoprene biosynthetic pathway is an endogenous polypeptide. In some aspects, the endogenous nucleic acid encoding a polypeptide of an isoprene biosynthetic pathway is operably linked to a constitutive promoter. In some aspects, the endogenous nucleic acid encoding a polypeptide of an isoprene biosynthetic pathway is operably linked to an inducible promoter. In some aspects, the endogenous nucleic acid encoding a polypeptide of an isoprene biosynthetic pathway is operably linked to a strong promoter. In a particular aspect, the cells are engineered to overexpress the endogenous polypeptide of an isoprene biosynthetic pathway relative to wild-type cells. In some aspects, the endogenous nucleic acid encoding a polypeptide of an isoprene biosynthetic pathway is operably linked to a weak promoter.

In some aspects, the polypeptide of an isoprene biosynthetic pathway is a heterologous polypeptide. In some aspects, the cells comprise more than one copy of a heterologous nucleic acid encoding a polypeptide of an isoprene biosynthetic pathway. In some aspects, the heterologous nucleic acid encoding a polypeptide of an isoprene biosynthetic pathway is operably linked to a constitutive promoter. In some aspects, the heterologous nucleic acid encoding a polypeptide of an isoprene biosynthetic pathway is operably linked to an inducible promoter. In some aspects, the heterologous nucleic acid encoding a polypeptide of an isoprene biosynthetic pathway is operably linked to a strong promoter. In some aspects, the heterologous nucleic acid encoding a polypeptide of an isoprene biosynthetic pathway is operably linked to a weak promoter.

The nucleic acids encoding a polypeptide(s) of an isoprene biosynthetic pathway can be integrated into a genome of the host cells or can be stably expressed in the cells. The nucleic acids encoding a polypeptide(s) of an isoprene biosynthetic pathway can additionally be on a vector.

Exemplary nucleic acids encoding a polypeptide(s) of an isoprene biosynthetic pathway include nucleic acids that encode a polypeptide, fragment of a polypeptide, peptide, or fusion polypeptide that has at least one activity of a polypeptide of an isoprene biosynthetic pathway such as a 2-methyl-3-buten-2-ol dehydratase polypeptide, 2-methyl-3-butene-2-ol isomerase polypeptide, and 3-methyl-2-buten-1-ol synthase polypeptide. Exemplary polypeptide(s) of an isoprene biosynthetic pathway and nucleic acids encoding polypeptide(s) of an isoprene biosynthetic pathway include naturally-occurring polypeptides and nucleic acids from any of the source organisms described herein. In addition, variants of polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide) can possess improved activity such as improved enzymatic activity.

In some aspects, a polypeptide of an isoprene biosynthetic pathway is a phosphatase. Exemplary phosphatases include a phosphatase from *Bacillus subtilis* or *Escherichia coli*. In some embodiments, the phosphatase is a 3-methyl-2-buten-1-ol synthase polypeptide or variant thereof. In some aspects, a polypeptide of an isoprene biosynthetic pathway is a terpene synthase (e.g., a geraniol synthase, farnesol synthase, linalool synthase or nerolidol synthase). Exemplary terpene synthases include a terpene synthase from *Ocimum basilicum, Perilla citriodora, Perilla frutescans, Cinnamomom tenuipile, Zea mays* or *Oryza sativa*. Additional exemplary terpene synthases include a terpene synthase from *Clarkia breweri, Arabidopsis thaliana, Perilla setoyensis, Perilla frutescens, Actinidia arguta, Actinidia polygama, Artemesia annua, Ocimum basilicum, Mentha aquatica, Solanum lycopersicum, Medicago trunculata, Populus trichocarpa, Fragaria vesca, or Fragraria ananassa*. In some embodiments, the terpene synthase is a 3-methyl-2-buten-1-ol synthase polypeptide or variant thereof. For example, a terpene synthase described herein can catalyze the conversion of dimethylallyl diphosphate to 3-methyl-2-buten-1-ol (e.g., a 3-methyl-2-buten-1-ol synthase). In some aspects, a terpene synthase described herein can catalyze the conversion of dimethylallyl diphosphate to 2-methyl-3-buten-2-ol (e.g., a 2-methyl-3-buten-2-ol synthase). In some aspects, a polypeptide of an isoprene biosynthetic pathway is a 2-methyl-3-buten-2-ol dehydratase polypeptide (e.g., a 2-methyl-3-buten-2-ol dehydratase polypeptide from *Aquincola tertiaricarbonis*) or variant thereof. In some aspects, the 2-methyl-3-buten-2-ol dehydratase polypeptide is a linalool dehydratase-isomerase polypeptide (e.g., a linalool dehydratase-isomerase polypeptide from *Castellaniella defragrans* Genbank accession number FR669447) or variant thereof. In some aspects, a polypeptide of an isoprene biosynthetic pathway is a 2-methyl-3-buten-2-ol isomerase polypeptide or variant thereof. In some aspects, the 2-methyl-3-butene-2-ol isomerase polypeptide is a linalool dehydratase-isomerase polypeptide (e.g., a linalool dehydratase-isomerase polypeptide from *Castellaniella defragrans* Genbank accession number FR669447) or variant thereof.

Standard methods can be used to determine whether a polypeptide has the desired isoprene biosynthetic pathway enzymatic activity (e.g., a 2-methyl-3-buten-2-ol dehydratase activity, 2-methyl-3-butene-2-ol isomerase activity, and 3-methyl-2-buten-1-ol activity) by measuring the ability of the polypeptide to convert DMAPP into isoprene in vitro, in a cell extract, or in vivo. See for example, U.S. Patent Application Publication No.: US 20130309742 A1 and U.S. Patent Application Publication No.: US 20130309741 A1.

In some aspects, the polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide) is a variant. In some aspects, polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-olsynthase polypeptide) is a variant of a wild-type or naturally occurring polypeptide(s) of an isoprene biosynthetic pathway. In some aspects, the variant has improved activity such as improved catalytic activity compared to the wild-type or naturally occurring polypeptide(s) of an isoprene biosynthetic pathway. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring polypeptide(s) of an isoprene biosynthetic pathway. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the polypeptide(s) of an isoprene biosynthetic pathway is a variant of naturally occurring polypeptide(s) of an isoprene biosynthetic pathway and has improved stability (such as thermo-stability) compared to the naturally occurring polypeptide(s) of an isoprene biosynthetic pathway.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). The variant can share sequence similarity with a wild-type or naturally occurring polypeptide(s) of an isoprene biosynthetic pathway. In some aspects, a variant of a wild-type or naturally occurring polypeptide(s) of an isoprene biosynthetic pathway can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). In some aspects, a variant of a wild-type or naturally occurring polypeptide(s) of an isoprene biosynthetic pathway has any of about 70% to about 99.9%, about 75% to about 99%, about 80% to about 98%, about 85% to about 97%, or about 90% to about 95% amino acid sequence identity as that of the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide).

In some aspects, the variant comprises a mutation in the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring polypeptide(s) of an isoprene biosynthetic pathway can be one or more, e.g. 1, 2, 3, 4, 5, 10, 15, 20, 30, 40, 50, or more amino acid residues. In some aspects, the nucleic acid encoding the variant (e.g., a 2-methyl-3-buten-2-ol dehydratase polypeptide, 2-methyl-3-butene-2-ol isomerase polypeptide, and 3-methyl-2-buten-1-ol synthase polypeptide) is codon optimized (for example, codon optimized based on host cells where the heterologous polypeptide(s) of an isoprene biosynthetic pathway is expressed).

Any one of the promoters described herein (e.g., promoters described herein and identified in the Examples of the present disclosure including inducible promoters and constitutive promoters) can be used to drive expression of any of the polypeptides of an isoprene biosynthetic pathway described herein.

Nucleic Acids Encoding DXP Pathway Polypeptides

In some aspects of the invention, the cells described in any of the compositions or methods described herein (including host cells that have been engineered for increased carbon flux through the phosphoketolase pathway as described herein) further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication Nos. WO 2009/076676, WO 2010/003007, WO 2009/132220, and U.S. Patent Publ. Nos. US 2009/0203102, 2010/0003716 and 2010/0048964.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No. WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, WO 2010/003007, WO 2009/132220, and U.S. Patent Publ. Nos. US 2009/0203102, 2010/0003716, and 2010/0048964.

In particular, DXS polypeptides convert pyruvate and D-glyceraldehyde 3-phosphate into 1-deoxy-D-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-D-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for Lower MVA Pathway, Isoprene Synthase, IDI, and DXP Pathway Polypeptides Isoprene synthase, IDI, DXP pathway, and/or lower MVA pathway nucleic acids (and their encoded polypeptides) can be obtained from any organism that naturally contains isoprene synthase, IDI, DXP pathway, and/or lower MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of *Archaea* such as *Methanosarcina mazei*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some aspects, the source organism is a gram-positive bacterium. Non-limiting examples include strains of *Streptomyces* (e.g., *S. lividans, S. coelicolor*, or *S. griseus*) and *Bacillus*. In some aspects, the source organism is a gram-negative bacterium, such as *E. coli* or *Pseudomonas* sp.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales, Pleurocapsales, Oscillatoriales, Nostocales*, or *Stigonematales*.

Recombinant Cells Capable of Increased Production of Isoprene

The recombinant cells described herein (including host cells that have been engineered for increased carbon flux through the phosphoketolase pathway as described herein) have the ability to produce isoprene concentration greater than that of the same cells lacking one or more copies of a heterologous nucleic acid phosphoketolase polypeptides, one or more copies of a heterologous nucleic acid encoding a MVA pathway polypeptide, and one or more heterologous nucleic acids encoding an isoprene synthase polypeptide when cultured under the same conditions. The cells can further comprise one or more heterologous nucleic acids encoding an IDI polypeptide. In certain embodiments, the phosphoketolase polypeptide is from *Burkholderia phyto-*

*firmans, Lactobacillus buchneri, Bifidobacterium gallicum, Bifidobacterium dentium, Bifidobacterium bifidum*, and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In other embodiments, the phosphoketolase polypeptide is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cell is a *Corynebacteria* spp. (e.g., *C. glutamicum*).

In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In some aspects, the one or more copies of a heterologous nucleic acid encoding phosphoketolase, one or more copies of a heterologous nucleic acid encoding a MVA pathway polypeptide, and one or more heterologous nucleic acids encoding an isoprene synthase polypeptide are heterologous nucleic acids that are integrated into the host cell's chromosomal nucleotide sequence. In other aspects, the one or more heterologous nucleic acids are integrated into plasmid. In still other aspects, at least one of the one or more heterologous nucleic acids is integrated into the cell's chromosomal nucleotide sequence while at least one of the one or more heterologous nucleic acid sequences is integrated into a plasmid. The recombinant cells can produce at least 5% greater amounts of isoprene compared to isoprene-producing cells that do not comprise the phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, provided herein are recombinant cells comprising one or more heterologous nucleic acids encoding a phosphoketolase polypeptide as described herein, one or more heterologous nucleic acids encoding a mevalonate (MVA) pathway polypeptide(s), one or more heterologous nucleic acids encoding a DXP pathway polypeptide(s), and one or more heterologous nucleic acids encoding an isoprene synthase polypeptide. The cells can further comprise one or more heterologous nucleic acids encoding an IDI polypeptide. Any of the one or more heterologous nucleic acids can be operably linked to constitutive promoters, can be operably linked to inducible promoters, or can be operably linked to a combination of inducible and constitutive promoters. The one or more heterologous nucleic acids can additionally be operably linked to strong promoters, weak promoters, and/or medium promoters. One or more of the heterologous nucleic acids encoding phosphoketolase, a mevalonate (MVA) pathway polypeptide(s), a DXP pathway polypeptide(s), and an isoprene synthase polypeptide can be integrated into a genome of the host cells or can be stably expressed in the cells. The one or more heterologous nucleic acids can additionally be on a vector.

The production of isoprene by the cells according to any of the compositions or methods described herein can be enhanced (e.g., enhanced by the expression of one or more heterologous nucleic acids encoding a phosphoketolase polypeptide, an isoprene synthase polypeptide, MVA pathway polypeptide(s), and/or a DXP pathway polypeptide(s)). As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase peptide. In certain embodiments described herein, the host cells have been further engineered increased carbon flux through the phosphoketolase pathway for E4P, GAP, Ac-P, and/or, acetyl-CoA production.

The production of isoprene by the recombinant cells described herein can be enhanced by about 5% to about 1,000,000 folds. In certain aspects, the production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more heterologous nucleic acids encoding phosphoketolase peptide. In certain embodiments described herein, the host cells have been further engineered to increased carbon flux through the phosphoketolase pathway to MVA production thereby providing enhanced production of isoprene as compared to the production of isoprene by cells that do not express one or more heterologous nucleic acids encoding phosphoketolase peptide and which have not been engineered for increased carbon flux through the phosphoketolase pathway to mevalonate production.

In other aspects, the production of isoprene by the recombinant cells described herein can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds as compared to the production of isoprene by cells that do not express one or more heterologous nucleic acids encoding phosphoketolase peptide. In certain embodiments described herein, the host cells have been further engineered increased carbon flux through the phosphoketolase pathway to MVA production thereby providing enhanced production of isoprene as compared to the production of isoprene by cells that do not express one or more heterologous nucleic acids encoding phosphoketolase peptide and which have not been engineered for increased carbon flux through the phosphoketolase pathway to mevalonate production.

Also provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other embodiments, the Performance Index value parameters further include (e) isoprene yield protein solubility or (f) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In other embodiments, the Performance Index value parameters further include (d) isoprene yield protein solubility or (e) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other embodiments, the Performance Index value parameters further include (e) isoprene yield protein solubility or (f) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In other embodiments, the Performance Index value parameters further include (d) isoprene yield protein solubility or (e) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using the Recombinant Cells to Produce Isoprene

Also provided herein are methods for producing isoprene comprising culturing any of the recombinant cells described herein. In one aspect, isoprene can be produced by culturing recombinant cells comprising one or more heterologous nucleic acids encoding any phosphoketolase polypeptide as described herein, one or more MVA pathway polypeptides, and an isoprene synthase polypeptide. In certain embodiments, the recombinant cells described herein comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma*

*hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum.*

In another aspect, isoprene can be produced by culturing recombinant cells comprising modulation in any of the enzymatic pathways described herein and one or more heterologous nucleic acids encoding a phosphoketolase peptide, a MVA pathway polypeptide, and an isoprene synthase polypeptide. In certain embodiments, the recombinant cells described herein comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. The isoprene can be produced from any of the cells described herein and according to any of the methods described herein. Any of the cells can be used for the purpose of producing isoprene from carbohydrates, including, but not limited to, six carbon sugars such as glucose and/or five carbon sugars such as xylose.

Thus, provided herein are methods of producing isoprene comprising culturing cells comprising one or more heterologous nucleic acids encoding a phosphoketolase polypeptide and an isoprene synthase in a suitable condition for producing isoprene and (b) producing isoprene. In certain embodiments, the recombinant cells described herein comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicumi*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum.*

The cells can further comprise one or more nucleic acid molecules encoding the MVA pathway polypeptide(s) described above (e.g., the complete MVA pathway) and any of the isoprene synthase polypeptide(s) described above (e.g. *Pueraria* isoprene synthase). In some aspects, the recombinant cells can be one of any of the cells described herein. Any of the isoprene synthases or variants thereof described herein, any of the host cell strains described herein, any of the promoters described herein, and/or any of the vectors described herein can also be used to produce isoprene using any of the energy sources (e.g. glucose or xylose) described herein can be used in the methods described herein. In some aspects, the method of producing isoprene further comprises a step of recovering the isoprene. In other embodiments, the phosphoketolase polypeptide is from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum.*

In certain aspects, provided herein are methods of making isoprene comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, an mvaE and an mvaS polypeptide from *L. grayi, E. faecium, E. gallinarum, E. casseliflavus*, and/or *E. faecalis*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein.

In certain aspects, provided herein are methods of making isoprene comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein.

The recombinant cells described herein that have various enzymatic pathways manipulated for increased carbon flow through the phosphoketolase pathway to mevalonate production can be used to produce isoprene. In some aspects, the recombinant cells can be further engineered to increase the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), $EIICB^{Glc}$ (ptsG), $EIIA^{Glc}$ (crr), and/or HPr (ptsH).

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In certain embodiments, the methods of producing isoprene can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with (i) one or more nucleic acids expressing one or more MVA pathway peptides and (ii) an isoprene synthase and (b) producing isoprene, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Also provided herein are methods for the production of isoprene comprising cells having enhanced isoprene production capabilities. The production of isoprene by the cells described herein can be enhanced by the expression of one or more heterologous nucleic acids encoding a phosphoketolase polypeptide, one or more copies of a heterologous nucleic acid encoding one or more polypeptides of the complete MVA pathway polypeptide, and one or more heterologous nucleic acids encoding an isoprene synthase polypeptide. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the phosphoketolase is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In yet other embodiments, the phosphoketolase is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase polypeptide, a MVA pathway polypeptide(s) and an isoprene synthase polypeptide. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the isoprene-producing cells that do not endogenously express phosphoketolase enzyme. In certain embodiments described herein, the methods described herein comprise host cells have been further engineered to increased carbon flux through the phosphoketolase pathway to MVA production thereby providing enhanced production of isoprene as compared to the production of isoprene by isoprene-producing cells that do not express one or more heterologous nucleic acids encoding phosphoketolase peptide and which have not been engineered for increased carbon flux through the phosphoketolase pathway to mevalonate production.

In other aspects, the methods described herein are directed to the enhanced production of isoprene by the cells described herein (e.g., enhanced by the expression of one or more heterologous nucleic acids encoding a phosphoketolase polypeptide). In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the phosphoketolase is from *Enterococcus faecium, Listeria grayi, Enterococcus gallinarum, Enterococcus saccharolyticus, Enterococcus casseliflavus,*

*Mycoplasma alligatoris, Carnobacterium* sp., *Melissococcus plutonius, Tetragenococcus halophilus*, and/or *Mycoplasma arthritidis*. In yet other embodiments, the phosphoketolase is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by an isoprene-producing cells without the expression of one or more heterologous nucleic acids encoding a phosphoketolase polypeptide. The production of isoprene can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by isoprene-producing cells without the expression of one or more heterologous nucleic acids encoding phosphoketolase. In certain embodiments described herein, the methods described herein comprise host cells have been further engineered to increased carbon flux to MVA production thereby providing enhanced production of isoprene as compared to the production of isoprene by cells that do not express one or more heterologous nucleic acids encoding phosphoketolase peptide and which have not been engineered for increased carbon flux to mevalonate production.

In addition, more specific cell culture conditions can be used to culture the cells in the methods described herein. For example, in some aspects, the method for the production of isoprene comprises the steps of (a) culturing recombinant cells (including, but not limited to, *E. coli* cells) that do not endogenously have a phosphoketolase gene in minimal medium at 34° C., wherein the recombinant cells heterologously express (i) one or more copies of a heterologous gene encoding a phosphoketolase polypeptide on a low to medium copy plasmid and under the control of a strong promoter, (ii) one or more copies of a heterologous nucleic acid encoding one or more polypeptides of the MVA pathway polypeptide (upper MVA pathway and lower MVA pathway), and (iii) one or more heterologous nucleic acids encoding an isoprene synthase polypeptide; and (b) producing isoprene. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the phosphoketolase is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In yet other embodiments, the phosphoketolase is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some aspects, the method of producing isoprene further comprises a step of recovering the isoprene.

Also provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said isoprene. In other embodiments, the Performance Index value parameters further include (e) isoprene yield protein solubility or (f) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said isoprene. In other embodiments, the Performance Index value parameters further include (d) isoprene yield protein solubility or (e) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing isoprene comprising culturing recombinant cells capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said isoprene. In other embodiments, the Performance Index value parameters further include (e) isoprene yield protein solubility or (f) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said isoprene. In other embodiments, the Performance Index value parameters further include (d) isoprene yield protein solubility or (e) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Capable of Increased Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., *Plant Physiol.* 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_5$-IPP) (Hsieh et al., *Plant Physiol.* 2011 March; 155(3):1079-90).

Production of isoprenoid precursors and/or isoprenoids can be made by using any of the recombinant host cells that comprise one or more copies of a heterologous nucleic acid encoding a phosphoketolase for increased production of isoprenoid precursors and/or isoprenoids. In some aspects, these cells further comprise one or more heterologous nucleic acids encoding polypeptides of the MVA pathway, IDI, and/or the DXP pathway, as described above, and a heterologous nucleic acid encoding a polyprenyl pyrophosphate synthase polypeptide. Without being bound to theory, it is thought that increasing the cellular production of mevalonate in recombinant cells by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production. The recombinant cells described herein that have various enzymatic pathways manipulated for increased carbon flow to mevalonate production can be used to produce isoprenoid precursors and/or isoprenoids. In some aspects, the recombinant cells can be further engineered to increase the activity of one or more of the following genes selected from the group consisting of rpiA, rpe, tktA, tal B, pta and/or eutD. In another aspect, these strains can be further engineered to decrease the activity of one or more genes of the following genes including zwf, pfkA, fba, gapA, ackA, gltA and/or pts.

Types of Isoprenoids

The recombinant cells of the present invention are capable of increased production of isoprenoids and the isoprenoid precursor molecules DMAPP and IPP. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

In other embodiments the isoprenoid can be a form of Vitamin A, such as, without limitation, retinol, retinyl palmitate, retinoic acid, alpha-carotene, beta-carotene, gamma-carotene, or the xanthophyll beta-cryptoxanthin. In yet other embodiments, the isoprenoid can be a form of Vitamin E, such as, without limitation a tocopherol (e.g., alpha-tocopherol, beta-tocopherol, gamma-tocopherol, or delta-tocopherol) or a tocotrienol (e.g., alpha-tocotrienol, beta-tocotrienol, gamma-tocotrienol, or delta-tocotrienol).

Heterologous Nucleic Acids Encoding Polyprenyl Pyrophosphate Synthases Polypeptides In some aspects of the invention, the cells described in any of the compositions or methods herein further comprise one or more nucleic acids encoding a phosphoketolase polypeptide, as described above, as well as one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosposphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in *E. coli*. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köliner & Boland, *J Org Chem.* 2010 Aug. 20; 75(16):5590-600.

Recombinant Cells Capable of Increased Production of Isoprenoid Precursors and/or Isoprenoids The recombinant cells (e.g., recombinant bacterial cells) described herein (including host cells that have been engineered for increased carbon flux through the phosphoketolase pathway as described herein) have the ability to produce isoprenoid precursors and/or isoprenoids at an amount and/or concentration greater than that of the same cells lacking one or more copies of a heterologous nucleic acid encoding phosphoketolase, one or more copies of a heterologous nucleic acid encoding a MVA pathway polypeptide, and one or more heterologous nucleic acids encoding a polyprenyl pyrophosphate synthase polypeptide when cultured under the same conditions. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In other embodiments, the phosphoketolase polypeptide is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacte-*

*rium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In one embodiment, the recombinant cells comprise one or more copies of a heterologous nucleic acid encoding a phosphoketolase isolated from *Burkholderia* phytofirmans. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In another embodiment, the recombinant cell is a *Corynebacteria* spp. (e.g., *C. glutamicum*).

In some aspects, the one or more copies of a heterologous nucleic acid encoding phosphoketolase, one or more copies of a heterologous nucleic acid encoding a MVA pathway polypeptide, and one or more heterologous nucleic acids encoding a polyprenyl pyrophosphate synthase polypeptide are heterologous nucleic acids that are integrated into the host cell's chromosomal nucleotide sequence. In other aspects, the one or more heterologous nucleic acids are integrated into plasmid. In still other aspects, at least one of the one or more heterologous nucleic acids is integrated into the cell's chromosomal nucleotide sequence while at least one of the one or more heterologous nucleic acid sequences is integrated into a plasmid. The recombinant cells can produce at least 5% greater amounts of isoprenoid precursors and/or isoprenoids compared to isoprenoid precursor and/or isoprenoid-producing cells that do not comprise the phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive, as well as any numerical value in between these numbers.

In one aspect of the invention, provided herein are recombinant cells comprising one or more heterologous nucleic acids encoding a phosphoketolase polypeptide as described herein, one or more heterologous nucleic acids encoding a mevalonate (MVA) pathway polypeptide(s), one or more heterologous nucleic acids encoding a DXP pathway polypeptide(s), and one or more heterologous nucleic acids encoding a polyprenyl pyrophosphate synthase polypeptide. The cells can further comprise one or more heterologous nucleic acids encoding an IDI polypeptide. Any of the one or more heterologous nucleic acids can be operably linked to constitutive promoters, can be operably linked to inducible promoters, or can be operably linked to a combination of inducible and constitutive promoters. The one or more heterologous nucleic acids can additionally be operably linked to strong promoters, weak promoters, and/or medium promoters. One or more of the heterologous nucleic acids encoding phosphoketolase, a mevalonate (MVA) pathway polypeptide(s), a DXP pathway polypeptide(s), and an polyprenyl pyrophosphate synthase polypeptide can be integrated into a genome of the host cells or can be stably expressed in the cells. The one or more heterologous nucleic acids can additionally be on a vector.

The production of isoprenoids and/or isoprenoid precursors by the cells according to any of the compositions or methods described herein can be enhanced (e.g., enhanced by the expression of one or more heterologous nucleic acids encoding a phosphoketolase polypeptide, a polyprenyl pyrophosphate synthase polypeptide, MVA pathway polypeptide(s), and/or a DXP pathway polypeptide(s)). As used herein, "enhanced" isoprenoid precursors and/or isoprenoids production refers to an increased cell productivity index (CPI) for isoprenoid precursors and/or isoprenoids, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase peptide. In certain embodiments described herein, the host cells have been further engineered increased carbon flux through the phosphoketolase pathway for E4P, GAP, Ac-P, and/or, acetyl-CoA production.

The production of isoprenoid precursors and/or isoprenoids by the recombinant cells described herein can be enhanced by about 5% to about 1,000,000 folds. In certain aspects, the production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by cells that do not express one or more heterologous nucleic acids encoding phosphoketolase peptide. In certain embodiments described herein, the host cells have been further engineered to increased carbon flux through the phosphoketolase pathway to MVA production thereby providing enhanced production of isoprenoid precursors and/or isoprenoids as compared to the production of isoprenoid precursors and/or isoprenoids by cells that do not express one or more heterologous nucleic acids encoding phosphoketolase peptide and which have not been engineered for increased carbon flux through the phosphoketolase pathway to mevalonate production.

In other aspects, the production of isoprenoid precursors and/or isoprenoids by the recombinant cells described herein can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds as compared to the production of isoprenoid precursors and/or isoprenoids by cells that do not express one or more heterologous nucleic acids encoding phosphoketolase peptide. In certain embodiments described herein, the host cells have been further engineered increased carbon flux through the phosphoketolase pathway to MVA production thereby providing enhanced production of isoprenoid precursors and/or isoprenoids as compared to the production of isoprenoid precursors and/or isoprenoids by cells that do not express one or more heterologous nucleic acids encoding phosphoketolase peptide and which have not been engineered for increased carbon flux through the phosphoketolase pathway to mevalonate production.

In one aspect of the invention, there are provided recombinant cells comprising one or more heterologous nucleic acids encoding a phosphoketolase polypeptide, one or more heterologous nucleic acids encoding one or more complete MVA pathway polypeptide(s) (i.e., the upper MVA pathway and the lower MVA pathway), one or more heterologous nucleic acids encoding polyprenyl pyrophosphate synthase and/or one or more heterologous nucleic acids encoding a DXP pathway polypeptide(s). The cells can further comprise one or more heterologous nucleic acids encoding an IDI polypeptide. Additionally, the polyprenyl pyrophosphate synthase polypeptide can be an FPP synthase polypeptide. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In other embodiments, the phosphoketolase polypeptide is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In another embodiment, the recombinant cell is a *Corynebacteria* spp. (e.g., *C. glutamicum*). The one or more heterologous nucleic acids can additionally be on one or more vectors.

Provided herein are recombinant cells which can provide enhanced isoprenoid precursor and/or isoprenoid production. The production of isoprenoid precursors and/or isoprenoids by the cells can be enhanced by the expression of one or more heterologous nucleic acids encoding a phosphoketolase polypeptide, one or more heterologous nucleic acids encoding one or more polypeptide(s) of the complete MVA pathway (i.e., the upper MVA pathway and lower MVA pathway), and one or more heterologous nucleic acids encoding a polyprenyl pyrophosphate synthase polypeptide. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In other embodiments, the phosphoketolase polypeptide is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In another embodiment, the recombinant cell is a *Corynebacteria* spp. (e.g., *C. glutamicum*). As used herein, “enhanced” isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, one or more polypeptide(s) of the complete MVA pathway, and a polyprenyl pyrophosphate synthase polypeptide. The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid and/or isoprenoid precursors by cells without the expression of one or more heterologous nucleic acids encoding a phosphoketolase. In certain embodiments described herein, the recombinant host cells have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase polypeptide and which have not been engineered for increased carbon flux to mevalonate production.

The production of isoprenoid precursors and/or isoprenoids by the cells described herein can be enhanced (e.g., enhanced by the expression of one or more heterologous nucleic acids encoding the phosphoketolase polypeptides from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fis-*

*cheri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, one or more heterologous nucleic acids encoding a lower MVA pathway polypeptide, and one or more heterologous nucleic acids encoding a polyprenyl pyrophosphate synthase polypeptide). The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by naturally-occurring cells (e.g., cells without the expression of one or more heterologous nucleic acids encoding phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum* along with one or more heterologous nucleic acids expressing one or more MVA pathway peptides and which have not been engineered for increased carbon flux to mevalonate production.

In other embodiments, the recombinant cells described herein can provide for the production of isoprenoid precursors and/or isoprenoids can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursors and/or isoprenoids by isoprenoid precursors and/or isoprenoids producing recombinant cells which do not express of one or more heterologous nucleic acids encoding a phosphoketolase polypeptide.

Also provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are isoprenoid precursor and/or isoprenoid-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using the Recombinant Cells to Produce Isoprenoids and/or Isoprenoid Precursor Molecules Also provided herein are methods of producing isoprenoid precursor molecules and/or isoprenoids comprising culturing recombinant cells (e.g., recombinant bacterial cells) that comprise one or more heterologous nucleic acids encoding a phosphoketolase and an polyprenyl pyrophosphate synthase polypeptide. In certain embodiments, the recombinant cells further comprise one or more one or more heterologous nucleic acids encoding an upper MVA pathway polypeptide and a lower MVA pathway polypeptide. The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, including six carbon sugars such as glucose.

In certain aspects, provided herein are methods of making isoprenoid precursor molecules and/or isoprenoids comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, an mvaE and an mvaS polypeptide from *L. grayi, E. faecium, E. gallinarum, E. casseliflavus*, and/or *E. faecalis*, in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

In certain aspects, provided herein are methods of making isoprenoid precursor molecules and/or isoprenoids comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, an mvaE and an mvaS polypeptide from *L. grayi, E. faecium, E. gallinarum, E. casseliflavus*, and/or *E. faecalis*, in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

The method of producing isoprenoid precursor molecules and/or isoprenoids can similarly comprise the steps of: (a) culturing recombinant cells (including, but not limited to, *E. coli* cells) that do not endogenously have a phosphoketolase, wherein the recombinant cells heterologously express one or more copies of a gene encoding a phosphoketolase polypeptide; and (b) producing isoprenoid precursor molecules and/or isoprenoids, wherein the recombinant cells produce greater amounts of isoprenoid precursors and/or isoprenoids when compared to isoprenoids and/or isoprenoid precursor-producing cells that do not comprise the phosphoketolase polypeptide.

The instant methods for the production of isoprenoid precursor molecules and/or isoprenoids can produce at least 5% greater amounts of isoprenoid precursors and/or isoprenoids when compared to isoprenoids and/or isoprenoid precursor-producing recombinant cells that do not comprise a phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells described above for enhanced isoprenoid and/or isoprenoid precursor molecule production. The production of isoprenoid precursor molecules and/or isoprenoids by the cells can be enhanced by the expression of one or more heterologous nucleic acids encoding phosphoketolase, and/or the mvaE and mvaS polypeptides from *L. grayi, E. faecium, E. gallinarum, E. casseliflavus*, and/or *E. faecalis*, one or more heterologous nucleic acids encoding a lower MVA pathway polypeptide, and one or more heterologous nucleic acids encoding a polyprenyl pyrophosphate synthase polypeptide. As used herein, “enhanced” isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, a polyprenyl pyrophosphate synthase polypeptide, a lower MVA pathway polypeptide(s), the mvaE and mvaS polypeptides from *L. grayi, E. faecium, E. gallinarum, E. casseliflavus*. The production of isoprenoid precursor molecules and/or isoprenoids can be enhanced by about 5% to about 1,000,000 folds. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

The production of isoprenoid precursor molecules and/or isoprenoids can also enhanced by the methods described herein by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by isoprenoid precursors and/or isoprenoid-producing cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

In addition, more specific cell culture conditions can be used to culture the cells in the methods described herein. For example, in some aspects, the method for the production of isoprenoid precursor molecules and/or isoprenoids comprises the steps of (a) culturing recombinant cells (including, but not limited to, *E. coli* cells) which comprise a heterologous nucleic acid which encodes a phosphoketolase polypeptide and that do not endogenously have an mvaE gene and an mvaS gene from *L. grayi, E. faecium, E. gallinarum, E. casseliflavus*, and/or *E. faecalis* in minimal medium at 34° C., wherein the recombinant cells heterologously express one or more copies of a gene encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum* on a low to medium copy plasmid and under the control of a strong promoter; and (b) producing isoprenoid precursor molecules and/or isoprenoids. In some aspects, the methods further comprise a step of recovering the isoprenoid precursor molecules and/or isoprenoids.

Also provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing isoprenoid precursors and/or isoprenoids. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing isoprenoid precursors and/or isoprenoids. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing isoprenoid precursors and/or isoprenoids. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing isoprenoid precursors and/or isoprenoids. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Vectors

Suitable vectors can be used for any of the compositions and methods described herein. For example, suitable vectors can be used to optimize the expression of one or more copies of a gene encoding a phosphoketolase, an upper MVA pathway polypeptide including, but not limited to, mvaE and an mvaS polypeptide, a lower MVA pathway polypeptide, an isoprene synthase, or a polyprenyl pyrophosphate synthase in a particular host cell (e.g., *E. coli*). In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of a phosphoketolase, an upper MVA pathway polypeptide including, but not limited to, mvaE and an mvaS polypeptide, a lower MVA pathway polypeptide, an mvaE and an mvaS nucleic acid from *L. grayi, E. faecium, E. gallinarum, E. casseliflavus*, and/or *E. faecalis*, an isoprene synthase, or a polyprenyl pyrophosphate synthase nucleic acid(s) integrate into the genome of host cells without a selective marker.

Any one of the vectors characterized herein or used in the Examples of the present disclosure can be used in the present invention.

Transformation Methods

Nucleic acids encoding one or more copies of a phosphoketolase, an upper MVA pathway polypeptide including, but not limited to, mvaE and an mvaS polypeptide, a lower MVA pathway polypeptide, and/or lower MVA pathway polypeptides can be inserted into a cell using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual,* $2^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. Patent Publ. No. 2009/0203102, WO 2010/003007, US Publ. No. 2010/0048964, WO 2009/132220, and US Publ. No. 2010/0003716.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any cell or progeny thereof that can be used to heterologously express genes can be used to express one or more a phosphoketolase. In certain embodiments, the cells (e.g., recombinant cells) comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24.

The cells (e.g., recombinant cells) with heterologous nucleic acid encoding a phosphoketolase as described above and herein can also be engineered with one or more heterologous nucleic acids expressing one or more MVA pathway peptides, isoprene synthase, IDI, DXP pathway polypeptide (e), and/or polyprenyl pyrophosphate synthase polypeptides. In some embodiments, the host cell is a gram-positive bacterium. Non-limiting examples include strains of *Corynebacteria* (e.g. *C. glutamicum*), *Streptomyces* (e.g., *S. lividans, S. coelicolor*, or *S. griseus*), *Bacillus, Listeria* (e.g., *L. monocytogenes*) or *Lactobacillus* (e.g., L. spp). In some embodiments, the source organism is a gram-negative bacterium, such as *E. coli*, *Pseudomonas* sp, or *H. pylori*.

Bacteria cells, including gram positive or gram negative bacteria can be used to express any of the heterologous genes described above. In particular, the mvaE and mvaS genes can be expressed in any one of *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprenoid precursors, isoprene, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprenoid precursors, isoprene, and isoprenoids. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum*, *T. viride*, *T. koningii*, *T. harzianum*, *Penicillium* sp., *Humicola insolens*, *H. lanuginose*, *H. grisea*, *Chrysosporium* sp., *C. lucknowense*, *Gliocladium* sp., *Aspergillus* sp., such as *A. oryzae*, *A. niger*, *A sojae*, *A. japonicus*, *A. nidulans*, or *A. awamori*, *Fusarium* sp., such as *F. roseum*, *F. graminum F. cerealis*, *F. oxysporuim*, or *F. venenatum*, *Neurospora* sp., such as *N. crassa*, *Hypocrea* sp., *Mucor* sp., such as *M. miehei*, *Rhizopus* sp. or *Emericella* sp. In some aspects, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6):423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: *Chlorococcales, Pleurocapsales, Oscillatoriales, Nostocales, or Stigonematales* (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* host cells can be used to express one or more phosphoketolase enzymes from any number of organisms. In certain embodiments, the cells (e.g., recombinant cells) comprise one or more copies of a heterologous nucleic acid encoding a phosphoketolase isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In some embodiments, the recombinant cells comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oralis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24.

These cells can also be engineered with one or more heterologous nucleic acids encoding one or more MVA pathway polypeptides, isoprene synthase, IDI, DXP pathway polypeptide(s), and/or polyprenyl pyrophosphate synthase polypeptides. In one aspect, the host cell is a recombinant cell of an *Escherichia coli* (*E. coli*) strain, or progeny thereof, capable of producing mevalonate that expresses one or more nucleic acids encoding phosphoketolase described above and herein along with one or more heterologous nucleic acids expressing one or more MVA pathway peptides. The *E. coli* host cells can produce mevalonate in amounts, peak titers, and cell productivities greater than that of the same cells lacking one or more heterologously expressed nucleic acids encoding phosphoketolase polypeptides described above and herein along with one or more heterologous nucleic acids expressing one or more MVA pathway peptides. In addition, the one or more heterologously expressed nucleic acids encoding phosphoketolase polypeptide described above and herein along with one or more heterologous nucleic acids expressing one or more MVA pathway peptides in *E. coli* can be chromosomal copies (e.g., integrated into the *E. coli* chromosome). In other aspects, the *E. coli* cells are in culture. In some aspects the one or more phosphoketolase enzymes is from *Clostridium acetobutylicum*, *Bifidobacterium longum*, and/or *Enterococcus gallinarum*. In any aspects, the one or more phosphoketolase enzymes are any phosphoketolase enzymes as disclosed herein.

Exemplary Host Cell Modifications

Citrate Synthase Pathway

Citrate synthase catalyzes the condensation of oxaloacetate and acetyl-CoA to form citrate, a metabolite of the tricarboxylic acid (TCA) cycle (Ner, S. et al. 1983. *Biochemistry*, 22: 5243-5249; Bhayana, V. and Duckworth, H. 1984. Biochemistry 23: 2900-2905). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate, isoprene and isoprenoids. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The gene encoding citrate synthase can also be deleted. The decrease of the activity of citrate synthase can result in more carbon flux into the mevalonate dependent biosynthetic pathway in comparison to cells that do not have decreased expression of citrate synthase. In any aspects of the invention, provided herein are recombinant cells comprising one or more heterologously expressed nucleic acids encoding phosphoketolase polypeptides as disclosed herein and further engineered to decrease the activity of citrate synthase (gltA). Activity modulation (e.g., decreased) of citrate synthase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a citrate synthase isozyme.

Pathways Involving Phosphotransacetylase and/or Acetate Kinase

Phosphotransacetylase ((encoded in *E. coli* by (i) pta (Shimizu et al. 1969. Biochim. Biophys. Acta 191: 550-558 or (ii) eutD (Bologna et al. 2010. J of Microbiology. 48:629-636) catalyzes the reversible conversion between acetyl-CoA and acetyl phosphate (acetyl-P), while acetate kinase (encoded in *E. coli* by ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, it is possible to increase the amount of acetyl-P going towards acetyl-CoA by enhancing the activity of phosphotransacetylase. In certain embodiments, enhancement is achieved by placing an upregulated promoter upstream of the gene in the chromosome, or to place a copy of the gene behind an adequate promoter on a plasmid. In order to decrease the amount of acetyl-coA going towards acetate, the activity of acetate kinase gene (e.g., the endogenous acetate kinase gene) can be decreased or attenuated. In certain embodiments, attenuation is achieved by deleting acetate kinase (ackA). This is done by replacing the gene with a chloramphenicol cassette followed by looping out of the cassette. In some aspects, the activity of acetate kinase is modulated by decreasing the activity of an endogenous acetate kinase. This can be accomplished by replacing the endogenous acetate kinase gene promoter with a synthetic constitutively low expressing promoter. In certain embodiments, it the attenuation of the acetated kinase gene should be done disrupting the expression of the phosphotransacetylase (pta) gene. Acetate is produced by *E. coli* for a variety of reasons (Wolfe, A. 2005. Microb. Mol. Biol. Rev. 69:12-50). Without being bound by theory, deletion of ackA could result in decreased carbon being diverted into acetate production (since ackA use acetyl-CoA) and thereby increase the yield of mevalonate, isoprenoid precursors, isoprene and/or isoprenoids.

In some aspects, the recombinant cells described herein produce decreased amounts of acetate in comparison to cells that do not have attenuated endogenous acetate kinase gene expression or enhanced phosphotransacetylase. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done to the endogenous acetate kinase gene expression or phosphotransacetylase gene expression.

The activity of phosphotransacetylase (pta and/or eutD) can be increased by other molecular manipulations of the enzymes. The increase of enzyme activity can be an increase in any amount of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In one embodiment the activity of pta is increased by altering the promoter and/or rbs on the chromosome, or by expressing it from a plasmid. In any aspects of the invention, provided herein are recombinant cells comprising one or more heterologously expressed nucleic acids encoding phosphoketolase polypeptides as disclosed herein and further engineered to increase the activity of phosphotransacetylase (pta and/or eutD). Activity modulation (e.g., increased) of phosphotransacetylase isozymes is also contemplated herein. In any aspects of the invention, provided herein are recombinant cells comprising one or more heterologously expressed nucleic acids encoding phosphoketolase polypeptides as disclosed herein and further engineered to increase the activity of a phosphotransacetylase (pta and/or eutD) isozyme.

The activity of acetate kinase (ackA) can also be decreased by other molecular manipulations of the enzymes. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of acetate kinase (ackA). Activity modulation (e.g., decreased) of acetate kinase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a acetate kinase isozyme.

In some cases, attenuating the activity of the endogenous acetate kinase gene results in more carbon flux into the mevalonate dependent biosynthetic pathway in comparison to cells that do not have attenuated endogenous acetate gene expression.

Pathways Involving Lactate Dehydrogenase

In *E. coli*, D-Lactate is produced from pyruvate through the enzyme lactate dehydrogenase (encoded by ldhA—FIG. 1) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor and isoprenoids production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant cell produces decreased amounts of lactate in comparison to cells that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to cells that do not have attenuated endogenous lactate dehydrogenase gene expression.

Pathways Involving Glyceraldehyde 3-Phosphate

Glyceraldehyde 3-phosphate dehydrogenase (gapA and/or gapB) is a crucial enzyme of glycolysis catalyzes the conversion of glyceraldehyde 3-phosphate into 1,3-biphospho-D-glycerate (Branlant G. and Branlant C. 1985. Eur. J. Biochem. 150:61-66).

In order to direct carbon towards the phosphoketolase enzyme, glyceraldehyde 3-phosphate dehydrogenase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of glyceraldehyde 3-phosphate dehydrogenase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of glyceraldehyde 3-phosphate dehydrogenase is modulated by decreasing the activity of an endogenous glyceraldehyde 3-phosphate dehydrogenase. This can be accomplished by replacing the endogenous glyceraldehyde 3-phosphate dehydrogenase gene promoter with a synthetic constitutively low expressing promoter. The gene encoding glyceraldehyde 3-phosphate dehydrogenase can also be deleted. The gene encoding glyceraldehyde 3-phosphate dehydrogenase can also be replaced by a *Bacillus* enzyme catalyzing the same reaction but producing NADPH rather than NADH. The decrease of the activity of glyceraldehyde 3-phosphate dehydrogenase can result in more carbon flux into the mevalonate-dependent biosynthetic pathway in comparison to cells that do not have decreased expression of glyceraldehyde 3-phosphate dehydrogenase. In any aspects of the invention, provided herein are recombinant cells comprising one or more heterologously expressed nucleic acids encoding phosphoketolase polypeptides as disclosed herein and further engineered to decrease the activity of glyceraldehyde 3-phosphate dehydrogenase (gapA and/or gapB). Activity modulation (e.g., decreased) of glyceraldehyde 3-phosphate dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glyceraldehyde 3-phosphate dehydrogenase (gapA and/or gapB) isozyme.

Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803). Fructose bisphophate aldolase (fba, fbaA, fbaB, and/or fbaC) interacts with the Entner-Doudoroff pathway and reversibly catalyzes the conversion of fructose 1,6-bisphosphate into dihydroxyacetone phosphate (DHAP) and glyceraldehyde 3-phosphate (GAP) (Baldwin S. A., et. al., Biochem J. (1978) 169(3):633-41).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Metabolites that can be directed into the phosphoketolase pathway can also be diverted into the ED pathway or EMP pathway. To avoid metabolite loss and to increase fructose-6-phosphate (F6P) concentration, fructose bisphophate aldolase (e.g., the endogenous fructose bisphophate aldolase) activity is attenuated. In some cases, attenuating the activity of the endogenous fructose bisphophate aldolase (fba, fbaA, fbaB, and/or fbaC) gene results in more carbon flux into the mevalonate dependent biosynthetic pathway in comparison to cells that do not have attenuated endogenous fructose bisphophate aldolase (fba, fbaA, fbaB, and/or fbaC) gene expression. In some aspects, attenuation is achieved by deleting fructose bisphophate aldolase (fba, fbaA, fbaB, and/or fbaC). Deletion can be accomplished by replacing the gene with a chloramphenicol or kanamycin cassette followed by looping out of the cassette. In some aspects, the activity of fructose bisphophate aldolase is modulated by decreasing the activity of an endogenous fructose bisphophate aldolase. This can be accomplished by replacing the endogenous fructose bisphophate aldolase gene promoter with a synthetic constitutively low expressing promoter. Without these enzymatic activities, more carbon can flux through the phosphoketolase enzyme, thus increasing the yield of mevalonate, isoprene or isoprenoids. The activity of fructose bisphophate aldolase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of fructose bisphophate aldolase (fba, fbaA, fbaB, and/or fbaC). Activity modulation (e.g., decreased) of fructose bisphophate aldolase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose bisphophate aldolase isozyme.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA and/or tktB), transaldolase (talA or talB), ribulose-5-phosphate-epimerase and (or) ribose-5-phosphate epimerase, ribose-5-phosphate isomerase (rpiA and/or rpiB) and/or ribulose-5-phosphate 3-epimerase (rpe)) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase, ribose-5-phosphate isomerase A, ribose-5-phosphate isomerase B, and/or ribulose-5-phosphate 3-epimerase) expression can be modulated (e.g., increase enzyme activity) to allow more carbon to flux towards fructose 6-phosphate and xylulose 5-phosphate, thereby increasing the eventual production of mevalonate, isoprene and isoprenoids.

Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

In any aspects of the invention, provided herein are recombinant cells comprising one or more heterologously expressed nucleic acids encoding phosphoketolase polypeptides as disclosed herein and further engineered to increase the activity of transketolase (tktA and/or tktB). In any aspects of the invention, provided herein are recombinant cells comprising one or more heterologously expressed nucleic acids encoding phosphoketolase polypeptides as disclosed herein and further engineered to decrease the activity of transketolase (tktA and/or tktB). In any aspects of the invention, provided herein are recombinant cells comprising one or more heterologously expressed nucleic acids encoding phosphoketolase polypeptides as disclosed herein and further engineered to increase the activity of transaldolase (talA or talB). In any aspects of the invention, provided herein are recombinant cells comprising one or more heterologously expressed nucleic acids encoding phosphoketolase polypeptides as disclosed herein and further engineered to increase the activity of ribose-5-phosphate isomerase (rpiA and/or rpiB). In any aspects of the invention, provided herein are recombinant cells comprising one or more heterologously expressed nucleic acids encoding phosphoketolase polypeptides as disclosed herein and further engineered to increase the activity of ribulose-5-phosphate 3-epimerase (rpe). Activity modulation (e.g., decreased or increased) of glucose 6-phosphate 1-dehydrogenase (zwf), 6-phosphogluconolactonase (pgl), 6-phosphogluconate dehydrogenase (gnd), transketolase (tktA and/or tktB), transaldolase (talA or talB), ribulose-5-phosphate-epimerase, ribose-5-phosphate epimerase, ribose-5-phosphate isomerase (rpiA and/or rpiB) and/or ribulose-5-phosphate 3-epimerase (rpe) isozymes is also contemplated herein. In any aspects of the invention, provided herein are recombinant cells comprising one or more heterologously expressed nucleic acids encoding phosphoketolase polypeptides as disclosed herein and further engineered to increase the activity of a glucose 6-phosphate 1-dehydrogenase (zwf) isozyme. In any aspects of the invention, provided herein are recombinant cells comprising one or more heterologously expressed nucleic acids encoding phosphoketolase polypeptides as disclosed herein and further engineered to increase the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to decrease the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to increase the activity of a transaldolase (talA or talB) isozyme. In any aspects of the invention, provided herein are recombinant cells comprising one or more heterologously expressed nucleic acids encoding phosphoketolase polypeptides as disclosed herein and further engineered to increase the activity of a ribose-5-phosphate isomerase (rpiA and/or rpiB) isozyme. In any aspects of the invention, provided herein are recombinant cells comprising one or more heterologously expressed nucleic acids encoding phosphoketolase polypeptides as disclosed herein and further engineered to increase the activity of a ribulose-5-phosphate 3-epimerase (rpe) isozyme.

In order to direct carbon towards the phosphoketolase enzyme, glucose 6-phosphate 1-dehydrogenase can be modulated (e.g., decrease enzyme activity). In some aspects, the activity of glucose 6-phosphate 1-dehydrogenase (zwf) (e.g., the endogenous glucose 6-phosphate 1-dehydrogenase gene) can be decreased or attenuated. In certain embodiments, attenuation is achieved by deleting glucose 6-phosphate 1-dehydrogenase. In some aspects, the activity of glucose 6-phosphate 1-dehydrogenase is modulated by decreasing the activity of an endogenous glucose 6-phosphate 1-dehydrogenase. This can be accomplished by replacing the endogenous glucose 6-phosphate 1-dehydrogenase gene promoter with a synthetic constitutively low expressing promoter. In any aspects of the invention, provided herein are recombinant cells comprising one or more heterologously expressed nucleic acids encoding phosphoketolase polypeptides as disclosed herein and further engineered to decrease the activity of glucose 6-phosphate 1-dehydrogenase (zwf). Activity modulation (e.g., decreased) of glucose 6-phosphate 1-dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glucose 6-phosphate 1-dehydrogenase isozyme.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975 Biochim. Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

In any aspects of the invention, provided herein are recombinant cells comprising one or more heterologously expressed nucleic acids encoding phosphoketolase polypeptides as disclosed herein and further engineered to decrease the activity of fructose 6-phosphate (pfkA and/or pfkB). Activity modulation (e.g., decreased) of fructose 6-phosphate isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose 6-phosphate isozyme.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcggtgataaattatctctggcggtgttgacataaataccactggcggtgatactgagcac atcagcaggacgcactgaccaccatgaaggtg—lambda promoter, GenBank NC_001416, SEQ ID NO:14), in front of the operon or using one or more synthetic constitutively expressing promoters.

Accordingly, in one aspect, the activity of pyruvate dehydrogenase is modulated by increasing the activity of one or more enzymes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of the genes encoding these enzymes can be manipulated for increasing activity of pyruvate dehydrogenase. In another aspect, the activity of the pyruvate dehydrogenase complex can be modulated by attenuating the activity of an endogenous pyruvate dehydrogenase complex repressor, further detailed below. The activity of an endogenous pyruvate dehydrogenase complex repressor can be attenuated by deletion of the endogenous pyruvate dehydrogenase complex repressor gene.

In some cases, one or more genes encoding the pyruvate dehydrogenase complex are endogenous genes. Another way to increase the activity of the pyruvate dehydrogenase complex is by introducing into the cell one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant cells can produce increased amounts of acetyl Co-A in comparison to cells wherein the activity of pyruvate dehydrogenase is not modulated. Modulating the activity of pyruvate dehydrogenase can result in more carbon flux into the mevalonate dependent biosynthetic pathway in comparison to cells that do not have modulated pyruvate dehydrogenase expression.

Pathways Involving the Phosphotransferase System

The phosphoenolpyruvate dependent phosphotransferase system (PTS) is a multicomponent system that simultaneously transports and phosphorylates its carbohydrate substrates across a membrane in a process that is dependent on energy provided by the glycolytic intermediate phosphoenolpyruvate (PEP). The genes that regulate the PTS are mostly clustered in operons. For example, the pts operon (ptsHIcrr) of *Escherichia coli* is composed of the ptsH, ptsI and crr genes coding for three proteins central to the phosphoenolpyruvate dependent phosphotransferase system (PTS), the HPr (ptsH), enzyme I (ptsI) and EIIIGlc (crr) proteins. These three genes are organized in a complex operon in which the major part of expression of the distal gene, crr, is initiated from a promoter region within ptsI. In addition to the genes of the pts operon, ptsG encodes the glucose-specific transporter of the phosphotransferase system, ptsG Transcription from this promoter region is under the positive control of catabolite activator protein (CAP)-cyclic AMP (cAMP) and is enhanced during growth in the presence of glucose (a PTS substrate). Furthermore, the ppsA gene encodes for phosphoenolpyruvate synthetase for the production of phosphoenolpyruvate (PEP) which is required for activity of the phosphotransferase system (PTS). Carbon flux is directed by the phosphoenolpyruvate synthetase through the pyruvate dehydrogenase pathway or the PTS pathway. See Postma, P. W., et al., Microbiol Rev. (1993), 57(3):543-94) which is incorporated herein by reference in its entirety.

In certain embodiments described herein, the down regulation (e.g. attenuation) of the pts operon can enhance acetate utilization by the host cells. The down regulation of PTS operon activity can be any amount of reduction of specific activity or total activity as compared to when no manipulation has been effectuated. In some instances, the decrease of activity of the complex is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In certain embodiments, attenuation is achieved by deleting the pts operon. In some aspects, the activity of the PTS system is modulated by decreasing the activity of an endogenous pts operon. This can be accomplished by replacing the endogenous promoter(s) within the pts operon with synthetic constitutively low expressing promoter(s). In any aspects of the invention, provided herein are recombinant cells comprising one or more heterologously expressed nucleic acids encoding phosphoketolase polypeptides as disclosed herein and further engineered to decrease the activity of the pts operon. In any aspects of the invention, provided herein are recombinant cells comprising one or more heterologously expressed nucleic acids encoding phosphoketolase polypeptides as disclosed herein and further engineered to decrease the activity of EI (ptsI). In any aspects of the invention, provided herein are recombinant cells comprising one or more heterologously expressed nucleic acids encoding phosphoketolase polypeptides as disclosed herein and further engineered to decrease the activity of $EIICB^{Glc}$ (ptsG). In any aspects of the invention, provided herein are recombinant cells comprising one or more heterologously expressed nucleic acids encoding phosphoketolase polypeptides as disclosed herein and further engineered to decrease the activity of $EIIA^{Glc}$ (crr). In any aspects of the invention, provided herein are recombinant cells comprising one or more heterologously expressed nucleic acids encoding phosphoketolase polypeptides as disclosed herein and further engineered to decrease the activity of HPr (ptsH). To decrease carbon loss through pyruvate dehydrogenase while increasing the PEP pool for glucose uptake, the activity of phosphoenolpyruvate synthetase (ppsA) can be increased. In any aspects of the invention, provided herein are recombinant cells comprising one or more heterologously expressed nucleic acids encoding phosphoketolase polypeptides as disclosed herein and further engineered to increase the activity of phosphoenolpyruvate synthetase (ppsA). In any further aspect of the invention, the PTS is downregulated and a glucose transport pathway is upregulated. A glucose transport pathway includes, but is not limited to, galactose (galP) and glucokinase (glk). In some embodiments, the pts operon is downregulated, the galactose (galP) gene is upregulated, and the glucokinase (glk) gene is upregulated. Activity modulation (e.g., decreased) of isozymes of the PTS is also contemplated herein. In any aspects of the invention, provided herein are recombinant cells comprising one or more heterologously expressed nucleic acids encoding phosphoketolase polypeptides as disclosed herein and further engineered to decrease the activity of PTS isozymes.

Pathways Involving Xylose Utilization

In certain embodiments described herein, the utilization of xylose is desirable to convert sugar derived from plant biomass into desired products, such as mevalonate, such as isoprenoid precursors, isoprene and/or isoprenoids. In some organisms, xylose utilization requires use of the pentose phosphate pathway for conversion to fructose-6-phosphate for metabolism. Organisms can be engineered for enhanced xylose utilization, either by deactivating the catabolite repression by glucose, or by heterologous expression of genes from the xylose operon found in other organisms. The xylulose pathway can be engineered as described below to enhance production of mevalonate, isoprenoid precursors, isoprene and/or isoprenoids via the phosphoketolase pathway.

Enhancement of xylose uptake and conversion to xylulose-5-phosphate followed by direct entry into the phosphoketolase pathway would be a benefit. Without being bound by theory, this allows the carbon flux to bypass the pentose phosphate pathway (although some glyceraldehyde-3-phosphate may be cycled into PPP as needed). Enhanced expression of xyulokinase can be used to increase the overall production of xylulose-5-phosphate. Optimization of xyluokinase expression and activity can be used to enhance xylose utilization in a strain with a phosphoketolase pathway. The desired xyulokinase may be either the endogenous host's enzyme, or any heterologous xyulokinase compatible with the host. In one embodiment, other components of the xylose operon can be overexpressed for increased benefit (e.g., xylose isomerase). In another embodiment, other xylose pathway enzymes (e.g. xylose reductase) may need to be attenuated (e.g., reduced or deleted activity).

Accordingly, the host cells engineered to have phosphoketolase enzymes as described herein can be further engineered to overexpress xylulose isomerase and/or xyulokinase, either the endogenous forms or heterologous forms, to improve overall yield and productivity of mevalonate, isoprenoid precursors, isoprene and/or isoprenoids.

Pathways Involving Transaldolase and Transketolase Enzymes of Pentose Phosphate Pathway Some microorganisms capable of anaerobic or heterofermentative growth incorporate a phosphoketolase pathway instead of or in addition to a glycolytic pathway. This pathway depends on the activity of the pentose phosphate pathway enzymes transaldolase and transketolase. Accordingly, the host cells engineered to have phosphoketolase enzymes as described herein can be further engineered to overexpress a transketolase and transaldolase, either the endogenous forms or heterologous forms, to improve pathway flux, decrease the levels of potentially toxic intermediates, reduce the diversion of intermediates to non-productive pathways, and improve the overall yield and productivity of mevalonate, isoprenoid precursors, isoprene and/or isoprenoids.

Combinations of Mutations

It is understood that for any of the enzymes and/or enzyme pathways described herein, molecular manipulations that modulate any combination (two, three, four, five, six, seven, eight, nine, ten, eleven, twelve, thirteen, or fourteen) of the enzymes and/or enzyme pathways described herein is expressly contemplated. For ease of the recitation of the combinations, citrate synthase (gltA) is designated as A, phosphotransacetylase (pta) is designated as B, acetate kinase (ackA) is designated as C, lactate dehydrogenase (ldhA) is designated as D, glyceraldehyde 3-phosphate dehydrogenase (gap) is designated as E, and pyruvate decarboxylase (aceE, aceF, and/or lpdA) is designated as F, phosphogluconate dehydratase (edd) is designated as G, 2-keto-3-deoxygluconate 6-phosphate aldolase (eda) is designated as H phosphofructokinase is designated as I, transaldolase is designated as J, transketolase is designated as K, ribulose-5-phosphate-epimerase is designated as L, ribose-5-phosphate epimerase is designated as M, xylukinase is designated as N, xylose isomerase is designated as O, and xylitol reductase is designated as P, ribose-5-phosphate isomerase (rpi) is designated as Q, D-ribulose-5-phosphate 3-epimerase (rpe) is designated as R, phosphoenolpyruvate synthetase (pps) is designated as S, fructose bisphosphate aldolase (fba) is designated as T, EI (ptsI) is designated as U, $EIICB^{Glc}$ (ptsG) is designated as V, $EIIA^{Glc}$ (crr) is designated as W, HPr (ptsH) is designated as X, galactose (galP) is designated as Y, glucokinase (glk) is designated as Z, glucose-6-phosphate dehydrogenase (zwf) is designated as AA. As discussed above, aceE, aceF, and/or lpdA enzymes of the pyruvate decarboxylase complex can be used singly, or two of three enzymes, or three of three enzymes for increasing pyruvate decarboxylase activity. Thus, any and all combination of enzymes designated as A-M herein is expressly contemplated as well as any and all combination of enzymes designated as A-AA. Furthermore, any combination described above can be used in combination with any of the enzymes and/or enzyme pathways described herein (e.g., phosphoketolase, MVA pathway polypeptides, isoprene synthase, DXP pathway polypeptides).

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. The gene pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production of mevalonate, isoprenoid precursors, isoprene, and isoprenoids.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

In other aspects, the host cells can be further engineered to increase intracellular acetyl-phosphate concentrations by introducing heterologous nucleic acids encoding sedoheptulose-1,7-bisphosphatase/fructose-1,6-bisphosphate aldolase and sedoheptulose-1,7-bisphosphatase/fructose-1,6-bisphosphate phosphatase. In certain embodiments, the host cells having these molecular manipulations can be combined with attenuated or deleted transaldolase (talB) and phosphofructokinase (pfkA and/or pfkB) genes, thereby allowing faster conversion of erythrose 4-phosphate, dihydroxyacetone phosphate, and glyceraldehyde 3-phosphate into sedoheptulose 7-phosphate and fructose 1-phosphate (see FIG. 5).

In other aspects, the introduction of 6-phosphogluconolactonase (PGL) into cells (such as various *E. coli* strains) which lack PGL can be used to improve production of mevalonate, isoprenoid precursors, isoprene, and isoprenoids. PGL may be introduced by introduction of the encoding gene using chromosomal integration or extra-chromosomal vehicles, such as plasmids.

In addition to the host cell (e.g., bacterial host cell) mutations for modulating various enzymatic pathways described herein that increases carbon flux towards mevalonate production, the host cells described herein comprise genes encoding phosphoketolase polypeptide, as well as other enzymes from the upper and lower MVA pathway, including but not limited to, the mvaE and mvaS gene products. Non-limiting examples of MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. MVA pathway polypeptides can include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein.

Non-limiting examples of MVA pathway polypeptides which can be used are described in International Patent Application Publication No. WO2009/076676; WO2010/003007 and WO2010/148150

Exemplary Cell Culture Media

As used herein, the terms "minimal medium" or "minimal media" refer to growth media containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 1001.11 of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. Patent Publ. No. 2009/0203102, WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of phosphoketolase polypeptide, as well as other enzymes from the upper and lower MVA pathway, including but not limited to, the mvaE and mvaS gene products, isoprene synthase, DXP pathway (e.g., DXS), IDI, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the recombinant cells (such as *E. coli* cells) comprise one or more heterologous nucleic acids encoding a phosphoketolase polypeptide, as well as enzymes from the upper, including but not limited to, the mvaE and mvaS gene products mvaE and mvaS polypeptides from *L. grayi, E. faecium, E. gallinarum, E. casseliflavus* and/or *E. faecalis* under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. Patent Publ. No. 2009/0203102, WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the recombinant cells are grown in batch culture. The recombinant cells can also be grown in fed-batch culture or in continuous culture. Additionally, the recombinant cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., U.S. Publ. No. 2011/0178261). In some aspects, any of the methods described herein further include a step of recovering the heterologous polypeptide. In some aspects, any of the methods described herein further include a step of recovering the terpenoid or carotenoid.

Suitable purification methods are described in more detail in U.S. Patent Application Publication US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

Example 1: Identification of Phosphoketolases

Figure 2:
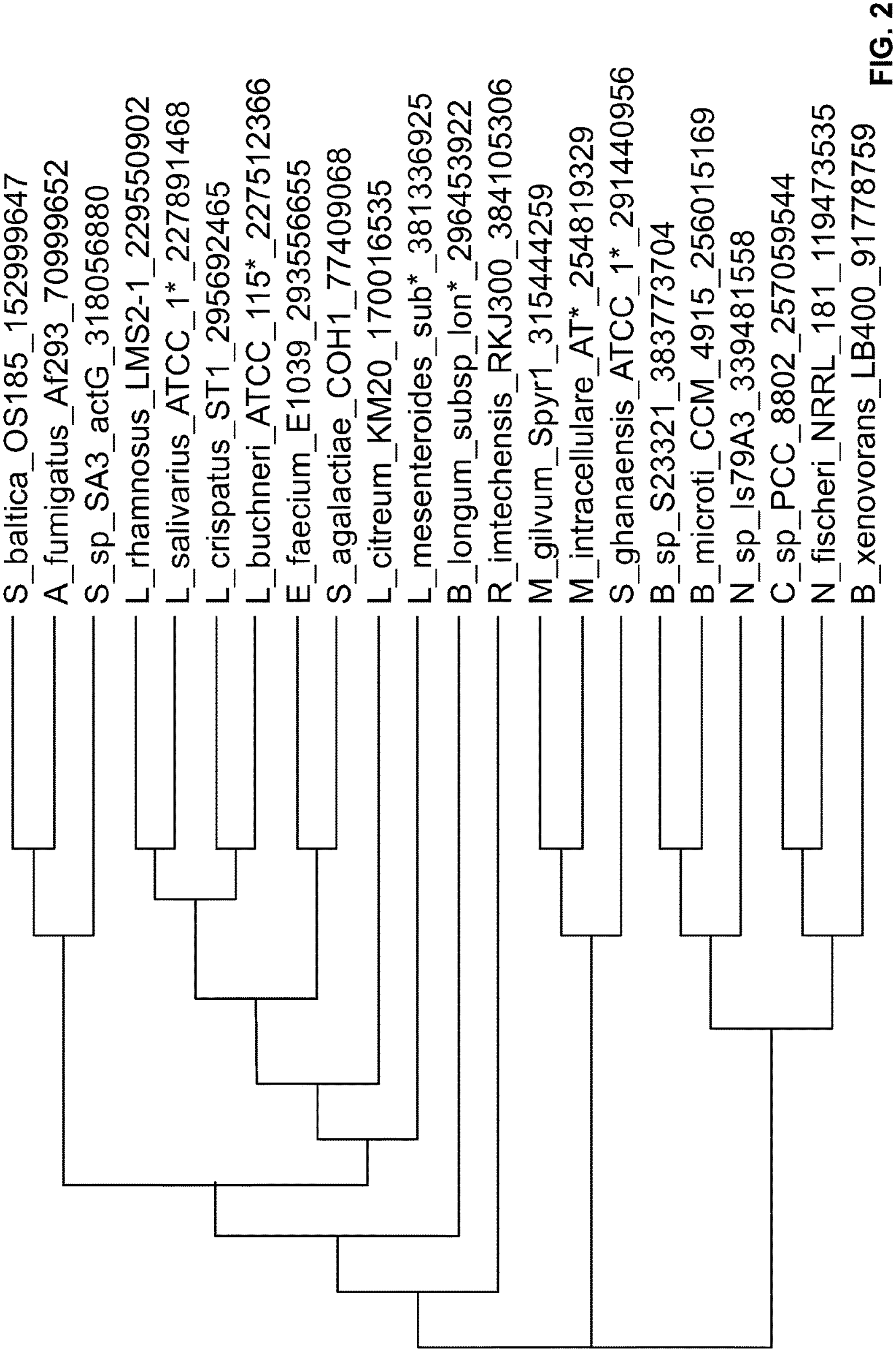
FIG. 2 is a diagram of the center representative sequences of the 22 Clusters of identified PKLs.
Figure 3:
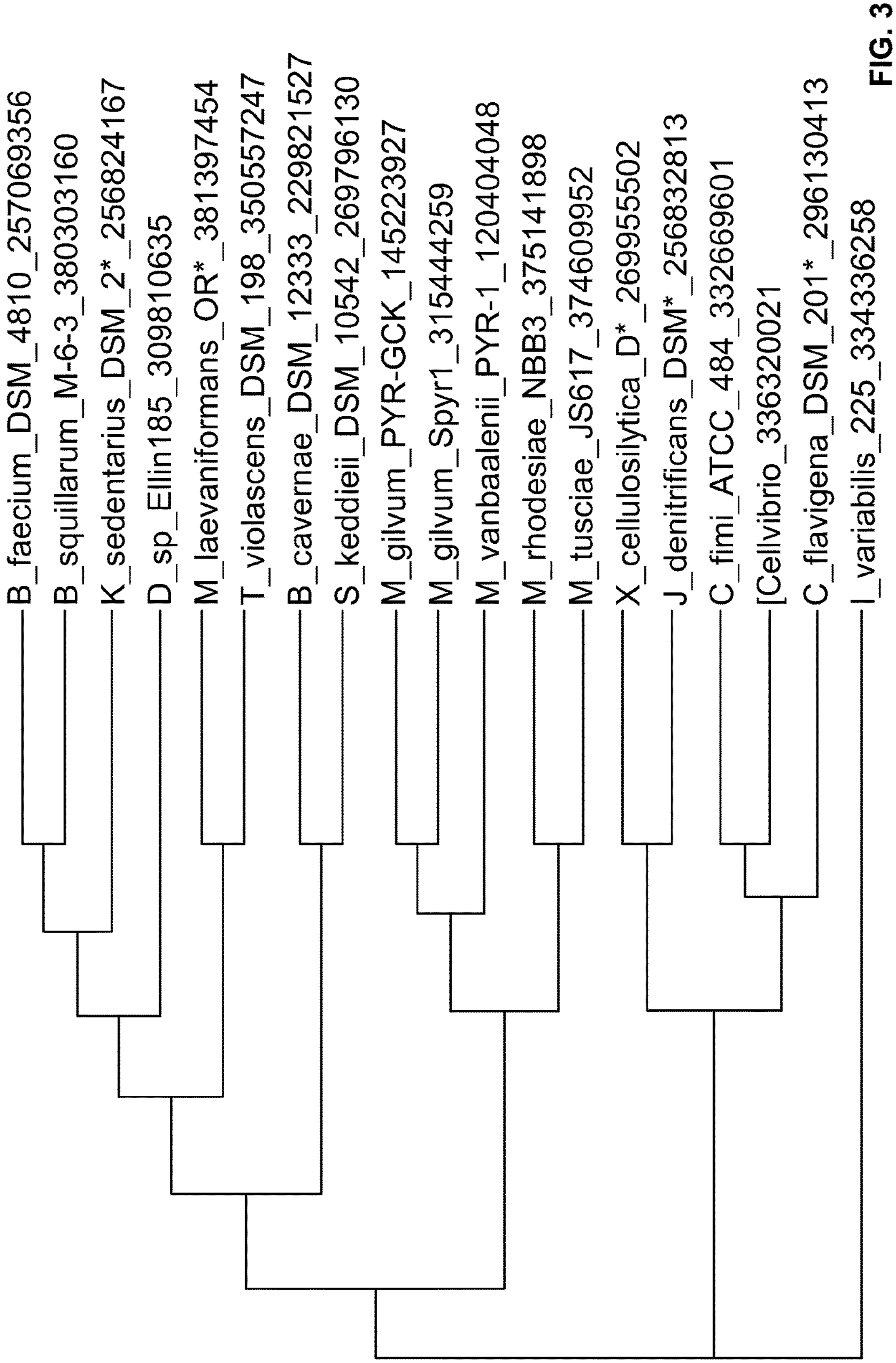
FIG. 3 is a diagram of identified phosphoketolases in Cluster 1.
Figure 4:
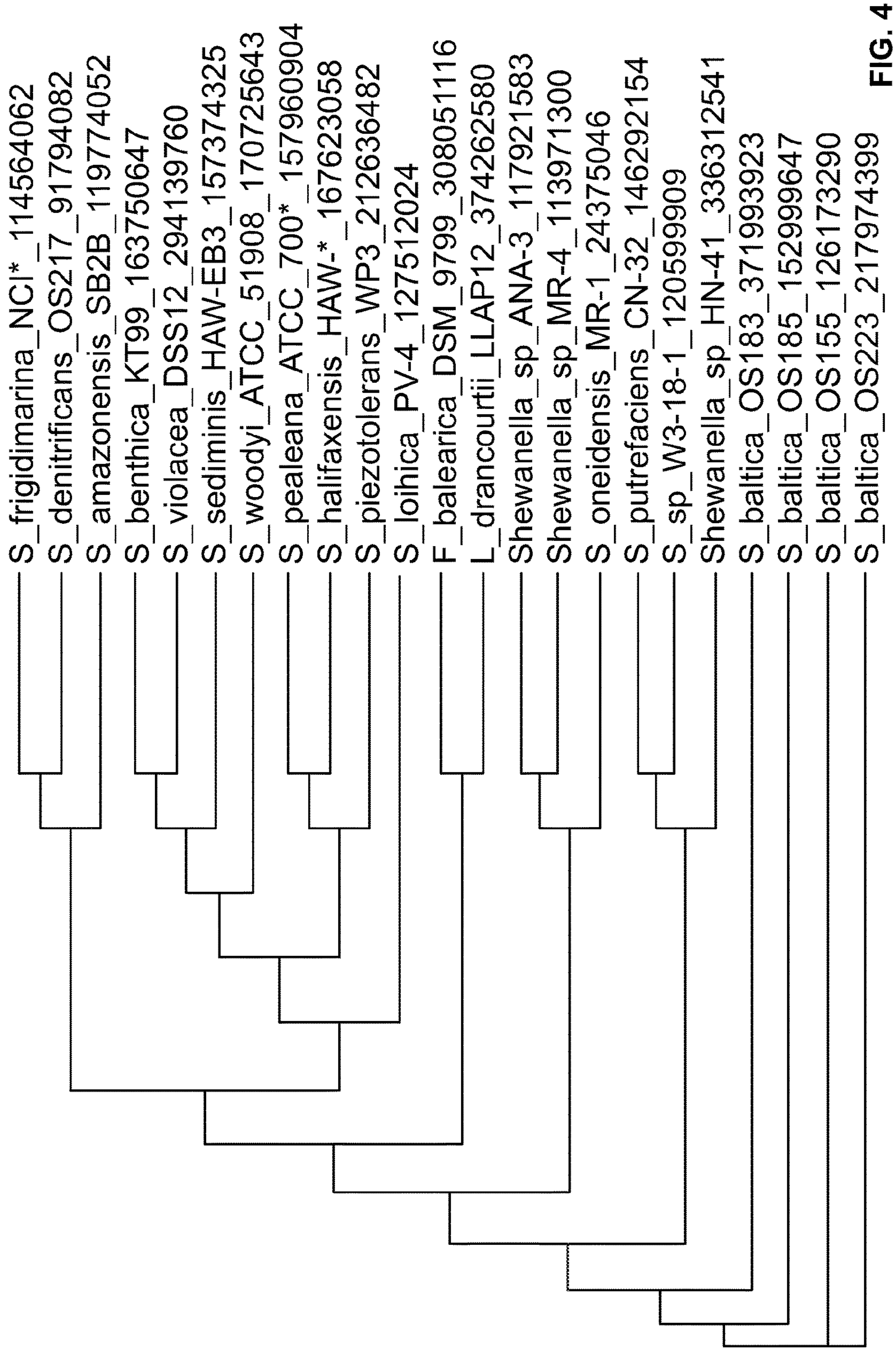
FIG. 4 is a diagram of identified phosphoketolases in Cluster 2.
Figure 5:
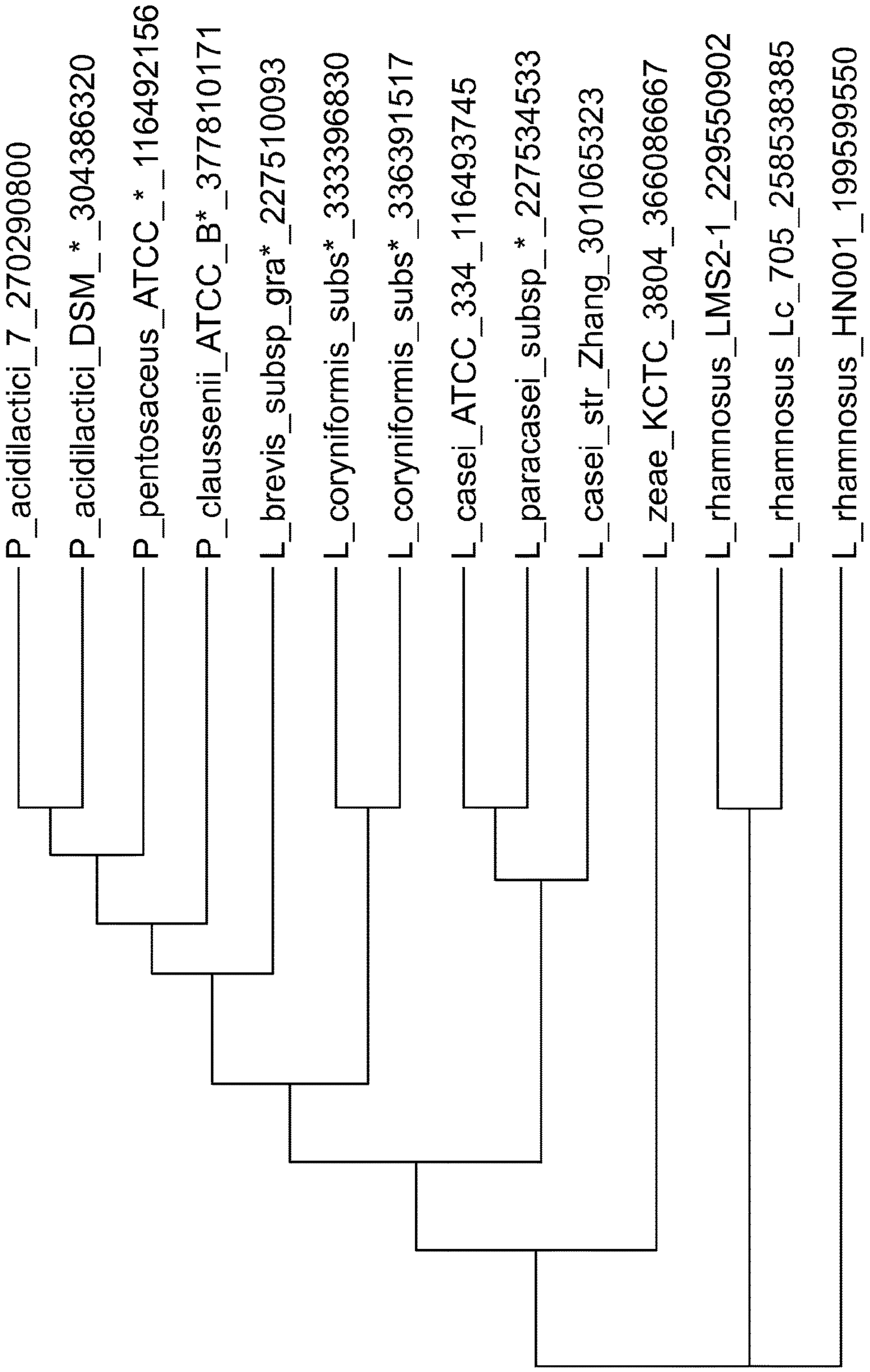
FIG. 5 is a diagram of identified phosphoketolases in Cluster 3.
Figure 6:
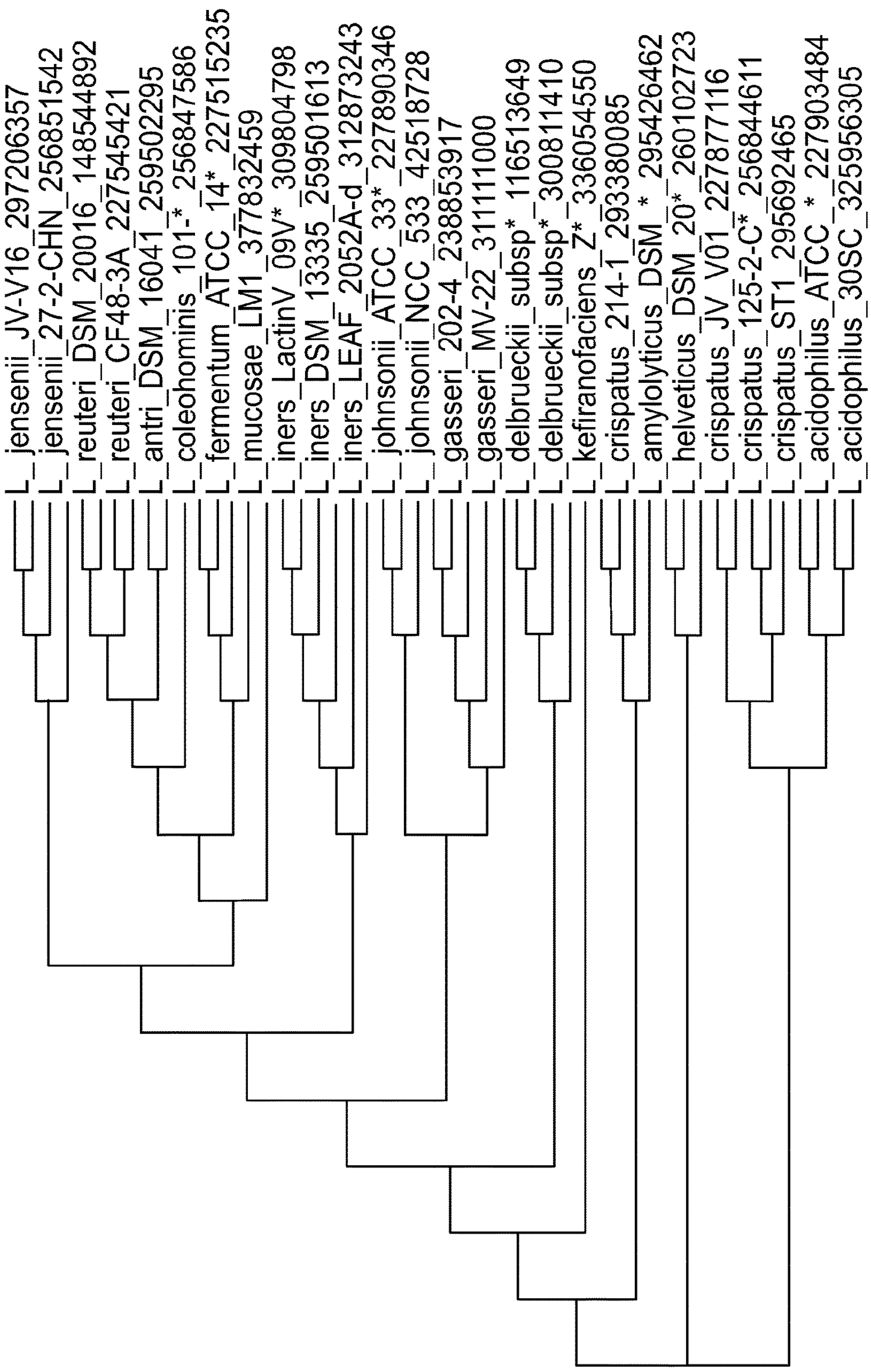
FIG. 6 is a diagram of identified phosphoketolases in Cluster 4.
Figure 7:
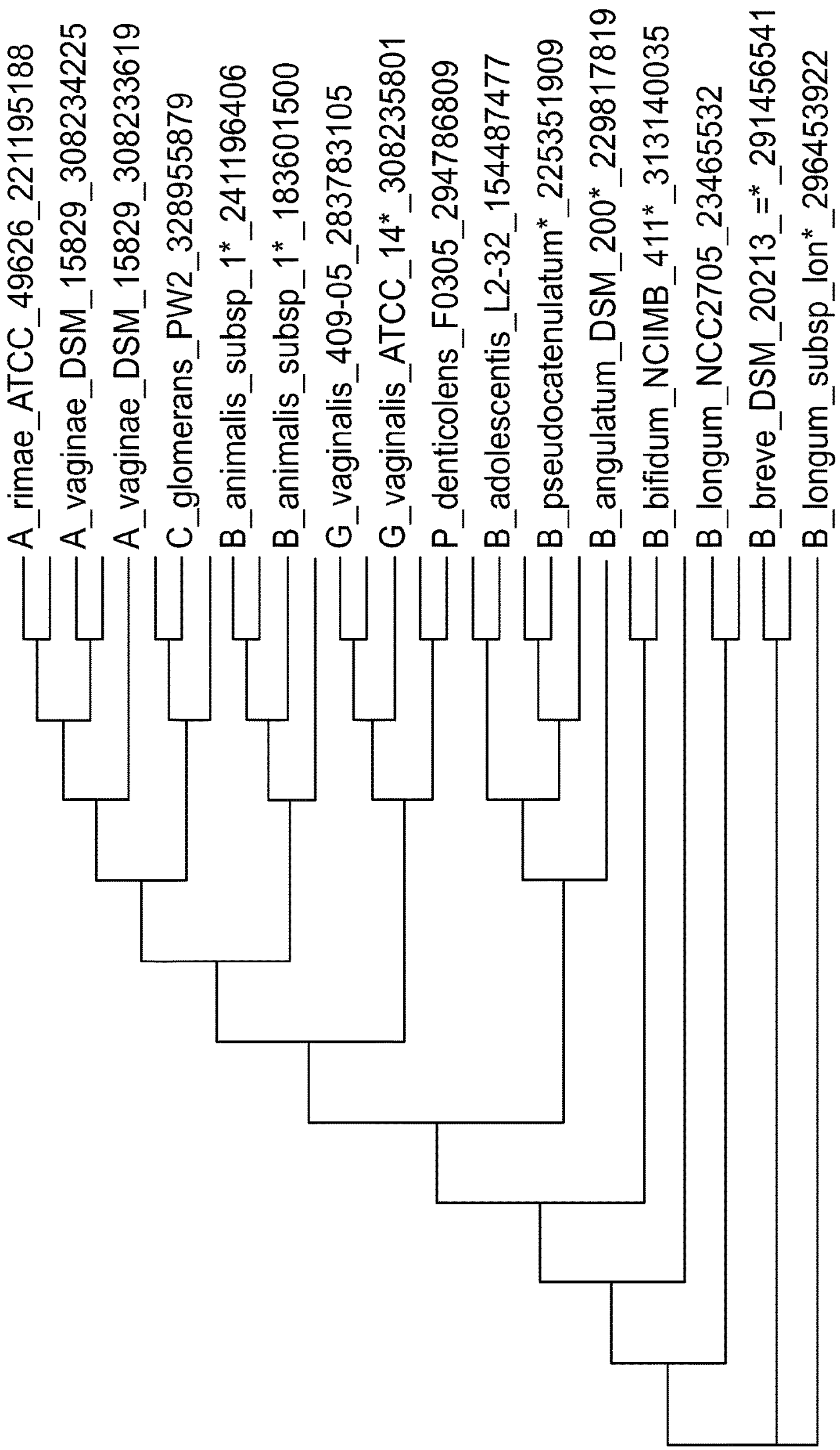
FIG. 7 is a diagram of identified phosphoketolases in Cluster 5.
Figure 8:
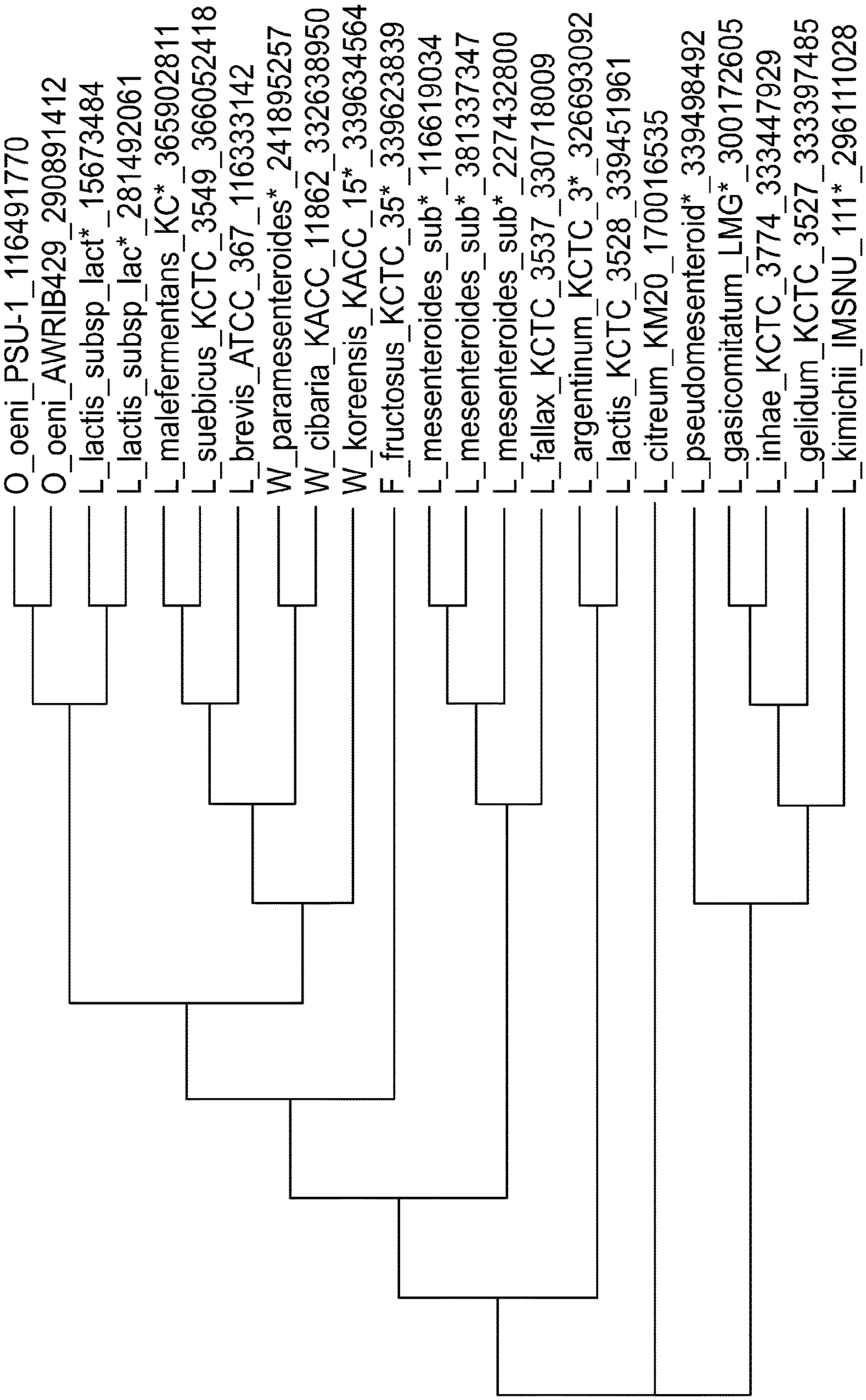
FIG. 8 is a diagram of identified phosphoketolases in Cluster 6.
Figure 9:
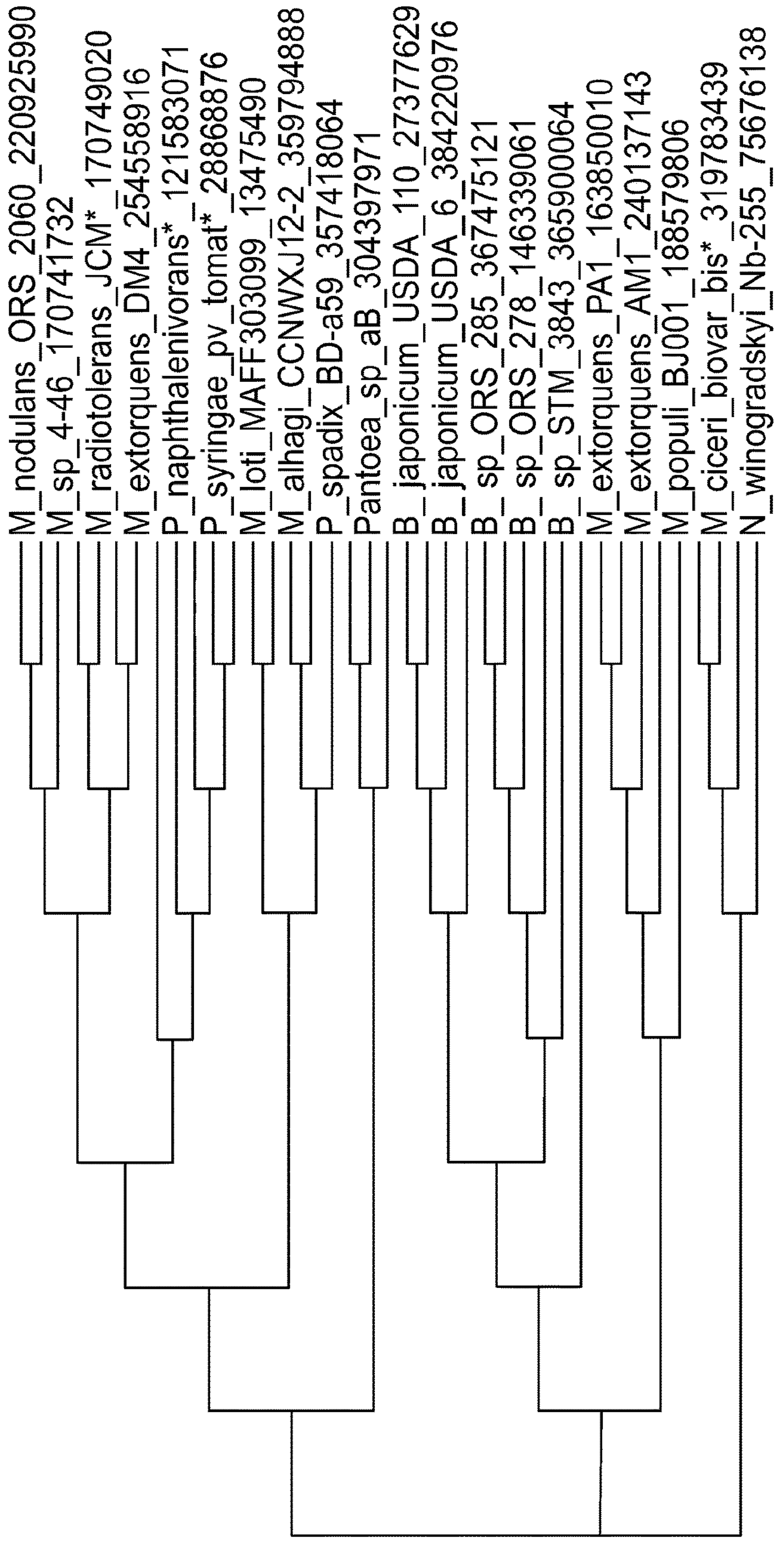
FIG. 9 is a diagram of identified phosphoketolases in Cluster 7.
Figure 10:
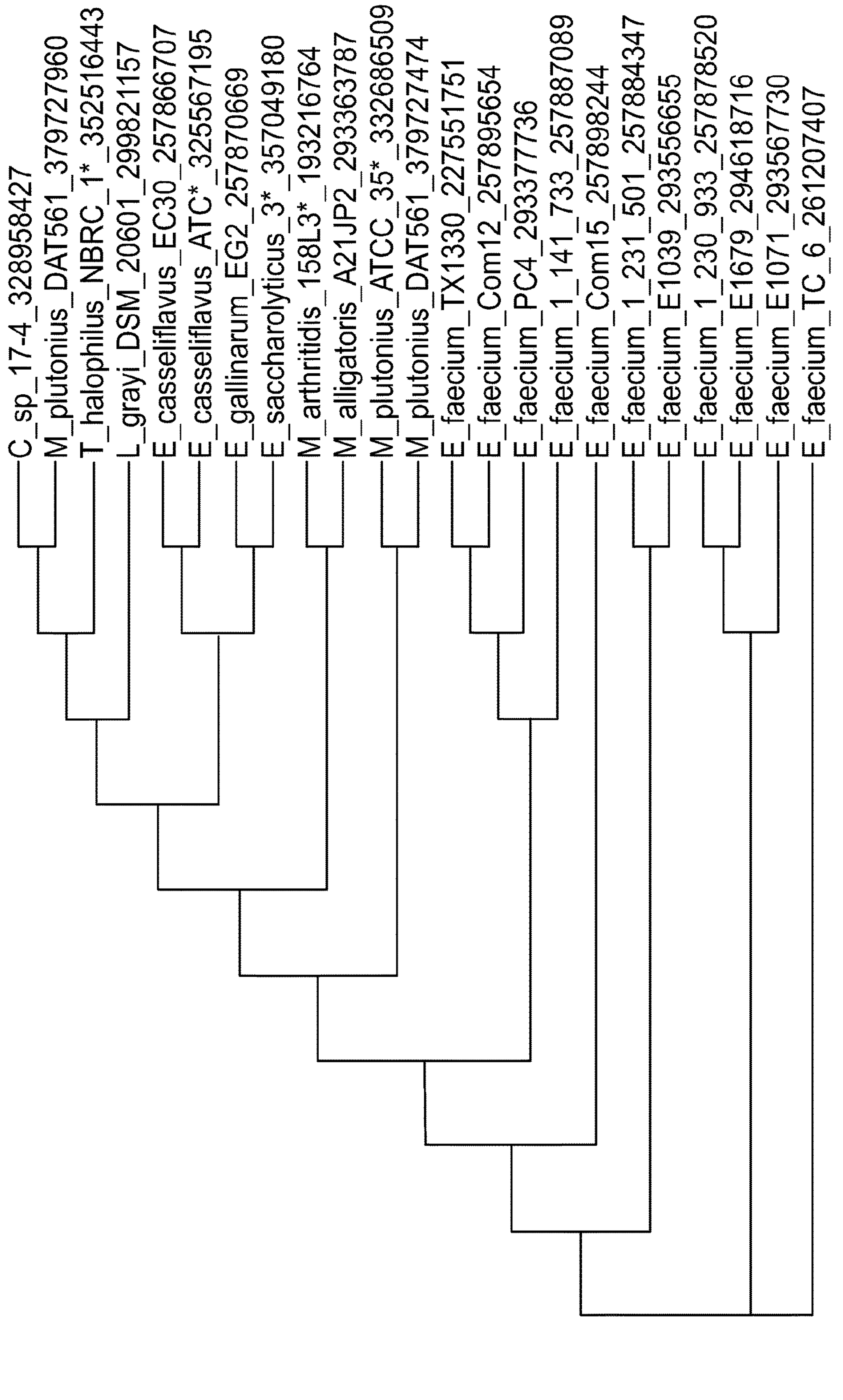
FIG. 10 is a diagram of identified phosphoketolases in Cluster 8.
Figure 11:
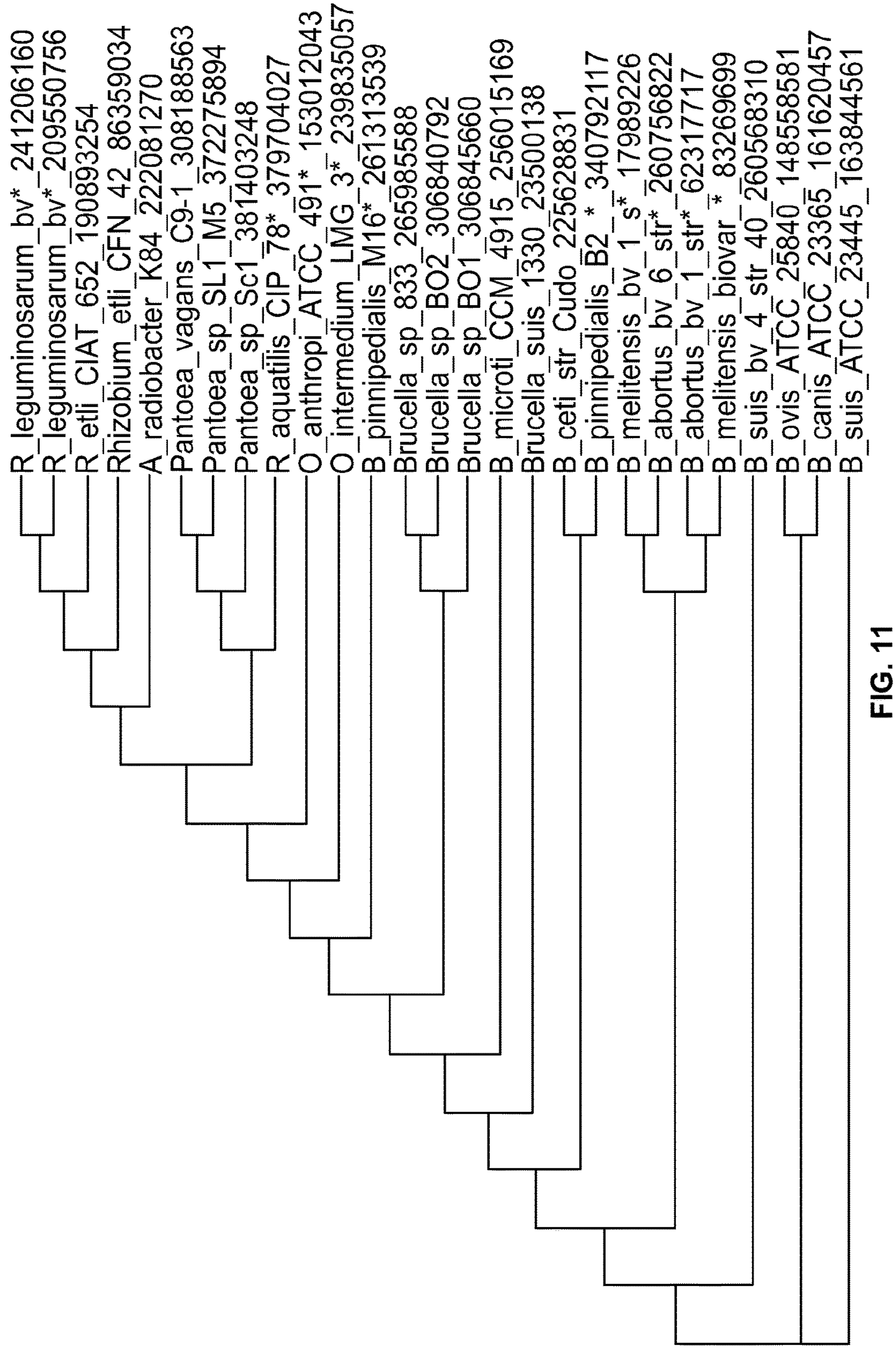
FIG. 11 is a diagram of identified phosphoketolases in Cluster 9.
Figure 12:
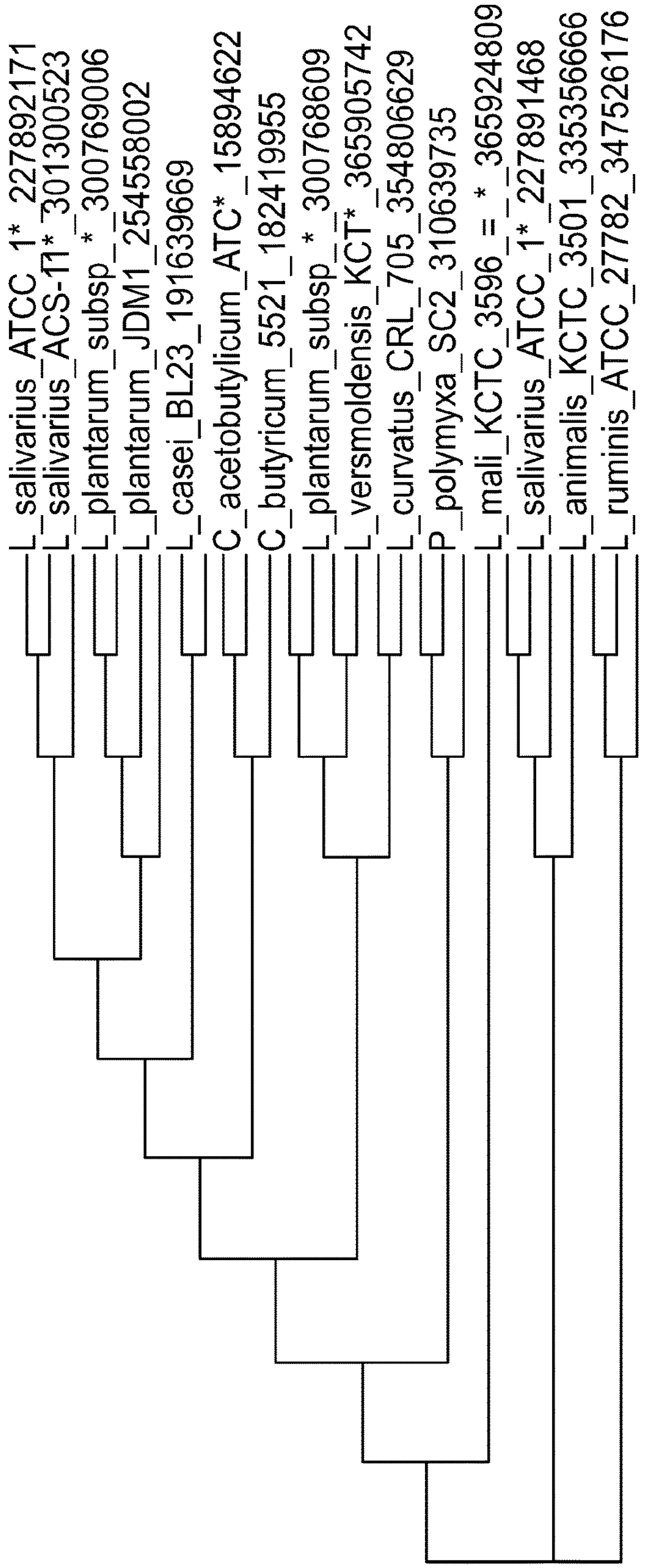
FIG. 12 is a diagram of identified phosphoketolases in Cluster 10.
Figure 13:
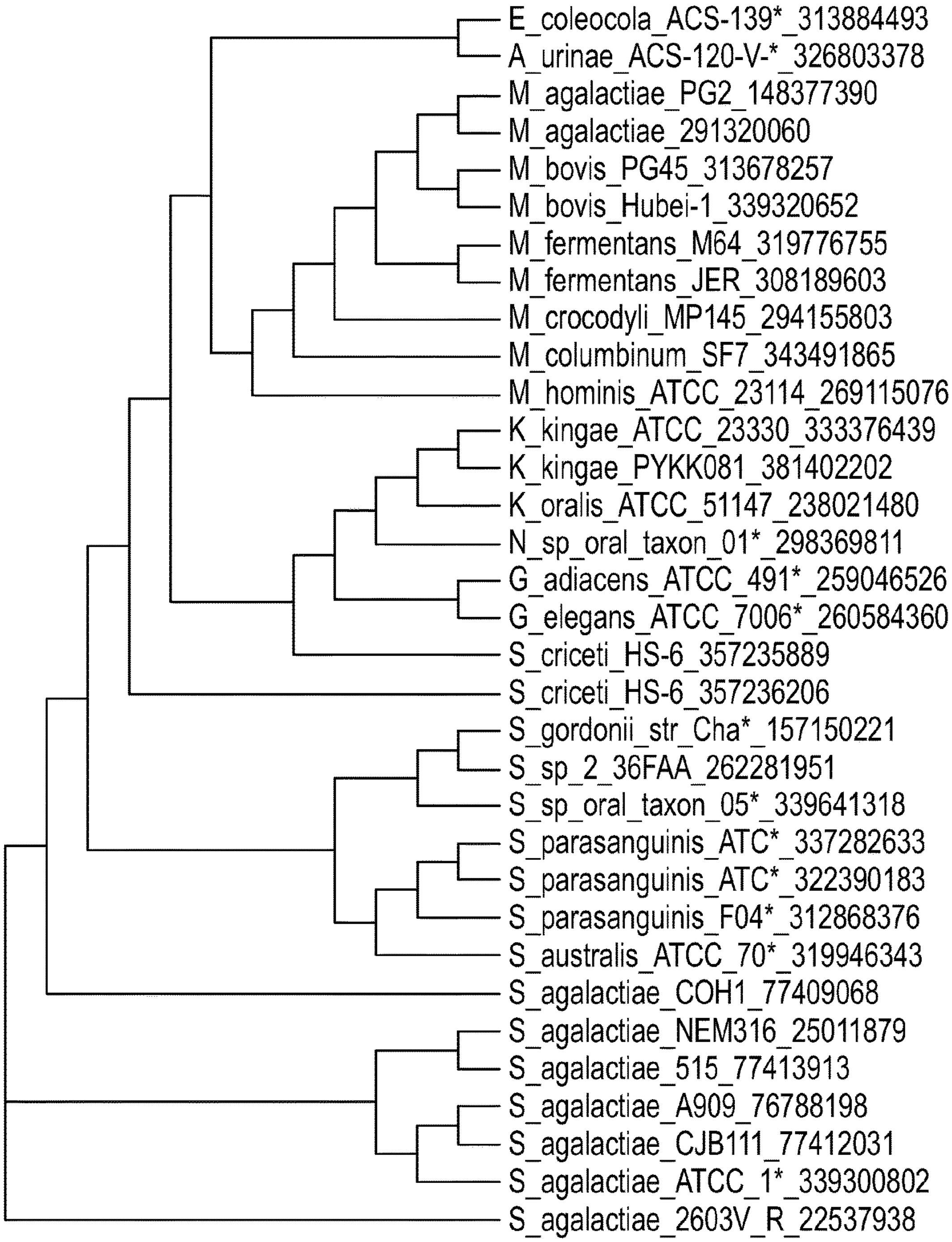
FIG. 13 is a diagram of identified phosphoketolases in Cluster 11.
Figure 14:
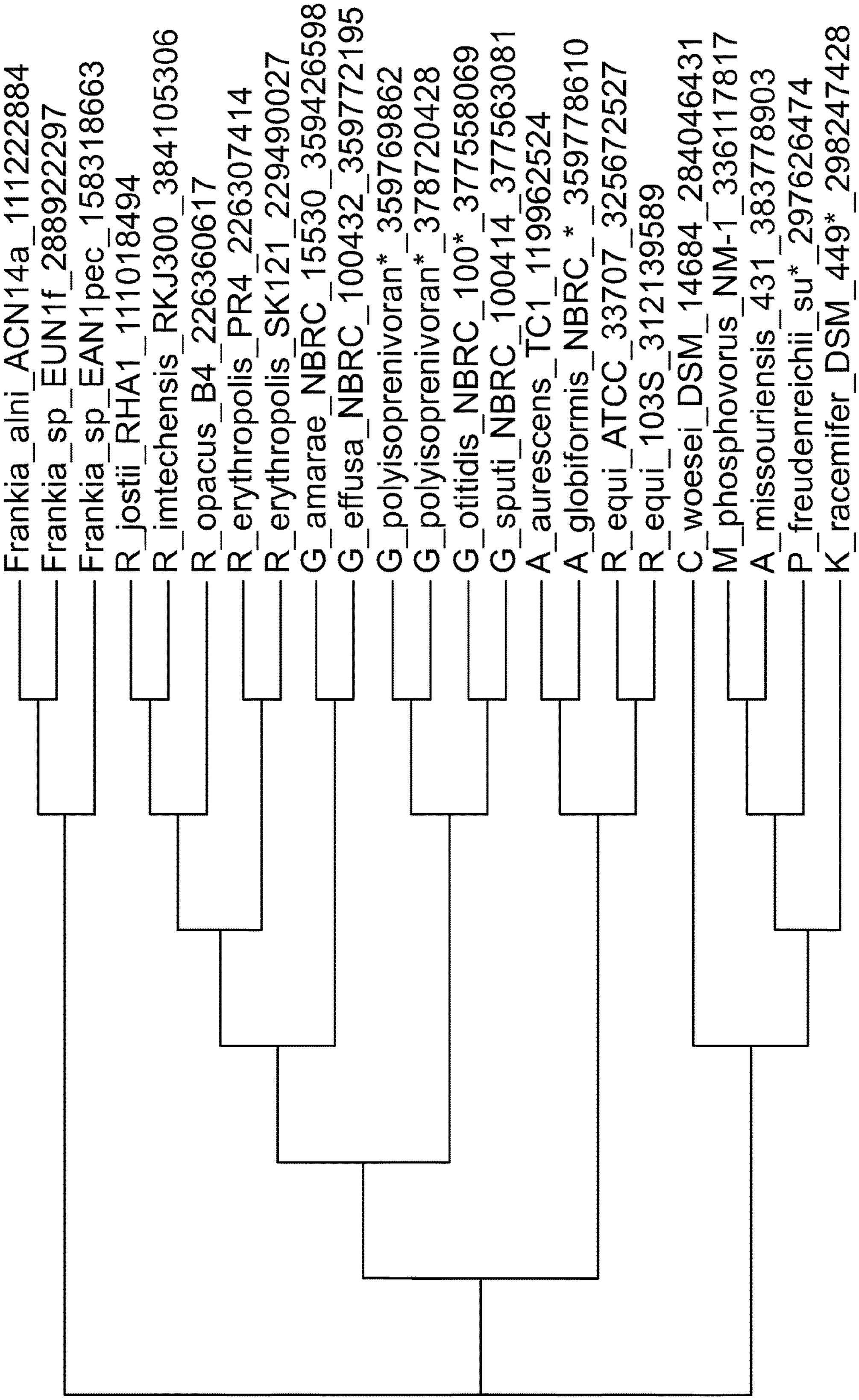
FIG. 14 is a diagram of identified phosphoketolases in Cluster 12.
Figure 15:
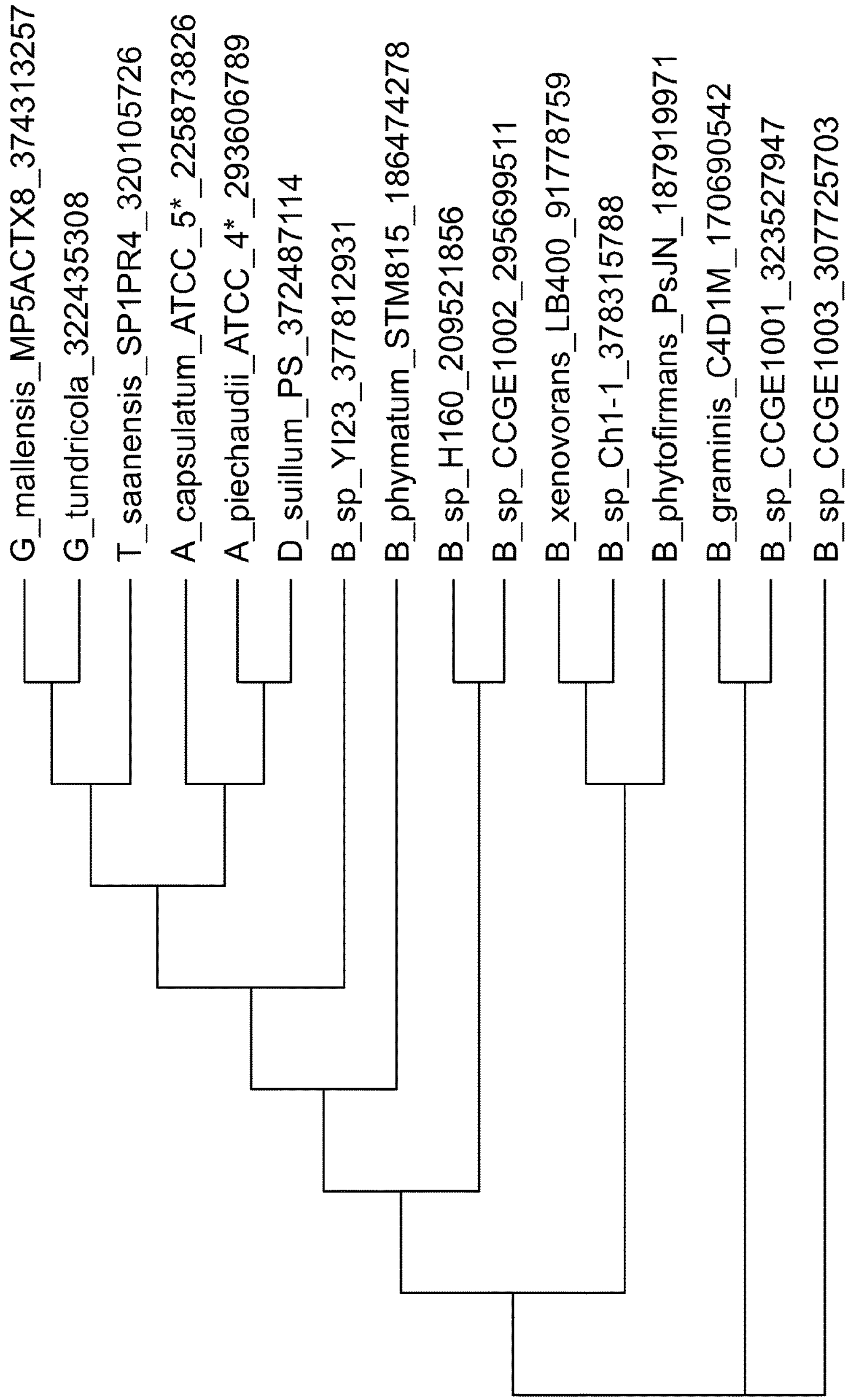
FIG. 15 is a diagram of identified phosphoketolases in Cluster 13.
Figure 16:
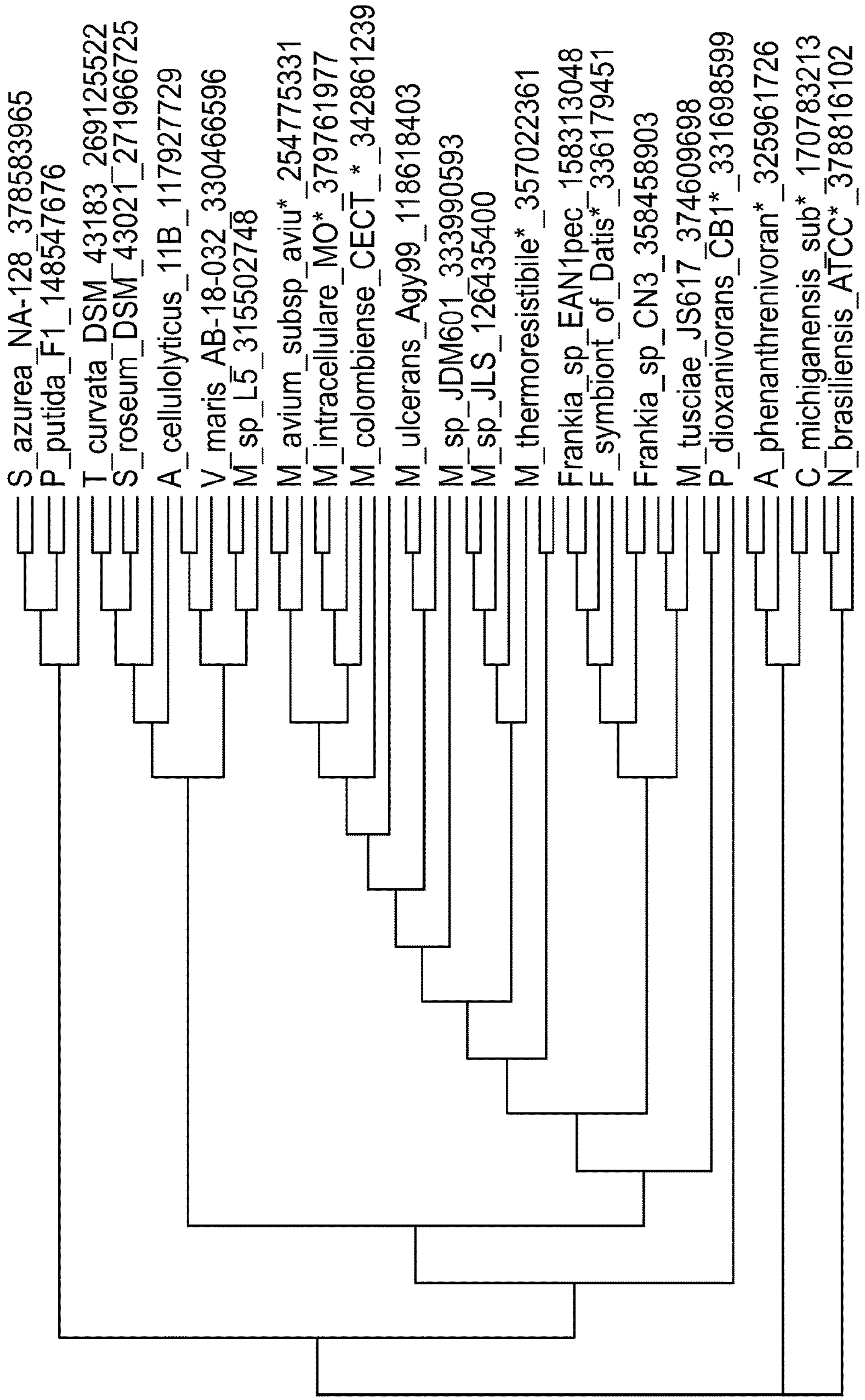
FIG. 16 is a diagram of identified phosphoketolases in Cluster 14.
Figure 17:
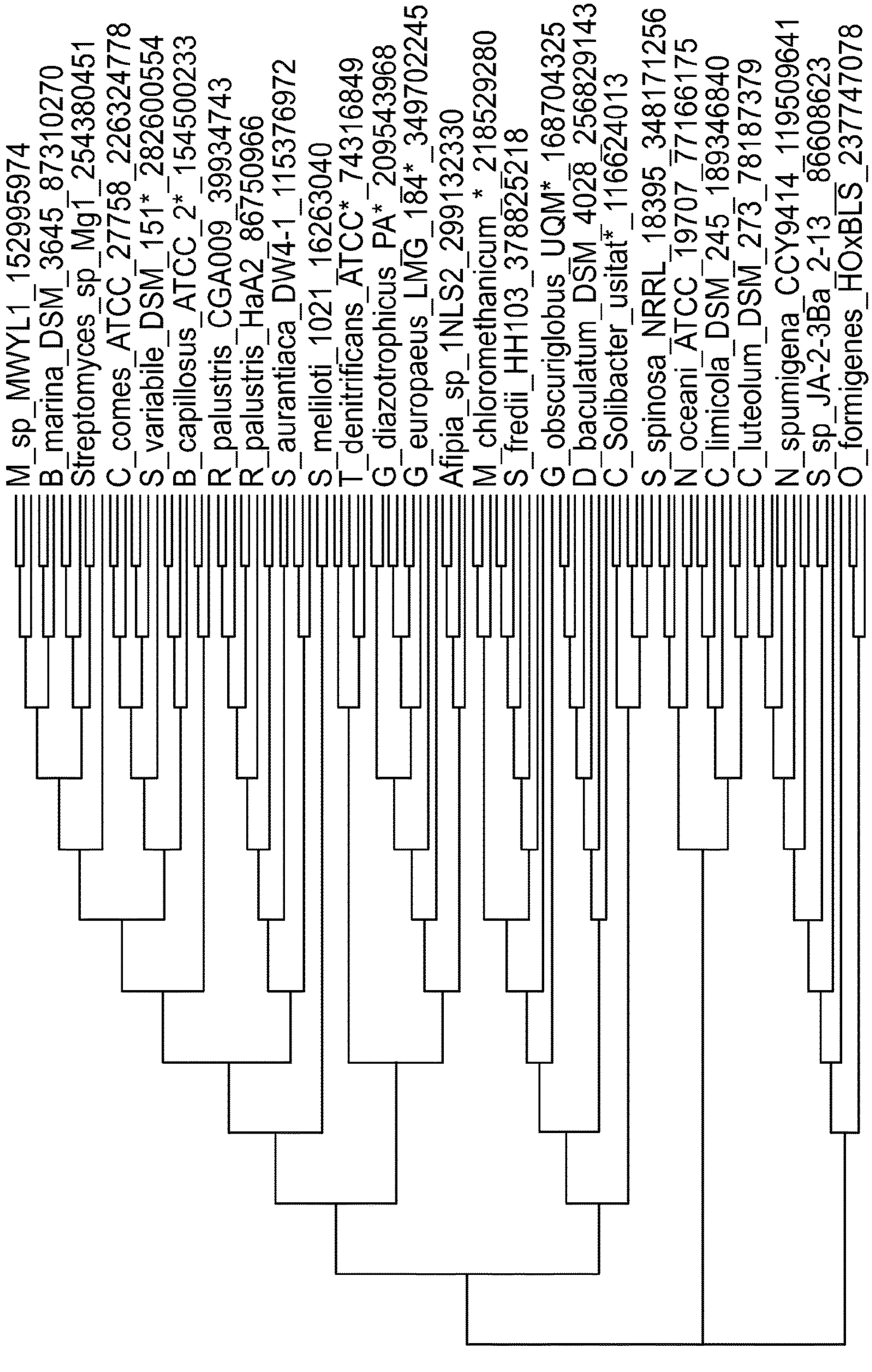
FIG. 17 is a diagram of identified phosphoketolases in Cluster 15.
Figure 18:
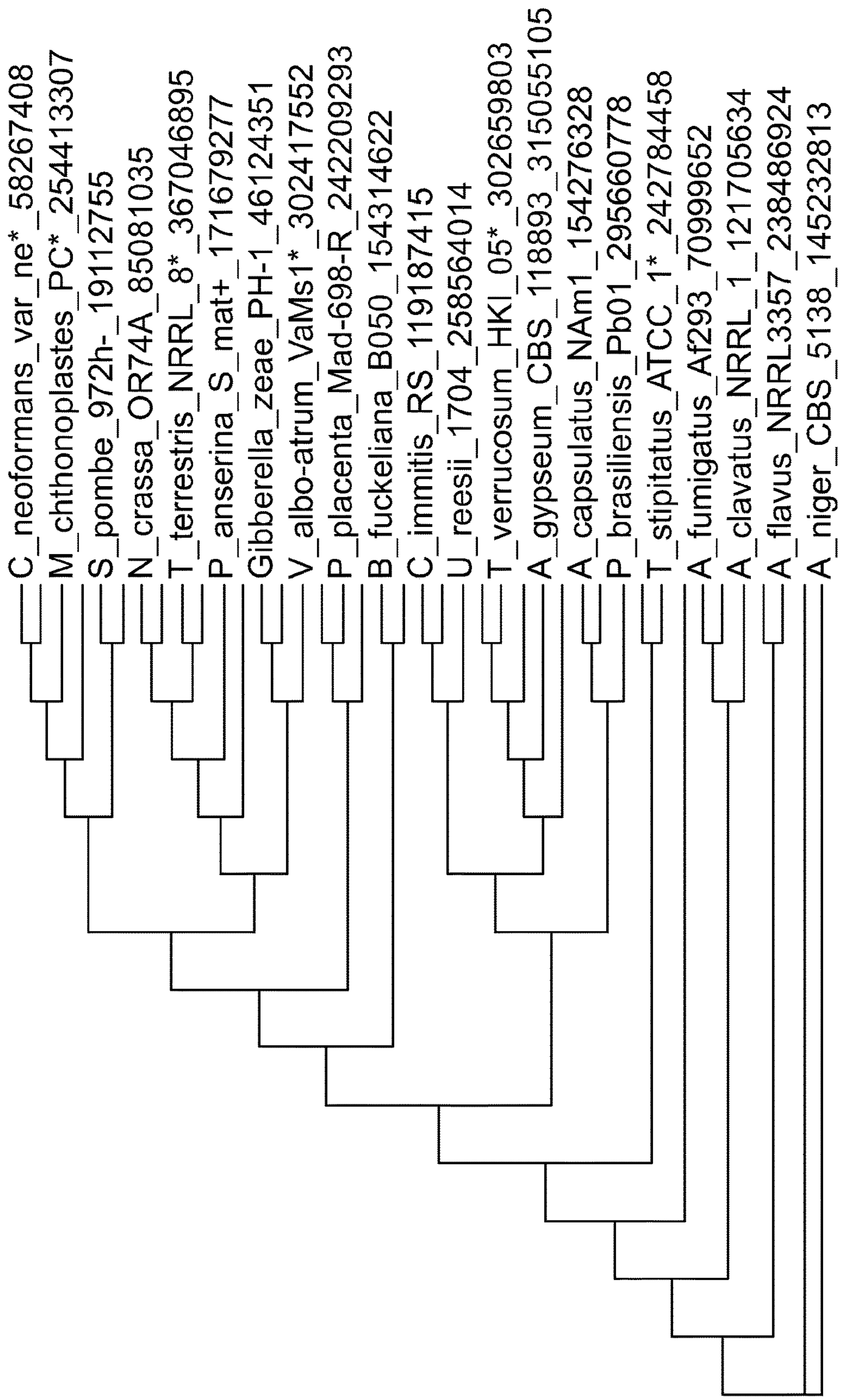
FIG. 18 is a diagram of identified phosphoketolases in Cluster 16.
Figure 19:
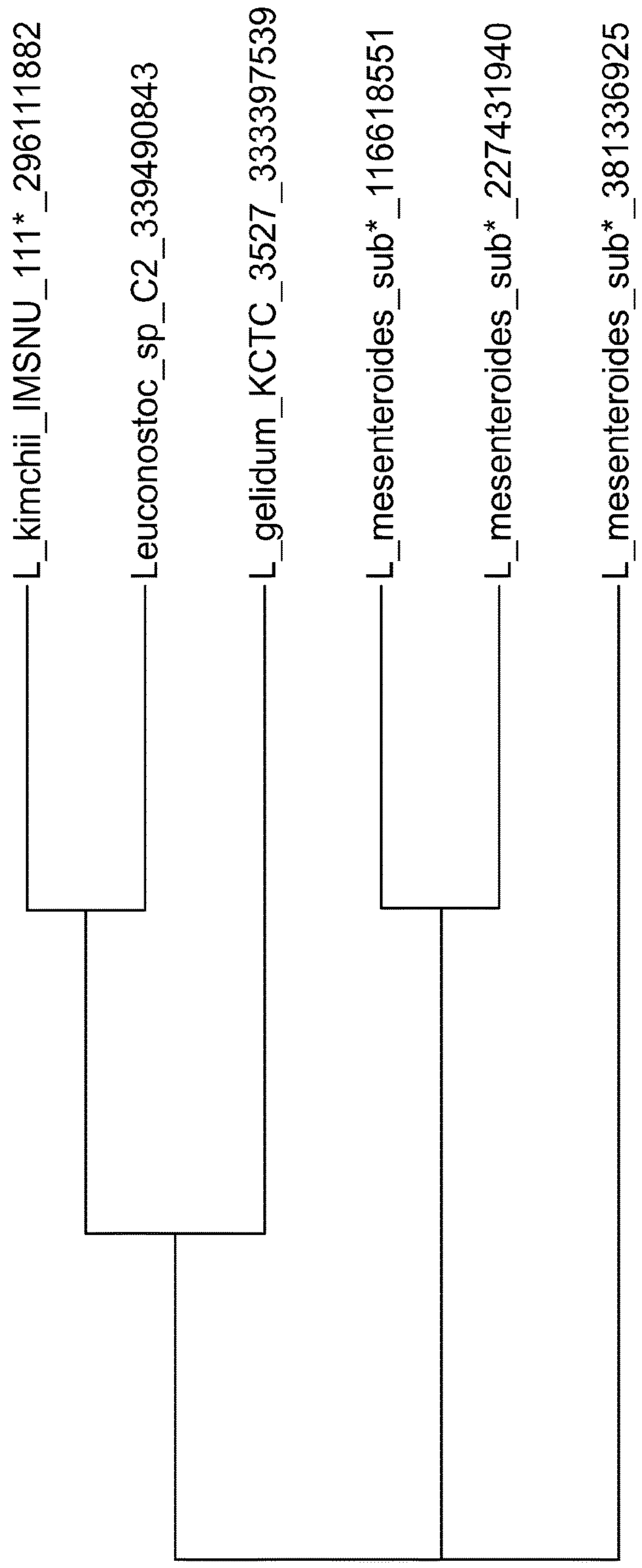
FIG. 19 is a diagram of identified phosphoketolases in Cluster 17.
Figure 20:
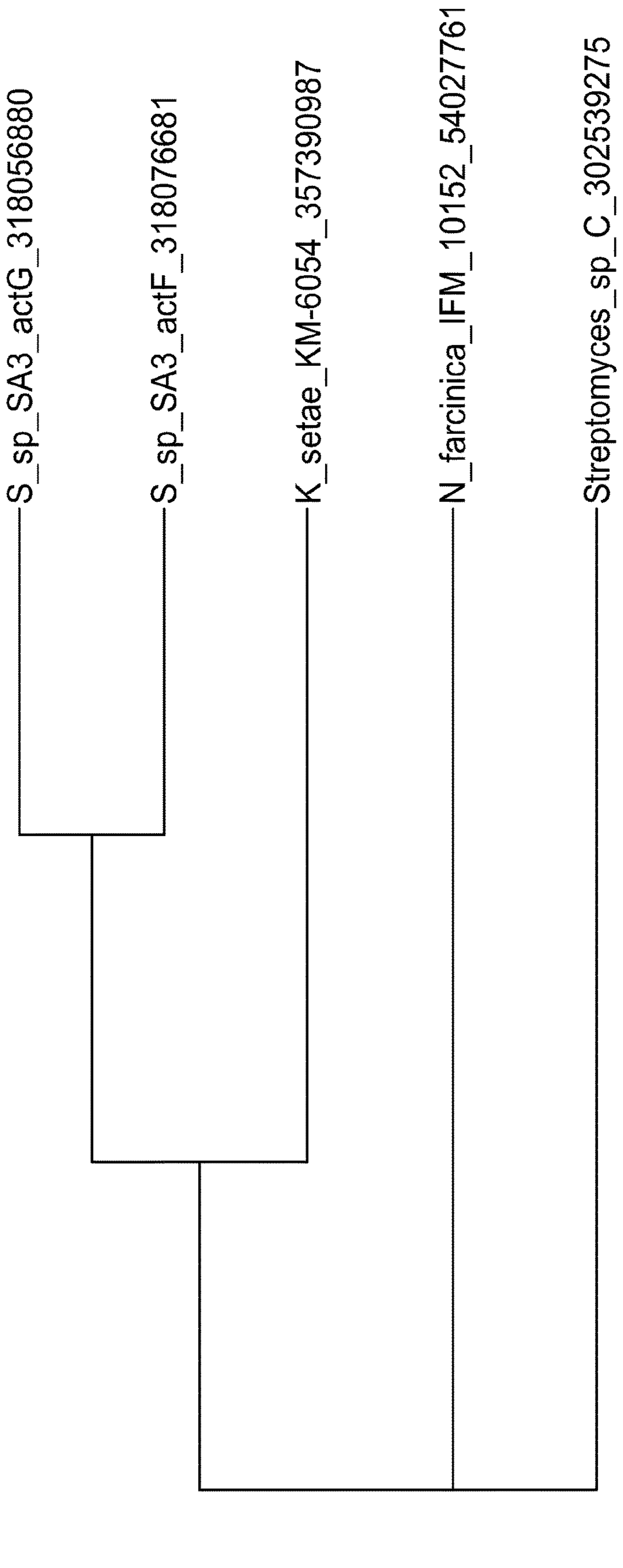
FIG. 20 is a diagram of identified phosphoketolases in Cluster 18.
Figure 21:
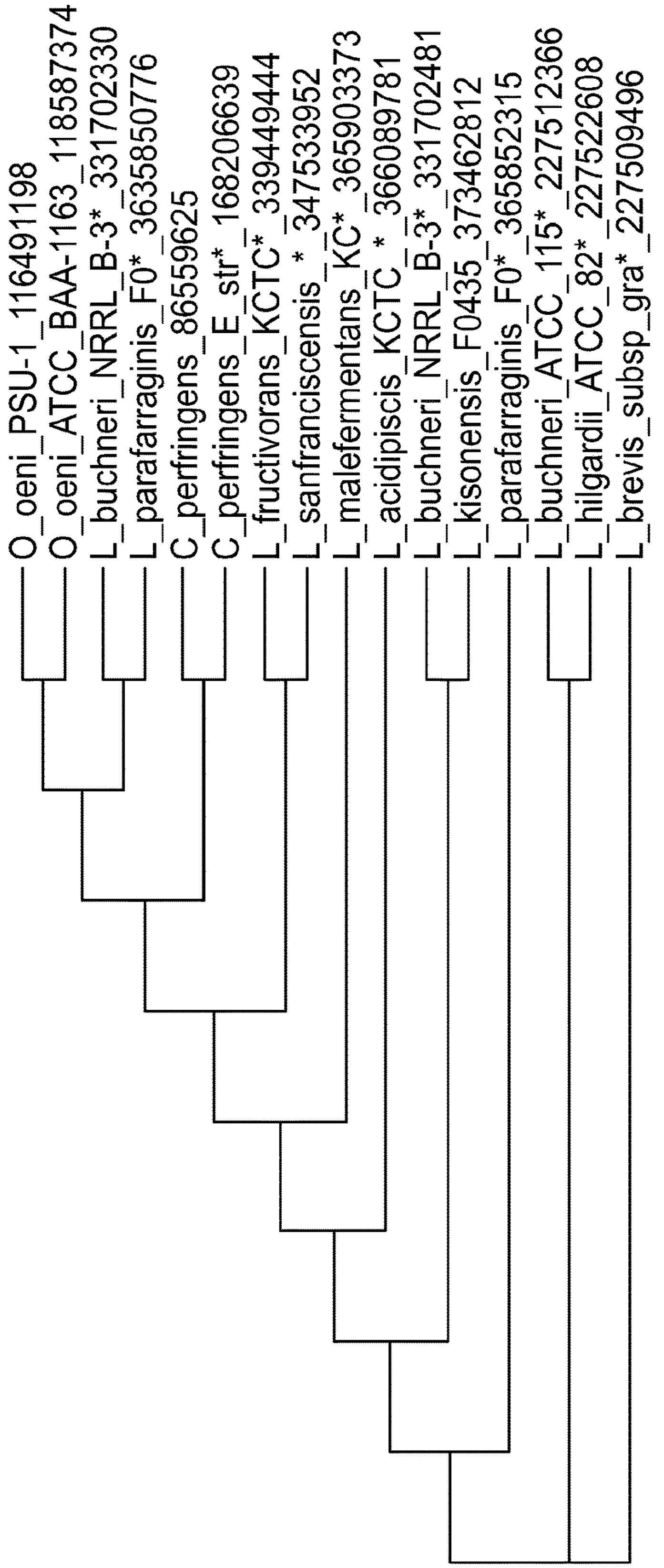
FIG. 21 is a diagram of identified phosphoketolases in Cluster 19.
Figure 22:
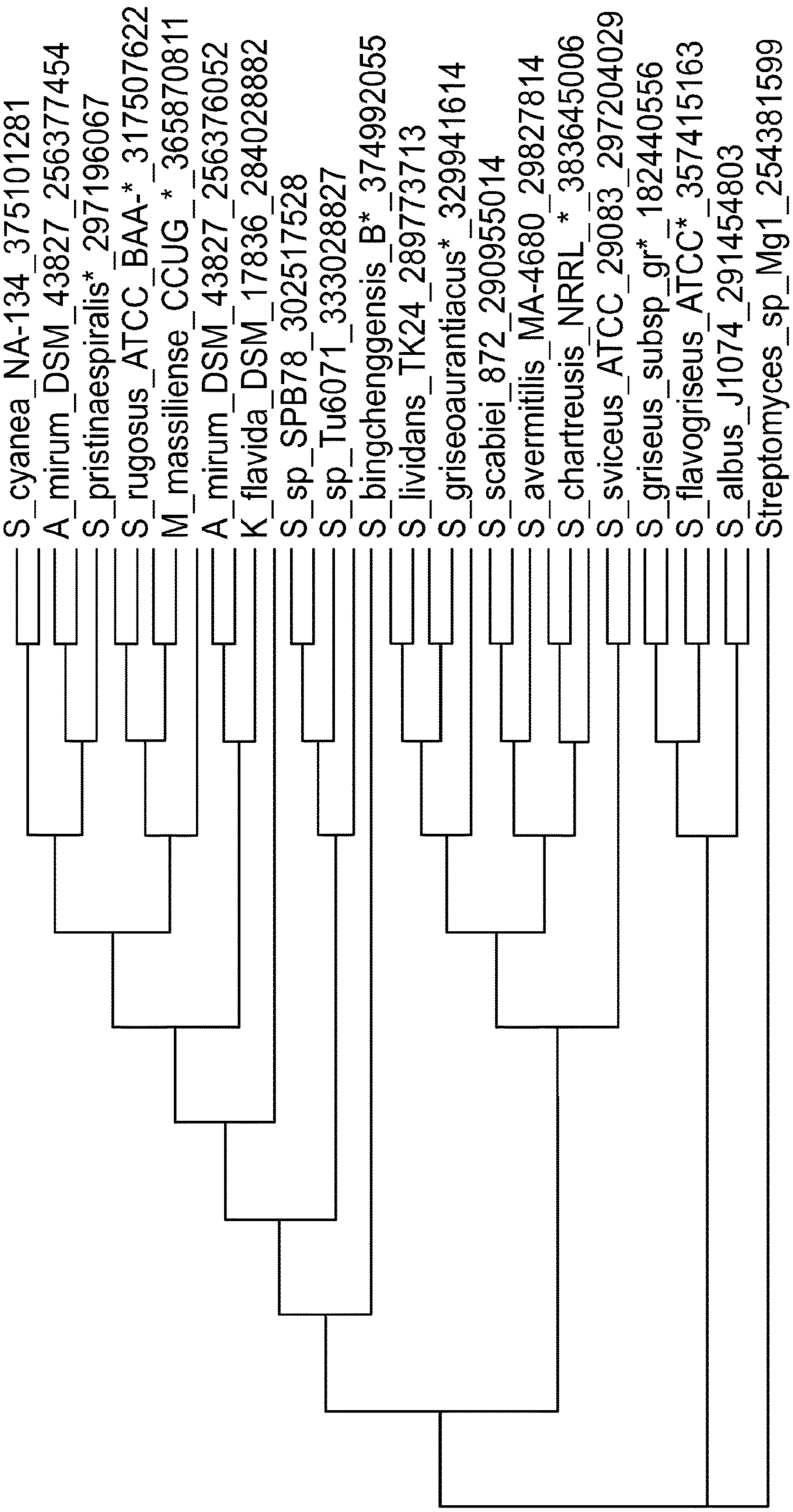
FIG. 22 is a diagram of identified phosphoketolases in Cluster 20.
Figure 23:
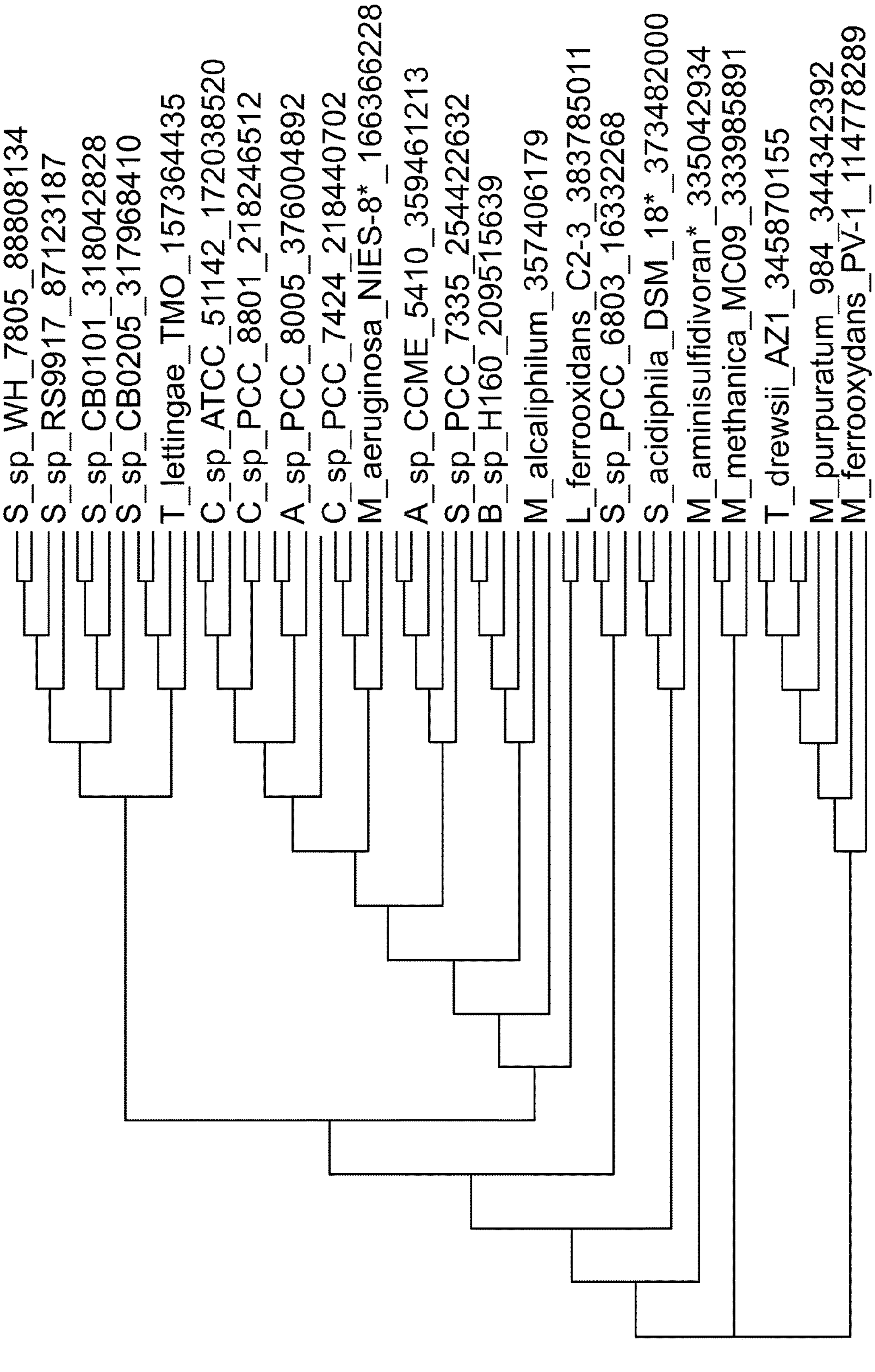
FIG. 23 is a diagram of identified phosphoketolases in Cluster 21.
Figure 24:
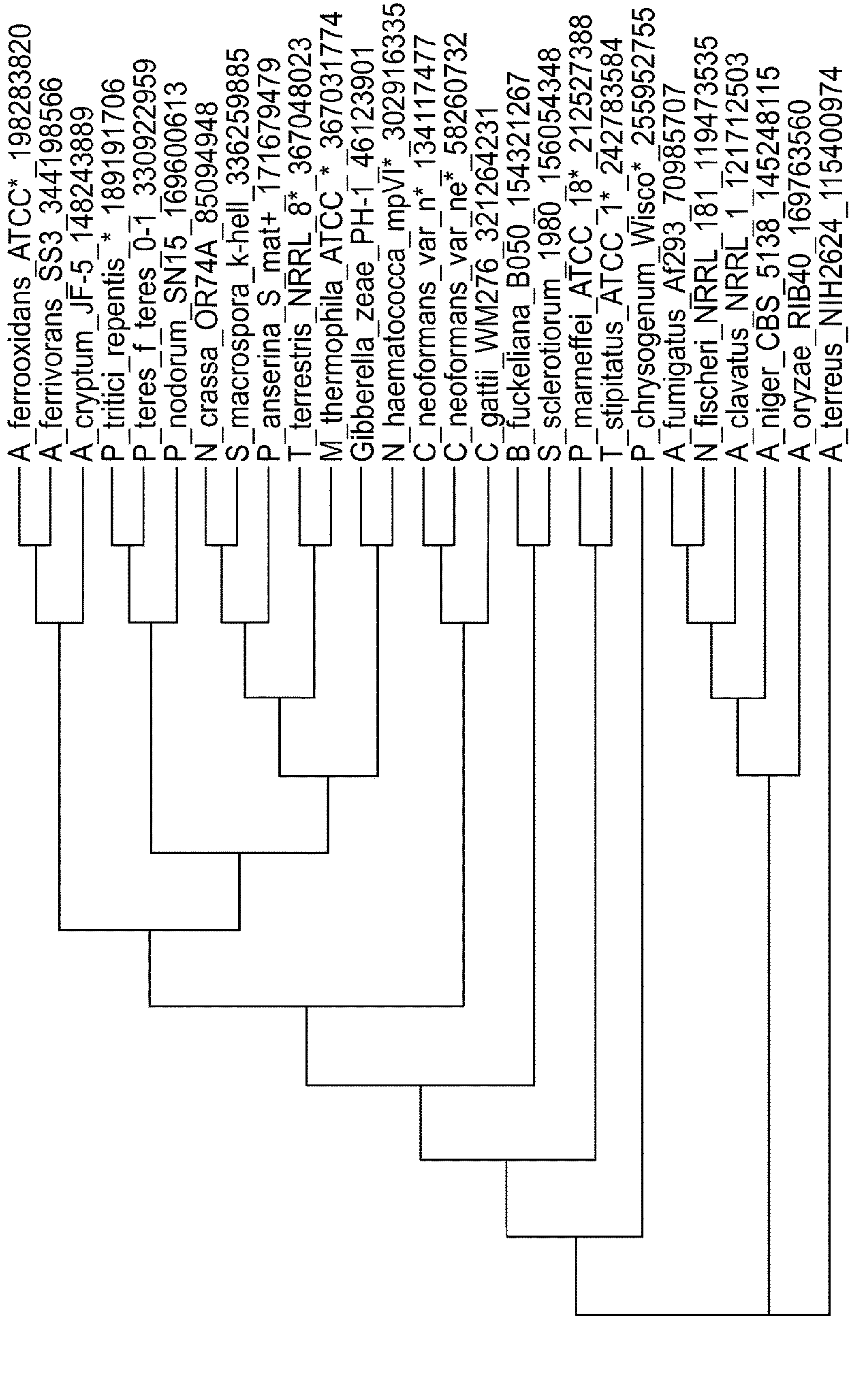
FIG. 24 is a diagram of identified phosphoketolases in Cluster 22.

To identify phosphoketolases that could be used for improved production of acetyl coenzyme A-derived (acetyl-CoA-derived) metabolites, isoprene, isoprenoid precursors, and isoprenoids in recombinant cells, the CDART program within the NCBI website was used to select all gene products that were consistent with the known phosphoketolase domain architecture (Geer L et al. (2002), "*CDART: protein homology by domain architecture.*", Genome Res. 12(10) 1619-23). Sequences were further refined by selecting the refseq sequences from the original domain architecture search. Next, the sequences were clustered into 22 distinct groups based on sequence similarity (Clustering by Passing Messages Between Data Points. Brendan J. Frey and Delbert Dueck, University of Toronto *Science* 315, 972-976, February 2007). Briefly, the amino acid sequences were multiply aligned using ClustalW. Pairwise percent identities (PIDs) were calculated. This was operationally defined and in this case it was the number of residues that were identical over residues that were aligned. The PIDs were converted to distances by way of the formula $K=-Ln(1-D-(D.D)/5)$ (Kimura, M. The neutral Theory of Molecular Evolution, Camb. Univ. Press, 1983, page 75). Negative distances were used as similarity score in the above algorithm. Medium similarities were used as preferences for each data point. 22 clusters were defined using this method (FIGS. 3-24). DNA encoding the amino acid sequence of the central representative sequence from each cluster was synthesized (FIG. 2 and Table 1). In cases where the central representative from a cluster was determined to be unlikely to represent an active phosphoketolase due to the absence of complete phosphoketolase domains, an alternate phosphoketolase from that cluster was selected for DNA synthesis (Table 1).

TABLE 1

| Central representative sequence | | | | |
|---|---|---|---|---|
| Cluster | Organism | NCBI identifier number | Amino acid SEQ ID NO | Nucleic Acid SEQ ID NO |
| 1 | *Mycobacterium gilvum* Spyr1 | 315444259 | 1 | 52 |
| 2 | *Shewanella baltica* OS185 | 152999647 | 2 | 53 |
| 3 | *Lactobacillus rhamnosus* LMS2-1 | 229550902 | 3 | 54 |
| 4 | *Lactobacillus crispatus* ST1 | 295692465 | 4 | 55 |
| 5 | *Bifidobacterium longum* subsp. *longum* JDM301 | 296453922 | 5 | N/D |
| 6 | *Leuconostoc citreum* KM20 | 170016535 | 6 | 56 |
| 7 | *Bradyrhizobium* sp. S23321 | 383773704 | 7 | 57 |
| 8 | *Enterococcus faecium* E1039 | 293556655 | 8 | N/D |
| 9 | *Brucella microti* CCM 4915 | 256015169 | 9 | 58 |
| 10 | *Lactobacillus salivarius* ATCC 11741 | 227891468 | 10 | 59 |
| 11 | *Streptococcus agalactiae* COH1 | 77409068 | 11 | N/D |
| 12 | *Rhodococcus imtechensis* RKJ300 | 384105306 | 12 | 60 |
| 13 | *Burkholderia xenovorans* LB400 | 91778759 | 13 | 61 |
| 14 | *Mycobacterium intracellulare* ATCC 13950 | 254819329 | 14 | 62 |
| 15 | *Nitrosomonas* sp. Is79A3 | 339481558 | 15 | 63 |
| 16* | *Schizosaccharomyces pombe* 972h- | 19112755 | 16 | 64 |
| 17 | *Leuconostoc mesenteroides* subsp. *mesenteroides* J18 | 381336925 | 17 | N/D |
| 18 | *Streptomyces* sp. SA3_actG | 318056880 | 18 | N/D |
| 19 | *Lactobacillus buchneri* ATCC 11577 | 227512366 | 19 | 65 |
| 20 | *Streptomyces ghanaensis* ATCC 14672 | 291440956 | 20 | 66 |
| 21 | *Cyanothece* sp. PCC 8802 | 257059544 | 21 | 67 |
| 22 | *Neosartorya fischeri* NRRL 181 | 119473535 | 22 | 68 |

N/D indicates not done
*Replaced the central representative *Aspergillus fumigatus* Af293 (NCBI number 70999652)

DNA encoding the protein sequences that were less than 90% identical to each other by pairwise alignment using ClustalW within Cluster 8, which contained the *Enterococcus gallinarum* phosphoketolase, and to Cluster 11, which shared the most homology with Cluster 8, were designed for protein synthesis (Table 2).

TABLE 2

| Sequences from Cluster 8 and Cluster 11 | | | |
|---|---|---|---|
| Organism | NCBI identifier number | Amino acid SEQ ID NO | Nucleic Acid SEQ ID NO |
| Cluster 8 | | | |
| *Enterococcus faecium* TX1330 | 227551751 | 23 | 69 |
| *Listeria grayi* DSM 20601 | 299821157 | 24 | 70 |
| *Enterococcus casseliflavus* EC30 | 257866707 | 25 | 71 |

TABLE 2-continued

| Sequences from Cluster 8 and Cluster 11 | | | |
|---|---|---|---|
| Organism | NCBI identifier number | Amino acid SEQ ID NO | Nucleic Acid SEQ ID NO |
| *Mycoplasma alligatoris* A21JP2 | 293363787 | 26 | 72 |
| *Carnobacterium* sp. 17-4 | 328958427 | 27 | 73 |
| *Melissococcus plutonius* ATCC 35311 | 332686509 | 28 | 74 |
| *Tetragenococcus halophilus* NBRC 12172 | 352516443 | 29 | 75 |
| *Melissococcus plutonius* DAT561 | 379727960 | 30 | 76 |
| *Mycoplasma arthritidis* 158L3-1 | 193216764 | 31 | 77 |
| Cluster 11 | | | |
| *Streptococcus agalactiae* NEM316 | 25011879 | 32 | 78 |
| *Mycoplasma agalactiae* PG2 | 148377390 | 33 | 79 |
| *Streptococcus gordonii* str. *Challis* substr. CH1 | 157150221 | 34 | 80 |
| *Kingella oralis* ATCC 51147 | 238021480 | 35 | 81 |
| *Mycoplasma fermentans* M64 | 319776755 | 36 | 82 |
| *Granulicatella adiacens* ATCC 49175 | 259046526 | 37 | 83 |
| *Mycoplasma hominis* ATCC 23114 | 269115076 | 38 | 84 |
| *Mycoplasma crocodyli* MP145 | 294155803 | 39 | 85 |
| *Neisseria* sp. oral taxon 014 str. F0314 | 298369811 | 40 | 86 |
| Eremococcus *coleocola* ACS 139-V-Col8 | 313884493 | 41 | 87 |
| *Aerococcus urinae* ACS-120-V-Col10a | 326803378 | 42 | 88 |
| *Kingella kingae* ATCC 23330 | 333376439 | 43 | 89 |
| *Streptococcus criceti* HS-6 | 357236206 | 44 | 90 |
| *Streptococcus criceti* HS-6 | 357235889 | 45 | 91 |
| *Mycoplasma columbinum* SF7 | 343491865 | 46 | 92 |

TABLE 3

| Sequences from Cluster 8-Amino Acid Percent Sequence Identity | | |
|---|---|---|
| Cluster 8 Reference AA | Phosphoketolase AA Sequence | Amino Acid % Identity |
| SEQ ID NO: 8 | SEQ ID NO: 23 | 98 |
| SEQ ID NO: 8 | SEQ ID NO: 24 | 73 |
| SEQ ID NO: 8 | SEQ ID NO: 25 | 74 |
| SEQ ID NO: 8 | SEQ ID NO: 26 | 67 |
| SEQ ID NO: 8 | SEQ ID NO: 27 | 71 |
| SEQ ID NO: 8 | SEQ ID NO: 28 | 72 |
| SEQ ID NO: 8 | SEQ ID NO: 29 | 70 |
| SEQ ID NO: 8 | SEQ ID NO: 30 | 72 |
| SEQ ID NO: 8 | SEQ ID NO: 31 | 70 |

TABLE 4

| Sequences from Cluster 11-Amino Acid Percent Sequence Identity | | |
|---|---|---|
| Cluster 11 Reference AA | Phosphoketolase AA Sequence | Amino Acid % Identity |
| SEQ ID NO: 11 | SEQ ID NO: 32 | 99 |
| SEQ ID NO: 11 | SEQ ID NO: 33 | 65 |
| SEQ ID NO: 11 | SEQ ID NO: 34 | 89 |
| SEQ ID NO: 11 | SEQ ID NO: 35 | 74 |
| SEQ ID NO: 11 | SEQ ID NO: 36 | 69 |
| SEQ ID NO: 11 | SEQ ID NO: 37 | 79 |
| SEQ ID NO: 11 | SEQ ID NO: 38 | 65 |
| SEQ ID NO: 11 | SEQ ID NO: 39 | 68 |

TABLE 4-continued

| Sequences from Cluster 11-Amino Acid Percent Sequence Identity | | |
|---|---|---|
| Cluster 11 Reference AA | Phosphoketolase AA Sequence | Amino Acid % Identity |
| SEQ ID NO: 11 | SEQ ID NO: 40 | 77 |
| SEQ ID NO: 11 | SEQ ID NO: 41 | 67 |
| SEQ ID NO: 11 | SEQ ID NO: 42 | 68 |
| SEQ ID NO: 11 | SEQ ID NO: 43 | 74 |
| SEQ ID NO: 11 | SEQ ID NO: 44 | 84 |
| SEQ ID NO: 11 | SEQ ID NO: 45 | 79 |
| SEQ ID NO: 11 | SEQ ID NO: 46 | 66 |

Example 2: Identification of Phosphoketolases in Bacterial Genomes Lacking Phosphofructokinase A search was conducted for bacterial genomes that had an annotated phosphoketolase (PKL) but did not have an annotated phosphofructokinase (PFK), a critical enzyme for carbon flux through glycolysis. Several organisms that fit these criteria, and from this list five PKLs, specifically PKLs from *Burkholderia phytofirmans* PsJN (SEQ ID NO:47), *Lactobacillus buchneri* NRRL B-30929 (SEQ ID NO:48), *Bifidobacterium gallicum* DSM 20093 (SEQ ID NO:49), *Bifidobacterium dentium* Bd1 (SEQ ID NO:50), and *Bifidobacterium bifidum* IPLA 20015 (SEQ ID NO:51), were chosen for investigation of high activity and increased yield of isoprene from glucose. Since most of the PKLs from the full list of organisms have not been characterized, the five PKLs that were chosen were based on sequence diversity and the best circumstantial evidence of high activity that could be obtained in the literature. The PKL from *Bifidobacterium dentium* displayed a pH optimum of 7 (Sgorbati B., et al., *Antonie van Leeuwenhoek* 1976 (42), 49-57), whereas the pH optima for other PKLs is typically around 6 (Heath E C., et al., *J Bio Chem* 1957, 1009-1029). *Lactobacillus buchneri* was isolated as a contaminant from a fuel ethanol plant, and was shown to grow on both glucose and xylose, presumably by activity of PKL on either F6P or X5P for cell mass and energy (Liu S., et al., *J Ind Microbiol Biotechnol* 2008 (35), 75-81). The PKLs from *Bifidobacterium bifidum* and *Bifidobacterium gallicum* were chosen because these strains were able to grow well on either glucose or xylose as the sole carbon source (Palframan R J., et al., *Curr Issues Intest Microbiol* 2003 (4), 71-75).

Example 3: Cloning of Identified Phosphoketolase Enzymes

PKLs obtained from *Bifidobacterium longum* subsp. *infantis, Enterococcus gallinarum*, and *Clostridium acetobutylicum* were each assayed for enzyme activity. *Bifidobacterium longum* subsp. *infantis* PKL had a Km of 5.7±1.16 mM, a kcat of 4.56±0.2 $sec^{-1}$, and a kcat/Km of 0.79±0.2 $mM^{-1}$ $sec^{-1}$, *Enterococcus gallinarum* PKL had a Km of 10.4±1.03 mM, a kcat of 1.35±0.04 $sec^{-1}$, and a kcat/Km of 0.13±0.1 $mM^{-1}$ $sec^{-1}$, and *Clostridium acetobutylicum* PKL was found to have a Km of 10.3±0.67 mM, a kcat of 2.18±0.05 $sec^{-1}$, and a kcat/Km of 0.21±0.06 $mM^{-1}$ $sec^{-1}$. A construct encoding the *Bifidobacterium longum* subsp. *infantis, Enterococcus gallinarum*, or *Clostridium acetobutylicum* PKLs was used as a control to screen the candidate PKL enzymes for in vitro and in vivo activity.

Figure 25:
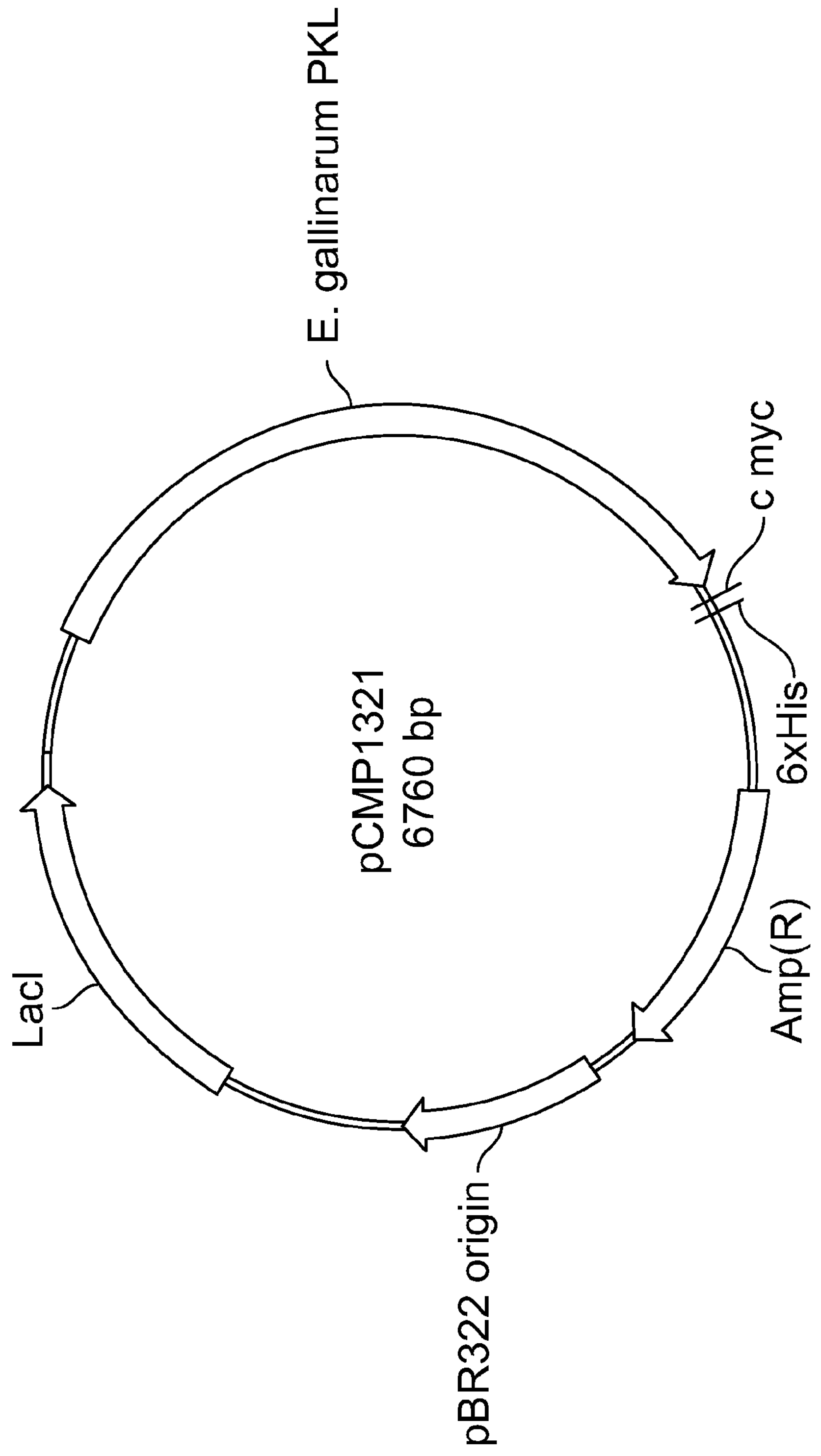
FIG. 25 depicts the plasmid map of pCMP1321, expressing *Enterococcus gallinarum* phosphoketolase.
Figure 26:
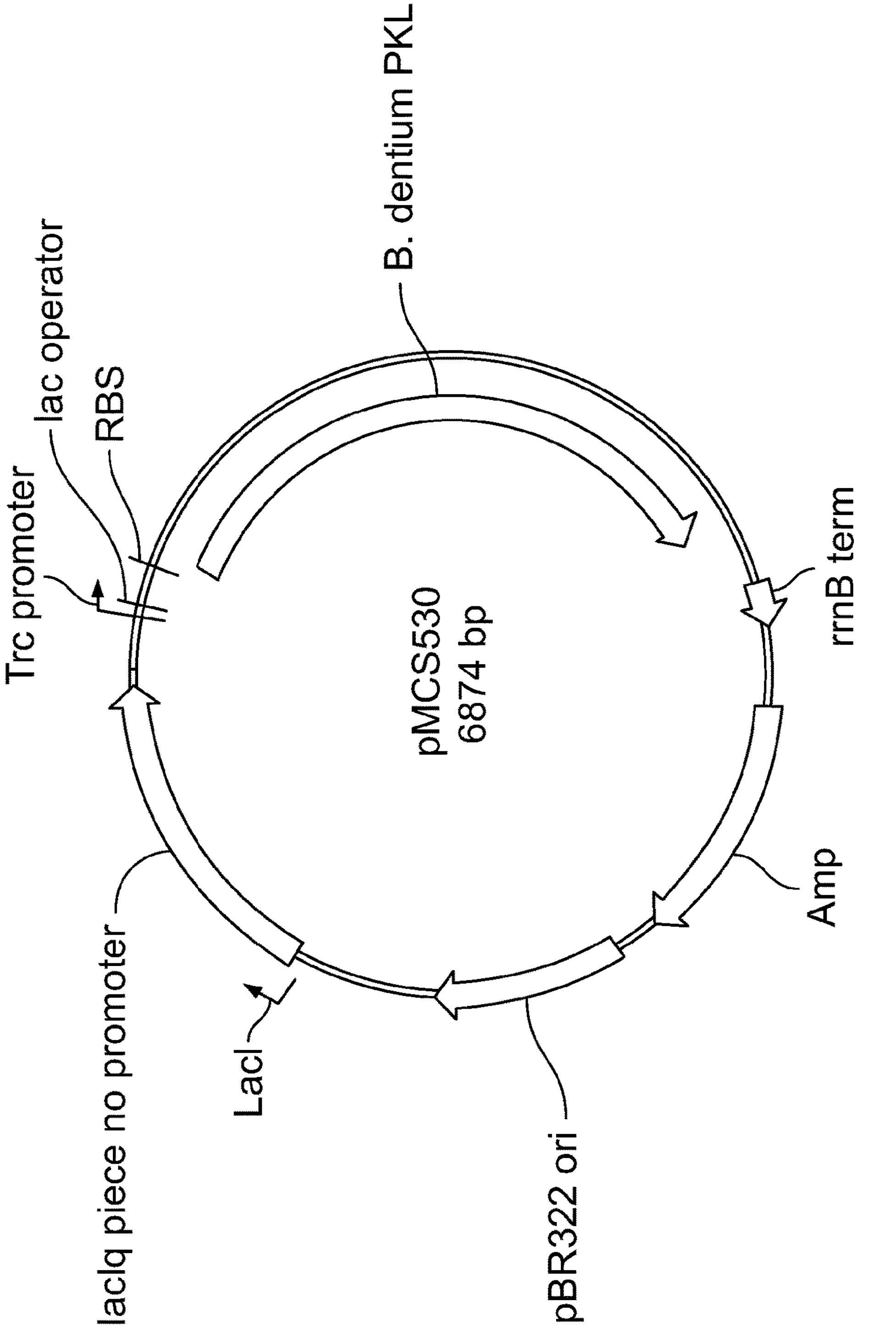
FIG. 26 depicts the plasmid map of pMCS530, expressing *Bifidobacterium dentium* phosphoketolase.
Figure 27:
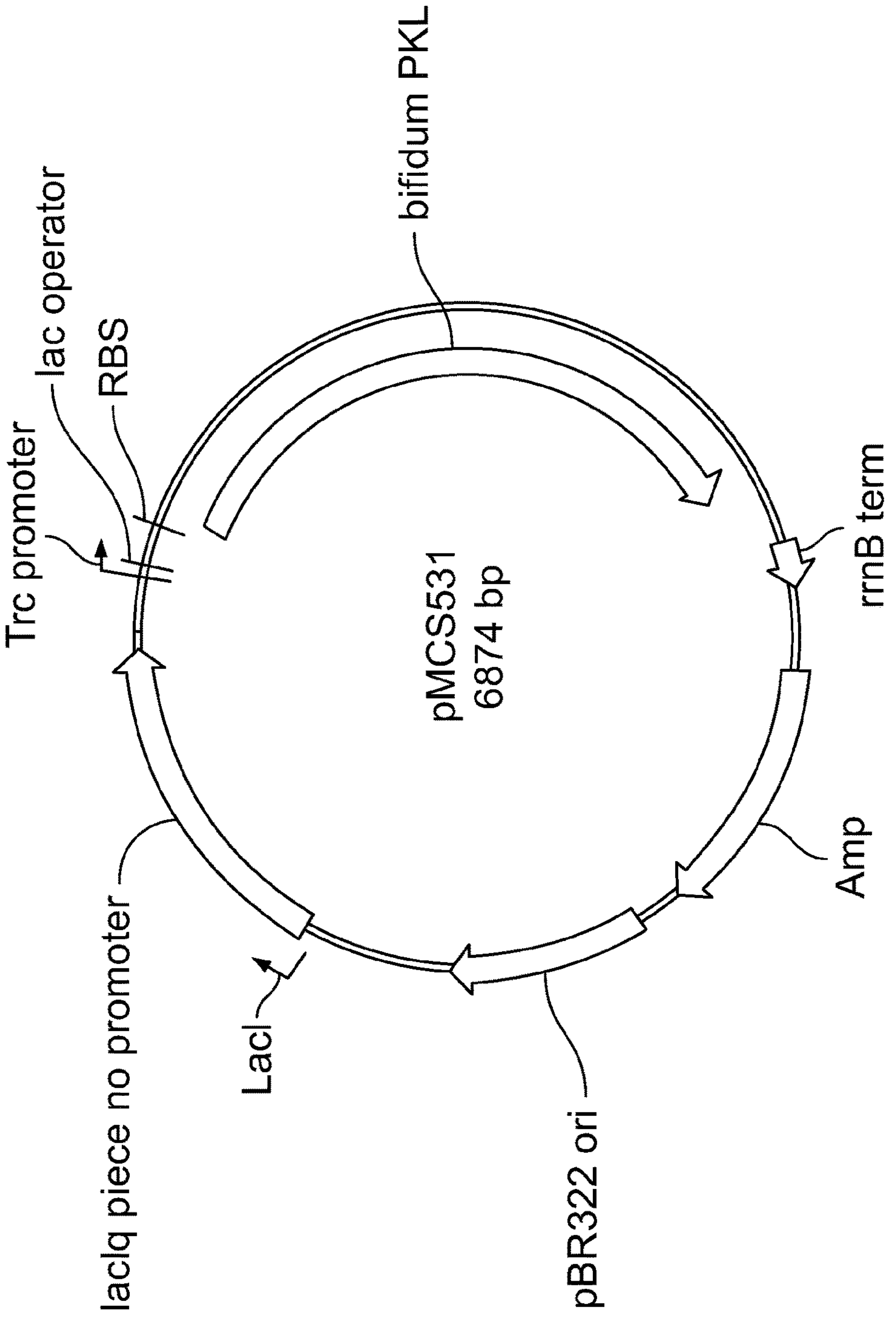
FIG. 27 depicts the plasmid map of pMCS531, expressing *Bifidobacterium bifidum* phosphoketolase.
Figure 28:
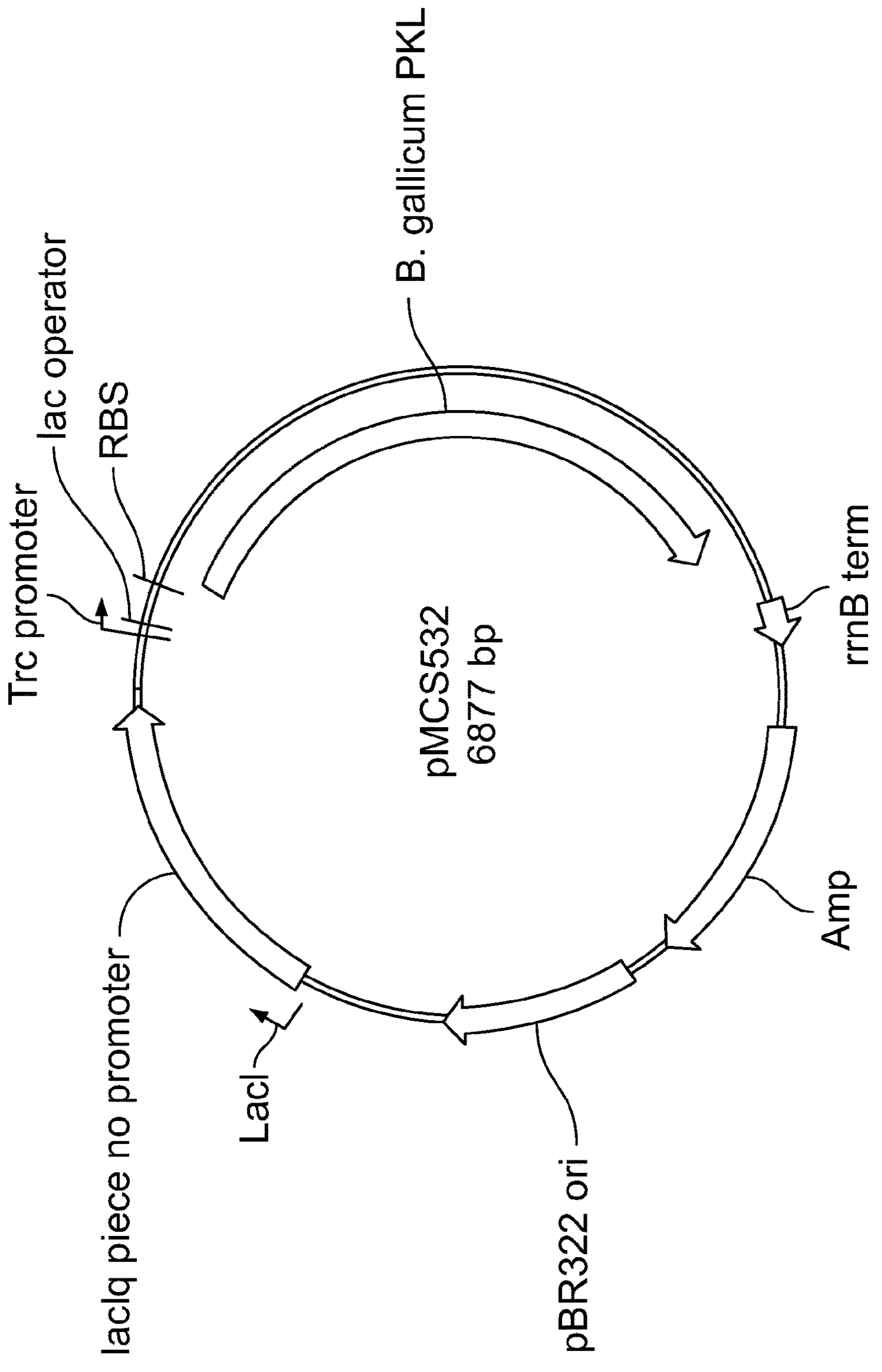
FIG. 28 depicts the plasmid map of pMCS532, expressing *Bifidobacterium gallicum* phosphoketolase.
Figure 29:
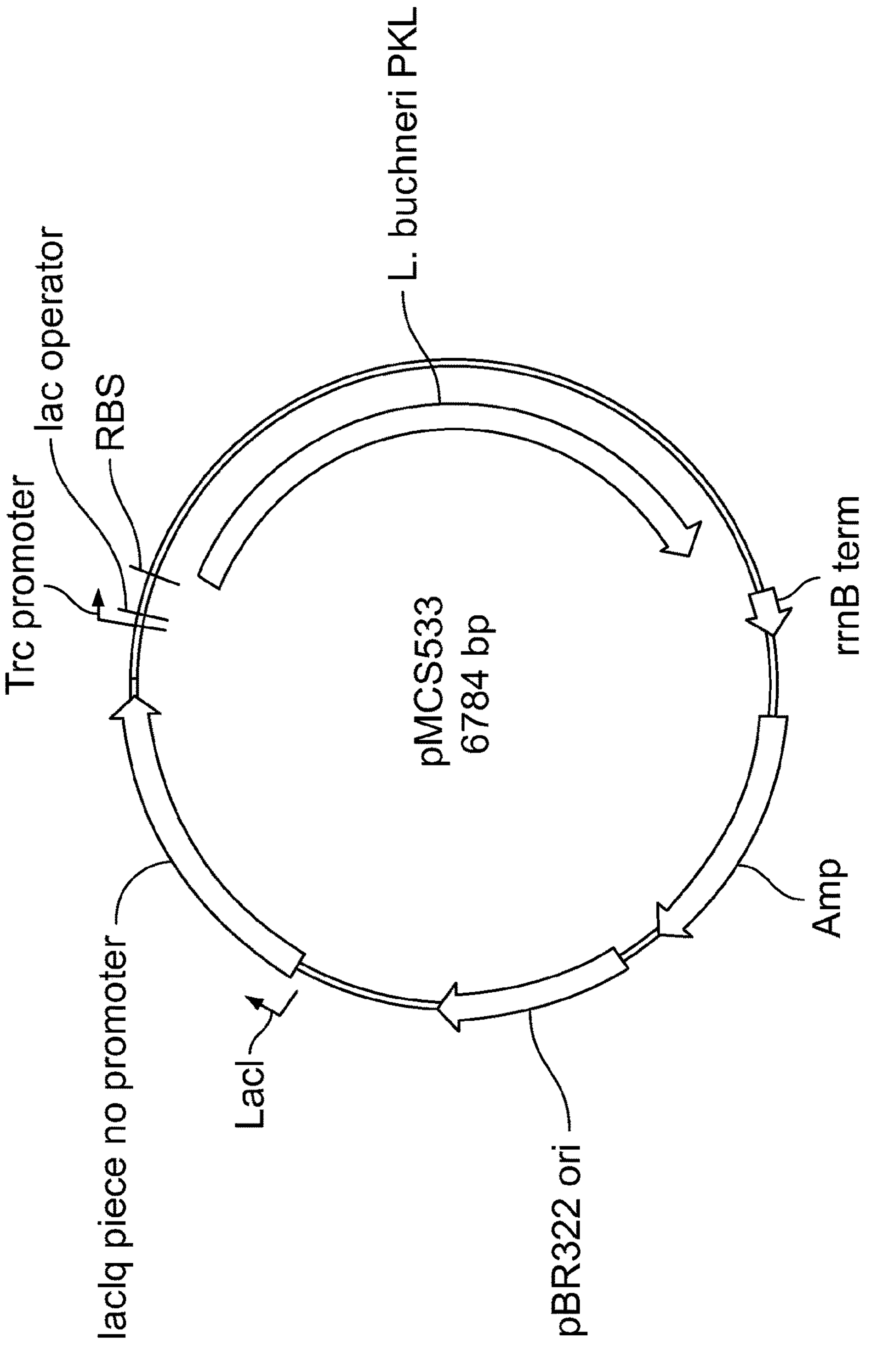
FIG. 29 depicts the plasmid map of pMCS533, expressing *Lactobacillus buchneri* phosphoketolase.
Figure 30:
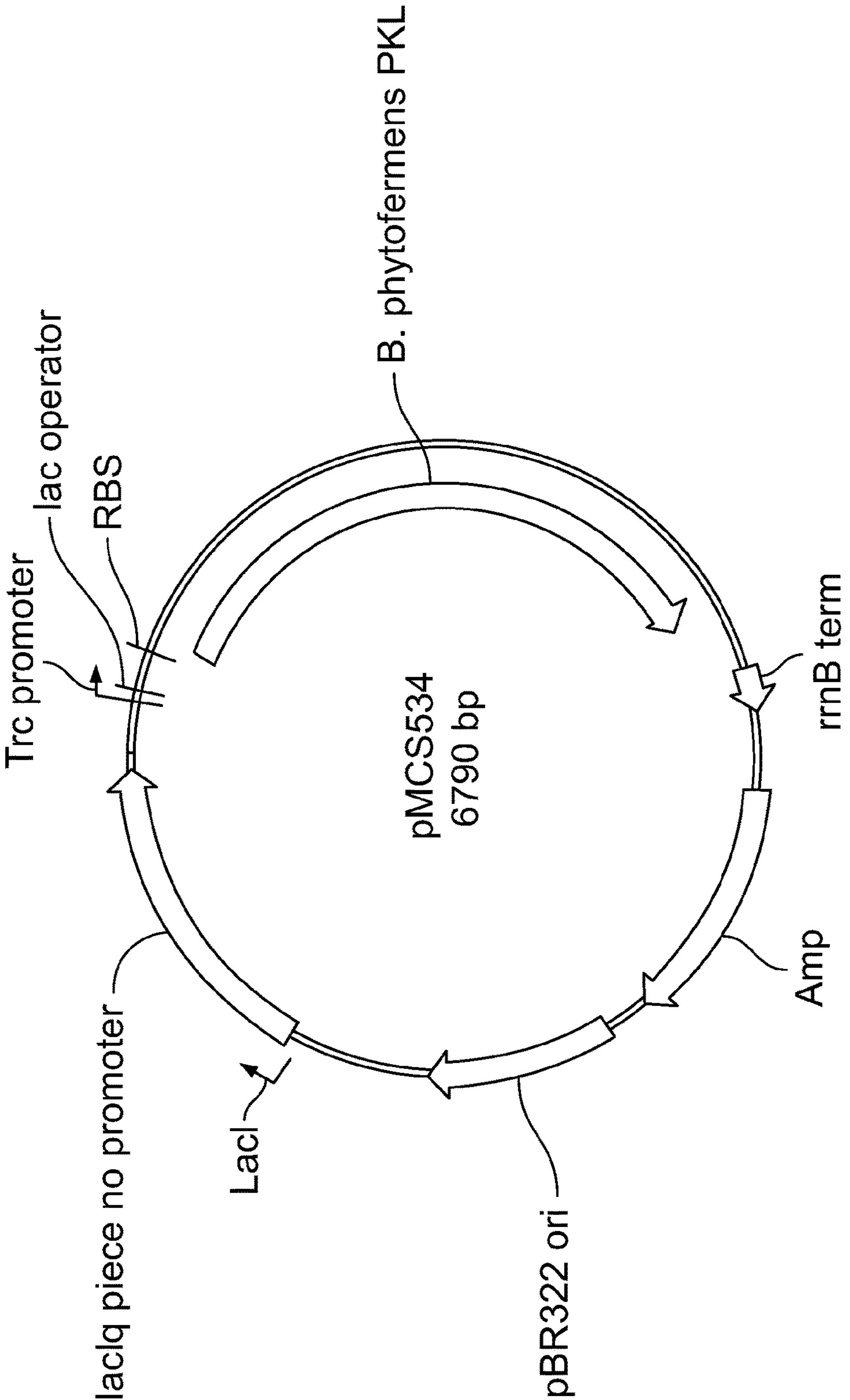
FIG. 30 depicts the plasmid map of pMCS534, expressing *Burkholderia* phytofermans phosphoketolase.
Figure 31:
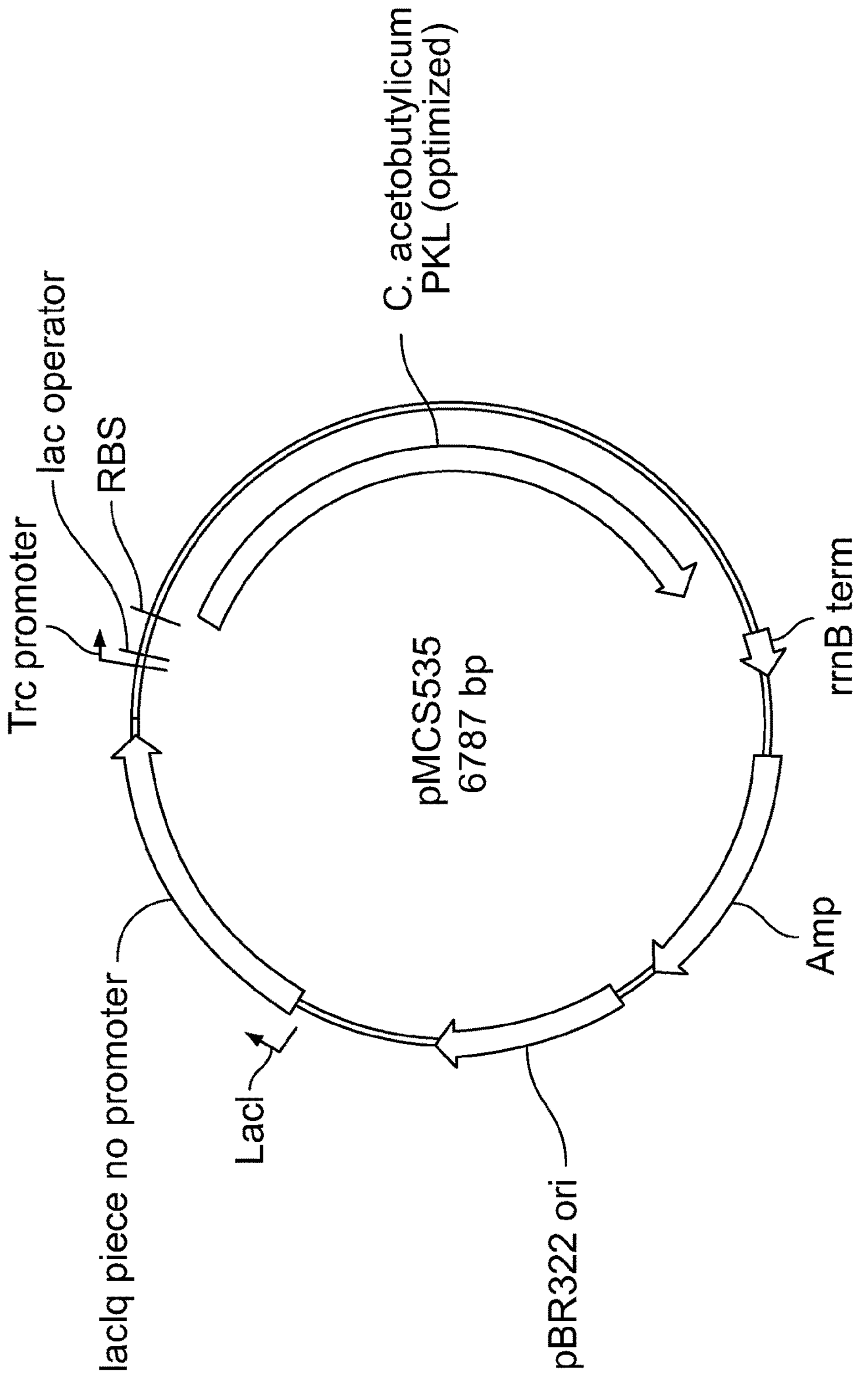
FIG. 31 depicts the plasmid map of pMCS535, expressing *Clostridium acetobutylicum* optimized phosphoketolase.

The amino acid sequence of *Enterococcus gallinarum* PKL (SEQ ID NO: 93) was obtained from GenBank and was processed in GeneArt optimization software for optimized expression in *E. coli*. Two base pairs were added in front of the PKL gene to form a BspHI site and a SacI site was inserted just after the stop codon. The synthesized PKL gene was cloned into GeneArt kanamycin-resistant cloning plasmid. The *E. gallinarum* PKL gene was then subcloned into a NcoI/SacI-digested pTrcHis2B vector (Life Technologies, Carlsbad, Calif.) to form plasmid pCMP1321 (Table 5, FIG. 25).

Chromosomal DNA of strain ATCC15697, *Bifidobacterium longum* subsp. *infantis* was obtained from ATCC (Manassas, Va.). The gene encoding *B. longum* PKL was amplified by polymerase chain reaction (PCR) from the chromosomal DNA using primers CMP283: 5'-ctgtatTCAT-GAcgagtcctgttattggcacc-3' (SEQ ID NO: 107) and CMP284: 5'-ctctatGAATTCTCACTCGTTGTCGCCAGCG-3' (SEQ ID NO: 108), and the polymerase Herculase according to the manufacturer's protocol (Life Technologies, Carlsbad, Calif.). The PCR product was digested with EcoRI and BspHI restriction enzymes before purification. After purification, the approximately 2500 bp fragment was assembled into EcoRI/NcoI-digested pTrcHis2B (Invitrogen, Carlsbad, Calif.) using the GENEART seamless cloning kit (Invitrogen, Carlsbad, Calif.) to form plasmid pCMP1090 (Table 5).

For construction of the control plasmid encoding a *Clostridium acetobutylicum* PKL, chromosomal DNA of strain ATCC BAA-98 was obtained from ATCC (Manassas, Va.). The gene encoding *Clostridium acetobutylicum* PKL was amplified by polymerase chain reaction (PCR) from the chromosomal DNA using primers CacetpTrcHisBF: 5'-taaggaggaataaaccatgcaaagtataataggaaaacataaggatgaagg-3' (SEQ ID NO: 109) and CacetpTrcHisBR: 5'-ttctagaaagct-tcgttatacatgccactgccaattagttatttc-3' (SEQ ID NO: 110), and the polymerase Herculase according to the manufacturer's protocol (Life Technologies, Carlsbad, Calif.). The PCR product was purified and assembled into EcoRI/NcoI-digested pTrcHis2B (Invitrogen, Carlsbad, Calif.) using the GENEART seamless cloning kit (Invitrogen, Carlsbad, Calif.) to form plasmid pCMP1364 (Table 3).

The nucleic acid sequence encoding a PKL protein derived from each of *Bifidobacterium dentium*, *Bifidobacterium bifidum*, *Bifidobacterium gallicum*, *Lactobacillus buchneri*, *Burkholderia phytofermans*, and *Clostridium acetobutylicum* (SEQ ID NO:94) were codon optimized for expression in *E. coli*, and synthesized by Gene Oracle (Mountain View, Calif.). These codon-optimized PKL genes were amplified by PCR and subcloned into the pTrcHis2B expression plasmid using the GeneArt Seamless Cloning Kit (Life Technologies), according to the manufacturer's recommended protocol. Table 5 below lists the primers used for construction of plasmids pMCS530 through pMCS535. The PKL enzymes were cloned downstream of the pTrc promoter to permit inducible expression of the phosphoketolase genes by IPTG (Table 6, FIGS. 26-31).

TABLE 5

Primers used for construction of plasmids

| Primer | Sequence | Description |
|---|---|---|
| *Bifidobacterium dentium* | | |
| o430 | tgataacgaataagagctcgagatctgcagctggtacc (SEQ ID NO: 111) | DentiumPKL into pTrcHis2B, plasmid Forward primer |
| o431 | gactcgtcatggtttattcctccttatttaatcgatacattaatatatacc (SEQ ID NO: 112) | DentiumPKL into pTrcHis2B, plasmid Reverse primer |
| o432 | ggaataaaccatgacgagtccagttattggaacaccc (SEQ ID NO: 113) | DentiumPKL into pTrcHis2B, PKL Forward primer |
| o433 | tctcgagctcttattcgttatcacccgcagtagcgg (SEQ ID NO: 114) | DentiumPKL into pTrcHis2B, PKL Reverse primer |
| *Bifidobacterium bifidum* | | |
| o434 | cgacaacgagtaagagctcgagatctgcagctggtacc (SEQ ID NO: 115) | Bifidum PKL into pTrcHis2B, plasmid Forward primer |
| o435 | gagaggtcatggtttattcctccttatttaatcgatacattaatatatacc (SEQ ID NO: 116) | Bifidum PKL into pTrcHis2B, plasmid Reverse primer |
| o436 | ggaataaaccatgacctctccagtaattggcactcc (SEQ ID NO: 117) | Bifidum PKL into pTrcHis2B, PKL Forward primer |
| o437 | tctcgagctcttactcgttgtcgcctgccgtg (SEQ ID NO: 118) | Bifidum PKL into pTrcHis2B, PKL Reverse primer |
| *Bifidobacterium gallicum* | | |
| o438 | cgataatgaataagagctcgagatctgcagctggtacc (SEQ ID NO: 119) | Gallicum PKL into pTrcHis2B, plasmid Forward primer |
| o439 | gagaagtcatggtttattcctccttatttaatcgatacattaatatatacc (SEQ ID NO: 120) | Gallicum PKL into pTrcHis2B, plasmid Reverse primer |
| o440 | ggaataaaccatgacttctcccgtgattggtactcc (SEQ ID NO: 121) | Gallicum PKL into pTrcHis2B, PKL Forward primer |
| o441 | tctcgagctcttattcattatcgcccgccgtagc (SEQ ID NO: 122) | Gallicum PKL into pTrcHis2B, PKL Reverse primer |

TABLE 5-continued

| Primers used for construction of plasmids | | |
|---|---|---|
| Primer | Sequence | Description |
| | *Lactobacillus buchneri* | |
| o442 | gctgaaaaaataagagctcgagatctgcagctggtacc (SEQ ID NO: 123) | *Buchneri* PKL into pTrcHis2B, plasmid Forward primer |
| o443 | ccactgtcatggtttattcctccttatttaatcgatacattaatatatacc (SEQ ID NO: 124) | *Buchneri* PKL into pTrcHis2B, plasmid Reverse primer |
| o444 | ggaataaaccatgacagtggactatgactcaaaagagtacttagag (SEQ ID NO: 125) | *Buchneri* PKL into pTrcHis2B, PKL Forward primer |
| o445 | tctcgagctcttattttttcagcccttcccatttcc (SEQ ID NO: 126) | *Buchneri* PKL into pTrcHis2B, PKL Reverse primer |
| | *Burkholderia phytofermans* | |
| o446 | ctggaaaggttaagagctcgagatctgcagctggtacc (SEQ ID NO: 127) | *Phytofermans* PKL into pTrcHis2B, plasmid Forward primer |
| o447 | cttcagccatggtttattcctccttatttaatcgatacattaatatatacc (SEQ ID NO: 128) | *Phytofermans* PKL into pTrcHis2B, plasmid Reverse primer |
| o448 | ggaataaaccatggctgaagccactgcccatc (SEQ ID NO: 129) | *Phytofermans* PKL into pTrcHis2B, PKL Forward primer |
| o449 | tctcgagctcttaacctttccaggtccaattccggattt (SEQ ID NO: 130) | *Phytofermans* PKL into pTrcHis2B, PKL Reverse primer |
| | *Clostridium acetobutylicum* | |
| o450 | atggcatgtataagagctcgagatctgcagctggtacc (SEQ ID NO: 131) | *Acetobutylicum* optimized PKL into pTrcHis2B, plasmid Forward primer |
| o451 | ttgattgcatggtttattcctccttatttaatcgatacattaatatatacc (SEQ ID NO: 132) | *Acetobutylicum* optimized PKL into pTrcHis2B, plasmid Reverse primer |
| o452 | ggaataaaccatgcaatcaatcatcggcaaacac (SEQ ID NO: 133) | *Acetobutylicum* optimized PKL into pTrcHis2B, PKL Forward primer |
| o453 | tctcgagctcttatacatgccattgccagtttgtgatc (SEQ ID NO: 134) | *Acetobutylicum* optimized PKL into pTrcHis2B, PKL Reverse primer |

TABLE 6

| Plasmids encoding PKLs | |
|---|---|
| Plasmid | Description |
| pCMP1321 | pTrcHis2B *E. gallinarum* PKL, Carb |
| pCMP1090 | pTrcHis2B *B. longum* PKL, Carb |
| pCMP1364 | pTrcHis2B *C. acetobutylicum* PKL, Carb |
| pMCS530 | pTrcHis2B *B. dentium* PKL, Carb |
| pMCS531 | pTrcHis2B *B. bifidum* PKL, Carb |
| pMCS532 | pTrcHis2B *B. gallicum* PKL, Carb |
| pMCS533 | pTrcHis2B *L. buchneri* PKL, Carb |
| pMCS534 | pTrcHis2B *B. phytofermans* PKL, Carb |
| pMCS535 | pTrcHis2B *C. acetobutylicum* PKL optimized, Carb |

Carb indicates carbenicillin

The nucleic acid sequence encoding a PKL protein derived from each of the organisms listed in Table 1, Table 2, and Clusters 1-22 (see FIGS. 3-24) are codon optimized for expression in *E. coli* and synthesized. These codon-optimized PKL genes are subcloned into the pTrcHis2B expression plasmid downstream of the pTrc promoter to permit inducible expression of the phosphoketolase gene by IPTG.

Example 4: Construction of Strains Expressing Identified PKLs for In Vitro Studies PKL expressing strains were constructed by transforming strain CMP1133 (BL21, Δpgl PL.2mKKDy1, GI1.2gltA, yhfSFRTPyddVIspAyhfS, thiFRTtruncIspA) with the plasmids listed on Table 5 and selecting for colonies on Luria-Bertani plates containing 20 μg/ml kanamycin. The kanamycin marker was removed using the protocol recommended by the manufacturer (Gene Bridges, Heidelberg, Germany) to form the indicated strains (Table 7).

TABLE 7

| Description of *E. coli* strains | |
|---|---|
| Strain Name | Genotype |
| CMP1183 | BL21, Δpgl PL.2mKKDyl, GI1.2gltA, yhfSFRTPyddVIspAyhfS, thiFRTtruncIspA, pCMP1090 (pTrcPKL *B. longum*) |
| CMP1328 | BL21, Δpgl PL.2mKKDyl, GI1.2gltA, yhfSFRTPyddVIspAyhfS, thiFRTtruncIspA, pCMP1321 (pTrcPKL *E. gallinarum*) |
| CMP1366 | BL21, Δpgl PL.2mKKDyl, GI1.2gltA, yhfSFRTPyddVIspAyhfS, thiFRTtruncIspA, pCMP1364 (pTrcPKL *C. acetobutylicum*) |

TABLE 7-continued

| Description of *E. coli* strains | |
|---|---|
| Strain Name | Genotype |
| MCS545 | BL21, Δpgl PL.2mKKDyl, GI1.2gltA, yhfSFRTPyddVIspAyhfS, thiFRTtruncIspA, pMCS530 (pTrcPKL *B. dentium*) |
| MCS546 | BL21, Δpgl PL.2mKKDyl, GI1.2gltA, yhfSFRTPyddVIspAyhfS, thiFRTtruncIspA, pMCS531 (pTrcPKL *B. bifidum*) |
| MCS547 | BL21, Δpgl PL.2mKKDyl, GI1.2gltA, yhfSFRTPyddVIspAyhfS, thiFRTtruncIspA, pMCS532 (pTrcPKL *B. gallicum*) |
| MCS548 | BL21, Δpgl PL.2mKKDyl, GI1.2gltA, yhfSFRTPyddVIspAyhfS, thiFRTtruncIspA, pMCS533 (pTrcPKL *L. buchneri*) |
| MCS549 | BL21, Δpgl PL.2mKKDyl, GI1.2gltA, yhfSFRTPyddVIspAyhfS, thiFRTtruncIspA, pMCS534 (pTrcPKL *B. phytofermans*) |
| MCS550 | BL21, Δpgl PL.2mKKDyl, GI1.2gltA, yhfSFRTPyddVIspAyhfS, thiFRTtruncIspA, pMCS535 (pTrcPKL *C. acetobutylicum* optimized) |

PKL expressing strains, each expressing an identified PKL, are constructed by transforming strain CMP1133 (BL21, Δpgl PL.2mKKDy1, GI1.2gltA, yhfSFRTPyddVIspAyhfS, thiFRTtruncIspA) with a plasmid encoding a PKL listed on Table 1, Table 2, and Clusters 1-22 (see FIGS. 3-24) and is selected for colonies on Luria-Bertani plates containing 20 μg/ml kanamycin. The kanamycin marker is removed using the protocol recommended by the manufacturer (Gene Bridges, Heidelberg, Germany).

Example 5: Comparison of Expression and Solubility of Identified PKLs

Strains expressing pTrcHis2B *B. longum* (strain CMP1183), pTrcHis2B *E. gallinarum* (strain CMP1328), pTrcHis2B *C. acetobutylicum* (strain CMP1366), pTrcHis2B *B. dentium* PKL (strain MCS545), pTrcHis2B *B. bifidum* (strain MCS546), pTrcHis2B *B. gallicum* PKL (strain MCS547), pTrcHis2B *L. buchneri* PKL (strain MCS548), pTrcHis2B *B. phytofermans* PKL (strain MCS549), or pTrcHis2B *C. acetobutylicum* PKL optimized (strain MCS550) were grown in LB media, induced at $OD_{600}$~0.5 with 200 μM IPTG, and induced for 4 hours at a temperature of 30° C. or 34° C. Cells were harvested by centrifuging 4 ml culture broth at 3000 rpm for 10 minutes. Cell pellets were re-suspended in 2 ml of 50 mM MES, 50 mM NaCl pH6.0 with 0.1% DNAase and 0.5 mM AEBSF. The cell suspension was lysed using a french pressure cell at 14,000 psi (American Instrument Company). The lysate was then centrifuged at 15,000 RPM for 10 minutes at 4° C. in an Eppendorf 5804R centrifuge. The supernatant and pellet were separated. The pellets were resuspended in the lysis 50 mM MES, 50 mM NaCl pH6.0 buffer. Supernatant and pellet samples were analyzed by 4-12% SDS-PAGE gel electrophoresis. Solubility was assessed by comparison of soluble versus pellet (insoluble) phosphoketolase fractions.

Figure 32A:
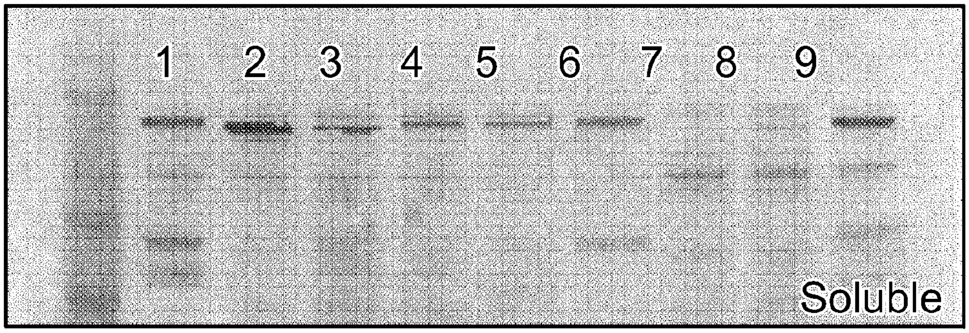
FIG. 32 is a series of SDS-PAGE coomasie stained gels showing protein expression in strains expressing phosphoketolase. A) soluble protein and B) insoluble protein from cells expressing *B. longum* PKL (lane 1), *E. gallinarum* PKL (lane 2), *C. acetobutylicum* PKL (lane 3), *B. dentium* PKL (lane 4), *B. bifidum* PKL (lane 5), *B. gallicum* PKL (lane 6), *L. buchneri* PKL (lane 7), *B. phytofermans* PKL (lane 8), and *C. acetobutylicum* codon optimized PKL (lane 9).
Figure 32B:
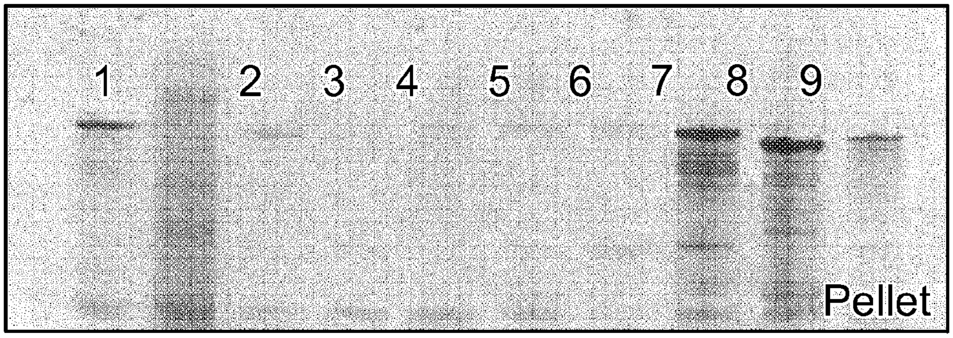

The results showed that optimized *C. acetobutylicum* PKL (FIG. 32A, lane 9) was expressed at a higher level as compared to *C. acetobutylicum* PKL that had not been codon-optimized (FIG. 32A, lane 3). *B. dentium* (FIG. 32A, lane 4), B. bifidium (FIG. 32A, lane 5), and *B. gallicum* (FIG. 32A, lane 6) PKLs were all expressed at a similar level to *C. acetobutylicum* PKL (FIG. 32A, lane 3) and were mostly soluble (FIG. 32B). In comparison, *L. buchneri* (lane 7) and *B. phytofermans* (lane 8) were almost completely insoluble (FIG. 32B).

Strains expressing an identified PKL listed on Table 1, Table 2, and Clusters 1-22 (see FIGS. 3-24) are grown in LB media, induced at $OD_{600}$~0.5 with 200 μM IPTG, and induced for 4 hours at a temperature of 30° C. or 34° C. Cells are harvested by centrifuging 4 ml culture broth at 3000 rpm for 10 minutes. Cell pellets are re-suspended in 2 ml of 50 mM MES, 50 mM NaCl pH6.0 with 0.1% DNAase and 0.5 mM AEBSF. The cell suspension is lysed using a french pressure cell at 14,000 psi (American Instrument Company). The lysate is then centrifuged at 15,000 RPM for 10 minutes at 4° C. in an Eppendorf 5804R centrifuge. The supernatant and pellet are separated. The pellets are resuspended in the lysis buffer (50 mM MES, 50 mM NaCl pH6.0). Supernatant and pellet samples are analyzed by 4-12% SDS-PAGE gel electrophoresis. Solubility is assessed by comparison of soluble versus pellet (insoluble) phosphoketolase fractions.

Example 6: In Vitro Screen for Phosphoketolase Activity in Strains Expressing Identified PKLs Strains expressing pTrcHis2B *B. longum* (strain CMP1183), pTrcHis2B *E. gallinarum* (strain CMP1328), pTrcHis2B *C. acetobutylicum* (strain CMP1366), pTrcHis2B *B. dentium* PKL (strain MCS545), pTrcHis2B *B. bifidum* (strain MCS546), pTrcHis2B *B. gallicum* PKL (strain MCS547), pTrcHis2B *L. buchneri* PKL (strain MCS548), pTrcHis2B *B. phytofermans* PKL (strain MCS549), or pTrcHis2B *C. acetobutylicum* PKL optimized (strain MCS550) were grown in LB medium with 50 μg/ml carbenicillin at 37° C. prior to induction. Following induction with 10 μM, 25 μM, 50 μM, or 100 μM IPTG, cultures were transferred to a 34° C. shaker for 30 minutes. Cells were harvested by centrifugation at 10,000 rpm for 10 min at 4° C. Cell pellets were stored at −80° C. prior to purification. For purification, PKL cell pellets were resuspended in 50 mM MES pH 6.0, 50 mM NaCL, 0.5 mM AEBSF, 0.1 mg/ml DNaseI. Cells were lysed by repeated passage through a French press and clarified by ultracentrifugation at 50,000 rpm for 60 min. Clarified lysate containing the PKL from *B. longum, E. gallinarum, C. acetobutylicum, B. dentium, B. bifidum, B. gallicum, L. buchneri, B. phytofermans*, or *C. acetobutylicum* were loaded onto a DEAE HiTrap FF column equilibrated in 50 mM MES, 50 mM NaCl, pH 6 and eluted with a gradient to 50 mM MES, 1M NaCl, pH 6. The resulting fractions were analyzed by SDS-PAGE. Fractions containing PKL were pooled and desalted using a G25 desalting column into 50 mM MES, 50 mM NaCL pH 6.0. Further purification was achieved using a MonoQ 10/100 GL column equilibrated in 50 mM MES, 50 mM NaCL, pH 6 with a salt gradient to 1M NaCl. The amount of AcP formed by each PKL was measured using a scaled down version of hydroxamate assay described in L. Meile et. al., *Bacteriol.*, 2001, 183:2929-2936 and Frey et. al., *Bioorganic Chem.*, 2008, 36:121-127, which are incorporated herein in their entirety by reference. The assays were performed in a 96-well plate (Costar catalog #9017) format, at 37° C. Each 300 μl reaction contained 1 mM TPP, 10 mM potassium phosphate pH 6.0, 50 mM MES pH 6, 10 mM MgCl2, 5 mM F6P and PKL at concentration of 250 nM. Time points were taken at various intervals. In order to stop the reaction 60 μl of the reaction mixture was mixed with 60 μl of 2M hydroxylamine at pH 6.5, incubated for 10 min at room temperature. Addition of 40 μl of 15% TCA, 40 μl of 4M HCl, and 40 μl of 5% $FeCl_3$ in 0.1 M HCl was used to precipitate the protein and allow AcP detection. The samples were then centrifuged at 3000 rpm for 10 min. A 200 μl sample of supernatant was transferred to a microtiter plate and a plate reader, and absorbance changes associated with the amount of AcP formed were monitored at 505 nm.

Figure 33:
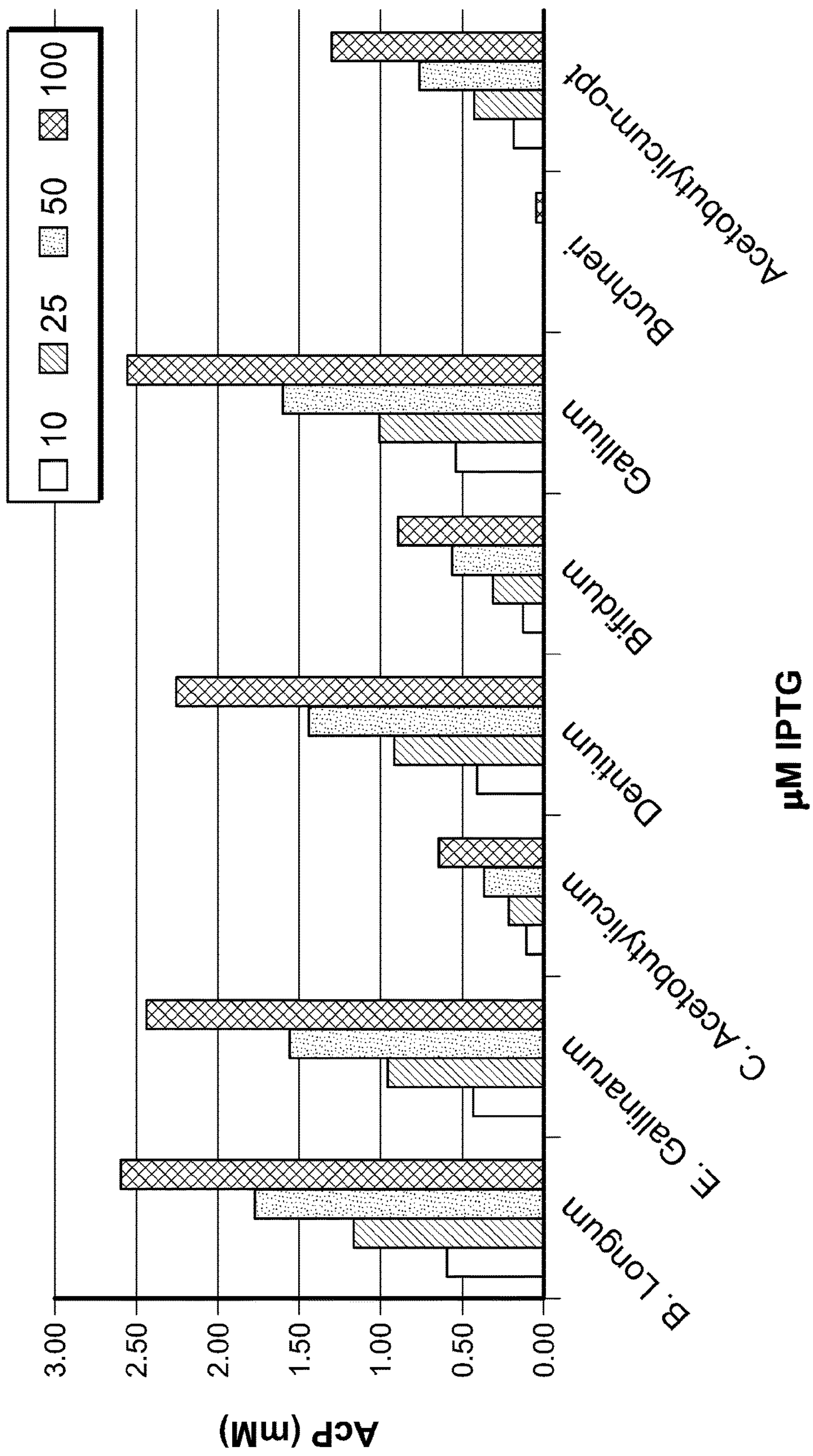
FIG. 33 is a graph showing in vitro activity of *B. longum* PKL, *E. gallinarum* PKL, *C. acetobutylicum* PKL, *B. dentium* PKL, *B. bifidum* PKL, *B. gallicum* PKL, *L. buchneri* PKL, *B. phytofermens* PKL, and *C. acetobutylicum* codon optimized PKL in the presence of F6P substrate as measured by Ac-P yield.

The results showed that optimized *C. acetobutylicum* PKL had F6P activity and produced greater amounts of AcP as compared to *C. acetobutylicum* PKL that had not been codon-optimized (FIG. 33). *B. dentium* had similar PKL F6P activity as *C. acetobutylicum* PKL that had not been codon-optimized. *B. dentium* and *B. gallicum* PKLs had significant F6P activity and were comparable to *E. gallinarum* PKL F6P activity. In comparison, *L. buchneri* PKL (FIG. 33) and *B. phytofermans* PKL did not demonstrate F6P activity which is supported by the finding that these PKLs are almost completely insoluble.

Strains expressing an identified PKL listed on Table 1, Table 2, and Clusters 1-22 (see FIGS. 3-24) are grown in LB medium with 50 μg/ml carbenicillin at 37° C. prior to induction. Following induction with 10 μM, 25 μM, 50 μM, or 100 μM IPTG, cultures are transferred to a 34° C. shaker for 30 minutes. Cells are harvested by centrifugation at 10,000 rpm for 10 min at 4° C. For purification, PKL cell pellets are resuspended in 50 mM MES pH 6.0, 50 mM NaCL, 0.5 mM AEBSF, 0.1 mg/ml DNaseI. Cells are lysed by repeated passage through a French press and clarified by ultracentrifugation at 50,000 rpm for 60 min. Clarified lysate containing the PKLs are loaded onto a DEAE HiTrap FF column equilibrated in 50 mM MES, 50 mM NaCl, pH 6 and eluted with a gradient to 50 mM MES, 1M NaCl, pH 6. The resulting fractions are analyzed by SDS-PAGE. Fractions containing PKL are pooled and desalted using a G25 desalting column into 50 mM MES, 50 mM NaCL pH 6.0. Further purification is achieved using a MonoQ 10/100 GL column equilibrated in 50 mM MES, 50 mM NaCL, pH 6 with a salt gradient to 1M NaCl. The amount of AcP formed by each PKL is measured using a scaled down version of hydroxamate assay described in L. Meile et. al., *Bacteriol.,* 2001, 183:2929-2936 and Frey et. al., *Bioorganic Chem.,* 2008, 36:121-127. The assays are performed in a 96-well plate (Costar catalog #9017) format, at 37° C. Each 300 μl reaction contains 1 mM TPP, 10 mM potassium phosphate pH 6.0, 50 mM MES pH 6, 10 mM MgCl2, 5 mM F6P and PKL at a concentration of 250 nM. Time points are taken at various intervals. In order to stop the reaction, 60 μl of the reaction mixture is mixed with 60 μl of 2M hydroxylamine at pH 6.5, incubated for 10 min at room temperature. Addition of 40 μl of 15% TCA, 40 μl of 4M HCl, and 40 μl of 5% $FeCl_3$ in 0.1 M HCl is used to precipitate the protein and allow AcP detection. The samples are then centrifuged at 3000 rpm for 10 min. A 200 μl sample of supernatant is transferred to a microtiter plate and a plate reader, and absorbance changes associated with the amount of AcP formed are monitored at 505 nm.

Example 7: In Vivo Screen for Phosphoketolase Activity in Strains Expressing Identified Phosphoketolases (PKLs)

The in vivo activities of phosphoketolase (PKL) enzymes were evaluated in a mutant strain that has no transketolase (tkt) activity. Transketolase is responsible for producing erythrose-4-phosphate (E4P), the substrate for all aromatic vitamins and amino acids in *E. coli*. Growth of *E. coli* on minimal medium with glucose as a carbon source in the absence of transketolase activity is therefore not possible due to aromatic auxotrophy (Zhao and Winkler 1994). Transketolase is also involved in the interconversion of xylulose-5-phosphate (X5P) with sedoheptulose-7-phosphate (S7P) and glyceraldehyde-3-phosphate (GAP), and growth of a tkt mutant on minimal medium with xylose as a carbon source is also not possible, since tkt activity is the only outlet back into glycolysis from the pentose phosphate pathway. Since phosphoketolase produces E4P from F6P, and GAP from X5P, functional enzymes can rescue the growth defects of a tkt mutant when grown on glucose (indicating F6P activity) or xylose (indicating both X5P and F6P activity). Growth of complemented mutants therefore can be used to test the different in vivo activities of phosphoketolase enzymes.

Strain Construction

Standard molecular biology techniques to amplify mutations from the Keio collection by PCR, perform P1 transduction, perform GeneBridges insertions (manufacturer's protocol), PCR amplification (Pfu Turbo or Herculase, manufacturer's protocol), transform plasmids, and to grow and propagate strains were used. Briefly, since there are two transketolase enzymes in the genome of *E. coli*, both had to be knocked out to generate a transketolase null mutant. The kanamycin insert in tktB was amplified by PCR from the Keio collection and introduced by recombineering into BL21. The antibiotic resistance cassette in tktB was confirmed by PCR and then looped out using the pCP20 plasmid (Table 5). The tktA mutation was then introduced into BL21 by the same method and subsequently introduced into the tktB mutant by P1 transduction to generate a transketolase null mutant strain (Table 6). This strain, DW809, only grew on M9 glucose minimal medium with casamino acids that did not contribute substantially to the aromatic amino acid supply and an additional supplement of all aromatic compounds, including tyrosine, phenylalanine, tryptophan, p-aminobenzoate, 2-3-dihydroxybenzoate, p-hydroxybenzoate, and pyridoxine (as indicated in Zhao and Winkler, 1994). This combination of six aromatic compounds and pyridoxine is subsequently referred to herein as the "aromatic supplement." Plasmids harboring different phosphoketolase enzymes were then transformed into the transketolase mutant strain, and selected for growth on M9 glucose casamino acids with the aromatic supplement and carbenicillin (Table 6). Strains were then assayed for growth on an Enzyscreen Growth Profiler (Enzyscreen, BV) on either M9 glucose or xylose without the aromatic supplement and compared to the control strain that did not express a phosphoketolase enzyme. Phosphoketolase enzymes were induced in the transketolase null mutant at two different concentrations of IPTG, 20 μM and 60 μM.

The transektolase null mutant strain is transformed with an identified PKL listed on Table 1, Table 2, or Clusters 1-22 (see FIGS. 3-24) and selected for growth on M9 glucose casamino acids with the aromatic supplement and carbenicillin. Strains are then assayed for growth on an Enzyscreen Growth Profiler (Enzyscreen, BV) on either M9 glucose or xylose without the aromatic supplement and compared to the control strain that did not express a phosphoketolase enzyme. Phosphoketolase enzymes are induced in the transketolase null mutant at two different concentrations of IPTG, 20 μM and 60 μM.

TABLE 8

Primers for testing presence of tktA and tktB mutations

| Primer Name | Sequence |
|---|---|
| tktA test for | catgcgagcatgatccagagatttctga (SEQ ID NO: 135) |

TABLE 8-continued

| Primers for testing presence of tktA and tktB mutations | |
|---|---|
| Primer Name | Sequence |
| tktA test rev | gcttgtccgcaaacggacatatcaaggt (SEQ ID NO: 136) |
| tktB test for | cagctcccatgagcgaagcggagt (SEQ ID NO: 137) |
| tktB test rev | gacgcgtcagcgtcgcatccggca (SEQ ID NO: 138) |
| tktB B test for | gctgcgatcgactgactatcgcaccga (SEQ ID NO: 139) |
| tktB B test rev | cagacgcctggcccacgttgtggatca (SEQ ID NO: 140) |
| tktA B test for | gcagcggacgggcgagtagattgcgca (SEQ ID NO: 141) |
| tktA B test rev | gtgatctacaacacgccttatctat (SEQ ID NO: 142) |

TABLE 9

| Engineered strains expressing PKLs | |
|---|---|
| Strain | Description |
| DW809 | BL21 ΔtktA ΔtktB, Kan (antibiotic marker in tktA from Keio) |
| DW816 | BL21 ΔtktA ΔtktB, pCMP1321, Kan Carb |
| DW830 | BL21 ΔtktA ΔtktB, pMCS530, Kan Carb |
| DW831 | BL21 ΔtktA ΔtktB, pMCS531, Kan Carb |
| DW832 | BL21 ΔtktA ΔtktB, pMCS532, Kan Carb |
| DW833 | BL21 ΔtktA ΔtktB, pMCS533, Kan Carb |
| DW834 | BL21 ΔtktA ΔtktB, pMCS534, Kan Carb |
| DW835 | BL21 ΔtktA ΔtktB, pMCS535, Kan Carb |

Results

Figure 34:
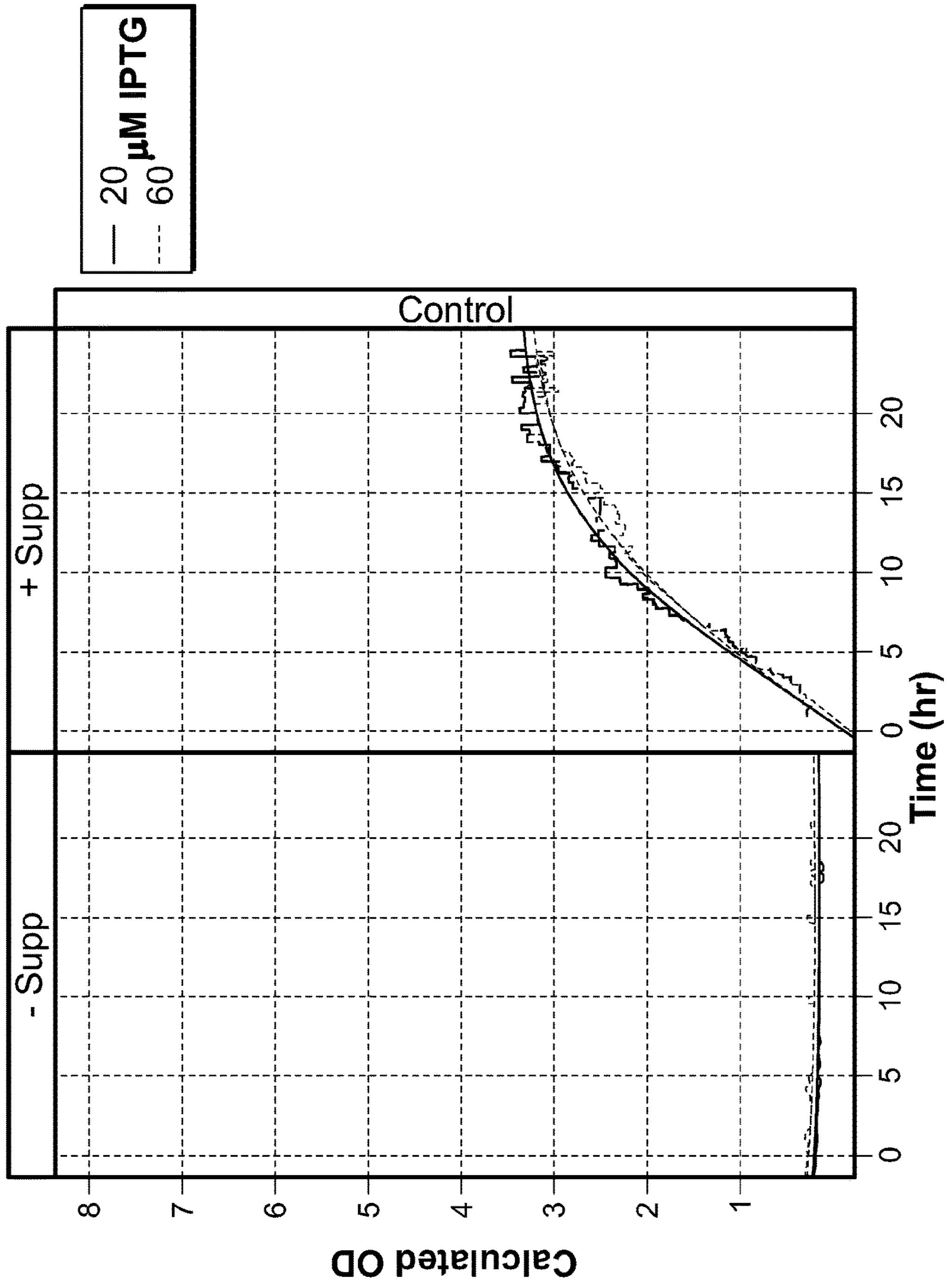
FIG. 34 is a graph showing that the transketolase mutant grew on glucose only with supplement containing six aromatic compounds and pyridoxine.
Figure 35:
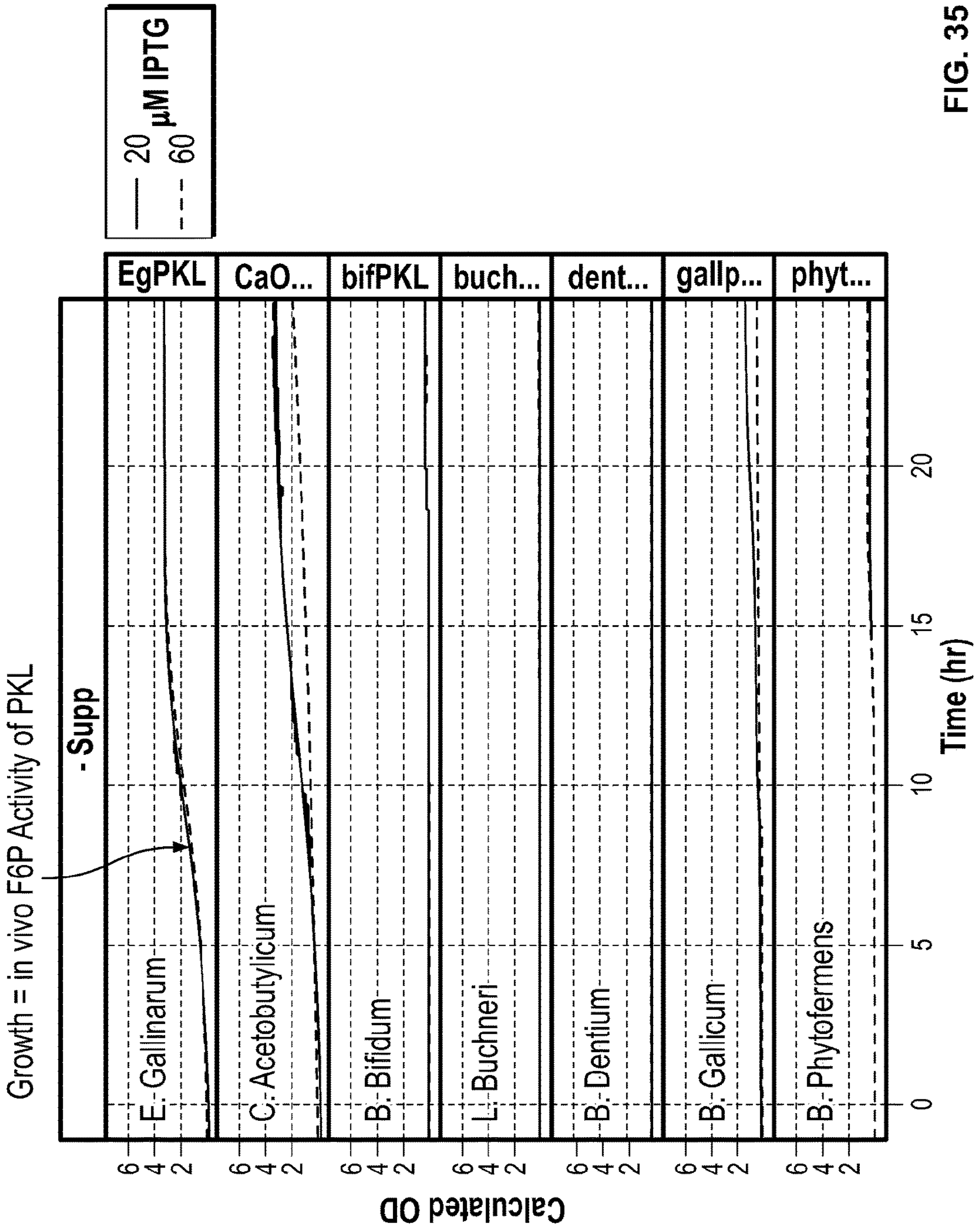
FIG. 35 is a graph showing that phosphoketolases from *E. gallinarum* and *C. acetobutylicum* restored growth to the transketolase mutant on glucose without supplement.
Figure 36:
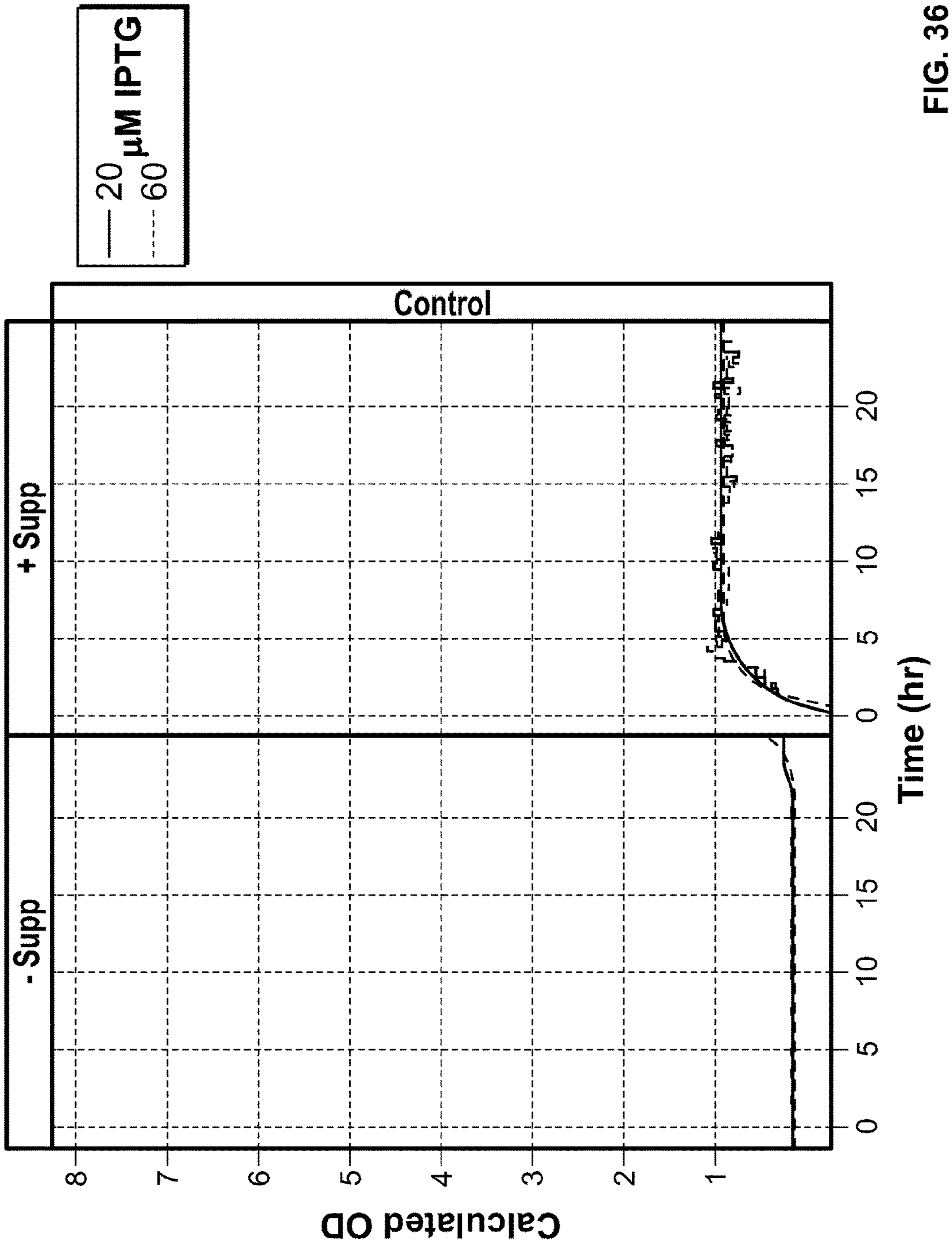
FIG. 36 is a graph showing that the transketolase mutant did not grow on xylose with or without supplement containing six aromatic compounds and pyridoxine.
Figure 37:
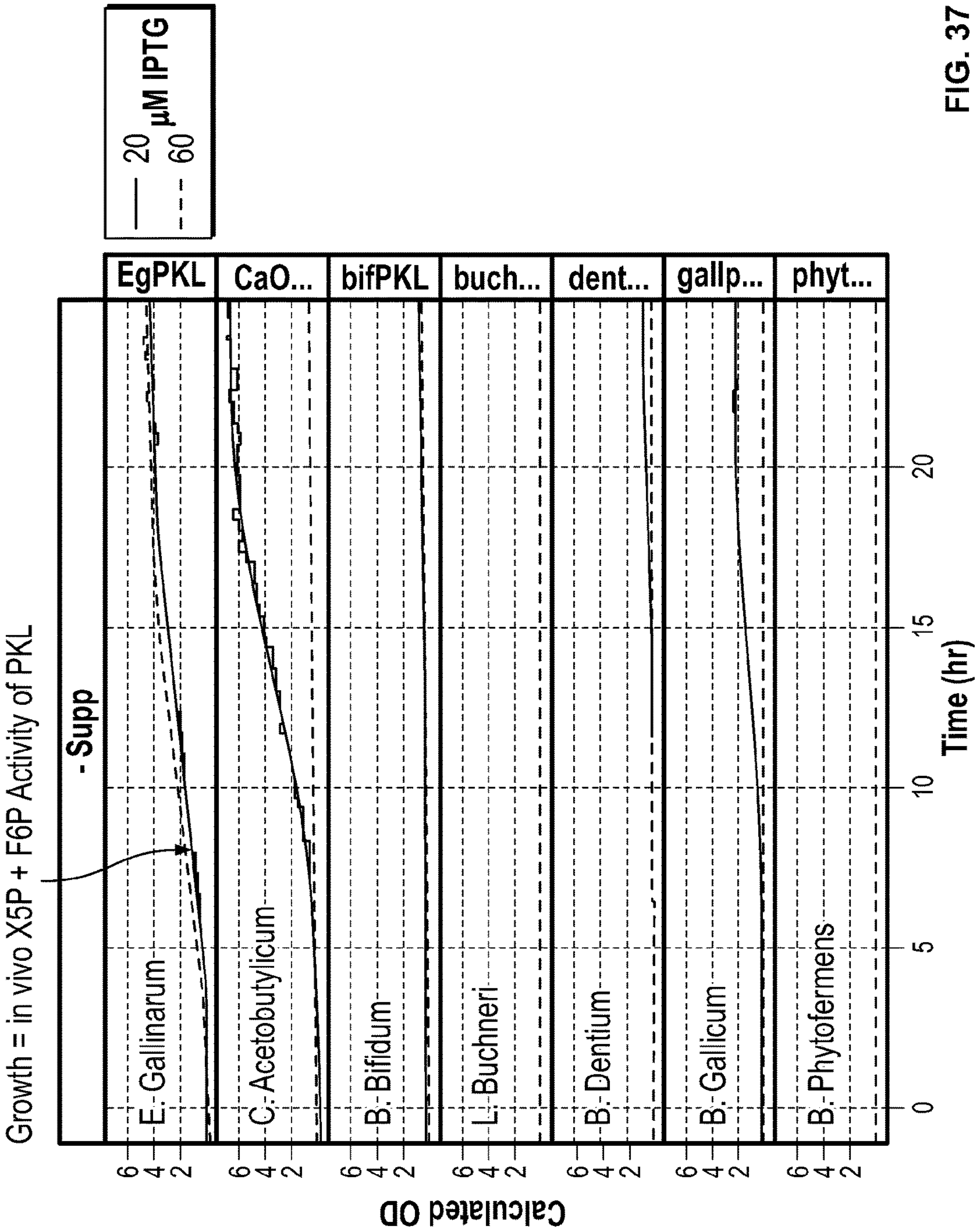
FIG. 37 is a graph showing that phosphoketolases from *E. gallinarum* and *C. acetobutylicum* restored growth to the transketolase mutant on xylose without supplement.

In this assay, the transketolase mutant grew on glucose only with supplement (FIG. 34) and did not grown on xylose with or without supplement (FIG. 36). Growth of the transketolase null mutant expressing different phosphoketolases highlighted the differential in vivo behavior of these enzymes. *E. gallinarum* PKL displayed the best performance on both glucose and xylose, indicating sufficient F6P and X5P activity to maintain growth of the transketolase mutant in the absence of supplement (see FIGS. 35 and 37). The *C. acetobutylicum* PKL also allowed for growth of the transketolase mutant in the absence of aromatic supplement on glucose and xylose (FIGS. 35 and 37), but appeared to have a deleterious effect on cell growth at the 60 μM IPTG concentration when grown on glucose (FIG. 35).

Example 8: Measurement of Intracellular Acetyl Phosphate in Strains Expressing PKLs Isoprene producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24). Strains that did not express a phophoketolase are used as controls.

(i) Materials

TM3 Media Recipe (Per Liter Fermentation Media):

$K_2HPO_4$ 13.6 g, $KH_2PO_4$ 13.6 g, $MgSO_4$*$7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.

1000× Trace Metal Solution (Per Liter Fermentation Media)

Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells expressing the complete MVA pathway and a PKL from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24) are grown overnight in Luria-Bertani broth+antibiotics. The day after, they are diluted to an OD600 of 0.05 in 20 mL TM3 medium containing 50 ug/mL carbenicillin (in a 250-mL baffled Erlenmeyer flask), and incubated at 34° C. and 200 rpm. After 2 h of growth, OD600 is measured and 200 uM IPTG is added. After 3.5 more hours, 1.5 ml sample is centrifuged, the supernatant is discarded and the pellet is resuspended in 100 uL dry-ice cold methanol.

(iii) Intracellular Acetyl-Phosphate Determination.

To extract acetyl-phosphate, 1.5 mL of *E. coli* cells grown to OD 0.57-2.26 is spun down by centrifugation and 100 μL of dry-ice cold methanol is added to the pellets. Methanol-quenched samples are stored at −20° C. for several days. Further sample processing includes gentle cell re-suspension, 5-min centrifugation at −9° C. and aspiration of the supernatant into clean vials. The pellet is re-extracted twice with 75 μL of water containing 2% acetic acid. After each extraction, cell debris are pelleted by centrifugation at −9° C., the supernatants from all three extractions are pooled together and spiked with 1 μL of tributylamine. Mass spectrometric analysis of acetyl phosphate by LCMS is carried out using a Thermo Finnigan TSQ system (Thermo Electron Corporation, San Jose, Calif.). The system control, data acquisition, and mass spectral data evaluation are performed using XCalibur and LCQuan software (Thermo Electron Corp). A mobile phase gradient is applied to a Synergi MAX-RP 5 μM HPLC column (150×2 mm, Phenomenex) at a flow rate of 0.4 mL/min. The applied gradient profile is 99% A and 1% B at t=0-1 min; 80% A and 20% B at t=11 min; 75% B and 25% Cat t=12-14 min; 99% A and 1% B at t=15-16 min, where solvent A is 15 mM tributylamine/10 mM acetic acid in water, solvent B is methanol, and solvent C is water. Mass detection of acetyl phosphate is carried out using electrospray ionization (ESI-MS/MS) in the negative mode (ESI spray voltage of 2.5-3.0 kV, ion transfer tube temperature 390° C.) with m/z value for the precursor ion of 138.9. Concentration of acetyl phosphate is determined based on the integrated intensity of peak generated by $PO_3^-$ product ion (m/z=79.0, collision energy 20 V, collision gas pressure 1.7 mTorr, $R_t$=13.2 min). A calibration curve obtained by injection of acetyl phosphate standard (Sigma-Aldrich) is used to calculate concentration of the metabolite in cell extracts. Intracellular concentration of acetyl phosphate is determined based on the assumption that in 1 mL of the culture at OD=200 the integrated volume of all cells is 50 Ml. Produced acetyl phosphate is assessed in strains expressing a PKL as compared to control strain not expressing phosphoketolase.

Example 9: Production of Isoprene in Recombinant Host Cells Expressing Phosphoketolase at Small Scale Isoprene producing *E. coli* strains are constructed to express a phosphoketolase from *Burkholderia* phytofirmans PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and an isoprene synthase. Isoprene producing strains that did not express a phophoketolase are used as controls.

TM3 Media Recipe (Per Liter Fermentation Media):

$K_2HPO_4$ 13.6 g, $KH_2PO_4$ 13.6 g, $MgSO_4$*7$H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in di$H_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media)

Citric Acid*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, $NaMoO_4$*2$H_2O$ 100 mg. Each component is dissolved one at a time in di$H_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. A 100 μl sample of whole broth is placed in a 96-well glass block. The glass block is sealed with aluminum foil and incubated at 34° C. while shaking at 450 rpm, for 30 minutes using a Thermomixer. After 30 minutes, the block is kept at 70° C. water bath for 2 minutes and levels of isoprene in the headspace measurement are determined using gas chromatography-mass spectrometry. The reported specific productivity is the amount of isoprene in ug/L read by the GC divided by the incubation time (30 min) and the measured OD600.

Example 10: Production of Isoprene in Recombinant Host Cells Expressing Phosphoketolase at 15-L Scale Isoprene producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and an isoprene synthase. Isoprene producing strains that did not express a phophoketolase are used as controls in a 15 Liter scale experiment for production of isoprene.

(i) Materials

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components are added together and dissolved in Di H2O. This solution is heat sterilized (123° C. for 20 minutes). The pH is adjusted to 7.0 with ammonium hydroxide (28%) and q.s. to volume. Glucose 10 g, Vitamin Solution 8 mL, and antibiotics are added after sterilization and pH adjustment.

1000× Modified Trace Metal Solution (Per Liter):

Citric Acids*$H_2O$ 40 g, MnSO4*$H_2O$ 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di $H_2O$ 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Analysis

Isoprene, Oxygen, Nitrogen, and Carbon Dioxide levels in the off-gas are determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth are determined in broth samples taken at 4 hour intervals by an HPLC analysis. Concentration in broth samples are determined by comparison of the refractive index response versus a previously generated calibration curve using standard of a known concentration.

Example 11: Production of Amorphadiene or Farnesene in Strains Expressing an Identified Phosphoketolase Isoprenoid producing *E. coli* strains are constructed to express a phosphoketolase from *Burkholderia phytofirmans* PsJN, *Lactobacillus buchneri* NRRL B-30929, *Bifidobacte-*

*rium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and a codon-optimized gene coding for farnesene synthase or amorphadiene synthase. Isoprenoid producing strains that did not express a phophoketolase are used as controls in an experiment for production of amorphadine or farnesene.

(i) Materials

TM3 Media Recipe (Per Liter Fermentation Media):

$K_2HPO_4$ 13.6 g, $KH_2PO_4$ 13.6 g, $MgSO_4$*7$H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in di$H_2O$. The pH is adjusted to 6.8 with ammonium hydroxide (30%) and brought to volume. Media is then filter-sterilized with a 0.22 micron filter. Glucose 10.0 g and antibiotics are added after sterilization and pH adjustment.

1000× Trace Metal Solution (Per Liter Fermentation Media):

Citric Acid*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, $NaMoO_4$*2$H_2O$ 100 mg. Each component is dissolved one at a time in di$H_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.05 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et. al., 2006).

After 2 h of growth, OD600 is measured and 0.05-0.40 mM isopropyl β-D-1-thiogalactopyranoside (IPTG) is added. Samples are taken regularly during the course of the fermentation. At each timepoint, OD600 is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., Nat. Biotechnol. 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

Figure 38:
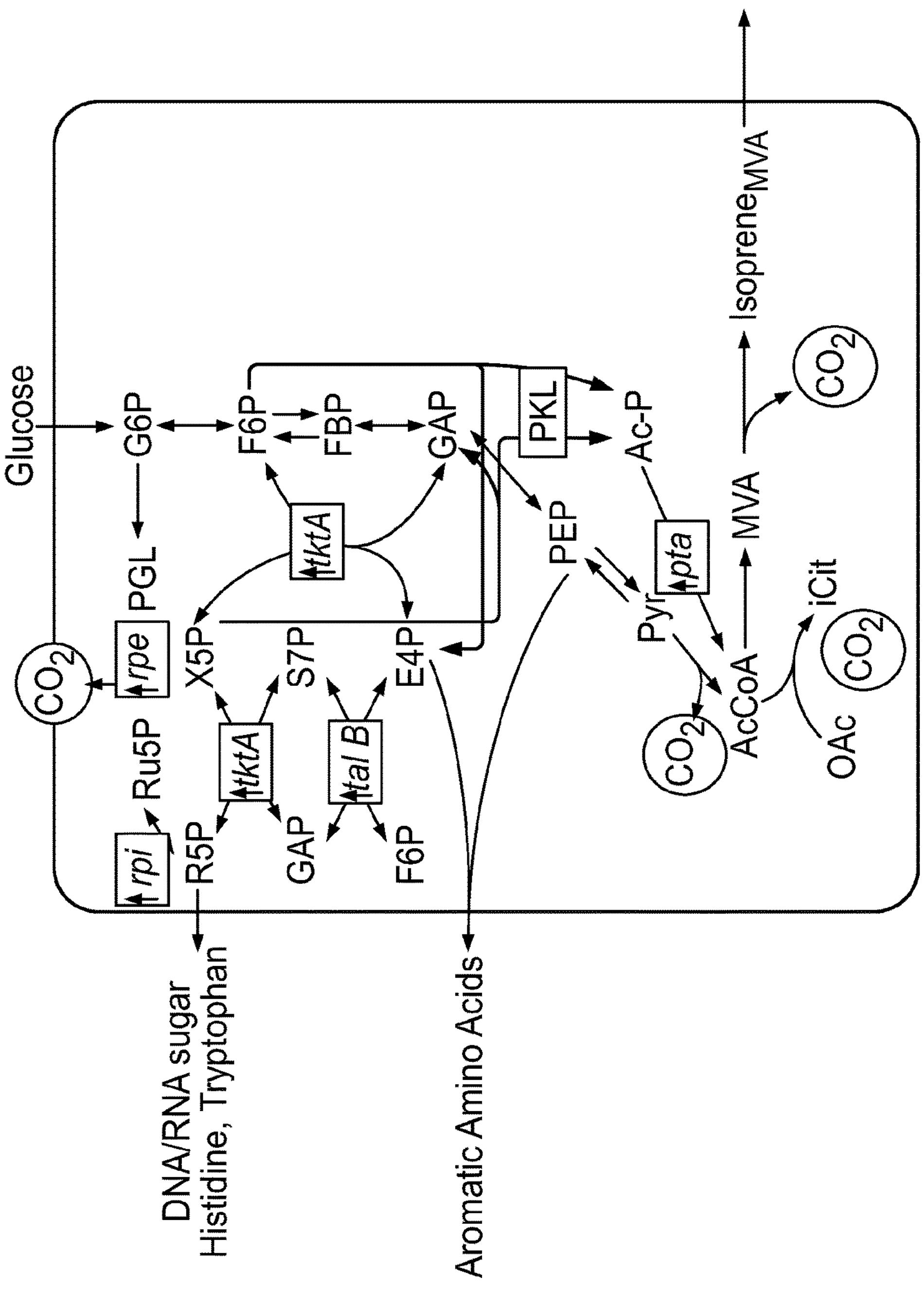
FIG. 38 is a diagram depicting host mutations that are preferably upregulated to increase carbon flux through the phosphoketolase pathway. Genes of interest for modulating carbon flux include moduribose-5-phosphate isomerase A (rpiA), D-ribulose-5-phosphate 3-epimerase (rpe), transketolase A (tktA), transaldolase B (tal B), and/or phosphate acetyltransferase (pta).

Example 12: Construction of Phosphoketolase-Expressing Strains Harboring Host Mutations for Producing Isoprene Isoprene-producing strains comprising a PKL from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24) can be further engineered to increase the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphoenolpyruvate synthetase (ppsA), phosphate acetyltransferase (pta and/or eutD) to improve carbon flux through the phosphoketolase pathway (FIG. 38). In certain aspects, the activity of the following genes rpiA, rpiB, rpe, tktA, tktB, tal B, ppsA, eutD, and/or pta can be increased by altering the promoter and/or rbs on the chromosome, or by expressing it from a plasmid. In one embodiment the activity of ribose-5-phosphate isomerase (rpiA and/or rpiB) is increased by altering the promoter and/or rbs on the chromosome, or by expressing it from a plasmid. In another embodiment the activity of D-ribulose-5-phosphate 3-epimerase (rpe) is increased by altering the promoter and/or rbs on the chromosome, or by expressing it from a plasmid. In another embodiment the activity of transketolase (tktA and/or tktB) is increased by altering the promoter and/or rbs on the chromosome, or by expressing it from a plasmid. In yet another embodiment the activity of transaldolase B (tal B) is increased by altering the promoter and/or rbs on the chromosome, or by expressing it from a plasmid. In another embodiment the activity of phosphoenolpyruvate synthetase (ppsA) is increased by altering the promoter and/or rbs on the chromosome, or by expressing it from a plasmid. In still other embodiments the activity of phosphate acetyltransferase (pta and/or eutD) is increased by altering the promoter and/or rbs on the chromosome, or by expressing it from a plasmid. In certain aspects, isozymes of the following genes rpiA, rpiB, rpe, tktA, tktB, tal B, ppsA, eutD, and/or pta can be increased by altering the promoter and/or rbs on the chromosome, or by expressing it from a plasmid.

Figure 39:
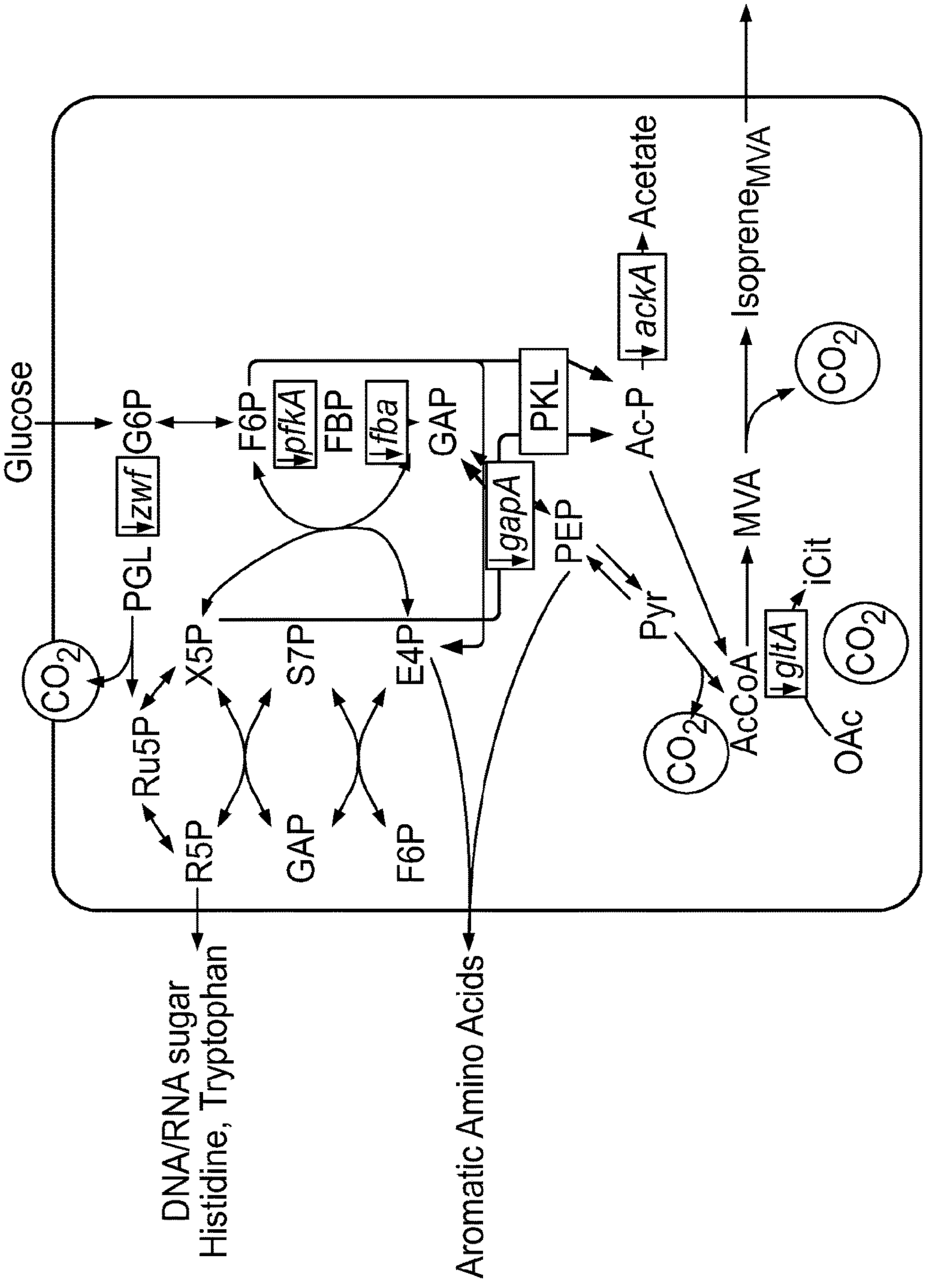
FIG. 39 is a diagram depicting host mutations that are preferably downregulated to increase carbon flux through the phosphoketolase pathway. Genes of interest for modulating carbon flux include glucose-6-phosphate dehydrogenase (zwf), 6-phosphofructokinase-1 (pfkA), fructose bisphosphate aldolase (fba), glyceraldehyde-3-phosphate dehydrogenase A (gapA), Acetate kinase (ackA), citrate synthase (gltA) and/or the pts operon.

These strains can be further engineered to decrease the activity of one or more of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), transketolase (tktA and/or tktB), EI (ptsI), $EIICB^{Glc}$ (ptsG), $EIIA^{Glc}$ (crr), and/or HPr (ptsH) to increase carbon flux into the phosphoketolase pathway (FIG. 39). In one embodiment, a zwf gene encoding glucose-6-phosphate dehydrogenase is downregulated. In another embodiment, a pfkA gene encoding 6-phosphofructokinase-1 A is downregulated. In another embodiment, a gapA gene encoding glyceraldehyde-3-phosphate dehydrogenase A is downregulated. In another embodiment, a fba gene encoding fructose bisphosphate aldolase is downregulated. In yet another embodiment, a gltA gene encoding citrate synthase is downregulated. In an embodiment, a ackA gene encoding acetate kinase is downregulated. In another embodiment, a ptsI gene encoding EI is downregulated. In an embodiment, a ptsH gene encoding HPr is downregulated. In another embodiment, a ptsG gene encoding $EIICB^{Glc}$ is downregulated. In a yet another embodiment, a crr gene encoding $EIIA^{Glc}$ is downregulated. The pts operon encodes genes of the phosphotransferase system. In some embodiments, the strains can be engineered to decrease activity of the phosphotransferase system (PTS) to increase carbon flux into the phosphoketolase pathway. In some embodiments, the PTS is downregulated by downregulation of the pts operon. In certain aspects, the PTS is downregulated and a glucose transport pathway is upregulated. A glucose transport pathway includes, but is not limited to, galactose (galP) and glucokinase (glk) genes. In some embodiments, the pts operon is downregulated, the galactose (galP) gene is upregulated, and the glucokinase (glk) gene is upregulated. In certain aspects, isozymes of proteins encoded by the following genes zwf, pfkA, fba, gapA, ackA, gltA, tktA, ptsG, ptsH, ptsI, and/or crr can be downregulated to increase carbon flux into the phosphoketolase pathway. In some embodiments, the pfkB gene is downregulated. In some embodiments, the glyceraldehyde-3-phosphate dehydrogenase B (gapB) gene is downregulated. In some embodiments, the transketolase B (tktB) gene is downregulated.

Example 13: Production of Isoprene by Phosphoketolase-Expressing Strains Harboring Host Mutations at Small Scale The isoprene producing strains described in Example 12 are evaluated for isoprene production at small scale.

(i) Materials

TM3 Media Recipe (Per Liter Fermentation Media):

$K_2HPO_4$ 13.6 g, $KH_2PO_4$ 13.6 g, $MgSO_4$*7$H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in di$H_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media)

Citric Acid*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, $NaMoO_4$*2$H_2O$ 100 mg. Each component is dissolved one at a time in di$H_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in ug/L read by the GC divided by the incubation time (30 min) and the measured OD600.

Example 14: Production of Isoprene by Phosphoketolase-Expressing Strains Harboring Host Mutations at 15-L Scale The isoprene producing strains described in Example 12 are evaluated for isoprene production at 15-L scale.

(i) Materials

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*$H_2O$ 40 g, MnSO4*$H_2O$ 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di $H_2O$ 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Analysis

Isoprene, Oxygen, Nitrogen, and Carbon Dioxide levels in the off-gas are determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth arephytofermans determined in broth samples taken at 4 hour intervals by an HPLC analysis. Concentration in broth samples are determined by comparison of the refractive index response versus a previously generated calibration curve using standard of a known concentration.

Example 15: Strains Used for Small Scale Evaluation of Phosphoketolases

The phosphoketolase expressing strains were generated using standard molecular biology techniques where the specified PKL was transformed into MD-891 (BL2+ GI1.2gltA yhfSFRTPyddVIspAyhfS thiFRTtruncIspA pgl ML+FRT-PL.2-3cis-RBS10000-mvk(burtonii) ackA::FRT) together with MCM-1225 (pMCM1225-pCL Ptrc-*E. gallinarum* Upper MVA)). Strains are listed in Table 10.

TABLE 10

Strains used for Small Scale Evaluation of Phosphoketolases

| Source | PKL # | Amino Acid SEQ ID NO: | pTrc_ IspS_IDI plasmid | MD891 strain | (MCM1225) |
|---|---|---|---|---|---|
| *E. faecium* | 1 | 23 | MCS811 | MCS865 | MCS932 |
| *L. grayi* | 2 | 24 | MCS812 | MCS866 | MCS933 |
| *E. casseliflavus* | 3 | 25 | MCS813 | MCS867 | MCS934 |

TABLE 10-continued

| Strains used for Small Scale Evaluation of Phosphoketolases | | | | | |
|---|---|---|---|---|---|
| Source | PKL # | Amino Acid SEQ ID NO: | pTrc_ IspS_IDI plasmid | MD891 strain | (MCM1225) |
| *M. alligatoris* | 4 | 26 | MCS814 | MCS868 | MCS935 |
| *Carnobacterium* | 5 | 27 | MCS815 | MCS869 | MCS936 |
| *M. plutonius* ATCC | 6 | 28 | MCS816 | MCS870 | MCS937 |
| *T. halophilus* | 7 | 29 | MCS817 | MCS871 | MCS938 |
| *M. plutonius* DAT | 8 | 30 | MCS818 | MCS872 | MCS939 |
| *M. arthritidis* | 9 | 31 | MCS819 | MCS873 | MCS940 |
| *S. agalactiae* | 10 | 32 | MCS820 | MCS874 | MCS941 |
| *M. agalacticae* | 11 | 33 | MCS821 | MCS875 | MCS942 |
| *S. gordonii* | 12 | 34 | MCS822 | MCS876 | MCS943 |
| *K. oralis* | 13 | 35 | MCS823 | MCS877 | MCS944 |
| *M. fermentans* | 14 | 36 | MCS824 | MCS878 | MCS945 |
| *G. adiacens* | 15 | 37 | MCS825 | MCS879 | MCS946 |
| *M. hominis* | 16 | 38 | MCS826 | MCS880 | MCS947 |
| *M. crocodyli* | 17 | 39 | MCS827 | MCS881 | MCS948 |
| *Neisseria* | 18 | 40 | MCs828 | MCS882 | MCS949 |
| *E. coleocola* | 19 | 41 | MCS829 | MCS883 | MCS950 |
| *A. urinae* | 20 | 42 | MCS830 | MCS884 | MCS951 |
| *K. kingae* | 21 | 43 | MCS831 | MCS885 | MCS952 |
| *S. criceti* (#1) | 22 | 44 | MCS832 | MCS886 | MCS953 |
| *S. criceti* (#2) | 23 | 45 | MCS833 | MCS887 | MCS954 |
| *M. columbinum* | 24 | 46 | MCS834 | MCS888 | MCS955 |
| *M. gilvum* | 25 | 1 | MCS835 | MCS889 | MCS956 |
| *S. baltica* | 26 | 2 | MCs836 | MCS890 | MCS957 |
| *L. rhamnosus* | 27 | 3 | MCS837 | MCS891 | MCS958 |
| *L. crispatus* | 28 | 4 | MCS838 | MCS892 | MCS959 |
| *L. citreum* | 29 | 6 | MCS839 | MCS893 | MCS960 |
| *Bradyrhizobium* sp. | 30 | 7 | MCS840 | MCS894 | MCS961 |
| *B. microti* | 31 | 9 | MCS841 | MCS895 | MCS962 |
| *L. salivarius* | 32 | 10 | MCS842 | MCS896 | MCS963 |
| *R. imtechensis* | 33 | 12 | MCS843 | MCS897 | MCS964 |
| *B. xenovorans* | 34 | 13 | MCS844 | MCS898 | MCS965 |
| *M. intracellulare* | 35 | 14 | MCS845 | MCS899 | MCS966 |
| *Nitrosomonas* sp. | 36 | 15 | MCS846 | MCS900 | MCS967 |
| *S. pombe* | 37 | 16 | MCS847 | MCS901 | MCS968 |
| L. *buchneri* | 38 | 19 | MCS848 | MCS902 | MCS969 |
| *S. ghanaensis* | 39 | 20 | MCs849 | MCS903 | MCS970 |
| *Cyanothece* sp. | 40 | 21 | MCS850 | MCS904 | MCS971 |
| *N. fischeri* | 41 | 22 | MCS851 | MCS905 | MCS972 |
| *L. lactis* | 42 | 105 | MCS852 | MCS906 | MCS973 |
| *E. gallinarum* (CON) | | 93 | EWL1421 | MCS908 | MCS975 |

Example 16: In Vivo Screen for Phosphoketolase Activity in Expressing Identified Phosphoketolases (PKLs)

The following in vivo screen for phosphoketolase activity was performed as set forth above in Example 7. The host cell background is DW-809 with plasmids pMCS811-pMCS852 containing distinct phosphoketolases.

For in vivo growth evaluation of this set of phosphoketolase (PKL) enzymes, strain DW809, the transketolase double mutant strain as describe in Example 7, was transformed with plasmids expressing both PKL and isoprene synthase from an IPTG-inducible promoter (see Table 11 for complete list). Individual transformants were identified by growth on M9 glucose minimal medium plates with the aromatic supplement, grown overnight, and then assayed on the Enzyscreen Growth Profiler for growth performance on either glucose or xylose without the aromatic supplement, as described in Example 7. The range of IPTG concentrations used for induction was 0, 20, 40, 60, 80, 100, 200, and 400 μM. To calculate performance index (PI) for growth on glucose or xylose, the OD of each experimental strain was normalized to the OD of the control at a specific time point in the growth curve (typically between 30 and 40 hours). The experimental strains that displayed the highest PIs for growth expressed PKL enzymes with the most preferred in vivo activity, whereas the strains with low PIs expressed PKLs that did performed as well in this assay. PIs at 0, 100, and 400 μM were calculated, and were representative of overall growth performance at different induction levels. These are illustrated in Table 11.

TABLE 11

| Performance indices (PI) for growth on glucose or xylose | | | | | | | | |
|---|---|---|---|---|---|---|---|---|
| Source | PKL # | DW-809 strain | PI 0 Glucose | PI 100 Glucose | PI 400 Glucose | PI 0 Xylose | PI 100 Xylose | PI 400 Xylose |
| *E. faecium* | 1 | MCS811 | 0.55 | 0.69 | 0.93 | 0.84 | 0.67 | 0.77 |
| *L. grayi* | 2 | MCS812 | 0.76 | 0.84 | 0.67 | 1.14 | 0.50 | 0.45 |
| *E. casseliflavus* | 3 | MCS813 | 4.73 | 0.50 | 0.47 | 2.27 | 0.77 | 0.36 |
| *M. alligatoris* | 4 | MCS814 | 4.54 | 0.66 | 0.99 | 1.10 | 1.11 | 1.20 |
| *Carnobacterium* | 5 | MCS815 | 0.72 | 0.06 | 0.06 | 0.49 | 0.09 | 0.17 |
| *M. plutonius* ATCC | 6 | MCS816 | 0.13 | 0.30 | 0.11 | 0.47 | 0.16 | 0.30 |
| *T. halophilus* | 7 | MCS817 | 0.06 | 0.02 | 0.03 | 0.39 | 0.07 | 0.05 |
| *M. plutonius* DAT | 8 | MCS818 | 0.17 | 0.11 | 0.08 | 0.85 | 0.18 | 0.15 |
| *M. arthritidis* | 9 | MCs819 | 2.26 | 0.43 | 0.66 | 9.52 | 1.33 | 0.95 |
| *S. agalactiae* | 10 | MCS820 | 3.23 | 0.96 | 0.79 | 0.64 | 0.61 | 0.59 |
| *M. agalacticae* | 11 | MCS821 | 1.26 | 0.94 | 1.19 | 11.47 | 0.88 | 0.38 |
| *S. gordonii* | 12 | MCS822 | 3.46 | 0.55 | 0.54 | 2.66 | 1.08 | 0.65 |
| *K. oralis* | 13 | MCS823 | 4.39 | 0.67 | 0.59 | 2.49 | 0.82 | 0.57 |
| *M. fermentans* | 14 | MCS824 | 1.48 | 0.34 | 0.32 | 5.70 | 0.12 | 0.15 |
| *G. adiacens* | 15 | MCS825 | 3.87 | 0.63 | 0.65 | 2.48 | 0.59 | 0.49 |
| *M. hominis* | 16 | MCS826 | 1.83 | 0.92 | 0.83 | 18.42 | 2.79 | 0.54 |
| *M. crocodyli* | 17 | MCS827 | 0.08 | 0.05 | 0.06 | 0.54 | 0.08 | 0.07 |
| *Neisseria* | 18 | MCs828 | 1.30 | 0.60 | 0.84 | 11.47 | 0.54 | 0.24 |
| *E. coleocola* | 19 | MCS829 | 0.10 | 0.08 | 0.13 | 1.18 | 0.09 | 0.05 |
| *A. urinae* | 20 | MCS830 | 3.79 | 0.81 | 0.84 | 2.75 | 0.53 | 1.10 |

TABLE 11-continued

| Performance indices (PI) for growth on glucose or xylose | | | | | | | | |
|---|---|---|---|---|---|---|---|---|
| Source | PKL # | DW-809 strain | PI 0 Glucose | PI 100 Glucose | PI 400 Glucose | PI 0 Xylose | PI 100 Xylose | PI 400 Xylose |
| *K. kingae* | 21 | MCS831 | 5.09 | 0.81 | 1.06 | 2.36 | 0.98 | 1.28 |
| *S. criceti* #1 | 22 | MCS832 | 1.22 | 0.50 | 0.52 | 7.44 | 0.28 | 0.61 |
| *S. criceti* #2 | 23 | MCS833 | 1.46 | 1.52 | 1.44 | 16.23 | 0.64 | 0.30 |
| *M. columbinum* | 24 | MCS834 | 1.47 | 0.13 | 0.30 | 2.96 | 0.30 | 0.46 |
| *M. gilvum* | 25 | MCS835 | 0.34 | 0.08 | 0.09 | 1.38 | 0.10 | 0.16 |
| *S. baltica* | 26 | MCs836 | 0.11 | 0.04 | 0.08 | 1.17 | 0.07 | 0.03 |
| *L. rhamnosus* | 27 | MCS837 | 0.43 | 0.11 | 0.13 | 0.58 | 0.39 | 0.70 |
| *L. crispatus* | 28 | MCS838 | 1.02 | 0.19 | 0.25 | 0.37 | 0.05 | 0.12 |
| *L. citreum* | 29 | MCS839 | 1.34 | 0.84 | 0.67 | 1.43 | 0.36 | 0.75 |
| *Bradyrhizobium* sp. | 30 | MCS840 | 0.38 | 0.09 | 0.10 | 0.39 | 0.11 | 0.17 |
| *B. microti* | 31 | MCS841 | 0.38 | 0.12 | 0.10 | 0.64 | 0.13 | 0.22 |
| *L. salivarius* | 32 | MCS842 | 0.48 | 1.33 | 2.39 | 1.92 | 2.20 | 0.99 |
| *R. imtechensis* | 33 | MCS843 | 0.22 | 1.36 | 0.06 | 0.38 | 0.01 | 0.01 |
| *B. xenovorans* | 34 | MCS844 | 0.72 | 0.25 | 0.25 | 0.37 | 0.07 | 0.15 |
| *M. intracellulare* | 35 | MCS845 | 0.12 | 0.03 | 0.07 | 0.74 | 0.11 | 0.13 |
| *Nitrosomonas* sp. | 36 | MCS846 | 0.08 | 0.04 | 0.07 | 0.71 | 0.13 | 0.12 |
| *S. pombe* | 37 | MCS847 | 0.83 | 0.27 | 0.23 | 0.43 | 0.07 | 0.12 |
| *L. buchneri* | 38 | MCS848 | 0.75 | 0.23 | 0.26 | 1.63 | 0.07 | 0.15 |
| *S. ghanaensis* | 39 | MCs849 | 0.70 | 0.28 | 0.00 | 0.33 | 0.10 | 0.12 |
| *N. fischeri* | 41 | MCS851 | 0.32 | 0.07 | 0.06 | 0.54 | 0.01 | 0.01 |
| *L. lactis* | 42 | MCS852 | 0.82 | 0.37 | 0.06 | 0.33 | 0.13 | 0.14 |
| *E. gallinarum* (CON) | | EWL1421 | 1.00 | 1.00 | 1.00 | 1.00 | 1.00 | 1.00 |

Example 17: Small Scale Evaluation of Isoprene Yield and Isoprene Specific Productivity in Strains Expressing Phosphoketolase The isoprene producing strains described in Example 15 were evaluated for isoprene production at small scale.

(i) Materials and methods

Yeast extract, $MgSO_4$, glucose, IPTG, spectinomycin, and carbenicillin were purchased from Sigma. Aluminum foil seal, 48-well sterile 5 mL block, Breathe Easier sealing membrane, 96-well micro titer plates, and 96-well conical bottom plates were purchased from VWR. 96-well glass blocks were purchased from Zinsser Analytic. Equipment: Agilent 6890 GC equipped with a 5973N mass spectrometer, Eppendorf centrifuge 5417R, Sorvall legend RT.

Growth Rate Measurement:

Shake tubes containing 3 ml LB media, with appropriate antibiotics, were inoculated with glycerol culture stocks. Cultures were incubated for approximately 15 hours at 30° C., 220 rpm.

Supplemented TM3 media was prepared by combining TM3 media (without $MgSO_4$ and yeast extract), 1% Glucose, 8 mM $MgSO_4$, 0.02% yeast extract and appropriate antibiotics. 2 mL of supplemented TM3 were inoculated with overnight cultures in each well of a 48-well sterile block to a final $OD_{600}$ of 0.2. Blocks were sealed with Breathe Easier membranes and incubated for 2 hours at 34° C. at 600 rpm. After 2 hours of growth, the $OD_{600}$ was measured in the microtiter plate and cells were induced with various concentrations of IPTG. $OD_{600}$ readings were taken every hour after the IPTG induction for 4 hrs. $OD_{600}$ measurements were determined using a SpectraMax Plus190 (Molecular Devices).

Isoprene Yield Assay:

Supplemented TM3 media was prepared by combining TM3 media (without $MgSO_4$ and yeast extract), 1% Glucose, 8 mM $MgSO_4$, 0.02% yeast extract and appropriate antibiotics. 2 mL of supplemented TM3 media were inoculated in each well of a 48-well sterile block to a final $OD_{600}$ of 0.2. 10 µL of the inoculated cultures were transferred to 90 µL of TM3 media without glucose or yeast extract and sealed with aluminum foil in a 96-well glass block (Zinsser) and incubated at 34° C. and 450 rpm for 24 hours. After 24 hours, the amount of isoprene in the headspace was measured by GC/MS and amount of glucose left in the media in the media to calculate isoprene yield.

Isoprene Specific Productivity Measurement:

100 µl of culture was collected in a 96-well glass block. The glass block was sealed with aluminum foil seal and incubated at 34° C. while shaking at 450 rpm for 30 minutes using a Thermomixer (Eppendorf). After 30 minutes, the block was incubated at 70° C. water bath for 2 minutes. The glass block was allowed to cool to room temperature and then isoprene in the headspace of the wells was measured by GC/MS.

Glucose Measurement:

Glucose samples were collected by centrifuging 300 µl of cell culture in the 96-well conical bottom plate for 10 min at 4° C., 3000 rpm. The supernatant was diluted 10-fold in DI water and the glucose concentration was measured using the described glucose oxidase assay.

Glucose Oxidase Assay:

ABTS was solubilized in 50 mM sodium acetate pH 5. Glucose oxidase (GOX) and horse radish peroxidase (HRP) were added to the following concentration: 2.74 mg/ml ABTS (powder), 0.1 U/ml HRP, 1 U/ml GOX. The container was wrapped in tin foil to protect from light and stored up to 7 days at 4° C. The glucose standard was prepared by dissolving glucose in MilliQ water across the desired concentration range (i.e serial 2× dilution from 1 mg/ml). 10 µl of test sample was added (dilute reaction supernatant) and/or glucose standard to a well of a microtiter plate. 90 µl of the ABTS reagent was added and quickly mixed on a plate mixer. The assay plate was transferred to the plate reader and absorbance was monitored at 420 nm for 3-5 minutes. The data file was exported to Excel. The glucose calibration curve was used to calculate the amount of glucose in each well.

TABLE 12

| Parameters for isoprene detection by GC/MS | | |
|---|---|---|
| GCMS Paramaters: | | |
| Column: | | |
| ZB-5ms 15 m × 0.25 mm × 0.25 μm | | |
| Oven: | | |
| Ramp (° C./min) | Temperature (° C.) | Hold Time (min) |
| 0 | 37 | 0.6 |
| Total Run Time: | | 0.6 minutes |
| Front Inlet Temperature: | | 110° C. |
| Split Ratio: | | 50:1 |
| Flow Rate: | | 2 mL/min |
| Injection Volume: | | 100 μL |
| MS Mode: | | EI |
| MS Source: | | 230° C. |
| MS Quadrupole: | | 150° C. |
| MSD Transfer Line Heater (Aux2): | | 280° C. |
| SIM Mode: | | 67 amu |

(ii) Results

To calculate performance index (PI) for each of: (i) Isoprene Specific Productivity at 2 hours; (ii) Isoprene Specific Productivity at 4 hours; (iii) Growth rate; and (iv) Isoprene yield, each experimental strain was normalized to the specific parameter of the control at a specific time point in the growth curve (typically between 15-24 hours). The experimental strains that displayed PI values greater than 1.0 for these evaluated parameters indicated better performance of the evaluated PKL in this isoprene production assay.

TABLE 13

PI for each of: (i) Isoprene Specific Productivity at 2 hours; (ii) Isoprene Specific Productivity at 4 hours; (iii) Growth rate; and (iv) Isoprene yield

| Source | PKL # | MD891 strain | PI S. Prod. 2 h(mg/L/h/OD)-MTP | PI S. Prod. 4 h (mg/L/h/OD)-MTP | PI Growth rate (OD at 5 h)-MTP | PI Yield (24 h)-MTP |
|---|---|---|---|---|---|---|
| *E. faecium* | 1 | MCS865 | 1.29 | 1.02 | 1.01 | 1.07 |
| *L. grayi* | 2 | MCS866 | 1.24 | 0.75 | 0.99 | 0.73 |
| *E. casseliflavus* | 3 | MCS867 | 0.84 | 0.62 | 0.88 | 0.87 |
| *M. alligatoris* | 4 | MCS868 | 1.21 | 0.99 | 0.90 | 1.09 |
| *Carnobacterium* | 5 | MCS869 | 0.82 | 0.68 | 1.14 | 0.50 |
| *T. halophilus* | 7 | MCS871 | 1.21 | 1.17 | 1.10 | 0.99 |
| *M. plutonius* DAT | 8 | MCS872 | 0.00 | 0.00 | 0.00 | 0.00 |
| *M. arthritidis* | 9 | MCS873 | 0.61 | 0.34 | 0.72 | 0.64 |
| *S. agalactiae* | 10 | MCS874 | 1.06 | 0.93 | 0.95 | 1.13 |
| *K. oralis* | 13 | MCS877 | 0.92 | 0.71 | 0.86 | 0.99 |
| *M. fermentans* | 14 | MCS878 | 0.25 | 0.17 | 0.48 | 0.03 |
| *G. adiacens* | 15 | MCS879 | 1.02 | 0.85 | 0.86 | 0.96 |
| *M. crocodyli* | 17 | MCS881 | 0.67 | 0.42 | 0.68 | 1.03 |
| *E. coleocola* | 19 | MCS883 | 0.60 | 0.51 | 0.61 | 0.90 |
| *A. urinae* | 20 | MCS884 | 1.07 | 1.02 | 0.89 | 1.05 |
| *S. criceti* #1 | 22 | MCS886 | 1.06 | 0.83 | 0.85 | 0.85 |
| *M. columbinum* | 24 | MCS888 | 0.66 | 0.31 | 0.63 | 0.08 |
| *M. gilvum* | 25 | MCS889 | 1.00 | 1.02 | 1.00 | 0.95 |
| *L. rhamnosus* | 27 | MCS891 | 0.66 | 0.64 | 1.00 | 0.70 |
| *L. citreum* | 29 | MCS893 | 1.17 | 0.84 | 1.02 | 0.86 |
| *Bradyrhizobium* sp. | 30 | MCS894 | 1.10 | 1.15 | 1.06 | 0.98 |
| *B. microti* | 31 | MCS895 | 0.94 | 0.83 | 1.04 | 0.89 |
| *R. imtechensis* | 33 | MCS897 | 0.98 | 0.90 | 1.05 | 0.99 |
| *B. xenovorans* | 34 | MCS898 | 1.09 | 0.92 | 1.15 | 0.87 |
| *M. intracellulare* | 35 | MCS899 | 1.12 | 0.77 | 1.05 | 0.82 |
| *Nitrosomonas* sp. | 36 | MCS900 | 0.64 | 0.55 | 1.22 | 0.63 |
| *S. pombe* | 37 | MCS901 | 0.64 | 0.63 | 0.78 | 0.78 |
| *L. buchneri* | 38 | MCS902 | 0.92 | 0.74 | 1.17 | 0.65 |
| *S. ghanaensis* | 39 | MCS903 | 0.92 | 0.86 | 1.05 | 0.90 |
| *Cyanothece* sp. | 40 | MCS904 | 0.79 | 0.55 | 1.06 | 0.69 |
| *N. fischeri* | 41 | MCS905 | 0.79 | 0.58 | 1.19 | 0.58 |
| *L. lactis* | 42 | MCS906 | 1.02 | 0.85 | 1.17 | 0.72 |
| *E. gallinarum* (CON) | | MCS908 | 1.00 | 1.00 | 1.00 | 1.00 |

Example 18: Measurement of Intracellular Metabolites in Strains Expressing PKLs (i) Materials and Methods Metabolite Extraction:

The strains used for metabolite analysis were the same strains described in Example 17. Thus, these strains were grown under the growth conditions set forth in Example 17 and samples were taken after 4 hour of growth to determine relative concentrations of selected cellular metabolites 500 uL of cell cultures were collected by centrifugation, the supernatant was discarded, 100 uL of dry-ice-cold methanol was added to the pellets, and the tubes with the pellets were immediately frozen in dry ice and placed into a −80° C. refrigerator for storage. To extract metabolites, cell pellets covered with methanol were resuspended using glass rods, the tubes were centrifuged in microcentrifuge for 5 min and the resulting supernatants were removed and placed into clean tubes. Cell pellets obtained after the first extraction step were resuspended in 40 uL of 50% methanol/10 mM ammonium acetate mix, cell debris were centrifuged and the supernatants were collected and pooled together with the supernatants obtained after the first extraction. This extraction procedure was repeated one more time to ensure more complete removal of metabolites from cell debris.

During the extraction-centrifugation samples with cells were kept below 4° C. to minimize metabolites degradation. Final pooled extracts was mixed and then cleared by centrifugation.

Metabolite Measurements:

Analysis of metabolites was performed by LCMS on a TSQ Quantim triple quadrupole instrument (Thermo Scientific). System control, data acquisition, and data analysis were done with XCalibur and LCQuan software (Thermo Scientific). 10 uL samples were applied to a C18 Synergi MAX-RP HPLC column (150×2 mm, 4 uM, 80A, Phenomenex) equipped with the manufacturer-recommended guard cartridge. The column was eluted with a gradient of 15 mM acetic acid+10 mM tributylamine in MilliQ-grade water (solvent A) and LCMS-grade methanol from Honeywell, Burdick & Jackson (solvent B). The 22.5 min gradient was as follows: t=0 min, 5% B; t=2 min, 5% B; t=6 min, 10% B; t=12 min, 20% B; t=18 min, 67% B; t=19 min, 99% B; t=21 min, 99% B; t=21.5 min, 5% B; t=22.5 min, 5% B flow rate 0.4 mL/min, column temperature 35° C. Mass detection was carried out using electrospray ionization in the negative mode at ESI spray voltage of 3.0-3.5 kV and ion transfer tube temperature of 350° C. The following SRM transitions were selected for metabolites of interest: 25979 glucose-6-phosphate (G6P), 339→79 for fructose 1,6-bisphosphate, 167→79 for phosphoenolpyruvate, 275→79 for 6-phosphoglycerate, 259→79 eV for ribose-5-phosphate, 139→79 for acetyl-phosphate, and 199→79 for erythrose 4-phosphate. Scan time for each SRM transition was 0.1 s with a scan width set at 0.7 m/z. Argon was used as the collision gas at 1.7 mTorr, and the collision energies were optimized to get maximum signal intensities using corresponding standards purchased from Sigma-Aldrich. The same standards were used to verify the retention times of measured metabolites. Peaks with SRM transitions 369→79 were attributed to heptose-bisphosphates. Concentrations of measured metabolites were expressed as signal intensities normalized to optical densities of the cultures during sampling.

(ii) Results

To calculate performance index (PI) for the production of Acetyl-phosphate (AcP), the amount of each metabolite from the respective experimental strain was normalized to the specific parameter of the control at a specific time point in the growth curve (typically between 30 and 40 hours). The experimental strains that displayed PI values greater than 1.0 for these evaluated parameters indicated better performance of the evaluated PKL in this assay.

TABLE 14

PI for the production of: (i) acetyl-phosphate (AcP)

| Source | PKL # | MD891 strain | PI AcP (AU/OD)-MTP |
|---|---|---|---|
| *E. faecium* | 1 | MCS865 | 2.49 |
| *L. grayi* | 2 | MCS866 | 0.94 |
| *E. casseliflavus* | 3 | MCS867 | 2.12 |
| *M. alligatoris* | 4 | MCS868 | 1.75 |
| *Carnobacterium* | 5 | MCS869 | 0.35 |
| *M. plutonius* ATCC | 6 | MCS870 | 0.00 |
| *T. halophilus* | 7 | MCS871 | 0.48 |
| *M. plutonius* DAT | 8 | MCS872 | 0.00 |
| *M. arthritidis* | 9 | MCS873 | 1.51 |
| *S. agalactiae* | 10 | MCS874 | 1.06 |
| *M. agalacticae* | 11 | MCS875 | 0.00 |
| *S. gordonii* | 12 | MCS876 | 0.00 |
| *K. oralis* | 13 | MCS877 | 2.26 |
| *M. fermentans* | 14 | MCS878 | 0.54 |
| *G. adiacens* | 15 | MCS879 | 1.47 |
| *M. hominis* | 16 | MCS880 | 0.00 |
| *M. crocodyli* | 17 | MCS881 | 1.71 |
| *Neisseria* | 18 | MCS882 | 0.00 |
| *E. coleocola* | 19 | MCS883 | 2.93 |
| *A. urinae* | 20 | MCS884 | 0.98 |
| *K. kingae* | 21 | MCS885 | 0.00 |
| *S. criceti* #1 | 22 | MCS886 | 1.31 |
| *S. criceti* #2 | 23 | MCS887 | 0.00 |
| *M. columbinum* | 24 | MCS888 | 0.73 |
| *M. gilvum* | 25 | MCS889 | 0.52 |
| *S. baltica* | 26 | MCS890 | 0.00 |
| *L. rhamnosus* | 27 | MCS891 | 2.35 |
| *L. crispatus* | 28 | MCS892 | 0.00 |
| *L. citreum* | 29 | MCS893 | 0.76 |
| *Bradyrhizobium* sp. | 30 | MCS894 | 0.19 |
| *B. microti* | 31 | MCS895 | 0.31 |
| *L. salivarius* | 32 | MCS896 | 0.00 |
| *R. imtechensis* | 33 | MCS897 | 0.19 |
| *B. xenovorans* | 34 | MCS898 | 0.16 |
| *M. intracellulare* | 35 | MCS899 | 0.40 |
| *Nitrosomonas* sp. | 36 | MCS900 | 0.33 |
| *S. pombe* | 37 | MCS901 | 0.19 |
| *L. buchneri* | 38 | MCS902 | 0.19 |
| *S. ghanaensis* | 39 | MCS903 | 0.76 |
| *Cyanothece* sp. | 40 | MCS904 | 0.15 |
| *N. fischeri* | 41 | MCS905 | 0.15 |
| *L. lactis* | 42 | MCS906 | 0.19 |
| *E. gallinarum* (CON) | | MCS908 | 1.00 |

Example 19: Determination of Protein Expression and Solubility of Phosphoketolases (i) Materials and Methods The strains used to determine protein expression and solubility of the evaluated phosphoketolases were the same strains described in Example 17. The strains were grown in LB broth overnight at 34 C with appropriate antibiotics. The next day, 100 uL of the overnight culture was added to 5 mL of LB with appropriate antibiotics and grown at 34 C to an OD(600) of ~0.5. The cultures were then induced with 200 uM IPTG and incubated for an additional 6 hours at 34 C. The cells were then harvested by centrifugation, and the pellets were stored at −80 C.

The next day the pellets were allowed to thaw, and they were resuspended to an OD(600) of 4 in 100 mM Tris 100 mM NaCl pH 7.6 with 0.2 mg/ml DNaseI and 0.5 mM AEBSF. The cells were then individually lysed via French-press, and the cell debris was removed by centrifugation. The average total protein concentration of the soluble fraction was 0.56±0.22 mg/ml as determined by the standard Bradford assay. The pellet from centrifugation was resuspended in 100 mM Tris 100 mM NaCl pH 7.6 buffer and saved to determine the percent solubility of each phosphoketolase.

The lysate was then used to determine the amount phosphoketolase (PKL) activity on fructose 6-phosphate (F6P) per unit total protein (μmol/min/mg). The PKL activity on F6P was determined by following the amount of acetyl-phosphate (AcP) generated. The reaction mixture (200 uL) contained 10 mM MgCl2, 10 mM potassium phosphate (pH 7.6), 1 mM thiamine diphosphate, 10 mM F6P, 20 mM NaF, 8 mM iodoacetomide, 1 mM dithiothreitol in 100 mM Tris 100 mM NaCl pH 7.6 with 100 uL of lysate. These incubated for 30 minutes at 34 C and were quenched by adding 60 uL of the reaction mixture to 60 uL of 2 M hydroxylamine pH 6.5. This quenched mixture incubated at room temperature for 10 minutes, and then 40 uL of 15% TCA, 40 uL of 4 M HCl and 40 uL of 5% FeCl3 in 0.1 M HCl was added. This final mixture was then centrifuged at 3000 rpm for 5 min. The supernatant (200 uL) was removed, and the absorbance was measured at 505 nm. A calibration curve of AcP was used to calculate how much AcP was produced.

Relative expression and solubility of each PKL variant, relative to the *E. gallinarum* MCS908 control, was determined by densitometry. The soluble lysates of each sample were mixed 1:1 with gel loading dye and ran on SDS-PAGE gels. Each pellet, obtained from sample centrifugation post lysis via the French press (see above), was diluted 1:1 with gel loading dye and loaded on SDS-PAGE gels. A sample of *E. gallinarum* MCS908 soluble lysate was included on each gel as a control. Gels were developed using Coomassie Brilliant Blue stain, and analyzed using ImageQuantTL v2005 (GE Health Sciences) densitometry software. The percent of soluble protein expressed and the percent soluble to insoluble were determined relative to the control strain (*E. gallinarum* MCS908).

(ii) Results

To calculate performance index (PI) for each of: (i) (F6P) Specific Activity per unit total protein (μmol/min/mg); (ii) Expression level; and (iii) Solubility each experimental strain was normalized to the specific parameter of the control. The PI for F6P Specific Activity (Activity/Expression level) was determined by dividing the PI values for (i) by the PI value to (ii). The experimental strains that displayed a PI greater than 1.0 for these evaluated parameters indicated better performance of the evaluated PKL in this assay.

TABLE 15

Solubility and expression of each PKL

| Source | MD891 strain | PI F6P S.A. (μmol/min/mg total protein) | PI Expression level (% relative to control) | PI Solubility (% Soluble) | PI F6P Specific Activity (Activity/Expression level) |
|---|---|---|---|---|---|
| *L. grayi* | MCS866 | 1.22 | 0.33 | 0.30 | 3.69 |
| *E. casseliflavus* | MCS867 | 2.41 | 2.35 | 0.97 | 1.02 |
| *M. alligatoris* | MCS868 | 0.79 | 0.26 | 0.77 | 3.05 |
| *Carnobacterium* | MCS869 | 0.10 | 0.09 | 0.07 | 1.14 |
| *T. halophilus* | MCS871 | 0.15 | 0.05 | 0.16 | 3.06 |
| *M. arthritidis* | MCS873 | 2.52 | 1.78 | 0.87 | 1.41 |
| S. *agalactiae* | MCS874 | 1.25 | 0.49 | 0.82 | 2.56 |
| *K. oralis* | MCS877 | 2.29 | 1.81 | 0.96 | 1.26 |
| *M. fermentans* | MCS878 | 0.29 | 0.21 | 0.79 | 1.38 |
| *G. adiacens* | MCS879 | 1.87 | 1.04 | 0.99 | 1.79 |
| *M. crocodyli* | MCS881 | 2.21 | 1.16 | 0.61 | 1.90 |
| *E. coleocola* | MCS883 | 3.18 | 1.67 | 0.95 | 1.90 |
| *A. urinae* | MCS884 | 1.96 | 1.40 | 0.98 | 1.40 |
| *M. columbinum* | MCS888 | 1.77 | 1.75 | 1.06 | 1.01 |
| *M. gilvum* | MCS889 | 0.65 | 0.33 | 0.40 | 1.96 |
| *L. citreum* | MCS893 | 0.90 | 1.13 | 1.03 | 0.80 |
| *Bradyrhizobium* sp. | MCS894 | 0.11 | 0.10 | 0.29 | 1.10 |
| *B. microti* | MCS895 | 0.42 | 0.25 | 0.90 | 1.69 |
| *R. imtechensis* | MCS897 | 0.14 | 0.06 | 0.29 | 2.28 |
| *B. xenovorans* | MCS898 | 0.23 | 0.33 | 0.22 | 0.69 |
| *M. intracellulare* | MCS899 | 0.14 | 0.32 | 0.45 | 0.43 |
| *Nitrosomonas* sp. | MCS900 | 0.22 | 0.10 | 0.13 | 2.23 |
| *S. pombe* | MCS901 | 0.16 | 0.49 | 0.18 | 0.32 |
| *L. buchneri* | MCS902 | 0.06 | 0.06 | 0.08 | 0.97 |
| *S. ghanaensis* | MCS903 | 0.67 | 0.46 | 0.23 | 1.45 |
| *Cyanothece* sp. | MCS904 | 1.23 | 0.48 | 0.77 | 2.56 |
| *N. fischeri* | MCS905 | 0.07 | 0.44 | 0.27 | 0.15 |
| *L. lactis* | MCS906 | 0.23 | 0.07 | 0.07 | 3.24 |
| *E. gallinarum* (CON) | MCS908 | 1.00 | 1.00 | 1.00 | 1.00 |

Example 20: Phosphoketolase Activity on Fructose 6-Phosphate and Xylulose 5-Phosphate This example determined PKL activity when strains are grown on fructose 6-phosphate (F6P) or xylulose 5-phosphate (X5P).

(i) Materials and Methods

The strains were grown in LB broth overnight at 34 C with appropriate antibiotics. The next day, 200 uL of the overnight culture was added to 5 mL of TM3 with appropriate antibiotics and grown at 34 C for 2.5 hours. The cultures were then induced with 200 uM IPTG and incubated for an additional 4 hours at 34 C. The cells were then harvested by centrifugation, and the pellets were stored at −80 C.

The next day the pellets were allowed to thaw, and they were resuspended in 2 mL of 100 mM HEPES pH 7.8 with 0.2 mg/ml DNaseI and 0.5 mM AEBSF. The cells were then individually lysed via French-press, and the cell debris was removed by centrifugation.

Lysate Preparation and Enzyme Activity Determination:

The lysate was then used to determine the amount phosphoketolase (PKL) activity on fructose 6-phosphate (F6P) and xylulose 5-phosphate (X5P). The PKL activity on F6P and X5P was determined by following the amount of acetyl-phosphate (AcP) generated. The F6P reaction mixture (200 uL) contained 10 mM MgCl2, 10 mM potassium phosphate (pH 7.6), 1 mM thiamine diphosphate, 10 mM F6P, 20 mM NaF, 8 mM iodoacetomide, 1 mM dithiothreitol in 100 mM HEPES pH 7.8 with and 100 uL of lysate. These incubated for 30 minutes at 34 C and were quenched by adding 60 uL of the reaction mixture to 60 uL of 2 M hydroxylamine pH 6.5. This quenched mixture incubated at room temperature for 10 minutes, and then 40 uL of 15% TCA, 40 uL of 4 M HCl and 40 uL of 5% FeCl3 in 0.1 M HCl was added. This final mixture was then centrifuged at 3000 rpm for 5 min. The supernatant (200 uL) was removed, and the absorbance was measured at 505 nm. A calibration curve of AcP was used to calculate how much AcP was produced. The X5P activity was measured with a similar method. The X5P reaction mixture (200 uL) contained 10 mM MgCl2, 10 mM potassium phosphate (pH 7.6), 1 mM thiamine diphosphate, 10 mM ribose 5-phosphate, 60 ug/mL of ribulose-5-phosphate 3-epimerase, 200 ug/mL of ribose-5-phosphate isomerase A, 20 mM NaF, 8 mM iodoacetomide, 1 mM dithiothreitol in 100 mM HEPES pH 7.8 with and 20 uL of lysate. Due to the wide range of activities on X5P, the activities were measured at two concentrations of lysate: undiluted and five-fold diluted into 100 mM HEPES pH 7.8.

TABLE 16

PKL activity on F6P or X5P

| Strain Description (MD-891 Strain) | F6P AcP (mM) | F6P Spec Act | X5P (Undiluted) AcP (mM) | X5P (Undiluted) Spec Act | X5P (Diluted 5X) AcP (mM) | X5P (Diluted 5X) Spec Act | Ratio Undiluted (X/F) | Ratio Diluted (X/F) |
|---|---|---|---|---|---|---|---|---|
| pMCS842, pMCM1225 | 0.51 | 0.19 | 1.75 | 3.21 | 0.41 | 3.79 | 17.03 | 20.16 |
| pMCS836, pMCM1225 | 0.04 | 0.04 | 0.11 | 0.54 | 0.085 | 2.10 | 15.19 | 59.62 |
| pEWL1421, pMCM1225 | 1.19 | 0.65 | 3.59 | 9.74 | 0.76 | 10.37 | 15.06 | 16.04 |
| pMCS813, pMCM1225 | 1.99 | 1.06 | 4.97 | 13.19 | 1.26 | 16.76 | 12.49 | 15.88 |
| pMCS821, pMCM1225 | 1.98 | 1.20 | 4.82 | 14.59 | 1.27 | 19.16 | 12.20 | 16.022 |
| pMCS833, pMCM1225 | 2.02 | 1.14 | 4.70 | 13.28 | 1.12 | 15.83 | 11.68 | 13.91 |
| pMCS830, pMCM1225 | 1.45 | 0.63 | 3.10 | 6.73 | 0.81 | 8.77 | 10.67 | 13.90 |
| pMCS822, pMCM1225 | 1.52 | 1.27 | 3.23 | 13.48 | 0.67 | 13.86 | 10.61 | 10.91 |
| pMCS839, pMCM1225 | 0.37 | 0.37 | 0.77 | 3.85 | 0.19 | 4.88 | 10.45 | 13.25 |
| pMCS825, pMCM1225 | 2.02 | 1.26 | 4.14 | 12.92 | 1.16 | 18.08 | 10.22 | 14.30 |
| pMCS823, pMCM1225 | 2.51 | 1.02 | 4.65 | 9.48 | 1.25 | 12.70 | 9.28 | 12.43 |
| pMCS826, pMCM1225 | 2.43 | 1.81 | 4.36 | 16.19 | 0.94 | 17.50 | 8.95 | 9.68 |
| pMCS824, pMCM1225 | 0.37 | 6.81 | 0.64 | 59.24 | 0.19 | 89.62 | 8.69 | 13.15 |
| pMCS834, pMCM1225 | 2.04 | 1.16 | 3.39 | 9.61 | 0.87 | 12.30 | 8.32 | 10.64 |
| pMCS811, pMCM1225 | 0.87 | 0.33 | 1.45 | 2.80 | 0.39 | 3.79 | 8.31 | 11.24 |
| pMCS819, pMCM1225 | 3.53 | 1.85 | 5.13 | 13.45 | 1.34 | 17.65 | 7.26 | 9.52 |
| pMCS820, pMCM1225 | 0.81 | 0.32 | 1.16 | 2.26 | 0.32 | 3.12 | 7.18 | 9.91 |
| pMCS838, pMCM1225 | 0.24 | 0.15 | 0.34 | 1.06 | 0.16 | 2.49 | 7.05 | 16.62 |
| pMCS829, pMCM1225 | 3.30 | 2.15 | 4.45 | 14.46 | 1.16 | 18.93 | 6.73 | 8.81 |
| pMCS832, pMCM1225 | 2.10 | 1.78 | 2.76 | 11.73 | 0.69 | 14.62 | 6.59 | 8.21 |
| pMCS827, pMCM1225 | 1.33 | 2.28 | 1.73 | 14.84 | 0.36 | 15.45 | 6.51 | 6.78 |
| pMCS831, pMCM1225 | 0.78 | 0.64 | 0.99 | 4.08 | 0.23 | 4.63 | 6.41 | 7.282 |
| pMCS828, pMCM1225 | 2.62 | 2.32 | 3.30 | 14.62 | 0.87 | 19.25 | 6.31 | 8.31 |
| pMCS845, pMCM1225 | 0.19 | 0.12 | 0.17 | 0.53 | 0.09 | 1.40 | 4.36 | 11.52 |
| pMCS814, pMCM1225 | 0.54 | 0.30 | 0.37 | 1.01 | 0.17 | 2.37 | 3.36 | 7.87 |
| pMCS844, pMCM1225 | 0.21 | 0.16 | 0.12 | 0.47 | 0.09 | 1.79 | 2.89 | 11.07 |
| pMCS816, pMCM1225 | 0.19 | 0.11 | 0.11 | 0.33 | 0.12 | 1.74 | 2.87 | 15.25 |
| pMCS849, pMCM1225 | 0.82 | 0.38 | 0.47 | 1.08 | 0.14 | 1.62 | 2.83 | 4.23 |
| pMCS645, pMCM1225 | 0.22 | 0.20 | 0.13 | 0.56 | 0.10 | 2.31 | 2.81 | 11.57 |
| pMCS818, pMCM1225 | 0.18 | 0.19 | 0.09 | 0.48 | 0.10 | 2.67 | 2.54 | 13.99 |
| pMCS841, pMCM1225 | 0.78 | 0.45 | 0.37 | 1.09 | 0.11 | 1.66 | 2.42 | 3.69 |
| pMCS837, pMCM1225 | −0.07 | −0.03 | 0.61 | 1.17 | 0.10 | 1.01 | −43.14 | −37.25 |

Example 21: 14 L Evaluation of Isoprene Production in Strains Expressing Phosphoketolase This experiment was performed to evaluate the effect of expressing various phosphoketolase enzymes on isoprene production. All the strains in this experiment used a modified *E. coli* host (BL21 derived production host MD891) which expresses introduced genes from the mevalonate pathway, isoprene synthase and phosphoketolase (PKL), for strain details see Table 17. All of these isoprene producing strains were grown in fed-batch culture at the 15-L scale.

The relevant performance metrics are cumulative isoprene yield on glucose, and isoprene titer. The productivity metrics are found summarized in Table 18.

TABLE 17

| List of strains | | | |
|---|---|---|---|
| Strain Name | Host | IPTG inducible Upper pathway plasmid | IPTG inducible Isoprene synthase/Phosphoketolase plasmid. |
| MD13-896 | MD-891 | pMCM1225 | pEWL1418 (PTrc IspS-PKL_*B. longum*) |
| MD13-898 | MD-891 | pMCM1225 | pEWL1436 (PTrc IspS-PKL_*C. Acetobutylicum*) |
| MCS674 | MD-891 | pMCM1225 | (PTrc IspS-PKL_*Bifidobacterium bifidum*) |
| MCS675 | MD-891 | pMCM1225 | (PTrc IspS-PKL_*Bifidobacterium dentium*) |
| MCS676 | MD-891 | pMCM1225 | (PTrc IspS-PKL_*Bifidobacterium gallicum*) |
| MCS703 | MD-891 | pMCM1225 | pMCS668 (PTrc IspS-PKL_*E. gallinarum*-RBS 2300) |
| MCS704 | MD-891 | pMCM1225 | pMCS669 (PTrc IspS-PKL_*E. gallinarum*-RBS 7700) |
| MCS706 | MD-891 | pMCM1225 | pMCS671 (PTrc IspS-PKL_*E. gallinarum*-RBS 73300) |
| DW891-2 | MD-891 | pMCM1225 | pMCS822 (PTrc IspS-PKL_ *S. gordonii*) |
| DW892-1 | MD-891 | pMCM1225 | pMCS831 (PTrc IspS-PKL_ *K. kingae*) |
| MCS935 | MD-891 | pMCM1225 | pMCS814 (PTrc IspS-PKL4[*M. alligatoris*]) |
| MCS941 | MD-891 | pMCM1225 | pMCS820 (PTrc IspS-PKL10[*S. agalacticae*]) |
| MCS946 | MD-891 | pMCM1225 | pMCS825 (PTrc IspS-PKL15 [*G. adiacens*]) |
| MCS699 | MD-891 | pMCM1225 | pMCS666 (PTrc IspS-PKL_*E. gallinarum*_RBS2600) |
| MCS951 | MD-891 | pMCM1225 | pMCS830 (PTrc IspS-PKL_ *A. urinae*) |
| MCS944 | MD-891 | pMCM1225 | pMCS823 (PTrc IspS-PKL_ *K. oralis*) |
| MCS932 | MD-891 | pMCM1225 | pMCS811 (PTrc IspS-PKL_ *E. faecium*) |
| MCS934 | MD-891 | pMCM1225 | pMCS813 (PTrc IspS-PKL3[E. *casseliflavus*]) |
| MCS963 | MD-891 | pMCM1225 | pMCS842 (PTrc IspS-PKL_ *L. salivarus*) |
| MCS947 | MD-891 | pMCM1225 | pMCS826 (PTrc IspS-PKL_ *M. hominis*) |

(i) Materials and Methods

Medium Recipe (Per Liter Fermentation Medium):

$K_2HPO_4$ 7.5 g, $MgSO_4$*$7H_2O$ 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics (spectinomycin and carbenicillin) were added after sterilization and pH adjustment to a target concentration of 50 mg/L.

1000× Modified Trace Metal Solution (Per Liter):

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (Per Liter):

$MgSO_4$*$7H_2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di $H_2O$ 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml. For a target of 100 μM IPTG: 1.87 ml of a sterile 10 mg/ml solution is added per kilogram of feed.

This experiment was carried out to monitor isoprene production from glucose at the desired fermentation pH (7.0) and temperature (34° C.). To start each experiment, the appropriate frozen vial of the *E. coli* production strain was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by in house facilities that dilute the inlet gas to a known concentration (7.3 to 8.3 vol % oxygen).

The batched media had glucose batched in at 9.7 g/L. Induction was achieved by adding isopropyl-beta-D-1-thiogalactopyranoside (IPTG). A syringe containing a sterile solution of IPTG was added to bring the IPTG concentration to 100 μM when the cells were at an $OD_{550}$ of 6. Once the glucose was consumed by the culture, as signaled by a rise in pH, the glucose feed solution was fed to meet metabolic demands at rates less than or equal to 10 g/min. At a fixed time after dissolved oxygen limitation was established, the temperature was raised from 34° C. to 37° C. over the course of one hour. The fermentation was run long enough to determine the maximum cumulative isoprene mass yield on glucose, typically a total of 64 hrs elapsed fermentation time (EFT).

(ii) Results and Analysis

Isoprene, Oxygen, Nitrogen, and Carbon Dioxide levels in the off-gas were determined independently by a Hiden HPR20 (Hiden Analytical) mass spectrometer.

Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

HPLC Information

System: Waters Alliance 2695

Column: BioRad—Aminex HPX-87H Ion Exclusion Column 300 mm×7.8 mm Catalog #125-0140

Column Temperature: 50 C

Guard column: BioRad—Microguard Cation H refill 30 mm×4.6 mm Catalog #125-0129

Running buffer: 0.01N $H_2SO_4$

Running buffer flow rate: 0.6 ml/min

Approximate running pressure: ~1100-1200 psi

Injection volume: 20 microliters

Detector: Refractive Index (Knauer K-2301)

Runtime: 26 minute

Cumulative Isoprene yield on glucose is equal to Isoprene total weight (t)/[(Feed Wt(0)-Feed Wt(t)+83.5)*0.5826)], where 0.5826 is the wt % of glucose in the glucose feed solution and 83.5 is the grams of this feed batched into the fermentor at t=0. Units are $g_{isoprene}/g_{glucose}$*100, expressed as percentages.

IspER is the Isoprene Evolution Rate in (mmol/L/hr).

Specific productivity (mg/L/hr/OD)=IspER*68.117 g/mol/OD.

OD=optical density=Absorbance at 550 nm*dilution factor in water.

Smoothed Specific productivity (mg/L/hr/OD)=slope of milligrams isoprene produced per hour (averaged over 8 hour interval)/broth volume*OD.

Isoprene titer ($g_{Isoprene}/L_{average\ broth}$) is the total evolved isoprene per average broth volume. It is calculated by integrating the IspER and converting the isoprene unit from mmol to grams.

Figure 40:
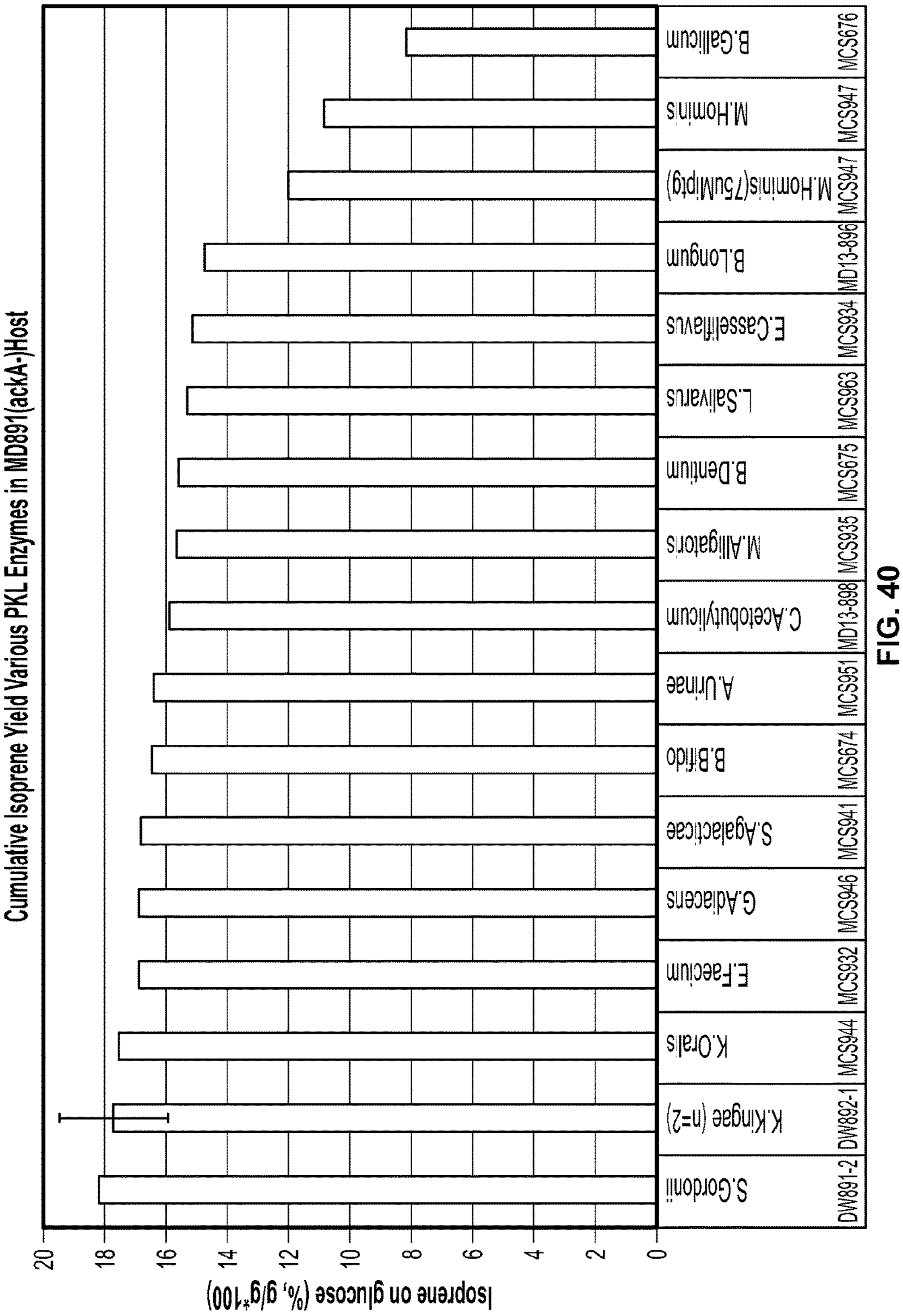
FIG. 40 depicts the cumulative isoprene yield of various PKL enzymes in an MD891(ackA-)host.
Figure 41:
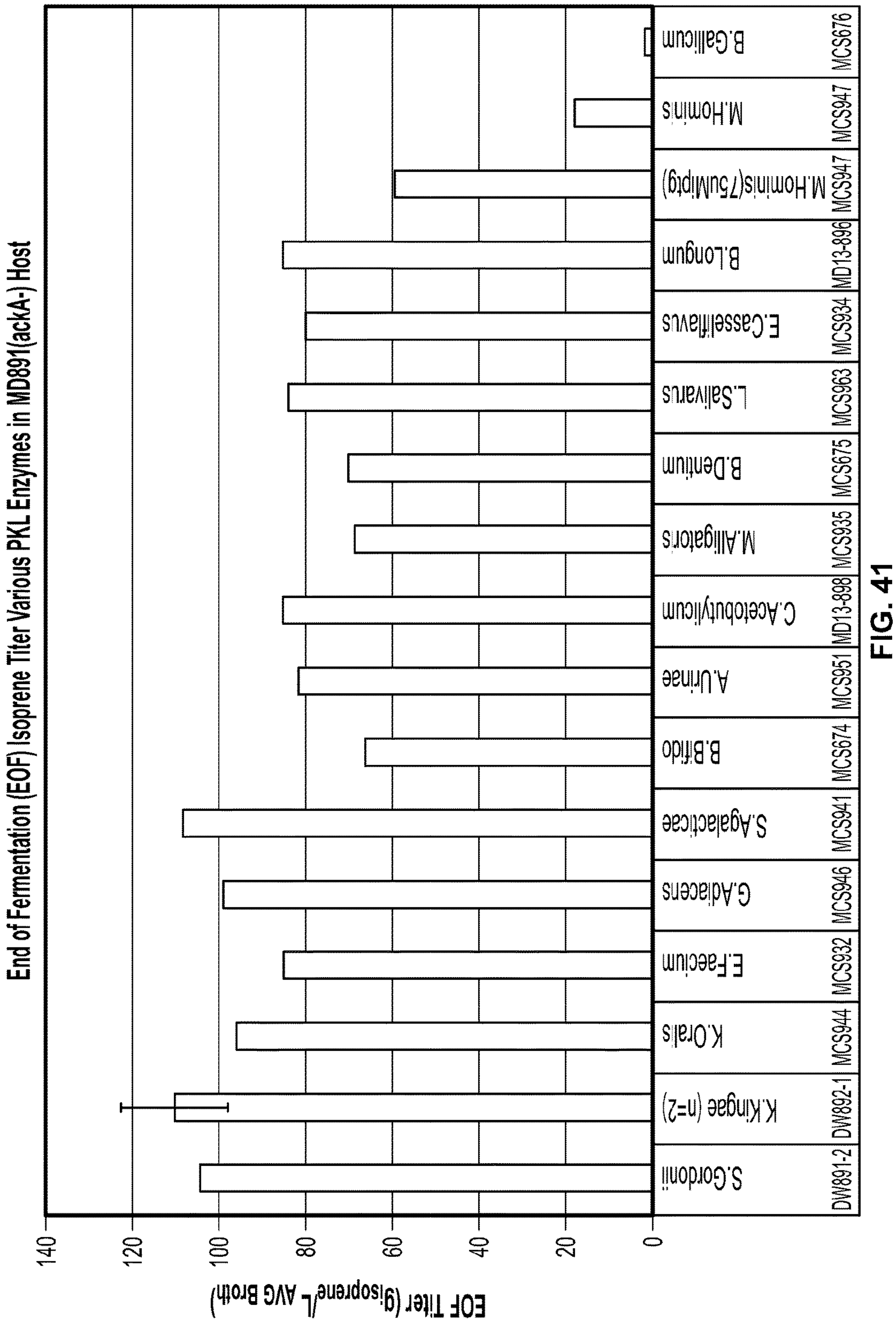
FIG. 41 depicts end of fermentation (EOF) isoprene titer of various PKL enzymes in an MD891(ackA-)host.
Figure 42:
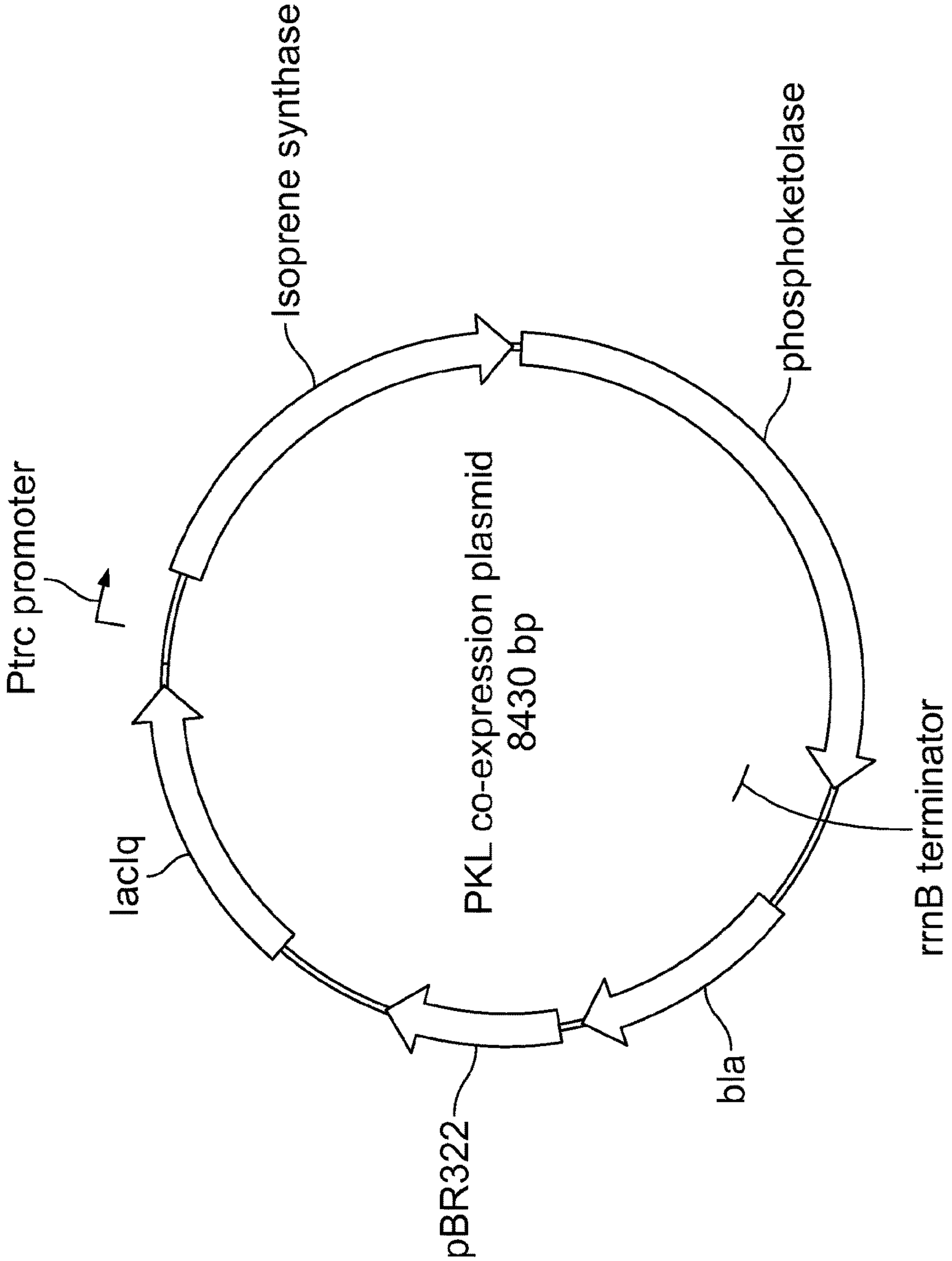
FIG. 42 depicts a generic plasmid map of a plasmid suitable for co-expression of PKL in accordance with any of the compositions, cells, or methods disclosed herein.

The results are depicted graphically in FIGS. 40 and 41 and illustrated in Table 15.

TABLE 18

Isoprene Productivity Metrics

| Strain Name | PKL (in MD891ackA- host) | Avg EOF Isoprene Titer (g/L) | Avg Cumulative Yield (g/g*100) |
|---|---|---|---|
| DW891-2 | *S. gordonii* | 104.36 | 18.20 |
| DW892-1 | *K. kingae* | 110.32 | 17.73 |
| MCS944 | *K. oralis* | 96.11 | 17.57 |
| MCS932 | *E. faecium* | 84.76 | 16.92 |
| MCS946 | *G. adiacens* | 99.20 | 16.86 |
| MCS941 | *S. agalacticae* | 108.37 | 16.83 |
| MCS674 | *B. bifido* | 66.12 | 16.46 |
| MCS951 | *A. urinae* | 81.77 | 16.41 |
| MD13-898 | *C. acetobutylicum* | 85.13 | 15.90 |
| MCS935 | *M. alligatoris* | 68.48 | 15.67 |
| MCS675 | *B. dentium* | 70.15 | 15.66 |
| MCS963 | *L. salivarus* | 83.91 | 15.32 |
| MCS934 | *E. casseliflavus* | 80.17 | 15.07 |
| MD13-896 | *B. longum* | 85.09 | 14.74 |
| MCS947 | *M. hominis* (decreased IPTG) | 59.42 | 12.04 |
| MCS947 | *M. hominis* | 17.69 | 10.84 |
| MCS676 | *B. gallicum* | 2.12 | 8.17 |

Example 22: In Vivo Evaluation of Growth in PKL Expressing Strains Blocked for Glycolysis and Pentose Phosphate Pathways For analysis of PKL enzyme activity in a strain blocked for glycolysis and pentose phosphate pathways, a subset of expression plasmids was transformed into strain MD1041 (HMB GI1.2gltA yhfSFRTPyddVIspAyhfS thiFRTtruncIspA pgl ML, FRT-PL.2-2cis-RBS10000-MVK(burtonii), t zwf::FRT, t pfkA::Frt+t ackA::FRT, t pfkB::Frt) using standard molecular biology techniques. Individual transformants were grown overnight in LB, diluted into TM3 medium with 1% glucose-6-phosphate (Sigma) as the carbon source, and induced with 0, 20, 40, 60, 80, 100, 200, or 400 μM IPTG. Strains were assayed for growth performance on the Enzyscreen Growth Profiler in comparison to MD1041 control strains that did not express any PKL (and therefore did not grow), expressed the PKL enzyme from *E. gallinarum* (and were representative of baseline performance), or WT strains that had no metabolic block in glycolysis or pentose phosphate pathways (as a control for optimal growth).

To calculate performance index (PI) for growth, MD1041 derivative strains that expressed experimental PKL enzymes were compared to MCS1148, a strain that expressed the PKL from *E. gallinarum* (see Table 1 for strain list). The 35 hour time point and 100 μM IPTG induction level were chosen as representative of general performance throughout the growth curve. To normalize values between assay plates, a correction factor, based on the difference between max OD values of WT strains, of 1.279 was applied to all values in the plate that did not contain the control strain expressing *E. gallinarum* PKL. PI was then calculated by dividing the corrected experimental OD value by the OD value of MCS1148 at the 35 hour time point. The PI of MCS1148 was therefore 1.0, and any value higher than this indicated an X-fold improvement to growth in this assay. PI values are shown in Table 19.

TABLE 19

PI values in PKL expressing strains Blocked for Glycolysis and Pentose Phosphate Pathways

| Strain | PKL | PI Growth at 35 hours |
|---|---|---|
| MD1059 | No PKL | 0.167 |
| MCS1106 | pMCS811 (pTrc_IspS_PKL1 [*E. faecium*]) | 0.606 |
| MCS1108 | pMCS813(pTrc_IspS_PKL3 [*E. casseliflavus*]) | 0.328 |
| MCS1109 | pMCS814(pTrc_IspS_PKL4[*M. alligatoris*]) | 0.740 |
| MCS1116 | pMCS821(pTrc_IspS_PKL11[*M. agalacticae*]) | 0.579 |
| MCS1118 | pMCS823 (pTrc_IspS_PKL13 [*K. orails*]) | 1.761 |
| MCS1120 | pMCS825 (pTrc_IspS_PKL15 [*G. adiacens*]) | 0.560 |
| MCS1121 | pMCS826 (pTrc_IspS_PKL16 [*M. hominis*]) | 0.824 |
| MCS1123 | pMCS828 (pTrc_IspS_PKL18 [*Neissaria*]) | 0.262 |
| MCS1124 | pMCS829 (pTrc_IspS_PKL19 [*E. coleocola*]) | 0.164 |
| MCS1125 | pMCS830 (pTrc_IspS_PKL20 [*A. urinae*]) | 1.090 |
| MCS1126 | pMCS831(pTrc_IspS_PKL21 [*K. kingae*]) | 0.607 |
| MCS1127 | pMCS832(pTrc_IspS_PKL22 [*S. criceti* #1]) | 0.099 |
| MCS1128 | pMCS833(pTrc_IspS_PKL23 [*S. criceti* #2]) | 0.587 |
| MCS1137 | pMCS842(pTrc_IspS_PKL32 [*L. salivarius*]) | 0.125 |
| MCS1148 | pMCS625 (pEWL1421 = pTrc_IspS_*gallinarum*PKL) | 1.000 |
| MCS1150 | pMCS644 (pTrc_IspS_*dentium*PKL) | 0.116 |
| MCS1152 | pMCS646 (pTrc_IspS_*acetobutylicum* optimizedPKL) | 0.163 |
| MCS1153 | pMCS647 (pTrc_IspS_truncatedmMVK; gi1.6_*acetobutylicum* optimized PKL | 1.727 |
| MCS1162 | pMCS1008 (pTrc_IspS_PKL-ANC110) | 0.239 |
| MCS1168 | pMCS1019 (pTrc_IspS_RBS3_PKL16 [*M. hominis*]) | 0.120 |

What is claimed is:

1. A recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 or SEQ ID NO:11 and (ii) one or more nucleic acids encoding one or more polypeptides of the complete mevalonate (MVA) pathway, wherein the recombinant cell is a recombinant *Escherichia coli* cell, and wherein (1) said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate, wherein the Performance Index value is calculated as activity per unit relative to a corresponding cell expressing a phosphoketolase from *E. gallinarum* or (2) said polypeptide having phosphoketolase activity of (i) has a Performance Index value of greater than 1.0 in one or more of the following parameters: (e) protein solubility, (f) protein expression, or (g) fructose-6-phosphate (F6P) Specific Activity, wherein the Performance Index value is calculated as activity per unit relative to a phosphoketolase from *E. gallinarum.*

2. The recombinant cell of claim 1, wherein the polypeptide comprises at least 65% sequence identity to SEQ ID NO:8 and wherein the polypeptide comprises at least 90% sequence identity to a polypeptide selected from the group consisting of SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

3. The recombinant cell of claim 1, wherein the polypeptide comprises at least 65% sequence identity to SEQ ID NO:11 and wherein the polypeptide comprises at least 90% sequence identity to a polypeptide selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

4. The recombinant cell of claim 1, wherein culturing of the recombinant cell in a suitable media increases one or more of an intracellular amount of erythrose 4-phosphate, an intracellular amount of glyceraldehyde 3-phosphate, or intracellular amount phosphate.

5. The recombinant cell of claim 1, wherein the polypeptide having phosphoketolase activity is capable of synthesizing glyceraldehyde 3-phosphate and acetyl phosphate from xylulose 5-phosphate.

6. The recombinant cell of claim 1, wherein the polypeptide having phosphoketolase activity is capable of synthesizing erythrose 4-phosphate and acetyl phosphate from fructose 6-phosphate.

7. The recombinant cell of claim 1, wherein the one or more polypeptides of the complete MVA pathway is selected from (a) acetyl-CoA acetyltransferase; (b) 3-hydroxy-3-methylglutaryl-CoA synthase; (c) 3-hydroxy-3-methylglutaryl-CoA reductase; (d) mevalonate kinase; (e) phosphomevalonate kinase; and (f) diphosphomevalonate decarboxylase.

8. The recombinant cell of claim 1, further comprising a heterologous nucleic acid encoding an isoprene synthase polypeptide, wherein culturing of the recombinant cell in a suitable media provides for the production of isoprene with a Performance Index value of greater than 1.0 in one or more of the following parameters: (h) isoprene yield or (i) isoprene specific productivity.

9. The recombinant cell of claim 8, wherein the isoprene synthase polypeptide is a plant isoprene synthase polypeptide.

10. The recombinant cell of claim 9, wherein the plant isoprene synthase polypeptide is a polypeptide from *Pueraria* or *Populus* or a hybrid, *Populus alba*×*Populus tremula.*

11. The recombinant cell of claim 9, wherein the plant isoprene synthase polypeptide is a polypeptide from *Pueraria montana, Pueraria lobata, Populus tremuloides, Populus alba, Populus nigra, or Populus trichocarpa.*

12. The recombinant cell of claim 8, wherein the recombinant cell further comprises one or more nucleic acids encoding one or more 1-deoxy-D-xylulose 5-phosphate (DXP) pathway polypeptides.

13. The recombinant cell of claim 1, further comprising a heterologous nucleic acid encoding a polyprenyl pyrophosphate synthase polypeptide, wherein culturing of the recombinant cell in a suitable media provides for the production of isoprenoids.

14. The recombinant cell of claim 1, wherein culturing of the recombinant cell in a suitable media provides for the production of an acetyl CoA-derived metabolite.

15. The recombinant cell of claim 13, wherein the isoprenoid is selected from the group consisting of monoterpenes, diterpenes, triterpenes, tetraterpenes, sequiterpene, and polyterpene.

16. The recombinant cell of claim 13, wherein the isoprenoid is selected from the group consisting of abietadiene, amorphadiene, carene, α-farnesene, 13-farnesene, farnesol, geraniol, geranylgeraniol, linalool, limonene, myrcene, nerolidol, ocimene, patchoulol, 13-pinene, sabinene, γ-terpinene, terpindene and valencene.

17. The recombinant cell of claim 14, wherein the acetyl CoA-derived metabolite is selected from the group consisting of polyketides, polyhydroxybutyrate, fatty alcohols, amino acids, and fatty acids.

18. The recombinant cell of claim 14, wherein the acetyl CoA-derived metabolite is selected from the group consisting of acetone, isopropanol, isobutene, and propene.

19. A method of producing isoprene comprising: (a) culturing the recombinant cell of claim 8 under conditions suitable for producing isoprene and (b) producing isoprene.

20. A method of producing an isoprenoid comprising: (a) culturing the recombinant cell of claim 13 under conditions suitable for producing an isoprenoid and (b) producing an isoprenoid.

* * * * *

SEQUENCE LISTING

<160> NUMBER OF SEQ ID NOS: 142

<210> SEQ ID NO 1
<211> LENGTH: 823

```
<212> TYPE: PRT
<213> ORGANISM: Mycobacterium gilvum Spyr1

<400> SEQUENCE: 1

Met Thr Thr Ala Thr Thr Ala Glu Arg Arg Pro Leu Ser Asp Gln Asp
 1               5                  10                  15

Val Asp Arg Leu Asp Arg Trp Trp Arg Ala Ala Asn Tyr Leu Ser Val
            20                  25                  30

Gly Gln Ile Tyr Leu Leu Asp Asn Pro Leu Leu Arg Thr Pro Leu Thr
        35                  40                  45

Arg Glu Asp Val Lys Pro Arg Leu Leu Gly His Trp Gly Thr Thr Pro
    50                  55                  60

Gly Leu Asn Phe Leu Tyr Ala His Leu Asn Arg Ala Ile Ala Gln Arg
65                  70                  75                  80

Gln Gln Ser Thr Ile Tyr Val Thr Gly Pro Gly His Gly Gly Pro Gly
                85                  90                  95

Leu Val Ala Asn Ala Tyr Leu Asp Gly Thr Tyr Ser Glu Ile Tyr Ser
            100                 105                 110

Asp Ile Thr Gln Asp Asp Glu Gly Leu Arg Arg Leu Phe Arg Gln Phe
        115                 120                 125

Ser Phe Pro Gly Gly Ile Pro Ser His Val Ala Pro Glu Thr Pro Gly
    130                 135                 140

Ser Ile His Glu Gly Gly Glu Leu Gly Tyr Ala Leu Ser His Ala Tyr
145                 150                 155                 160

Gly Ala Ala Phe Asp Asn Pro Asp Leu Leu Val Ala Ala Val Val Gly
                165                 170                 175

Asp Gly Glu Ala Glu Thr Gly Pro Leu Ala Thr Ser Trp His Ser Asn
            180                 185                 190

Lys Phe Val Asn Ala Ala Lys Asp Gly Ala Val Leu Pro Ile Leu His
        195                 200                 205

Leu Asn Gly Tyr Lys Ile Ala Asn Pro Thr Leu Leu Ala Arg Ile Pro
    210                 215                 220

Thr Asp Glu Leu Arg Ala Leu Met Val Gly Tyr Gly His His Pro Tyr
225                 230                 235                 240

Phe Phe Glu Val Pro Asp Asp Glu Gly Gly Pro Gly Val Asp His Ala
                245                 250                 255

Asp Ala His Arg Arg Phe Ala Arg Leu Leu Asp Asp Val Leu Asp Glu
            260                 265                 270

Ile Ala Asp Ile Lys Thr Arg Ala Arg Glu Gly Asp Glu Ser Arg Pro
        275                 280                 285

Ala Trp Pro Met Ile Val Phe Arg Thr Pro Lys Gly Trp Thr Gly Pro
    290                 295                 300

Asp Tyr Ile Asp Gly Lys Lys Thr Thr Gly Ser Trp Arg Ala His Gln
305                 310                 315                 320

Val Pro Leu Ser Asn Ala Arg Asp Thr Lys Glu His Leu Ala Val Leu
                325                 330                 335

Ser Asp Trp Leu Ser Ser Tyr Arg Pro Asp Glu Leu Phe Asp Ala Asp
            340                 345                 350

Gly Arg Leu Leu Pro Glu Ile Ala Glu Leu Ala Pro Ser Gly Gln Leu
        355                 360                 365

Arg Met Ser Asp Asn Ala His Ala Asn Gly Gly Leu Leu Leu Lys Asp
    370                 375                 380

Leu Arg Leu Pro Asp Phe Arg Glu Tyr Ala Val Asp Val Pro Ala Pro
385                 390                 395                 400
```

-continued

Gly Ala Thr Val Ala Glu Ala Thr Arg Val Leu Gly Gln Trp Leu Thr
405 410 415

Glu Val Ile Arg Leu Asn Pro Asp Asn Phe Arg Ile Phe Gly Pro Asp
420 425 430

Glu Thr Ala Ser Asn Arg Leu Gln Ala Val Tyr Asp Ala Thr Asp Lys
435 440 445

Gln Trp Asn Ala Glu Phe Phe Gly Ala Glu Val Asp Glu His Leu Ala
450 455 460

Arg Ala Gly Arg Val Val Glu Met Leu Ser Glu His Gln Cys Gln Gly
465 470 475 480

Trp Leu Glu Gly Tyr Leu Leu Thr Gly Arg His Gly Leu Phe Asn Cys
485 490 495

Tyr Glu Ala Phe Ile His Ile Val Asp Ser Met Leu Asn Gln His Ala
500 505 510

Lys Trp Leu Lys Val Thr Asn His Ile Pro Trp Arg Arg Pro Ile Ala
515 520 525

Ser Leu Asn Tyr Leu Leu Ser Ser His Val Trp Arg Gln Asp His Asn
530 535 540

Gly Phe Ser His Gln Asp Pro Gly Phe Ile Asp His Val Val Asn Lys
545 550 555 560

Ser Ala Lys Val Val Arg Val Tyr Leu Pro Pro Asp Ala Asn Thr Leu
565 570 575

Leu Ser Thr Tyr Asp His Cys Leu Arg Ser Arg Gln Tyr Val Asn Val
580 585 590

Val Val Ser Gly Lys Gln Pro Ser Pro Asn Phe Leu Thr Met Glu Gln
595 600 605

Ala Val Ala His Cys Thr Arg Gly Leu Gly Ile Trp Glu Trp Ala Gly
610 615 620

Ser Glu Glu Leu Gly Thr Asp Pro Asp Val Val Leu Ala Ser Ala Gly
625 630 635 640

Asp Ile Pro Thr Leu Glu Ala Leu Ala Ala Ala Asp Ile Leu Arg Gln
645 650 655

His Leu Pro Asp Leu Lys Val Arg Phe Val Asn Val Val Asp Leu Met
660 665 670

Arg Leu Gln Asp Ser Thr Glu His Pro His Gly Leu Pro Asp Arg Asp
675 680 685

Phe Asp Met Ile Phe Thr Thr Asp Arg Pro Ile Ile Phe Ala Tyr His
690 695 700

Gly Tyr Pro Trp Leu Ile His Arg Leu Thr Tyr Arg Arg Ala Gly His
705 710 715 720

Asp Asn Leu His Val Arg Gly Tyr Lys Glu Glu Gly Thr Thr Thr Thr
725 730 735

Pro Phe Asp Met Val Met Leu Asn Asp Leu Asp Arg Tyr His Leu Val
740 745 750

Met Asp Val Ile Asp Arg Val Pro Ser Leu Gly Ser Thr Cys Ala Ala
755 760 765

Leu Arg Gln Gln Met Ala Asp Lys Arg Ile Ala Ala Arg Glu Tyr Thr
770 775 780

Arg Ala His Gly Glu Asp Ile Pro Glu Val Lys Asp Trp Val Trp Pro
785 790 795 800

Ala Ala Arg Glu Ser Gly Phe Gly Thr Ala Gly Ala Asp Gly Ala Ser
805 810 815

Ser Thr Gly Gly Asp Asn Glu
820

<210> SEQ ID NO 2
<211> LENGTH: 788
<212> TYPE: PRT
<213> ORGANISM: Shewanella baltica OS185

<400> SEQUENCE: 2

Met Thr Gln Ile His Glu Ile Asn Ala Leu Lys Lys Tyr Val Arg Ala
1 5 10 15

Thr Asn Phe Leu Ala Thr Ser Gln Ile Tyr Leu Lys Gln Asn Val Leu
20 25 30

His Lys Arg Pro Leu Ala His Thr Asp Ile Lys Pro Arg Leu Leu Gly
35 40 45

His Trp Gly Thr Cys Pro Gly Ile Asn Phe Val Tyr Ala Asn Ile Asn
50 55 60

Arg Leu Ile Val Lys His Asn Arg Ser Phe Ile Tyr Leu Val Gly Pro
65 70 75 80

Gly His Gly Phe Pro Ala Val Gln Ala Asn Leu Phe Met Glu Gly Ser
85 90 95

Leu Ser His Phe Tyr Pro Glu Thr Ile Pro Tyr Asn Glu Thr Gly Ile
100 105 110

Glu Asp Ile Cys Lys Lys Phe Ser Ala Ala Tyr Gly Tyr Pro Ser His
115 120 125

Ala Asn Pro Glu Ala Pro Gly Gln Ile Leu Glu Gly Gly Glu Leu Gly
130 135 140

Tyr Ser Leu Ser Val Gly Trp Gly Ala Val Leu Asp Asn Pro Asp Leu
145 150 155 160

Ile Ala Thr Val Leu Ile Gly Asp Gly Glu Ala Glu Thr Gly Pro Leu
165 170 175

Ala Ala Ser Trp Tyr Ala Asn Arg Leu Val Ser Pro Ala Thr Ser Gly
180 185 190

Ala Val Leu Pro Ile Val His Ile Asn Gly Tyr Lys Ile Ser Gly Pro
195 200 205

Thr Arg Met Gly Arg Met Ser His Glu Glu Leu Asp Leu Glu Phe Arg
210 215 220

Gly Leu Gly Tyr Phe Pro Ile Ile Val Asp Asn Glu Leu Glu Glu Asp
225 230 235 240

Ile Tyr Val Gln Met Thr Asn Ala Met Asp Thr Ala Tyr Ala Met Ile
245 250 255

Asn Asp Ile Gln Arg Arg Ala Arg Ser Gly Glu Asp Val Val Lys Pro
260 265 270

Lys Trp Pro Val Ile Leu Met Arg Thr Ala Lys Gly Trp Thr Gly Val
275 280 285

Ser Glu Tyr Lys Gly Lys Lys Leu Glu Gly Asn Cys Glu Ser His Gln
290 295 300

Val Ile Val Asn Lys Cys Ala Thr Asp Lys Gly His Leu Asp Ala Leu
305 310 315 320

Asp Asn Trp Leu Ala Ser Tyr His Phe Gln Glu Leu Tyr Gln Met Asn
325 330 335

Asp Lys Gly Glu Leu Ile Phe Asp Ala Asp Ile Cys Ser Leu Ile Pro
340 345 350

Pro Lys Gln Leu Ala Cys Gly Arg Gln His Leu Thr Tyr Gly Gly Glu
355 360 365

-continued

```
Val Val Arg Ala Leu Thr Asn Pro Asp Leu Glu Lys Leu Ser Tyr Gly
    370                 375                 380

Pro Glu Val Pro Arg Gly His Arg Gly Tyr Ser Met Leu Lys Met Gly
385                 390                 395                 400

Glu Trp Met Arg Asp Ala Phe Lys Leu Asn Arg Asp Gln Arg Asn Leu
                405                 410                 415

Arg Ile Phe Ser Pro Asp Glu Thr Tyr Ser Asn Gln Leu Gln Ala Val
            420                 425                 430

Phe Glu Glu Thr Asp Arg Ala Trp Gln Trp Pro Ile Glu Ser Trp Asp
        435                 440                 445

Glu Asp Met Ser Arg Glu Gly Arg Val Ile Glu Leu Leu Ser Glu Asn
    450                 455                 460

Leu Leu Phe Gly Met Leu His Gly Tyr Thr Val Thr Gly Arg His Gly
465                 470                 475                 480

Met Phe Pro Thr Tyr Glu Ser Phe Ser Gln Val Ile Ser Ser Met Ala
                485                 490                 495

Asp Gln Tyr Cys Lys Tyr Val Tyr Ala Ser Gln Gly Val His Phe Arg
            500                 505                 510

Lys Pro Leu Pro Ser Cys Asn Val Val Leu Ser Ser Leu Leu Glu Arg
        515                 520                 525

Gln Asp His Asn Gly Tyr Ser His Gln Asn Pro Ser Phe Leu Gly Ala
    530                 535                 540

Met Leu Glu Lys His Pro Lys Ile Ile Ser Ala Tyr Leu Pro Ala Asp
545                 550                 555                 560

Ala Asn Ser Thr Leu Val Tyr Thr Glu Arg Ala Tyr Ala Asp Arg Asp
                565                 570                 575

Lys Leu Asn Ile Leu Val Ala Gly Lys Lys Glu Leu Pro Gln Trp Leu
            580                 585                 590

Ser Leu Glu Glu Ala Arg Lys Gln Ala Lys Asp Gly Val Met Val Trp
        595                 600                 605

Asp Phe Ala Ser Asp Glu Asn Pro Asp Ile Val Leu Ala Gly Cys Gly
    610                 615                 620

Asp Tyr Val Thr Gln Glu Cys Met Ala Ser Leu Val Leu Ile Arg Glu
625                 630                 635                 640

Leu Leu Pro Arg Val Lys Ile Arg Phe Val Ser Val Thr Glu Leu Ser
                645                 650                 655

Ser Asp Gly Leu Gly Ser Arg Lys Phe Lys Glu Lys Pro Trp Leu Met
            660                 665                 670

Asp Glu Ile Phe Thr Gln Asp Lys Gly Val Val Phe Asn Tyr His Gly
        675                 680                 685

Tyr Pro Asn Thr Ile Lys Lys Leu Ile Phe Asp Tyr Lys Gly Ser Arg
    690                 695                 700

Arg Phe Arg Ile Lys Gly Tyr Glu Glu Glu Gly Ser Thr Thr Thr Pro
705                 710                 715                 720

Phe Asp Met Gly Val Arg Asn Gly Thr Ser Arg Tyr His Leu Val Ile
                725                 730                 735

Asp Met Ala Tyr Lys Leu Phe Gln Gln Gly Val Ile Asp Glu Thr Met
            740                 745                 750

His Val Ser Ile Thr Thr Asp Met Leu Gln Arg Leu Val Asp His Arg
        755                 760                 765

Asn Tyr Ile Lys Ala Asn Gly Val Asp Pro Ile Glu Ile Glu Asn Trp
    770                 775                 780
```

```
Ile Trp Thr Arg
785


<210> SEQ ID NO 3
<211> LENGTH: 795
<212> TYPE: PRT
<213> ORGANISM: Lactobacillus rhamnosus LMS2-1

<400> SEQUENCE: 3

Met Ser Met Asp Thr Lys Val Lys Thr Val Asp Tyr Ser Ser Lys Glu
 1               5                  10                  15

Tyr Phe Asp Lys Met Thr Ala Tyr Trp Arg Ala Ala Asn Tyr Val Ser
            20                  25                  30

Val Gly Gln Leu Tyr Leu Lys Asp Asn Pro Leu Leu Glu Arg Pro Leu
        35                  40                  45

Lys Ser Glu Asp Val Lys Pro His Pro Ile Gly His Trp Gly Thr Ile
    50                  55                  60

Ala Gly Gln Asn Phe Ile Tyr Thr His Leu Asn Arg Val Ile Asn Lys
65                  70                  75                  80

Tyr Asp Leu Asn Met Phe Tyr Ile Glu Gly Pro Gly His Gly Gly Gln
                85                  90                  95

Val Met Val Ser Asn Ser Tyr Leu Asp Gly Ser Tyr Ser Glu Ile Tyr
            100                 105                 110

Pro Arg Val Ser Gln Asp Lys Glu Gly Met Lys Asn Leu Phe Thr Gln
        115                 120                 125

Phe Ser Trp Pro Gly Gly Val Ala Ser His Ala Ser Ala Gln Thr Pro
    130                 135                 140

Gly Ser Ile His Glu Gly Gly Glu Leu Gly Tyr Ala Leu Ser His Ala
145                 150                 155                 160

Thr Gly Ala Ile Leu Asp Asn Pro Asp Val Ile Ala Ala Val Val Thr
                165                 170                 175

Gly Asp Gly Glu Thr Glu Thr Gly Pro Leu Ala Ala Ser Trp Phe Ser
            180                 185                 190

Asn Thr Phe Ile Asn Pro Ile Ser Asp Gly Ala Ile Leu Pro Ile Val
        195                 200                 205

His Met Asn Gly Phe Lys Ile Ser Asn Pro Thr Ile Leu Ser Arg Lys
    210                 215                 220

Ser Asp Glu Asp Leu Thr Lys Tyr Phe Glu Gly Met Gly Trp Lys Pro
225                 230                 235                 240

Tyr Phe Val Glu Gly Asp Asp Pro Thr Lys Leu Asn Pro Glu Met Ala
                245                 250                 255

Lys Val Met Asp Ala Ala Ile Glu Glu Ile Lys Ala Ile Gln Lys His
            260                 265                 270

Ala Arg Glu Thr Gly Asp Thr Thr Met Pro His Trp Pro Val Ile Ile
        275                 280                 285

Phe Arg Ser Pro Lys Gly Trp Thr Gly Pro Lys Ser Trp Asn Gly Glu
    290                 295                 300

Pro Ile Glu Gly Ser Phe Arg Ala His Gln Ile Pro Ile Pro Val Asp
305                 310                 315                 320

Ala Glu Asp Met Glu His Ala Asp Ser Leu Ala Gly Trp Leu Lys Ser
                325                 330                 335

Tyr His Pro Glu Glu Leu Phe Asp Glu Asn Gly Lys Leu Ile Pro Glu
            340                 345                 350

Leu Ala Ala Leu Pro Pro Lys Gly Asp Lys Arg Met Ala Ala Asn Pro
        355                 360                 365
```

-continued

```
Ile Thr Asn Gly Gly Leu Asp Pro Lys Pro Leu Val Leu Pro Asp Tyr
    370                 375                 380

Arg Lys Tyr Ala Leu Asp Asn Lys Glu His Gly Lys Gln Ile Lys Gln
385                 390                 395                 400

Asp Met Ile Val Trp Ser Asp Tyr Leu Arg Asp Leu Ile Lys Leu Asn
                405                 410                 415

Pro His Asn Phe Arg Ile Phe Gly Pro Asp Glu Thr Met Ser Asn Arg
            420                 425                 430

Leu Tyr Ser Leu Phe Glu Val Thr Asn Arg Gln Trp Leu Glu Pro Ile
        435                 440                 445

Lys Glu Pro Ala Asp Gln Tyr Leu Ala Pro Ala Gly Arg Ile Ile Asp
    450                 455                 460

Ser Gln Leu Ser Glu His Gln Ser Glu Gly Phe Asn Glu Gly Tyr Thr
465                 470                 475                 480

Leu Thr Gly Arg His Gly Leu Phe Thr Ser Tyr Glu Ala Phe Leu Arg
                485                 490                 495

Val Val Asp Ser Met Leu Thr Gln His Phe Lys Trp Ile Arg Lys Ala
            500                 505                 510

His Glu Glu Pro Trp His Lys Ala Tyr Pro Ser Leu Asn Val Val Ser
        515                 520                 525

Thr Ser Thr Ser Phe Gln Gln Asp His Asn Gly Tyr Thr His Gln Asp
    530                 535                 540

Pro Gly Ile Leu Thr His Met Ala Glu Lys Lys Ala Glu Tyr Ile Arg
545                 550                 555                 560

Glu Tyr Leu Pro Ala Asp Ala Asn Ser Leu Leu Ala Ile Ser Pro Lys
                565                 570                 575

Leu Phe Ser Ser Gln Asn Thr Val Asn Val Leu Ile Thr Ser Lys Gln
            580                 585                 590

Pro Arg Pro Gln Phe Tyr Ser Ile Asp Glu Ala Thr Val Leu Ala Asn
        595                 600                 605

Ala Gly Leu Lys Arg Ile Asp Trp Ala Ser Asn Asp Asp Gly Val Glu
    610                 615                 620

Pro Asp Val Val Ile Ala Ala Ala Gly Thr Glu Pro Asn Met Glu Ser
625                 630                 635                 640

Leu Ala Ala Ile Asn Leu Leu His Asp Ala Phe Pro Asp Leu Lys Ile
                645                 650                 655

Arg Phe Ile Asn Val Leu Asp Leu Leu Lys Leu Arg Ser Pro Glu Ile
            660                 665                 670

Asp Pro Arg Gly Leu Ser Asp Ala Glu Phe Asn Ser Tyr Phe Thr Thr
        675                 680                 685

Asp Lys Pro Ile Leu Phe Ala Tyr His Gly Phe Glu Gly Leu Ile Arg
    690                 695                 700

Asp Ile Phe Phe Thr Arg Gln Asn Arg Asn Val Leu Ile His Gly Tyr
705                 710                 715                 720

Arg Glu Glu Gly Asp Ile Thr Thr Pro Phe Asp Met Arg Val Leu Asn
                725                 730                 735

Glu Leu Asp Arg Phe His Leu Ala Lys Asp Val Ile Gln His Val Pro
            740                 745                 750

Ala Tyr Ala Glu Lys Ala Ala Ala Phe Val Gln Lys Met Asp Asp Thr
        755                 760                 765

Leu Gln Tyr His His Asp Phe Ile Arg Ala Asn Gly Glu Asp Ile Pro
    770                 775                 780
```

Glu Val Gln Glu Trp Thr Trp Lys Ser Ile Lys
785 790 795

<210> SEQ ID NO 4
<211> LENGTH: 799
<212> TYPE: PRT
<213> ORGANISM: Lactobacillus crispatus ST1

<400> SEQUENCE: 4

Met Ala Val Asp Tyr Asp Ser Lys Asp Tyr Leu Lys Ser Val Asp Ala
1 5 10 15

Tyr Trp Arg Ala Ala Asn Tyr Leu Ser Val Gly Gln Leu Phe Leu Met
20 25 30

Lys Asn Pro Leu Leu Lys Thr Pro Leu Val Ala Glu Asp Val Lys Pro
35 40 45

Lys Pro Ile Gly His Trp Gly Thr Ile Ala Pro Gln Asn Phe Ile Tyr
50 55 60

Ala His Leu Asn Arg Val Leu Lys Lys Tyr Asp Leu Asn Met Phe Tyr
65 70 75 80

Ile Glu Gly Ser Gly His Gly Gly Gln Val Met Val Ser Asn Ser Tyr
85 90 95

Leu Asp Gly Ser Tyr Thr Glu Arg Tyr Pro Glu Ile Thr Gln Asp Glu
100 105 110

Lys Gly Met Ala Lys Leu Phe Lys Arg Phe Ser Phe Pro Gly Gly Val
115 120 125

Ala Ser His Ala Ala Pro Glu Thr Pro Gly Ser Ile His Glu Gly Gly
130 135 140

Glu Leu Gly Tyr Ser Leu Ser His Gly Thr Gly Ala Val Leu Asp Asn
145 150 155 160

Pro Asp Val Ile Ala Ala Val Glu Ile Gly Asp Gly Glu Ala Glu Thr
165 170 175

Gly Pro Leu Ala Ala Ser Trp Phe Ser Asp Lys Phe Ile Asn Pro Ile
180 185 190

Lys Asp Gly Ala Val Leu Pro Ile Leu Gln Ile Asn Gly Phe Lys Ile
195 200 205

Ser Asn Pro Thr Ile Val Ser Arg Met Ser Asp Gln Glu Leu Thr Glu
210 215 220

Tyr Phe Arg Gly Met Gly Trp Asp Pro His Phe Val Ser Val Phe Lys
225 230 235 240

Gly Gly Arg Phe Asp Gly Glu Lys Asp Pro Met Gln Val His Glu Glu
245 250 255

Met Ala Lys Thr Met Asp Glu Val Ile Glu Glu Ile Lys Ala Ile Gln
260 265 270

Lys His Ala Arg Glu Asn Asn Asp Ala Thr Leu Pro His Trp Pro Met
275 280 285

Ile Ile Phe Gln Cys Pro Lys Gly Trp Thr Gly Pro Lys Lys Asp Leu
290 295 300

Asp Gly Asn Pro Ile Glu Asn Ser Phe Arg Ala His Gln Ile Pro Ile
305 310 315 320

Pro Val Ala Gln Gly Asp Met Glu His Ala Asp Met Leu Thr Asp Trp
325 330 335

Leu Glu Ser Tyr Lys Pro Glu Glu Leu Phe Asn Glu Asp Gly Ser Pro
340 345 350

Lys Glu Ile Val Thr Glu Asn Thr Ala Lys Gly Asp His Arg Met Ala
355 360 365

```
Met Asn Pro Ile Thr Asn Gly Gly Ile Asp Pro Lys Arg Leu Asn Leu
    370                 375                 380

Pro Asp Tyr Arg Lys Phe Ala Leu Lys Phe Asp Lys Pro Gly Ser Val
385                 390                 395                 400

Glu Ala Gln Asp Met Val Glu Trp Ala Lys Tyr Leu Asp Glu Val Ala
                405                 410                 415

Lys Leu Asn Pro Thr Thr Phe Arg Gly Phe Gly Pro Asp Glu Ser Lys
            420                 425                 430

Ser Asn Arg Leu Phe Gln Leu Leu Asp Asp Gln Lys Arg Gln Trp Glu
        435                 440                 445

Pro Glu Val His Glu Pro Asn Asp Glu Asn Leu Ala Pro Ser Gly Arg
    450                 455                 460

Val Ile Asp Ser Gln Leu Ser Glu His Gln Asp Glu Gly Phe Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
            500                 505                 510

Arg Lys Ala Lys Glu Gln Tyr Trp Arg His Asp Tyr Pro Ser Leu Asn
        515                 520                 525

Phe Val Ala Thr Ser Thr Val Phe Gln Gln Asp His Asn Gly Tyr Thr
    530                 535                 540

His Gln Asp Pro Gly Ile Leu Thr His Leu Tyr Glu Lys Asn Arg Pro
545                 550                 555                 560

Asp Leu Val His Glu Tyr Leu Pro Ser Asp Thr Asn Thr Leu Leu Ala
                565                 570                 575

Val Gly Asp Lys Ala Leu Gln Asp Arg Glu Cys Ile Asn Val Leu Val
            580                 585                 590

Thr Ser Lys Gln Pro Arg Pro Gln Trp Phe Ser Ile Glu Glu Ala Lys
        595                 600                 605

Lys Leu Val Asp Lys Gly Leu Gly Tyr Ile Asp Trp Ala Ser Thr Asp
    610                 615                 620

Lys Gly Ala Lys Pro Asp Val Val Phe Ala Ser Thr Glu Thr Glu Pro
625                 630                 635                 640

Thr Ile Glu Thr Leu Ala Ala Ile Asp Ile Leu His Lys Lys Phe Pro
                645                 650                 655

Asp Leu Lys Ile Arg Tyr Ile Asn Val Val Asp Val Met Lys Leu Met
            660                 665                 670

Asp Pro Lys Asp Asn Lys Asn Gly Leu Ser Thr Glu Glu Phe Asp Arg
        675                 680                 685

Leu Phe Pro Lys Asp Val Pro Val Ile Phe Ala Trp His Gly Tyr Lys
    690                 695                 700

Ser Met Met Glu Ser Ile Trp Phe Ala Arg Lys Arg Tyr Asn Val His
705                 710                 715                 720

Ile His Cys Tyr Glu Glu Asn Gly Asp Ile Thr Thr Pro Phe Asp Met
                725                 730                 735

Arg Val Leu Asn His Leu Asp Arg Phe Asp Leu Ala Lys Asp Ala Val
            740                 745                 750

Glu Ser Ile Asp Lys Leu Lys Gly Lys Asn Ala Asp Phe Ile Ser His
        755                 760                 765

Met Asp Asp Leu Leu Glu Lys His His Gln Tyr Ile Arg Asp Asn Gly
    770                 775                 780
```

Lys Asp Met Pro Glu Val Thr Glu Trp Gln Trp Ser Gly Leu Lys
785 790 795

<210> SEQ ID NO 5
<211> LENGTH: 825
<212> TYPE: PRT
<213> ORGANISM: Bifidobacterium longum subsp. longum JDM301

<400> SEQUENCE: 5

Met Thr Ser Pro Val Ile Gly Thr Pro Trp Lys Lys Leu Asn Ala Pro
1 5 10 15

Val Ser Glu Glu Ala Leu Glu Gly Val Asp Lys Tyr Trp Arg Val Ala
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Phe Ile Ala Asp His Gly Gln Asn Thr Val Ile Ile Met Gly Pro Gly
85 90 95

His Gly Gly Pro Ala Gly Thr Ser Gln Ser Tyr Leu Asp Gly Thr Tyr
100 105 110

Thr Glu Thr Phe Pro Lys Ile Thr Lys Asp Glu Ala Gly Leu Gln Lys
115 120 125

Phe Phe Arg Gln Phe Ser Tyr Pro Gly Gly Ile Pro Ser His Phe Ala
130 135 140

Pro Glu Thr Pro Gly Ser Ile His Glu Gly Gly Glu Leu Gly Tyr Ala
145 150 155 160

Leu Ser His Ala Tyr Gly Ala Ile Met Asp Asn Pro Ser Leu Phe Val
165 170 175

Pro Ala Ile Val Gly Asp Gly Glu Ala Glu Thr Gly Pro Leu Ala Thr
180 185 190

Gly Trp Gln Ser Asn Lys Leu Val Asn Pro Arg Thr Asp Gly Ile Val
195 200 205

Leu Pro Ile Leu His Leu Asn Gly Tyr Lys Ile Ala Asn Pro Thr Ile
210 215 220

Leu Ser Arg Ile Ser Asp Glu Glu Leu His Glu Phe Phe His Gly Met
225 230 235 240

Gly Tyr Glu Pro Tyr Glu Phe Val Ala Gly Phe Asp Asp Glu Asp His
245 250 255

Met Ser Ile His Arg Arg Phe Ala Glu Leu Trp Glu Thr Ile Trp Asp
260 265 270

Glu Ile Cys Asp Ile Lys Ala Ala Ala Gln Thr Asp Asn Val His Arg
275 280 285

Pro Phe Tyr Pro Met Leu Ile Phe Arg Thr Pro Lys Gly Trp Thr Cys
290 295 300

Pro Lys Tyr Ile Asp Gly Lys Lys Thr Glu Gly Ser Trp Arg Ala His
305 310 315 320

Gln Val Pro Leu Ala Ser Ala Arg Asp Thr Glu Ala His Phe Glu Val
325 330 335

Leu Lys Asn Trp Leu Glu Ser Tyr Lys Pro Glu Glu Leu Phe Asp Ala
340 345 350

Asn Gly Ala Val Lys Asp Asp Val Leu Ala Phe Met Pro Lys Gly Glu
355 360 365

-continued

```
Leu Arg Ile Gly Ala Asn Pro Asn Ala Asn Gly Gly Val Ile Arg Asp
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Ala Trp Asp Trp Ala Ser Thr Ala Lys Asn Asn Asp Glu Ala
625                 630                 635                 640

Glu Val Val Leu Ala Ala Ala Gly Asp Val Pro Thr Gln Glu Ile Met
                645                 650                 655

Ala Ala Ser Asp Lys Leu Lys Glu Leu Gly Val Lys Phe Lys Val Val
            660                 665                 670

Asn Val Ala Asp Leu Leu Ser Leu Gln Ser Ala Lys Glu Asn Asp Glu
        675                 680                 685

Ala Leu Thr Asp Glu Glu Phe Ala Asp Ile Phe Thr Ala Asp Lys Pro
    690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp
        755                 760                 765

Lys Tyr Ala Asp Lys Ile Asp Glu Leu Glu Lys Phe Arg Asp Glu Ala
    770                 775                 780
```

```
Phe Gln Phe Ala Val Asp Lys Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Ala Thr Ala Gly Asp Asn Glu
            820                 825


<210> SEQ ID NO 6
<211> LENGTH: 817
<212> TYPE: PRT
<213> ORGANISM: Leuconostoc citreum KM20

<400> SEQUENCE: 6

Met Ala Asp Phe Asp Ser Lys Glu Tyr Leu Glu Leu Val Asp Lys Trp
 1               5                  10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Gln Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Asp Leu Asn Met
65                  70                  75                  80

Phe Tyr Ile Gly Gly Pro Gly His Gly Gly Gln Val Met Val Thr Asn
                85                  90                  95

Ala Tyr Leu Asp Gly Glu Tyr Thr Glu Asp Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Ile Ala Phe Ala Val Val Gly Asp Gly Glu Ala
                165                 170                 175

Glu Thr Gly Pro Ser Met Thr Ser Trp His Ser Thr Lys Phe Leu Asn
            180                 185                 190

Ala Lys Asn Asp Gly Ala Val Leu Pro Ile Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Ala Tyr His Glu Leu Ala Ala Lys Val
                245                 250                 255

Leu Asp Gln Ala Ile Glu Asp Ile Gln Ala Ile Gln Lys Asp Ala Arg
            260                 265                 270

Glu Asn Gly Lys Tyr Glu Asp Gly Thr Ile Pro Ala Trp Pro Val Ile
        275                 280                 285

Ile Ala Arg Leu Pro Lys Gly Trp Gly Gly Pro Thr His Asp Glu Asp
    290                 295                 300

Gly Asn Pro Ile Glu Asn Ser Phe Arg Ala His Gln Val Pro Leu Pro
305                 310                 315                 320

Leu Ala Gln Asn Lys Leu Glu Thr Leu Ser Gln Phe Glu Asp Trp Met
                325                 330                 335
```

-continued

```
Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Ala Asn Gly Gly Arg Arg Arg Gly Glu Glu Ala Thr Asp
    370                 375                 380

Leu Thr Leu Pro Asp Trp Arg Gln Phe Thr Asn Asp Ile Thr Asn Glu
385                 390                 395                 400

Asn Arg Gly His Glu Leu Pro Lys Val Thr Gln Asn Met Asp Met Thr
                405                 410                 415

Thr Leu Ser Asn Tyr Leu Glu Glu Val Ala Lys Leu Asn Pro Thr Ser
            420                 425                 430

Phe Arg Val Phe Gly Pro Asp Glu Thr Met Ser Asn Arg Leu Trp Ser
        435                 440                 445

Leu Phe Asn Thr Thr Asn Arg Gln Trp Met Glu Glu Val Lys Glu Pro
    450                 455                 460

Asn Asp Gln Tyr Val Gly Pro Glu Gly Arg Ile Ile Asp Ser Gln Leu
465                 470                 475                 480

Ser Glu His Gln Ala Glu Gly Trp Leu Glu Gly Tyr Thr Leu Thr Gly
                485                 490                 495

Arg Val Gly Ile Phe Ala Ser Tyr Glu Ser Phe Leu Arg Val Val Asp
            500                 505                 510

Thr Met Val Thr Gln His Phe Lys Trp Leu Arg His Ala Ser Glu Gln
        515                 520                 525

Ala Trp Arg Asn Asp Tyr Pro Ser Leu Asn Leu Ile Ala Thr Ser Thr
    530                 535                 540

Ala Phe Gln Gln Asp His Asn Gly Tyr Thr His Gln Asp Pro Gly Met
545                 550                 555                 560

Leu Thr His Leu Ala Glu Lys Lys Ser Asn Phe Ile Arg Glu Tyr Leu
                565                 570                 575

Pro Ala Asp Gly Asn Ser Leu Leu Ala Val Gln Asp Arg Ala Phe Ser
            580                 585                 590

Glu Arg His Lys Val Asn Leu Ile Ile Ala Ser Lys Gln Pro Arg Gln
        595                 600                 605

Gln Trp Phe Thr Ala Asp Glu Ala Asp Glu Leu Ala Asn Glu Gly Leu
    610                 615                 620

Lys Ile Ile Asp Trp Ala Ser Thr Ala Pro Ser Gly Asp Val Asp Ile
625                 630                 635                 640

Thr Phe Ala Ser Ser Gly Thr Glu Pro Thr Ile Glu Thr Leu Ala Ala
                645                 650                 655

Leu Trp Leu Ile Asn Gln Ala Phe Pro Glu Val Lys Phe Arg Tyr Val
            660                 665                 670

Asn Val Val Glu Leu Leu Arg Leu Gln Lys Lys Ser Glu Ser His Met
        675                 680                 685

Asn Asp Glu Arg Glu Leu Ser Asp Ala Glu Phe Asn Lys Phe Phe Gln
    690                 695                 700

Ala Asp Lys Pro Val Ile Phe Gly Phe His Ala Tyr Glu Asp Leu Ile
705                 710                 715                 720

Glu Ser Phe Phe Phe Glu Arg Lys Phe Lys Gly Asp Val Tyr Val His
                725                 730                 735

Gly Tyr Arg Glu Asp Gly Asp Ile Thr Thr Thr Tyr Asp Met Arg Val
            740                 745                 750
```

Tyr Ser Lys Leu Asp Arg Phe His Gln Ala Lys Glu Ala Ala Glu Ile
755 760 765

Leu Ser Ala Asn Ser Thr Ile Asp Gln Ala Ala Ala Asp Thr Phe Ile
770 775 780

Glu Lys Met Asp Ala Thr Leu Ala Lys His Phe Glu Val Thr Arg Asn
785 790 795 800

Glu Gly Arg Asp Ile Glu Glu Phe Thr Asp Trp Asn Trp Ser Ala Leu
805 810 815

Lys

<210> SEQ ID NO 7
<211> LENGTH: 795
<212> TYPE: PRT
<213> ORGANISM: Bradyrhizobium sp. S23321

<400> SEQUENCE: 7

Met Asn Asn Gln Gln Gln Ser Ala Leu Ser Arg Ser Asp Leu Asp Leu
1 5 10 15

Leu Asp Arg Tyr Trp Arg Ala Ala Asn Tyr Leu Ser Val Gly Gln Ile
20 25 30

Tyr Leu Leu Asp Asn Pro Leu Leu Arg Glu Pro Leu Arg Pro Glu His
35 40 45

Ile Lys Pro Arg Leu Leu Gly His Trp Gly Thr Thr Pro Gly Leu Asn
50 55 60

Phe Ile Tyr Ala His Leu Asn Arg Val Ile Arg Ala Leu Asp Leu Ser
65 70 75 80

Val Leu Tyr Val Cys Gly Pro Gly Asn Gly Gly Pro Gly Met Val Ala
85 90 95

Asn Thr Tyr Leu Glu Gly Ser Tyr Ser Glu Ile Tyr Pro Asn Ile Ala
100 105 110

Arg Asp Thr Asp Gly Leu Arg Lys Leu Phe Arg Gln Phe Ser Phe Pro
115 120 125

Gly Gly Ile Pro Ser His Ala Ala Pro Glu Thr Pro Gly Ser Ile His
130 135 140

Glu Gly Gly Glu Leu Gly Tyr Ala Leu Val His Ala Tyr Gly Ala Ala
145 150 155 160

Phe Asp Asn Pro Asp Leu Ile Val Ala Cys Val Val Gly Asp Gly Glu
165 170 175

Ala Glu Thr Gly Pro Leu Ala Ala Ser Trp His Ser Asn Lys Phe Leu
180 185 190

Asn Pro Val His Asp Gly Ala Val Leu Pro Ile Leu His Leu Asn Gly
195 200 205

Tyr Lys Ile Ala Asn Pro Thr Val Leu Gly Arg Met Arg Asp Glu Glu
210 215 220

Ile Arg Asp Leu Phe Arg Gly Phe Gly His Glu Pro Leu Phe Val Glu
225 230 235 240

Gly Asp Asp Pro Thr Leu Met His Gln Ala Met Ala Asp Ala Phe Asp
245 250 255

Val Ala Phe Ala Arg Ile Arg Ser Ile Gln Gln His Ala Arg Asp Gly
260 265 270

Arg Lys Glu Ile Glu Arg Pro Arg Trp Pro Met Ile Val Leu Arg Ser
275 280 285

Pro Lys Gly Trp Thr Gly Pro Lys Glu Val Asp Gly Leu Lys Val Glu
290 295 300

-continued

```
Gly Phe Trp Arg Ala His Gln Val Pro Val Ala Gly Cys Arg Glu Asn
305                 310                 315                 320

Pro Ala His Leu Lys Ile Leu Glu Asp Trp Met Arg Ser Tyr Glu Pro
                325                 330                 335

Glu Lys Leu Phe Asp Ala Ser Gly Ala Leu Ile Pro Glu Leu Gln Ala
            340                 345                 350

Leu Ala Pro Glu Gly Asn Arg Arg Met Gly Ala Asn Pro His Ala Asn
        355                 360                 365

Gly Gly Leu Leu Lys Lys Glu Leu Lys Leu Pro Asp Phe Arg Ser Phe
    370                 375                 380

Ala Leu Glu Val Pro Gln Pro Gly Gly Val Thr Gly Glu Ala Thr Arg
385                 390                 395                 400

Glu Leu Gly Lys Phe Leu Arg Asp Val Ile Arg Leu Asn Ala Ala Glu
                405                 410                 415

Arg Asn Phe Arg Ile Met Gly Pro Asp Glu Thr Ala Ser Asn Arg Leu
            420                 425                 430

Asp Ala Val Phe Glu Glu Thr Glu Arg Val Trp Met Glu Pro Ile Glu
        435                 440                 445

Pro Tyr Asp Val His Leu Ala Gln Asp Gly Arg Val Met Glu Val Leu
    450                 455                 460

Ser Glu His Leu Cys Gln Gly Trp Leu Glu Gly Tyr Leu Leu Thr Gly
465                 470                 475                 480

Arg His Gly Phe Phe Ser Cys Tyr Glu Ala Phe Ile His Ile Val Asp
                485                 490                 495

Ser Met Phe Asn Gln His Ala Lys Trp Leu Lys Val Thr Arg His Leu
            500                 505                 510

Pro Trp Arg Arg Pro Ile Ala Ser Leu Asn Tyr Leu Leu Thr Ser His
        515                 520                 525

Val Trp Arg Gln Asp His Asn Gly Phe Ser His Gln Asp Pro Gly Phe
    530                 535                 540

Val Asp Leu Val Ala Asn Lys Lys Ala Asp Ile Val Arg Ile Tyr Phe
545                 550                 555                 560

Pro Pro Asp Ala Asn Thr Leu Leu Trp Ile Ala Asp His Cys Leu Arg
                565                 570                 575

Thr Tyr Asn Arg Ile Asn Val Ile Val Ala Gly Lys Gln Pro Ala Pro
            580                 585                 590

Gln Trp Leu Ser Met Gln Asp Ala Ala Thr His Cys Asp Ala Gly Ile
        595                 600                 605

Gly Ile Trp Ser Trp Ala Gly Asn Glu Asp Ala Thr Gly Glu Pro His
    610                 615                 620

Val Val Met Ala Cys Ala Gly Asp Val Pro Thr Leu Glu Thr Leu Ala
625                 630                 635                 640

Ala Val Asp Leu Leu Arg Lys Ala Leu Pro Asp Leu Lys Ile Arg Val
                645                 650                 655

Val Asn Val Val Asp Leu Met Thr Leu Gln Pro Lys Glu Gln His Pro
            660                 665                 670

His Gly Leu Ser Asp Arg Asp Phe Asp Ser Leu Phe Thr Ser Asp Lys
        675                 680                 685

Pro Val Ile Phe Ala Tyr His Gly Tyr Pro His Leu Ile His Arg Leu
    690                 695                 700

Thr Tyr Asn Arg Thr Asn His Ala Gly Leu His Val Arg Gly Phe Ile
705                 710                 715                 720

Glu Glu Gly Thr Thr Thr Thr Pro Phe Asp Met Val Val Leu Asn Glu
```

725 730 735

Leu Asp Arg Tyr His Leu Ala Ile Glu Ala Ile Glu Arg Val Pro Gly
740 745 750

Leu Ala Ala Arg Ala Ala Ala Val Lys Gln Gln Phe Arg Asp Ala Leu
755 760 765

Ile Glu His Ser His Tyr Ile Arg Glu His Gly Glu Asp Met Pro Glu
770 775 780

Ile Arg Asp Trp Val Trp Pro Gly Lys Thr Gly
785 790 795

<210> SEQ ID NO 8
<211> LENGTH: 781
<212> TYPE: PRT
<213> ORGANISM: Enterococcus faecium E1039

<400> SEQUENCE: 8

Met Asp Tyr Ser Ser Lys Glu Tyr Phe Asp Lys Met Thr Ala Trp Trp
1 5 10 15

Arg Ala Ala Asn Tyr Leu Ser Val Gly Gln Leu Tyr Leu Lys Asp Asn
20 25 30

Pro Leu Leu Arg Arg Thr Leu Lys Pro Glu Asp Val Lys Lys His Pro
35 40 45

Ile Gly His Trp Gly Thr Ile Pro Gly Gln Asn Phe Ile Tyr Val His
50 55 60

Leu Asn Arg Val Ile Asn Lys Tyr Asp Leu Asn Met Phe Tyr Ile Glu
65 70 75 80

Gly Pro Gly His Gly Gly Gln Val Met Val Ser Asn Ala Tyr Leu Asp
85 90 95

Gly Ser Tyr Thr Glu Ile Tyr Pro Glu Val Thr Glu Asp Glu Thr Gly
100 105 110

Met Gln Lys Leu Phe Lys Arg Phe Ser Phe Pro Gly Gly Ile Ala Ser
115 120 125

His Ala Ala Pro Glu Thr Pro Gly Ser Ile His Glu Gly Gly Glu Leu
130 135 140

Gly Tyr Ser Leu Ser His Ala Val Gly Ala Val Leu Asp Asn Pro Glu
145 150 155 160

Val Ile Ser Ala Val Val Ile Gly Asp Gly Glu Ala Glu Thr Gly Pro
165 170 175

Leu Ala Gly Ser Trp Phe Ser Asn Val Phe Ile Asn Pro Val Ile Asp
180 185 190

Gly Ala Val Leu Pro Ile Leu His Leu Asn Gly Ala Lys Ile Ala Asn
195 200 205

Pro Thr Ile Leu Ala Arg Lys Ser Asp Gly Glu Leu Ala Asn Tyr Phe
210 215 220

Asn Gly Leu Gly Trp Glu Pro Phe Phe Ile Glu Gly Asn Asp Pro Glu
225 230 235 240

Lys Leu Asn Pro Val Met Ala Glu Lys Met Asp Gln Ala Ile Glu Lys
245 250 255

Ile Lys Ser Ile Gln Lys Glu Ala Arg Leu Lys Thr Ala Thr Asp Val
260 265 270

Val Met Pro Lys Trp Pro Val Leu Ile Val Arg Thr Pro Lys Gly Trp
275 280 285

Thr Gly Glu Pro Ile Glu Gly Thr Phe Arg Ala His Gln Val Pro Ile
290 295 300

-continued

```
Pro Val Asp Gln Glu His Met Asp His Ala Asp Ala Leu Leu Arg Trp
305                 310                 315                 320

Leu Lys Ser Tyr Glu Pro Glu Lys Leu Phe Asp Ala Gln Gly Arg Ile
                325                 330                 335

Leu Glu Glu Ile Arg Glu Ile Ala Pro Thr Gly Asp Gln Arg Met Ala
            340                 345                 350

Lys Asn Pro Ile Thr Asn Gly Gly Ile Asp Pro Lys Pro Leu Ile Met
        355                 360                 365

Pro Asp Trp Lys Lys Tyr Thr Leu Gln Phe Glu Lys Pro Gly Ser Ile
    370                 375                 380

Lys Ala Glu Asp Met Thr Glu Leu Gly Lys Phe Val Arg Glu Ile Ile
385                 390                 395                 400

Glu Lys Asn Pro Glu Asn Phe Arg Ile Phe Gly Pro Asp Glu Thr Lys
                405                 410                 415

Ser Asn Arg Leu Asn Gln Val Phe Lys Thr Thr Asn Arg Gln Trp Met
            420                 425                 430

Glu Lys Ile Glu Pro Glu Asn Asp Glu Trp Leu Ser Pro Ser Gly Arg
        435                 440                 445

Val Ile Asp Ser Gln Leu Ser Glu His Gln Asp Glu Gly Phe Leu Glu
    450                 455                 460

Gly Tyr Val Leu Thr Gly Arg His Gly Phe Phe Ala Ser Tyr Glu Ser
465                 470                 475                 480

Phe Leu Arg Val Val Asp Ser Met Leu Thr Gln His Phe Lys Trp Met
                485                 490                 495

Arg Lys Ser His Asp Leu Ser Trp Arg Asn Asp Tyr Pro Ser Leu Asn
            500                 505                 510

Leu Ile Ala Ser Ser Thr Val Phe Gln Gln Asp His Asn Gly Tyr Ser
        515                 520                 525

His Gln Asp Pro Gly Ile Leu Thr His Leu Ala Glu Lys Lys Ala Glu
    530                 535                 540

Phe Ile Arg Glu Tyr Leu Pro Ala Asp Ala Asn Thr Leu Leu Ala Val
545                 550                 555                 560

Met Asp Lys Ala Phe Arg Ser Ser Glu Lys Ile Asn Leu Ile Ile Ser
                565                 570                 575

Ser Lys His Pro Arg Ala Gln Phe Tyr Ser Ala Glu Glu Ala Ala Val
            580                 585                 590

Leu Val Asn Glu Gly Leu Lys Ile Ile Asp Trp Ala Ser Thr Ala Lys
        595                 600                 605

Glu Glu Glu Pro Glu Leu Val Ile Ala Ala Ala Gly Thr Glu Ser Asn
    610                 615                 620

Leu Glu Ala Leu Ala Ala Val Thr Leu Leu Leu Glu Glu Phe Pro Lys
625                 630                 635                 640

Leu Lys Ile Arg Phe Ile Asn Val Val Asp Leu Leu Lys Leu Arg His
                645                 650                 655

Pro Ser Gln Asp Pro Arg Gly Leu Ser Asp Glu Glu Phe Asp Gln Tyr
            660                 665                 670

Phe Thr Lys Asp Lys Pro Ile Leu Phe Ala Phe His Gly Tyr Glu Thr
        675                 680                 685

Leu Val Arg Thr Ile Phe Phe Asp Arg His Asn His His Leu Met Ile
    690                 695                 700

His Gly Tyr Lys Glu Asn Gly Asp Ile Thr Thr Pro Phe Asp Met Arg
705                 710                 715                 720

Val Val Asn Glu Leu Asp Arg Tyr His Leu Ala Lys Asp Ala Ala Leu
```

```
                725                 730                 735

Lys Ile Lys Gly Ser Gln Ala Glu Asp Phe Ala Glu Lys Met Asp Gln
            740                 745                 750

Lys Leu Gln Glu His Gln Asn Tyr Ile Arg Glu Asn Gly Ile Asp Leu
        755                 760                 765

Pro Glu Val Leu Asp Trp Lys Trp Lys Asn Leu Asp Gln
    770                 775                 780


<210> SEQ ID NO 9
<211> LENGTH: 789
<212> TYPE: PRT
<213> ORGANISM: Brucella microti CCM 4915

<400> SEQUENCE: 9

Met Pro Ala Lys Gly Pro Leu Thr Pro Gln Gln Leu Ser Leu Ile Asn
 1               5                  10                  15

Arg Tyr Trp Arg Ala Ala Asn Tyr Leu Ser Val Gly Gln Ile Tyr Leu
            20                  25                  30

Met Lys Asn Pro Leu Leu Arg Glu Pro Leu Gln Pro Glu His Ile Lys
        35                  40                  45

Pro Arg Leu Leu Gly His Trp Gly Thr Thr Pro Gly Leu Asn Phe Ile
    50                  55                  60

Tyr Ala His Leu Asn Arg Ile Ile Gln Gln Arg Asn Ala Asn Val Ile
65                  70                  75                  80

Tyr Ile Cys Gly Pro Gly His Gly Gly Pro Gly Met Val Ala Asn Thr
                85                  90                  95

Tyr Leu Glu Gly Thr Tyr Ser Glu Ile Tyr Pro Ala Ile Ser Glu Asp
            100                 105                 110

Glu Ala Gly Met Glu Arg Leu Phe Arg Gln Phe Ser Phe Pro Gly Gly
        115                 120                 125

Ile Pro Ser His Ala Ala Pro Glu Thr Pro Gly Ser Ile His Glu Gly
    130                 135                 140

Gly Glu Leu Gly Tyr Ala Leu Val His Ala Tyr Gly Ala Ala Phe Asp
145                 150                 155                 160

Asn Pro Asp Leu Val Val Ala Cys Val Val Gly Asp Gly Glu Ala Glu
                165                 170                 175

Thr Gly Ala Leu Ala Thr Ser Trp His Ser Asn Lys Phe Leu Asn Pro
            180                 185                 190

Ala Arg Asp Gly Ala Val Leu Pro Ile Leu His Leu Asn Gly Tyr Lys
        195                 200                 205

Ile Ala Asn Pro Thr Val Leu Ala Arg Leu Ser Asp Asp Leu Asp
    210                 215                 220

Asn Leu Phe Arg Gly Tyr Gly Tyr Glu Pro Phe Phe Val Glu Gly Ser
225                 230                 235                 240

Glu Pro Ala Asp Met His Gln Lys Met Ala Ala Thr Leu Asp Thr Ile
                245                 250                 255

Phe Gln Arg Ile Gln Asp Ile Lys Lys Asn Ala Asp Val His Ser Pro
            260                 265                 270

Glu Arg Pro Arg Trp Pro Met Ile Ile Leu Arg Ser Pro Lys Gly Trp
        275                 280                 285

Thr Gly Pro Lys Thr Val Asp Gly Leu Val Val Glu Asn Tyr Trp Arg
    290                 295                 300

Ala His Gln Val Pro Val Ala Asn Cys Arg Glu Asn Asp Ala His Arg
305                 310                 315                 320
```

-continued

```
Lys Ile Leu Glu Asp Trp Met Lys Ser Tyr Asp Pro Ser Asp Leu Phe
                325                 330                 335

Asp Glu Lys Gly Ala Leu Lys Pro Glu Leu Arg Ala Leu Ala Pro Lys
            340                 345                 350

Gly Glu Ala Arg Met Gly Ala Asn Pro His Ala Asn Gly Gly Leu Leu
        355                 360                 365

Arg Lys Glu Leu His Met Pro Asp Phe Arg Gln Tyr Ala Val Asn Val
    370                 375                 380

Thr Glu Pro Gly Ala Ile Glu Ala Gln Ser Thr Lys Ile Leu Gly Asp
385                 390                 395                 400

Phe Leu Arg Asp Val Met Lys Leu Asn Glu Thr Glu Lys Asn Phe Arg
                405                 410                 415

Ile Phe Gly Pro Asp Glu Thr Ala Ser Asn Arg Leu Gly Ser Val Leu
            420                 425                 430

Glu Ala Thr Asn Arg Val Trp Met Ala Glu Thr Leu Asp Met Asp Asp
        435                 440                 445

His Leu Ala Ala Asp Gly Arg Val Met Glu Val Leu Ser Glu His Leu
    450                 455                 460

Cys Gln Gly Trp Leu Glu Gly Tyr Leu Leu Ser Gly Arg His Gly Phe
465                 470                 475                 480

Phe Ser Cys Tyr Glu Ala Phe Ile His Ile Ile Asp Ser Met Phe Asn
                485                 490                 495

Gln His Ala Lys Trp Leu Gln Val Ala Arg Glu Leu Glu Trp Arg Lys
            500                 505                 510

Pro Ile Ser Ser Leu Asn Tyr Leu Leu Thr Ser His Val Trp Arg Gln
        515                 520                 525

Asp His Asn Gly Phe Ser His Gln Asp Pro Gly Phe Val Asp Leu Val
    530                 535                 540

Ala Asn Lys Ser Ala Asp Ile Val Arg Val Tyr Phe Pro Pro Asp Ala
545                 550                 555                 560

Asn Thr Leu Leu Trp Val Gly Asp His Cys Leu Lys Thr Trp Asn Arg
                565                 570                 575

Val Asn Val Ile Val Ala Gly Lys Gln Pro Glu Pro Gln Trp Leu Thr
            580                 585                 590

Met Ala Glu Ala Glu Lys His Cys Glu Ala Gly Leu Gly Ile Trp Glu
        595                 600                 605

Trp Ala Gly Thr Glu Asp Gly Leu Glu Pro Asp Ile Val Met Ala Cys
    610                 615                 620

Ala Gly Asp Val Pro Thr Met Glu Thr Leu Ala Ala Val Asp Leu Leu
625                 630                 635                 640

Arg Gln Ser Leu Pro His Leu Arg Ile Arg Val Val Asn Val Val Asp
                645                 650                 655

Leu Met Val Leu Gln Ser Pro His Gln His Pro His Gly Ile Ser Asp
            660                 665                 670

Glu Glu Phe Asp Arg Met Phe Thr Thr Asn Arg Pro Val Ile Phe Ala
        675                 680                 685

Tyr His Gly Tyr Pro Tyr Leu Ile His Arg Leu Val Tyr Lys Arg Thr
    690                 695                 700

Asn His Ser Asn Phe His Val Arg Gly Phe Ile Glu Gln Gly Thr Thr
705                 710                 715                 720

Thr Thr Pro Phe Asp Met Thr Val Leu Asn Glu Leu Asp Arg Phe His
                725                 730                 735

Leu Ala Met Glu Ala Val Glu Arg Leu Pro Leu Gly Glu Ser Val Ala
```

-continued

```
            740                 745                 750

Lys Pro Leu Ile Asp Asn Phe Thr Glu Lys Leu Ala Leu His Lys Asp
        755                 760                 765

Tyr Ile Arg Gln His Gly Glu Asp Met Pro Glu Ile Arg Asp Trp Lys
    770                 775                 780

Trp Thr Trp Pro Arg
785


<210> SEQ ID NO 10
<211> LENGTH: 786
<212> TYPE: PRT
<213> ORGANISM: Lactobacillus salivarius ATCC 11741

<400> SEQUENCE: 10

Met Thr Asp Tyr Ser Ser Gln Glu Tyr Leu Asp Lys Leu Asp Ala Tyr
 1               5                  10                  15

Trp Arg Ala Ala Asn Tyr Val Ser Val Gly Gln Leu Tyr Leu Lys Asp
            20                  25                  30

Asn Pro Leu Leu Arg Arg Pro Leu Lys Ala Glu Asp Val Lys Val Lys
        35                  40                  45

Pro Ile Gly His Trp Gly Thr Ile Ala Gly Gln Asn Phe Ile Tyr Ala
    50                  55                  60

His Leu Asn Arg Val Ile Asn Lys Tyr Asp Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Ser Glu Ile Tyr Pro Glu Ile Ser Gln Asp Glu Gln
            100                 105                 110

Gly Met Lys Arg Leu Phe Lys Arg Phe Ser Phe Pro Gly Gly Val Ala
        115                 120                 125

Ser His Ala Ala Pro Glu Thr Pro Gly Ser Ile His Glu Gly Gly Glu
    130                 135                 140

Leu Gly Tyr Ser Ile Ser His Ser Val Gly Ala Val Leu Asp Asn Pro
145                 150                 155                 160

Asp Leu Ile Val Ala Ala Val Val Gly Asp Gly Glu Ala Glu Thr Gly
                165                 170                 175

Pro Leu Ala Ala Ser Trp Gln Ser Asn Lys Phe Ile Asn Pro Ile His
            180                 185                 190

Asp Gly Ala Val Leu Pro Ile Leu Asp Leu Asn Gly Phe Lys Ile Ser
        195                 200                 205

Asn Pro Thr Ile Leu Ser Arg Glu Ser Asp Glu Thr Leu Thr Lys Tyr
    210                 215                 220

Phe Glu Gly Met Gly Trp His Pro Ile Phe Val Glu Gly Asp Asp Pro
225                 230                 235                 240

Lys Leu Met His Pro Ala Met Ala Lys Ala Met Asp Glu Ala Ile Glu
                245                 250                 255

Glu Ile Lys Ala Ile Gln Lys Asn Ala Arg Glu Asn Asn Asp Pro Ser
            260                 265                 270

Leu Pro Ala Trp Pro Val Ile Ile Phe Arg Ala Pro Lys Gly Trp Thr
        275                 280                 285

Gly Pro Lys Glu Trp Asp Gly Glu Pro Ile Glu Lys Ser Phe Arg Ala
    290                 295                 300

His Gln Ile Pro Ile Pro Val Asp Gln Asn Asp Met Gln His Ala Asp
305                 310                 315                 320
```

-continued

```
Ala Leu Val Asp Trp Leu Glu Ser Tyr Lys Pro Glu Glu Leu Phe Asp
                325                 330                 335

Glu Asn Gly Lys Leu Lys Ala Glu Ile Ala Glu Ile Thr Pro Lys Gly
            340                 345                 350

Asp Lys Arg Met Ala Ala Asn Pro His Thr Asn Pro Gly Lys Leu Ile
        355                 360                 365

Arg Glu Val Ile Lys Pro Asp Phe Arg Asp Phe Ala Val Asp Thr Ser
    370                 375                 380

Val Pro Gly Lys Glu Val Ala Gln Asp Met Thr Val Leu Gly Lys Tyr
385                 390                 395                 400

Leu Glu Lys Val Leu Ser Asp Asn Arg His Asn Tyr Arg Val Phe Gly
                405                 410                 415

Pro Asp Glu Thr Met Ser Asn Arg Leu Ala Pro Ile Phe Asp Val Thr
            420                 425                 430

Lys Arg Gln Trp Leu Ala Glu Ile Lys Glu Pro Asn Asp Gln Tyr Leu
        435                 440                 445

Ala Pro Ser Gly Gln Val Ile Asp Ser Gln Leu Ser Glu His Gln Ala
    450                 455                 460

Glu Gly Phe Leu Glu Gly Tyr Val Leu Thr Gly Arg His Gly Phe Phe
465                 470                 475                 480

Ala Ser Tyr Glu Ser Phe Leu Arg Val Val Asp Ser Met Leu Thr Gln
                485                 490                 495

His Phe Lys Trp Leu Arg Lys Ala Thr Glu Gln Pro Trp Arg Thr Ser
            500                 505                 510

Ile Pro Ser Leu Asn Val Ile Ala Thr Ser Thr Val Phe Gln Gln Asp
        515                 520                 525

His Asn Gly Tyr Thr His Gln Asp Pro Gly Ile Leu Gly His Leu Ala
    530                 535                 540

Asp Lys Lys Pro Glu Tyr Ile Arg Glu Tyr Leu Pro Ala Asp Ala Asn
545                 550                 555                 560

Ser Leu Leu Ala Val Phe Asp Lys Thr Ile Asn Asp Arg Asp Lys Ile
                565                 570                 575

Asn Leu Ile Val Ala Ser Lys His Pro Arg Gln Gln Phe Tyr Ser Ala
            580                 585                 590

Ala Glu Ala Lys Glu Leu Val Asp Lys Gly Leu Lys Ile Ile Asp Trp
        595                 600                 605

Ala Ser Thr Asp Lys Asn Ala Glu Pro Asp Val Val Ile Ala Ala Ala
    610                 615                 620

Gly Thr Glu Pro Asn Leu Glu Ala Leu Ala Ala Ile Ser Ile Leu His
625                 630                 635                 640

Glu Lys Leu Pro Asp Leu Lys Ile Arg Phe Ile Asn Val Val Asp Ile
                645                 650                 655

Leu Lys Leu Arg Ser Pro Lys Val Asp Pro Arg Gly Leu Ser Asp Asp
            660                 665                 670

Glu Phe Asp Ala Tyr Phe Thr Lys Asp Lys Pro Val Ile Phe Ala Phe
        675                 680                 685

His Gly Tyr Glu Gly Leu Leu Arg Asp Ile Phe Tyr Tyr Arg His Asn
    690                 695                 700

His Asn Val Ala Phe His Gly Tyr Arg Glu Asn Gly Asp Ile Thr Thr
705                 710                 715                 720

Pro Phe Asp Met Arg Val Leu Ser Gln Met Asp Arg Phe Asp Leu Val
                725                 730                 735

Lys Ser Val Ala Leu Ser Leu Pro Asp Ala Asp Lys Tyr Gly Gln Leu
```

```
            740                 745                 750

Val Ala Glu Met Asp Ala Lys Val Ala Lys His His Gln Tyr Ile Arg
        755                 760                 765

Asp Glu Gly Thr Asp Leu Pro Glu Val Glu Asn Trp Glu Trp Lys Pro
    770                 775                 780

Leu Asp
785


<210> SEQ ID NO 11
<211> LENGTH: 755
<212> TYPE: PRT
<213> ORGANISM: Streptococcus agalactiae COH1

<400> SEQUENCE: 11

Met Ser Glu Phe Asp Thr Lys Ser Tyr Leu Glu Lys Leu Asp Ala Trp
 1               5                  10                  15

Trp Arg Ala Ala Asn Tyr Ile Ser Ala Ala Gln Met Tyr Leu Lys Asp
            20                  25                  30

Asn Pro Leu Leu Arg Arg Glu Leu Val Glu Asn Asp Leu Lys Val His
        35                  40                  45

Pro Ile Gly His Trp Gly Thr Val Pro Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Asn Pro Asn Ile Glu Gln Thr Glu Asp
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Gly Glu Thr Gly
                165                 170                 175

Pro Leu Met Ala Gly Trp Leu Ser Asn Thr Phe Ile Asn Pro Val Asn
            180                 185                 190

Asp Gly Ala Val Leu Pro Ile Phe Tyr Leu Asn Gly Gly Lys Ile His
        195                 200                 205

Asn Pro Thr Ile Phe Glu Arg Lys Thr Asp Glu Glu Leu Ser Gln Phe
    210                 215                 220

Phe Glu Gly Leu Gly Trp Lys Pro Ile Phe Ala Asp Val Val Glu Leu
225                 230                 235                 240

Ser Glu Asp His Ala Ala Ala His Ala Leu Phe Ala Glu Lys Leu Asp
                245                 250                 255

Gln Ala Ile Gln Glu Ile Lys Thr Ile Gln Ser Glu Ala Arg Gln Lys
            260                 265                 270

Pro Ala Glu Glu Ala Ile Gln Ala Lys Phe Pro Val Leu Val Ala Arg
        275                 280                 285

Ile Pro Lys Gly Trp Thr Gly Pro Lys Ala Trp Glu Gly Thr Pro Ile
    290                 295                 300

Glu Gly Gly Phe Arg Ala His Gln Val Pro Ile Pro Val Asp Ala His
305                 310                 315                 320
```

-continued

His Met Glu His Val Asp Ser Leu Leu Ser Trp Leu Gln Ser Tyr Arg
325 330 335

Pro Glu Glu Leu Phe Asp Glu Asn Gly Lys Ile Val Asp Glu Ile Ala
340 345 350

Ala Ile Ser Pro Lys Gly Asp Arg Arg Met Ser Met Asn Pro Ile Thr
355 360 365

Asn Ala Gly Ile Val Lys Ala Met Asp Thr Ala Asp Trp Lys Lys Phe
370 375 380

Ala Leu Asp Ile Asn Val Pro Gly Gln Ile Met Ala Gln Asp Met Ile
385 390 395 400

Glu Phe Gly Lys Tyr Ala Ala Asp Leu Val Asp Ala Asn Pro Asp Asn
405 410 415

Phe Arg Ile Phe Gly Pro Asp Glu Thr Lys Ser Asn Arg Leu Gln Glu
420 425 430

Val Phe Thr Arg Thr Ser Arg Gln Trp Leu Gly Arg Arg Lys Pro Asp
435 440 445

Tyr Asp Glu Ala Leu Ser Pro Ala Gly Arg Val Ile Asp Ser Gln Leu
450 455 460

Ser Glu His Gln Ala Glu Gly Phe Leu Glu Gly Tyr Val Leu Thr Gly
465 470 475 480

Arg His Gly Phe Phe Ala Ser Tyr Glu Ser Phe Leu Arg Val Val Asp
485 490 495

Ser Met Val Thr Gln His Phe Lys Trp Leu Arg Lys Ser Lys Thr His
500 505 510

Thr Thr Trp Arg Lys Asn Tyr Pro Ala Leu Asn Leu Ile Ala Ala Ser
515 520 525

Thr Val Phe Gln Gln Asp His Asn Gly Tyr Thr His Gln Asp Pro Gly
530 535 540

Ile Leu Thr His Leu Ala Glu Lys Thr Pro Glu Tyr Ile Arg Glu Tyr
545 550 555 560

Leu Pro Ala Asp Thr Asn Ser Leu Leu Ala Val Met Asp Lys Ala Phe
565 570 575

Lys Ala Glu Asp Lys Ile Asn Leu Ile Val Thr Ser Lys His Pro Arg
580 585 590

Pro Gln Phe Tyr Ser Ile Ala Glu Ala Glu Glu Leu Val Ala Glu Gly
595 600 605

Tyr Lys Val Ile Asp Trp Ala Ser Asn Val Ser Leu Asn Gln Glu Pro
610 615 620

Asp Val Val Phe Ala Ala Ala Gly Thr Glu Pro Asn Leu Glu Ala Leu
625 630 635 640

Ala Ala Ile Ser Ile Leu His Lys Ala Phe Pro Glu Leu Lys Ile Arg
645 650 655

Phe Val Asn Val Leu Asp Ile Leu Lys Leu Arg His Pro Ser Gln Asp
660 665 670

Ala Arg Gly Leu Ser Asp Glu Glu Phe Asn Lys Val Phe Thr Thr Asp
675 680 685

Lys Pro Val Ile Phe Ala Phe His Gly Tyr Glu Asp Met Ile Arg Asp
690 695 700

Ile Phe Phe Ser Arg His Asn His Asn Leu His Thr His Gly Tyr Arg
705 710 715 720

Glu Asn Gly Asp Ile Thr Thr Pro Phe Asp Met Arg Val Met Ser Glu
725 730 735

Leu Asp Arg Phe His Leu Ala Gln Asp Ala Ala Leu Ala Ser Leu Gly

```
            740                 745                 750

Ile Lys His
        755


<210> SEQ ID NO 12
<211> LENGTH: 800
<212> TYPE: PRT
<213> ORGANISM: Rhodococcus imtechensis RKJ300

<400> SEQUENCE: 12

Met Thr Asp Gly Arg Gln Val Gly Ser Gln Asp Ser Asp Gly His Tyr
 1               5                  10                  15

Ser Asp Ser Asp Leu Asp Leu Asp Leu Arg Trp Trp Ala Ala Ala Asn
            20                  25                  30

Tyr Leu Thr Val Ala Gln Ile Tyr Leu Gln Asp Asn Ala Leu Leu Arg
        35                  40                  45

Ala Pro Leu Arg Pro Glu His Ile Lys Pro Arg Leu Leu Gly His Trp
    50                  55                  60

Gly Thr Ser Pro Gly Leu Ser Met Ile Tyr Ala Leu Leu Asn Arg Leu
65                  70                  75                  80

Ile Arg Arg Thr Asp Thr Asp Cys Leu Tyr Val Thr Gly Pro Gly His
                85                  90                  95

Gly Gly Pro Ala Leu Val Ala Ala Thr Tyr Leu Glu Gly Thr Tyr Ser
            100                 105                 110

Glu Val Tyr Pro Gly Val Ser Arg Asp Ala Ala Gly Ile His Arg Leu
        115                 120                 125

Cys Arg Gln Phe Ser Thr Pro Gly Gly Ile Pro Ser His Val Ser Val
    130                 135                 140

Gln Thr Pro Gly Ser Ile His Glu Gly Gly Glu Leu Gly Tyr Ala Leu
145                 150                 155                 160

Ala His Ala Ala Gly Ala Ala Phe Asp His Pro Asn Leu Leu Val Ala
                165                 170                 175

Cys Val Ile Gly Asp Gly Glu Ala Glu Thr Gly Pro Leu Ser Gly Ser
            180                 185                 190

Trp Lys Leu Pro Ala Phe Leu Asn Pro Glu Arg Asp Gly Ala Val Leu
        195                 200                 205

Pro Ile Leu His Val Asn Gly Ala Lys Ile Ala Gly Pro Thr Val Tyr
    210                 215                 220

Gly Arg Ser Ser Asp Ala Asp Val Glu Ala Phe Leu Gly Gly Gln Gly
225                 230                 235                 240

Trp Ala Pro Thr Val Val Ser Gly Asp Asp Pro Arg His Val Phe Pro
                245                 250                 255

Ala Leu His Arg Ala Leu Thr Asp Ala His Ala Ala Ile Ser Asp Leu
            260                 265                 270

Gln Arg Glu Ala Arg Ala Gly Arg Arg Ser Ala Ala Lys Trp Pro Ala
        275                 280                 285

Ile Val Leu Arg Thr Pro Lys Gly Trp Thr Gly Pro Arg Thr Val Asp
    290                 295                 300

Gly Val Leu Val Glu Gly Thr His Arg Ala His Gln Val Pro Leu Ser
305                 310                 315                 320

Gly Val Arg Thr Asp Glu Ala His Leu Arg Gln Leu Glu Glu Trp Met
                325                 330                 335

Arg Ser Tyr Gly Pro Gly Glu Leu Phe Asp Ser Ser Gly Ala Leu Val
            340                 345                 350
```

-continued

```
Pro Asp Leu Glu Arg Leu Ala Pro Gln Gly Asp Lys Arg Met Gly Ser
        355                 360                 365

Ser Pro Tyr Ala Asn Gly Gly Arg Leu Arg Ala Asp Leu Pro Val Pro
    370                 375                 380

Pro Leu Glu Lys Tyr Ala Leu Ala Ile Glu Lys Pro Gly Thr Thr Leu
385                 390                 395                 400

His Glu Thr Thr Arg Val Leu Gly Glu Leu Leu Arg Asp Leu Tyr Ala
                405                 410                 415

Ala Thr Ala Thr Pro Asp Gly Gly Gly Tyr Phe Arg Leu Phe Cys Pro
            420                 425                 430

Asp Glu Thr Ala Ser Asn Arg Leu Gly Ala Val Phe Glu Val Thr Asp
        435                 440                 445

Arg Cys Trp Gln Leu Pro Val Thr Asp Tyr Asp Asp Gly Leu Ser Ala
    450                 455                 460

Arg Gly Arg Val Met Glu Val Leu Ser Glu His Leu Cys Glu Gly Trp
465                 470                 475                 480

Leu Glu Gly Tyr Leu Leu Ser Gly Arg His Gly Leu Phe Ala Ser Tyr
                485                 490                 495

Glu Ala Phe Ala Met Val Ser Val Ser Met Leu Val Gln His Thr Lys
            500                 505                 510

Trp Leu Gln His Ala Val Asp Leu Pro Trp Arg Ala Pro Val Ala Ser
        515                 520                 525

Leu Asn Val Leu Leu Thr Ser Thr Cys Trp Arg Asn Asp His Asn Gly
    530                 535                 540

Phe Ser His Gln Gly Pro Gly Met Ile Asp Ala Val Ile Pro Leu Ala
545                 550                 555                 560

Pro Asp Val Val Arg Ile Trp Leu Pro Pro Asp Ser Asn Thr Leu Leu
                565                 570                 575

Ser Ile Ala Asp His Cys Leu Arg Ser Thr Asp His Val Asn Leu Ile
            580                 585                 590

Val Val Asp Lys Gln Pro His Leu Gln Tyr Leu Thr Leu Ala Glu Ala
        595                 600                 605

His Ala His Cys Ala Ala Gly Ala Ser Val Trp Glu Trp Ala Gly Thr
    610                 615                 620

Glu Gly Ala Val Gly Ala Asp Pro Asp Val Val Leu Ala Ala Ala Gly
625                 630                 635                 640

Asp Val Pro Thr Gln Glu Ile Leu Ala Ala Ala Gln Leu Leu Arg Glu
                645                 650                 655

His Thr Pro Asp Leu Val Thr Arg Val Val Asn Val Val Asp Leu Met
            660                 665                 670

Gly Leu Leu Thr Pro Thr Glu His Pro His Gly Phe Asp Ala Arg Met
        675                 680                 685

Phe Leu Asp Leu Phe Thr Ala Asp Thr Asp Val Val Phe Ala Phe His
    690                 695                 700

Gly Tyr Ser Arg Ala Val His Glu Leu Ile His Gly Arg Pro Ala Pro
705                 710                 715                 720

Asp Arg Phe His Val Arg Gly Phe Ser Glu Gln Gly Thr Thr Thr Thr
                725                 730                 735

Pro Phe Asp Met Val Val Leu Asn Arg Met Ser Arg Tyr His Leu Val
            740                 745                 750

Leu Glu Ala Leu Arg Arg Thr Arg Arg Glu Pro Ala Gly Ala Gly Glu
        755                 760                 765

Leu Ala Asp Phe Cys Leu Arg Gln Leu Glu Arg His Gly Glu Tyr Val
```

770 775 780

Val Ala His Leu Glu Asp Met Pro Glu Val Arg Asp Trp Thr Trp Ser
785 790 795 800

<210> SEQ ID NO 13
<211> LENGTH: 797
<212> TYPE: PRT
<213> ORGANISM: Burkholderia xenovorans LB400

<400> SEQUENCE: 13

Met Ala Glu Ala Ser Ser Arg Pro Thr Pro Pro Gln Val Leu Asp Ala
1 5 10 15

Asp Thr Leu Arg Asn Met Asp Arg Tyr Trp Arg Ala Cys Asn Tyr Leu
20 25 30

Ser Ala Gly Met Ile Tyr Leu Arg Asp Asn Pro Leu Leu Arg Glu Pro
35 40 45

Leu Lys Pro Glu His Ile Lys Asn Arg Leu Leu Gly His Trp Gly Ser
50 55 60

Asp Pro Gly Gln Ser Phe Leu Leu Val His Leu Asn Arg Leu Ile Arg
65 70 75 80

Lys Leu Asp Leu Asn Val Ile Tyr Val Ala Gly Pro Gly His Gly Ala
85 90 95

Pro Ala Thr Leu Ala His Cys Tyr Leu Glu Gly His Tyr Ser Glu Ile
100 105 110

Tyr Pro Asp Arg Ser Glu Asp Glu Ala Gly Met Gln Arg Phe Phe Arg
115 120 125

Gln Phe Ser Phe Pro Gly Gly Ile Gly Ser His Cys Thr Pro Glu Thr
130 135 140

Pro Gly Ser Ile His Glu Gly Gly Glu Leu Gly Tyr Ser Leu Ser His
145 150 155 160

Gly Tyr Gly Ala Ala Phe Asp Asn Pro Asp Leu Ile Val Thr Val Met
165 170 175

Ile Gly Asp Gly Glu Ala Glu Thr Gly Pro Leu Ala Thr Ser Trp His
180 185 190

Ser Asn Lys Phe Leu Asn Pro Val Arg Asp Gly Ala Val Leu Pro Val
195 200 205

Leu His Leu Asn Gly Tyr Lys Ile Ala Asn Pro Thr Ile Leu Ala Arg
210 215 220

Ile Pro Arg Glu Glu Leu Glu Ala Leu Leu Thr Gly Tyr Gly His Lys
225 230 235 240

Pro Tyr Phe Val Glu Gly Asp Asp Pro Ala Val Met His Gln Gln Met
245 250 255

Ala Ala Thr Leu Glu Gln Cys Ile Gly Glu Ile Arg Ala Ile Gln Gln
260 265 270

His Ala Arg Ala Asn Asn Asp Ala Thr Arg Pro Arg Trp Pro Met Ile
275 280 285

Val Leu Arg Ser Pro Lys Gly Trp Thr Gly Pro Lys Glu Val Asp Gly
290 295 300

His Lys Val Glu Gly Ser Trp Arg Ala His Gln Val Pro Val Leu Asp
305 310 315 320

Pro Val Thr Asn Gly Lys Ser Leu Lys Leu Val Glu Asn Trp Met Arg
325 330 335

Ser Tyr Glu Pro Glu Ser Leu Phe Asp Glu Ala Gly Arg Leu Val Glu
340 345 350

-continued

```
Glu Leu Arg Glu Leu Ala Pro Lys Gly Ala Arg Arg Ile Ser Ala Asn
        355                 360                 365

Pro His Ala Asn Gly Gly Leu Leu Cys Lys Thr Leu Asp Met Pro Ala
    370                 375                 380

Phe Gly Asp Tyr Ala Val Ala Val Lys Lys Pro Gly Gly Thr Tyr Thr
385                 390                 395                 400

Ser Pro Thr Glu Val Leu Gly Lys Phe Leu Cys Asp Val Met Arg Arg
                405                 410                 415

Asn Met Thr Asn Phe Arg Val Phe Gly Pro Asp Glu Thr Ala Ser Asn
            420                 425                 430

Lys Leu Thr Ala Ile Tyr Glu Ala Ser Glu Lys Thr Trp Leu Ala Gln
        435                 440                 445

Thr Glu Pro Ser Asp Ala Asp Gly Gly Asp Leu Ala Val Asp Gly Arg
    450                 455                 460

Val Met Glu Met Leu Ser Glu His Thr Leu Glu Gly Trp Phe Glu Gly
465                 470                 475                 480

Tyr Val Leu Thr Gly Arg His Gly Leu Phe Ala Thr Tyr Glu Ala Phe
                485                 490                 495

Val His Val Ile Asp Ser Met Phe Asn Gln His Ala Lys Trp Leu Glu
            500                 505                 510

Lys Ala Lys Arg Asp Leu Gly Trp Arg Gln Pro Val Pro Ser Ile Asn
        515                 520                 525

Leu Leu Ile Thr Ser Leu Val Trp Arg Gln Asp His Asn Gly Phe Thr
    530                 535                 540

His Gln Asp Pro Gly Phe Leu Asp Val Val Thr Asn Lys Ser Pro Asp
545                 550                 555                 560

Val Val Arg Ile Tyr Leu Pro Pro Asp Ala Asn Cys Leu Leu Ser Val
                565                 570                 575

Ala Asp His Cys Leu Arg Ser Arg Asp Tyr Val Asn Val Ile Val Ala
            580                 585                 590

Asp Lys Gln Pro His Leu Gln Tyr Leu Asp Met Asp Ala Ala Val Ile
        595                 600                 605

His Cys Thr Lys Gly Ile Gly Ile Trp Asp Trp Ala Ser Thr Asp Gln
    610                 615                 620

Gly Val Glu Pro Asp Val Val Ile Ala Ser Ala Gly Asp Ile Ala Thr
625                 630                 635                 640

Met Glu Ala Leu Ala Ala Val Gln Ile Leu Lys Glu Arg Phe Ala Asp
                645                 650                 655

Leu Lys Ile Arg Phe Val Asn Val Val Asp Leu Phe Arg Leu Met Pro
            660                 665                 670

Glu His Ala His Pro His Gly Leu Ser Asn Arg Asp Phe Asp Ser Leu
        675                 680                 685

Phe Thr Ala Thr Lys Pro Val Ile Phe Asn Phe His Ser Tyr Ala Ser
    690                 695                 700

Leu Val His Lys Leu Thr Tyr Asn Arg Thr Asn His Asp Asn Leu His
705                 710                 715                 720

Val His Gly Tyr His Glu Lys Gly Asn Ile Asn Thr Pro Leu Glu Leu
                725                 730                 735

Ala Ile Ile Asn Gln Val Asp Arg Phe Ser Leu Ala Ile Asp Val Ile
            740                 745                 750

Asp Arg Val Pro Lys Leu Arg Gly Val Gly Asp His Ala Lys Glu Trp
        755                 760                 765

Leu Arg Gly Gln Val Ile Glu His Leu Ala Tyr Ala His Ala Glu Gly
```

770 775 780

Ile Asp Arg Glu Glu Ile Arg Asn Trp Thr Trp Lys Gly
785 790 795

<210> SEQ ID NO 14
<211> LENGTH: 787
<212> TYPE: PRT
<213> ORGANISM: Mycobacterium intracellulare ATCC 13950

<400> SEQUENCE: 14

Met Thr His Ala Thr Ala Leu Ser Asp Asp Glu Leu Ala Leu Ile Asp
1 5 10 15

Lys Tyr Trp Arg Ala Ala Asn Tyr Leu Ser Val Gly Gln Ile Tyr Leu
20 25 30

Leu Asp Asn Pro Leu Leu Thr Glu Pro Leu Thr Ile Asp His Val Lys
35 40 45

Pro Arg Leu Leu Gly His Trp Gly Thr Thr Pro Gly Leu Asn Leu Val
50 55 60

Tyr Ala His Leu Asn Arg Val Ile Arg His Arg Asp Ala Asp Val Ile
65 70 75 80

Tyr Val Thr Gly Pro Gly His Gly Gly Pro Gly Leu Val Ala Asn Ala
85 90 95

Tyr Leu Glu Gly Thr Tyr Ser Glu Val Tyr Thr Gly Ile Glu Glu Asp
100 105 110

Thr Glu Gly Leu Arg Lys Leu Phe Arg Gln Phe Ser Phe Pro Gly Gly
115 120 125

Ile Pro Ser His Val Ala Ala Gln Thr Pro Gly Ser Ile His Glu Gly
130 135 140

Gly Glu Leu Gly Tyr Ala Leu Val His Ala Tyr Gly Ala Ala Leu Asp
145 150 155 160

Asn Pro Tyr Leu Val Val Ala Cys Val Val Gly Asp Gly Glu Ala Glu
165 170 175

Thr Gly Pro Leu Ala Ala Ser Trp His Ser Asn Lys Phe Leu Asn Pro
180 185 190

Val Thr Asp Gly Ala Val Leu Pro Ile Leu Ala Leu Asn Gly Tyr Lys
195 200 205

Ile Ala Asn Pro Thr Val Leu Ala Arg Ile Pro His Ala Glu Leu Glu
210 215 220

Ser Leu Leu Arg Gly Tyr Gly Tyr Arg Pro Ile Thr Val Ala Gly Asp
225 230 235 240

Asp Pro Ala Asp Val His Arg Gln Leu Ala Ala Ala Leu Asp Asp Ala
245 250 255

Phe Asp Asp Ile Ala Ala Ile Gln Ser Ala Ala Arg Gly Gly Asn Gly
260 265 270

Val Glu Arg Pro Val Trp Pro Met Ile Val Leu Arg Thr Pro Lys Gly
275 280 285

Trp Thr Gly Pro Lys Met Val Asp Gly Lys Lys Val Glu Gly Thr Trp
290 295 300

Arg Ser His Gln Val Pro Leu Ala Ala Thr Arg Asp Asn Pro Glu His
305 310 315 320

Arg Ala Gln Leu Glu Glu Trp Leu Arg Ser Tyr Gly Pro Gly Glu Leu
325 330 335

Phe Asp Glu Asn Gly Arg Leu Arg Pro Glu Leu Arg Ala Leu Ala Pro
340 345 350

```
Ser Gly Asp Arg Arg Met Ser Ala Asn Pro His Ala Asn Gly Gly Leu
        355                 360                 365

Leu Leu His Asp Leu Asp Leu Pro Asp Phe Arg Asp Tyr Ala Val Ala
    370                 375                 380

Val Glu Arg Pro Ala Ala Val Thr His Glu Ala Thr Arg Val Leu Gly
385                 390                 395                 400

Gly Phe Leu Arg Asp Val Ile Ala Arg Asn Lys Asp Arg Phe Arg Leu
                405                 410                 415

Met Gly Pro Asp Glu Thr Ala Ser Asn Arg Leu Asp Ala Val Tyr Gly
            420                 425                 430

Ser Thr Asp Lys Val Trp Leu Ser Glu Ile Glu Pro Asp Asp Glu His
        435                 440                 445

Leu Ala Pro Asp Gly Arg Val Met Glu Val Leu Ser Glu His Leu Cys
    450                 455                 460

Gln Gly Trp Leu Glu Gly Tyr Leu Leu Thr Gly Arg His Gly Leu Phe
465                 470                 475                 480

Asn Cys Tyr Glu Ala Phe Val His Ile Val Asp Ser Met Leu Asn Gln
                485                 490                 495

His Ala Lys Trp Leu Ala Thr Ser Arg Glu Leu Pro Trp Arg Arg Pro
            500                 505                 510

Ile Ala Ser Leu Asn Tyr Leu Leu Ser Ser His Val Trp Arg Gln Asp
        515                 520                 525

His Asn Gly Ala Ser His Gln Asp Pro Gly Phe Ile Asp Leu Val Ala
    530                 535                 540

Asn Lys Arg Pro Glu Leu Thr Arg Val Tyr Leu Pro Pro Asp Gly Asn
545                 550                 555                 560

Thr Leu Leu Ser Val Ala Asp His Cys Leu Arg Ser Arg Asp Tyr Ile
                565                 570                 575

Asn Val Ile Val Ala Gly Lys Gln Pro Ala Leu Ala Tyr Leu Asp Met
            580                 585                 590

Asp Glu Ala Val Ala His Cys Thr Arg Gly Leu Gly Ile Trp Glu Trp
        595                 600                 605

Ala Ser Thr Ala Thr Asp Asp Pro Asp Val Val Leu Ala Cys Ala Gly
    610                 615                 620

Asp Ile Pro Thr Leu Glu Thr Leu Ala Ala Ala Asp Ile Leu Arg Ser
625                 630                 635                 640

Glu Leu Pro Glu Leu Ala Val Arg Val Val Asn Val Val Asp Leu Met
                645                 650                 655

Arg Leu Gln Pro Asp Thr Glu His Pro His Gly Leu Pro Asp Arg Glu
            660                 665                 670

Phe Asp Ala Leu Phe Thr Pro Asp Arg Pro Val Ile Phe Ala Tyr His
        675                 680                 685

Gly Tyr Pro Trp Leu Ile His Arg Leu Thr Tyr Ser Arg Thr Asn His
    690                 695                 700

Ala His Met His Val Arg Gly Phe Lys Glu Arg Gly Thr Thr Thr Thr
705                 710                 715                 720

Pro Phe Asp Met Val Met Leu Asn Asp Leu Asp Arg Phe His Leu Val
                725                 730                 735

Met Asp Val Ile Asp Arg Val Asp Gly Leu Ala Ser Arg Ala Ala Met
            740                 745                 750

Leu Arg Gln Arg Met Val Asp Ala Arg Leu Ala Ala Arg Met Tyr Thr
        755                 760                 765

Arg Glu His Gly Glu Asp Asp Pro Lys Ile Ser Gly Trp Thr Trp Gly
```

770 775 780

Pro Ser Asp
785

<210> SEQ ID NO 15
<211> LENGTH: 789
<212> TYPE: PRT
<213> ORGANISM: Nitrosomonas sp. Is79A3

<400> SEQUENCE: 15

Met Lys Lys Asn Thr Lys Leu Leu Ser Pro Glu Leu Leu His Lys Met
1 5 10 15

Asp Ala Tyr Trp Arg Ala Ala Asn Tyr Leu Ser Val Gly Gln Ile Tyr
20 25 30

Leu Tyr Asp Asn Pro Leu Leu Lys Gln Pro Leu Lys Leu Ala His Ile
35 40 45

Lys Pro Arg Leu Leu Gly His Trp Gly Thr Thr Pro Gly Leu Asn Phe
50 55 60

Ile Tyr Val His Leu Asn Arg Ile Ile Lys Glu His Asp Leu Asn Val
65 70 75 80

Ile Tyr Ile Thr Gly Pro Gly His Gly Gly Pro Gly Leu Val Ala Asn
85 90 95

Thr Tyr Leu Glu Gly Thr Tyr Ser Glu Val Tyr Pro Asn Ile Ser Gln
100 105 110

Asp Glu Asp Gly Met Gln Arg Leu Phe Lys Gln Phe Ser Phe Pro Gly
115 120 125

Gly Ile Pro Ser His Val Ala Pro Glu Thr Pro Gly Ser Ile His Glu
130 135 140

Gly Gly Glu Leu Gly Tyr Ser Leu Ser His Ala Phe Gly Ala Ala Phe
145 150 155 160

Asp Asn Pro Gly Leu Leu Val Ala Cys Val Val Gly Asp Gly Glu Ala
165 170 175

Glu Thr Gly Pro Leu Ala Thr Ser Trp His Ser Asn Lys Phe Leu Asn
180 185 190

Pro Val His Asp Gly Ala Val Leu Pro Ile Leu His Leu Asn Gly Tyr
195 200 205

Lys Ile Ala Gly Pro Thr Val Leu Ala Arg Ile Pro Cys Asp Glu Leu
210 215 220

Glu Ala Leu Phe Arg Gly Tyr Gly Tyr Thr Pro Tyr Phe Ile Glu Gly
225 230 235 240

Asp Asp Pro Leu Glu Met His Gln Arg Met Ala Ala Thr Leu Asp Ala
245 250 255

Val Ile Ala Asn Ile Gln Ser Ile Gln Arg Asp Ala Arg Thr His Gly
260 265 270

Phe Thr Lys Arg Pro His Trp Pro Met Ile Ile Leu Arg Ser Pro Lys
275 280 285

Gly Trp Thr Gly Pro Lys Val Val Asp Gly Lys Pro Thr Glu Gly Thr
290 295 300

Phe Arg Ser His Gln Val Pro Met Gly Asp Met Ser Gln Pro Gly His
305 310 315 320

Val Lys Ile Leu Glu Lys Trp Leu Lys Ser Tyr Arg Pro Gln Glu Leu
325 330 335

Phe Asp Glu Thr Gly Lys Leu Leu Ala Glu Leu Ala Glu Leu Ala Pro
340 345 350

-continued

```
Gln Gly Ala Arg Arg Met Gly Ala Asn Pro His Ala Asn Gly Gly Met
        355                 360                 365

Leu Leu Arg Asp Leu Arg Leu Pro Asp Phe Arg Asp Tyr Ala Val Lys
    370                 375                 380

Val Ala Asn Pro Gly Thr Val Ser Ala Glu Ala Thr Arg Thr Gln Gly
385                 390                 395                 400

Glu Phe Ile Arg Asp Val Val Lys Leu Asn Ala Thr Asn Phe Arg Val
                405                 410                 415

Phe Ser Pro Asp Glu Thr Ala Ser Asn Arg Trp Gly Ala Val Phe Glu
            420                 425                 430

Val Thr Asn Arg Cys Ser Thr Ala Glu Ile Val Pro Gly Asp Asp His
        435                 440                 445

Val Ala Pro Asp Gly Arg Val Met Glu Met Leu Ser Glu His Gln Cys
    450                 455                 460

Glu Gly Trp Leu Glu Gly Tyr Leu Leu Thr Gly Arg His Gly Phe Phe
465                 470                 475                 480

Ser Cys Tyr Glu Ala Phe Ile His Ile Ile Asp Ser Met Phe Asn Gln
                485                 490                 495

His Ala Lys Trp Leu Lys Val Ala Asn Glu Ile Pro Trp Arg Arg Pro
            500                 505                 510

Ile Ala Ser Leu Asn Tyr Leu Leu Ser Ser His Val Trp Arg Gln Asp
        515                 520                 525

His Asn Gly Phe Ser His Gln Asp Pro Gly Phe Ile Asp His Val Ile
    530                 535                 540

Asn Lys Lys Ala Glu Ile Ile Arg Ile Tyr Leu Pro Pro Asp Ala Asn
545                 550                 555                 560

Thr Leu Leu Ser Val Thr Asp His Cys Leu Arg Ser Arg Asn Tyr Val
                565                 570                 575

Asn Val Ile Val Ala Gly Lys Gln Pro Gln Pro Gln Trp Leu Asp Met
            580                 585                 590

Asp Ala Ala Ile Lys His Cys Thr Ala Gly Ile Gly Ile Trp Glu Trp
        595                 600                 605

Ala Ser Asn Asp Gln Gly Glu Glu Pro Asp Val Val Met Ala Cys Ala
    610                 615                 620

Gly Asp Ala Pro Thr Ile Glu Thr Leu Ala Ala Val Glu Leu Leu Trp
625                 630                 635                 640

Lys His Phe Pro Glu Leu Lys Ile Arg Val Ile Asn Val Val Asp Leu
                645                 650                 655

Met Ser Leu Gln Pro Gln Ser Glu His Pro His Gly Leu Ser Asp Lys
            660                 665                 670

Asp Phe Asp Gly Leu Phe Thr Lys Asp Lys Pro Ile Ile Phe Ala Tyr
        675                 680                 685

His Gly Tyr Pro Trp Leu Ile His Arg Leu Thr Tyr Arg Arg Thr Asn
    690                 695                 700

His Asp Asn Leu His Val Arg Gly Tyr Lys Glu Glu Gly Thr Thr Ser
705                 710                 715                 720

Thr Pro Phe Asp Met Val Val Met Asn Asp Leu Asp Arg Phe His Leu
                725                 730                 735

Val Ala Asp Val Ile Asp Arg Val Pro Gln Leu Gly Ser Arg Ala Ala
            740                 745                 750

Tyr Val Lys Gln Ala Ile Arg Asp Lys Leu Ile Glu His Lys Gln Tyr
        755                 760                 765

Ile Asn Gln Tyr Gly Glu Asp Met Pro Glu Ile Arg Asn Trp Lys Trp
```

770 775 780

Lys Gly Ser Ser Val
785

<210> SEQ ID NO 16
<211> LENGTH: 825
<212> TYPE: PRT
<213> ORGANISM: Schizosaccharomyces pombe 972h-

<400> SEQUENCE: 16

Met Ala Thr Gln Asn Asp Ile Pro Asn Ser Thr Pro Glu Asp Leu Ala
1 5 10 15

Lys Gln Val Glu Ile Ala Glu Lys His Pro Asp Pro Pro Ala Met Pro
20 25 30

Ser Arg Leu Pro Asp Ser Leu Lys Thr Leu Glu Ala Lys Ile Asp Thr
35 40 45

Ser Lys Ile Thr Asp Glu Glu Val Ala Asn Val His Arg Phe Gln Arg
50 55 60

Ala Cys Asp Tyr Leu Ala Ala Ser Leu Ile Phe Leu Ser Asn Gly Leu
65 70 75 80

Tyr Thr Gly Gly Asp Leu Glu Glu Lys Asp Ile Lys Thr Arg Leu Leu
85 90 95

Gly His Trp Gly Thr Cys Pro Gly Leu Ser Ile Val Tyr Ser His Cys
100 105 110

Asn Arg Ile Ile Asn Lys Tyr Asp Leu Asn Met Leu Phe Val Val Gly
115 120 125

Pro Gly His Gly Ala Pro Ala Ile Leu Ser Ala Leu Phe Leu Glu Asp
130 135 140

Ser Leu Gly Pro Phe Tyr Pro Arg Tyr Gln Phe Thr Lys Glu Gly Leu
145 150 155 160

Asn Asn Leu Ile Asn Thr Phe Ser Leu Pro Gly Gly Phe Pro Ser His
165 170 175

Val Asn Ala Glu Val Pro Gly Ala Ile His Glu Gly Gly Glu Leu Gly
180 185 190

Tyr Ala Leu Ser Val Ser Tyr Gly Ala Val Leu Asp Arg Pro Asp Leu
195 200 205

Ile Val Thr Cys Val Val Gly Asp Gly Glu Ala Glu Thr Gly Pro Thr
210 215 220

Ala Thr Ser Trp His Ala His Lys Phe Leu Asp Pro Ala Glu Ser Gly
225 230 235 240

Ala Val Ile Pro Val Leu Glu Leu Asn Gly Tyr Lys Ile Ser Glu Arg
245 250 255

Thr Ile Tyr Gly Cys Met Asp Asp Ser Glu Leu Leu Ser Leu Phe Ser
260 265 270

Gly Phe Gly Tyr Glu Val Ala Ile Val Asn Asp Thr Pro Asp Gln Asn
275 280 285

Arg Val Met Ala Ala Thr Met Asp Trp Ala Val Glu Arg Ile His Asp
290 295 300

Ile Gln His Arg Ala Arg Val Asn Arg Glu Glu Ile Lys Pro Arg Trp
305 310 315 320

Pro Met Ile Ile Leu Arg Thr Pro Lys Gly Lys Gly Cys Pro Lys Tyr
325 330 335

Leu Asn Gly Lys Phe Leu Glu Gly Thr Phe Arg Ala His Gln Val Pro
340 345 350

```
Leu Lys Leu Ala Arg Thr Asp Thr Asn Gln Arg Asn Leu Leu Lys Asp
        355                 360                 365

Trp Leu Asn Ser Tyr Asn Cys Gln Asp Phe Leu Asp Glu His Gly Leu
    370                 375                 380

Pro Thr Lys Gly Ile Thr Glu His Leu Pro Pro Arg Glu Lys Arg Met
385                 390                 395                 400

Gly Gln Arg His Glu Thr Tyr Asn Ser Tyr Leu Pro Leu Lys Val Pro
                405                 410                 415

Asp Trp Lys Lys Tyr Gly Val Lys Lys Gly Glu Thr Thr Ser Ala Thr
            420                 425                 430

Ser Val Val Gly Gln Tyr Leu Asp Glu Leu Leu Val Thr Asn Asp Ser
        435                 440                 445

Thr Leu Arg Ile Phe Ser Pro Asp Glu Leu Glu Ser Asn Lys Leu Asp
    450                 455                 460

Gly Ala Leu Lys His Ser Tyr Arg Thr Met Gln Thr Asp Pro Glu Leu
465                 470                 475                 480

Met Ala Lys Arg Gly Arg Val Thr Glu Val Leu Ser Glu His Leu Cys
                485                 490                 495

Gln Gly Phe Met Gln Gly Tyr Thr Leu Thr Gly Arg Thr Ala Ile Phe
            500                 505                 510

Pro Ser Tyr Glu Ala Phe Met Thr Ile Val Val Ser Met Leu Val Gln
        515                 520                 525

Tyr Ser Lys Phe Leu Lys Met Gly Leu Glu Thr Gly Trp His Gly Lys
    530                 535                 540

Phe Gly Ser Leu Asn Tyr Val Thr Ser Ser Thr Trp Ala Arg Gln Glu
545                 550                 555                 560

His Asn Gly Phe Ser His Gln Ser Pro Arg Phe Ile Thr Thr Met Leu
                565                 570                 575

Ser Leu Lys Pro Gly Val Ser Arg Val Tyr Phe Pro Pro Asp Ala Asn
            580                 585                 590

Cys Phe Leu Ala Thr Val Ala Arg Cys Met Lys Ser Glu Asn Thr Ile
        595                 600                 605

Asn Leu Met Val Ser Ser Lys Asn Pro Gln Pro Ala Tyr Leu Ser Val
    610                 615                 620

Glu Glu Ala Glu His His Cys Lys Ala Gly Ala Ser Val Trp Lys Phe
625                 630                 635                 640

Ala Ser Thr Asp Asn Gly Glu Asn Pro Asp Val Val Ile Ala Gly Val
                645                 650                 655

Gly Asn Glu Ile Met Phe Glu Val Val Lys Ala Ala Glu Met Leu Gln
            660                 665                 670

Asn Asp Ile Pro Glu Leu Arg Val Arg Val Ile Asn Val Thr Asp Leu
        675                 680                 685

Met Val Leu Ser Ser Leu His Pro His Gly Met Asn Pro Ala Glu Phe
    690                 695                 700

Asp Ser Leu Phe Thr Lys Asp Arg His Val His Phe Asn Tyr His Gly
705                 710                 715                 720

Tyr Val Met Asp Leu Lys Ala Leu Leu Phe Asp Arg Ile Gln Gly Thr
                725                 730                 735

Arg Val Thr Met Glu Gly Tyr Arg Glu Glu Gly Thr Thr Thr Thr Pro
            740                 745                 750

Phe Asn Met Met Met Cys Asn Asn Thr Ser Arg Tyr His Val Ala Arg
        755                 760                 765

Met Ala Leu Gln His Ala Leu His Asn Pro Thr Val Ala Val Asn Cys
```

770 775 780

Asn Met Leu Cys Ala Lys Tyr Ala Trp Lys Leu Glu Glu Ile Glu Asn
785 790 795 800

Tyr Ile Met Glu Asn Lys Asp Asp Pro Pro Glu Ile Tyr Ala Ala Pro
805 810 815

Val Phe Lys Asn Lys Thr Ser Thr Leu
820 825

<210> SEQ ID NO 17
<211> LENGTH: 788
<212> TYPE: PRT
<213> ORGANISM: Leuconostoc mesenteroides subsp. mesenteroides J18

<400> SEQUENCE: 17

Met Asn Ile Asp Ser Thr Asp Tyr Leu Asn Asn Leu Asp Ala Tyr Trp
1 5 10 15

Arg Ala Thr Asn Tyr Leu Ser Val Gly Gln Leu Tyr Leu Leu Asp Asn
20 25 30

Pro Leu Leu Lys Glu Lys Leu Thr Ala Glu Gln Val Lys Ile His Pro
35 40 45

Ile Gly His Trp Gly Thr Ile Pro Ser Gln Asn Phe Ile Tyr Ala His
50 55 60

Leu Asn Arg Ala Ile Asn Lys Phe Asn Leu Asn Met Phe Tyr Ile Glu
65 70 75 80

Gly Pro Gly His Gly Gly Gln Val Met Ile Ser Asn Ala Tyr Leu Asp
85 90 95

Gly Ser Tyr Thr Glu Ala Phe Pro Glu Ile Thr Gln Asp Glu Ala Gly
100 105 110

Met Gln Lys Met Phe Lys Arg Phe Ser Phe Pro Gly Gly Val Ala Ser
115 120 125

His Ala Asp Pro Lys Val Pro Gly Ser Ile His Glu Gly Gly Ala Leu
130 135 140

Gly Tyr Ser Ile Leu His Gly Ala Gly Ala Val Leu Asp Asn Pro Asp
145 150 155 160

Leu Ile Ala Ala Val Val Val Gly Asp Gly Glu Ala Glu Thr Ala Pro
165 170 175

Leu Ala Thr Ser Trp His Val Asn Lys Phe Leu Asn Pro Lys Asn Asp
180 185 190

Gly Thr Val Leu Pro Ile Leu Asn Leu Asn Gly Phe Lys Ile Ala Asn
195 200 205

Pro Thr Val Leu Ser Arg Glu Ser Asp Glu Thr Leu Thr Glu Tyr Phe
210 215 220

His Ser Leu Gly Trp His Pro Tyr Phe Val Ser Ser Phe Asp Lys Pro
225 230 235 240

Ile Met Gln Val His Glu Glu Met Ala Lys Thr Met Asp Thr Val Phe
245 250 255

Thr Glu Ile Lys Asp Ile Arg Glu Lys Ala Val Gln Gln Thr Asn Glu
260 265 270

Glu Ile Thr Arg Pro Leu Trp Pro Met Ile Val Leu Arg Ser Pro Lys
275 280 285

Gly Trp Thr Gly Pro Lys Thr Trp Asp Asp Asn Pro Ile Glu Asn Ser
290 295 300

Phe Arg Ala His Gln Ile Pro Ile Pro Ala Asp Gln Asn His Pro Glu
305 310 315 320

-continued

```
Tyr Ile Pro Gln Leu Val Asp Trp Leu Gln Ser Tyr Lys Pro Asp Glu
                325                 330                 335

Leu Phe Asp Glu Asn Gly Gln Leu Thr Gln Ser Ile Gln Glu Val Leu
            340                 345                 350

Pro Lys Lys Glu Leu Arg Met Ala Asn Asn Ser Val Thr Asn Ala Gly
        355                 360                 365

Lys Ile Lys Pro Leu Ile Leu Pro Asp Ile Asp Asn Tyr Leu Val Glu
    370                 375                 380

Asn Asn Gln Pro Gly Asn Asn Leu Ala Gln Asp Ala Ile Leu Leu Gly
385                 390                 395                 400

Asp Tyr Leu Arg Asp Ile Ile Lys Leu Asn Pro Thr Asn Phe Arg Gly
                405                 410                 415

Phe Gly Pro Asp Glu Thr Ala Ser Asn Arg Phe Gln Asp Ile Phe Glu
            420                 425                 430

Thr Thr Asn Arg Gln Trp Leu Leu Pro Ile Lys Glu Pro Asn Asp Gln
        435                 440                 445

Phe Met Ala Pro Glu Gly Arg Ile Ile Asp Ser Met Leu Ser Glu His
    450                 455                 460

Tyr Asp Glu Gly Met Leu Glu Ala Tyr Thr Leu Thr Gly Arg His Gly
465                 470                 475                 480

Phe Phe Ala Ser Tyr Glu Val Phe Ile Arg Glu Val Asp Asp Met Ile
                485                 490                 495

Val Gln His Phe Lys Trp Leu Asn His Ser His Asp Val Ser Trp Arg
            500                 505                 510

Lys Asp Val Pro Ala Leu Asn Ile Ile Ala Asp Ser Thr Val Phe Gln
        515                 520                 525

Gln Asp His Asn Gly Tyr Ser His Gln Asp Pro Gly Val Thr Thr Met
    530                 535                 540

Leu Tyr Glu Lys Gln Pro Asp Phe Ile Arg Glu Phe Phe Pro Ala Asp
545                 550                 555                 560

Ala Asn Ser Leu Val Ala Thr Phe Glu His Ala Ala Gln Ala Thr Gln
                565                 570                 575

Gln Ile Asn Tyr Ile Val Ala Ser Lys His Pro Arg Leu Gln Trp Phe
            580                 585                 590

Ser Pro Thr Glu Ala Lys Gln Leu Val Thr Gln Gly Leu Arg Val Ile
        595                 600                 605

Asp Trp Ala Ser Thr Asp Lys Gly Glu Lys Pro Asp Ile Ile Ile Ser
    610                 615                 620

Ser Ala Gly Ser Glu Pro Thr Thr Glu Ser Leu Ala Ala Ile Gln Ile
625                 630                 635                 640

Leu His Glu His Ile Pro Ser Leu Lys Ile Arg Tyr Ile Asn Val Leu
                645                 650                 655

Asp Leu Phe Lys Leu Arg Ala Asp Ala Ser Tyr Gly Leu Ser Asp Asp
            660                 665                 670

Glu Phe Asp Ala Tyr Phe Thr Thr Asp Thr Pro Val Leu Phe Ala Phe
        675                 680                 685

His Gly Tyr Glu Pro Met Ile Glu Ser Ile Phe Phe Lys Arg His Asn
    690                 695                 700

His His Leu Ala Val His Gly Tyr Arg Glu Val Gly Asp Ile Thr Thr
705                 710                 715                 720

Pro Phe Asp Met Arg Val Leu Asn Lys Ile Asp Arg Phe Asn Leu Val
                725                 730                 735

Lys Ala Ala Ile Asn Leu Leu Pro Glu Asn Ile Arg Thr Lys Gln Ala
```

```
            740                 745                 750

 Ala Leu Val Gln Glu Met Thr Asp Lys Leu Asp Leu His Val Ala Tyr
        755                 760                 765

Thr Arg Ser Lys Gly Thr Asp Leu Pro Glu Val Glu Asp Trp Arg Trp
    770                 775                 780

Gln Pro Leu Lys
785


<210> SEQ ID NO 18
<211> LENGTH: 694
<212> TYPE: PRT
<213> ORGANISM: Streptomyces sp. SA3_actG

<400> SEQUENCE: 18

Met Ser Asp Ala Ser Val Ser Ala Val Ala Asp Ala Leu Asp Tyr Leu
 1               5                  10                  15

Cys Leu Ala Gln Leu Tyr Leu Arg Glu Asn Pro Leu Leu Ala Arg Pro
            20                  25                  30

Leu Thr Ser Ala His Val Lys Trp Arg Pro Ala Gly His Trp Gly Val
        35                  40                  45

Cys Pro Pro Val Asn Arg Met Leu Ala Ala Leu Gly Pro Val Gln Ala
    50                  55                  60

Ser Val Pro Asp Gly Tyr Glu Leu Arg Val Leu His Gly Ala Gly His
65                  70                  75                  80

Ala Gly Pro Ser Ala Leu Ala His Ala Tyr Leu Thr Gly Arg Leu Gly
                85                  90                  95

Arg Val Tyr Pro Asp Leu Ile Gln Ser Pro Ala Gly Leu Leu Glu Leu
            100                 105                 110

Val Ser Gly Phe Pro Arg Pro Glu Thr Gly Gly Glu Ile Thr Pro Met
        115                 120                 125

Ile Pro Gly His Leu His Thr Gly Gly Gln Leu Gly Ala Ala Leu Ala
    130                 135                 140

Ile Gly Gln Gly Thr Val Leu Asp Ala Pro Arg Arg Leu Thr Val Ala
145                 150                 155                 160

Leu Leu Gly Asp Gly Glu Cys Glu Thr Gly Thr Thr Ala Ala Ser Trp
                165                 170                 175

Leu Ala Ser Arg Ala Leu Arg Gly Thr Gly Asp His Gly Thr Val Leu
            180                 185                 190

Pro Val Val Leu Leu Asn Gly Met Arg Met Gly Gly Pro Ser Val Leu
        195                 200                 205

Ser Thr Leu Ser Arg Asp Glu Leu Thr Ala Tyr Phe Thr Gly Leu Gly
    210                 215                 220

His Gln Pro Val Tyr Ser Asp Gly Leu Asp Ile Ala Gln Leu Arg Gln
225                 230                 235                 240

Ala Ile Ala Glu Ala Val Ala Asp Ala Arg Pro Leu Gly Val Pro Gly
                245                 250                 255

Pro Ser Ser Val Leu Val Leu Thr Leu Glu Lys Gly Tyr Gly Ala Pro
            260                 265                 270

Ala Gly Leu Ala Ala Thr Pro Ala Val His Lys Thr Pro Leu His Asp
        275                 280                 285

Pro Ala Ser Val Pro Ser Glu Phe Asp Leu Leu Ser Glu Trp Leu Ala
    290                 295                 300

Ser Tyr Arg Pro Ala Gln Leu Leu Thr Pro Gly Gly Arg Pro Arg Pro
305                 310                 315                 320
```

-continued

```
His Leu Leu Pro Ala Leu Pro Arg Pro Arg Pro Glu Pro Gly Gly Leu
                325                 330                 335

Ser Ala Pro Arg Gly Cys Ile Ala Ala Ser Thr Gln Val Ala Asp His
            340                 345                 350

Ala Ser Gly Arg Ala Phe Ala Gln Val Val Pro Asp Val Leu Arg Ala
        355                 360                 365

Arg Ala Ala Gln Gly Pro Phe Arg Val Phe Ser Pro Asp Glu Leu Ala
    370                 375                 380

Ser Asn Arg Ile Asp Leu Thr Asp Gly Gln Gly Arg Thr Val Pro Trp
385                 390                 395                 400

Ala Val Glu Val Leu Ser Glu Glu Leu Cys His Ala Trp Ala Gln Gly
                405                 410                 415

Tyr Thr Glu Thr Gly Arg His Ala Leu Val Ala Thr Tyr Glu Ala Phe
            420                 425                 430

Ala Pro Ile Thr Leu Ser Leu Val Gln Gln Gln Leu Lys His Arg Ser
        435                 440                 445

Ala Arg Arg His Ala Gly Leu Ala Pro Leu Pro Ser Leu Val Tyr Leu
    450                 455                 460

Leu Thr Ser Leu Gly Trp His Asn Thr Phe Thr His Gln Asn Pro Ser
465                 470                 475                 480

Leu Ala Thr Ala Leu Leu Ala Gly Gly Asp Pro Ser Val His Val Leu
                485                 490                 495

Thr Pro Ala Asp Pro Ala Arg Ala Ala Ala Ala Leu Thr Phe Ala Leu
            500                 505                 510

Arg Lys Leu Asp Arg Cys Thr Leu Val Ile Ala Asp Lys His Ala Thr
        515                 520                 525

Val Gln His Pro Leu Glu Thr Leu Asp Glu Glu Leu Arg His Gly Met
    530                 535                 540

Ala Ile Trp Pro His Leu Ser Ala Pro Gly Pro Glu Glu Pro Asp Leu
545                 550                 555                 560

Ile Leu Ala Ser Ala Gly Asp Leu Pro Ala Glu Val Leu Thr Thr Leu
                565                 570                 575

Ala Arg Arg Leu Arg Asp Asp Arg Arg Glu Leu Arg Leu Arg Tyr Val
            580                 585                 590

His Ile His Asp Leu Thr Ala Leu Ala Glu Glu Asp Thr Arg Ser Leu
        595                 600                 605

Ala Leu Gly Pro Ala Ala Phe Thr His His Phe Gly Thr Thr Ala Pro
    610                 615                 620

Leu Val Leu Ala Thr Ser Gly His Pro Ala Asp Ile His Ala Leu Phe
625                 630                 635                 640

Gly Arg Arg His Pro Gly Pro Arg Leu Thr Val Leu Gly Tyr Arg Asp
                645                 650                 655

Pro Gly Arg Pro Val Ser Gln Thr His Leu Arg Gln Leu Cys Gly Leu
            660                 665                 670

Asp Asp Thr Ser Leu Trp His Leu Ala Thr Thr Leu Ile Asp Ala Ser
        675                 680                 685

Lys Glu Ile Pro Ala Pro
    690
```

<210> SEQ ID NO 19
<211> LENGTH: 796
<212> TYPE: PRT
<213> ORGANISM: Lactobacillus buchneri ATCC 11577

<400> SEQUENCE: 19

-continued

Met Thr Val Asp Tyr Asp Ser Lys Glu Tyr Leu Asp Leu Leu Asp Lys
1               5                   10                  15

Tyr Trp Arg Ala Ala Asn Tyr Leu Ser Val Gly Gln Leu Tyr Leu Arg
            20                  25                  30

Asp Asn Pro Leu Leu Lys Arg Pro Leu Lys Ser Asp Asp Val Lys Ile
        35                  40                  45

Lys Pro Ile Gly His Trp Gly Thr Ile Val Ser Gln Asn Phe Ile Tyr
    50                  55                  60

Ala Gln Leu Asn Arg Ala Ile Asn Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Ser Asp Ile Tyr Pro Asn Ile Ser Gln Asp Glu
            100                 105                 110

Lys Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Leu Ser His Gly Thr Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

Thr Asp Gly Ala Val Leu Pro Ile Ile Asn Met Asn Gly Phe Lys Ile
        195                 200                 205

Ser Asn Pro Thr Ile Leu Ser Arg Met Ser Asp Ala Asp Leu Thr Asp
    210                 215                 220

Tyr Phe Lys Gly Met Gly Trp Glu Ala His Phe Val Glu Ala Thr Ala
225                 230                 235                 240

Asp Thr Asp His Ala Lys Val Glu Ala Glu Phe Ala Lys Thr Leu Asp
                245                 250                 255

Thr Val Ile Glu Lys Ile Lys Ser Ile Gln Lys Asn Ala Arg Glu Asn
            260                 265                 270

Glu Thr Pro Asp Asn Val Lys Leu Pro Val Trp Pro Met Ile Ile Phe
        275                 280                 285

Arg Ser Pro Lys Gly Trp Thr Gly Pro Lys Lys Asp Leu Asp Gly Asn
    290                 295                 300

Pro Ile Glu Gly Ser Phe Arg Ala His Gln Val Pro Ile Pro Val Asp
305                 310                 315                 320

Ala Asn Asp Met Glu His Ala Asp Glu Leu Val Asp Trp Leu Lys Ser
                325                 330                 335

Tyr Lys Pro Glu Glu Leu Phe Asp Glu Asn Gly Thr Leu Lys Pro Glu
            340                 345                 350

Leu Arg Ala Leu Ala Pro Lys Gly Glu Gln Arg Met Ser Val Asn Pro
        355                 360                 365

Ile Thr Asn Gly Gly Ile Lys Pro Glu Pro Leu Lys Leu Pro Asn Val
    370                 375                 380

Arg Asp Phe Glu Val Lys Phe Asp Lys Arg Gly Thr Glu Gln Lys Gln
385                 390                 395                 400

Asp Met Ile Glu Trp Ser Lys Trp Leu Asp Ala Val Ala Lys Leu Asn
                405                 410                 415

```
Pro Thr Thr Phe Arg Gly Phe Gly Pro Asp Glu Thr Lys Ser Asn Arg
            420                 425                 430

Leu Tyr Ser Leu Leu Asp Asp Gly Lys Arg Gln Trp Met Glu Asp Ile
        435                 440                 445

His Glu Pro Tyr Asp Glu Asp Leu Ala Asn His Gly Arg Val Ile Asp
    450                 455                 460

Ser Gln Leu Ser Glu His Gln Ala Glu Gly Trp Leu Glu Gly Tyr Val
465                 470                 475                 480

Leu Thr Gly Arg His Gly Phe Phe Ala Thr Tyr Glu Ser Phe Gly Arg
                485                 490                 495

Val Val Asp Ser Met Leu Thr Gln His Phe Lys Trp Leu Arg Lys Ala
            500                 505                 510

Ser Glu Gln Tyr Trp Arg Lys Gln Tyr Pro Ser Leu Asn Phe Val Asp
        515                 520                 525

Thr Ser Thr Val Phe Gln Gln Asp His Asn Gly Tyr Thr His Gln Asp
    530                 535                 540

Pro Gly Leu Leu Thr His Leu Ala Glu Lys Lys Pro Glu Phe Ile Arg
545                 550                 555                 560

Glu Tyr Leu Pro Ala Asp Ala Asn Glu Leu Leu Ala Val Gly Asp Ser
                565                 570                 575

Ala Phe Arg Thr Tyr Glu Lys Ile Asn Leu Ile Val Thr Ser Lys His
            580                 585                 590

Pro Arg Arg Gln Trp Tyr Ser Met Asp Glu Ala Gln Asn Leu Val Lys
        595                 600                 605

Asn Gly Leu Gly Tyr Ile Asp Trp Ala Ser Thr Asp Gln Gly Gln Glu
    610                 615                 620

Pro Asp Val Val Phe Ala Ala Ala Gly Ser Glu Pro Asn Leu Glu Ala
625                 630                 635                 640

Leu Ala Ala Ile Ser Ile Leu Asn Lys Glu Phe Pro Glu Leu Lys Ile
                645                 650                 655

Arg Phe Ile Asn Val Val Asp Ile Leu Lys Leu Asn Ser Pro Lys Lys
            660                 665                 670

Asp Pro Arg Gly Leu Ser Asp Glu Glu Phe Asp Asn Leu Phe Thr Thr
        675                 680                 685

Asp Lys Pro Val Ile Phe Ala Trp His Gly Phe Glu Asp Met Ile Lys
    690                 695                 700

Asp Ile Phe Phe Asp Arg His Asn His Asn Leu Tyr Val His Gly Tyr
705                 710                 715                 720

Arg Glu Asn Gly Asp Ile Thr Thr Pro Phe Asp Met Arg Val Leu Asn
                725                 730                 735

Glu Leu Asp Arg Phe His Leu Ala Ala Asp Ala Ile Arg His Ile Pro
            740                 745                 750

Ala Tyr Ala Val Lys Gly Gly Tyr Phe Ile Gln Arg Met Asn Asn Ile
        755                 760                 765

Val Asp Lys His Asn Arg Tyr Ile Arg Glu Val Gly Thr Asp Leu Pro
    770                 775                 780

Glu Val Thr Ser Trp Asn Trp Glu Pro Leu Asn Lys
785                 790                 795
```

<210> SEQ ID NO 20
<211> LENGTH: 792
<212> TYPE: PRT
<213> ORGANISM: Streptomyces ghanaensis ATCC 14672

<400> SEQUENCE: 20

```
Met Pro Glu Ala Pro Asp Thr Arg Thr Val Leu Ser Asp Glu Glu Leu
 1               5                  10                  15

Arg Thr Leu Asp Ala His Trp Arg Ala Ala Asn Tyr Leu Ala Ala Gly
            20                  25                  30

Gln Ile Tyr Leu Leu Ala Asn Pro Leu Leu Thr Glu Pro Leu Arg Pro
        35                  40                  45

Glu His Ile Lys Pro Arg Leu Leu Gly His Trp Gly Thr Ser Pro Gly
    50                  55                  60

Leu Asn Leu Val Tyr Thr His Leu Asn Arg Val Ile Ala Gly Arg Gly
65                  70                  75                  80

Leu Asp Ala Leu Cys Ile Trp Gly Pro Gly His Gly Gly Pro Ser Val
                85                  90                  95

Leu Ala Asn Ser Trp Leu Glu Gly Ser Tyr Gly Glu Thr Tyr Pro Asp
            100                 105                 110

Val Gly Arg Asp Ala Ala Gly Met Glu Arg Leu Phe Arg Gln Phe Ser
        115                 120                 125

Phe Pro Gly Gly Val Pro Ser His Val Ala Pro Glu Val Pro Gly Ser
    130                 135                 140

Val His Glu Gly Gly Glu Leu Gly Tyr Ser Leu Ala His Ala Tyr Gly
145                 150                 155                 160

Ala Ala Leu Asp His Pro Gly Leu Leu Val Ala Cys Val Ile Gly Asp
                165                 170                 175

Gly Glu Ala Glu Thr Gly Pro Leu Ala Ala Ser Trp His Ser Asn Lys
            180                 185                 190

Phe Leu Asp Pro Val His Asp Gly Ala Val Leu Pro Ile Leu His Leu
        195                 200                 205

Asn Gly Tyr Lys Ile Ala Asn Pro Thr Val Leu Ala Arg Leu Pro Glu
    210                 215                 220

Asp Glu Leu Asp Ser Leu Leu Arg Gly Tyr Gly His Glu Pro Ile His
225                 230                 235                 240

Val Ser Gly Asp Asp Pro Ala Ala Val His Arg Ala Met Ala His Ala
                245                 250                 255

Met Asp Thr Ala Leu Asp Arg Ile Ala Glu Val Gln Arg Ala Ala Arg
            260                 265                 270

Glu Asp Gly Val Thr Glu Arg Ala Arg Thr Pro Val Ile Val Leu Arg
        275                 280                 285

Thr Pro Lys Gly Trp Thr Gly Pro Ala Glu Val Asp Gly Lys Pro Val
    290                 295                 300

Glu Gly Thr Trp Arg Ala His Gln Val Pro Leu Ala Gly Val Arg Asp
305                 310                 315                 320

Asn Pro Glu His Leu Arg Gln Leu Glu Ala Trp Leu Arg Ser Tyr Arg
                325                 330                 335

Pro Glu Glu Leu Phe Asp Asp Ala Gly Arg Pro Val Ala Asp Val Leu
            340                 345                 350

Ala Cys Leu Pro Glu Gly Asp Arg Arg Leu Gly Ser Thr Pro Tyr Ala
        355                 360                 365

Asn Gly Gly Leu Leu Val Arg Glu Leu Pro Met Pro Ala Leu Asp Asp
    370                 375                 380

Phe Ala Val Pro Val Asp Lys Pro Gly Thr Thr Leu His Glu Pro Thr
385                 390                 395                 400

Arg Ile Leu Gly Gly Leu Leu Glu Arg Ile Met Arg Asp Thr Ala Asp
                405                 410                 415
```

-continued

```
Arg Arg Asp Phe Arg Leu Val Gly Pro Asp Glu Thr Ala Ser Asn Arg
            420                 425                 430

Leu Glu Ala Val Tyr Asp Ala Ser Gly Lys Ala Trp Gln Ala Gly Thr
        435                 440                 445

Leu Asp Val Asp Glu His Leu Asp Arg His Gly Arg Val Met Glu Val
    450                 455                 460

Leu Ser Glu His Leu Cys Gln Gly Trp Leu Glu Gly Tyr Leu Leu Thr
465                 470                 475                 480

Gly Arg His Gly Leu Phe Ser Cys Tyr Glu Ala Phe Val His Ile Val
                485                 490                 495

Asp Ser Met Val Asn Gln His Ile Lys Trp Leu Lys Thr Ser Arg Glu
            500                 505                 510

Leu Pro Trp Arg Ala Pro Ile Ala Ser Leu Asn Tyr Leu Leu Thr Ser
        515                 520                 525

His Val Trp Arg Gln Asp His Asn Gly Phe Ser His Gln Asp Pro Gly
    530                 535                 540

Phe Val Asp His Val Leu Asn Lys Ser Pro Glu Val Val Arg Val Tyr
545                 550                 555                 560

Leu Pro Pro Asp Ala Asn Thr Leu Leu Ser Val Ala Asp His Ala Leu
                565                 570                 575

Arg Ser Arg Asp Tyr Val Asn Val Val Val Ala Gly Lys Gln Pro Cys
            580                 585                 590

Phe Asp Trp Leu Ser Ile Asp Glu Ala Arg Val His Cys Ala Arg Gly
        595                 600                 605

Ala Gly Ile Trp Glu Trp Ala Gly Thr Glu Asn Gly Gly Ala Pro Asp
    610                 615                 620

Val Val Leu Ala Cys Ala Gly Asp Val Pro Thr Gln Glu Val Leu Ala
625                 630                 635                 640

Ala Ala Gln Leu Leu Arg Arg His Leu Pro Glu Leu Ala Val Arg Val
                645                 650                 655

Val Asn Val Val Asp Ile Ala Arg Leu Met Pro Arg Glu Glu His Pro
            660                 665                 670

His Gly Met Thr Asp Phe Glu Tyr Asp Gly Leu Phe Thr Ala Asp Lys
        675                 680                 685

Pro Val Ile Phe Ala Tyr His Gly Tyr Pro Trp Leu Ile His Arg Leu
    690                 695                 700

Ala Tyr Arg Arg Asn Gly His Pro Asn Leu His Val Arg Gly Tyr Lys
705                 710                 715                 720

Glu Ser Gly Thr Thr Thr Thr Pro Phe Asp Met Val Val Arg Asn Asp
                725                 730                 735

Leu Asp Arg Tyr Arg Leu Val Met Asp Val Ile Asp Arg Val Pro Gly
            740                 745                 750

Leu Ala Val Arg Ala Ala Ala Val Arg Gln Arg Met Ala Asp Ala Arg
        755                 760                 765

Thr Arg His His Ala Trp Ile Arg Glu His Gly Thr Asp Leu Pro Glu
    770                 775                 780

Val Ala Glu Trp Ser Trp Asn Ala
785                 790
```

<210> SEQ ID NO 21
<211> LENGTH: 802
<212> TYPE: PRT
<213> ORGANISM: Cyanothece sp. PCC 8802

<400> SEQUENCE: 21

```
Met Val Ala Thr Pro Glu Arg Pro Thr Leu Glu Gln Thr Pro Leu Ser
 1               5                  10                  15

Ala Glu Glu Leu Arg Gln Ile Gln Ala Tyr Trp Arg Ala Cys Asn Tyr
            20                  25                  30

Leu Ala Val Gly Met Ile Tyr Leu Arg Asp Asn Pro Leu Leu Lys Asp
        35                  40                  45

Pro Leu Thr Glu Asp His Val Lys Asn Arg Leu Leu Gly His Trp Gly
    50                  55                  60

Ser Ser Pro Gly Leu Ser Phe Ile Tyr Ile His Leu Asn Arg Leu Ile
65                  70                  75                  80

Lys Lys Tyr Gly Leu Asp Val Ile Tyr Met Ala Gly Pro Gly His Gly
                85                  90                  95

Ala Pro Gly Ile Leu Gly Pro Val Tyr Leu Glu Gly Thr Tyr Ser Glu
            100                 105                 110

Thr Tyr Pro Asp Lys Ser Glu Asp Glu Glu Gly Met Lys Lys Phe Phe
        115                 120                 125

Lys Gln Phe Ser Phe Pro Gly Gly Ile Gly Ser His Cys Thr Pro Glu
    130                 135                 140

Thr Pro Gly Ser Ile His Glu Gly Gly Glu Leu Gly Tyr Ser Leu Ser
145                 150                 155                 160

His Ala Tyr Gly Ala Ala Leu Asp Asn Pro Asp Leu Ile Val Ala Ala
                165                 170                 175

Val Val Gly Asp Gly Glu Ala Glu Thr Gly Pro Leu Ala Thr Ala Trp
            180                 185                 190

His Ser Asn Lys Phe Ile Asn Pro Ile Arg Asp Gly Ala Val Leu Pro
        195                 200                 205

Ile Leu His Leu Asn Gly Tyr Lys Ile Ala Asn Pro Thr Ile Leu Ala
    210                 215                 220

Arg Ile Ser His Glu Glu Leu Glu Tyr Leu Phe Lys Gly Tyr Gly Tyr
225                 230                 235                 240

Lys Pro Tyr Phe Val Glu Gly Ser Asp Pro Glu Val Met His Gln Lys
                245                 250                 255

Met Ala Ala Thr Leu Glu Thr Ala Ile Ala Glu Ile Lys His Ile Gln
            260                 265                 270

Gln Glu Ala Arg Thr Ser Gly Val Ala Lys Arg Pro Ile Trp Pro Met
        275                 280                 285

Ile Val Leu Arg Ser Pro Lys Gly Trp Thr Gly Pro Ala Ser Val Asp
    290                 295                 300

Gly Lys Lys Thr Glu Asp Phe Trp Arg Ser His Gln Val Pro Leu Ser
305                 310                 315                 320

Gly Met His Gly Asn Pro Ala His Ile Lys Val Leu Glu Asp Trp Leu
                325                 330                 335

Lys Ser Tyr Thr Pro Glu Glu Leu Phe Asp Glu Asn Gly Thr Leu Ile
            340                 345                 350

Pro Glu Leu Lys Glu Leu Ala Pro Thr Gly His His Arg Met Ser Ala
        355                 360                 365

Asn Pro His Ala Asn Gly Gly Leu Leu Arg Lys Asp Leu Lys Met Pro
    370                 375                 380

Asp Phe Arg Asn Tyr Gly Val Glu Val Ala Lys Pro Gly Thr Val Glu
385                 390                 395                 400

Val Gly Asn Thr Ala Leu Leu Gly Asn Phe Leu Arg Asp Val Met Ala
                405                 410                 415
```

-continued

```
Asn Asn Met Thr Asn Phe Arg Val Phe Gly Pro Asp Glu Thr Ala Ser
            420                 425                 430

Asn Arg Leu Asn Ala Ile Tyr Glu Ile Ser Lys Lys Val Trp Met Gly
        435                 440                 445

Glu Ile Leu Pro Glu Asp Ala Asp Gly Thr Glu Ile Thr Thr Asp Gly
    450                 455                 460

Arg Val Met Glu Met Leu Ser Glu His Thr Leu Gln Gly Trp Leu Glu
465                 470                 475                 480

Gly Tyr Leu Leu Thr Gly Arg His Gly Phe Phe His Thr Tyr Glu Ala
                485                 490                 495

Phe Ala His Val Val Asp Ser Met Phe Asn Gln His Ala Lys Trp Leu
            500                 505                 510

Asp Ile Cys Lys Asn Glu Val Pro Trp Arg Ala Ser Val Ser Ser Leu
        515                 520                 525

Asn Ile Leu Leu Ser Ser Thr Val Trp Arg Gln Asp His Asn Gly Phe
    530                 535                 540

Ser His Gln Asp Pro Gly Tyr Val Asp Leu Val Thr Asn Lys Ser Ala
545                 550                 555                 560

Asp Val Val Arg Val Tyr Phe Pro Pro Asp Ala Asn Cys Leu Leu Ser
                565                 570                 575

Val Ala Asn His Cys Leu Lys Ser Thr Asp Tyr Val Asn Val Ile Val
            580                 585                 590

Ser Asp Lys Gln Ile His Leu Gln Tyr Leu Asn Met Asp Gln Ala Ile
        595                 600                 605

Lys His Cys Thr Lys Gly Ile Gly Ile Trp Asp Trp Ala Ser Asn Asp
    610                 615                 620

Asp Cys Gly Thr Glu Pro Asp His Pro Asp Val Ile Met Ala Ser Cys
625                 630                 635                 640

Gly Asp Val Ala Thr Lys Glu Ala Leu Ala Ala Thr Ala Ile Leu Arg
                645                 650                 655

Glu Glu Phe Pro Asp Leu Lys Val Arg Phe Ile Asn Val Val Asp Leu
            660                 665                 670

Phe Lys Leu Gln Ser Glu Ile Glu His Pro His Gly Leu Ser Asp Arg
        675                 680                 685

Asp Phe Asp Asn Leu Phe Thr Lys Asp Lys Pro Ile Ile Phe Asn Phe
    690                 695                 700

His Gly Tyr Pro Trp Leu Ile His Lys Leu Thr Tyr Arg Arg Thr Asn
705                 710                 715                 720

His His Asn Leu His Val Arg Gly Tyr Lys Glu Lys Gly Asn Ile Asn
                725                 730                 735

Thr Pro Leu Glu Leu Ala Ile Asn Asn Gln Ile Asp Arg Phe Asn Leu
            740                 745                 750

Val Ile Asp Val Ile Asn Arg Val Pro Lys Leu Gly Ser Ala Ala Ala
        755                 760                 765

Tyr Val Tyr Glu Arg Met Lys Asn Ala Ile Ile Glu His Arg Ala Tyr
    770                 775                 780

Ala Tyr Glu His Gly Ile Asp Lys Pro Glu Ile Asn Asn Trp Lys Trp
785                 790                 795                 800

Pro His


<210> SEQ ID NO 22
<211> LENGTH: 812
<212> TYPE: PRT
<213> ORGANISM: Neosartorya fischeri NRRL 181
```

-continued

<400> SEQUENCE: 22

Met Thr Ser Lys Gly Glu Ile Glu Ser Leu Ser Ala Tyr Gly Val Ala
1               5                   10                  15

Arg Ser Thr Ile Gln Gly Thr Pro Leu Ser Gln Asp Glu Leu Arg Lys
            20                  25                  30

Met Asp Ala Tyr Phe Arg Ala Ser Met Tyr Leu Cys Leu Gly Met Leu
        35                  40                  45

Tyr Leu Arg Asp Asn Pro Leu Leu Lys Glu Pro Leu Lys Val Glu His
    50                  55                  60

Leu Lys Ala Arg Leu Leu Gly His Trp Gly Ser Asp Ala Gly Gln Ser
65                  70                  75                  80

Phe Thr Trp Ile His Met Asn Arg Leu Ile Lys Lys Tyr Asp Leu Asp
                85                  90                  95

Val Leu Phe Ile Ser Gly Pro Gly His Gly Ala Pro Gly Ile Leu Ser
            100                 105                 110

Gln Ser Tyr Leu Glu Gly Val Tyr Thr Glu Val Tyr Pro Glu Lys Thr
        115                 120                 125

Gln Asp Glu Lys Gly Leu Gln Arg Phe Phe Lys Gln Phe Ser Phe Pro
    130                 135                 140

Gly Gly Ile Gly Ser His Ala Thr Pro Glu Thr Pro Gly Ser Ile His
145                 150                 155                 160

Glu Gly Gly Glu Leu Gly Tyr Ser Ile Ser His Ala Phe Gly Thr Val
                165                 170                 175

Phe Asp His Pro Asn Leu Ile Thr Leu Thr Met Val Gly Asp Gly Glu
            180                 185                 190

Ala Glu Thr Gly Pro Leu Ala Thr Ser Trp His Ser Asn Lys Phe Leu
        195                 200                 205

Asn Pro Ile Thr Asp Gly Ala Val Leu Pro Val Leu His Leu Asn Gly
    210                 215                 220

Tyr Lys Ile Asn Asn Pro Thr Ile Leu Ala Arg Ile Ser His Glu Glu
225                 230                 235                 240

Leu Glu Met Leu Leu Lys Gly Tyr Gly Trp Thr Pro Tyr Phe Val Glu
                245                 250                 255

Gly Ser Asp Arg Glu Ser Met His Gln Ala Met Ala Ala Thr Leu Glu
            260                 265                 270

His Cys Val Leu Glu Ile Lys Lys Ile Gln Lys Gln Ala Arg Glu Ser
        275                 280                 285

Asn Lys Ala Phe Arg Pro Leu Trp Pro Met Ile Val Leu Arg Ser Pro
    290                 295                 300

Lys Gly Trp Ser Ala Pro Arg Glu Ile Asp Gly Lys Tyr Leu Glu Gly
305                 310                 315                 320

Phe Trp Arg Ala His Gln Ile Pro Ile Thr Asp Val Gln Ser Lys Pro
                325                 330                 335

Glu His Leu Lys Val Leu Glu Asn Trp Met Lys Ala Tyr Lys Pro Glu
            340                 345                 350

Glu Val Phe Asp Lys Asn Gly Thr Leu Ile Pro Glu Leu Lys Glu Leu
        355                 360                 365

Ala Pro Thr Gly Thr Ser Arg Met Ser Ala Asn Pro Val Gly Asn Gly
    370                 375                 380

Gly Leu Leu Arg Arg Pro Met Asp Leu Pro Asp Phe Arg Asp Tyr Ala
385                 390                 395                 400

Leu Thr Asp Ile Glu Pro Gly Val Thr Ile Arg Pro Ser Met Ser Asn

```
                405                 410                 415

Met Ser Lys Tyr Leu Arg Asp Val Val Ala Arg Asn Met Thr Thr Phe
            420                 425                 430

Arg Val Phe Gly Pro Asp Glu Thr Glu Ser Asn Lys Leu Ala Glu Ile
        435                 440                 445

Tyr Lys Ala Gly Lys Lys Val Trp Met Ala Glu Tyr Phe Lys Glu Asp
    450                 455                 460

Glu Asp Gly Gly Asn Leu Asp Met Gln Gly Arg Val Met Glu Ile Leu
465                 470                 475                 480

Ser Glu His Thr Cys Glu Gly Trp Leu Glu Gly Tyr Ile Leu Ser Gly
                485                 490                 495

Arg His Gly Met Leu Asn Ser Tyr Glu Pro Phe Ile His Val Ile Asp
            500                 505                 510

Ser Met Val Asn Gln His Cys Lys Trp Ile Glu Lys Cys Leu Ala Val
        515                 520                 525

Glu Trp Arg Ala Lys Val Ser Ser Leu Asn Ile Leu Leu Thr Ala Thr
    530                 535                 540

Val Trp Arg Gln Asp His Asn Gly Phe Thr His Gln Asp Pro Gly Phe
545                 550                 555                 560

Leu Asp Val Val Ala Asn Lys Ser Pro Glu Val Val Arg Ile Tyr Leu
                565                 570                 575

Pro Pro Asp Gly Asn Thr Leu Leu Ser Thr Met Asn His Cys Phe Arg
            580                 585                 590

Ser Val Asn Tyr Val Asn Val Ile Val Ala Asp Lys Gln Glu His Val
        595                 600                 605

Gln Phe Leu Asn Met Glu Glu Ala Ile Glu His Cys Thr Lys Gly Val
    610                 615                 620

Gly Ile Trp Asp Trp Ala Ser Asn Asp Gln Gly Cys Glu Pro Asp Val
625                 630                 635                 640

Val Met Ala Ser Cys Gly Asp Val Ala Thr His Glu Ala Leu Ala Ala
                645                 650                 655

Thr Ala Leu Leu Arg Glu His Leu Pro Gln Leu Lys Val Arg Phe Val
            660                 665                 670

Asn Val Val Asp Leu Phe Arg Leu Ile Ser Asp Ile Asn His Pro His
        675                 680                 685

Gly Met Pro Asp Arg Gln Trp Gly Ala Ile Phe Thr Thr Asp Lys Pro
    690                 695                 700

Ile Ile Phe Asn Phe His Ser Tyr Pro Trp Leu Ile His Arg Leu Thr
705                 710                 715                 720

Tyr Lys Arg Pro Gly Gln His Asn Leu His Val Arg Gly Tyr Lys Glu
                725                 730                 735

Lys Gly Asn Ile Asp Thr Pro Phe Glu Leu Ala Val Arg Asn Gln Thr
            740                 745                 750

Asp Arg Tyr Ser Leu Ala Ile Asp Ala Ile Asp Arg Ile Pro Ser Leu
        755                 760                 765

Gly Asn Thr Ala Ser Gly Val Arg Glu Arg Leu Ile Asn Leu Gln Leu
    770                 775                 780

Ala Ala Lys Asn Lys Ala Phe Asp Asp Gly Ile Asp Pro Asp Tyr Ile
785                 790                 795                 800

Arg Asn Trp Thr Trp Asp Tyr Pro Arg Lys Lys Cys
                805                 810
```

<210> SEQ ID NO 23

<211> LENGTH: 787
<212> TYPE: PRT
<213> ORGANISM: Enterococcus faecium TX1330

<400> SEQUENCE: 23

Met Asp Tyr Ser Ser Lys Glu Tyr Phe Asp Lys Met Thr Ala Trp Trp
1 5 10 15

Arg Ala Ala Asn Tyr Leu Ser Val Gly Gln Ile Tyr Leu Lys Asp Asn
20 25 30

Pro Leu Leu Arg Arg Thr Leu Lys Pro Glu Asp Val Lys Lys His Pro
35 40 45

Ile Gly His Trp Gly Thr Ile Pro Gly Gln Asn Phe Ile Tyr Val His
50 55 60

Leu Asn Arg Val Ile Asn Lys Tyr Asp Leu Asn Met Phe Tyr Ile Glu
65 70 75 80

Gly Pro Gly His Gly Gly Gln Val Met Val Ser Asn Ala Tyr Leu Asp
85 90 95

Gly Ser Tyr Thr Glu Ile Tyr Pro Glu Val Thr Glu Asp Glu Thr Gly
100 105 110

Met Gln Lys Leu Phe Lys Arg Phe Ser Phe Pro Gly Gly Ile Ala Ser
115 120 125

His Ala Ala Pro Glu Thr Pro Gly Ser Ile His Glu Gly Gly Glu Leu
130 135 140

Gly Tyr Ser Leu Ser His Gly Val Gly Ala Val Leu Asp Asn Pro Glu
145 150 155 160

Val Ile Ser Ala Val Val Ile Gly Asp Gly Glu Ala Glu Thr Gly Pro
165 170 175

Leu Ala Gly Ser Trp Phe Ser Asn Val Phe Ile Asn Pro Val Thr Asp
180 185 190

Gly Ala Val Leu Pro Ile Leu His Leu Asn Gly Ala Lys Ile Ala Asn
195 200 205

Pro Thr Ile Leu Ala Arg Lys Ser Asp Gly Glu Leu Ala Asn Tyr Phe
210 215 220

Asn Gly Leu Gly Trp Glu Pro Phe Phe Ile Glu Gly Asn Asp Pro Glu
225 230 235 240

Lys Leu Asn Pro Val Met Ala Glu Lys Met Asp Gln Ala Ile Glu Lys
245 250 255

Ile Lys Ser Ile Gln Lys Glu Ala Arg Leu Lys Thr Ala Ala Asp Ala
260 265 270

Met Met Pro Lys Trp Pro Val Leu Ile Val Arg Thr Pro Lys Gly Trp
275 280 285

Thr Gly Pro Glu Glu Trp Asp Gly Glu Pro Ile Glu Gly Thr Phe Arg
290 295 300

Ala His Gln Val Pro Ile Pro Val Asp Gln Glu His Met Asp His Ala
305 310 315 320

Asp Ala Leu Leu Arg Trp Leu Lys Ser Tyr Glu Pro Glu Lys Leu Phe
325 330 335

Asp Ala Gln Gly Arg Ile Leu Glu Glu Ile Arg Glu Ile Ala Pro Thr
340 345 350

Gly Asp His Arg Met Ala Lys Asn Pro Ile Thr Asn Gly Gly Met Asp
355 360 365

Pro Lys Pro Leu Ile Met Pro Asp Trp Lys Arg Tyr Thr Leu Gln Phe
370 375 380

Glu Lys Pro Gly Ser Val Thr Ala Glu Asp Met Thr Glu Leu Gly Lys

```
385                 390                 395                 400

Phe Val Arg Glu Ile Ile Glu Lys Asn Pro Glu Asn Phe Arg Ile Phe
                405                 410                 415

Gly Pro Asp Glu Thr Lys Ser Asn Arg Leu Asn Gln Val Phe Lys Thr
            420                 425                 430

Thr Asn Arg Gln Trp Met Glu Lys Ile Glu Pro Glu Asn Asp Glu Trp
        435                 440                 445

Leu Ser Pro Ser Gly Arg Val Ile Asp Ser Gln Leu Ser Glu His Gln
    450                 455                 460

Asp Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Met Arg Lys Ser Arg Asp Leu Ser Trp Arg Asn
            500                 505                 510

Asn Tyr Pro Ser Leu Asn Leu Ile Ala Ser Ser Thr Val Phe Gln Gln
        515                 520                 525

Asp His Asn Gly Tyr Ser His Gln Asp Pro Gly Ile Leu Thr His Leu
    530                 535                 540

Ala Glu Lys Lys Ala Glu Phe Ile Arg Glu Tyr Leu Pro Ala Asp Ala
545                 550                 555                 560

Asn Thr Leu Leu Ala Val Met Asp Lys Ala Phe Arg Ser Ser Glu Lys
                565                 570                 575

Ile Asn Leu Ile Ile Ser Ser Lys His Pro Arg Ala Gln Phe Tyr Ser
            580                 585                 590

Ala Glu Glu Ala Ala Val Leu Val Asn Glu Gly Leu Lys Ile Ile Asp
        595                 600                 605

Trp Ala Ser Thr Ala Lys Glu Glu Glu Pro Glu Leu Val Ile Ala Ala
    610                 615                 620

Ala Gly Thr Glu Ser Asn Leu Glu Ala Leu Ala Ala Val Thr Leu Leu
625                 630                 635                 640

Leu Glu Glu Phe Pro Lys Leu Lys Ile Arg Phe Ile Asn Val Val Asp
                645                 650                 655

Leu Leu Lys Leu Arg His Pro Ser Gln Asp Pro Arg Gly Leu Ser Asp
            660                 665                 670

Glu Glu Phe Asp Lys Tyr Phe Thr Lys Asp Lys Pro Ile Leu Phe Ala
        675                 680                 685

Phe His Gly Tyr Glu Thr Leu Ile Arg Thr Ile Phe Phe Asp Arg His
    690                 695                 700

Asn His His Leu Met Ile His Gly Tyr Lys Glu Asn Gly Asp Ile Thr
705                 710                 715                 720

Thr Pro Phe Asp Met Arg Val Val Asn Glu Leu Asp Arg Tyr His Leu
                725                 730                 735

Ala Lys Asp Ala Ala Leu Lys Ile Lys Gly Ser Gln Ala Glu Asp Phe
            740                 745                 750

Ala Lys Lys Met Asp Gln Lys Leu Gln Glu His Gln Asn Tyr Ile Arg
        755                 760                 765

Glu Asn Gly Ile Asp Leu Pro Glu Val Leu Asp Trp Lys Trp Lys Asn
    770                 775                 780

Leu Asp Gln
785

<210> SEQ ID NO 24
```

-continued

<211> LENGTH: 791
<212> TYPE: PRT
<213> ORGANISM: Listeria grayi DSM 20601

<400> SEQUENCE: 24

```
Met Thr Asp Tyr Ser Ser Pro Asn Tyr Leu Ala Lys Val Asp Ala Trp
 1               5                  10                  15

Trp Arg Ala Ala Asp Phe Ile Ser Val Gly Gln Leu Tyr Leu Lys Gly
            20                  25                  30

Asn Pro Leu Leu Arg Arg Pro Leu Glu Lys Glu Asp Leu Lys Val His
        35                  40                  45

Pro Ile Gly His Trp Gly Thr Ile Ser Gly Gln Asn Phe Ile Tyr Ala
    50                  55                  60

His Leu Asn Arg Val Ile Asn Lys Tyr Asp Leu Asn Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Asp Thr Tyr Pro Thr Ile Thr Gln Asp Glu Val
            100                 105                 110

Gly Leu Thr Lys Leu Tyr Lys Gln Phe Ser Phe Pro Gly Gly Ile Ala
        115                 120                 125

Ser His Ala Ala Pro Glu Thr Pro Gly Ser Leu His Glu Gly Gly Glu
    130                 135                 140

Leu Gly Tyr Ala Leu Ser His Ala Thr Gly Ser Ile Leu Asp Asn Pro
145                 150                 155                 160

Asp Val Ile Ala Ala Thr Val Ile Gly Asp Gly Glu Ala Glu Thr Gly
                165                 170                 175

Pro Leu Ser Ala Gly Trp Phe Ser Asn Thr Phe Ile Asn Pro Val Asn
            180                 185                 190

Asp Gly Ala Val Leu Pro Ile Leu Tyr Leu Asn Gly Ala Lys Ile Ser
        195                 200                 205

Asn Pro Thr Ile Leu Ser Arg Lys Thr Asp Lys Glu Leu Thr Ser Phe
    210                 215                 220

Phe Gln Gly Leu Gly Trp Asp Pro Ile Phe Val Glu Gly Glu Asp Pro
225                 230                 235                 240

Ala Lys Val His Pro Leu Met Ala Glu Lys Leu Asp Gln Ala Ile Glu
                245                 250                 255

Lys Ile Lys Ala Ile Gln Thr Glu Ala Arg Lys Glu Ala Ala Asp Lys
            260                 265                 270

Ala Thr Met Pro Thr Trp Pro Val Ile Leu Phe Arg Thr Pro Lys Gly
        275                 280                 285

Trp Thr Gly Pro Lys Glu Trp Asn Asn Glu Pro Ile Glu Gly Ser Phe
    290                 295                 300

Arg Ala His Gln Val Pro Ile Pro Val Asp Gln His His Phe Asp His
305                 310                 315                 320

Val Asp Ala Leu Glu Asn Trp Leu Gln Ser Tyr Arg Pro Glu Glu Leu
                325                 330                 335

Phe Thr Glu Glu Gly Ser Leu Lys Glu Glu Ile Lys Ser Leu Ala Pro
            340                 345                 350

Lys Asn Arg Met Ala Thr Asn Pro Ile Thr Asn Gly Gly Ile Asp Pro
        355                 360                 365

Gln Pro Leu Arg Leu Pro Ser Trp Lys Asp Tyr Ala Val Glu Thr Ala
    370                 375                 380

Asn Lys Asp Val Ile Thr Gln Asp Met Ile Glu Leu Gly Gly Phe Val
```

385 390 395 400

Arg Asp Ile Val Lys Glu Asn Pro Asp Asn Phe Arg Ile Phe Gly Pro
405 410 415

Asp Glu Thr Lys Ser Asn Arg Leu Asn Lys Val Phe Glu Val Thr Asn
420 425 430

Arg Gln Trp Met Ser Lys Ala Glu Phe Pro Arg Asp Glu Trp Leu Ala
435 440 445

Pro Ala Gly Arg Ile Ile Asp Gly Gln Leu Ser Glu His Gln Ala Glu
450 455 460

Gly Phe Leu Glu Gly Tyr Val Leu Thr Gly Arg His Gly Phe Phe Ala
465 470 475 480

Ser Tyr Glu Ser Phe Leu Arg Val Val Asp Ser Met Leu Thr Gln His
485 490 495

Phe Lys Trp Leu Arg Lys Ala Lys Glu Gln Thr Trp Arg Asn Ser Tyr
500 505 510

Pro Ser Leu Asn Val Ile Ala Thr Ser Thr Val Phe Gln Gln Asp His
515 520 525

Asn Gly Tyr Thr His Gln Asp Pro Gly Val Leu Thr His Leu Ala Glu
530 535 540

Lys Lys Pro Glu Phe Ile Arg Glu Tyr Leu Pro Ala Asp Thr Asn Ser
545 550 555 560

Leu Leu Ala Val Met Asn Glu Ala Phe Arg Ser Glu Glu Leu Ile Asn
565 570 575

Leu Ile Val Ser Ser Lys His Pro Arg Pro Gln Phe Tyr Ser Ala Glu
580 585 590

Glu Ala Glu Ile Leu Val Lys Asp Gly Leu Lys Ile Ile Asp Trp Ala
595 600 605

Ser Thr Val Ser Glu Ala Glu Glu Pro Asp Val Val Ile Ala Ser Ala
610 615 620

Gly Thr Glu Pro Asn Leu Glu Ala Leu Ala Ala Val Thr Leu Leu Asn
625 630 635 640

Glu Ala Phe Pro Ser Leu Lys Ile Arg Phe Ile Asn Ile Val Asp Ile
645 650 655

Leu Lys Leu Arg His Pro Asp Ile Asp Pro Arg Gly Leu Thr Asp Glu
660 665 670

Glu Phe Asp Arg Tyr Phe Thr Thr Asp Lys Pro Ile Ile Phe Ala Phe
675 680 685

His Ser Tyr Glu Gly Met Val Arg Asp Ile Phe Phe Asn Arg His Asn
690 695 700

His Asn Leu Phe Ile His Gly Tyr Arg Glu Asn Gly Asp Ile Thr Thr
705 710 715 720

Pro Phe Asp Met Arg Val Leu Ser Glu Met Asp Arg Phe His Leu Ala
725 730 735

Lys Asp Ala Ala Glu Ala Val Tyr Gly Glu Ile Ala Thr Ser Phe Ala
740 745 750

Ala Glu Met Asp Ala Val Leu Ser Lys His His His Phe Ile Arg Glu
755 760 765

Asn Gly Glu Asp Leu Pro Glu Val Glu Asn Trp Lys Trp Gln Ala Leu
770 775 780

Lys Thr Asp Leu Leu Glu Val
785 790

<210> SEQ ID NO 25

<211> LENGTH: 788
<212> TYPE: PRT
<213> ORGANISM: Enterococcus casseliflavus EC30

<400> SEQUENCE: 25

```
Met Lys Thr Thr Tyr Asp Thr Pro Glu Tyr Tyr Gln Lys Met Asn Ala
1               5                   10                  15

Trp Trp Arg Ala Ala Asn Tyr Leu Ser Val Gly Gln Ile Tyr Leu Lys
            20                  25                  30

Asp Asn Pro Leu Leu Arg Arg Pro Ile Glu Glu Lys Asp Leu Lys Val
        35                  40                  45

Asn Pro Ile Gly His Trp Gly Thr Ile Ala Gly Gln Asn Phe Ile Tyr
    50                  55                  60

Thr His Leu Asn Arg Val Ile Asn Lys Tyr Asp Leu Asn Met Phe Tyr
65                  70                  75                  80

Ile Glu Gly Pro Gly His Gly Gly Gln Val Met Val Ala Asn Ala Tyr
                85                  90                  95

Leu Asp Gly Ser Tyr Ser Glu Ile Tyr Pro Lys Ala Thr Gln Asp Glu
            100                 105                 110

Ala Gly Met Lys His Leu Phe Lys Thr Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ala His Ala Thr Gly Ala Ile Leu Asp Asn
145                 150                 155                 160

Pro Asp Val Ile Ala Ala Val Val Val Gly Asp Gly Glu Ala Glu Thr
                165                 170                 175

Gly Pro Leu Ala Gly Ser Trp Phe Ser Asn Thr Phe Ile Asn Pro Val
            180                 185                 190

Asn Asp Gly Ala Ile Leu Pro Ile Leu His Leu Asn Gly Ala Lys Ile
        195                 200                 205

Ala Asn Pro Thr Ile Leu Ala Arg Lys Ser Asp Gln Asp Leu Thr Lys
    210                 215                 220

Tyr Phe Glu Gly Met Gly Trp Thr Pro Tyr Phe Val Glu Gly Asp Asp
225                 230                 235                 240

Pro Glu Ala Val His Pro Gln Leu Ala Gln Lys Met Asp Gln Ala Ile
                245                 250                 255

Glu Gln Ile His Ala Ile Gln Ala Glu Ala Arg Lys Gly Ser Ala Glu
            260                 265                 270

Glu Ala Ala Met Pro His Trp Pro Val Leu Ile Val Arg Thr Pro Lys
        275                 280                 285

Gly Trp Thr Gly Pro Lys Val Trp Asp Gly Glu Pro Ile Glu Gly Gly
    290                 295                 300

Phe Arg Ala His Gln Val Pro Ile Pro Val Asn Ala Lys His Met Glu
305                 310                 315                 320

His Val Asp Ala Leu Thr Asp Trp Leu Gln Ser Tyr Arg Pro Glu Glu
                325                 330                 335

Leu Phe Asp Glu Asn Gly Arg Ile Lys Ala Glu Ile Gln Glu Leu Ala
            340                 345                 350

Pro Lys Gly Glu Gln Arg Met Ala Val Asn Pro Ile Thr Asn Gly Gly
        355                 360                 365

Ile Asp Pro Gln Pro Leu Arg Leu Pro Asp Trp Gln Ala His Ala Ile
    370                 375                 380

Ala Ile Glu Thr Pro Gly Glu Thr Thr Ala Gln Asp Met Met Val Phe
```

-continued

```
385                 390                 395                 400

Gly Lys Phe Ala Arg Asp Ile Ile Lys Glu Asn Pro Asp Asn Phe Arg
                405                 410                 415

Ile Phe Gly Pro Asp Glu Ala Lys Ser Asn Arg Leu Asn His Val Phe
            420                 425                 430

Glu Val Thr Asp Arg Gln Trp Leu Glu Pro Lys His Pro Asp Tyr Asp
        435                 440                 445

Glu Trp Leu Ser Ser Val Gly Arg Val Ile Asp Ser Gln Leu Ser Glu
    450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ile Thr Gln His Phe Lys Trp Leu Arg Lys Ala His Asp Leu Asp Trp
            500                 505                 510

Arg Asn Pro Tyr Pro Ser Leu Asn Leu Ile Ala Ser Ser Thr Val Phe
        515                 520                 525

Gln Gln Asp His Asn Gly Tyr Thr His Gln Asp Pro Gly Ile Met Thr
    530                 535                 540

His Ile Ala Glu Lys Lys Ala Asp Phe Val Arg Val Tyr Leu Pro Ala
545                 550                 555                 560

Asp Ala Asn Ser Leu Met Ala Val Met Ala Glu Thr Leu Ala Ser Glu
                565                 570                 575

Glu Lys Ile Asn Leu Val Val Ser Ser Lys His Pro Arg Pro Gln Phe
            580                 585                 590

Tyr Ser Ala Asp Glu Ala Lys Val Leu Val Lys Asp Gly Leu Lys Val
        595                 600                 605

Ile Asp Trp Ala Ser Thr Asp Glu Gly Gln Glu Pro Asp Ile Val Ile
    610                 615                 620

Ala Ala Ala Gly Thr Glu Pro Asn Leu Glu Ala Leu Ala Ala Val Ser
625                 630                 635                 640

Leu Leu Ile Glu Ala Phe Pro Glu Leu Lys Val Arg Phe Ile Asn Val
                645                 650                 655

Val Asp Leu Leu Lys Leu Arg Arg Pro Glu Val Asp Pro Arg Gly Leu
            660                 665                 670

Ser Asp Glu Ala Phe Glu Ala Tyr Phe Thr Lys Asp Lys Pro Ile Val
        675                 680                 685

Phe Ala Phe His Gly Tyr Glu Gly Leu Ile Arg Asp Ile Phe Phe Gly
    690                 695                 700

Arg Arg Asn Gln Gln Leu His Ile His Gly Tyr Arg Glu Asn Gly Asp
705                 710                 715                 720

Ile Thr Thr Pro Phe Asp Met Arg Ile Leu Ser Glu Leu Asp Arg Phe
                725                 730                 735

His Leu Ala Lys Asp Ala Ala Glu Trp Val Tyr Gly Glu Lys Ala Thr
            740                 745                 750

Asp Phe Ala Gln Lys Met Ala Asp Thr Val Ala Tyr His His Asp Phe
        755                 760                 765

Ile Arg Glu Asn Gly Tyr Asp Ile Ala Glu Val Glu Glu Trp Glu Trp
    770                 775                 780

Lys Pro Leu Arg
785

<210> SEQ ID NO 26
```

<211> LENGTH: 792
<212> TYPE: PRT
<213> ORGANISM: Mycoplasma alligatoris A21JP2

<400> SEQUENCE: 26

```
Met Lys Lys Asn Thr Phe Asp Thr Gln Asp Tyr Leu Asp Lys Val Asp
 1               5                  10                  15

Ala Trp Phe Arg Ala Ala Asn Tyr Leu Ser Val Gly Gln Met Tyr Leu
            20                  25                  30

Arg Asn Asn Pro Leu Leu Arg Ser Lys Ile Thr Ser Asp Asp Val Lys
        35                  40                  45

Val Tyr Pro Ile Gly His Trp Gly Thr Ile Pro Gly Gln Asn Phe Ala
    50                  55                  60

Tyr Ala His Leu Asn Arg Val Ile Asn Lys Tyr Asn Leu Asn Met Phe
65                  70                  75                  80

Tyr Ile Glu Gly Pro Gly His Gly Gly Gln Val Met Thr Ser Asn Ser
                85                  90                  95

Tyr Leu Asp Gly Ser Tyr Thr Glu Leu Phe Pro His Val Thr Gln Asp
            100                 105                 110

Val Ala Gly Met Lys His Leu Phe Lys Tyr Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Leu Ser His Ala Thr Gly Ala Ile Leu Asp
145                 150                 155                 160

Asn Pro Asn Val Ile Ala Ala Thr Ile Val Gly Asp Gly Glu Ala Glu
                165                 170                 175

Thr Gly Pro Leu Ala Ala Ser Trp Phe Ser Asn Ser Phe Ile Asn Pro
            180                 185                 190

Val Asn Asp Gly Ala Val Leu Pro Ile Leu His Leu Asn Gly Gly Lys
        195                 200                 205

Ile Ser Asn Pro Thr Ile Leu Cys Arg Lys Ser Asn Lys Glu Leu Thr
    210                 215                 220

Asp Tyr Phe Ala Gly Met Gly Trp Glu Ala Val Phe Val Glu Gly Ser
225                 230                 235                 240

Asp Glu Lys Glu Met His Lys Val Met Ala Gln Lys Leu Asp Tyr Val
                245                 250                 255

Ile Glu Lys Ile Gln Ser Ile Gln Asn Glu Ala Arg Lys Lys Pro Ala
            260                 265                 270

Asn Gln Ala Thr Arg Pro Ile Trp Pro Met Met Val Leu Arg Thr Pro
        275                 280                 285

Lys Gly Trp Thr Gly Pro Asp Ser Trp Asn Lys Asp Lys Ile Val Gly
    290                 295                 300

Ser Phe Arg Ala His Gln Val Pro Ile Pro Val Asn Ser Ala Asn Met
305                 310                 315                 320

Glu His Ile Asp Ala Leu Leu Asp Trp Leu Lys Ser Tyr Lys Val Asp
                325                 330                 335

Asn Leu Phe Asp Lys Asn Gly Lys Leu Val Asp Glu Ile Ala Gln Ile
            340                 345                 350

Ala Pro Lys Gly Asp Gln Arg Met Gly Met Asn Pro Ile Thr Asn Gly
        355                 360                 365

Gly Leu Asn Pro Lys Lys Leu Val Met Pro Arg Trp Gln Asp Phe Ala
    370                 375                 380

Leu Lys Phe Ser Lys Pro Gly Glu Leu Val Asn Gln Asp Met Val Glu
```

```
385                 390                 395                 400

Leu Gly Thr Tyr Phe Ala Lys Met Met Glu Leu Asn Lys Asp Asn Phe
                405                 410                 415

Arg Leu Phe Gly Pro Asp Glu Thr Lys Ser Asn Arg Leu Tyr Asn Val
            420                 425                 430

Phe Lys Val Thr Lys Arg Gln Trp Leu Glu Pro Ile Ser Pro Ile Leu
        435                 440                 445

Asp Glu Ala Leu Ser Pro Glu Gly Arg Val Ile Asp Ser Gln Leu Ser
    450                 455                 460

Glu His Gln Ala Glu Gly Phe Leu Glu Gly Tyr Val Leu Thr Gly Arg
465                 470                 475                 480

His Gly Val Phe Ala Ser Tyr Glu Ser Phe Leu Arg Val Val Asp Ser
                485                 490                 495

Met Leu Thr Gln His Leu Lys Trp Leu Lys Lys Ala Lys Asp Val His
            500                 505                 510

Trp Arg Asn Asp Tyr Pro Ser Leu Asn Val Ile Ala Thr Ser Thr Ala
        515                 520                 525

Phe Gln Gln Asp His Asn Gly Tyr Thr His Gln Asp Pro Gly Leu Ile
    530                 535                 540

Gly His Leu Ala Asp Lys Thr Pro Glu Ile Ile Arg Gln Tyr Leu Pro
545                 550                 555                 560

Ala Asp Thr Asn Thr Leu Leu Ala Val Met Asp Lys Ser Leu Lys Glu
                565                 570                 575

Arg Asn Val Ile Asn His Ile Ile Ala Ser Lys Gln Pro Arg Glu Gln
            580                 585                 590

Phe Tyr Ser Glu Gln Glu Ala Ala Glu Leu Val Glu Lys Gly Leu Lys
        595                 600                 605

Val Ile Asp Trp Ala Ser Thr Thr Lys Gly Asn Glu Glu Pro Glu Leu
    610                 615                 620

Val Val Val Ala Ala Gly Thr Glu Pro Asn Leu Glu Ala Leu Ala Ala
625                 630                 635                 640

Val Thr Ile Leu Asn Lys Glu Tyr Pro Ser Leu Lys Ile Arg Phe Val
                645                 650                 655

Asn Val Val Asp Leu Met Lys Leu Arg His Pro Ser Leu Asp Pro Arg
            660                 665                 670

Gly Leu Ser Asp Lys Glu Phe Asp Ala Ile Phe Thr Ser Asn Lys Pro
        675                 680                 685

Ile Val Phe Ala Phe His Gly Tyr Glu Gly Ile Leu Arg Asp Met Phe
    690                 695                 700

Phe Lys Arg Asn Asn His Asn Leu Ile Thr His Gly Tyr Arg Glu Asn
705                 710                 715                 720

Gly Asp Ile Thr Thr Ser Phe Asp Ile Arg Gln Leu Ser His Met Asp
                725                 730                 735

Arg Phe His Ile Ser Ala Ser Ala Ala Lys Ala Val Tyr Gly Asn Lys
            740                 745                 750

Ala Gln Glu Phe Glu Asp Lys Met Ile Gln Thr Ile Asp Phe His Thr
        755                 760                 765

Lys Tyr Ile Arg Glu Tyr Gly Thr Asp Ile Pro Glu Val Lys Glu Trp
    770                 775                 780

Lys Trp Ala Asp Leu Thr Arg Lys
785                 790
```

<210> SEQ ID NO 27

<211> LENGTH: 785
<212> TYPE: PRT
<213> ORGANISM: Carnobacterium sp. 17-4

<400> SEQUENCE: 27

```
Met Lys Asn Tyr Asp Ser Lys Asp Tyr Leu Lys Lys Val Asp Ala Phe
 1               5                  10                  15

Trp Arg Ala Ala Asn Tyr Leu Ser Val Gly Gln Leu Tyr Leu Arg Asp
            20                  25                  30

Asn Pro Leu Leu Gln Arg Pro Leu Lys Ser Thr Asp Val Lys Ala His
        35                  40                  45

Pro Ile Gly His Trp Gly Thr Ile Ser Gly Gln Asn Phe Ile Tyr Ala
    50                  55                  60

His Leu Asn Arg Val Ile Asn Lys Tyr Asp Leu Asn Met Phe Tyr Ile
65                  70                  75                  80

Glu Gly Pro Gly His Gly Gly Gln Val Met Ile Ser Asn Ala Tyr Leu
                85                  90                  95

Asp Gly Ser Tyr Thr Glu Ile Tyr Pro Asp Ile Thr Glu Asn Lys Glu
            100                 105                 110

Gly Met Lys Lys Leu Phe Lys Gln Phe Ser Ser Pro Gly Gly Val Ala
        115                 120                 125

Ser His Ala Ala Pro Glu Thr Pro Gly Ser Ile His Glu Gly Gly Glu
    130                 135                 140

Leu Gly Tyr Ser Leu Ser His Ala Thr Gly Ala Ile Leu Asp Asn Pro
145                 150                 155                 160

Asp Val Ile Ala Ala Thr Val Ile Gly Asp Gly Glu Ala Glu Thr Gly
                165                 170                 175

Pro Leu Ala Ala Gly Trp Phe Ser Asn Asn Phe Ile Asn Pro Val Asn
            180                 185                 190

Asp Gly Ala Val Leu Pro Ile Leu Tyr Leu Asn Gly Gly Lys Ile Ser
        195                 200                 205

Asn Pro Thr Ile Leu Ala Arg Lys Ser Asn Glu Asp Leu Lys Lys Tyr
    210                 215                 220

Phe Glu Gly Met Gly Trp Lys Pro Tyr Phe Val Glu Gly Thr Asp Pro
225                 230                 235                 240

Glu Lys Val His Pro Val Met Ala Asn Thr Leu Asp Val Val Ile Glu
                245                 250                 255

Glu Ile Arg Ser Ile Gln Asn Glu Ala Arg Lys Gly Lys Ala Glu Asp
            260                 265                 270

Val Glu Met Pro His Trp Pro Val Met Ile Ile Arg Thr Pro Lys Gly
        275                 280                 285

Trp Thr Gly Pro Lys Glu Trp Asp Asn Lys Lys Ile Glu Gly Thr Phe
    290                 295                 300

Arg Ala His Gln Val Pro Ile Pro Val Asp Ala Glu His Met Glu Tyr
305                 310                 315                 320

Val Asn Lys Leu Val Asp Trp Leu Lys Ser Tyr Arg Pro Glu Glu Leu
                325                 330                 335

Phe Thr Glu Asn Gly Lys Leu Ile Asp Asp Leu Lys Glu Leu Thr Pro
            340                 345                 350

Lys Gly Asn Lys Arg Met Ala Thr Asn Pro Ile Thr Asn Gly Gly Ile
        355                 360                 365

Asn Ala Lys Ala Leu Ile Ile Pro Asn Trp Lys Gln His Ala Ile Asp
    370                 375                 380

Thr Thr Ile Pro Gly Ala Val Ile Ala Gln Asp Met Asp Val Phe Gly
```

```
385                 390                 395                 400

Glu Gln Ala Arg Asp Leu Ile Val Lys Asn Pro Asn Asn Phe Arg Ile
                405                 410                 415

Phe Gly Pro Asp Glu Thr Lys Ser Asn Arg Leu Asp Lys Ile Phe Glu
            420                 425                 430

Val Thr Asn Arg Gln Trp Leu Glu Ser Lys Glu Leu Thr Asp Glu Trp
        435                 440                 445

Gln Ser Ser Ala Gly Arg Val Ile Asp Gly Gln Leu Ser Glu His Gln
    450                 455                 460

Ala Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Leu Arg Lys Ala Thr Asp Gln Lys Trp Arg Asn
            500                 505                 510

Asn Tyr Pro Ser Leu Asn Val Ile Ala Thr Ser Thr Val Phe Gln Gln
        515                 520                 525

Asp His Asn Gly Tyr Thr His Gln Asp Pro Gly Ile Leu Thr His Leu
    530                 535                 540

Ala Glu Lys Lys Pro Glu Phe Ile Arg Glu Tyr Leu Pro Ala Asp Ala
545                 550                 555                 560

Asn Ser Leu Met Ala Val Met Asp Lys Thr Leu Gln Glu Glu Gln Leu
                565                 570                 575

Ile Asn Leu Ile Ile Ser Ser Lys His Pro Arg Pro Gln Phe Tyr Ser
            580                 585                 590

Val Glu Glu Ala Glu Ile Leu Val Lys Asp Gly Leu Lys Ile Ile Asp
        595                 600                 605

Trp Ala Ser Thr Asp Asn Asp Ser Glu Pro Asp Leu Val Ile Ala Ala
    610                 615                 620

Ala Gly Thr Glu Pro Asn Leu Glu Ala Leu Ala Ala Met Ser Ile Leu
625                 630                 635                 640

His Lys Ala Phe Pro Glu Leu Lys Ile Arg Phe Ile Asn Ile Val Asp
                645                 650                 655

Ile Leu Lys Leu Arg His Pro Asp Ile Asp Ser Arg Gly Leu Thr Asp
            660                 665                 670

Glu Lys Phe Asp Ser Tyr Phe Thr Lys Glu Gln Pro Ile Ile Phe Ala
        675                 680                 685

Phe His Gly Phe Glu Gly Leu Ile Arg Asp Ile Phe Phe Asn Arg His
    690                 695                 700

Asn His Asn Leu Arg Ile His Gly Tyr Arg Glu Asn Gly Asp Ile Thr
705                 710                 715                 720

Thr Pro Phe Asp Met Arg Val Leu Asn Glu Met Asp Arg Phe His Leu
                725                 730                 735

Ala Lys Asp Ala Ala Lys Ala Val Tyr Gly Leu Lys Ala Asn Lys Phe
            740                 745                 750

Met Gln Glu Met Glu Asn Thr Val Asn Phe His His Gln Tyr Ile Arg
        755                 760                 765

Glu Asn Gly Ile Asp Ile Pro Glu Val Ile Asn Trp Lys Trp Glu Lys
    770                 775                 780

Ile
785
```

<210> SEQ ID NO 28

<211> LENGTH: 799
<212> TYPE: PRT
<213> ORGANISM: Melissococcus plutonius ATCC 35311

<400> SEQUENCE: 28

Met Glu Lys Asp Lys Tyr Ser Ser Thr Glu Tyr Leu Asp Lys Ile Asp
1 5 10 15

Lys Trp Trp Arg Ala Ala Asn Tyr Leu Ser Ile Gly Gln Leu Tyr Leu
20 25 30

Lys Asp Asn Pro Leu Leu Lys Arg Lys Ile Arg Ser Glu Asp Val Lys
35 40 45

Tyr His Pro Ile Gly His Trp Gly Thr Ile Ala Gly Gln Asn Phe Ile
50 55 60

Tyr Ala His Leu Asn Arg Ile Ile Asn Lys Tyr Asp Leu Asn Met Phe
65 70 75 80

Tyr Ile Glu Gly Pro Gly His Gly Gly Gln Val Met Val Ser Asn Ser
85 90 95

Tyr Leu Asp Gly Ser Tyr Thr Glu Ile Tyr Pro Ala Val Thr Glu Asp
100 105 110

Glu Ala Gly Met Gln Lys Leu Phe Lys Arg Phe Ser Phe Pro Gly Gly
115 120 125

Val Ser Ser His Ala Ala Pro Glu Thr Pro Gly Ser Ile His Glu Gly
130 135 140

Gly Glu Leu Gly Tyr Ser Leu Ser His Gly Val Gly Ala Ile Leu Asp
145 150 155 160

Asn Pro Glu Val Ile Ser Ala Val Val Ile Gly Asp Gly Glu Ser Glu
165 170 175

Thr Gly Pro Leu Ala Thr Ser Trp Phe Ser Asn Thr Phe Ile Asn Pro
180 185 190

Val Thr Asp Gly Ala Val Leu Pro Ile Leu His Leu Asn Gly Ala Lys
195 200 205

Ile Ala Asn Pro Thr Ile Leu Gly Arg Lys Ser Asp Lys Glu Leu Glu
210 215 220

Gln Tyr Phe Arg Gly Met Gly Trp Ile Pro Tyr Phe Val Glu Gly Asn
225 230 235 240

Asp Pro Asn Gln Met His Pro Leu Met Ala Lys Thr Leu Asp Gln Val
245 250 255

Ile Glu Lys Ile His Ser Ile Gln Glu Thr Ala Arg Lys Gln Thr Ala
260 265 270

Glu Thr Ala Ser Ile Gln Lys Trp Pro Leu Ile Val Leu Arg Thr Pro
275 280 285

Lys Gly Trp Thr Gly Pro Lys Glu Trp Asp Gly Lys Pro Ile Glu Val
290 295 300

Thr Phe Arg Ala His Gln Val Pro Ile Pro Ile Asp Gln Asp His Met
305 310 315 320

Glu His Val Asp Gln Leu Val Asn Trp Leu Lys Ser Tyr Lys Pro Glu
325 330 335

Glu Leu Phe Asp Glu Thr Gly Arg Leu Asn Ser Glu Ile Arg Ala Ile
340 345 350

Ala Pro Met Asn Asp Lys Arg Met Ala Met Asn Pro Ile Thr Asn Gly
355 360 365

Gly Ile Asn Pro Lys Pro Leu Gln Met Pro Asp Trp Arg Glu Phe Asp
370 375 380

Leu His Ile Ser Lys Pro Gly Glu Leu Val Ala Gln Asp Met Leu Glu 385 390 395 400

Phe Gly Lys Met Val Ala Ala Ile Ile Lys Lys Asn Pro Gln Asn Phe
405 410 415

Leu Ile Phe Gly Pro Asp Glu Thr Lys Ser Asn Leu Leu Asn Asp Ala
420 425 430

Phe Ser Val Thr Ser Arg Gln Trp Leu Glu Pro Ile Tyr Glu Pro Gln
435 440 445

Asp Glu Trp Leu Ala Pro Ser Gly Arg Ile Ile Asp Ser Gln Leu Ser
450 455 460

Glu His Gln Asp Glu Gly Ile Leu Glu Gly Tyr Val Leu Thr Gly Arg
465 470 475 480

His Gly Phe Phe Ala Ser Tyr Glu Ala Phe Ile Arg Ile Val Asp Ser
485 490 495

Met Ile Ala Gln His Ile Lys Trp Met Arg Lys Ala Met Asp Leu Pro
500 505 510

Trp Arg Asn Gly Tyr Ser Ser Leu Asn Leu Ile Ala Ser Ser Thr Ala
515 520 525

Phe Gln Gln Asp His Asn Gly Tyr Thr His Gln Asp Pro Gly Ile Leu
530 535 540

Ser His Leu Ala Glu Lys Glu Ala Asp Phe Ile His Glu Tyr Val Pro
545 550 555 560

Ala Asp Thr Asn Ser Leu Leu Ala Val Met Asp Lys Val Leu Lys Ser
565 570 575

Gln Gly Lys Val Asn Leu Val Ile Ser Ser Lys His Pro Arg Pro Gln
580 585 590

Phe Tyr Ser Pro Glu Glu Ala Gln Glu Leu Val Asn Arg Gly Leu Met
595 600 605

Glu Ile Asp Trp Ala Ser Thr Val Ala Glu Asn Gly Thr Pro Glu Ile
610 615 620

Val Ile Val Ala Ala Gly Thr Glu Pro Asn Met Glu Ala Leu Ala Ala
625 630 635 640

Ile Asn Leu Ile Asn Gln Ser Phe Pro Lys Leu Gln Phe Arg Phe Ile
645 650 655

Asn Val Val Asp Leu Leu Lys Leu Arg His Pro Ala Val Asp Ser Arg
660 665 670

Gly Ile Ser Glu Val Glu Tyr Asn His Leu Phe Thr Val Asp Ser Pro
675 680 685

Ile Ile Phe Val Cys Gln Gly Tyr Ser Ser Leu Ile Arg Ser Leu Phe
690 695 700

Tyr Asp Arg Lys Asn Arg Pro Val Ser Ile His Ser Tyr Gln Glu Asn
705 710 715 720

Gly Ala Ile Thr Thr Pro Phe Asp Met Arg Val Leu Asn Lys Ile Asp
725 730 735

Arg Tyr His Leu Ala Lys Asp Ile Ala Leu Thr Ala Tyr Gly Ser Arg
740 745 750

Gly Glu Asp Phe Ala Arg Ala Met Asp Thr Ile Leu Glu Lys His Asn
755 760 765

Gln Tyr Ile Arg Glu Thr Gly Lys Asp Leu Pro Glu Val Leu Asn Trp
770 775 780

Lys Trp Ala Pro Leu His Ile Tyr Asn Glu Asn Ile Glu Gln Asp
785 790 795

<210> SEQ ID NO 29

<211> LENGTH: 787
<212> TYPE: PRT
<213> ORGANISM: Tetragenococcus halophilus NBRC 12172

<400> SEQUENCE: 29

```
Met Ser Val Asn Ile Asp Ser Lys Glu Tyr Leu Glu Arg Met Asn Ala
1               5                   10                  15

Trp Trp Arg Ala Ala Asn Tyr Ile Ser Val Ala Gln Ile Phe Leu Arg
            20                  25                  30

Asp Asn Pro Leu Leu Arg Arg Pro Leu Glu Lys Glu Asp Ile Lys Ile
        35                  40                  45

Asn Pro Ile Gly His Trp Gly Thr Ile Ser Gly Gln Asn Phe Ile Tyr
    50                  55                  60

Val His Leu Asn Arg Val Ile Asn Lys Tyr Gly Leu Asn Met Phe Tyr
65                  70                  75                  80

Ile Glu Gly Pro Gly His Gly Gly Gln Val Met Val Ser Asn Ser Tyr
                85                  90                  95

Ile Asp Gly Ser Tyr Ser Glu Ile Tyr Pro Asp Val Thr Gln Asp Glu
            100                 105                 110

Ala Gly Leu Lys Lys Leu Phe Lys Gln Phe Ser Phe Pro Gly Gly Met
        115                 120                 125

Gly Ser His Ala Ala Pro Glu Thr Pro Gly Ser Ile His Glu Gly Gly
    130                 135                 140

Glu Leu Gly Tyr Ser Met Ser His Ala Val Gly Ala Val Leu Asp Asn
145                 150                 155                 160

Pro Asp Val Ile Ala Ala Thr Val Ile Gly Asp Gly Glu Ala Glu Thr
                165                 170                 175

Gly Pro Leu Ala Ala Ser Trp Met Ser Asn Asn Phe Ile Asn Pro Val
            180                 185                 190

Asn Asp Gly Ala Val Leu Pro Ile Leu Asn Leu Asn Gly Ala Lys Ile
        195                 200                 205

Ala Asn Pro Thr Val Leu Ala Arg Lys Ser Asp Lys Asp Leu Gln Lys
    210                 215                 220

Tyr Phe Glu Gly Leu Gly Trp Lys Pro Tyr Phe Val Glu Gly Asp Asn
225                 230                 235                 240

Pro Glu Lys Met His Pro Leu Met Ala Glu Thr Leu Asp Ala Val Ile
                245                 250                 255

Asn Glu Ile Gln Ser Ile Gln Lys Glu Ala Arg Lys Gly Ser Ala Glu
            260                 265                 270

Asp Val Thr Met Pro His Trp Pro Val Ile Val Phe Arg Thr Pro Lys
        275                 280                 285

Gly Trp Glu Gly Pro Glu Lys Trp Asp Asn Glu Gln Ile Ala Gly Thr
    290                 295                 300

Phe Arg Ala His Gln Val Pro Ile Pro Ile Asp Ala Ser His Met Glu
305                 310                 315                 320

Tyr Ala Asn Asp Leu Ala Lys Trp Leu Lys Ser Tyr Arg Pro Glu Glu
                325                 330                 335

Leu Phe Asp Glu Asn Gly Thr Ile Ile Asp Ala Ile Lys Glu Leu Ser
            340                 345                 350

Pro Lys Gly Asp Asn Arg Met Ser Val Asn Pro Ile Thr Asn Gly Gly
        355                 360                 365

Leu Asp Pro Lys Ala Leu Asn Met Pro Asp Trp His Thr His Ala Val
    370                 375                 380

Asp Thr Ser Lys Arg Gly Thr Asp Lys Ala Gln Asp Met Ser Val Leu
```

```
385                 390                 395                 400

Gly Gly Phe Ile Ala Asp Ile Met Glu Asn Asn Pro Lys Asn Phe Arg
                405                 410                 415

Ile Phe Gly Pro Asp Glu Thr Lys Ser Asn Arg Leu Asn Lys Val Phe
            420                 425                 430

Asp Val Thr Asn Arg Gln Trp Val Glu Pro Arg Glu Leu Ser Asp Glu
        435                 440                 445

Trp Gln Ser Ala Val Gly Arg Val Ile Asp Gly Gln Leu Ser Glu His
    450                 455                 460

Gln Ala Glu Gly Phe Leu Glu Gly Tyr Thr Leu Thr Gly Arg His Gly
465                 470                 475                 480

Phe Phe Ala Ser Tyr Glu Ala Phe Leu Arg Ile Val Asp Ser Met Leu
                485                 490                 495

Thr Gln His Phe Lys Trp Ile Arg Lys Ala Asn Glu Lys Ser Trp Arg
            500                 505                 510

Lys Lys Tyr Pro Ser Leu Asn Val Ile Ser Ser Ser Thr Ala Phe Gln
        515                 520                 525

Gln Asp His Asn Gly Tyr Thr His Gln Asp Pro Gly Val Ile Thr His
    530                 535                 540

Leu Ala Glu Lys Lys Pro Glu Tyr Ile Arg Glu Tyr Phe Pro Ala Asp
545                 550                 555                 560

Ala Asn Ser Leu Met Ala Val Met Asp Lys Ala Leu Lys Asp Glu Asn
                565                 570                 575

Val Ile Asn Leu Ile Thr Ser Ser Lys His Pro Arg Pro Gln Phe Tyr
            580                 585                 590

Ser Val Glu Glu Ala Gln Glu Leu Val Asp Tyr Gly Val Lys Lys Ile
        595                 600                 605

Asp Trp Ala Ser Asn Asp Gln Asp Ser Glu Pro Asp Ile Val Phe Ala
    610                 615                 620

Ala Ala Gly Ser Glu Pro Asn Leu Glu Ala Leu Ala Ala Ile Ser Ile
625                 630                 635                 640

Leu His Glu Gln Phe Pro Glu Met Lys Ile Arg Phe Ile Asn Val Val
                645                 650                 655

Asp Leu Leu Lys Leu Arg His Pro Asp Val Asp Pro Arg Gly Leu Ser
            660                 665                 670

Asp Glu Ala Phe Asp Glu Leu Phe Thr Thr Asp Lys Pro Val Ile Phe
        675                 680                 685

Asn Phe His Gly Tyr Glu Gly Leu Ile Arg Asp Ile Phe Phe Thr Arg
    690                 695                 700

His Asn Arg Asn Leu Ser Ile His Gly Tyr Arg Glu Asp Gly Asp Ile
705                 710                 715                 720

Thr Thr Pro Phe Asp Met Arg Val Lys Asn Glu Leu Asp Arg Phe His
                725                 730                 735

Leu Ala Lys Asp Ala Ala Asn Thr Ile Tyr Ala Glu Lys Ala Ala Asp
            740                 745                 750

Phe Ile Gln Glu Met Asp Lys Thr Leu Gln Tyr His His Asp Tyr Ile
        755                 760                 765

Arg Glu Asn Gly Asp Asp Ile Ser Glu Val Gln Asn Trp Glu Trp Lys
    770                 775                 780

Asp Leu Lys
785
```

<210> SEQ ID NO 30

<211> LENGTH: 793
<212> TYPE: PRT
<213> ORGANISM: Melissococcus plutonius DAT561

<400> SEQUENCE: 30

```
Met Thr Lys Tyr Asp Ser Lys Glu Tyr Leu Ala Lys Val Asp Ala Phe
 1               5                  10                  15

Trp Arg Ala Ala Asn Tyr Ile Ser Val Gly Gln Leu Tyr Leu Lys Asp
            20                  25                  30

Asn Pro Leu Leu Asp Arg Pro Ile Glu Thr Thr Asp Val Lys Val His
        35                  40                  45

Pro Ile Gly His Trp Gly Thr Ile Ser Gly Gln Asn Phe Ile Tyr Ala
    50                  55                  60

His Leu Asn Arg Val Ile Asn Lys Tyr Asp Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Thr Glu Ile Tyr Pro Glu Ile Thr Glu Asp Lys Glu
            100                 105                 110

Gly Leu Lys Lys Leu Phe Lys Gln Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ser Ile Ser His Ala Thr Gly Ala Ile Leu Asp Asn Pro
145                 150                 155                 160

Asp Val Ile Ala Ala Thr Val Val Gly Asp Gly Glu Ala Glu Thr Gly
                165                 170                 175

Pro Leu Ser Ala Gly Trp Phe Ala Asn Thr Phe Ile Asn Pro Val Asn
            180                 185                 190

Asp Gly Ala Ile Leu Pro Ile Leu Tyr Leu Asn Gly Gly Lys Ile Ser
        195                 200                 205

Asn Pro Thr Ile Leu Glu Arg Lys Ser Asp Glu Glu Leu Thr Lys Tyr
    210                 215                 220

Phe Glu Gly Met Gly Trp Lys Pro Tyr Phe Val Glu Gly Thr Val Pro
225                 230                 235                 240

Asp Lys Val His Pro Leu Met Ala Lys Ile Leu Asp His Ile Ile Glu
                245                 250                 255

Glu Ile Lys Asp Ile Gln Lys Glu Ala Arg Lys Asp Lys Ala Glu Asn
            260                 265                 270

Ala Lys Met Pro His Trp Pro Val Leu Ile Met Arg Thr Pro Lys Gly
        275                 280                 285

Trp Thr Gly Pro Lys Ile Trp Asp Asp Glu Lys Ile Glu Gly Thr Phe
    290                 295                 300

Arg Ala His Gln Val Pro Ile Pro Val Asp Ala Glu His Met Glu His
305                 310                 315                 320

Ile Asp Ala Leu Val Asp Trp Leu Lys Ser Tyr His Pro Glu Glu Leu
                325                 330                 335

Phe Asp Lys Asn Gly Thr Leu Lys Pro Glu Leu Lys Glu Leu Val Pro
            340                 345                 350

Lys Gly Asp Arg Arg Met Ala Lys Asn Pro Ile Thr Asn Gly Gly Leu
        355                 360                 365

Asp Pro Lys Pro Leu Lys Met Asn Gly Trp Glu Gln His Ala Ile Asp
    370                 375                 380

Thr Ser Thr Pro Gly Met Val Thr Ala Gln Asp Met Ile Val Phe Gly
```

```
385                 390                 395                 400

Asn Tyr Val Glu Asp Leu Ile Lys Ala Asn Pro Thr Asn Phe Arg Ile
                405                 410                 415

Phe Gly Pro Asp Glu Thr Lys Ser Asn Arg Leu Asn Lys Val Phe Asp
            420                 425                 430

Ser Thr Asp Arg Gln Trp Met Glu Pro Ile Ser Asn Ala Asp Glu Trp
        435                 440                 445

Gln Ser Ser Val Gly Arg Val Ile Asp Gly Gln Leu Ser Glu His Gln
    450                 455                 460

Ala Glu Gly Phe Leu Glu Gly Tyr Ile Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Leu Arg Lys Ala Lys Glu Gln Ser Trp Arg Lys
            500                 505                 510

Glu Tyr Pro Ala Leu Asn Ile Ile Ala Thr Ser Thr Val Phe Gln Gln
        515                 520                 525

Asp His Asn Gly Tyr Thr His Gln Asp Pro Gly Ile Leu Thr His Leu
    530                 535                 540

Ala Glu Lys Lys Ala Glu Tyr Ile Arg Glu Tyr Leu Pro Ala Asp Ala
545                 550                 555                 560

Asn Cys Leu Met Ala Val Met Asp Lys Ala Phe Gln Glu Asn Glu Val
                565                 570                 575

Ile Asn Leu Ile Val Ser Ser Lys His Pro Arg Pro Gln Phe Tyr Ser
            580                 585                 590

Val Thr Glu Ala Lys Glu Leu Val Asp Lys Gly Val Lys Val Ile Asp
        595                 600                 605

Trp Ala Ser Asn Asp Glu Gly Gln Thr Pro Asp Ile Val Ile Ala Ala
    610                 615                 620

Ser Gly Thr Glu Pro Asn Leu Glu Ala Leu Ala Ala Ile Thr Leu Leu
625                 630                 635                 640

Asn Lys Glu Phe Ile Asp Leu Lys Ile Arg Phe Val Asn Val Val Asp
                645                 650                 655

Ile Leu Lys Leu Arg His Pro Ser Ile Asp Pro Arg Gly Leu Thr Asp
            660                 665                 670

Glu Glu Phe Asp Ala Ile Phe Thr Lys Asp Lys Pro Ile Val Phe Ala
        675                 680                 685

Phe His Gly Phe Glu Gly Leu Ile Arg Asp Ile Phe Phe Ser Arg Ser
    690                 695                 700

Asn His Gln Leu Phe Val His Gly Tyr Arg Glu Lys Gly Asp Ile Thr
705                 710                 715                 720

Thr Pro Phe Asp Met Arg Val Leu Ser Glu Met Asp Arg Phe His Leu
                725                 730                 735

Ala Lys Asp Val Ala Asp Lys Val Tyr Asn Glu Gln Ala Ala Asp Phe
            740                 745                 750

Met Asn Arg Met Asp Glu Ile Leu Ala Phe His His Gln Tyr Ile Arg
        755                 760                 765

Lys Asn Gly Ile Asp Ile Pro Glu Val Val Asn Trp Lys Trp Glu Asp
    770                 775                 780

Leu Arg Lys Lys Thr Ile Cys Phe Asn
785                 790

<210> SEQ ID NO 31
```

<211> LENGTH: 793
<212> TYPE: PRT
<213> ORGANISM: Mycoplasma arthritidis 158L3-1

<400> SEQUENCE: 31

```
Met Lys Lys Thr Asn Tyr Asp Ser Asn Glu Tyr Phe Asn Leu Ile Asp
 1               5                  10                  15

Lys Trp Phe Arg Ala Ala Asn Tyr Leu Ser Val Gly Gln Ile Tyr Leu
            20                  25                  30

Arg Asn Asn Pro Leu Leu Lys Thr Lys Leu Val Ala Asp Asp Val Lys
        35                  40                  45

Ile Tyr Pro Ile Gly His Trp Gly Thr Ile Pro Gly Gln Asn Phe Ile
    50                  55                  60

Tyr Ala His Leu Asn Arg Val Ile Asn Lys Tyr Asp Leu Glu Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Thr Glu Ile Tyr Pro Glu Ile Thr Glu Asp
            100                 105                 110

Glu Ala Gly Leu Lys Thr Met Phe Lys Arg Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ala Leu Ser His Ala Thr Gly Ala Ile Leu Asp
145                 150                 155                 160

Asn Pro Asn Val Ile Ala Ala Thr Val Ile Gly Asp Gly Glu Ala Glu
                165                 170                 175

Thr Gly Pro Leu Ala Ala Gly Trp Phe Ser Asn Ser Phe Ile Asn Pro
            180                 185                 190

Val Asn Asp Gly Ala Val Leu Pro Ile Ile His Leu Asn Gly Ala Lys
        195                 200                 205

Ile Ser Asn Pro Thr Ile Leu Ser Arg Lys Ser Asn Gln Glu Leu Glu
    210                 215                 220

Asn Tyr Phe Ser Gly Leu Gly Trp Glu Pro Leu Phe Val Glu Gly Asp
225                 230                 235                 240

Asp Pro Lys Leu Met His Pro Leu Met Ala Lys Lys Leu Asp Glu Ala
                245                 250                 255

Ile Glu Lys Ile Gln Met Ile Gln Ala Ser Ala Arg Lys His Lys Ala
            260                 265                 270

Ser Glu Ala Thr Arg Pro Val Trp Pro Met Leu Ile Val Arg Thr Pro
        275                 280                 285

Lys Gly Trp Thr Gly Pro Lys Asp Trp Asn Gly Glu Val Val Glu Gly
    290                 295                 300

Ser Phe Arg Ala His Gln Val Pro Ile Pro Val Asn Ala Leu Asn Met
305                 310                 315                 320

Thr His Ile Asp Lys Leu Glu Ala Trp Leu Thr Ser Tyr His Pro Glu
                325                 330                 335

Glu Leu Phe Asp Lys Asn Gly Lys Ile Leu Glu Glu Ile Arg Ala Leu
            340                 345                 350

Ala Pro Lys Gly Leu Lys Arg Met Ala Val His Pro Ile Thr Asn Gly
        355                 360                 365

Gly Ile Asn Pro Arg Thr Leu Lys Leu Ser Ser Trp Glu Lys Phe Ala
    370                 375                 380

Thr Lys Phe Glu Thr Pro Gly Gln Ile Lys Gly Gln Asp Met Ile Glu
```

```
385                 390                 395                 400

Leu Gly Lys Tyr Phe Ala Glu Ile Ile Thr Leu Asn Lys Asp Asn Phe
                405                 410                 415

Arg Ile Phe Gly Pro Asp Glu Thr Lys Ser Asn Arg Met Asn Ala Val
            420                 425                 430

Phe Asn Val Thr Lys Arg Gln Trp Leu Glu Lys Ile Ala Pro Thr Tyr
        435                 440                 445

Asp Glu Trp Met Ser Pro Glu Gly Arg Val Ile Asp Ser Gln Leu Ser
    450                 455                 460

Glu His Gln Ala Glu Gly Phe Leu Glu Gly Tyr Val Ile Thr Gly Arg
465                 470                 475                 480

His Gly Val Phe Ala Ser Tyr Glu Ala Phe Leu Arg Val Val Asp Ser
                485                 490                 495

Met Leu Thr Gln His Met Lys Trp Met Lys Lys Ser Leu Glu Leu Pro
            500                 505                 510

Trp Arg Lys Asp Phe Pro Ser Leu Asn Val Ile Ala Thr Ser Thr Ala
        515                 520                 525

Phe Gln Gln Asp His Asn Gly Tyr Thr His Gln Asp Pro Gly Leu Leu
    530                 535                 540

Gly His Leu Ala Asp Lys Arg Pro Glu Leu Ile Arg Glu Tyr Leu Pro
545                 550                 555                 560

Ala Asp Thr Asn Cys Leu Leu Ala Thr Met Glu Lys Ala Leu Lys Asp
                565                 570                 575

Arg Asn Val Ile Asn Leu Ile Val Ala Ser Lys Gln Pro Arg Glu Gln
            580                 585                 590

Phe Tyr Ser Val Glu Glu Ala Ser Glu Leu Val Gln Lys Gly Tyr Lys
        595                 600                 605

Ile Ile Asn Trp Ala Ser Asn Val Ser Lys Asn Glu Glu Pro Asp Val
    610                 615                 620

Val Phe Ala Ala Ala Gly Val Glu Pro Asn Leu Glu Ala Leu Ala Ala
625                 630                 635                 640

Ile Ser Ile Leu Asn Lys Glu Phe Pro Asn Leu Lys Ile Arg Phe Val
                645                 650                 655

Asn Val Leu Asp Leu Leu Lys Leu Lys Ser Pro Lys His Asp Pro Arg
            660                 665                 670

Gly Ile Ser Asp Glu Glu Phe Asp Gln Ile Phe Thr Lys Asn Lys Pro
        675                 680                 685

Ile Ile Phe Ala Phe His Gly Tyr Glu Gly Leu Leu Arg Asp Ile Phe
    690                 695                 700

Phe Asp Arg His Asn His Asn Leu Ile Thr His Gly Tyr Arg Glu Asn
705                 710                 715                 720

Gly Asp Ile Thr Thr Ser Phe Asp Ile Arg Gln Leu Ser His Met Asp
                725                 730                 735

Arg Phe His Ile Ala Lys Asp Ala Ala Ile Ala Ala Leu Gly Lys Asp
            740                 745                 750

Gly Glu Met Phe Ala Lys Lys Met Asp Ser Lys Leu Gln Glu His Thr
        755                 760                 765

Ser Tyr Val Arg Glu Tyr Gly Tyr Asp Leu Pro Glu Val Val Asn Trp
    770                 775                 780

Lys Trp Thr Asn Leu Lys Pro Ile Lys
785                 790
```

<210> SEQ ID NO 32

<211> LENGTH: 792
<212> TYPE: PRT
<213> ORGANISM: Streptococcus agalactiae NEM316

<400> SEQUENCE: 32

```
Met Ser Glu Phe Asp Thr Lys Ser Tyr Leu Glu Lys Leu Asp Ala Trp
 1               5                  10                  15

Trp Arg Ala Ala Asn Tyr Ile Ser Ala Ala Gln Met Tyr Leu Lys Asp
            20                  25                  30

Asn Pro Leu Leu Arg Arg Glu Leu Val Glu Asn Asp Leu Lys Val His
        35                  40                  45

Pro Ile Gly His Trp Gly Thr Val Pro Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Asn Pro Asn Ile Glu Gln Thr Glu Asp
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Gly Glu Thr Gly
                165                 170                 175

Pro Leu Met Ala Gly Trp Leu Ser Asn Thr Phe Ile Asn Pro Val Asn
            180                 185                 190

Asp Gly Ala Val Leu Pro Ile Phe Tyr Leu Asn Gly Gly Lys Ile His
        195                 200                 205

Asn Pro Thr Ile Phe Glu Arg Lys Thr Asp Glu Glu Leu Ser Gln Phe
    210                 215                 220

Phe Glu Gly Leu Gly Trp Lys Pro Ile Phe Ala Asp Val Val Glu Leu
225                 230                 235                 240

Ser Glu Asp His Ala Ala Ala His Ala Leu Phe Ala Glu Lys Leu Asp
                245                 250                 255

Gln Ala Ile Gln Glu Ile Lys Thr Ile Gln Ser Glu Ala Arg Gln Lys
            260                 265                 270

Pro Ala Glu Glu Ala Ile Gln Ala Lys Phe Pro Val Leu Val Ala Arg
        275                 280                 285

Ile Pro Lys Gly Trp Thr Gly Pro Lys Ala Trp Glu Gly Thr Pro Ile
    290                 295                 300

Glu Gly Gly Phe Arg Ala His Gln Val Pro Ile Pro Val Asp Ala His
305                 310                 315                 320

His Met Glu His Val Asp Ser Leu Leu Ser Trp Leu Gln Ser Tyr Arg
                325                 330                 335

Pro Glu Glu Leu Phe Asp Glu Ser Gly Lys Ile Val Asp Glu Ile Ala
            340                 345                 350

Ala Ile Ser Pro Lys Gly Asp Arg Arg Met Ser Met Asn Pro Ile Thr
        355                 360                 365

Asn Ala Gly Ile Val Lys Ala Met Asp Thr Ala Asp Trp Lys Lys Phe
    370                 375                 380

Ala Leu Asp Ile Asn Val Pro Gly Gln Ile Met Ala Gln Asp Met Ile
```

385 390 395 400

Glu Phe Gly Lys Tyr Ala Ala Asp Leu Val Asp Ala Asn Pro Asp Asn
405 410 415

Phe Arg Ile Phe Gly Pro Asp Glu Thr Lys Ser Asn Arg Leu Gln Glu
420 425 430

Val Phe Thr Arg Thr Ser Arg Gln Trp Leu Gly Arg Arg Lys Pro Asp
435 440 445

Tyr Asp Glu Ala Leu Ser Pro Ala Gly Arg Val Ile Asp Ser Gln Leu
450 455 460

Ser Glu His Gln Ala Glu Gly Phe Leu Glu Gly Tyr Val Leu Thr Gly
465 470 475 480

Arg His Gly Phe Phe Ala Ser Tyr Glu Ser Phe Leu Arg Val Val Asp
485 490 495

Ser Met Val Thr Gln His Phe Lys Trp Leu Arg Lys Ser Lys Thr His
500 505 510

Thr Thr Trp Arg Lys Asn Tyr Pro Ala Leu Asn Leu Ile Ala Ala Ser
515 520 525

Thr Val Phe Gln Gln Asp His Asn Gly Tyr Thr His Gln Asp Pro Gly
530 535 540

Ile Leu Thr His Leu Ala Glu Lys Thr Pro Glu Tyr Ile Arg Glu Tyr
545 550 555 560

Leu Pro Ala Asp Thr Asn Ser Leu Leu Ala Val Met Asp Lys Ala Phe
565 570 575

Lys Ala Glu Asp Lys Ile Asn Leu Ile Val Thr Ser Lys His Pro Arg
580 585 590

Pro Gln Phe Tyr Ser Ile Ala Glu Ala Glu Glu Leu Val Ala Glu Gly
595 600 605

Tyr Lys Val Ile Asp Trp Ala Ser Asn Val Ser Leu Asn Gln Glu Pro
610 615 620

Asp Val Val Phe Ala Ala Ala Gly Thr Glu Pro Asn Leu Glu Ala Leu
625 630 635 640

Ala Ala Ile Ser Ile Leu His Lys Ala Phe Pro Glu Leu Lys Ile Arg
645 650 655

Phe Val Asn Val Leu Asp Ile Leu Lys Leu Arg His Pro Ser Gln Asp
660 665 670

Ala Arg Gly Leu Ser Asp Glu Glu Phe Asp Lys Val Phe Thr Thr Asp
675 680 685

Lys Pro Val Ile Phe Ala Phe His Ser Tyr Glu Asp Met Ile Arg Asp
690 695 700

Ile Phe Phe Ser Arg His Asn His Asn Leu His Thr His Gly Tyr Arg
705 710 715 720

Glu Asn Gly Asp Ile Thr Thr Pro Phe Asp Met Arg Val Met Ser Glu
725 730 735

Leu Asp Arg Phe His Leu Ala Gln Asp Ala Ala Leu Ala Ser Leu Gly
740 745 750

Asn Glu Ala Gln Ala Phe Ser Asp Glu Met Asn Gln Met Val Ala Tyr
755 760 765

His Lys Asp Tyr Ile Arg Glu His Gly Asp Asp Ile Pro Glu Val Gln
770 775 780

Asn Trp Lys Trp Glu Asn Ile Lys
785 790

<210> SEQ ID NO 33

<211> LENGTH: 795
<212> TYPE: PRT
<213> ORGANISM: Mycoplasma agalactiae PG2

<400> SEQUENCE: 33

Met Lys Lys Ser His Asp Phe Asp Ser Lys Glu Tyr Leu Asn Leu Val
1               5                   10                  15

Asp Ala Trp Trp Arg Ala Ala Asn Tyr Leu Ser Val Gly Gln Met Tyr
            20                  25                  30

Leu Arg Asn Asn Pro Leu Leu Lys Ile Pro Leu Thr Ser Asn Asp Val
        35                  40                  45

Lys Ile Tyr Pro Ile Gly His Trp Gly Thr Val Pro Gly Gln Asn Phe
    50                  55                  60

Ile Tyr Ala His Leu Asn Arg Ile Ile Asn Lys Tyr Asp Leu Asn Met
65                  70                  75                  80

Phe Phe Ile Ser Gly Pro Gly His Gly Gly Gln Val Ile Ala Ser Asn
                85                  90                  95

Thr Tyr Leu Asp Gly Ser Tyr Thr Glu Leu Phe Pro His Val Thr Lys
            100                 105                 110

Asp Ile Lys Gly Met Thr His Leu Phe Lys Tyr Phe Ser Phe Pro Gly
        115                 120                 125

Gly Thr Ala Ser His Ala Ala Pro Glu Cys Pro Gly Ser Ile His Glu
    130                 135                 140

Gly Gly Glu Leu Gly Tyr Ser Leu Ser His Ala Ala Gly Ala Val Leu
145                 150                 155                 160

Asp Asn Pro Asp Val Ile Ala Ala Thr Val Ile Gly Asp Gly Glu Ser
                165                 170                 175

Glu Thr Gly Pro Leu Ser Ala Gly Trp Phe Ile Asn Ser Phe Ile Asn
            180                 185                 190

Pro Ala Asn Asp Gly Ala Val Leu Pro Ile Leu His Val Asn Gly Gly
        195                 200                 205

Lys Ile Ser Asn Pro Thr Ile Trp Ser Arg Arg Ser Asn Glu Glu Leu
    210                 215                 220

Val Ser Tyr Phe Thr Gly Ala Gly Trp Lys Pro Phe Ile Val Glu Gly
225                 230                 235                 240

Asn Glu Pro Glu Tyr Met His His Glu Met Ala Lys Ala Leu Asp Ala
                245                 250                 255

Ser Val Glu Leu Ile Lys Gln Tyr Gln Ala Glu Ala Arg Lys Asn Gly
            260                 265                 270

Ala Asn Lys Ala Lys Arg Pro Gln Trp Pro Met Ile Val Leu Lys Ser
        275                 280                 285

Pro Lys Gly Trp Thr Gly Pro Lys Glu Trp Asn His Glu Ala Ile Glu
    290                 295                 300

Gly Ser Phe Arg Ala His Gln Val Pro Val Pro Val Ser Ala Glu Lys
305                 310                 315                 320

Met Gln His Ile Asp Ala Leu Glu Asn Trp Leu Arg Ser Tyr Arg Pro
                325                 330                 335

Glu Glu Leu Phe Asp Glu Asn Ala Gln Leu Lys Pro Glu Ile Ala Ala
            340                 345                 350

Ile Ala Pro Lys Gly Asp Arg Arg Met Gly Lys Asn Pro Ile Ala Asn
        355                 360                 365

Gly Gly Ile Asn Pro Arg Ala Ile Asn Val Gly Asp Trp Thr Lys Phe
    370                 375                 380

Ala Leu Asp Ile Lys Gln Pro Gly Lys Val Ile Asn Gln Asp Met Val

-continued

```
385                 390                 395                 400

Thr Leu Gly Ser Tyr Leu Gly Glu Leu Ser Leu Leu Asn Lys Asp Asn
                405                 410                 415

Phe Arg Val Trp Gly Pro Asp Glu His Lys Ser Asn Arg Leu Tyr Glu
            420                 425                 430

Met Phe Lys Val Thr Asp Arg Gln Trp Leu Asp Arg Ile Asp Glu Lys
        435                 440                 445

Tyr Asp Glu Phe Leu Ser Ser Val Gly Arg Ile Ile Asp Ser Gln Leu
    450                 455                 460

Ser Glu His Gln Ala Glu Gly Met Leu Glu Gly Tyr Val Leu Thr Gly
465                 470                 475                 480

Arg His Gly Val Phe Ala Ser Tyr Glu Ser Phe Leu Arg Val Val Asp
                485                 490                 495

Ser Met Leu Thr Gln His Met Lys Trp Val Lys Lys Ala Leu Asp Ile
            500                 505                 510

Pro Trp Arg Asn Asp Tyr Pro Ser Leu Asn Val Ile Ala Thr Ser Asn
        515                 520                 525

Ala Phe Gln Gln Asp His Asn Gly Tyr Thr His Gln Asp Pro Gly Leu
    530                 535                 540

Ile Gly His Leu Ala Asp Lys Arg Pro Glu Leu Ile Arg Glu Tyr Leu
545                 550                 555                 560

Pro Ala Asp Thr Asn Thr Leu Leu Ala Thr Met Ala Lys Ala Leu Gln
                565                 570                 575

Asp Arg Asn Val Ile Asn Leu Ile Ile Ser Ser Lys Gln Pro Arg His
            580                 585                 590

Gln Phe Phe Ser Ile Glu Glu Ala Thr Glu Leu Val Glu Lys Gly Ile
        595                 600                 605

Lys Ile Ile Asp Trp Ala Ser Asn Ile Lys Pro Asn Glu Glu Pro Asp
    610                 615                 620

Leu Val Val Ala Ala Ser Gly Thr Glu Ser Thr Ile Glu Ser Leu Ala
625                 630                 635                 640

Thr Ile Thr Tyr Leu Arg Ala His Phe Pro Glu Leu Lys Ile Arg Phe
                645                 650                 655

Val Asn Val Leu Asp Leu Leu Lys Leu Arg His Pro Ser Ile Asp Pro
            660                 665                 670

Arg Gly Leu Ser Asp Ser Glu Phe Asp Ser Ile Phe Thr Lys Asp Lys
        675                 680                 685

Pro Ile Leu Phe Ala Phe His Gly Tyr Glu Ala Ile Leu Arg Asp Ile
    690                 695                 700

Phe Phe Leu Arg Ser Asn His Asn Ile Ile Thr His Gly Tyr Arg Glu
705                 710                 715                 720

Asn Gly Asp Ile Thr Thr Ala Phe Asp Ile Arg Leu Leu Ser Glu Met
                725                 730                 735

Asp Arg Phe His Met Thr Ala Asn Val Ala Lys Lys Leu Ala Pro Val
            740                 745                 750

Val Gly Glu Ser Lys Ala Asn Glu Leu Val Lys Leu Met Glu Asp Lys
        755                 760                 765

Ile Lys Glu His Arg Ala Tyr Ile Lys Glu Tyr Gly Thr Asp Leu Pro
    770                 775                 780

Glu Val Lys Glu Trp Glu Trp Thr Pro Tyr Lys
785                 790                 795
```

<210> SEQ ID NO 34

<211> LENGTH: 794
<212> TYPE: PRT
<213> ORGANISM: Streptococcus gordonii str. Challis substr. CH1

<400> SEQUENCE: 34

```
Met Thr Thr Asp Tyr Asn Ser Lys Ala Tyr Leu Glu Lys Val Asp Ala
 1               5                  10                  15

Trp Trp Arg Ala Ala Asn Tyr Ile Ser Ala Ala Gln Met Tyr Leu Lys
            20                  25                  30

Asp Asn Pro Leu Leu Lys Arg Asp Val Val Ala Asn Asp Leu Lys Ala
        35                  40                  45

His Pro Ile Gly His Trp Gly Thr Val Pro Gly Gln Asn Phe Ile Tyr
    50                  55                  60

Ala His Leu Asn Arg Thr Ile Asn Lys Tyr Asp Leu Asp Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Thr Glu Leu Asn Pro Asn Ile Pro Gln Asn Glu
            100                 105                 110

Glu Gly Phe Lys His Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Ala Gly Ala Ile Leu Asp Asn
145                 150                 155                 160

Pro Asp Val Ile Ala Ala Thr Val Ile Gly Asp Gly Glu Gly Glu Thr
                165                 170                 175

Gly Pro Leu Met Ala Gly Trp Leu Ser Asn Thr Phe Ile Asn Pro Val
            180                 185                 190

Asn Asp Gly Ala Ile Leu Pro Ile Phe Tyr Leu Asn Gly Gly Lys Ile
        195                 200                 205

His Asn Pro Thr Ile Phe Glu Arg Lys Thr Asp Glu Glu Leu Thr Leu
    210                 215                 220

Phe Phe Glu Gly Leu Gly Trp Lys Pro Ile Phe Ala Asp Val Thr Ala
225                 230                 235                 240

Ile Ser Glu Asn His Glu Ala Ala His Ala Leu Phe Ala Ala Lys Leu
                245                 250                 255

Asp Glu Ala Ile Glu Glu Ile Lys Lys Val Gln Ala Glu Ala Arg Lys
            260                 265                 270

Gly Ser Ala Glu Glu Ala Thr Gln Ala Ile Phe Pro Val Leu Val Ala
        275                 280                 285

Arg Ile Pro Lys Gly Trp Thr Gly Pro Lys Ser Trp Glu Gly Thr Pro
    290                 295                 300

Ile Glu Gly Gly Phe Arg Ala His Gln Val Pro Ile Pro Val Asp Ala
305                 310                 315                 320

His His Met Glu His Val Asp Ala Leu Leu Asn Trp Leu Lys Ser Tyr
                325                 330                 335

Arg Pro Glu Glu Leu Phe Asp Glu Ser Gly Lys Val Leu Pro Glu Ile
            340                 345                 350

Ala Ala Ile Gly Pro Lys Gly Asp Arg Arg Met Ala Met Asn Pro Ile
        355                 360                 365

Thr Asn Ala Gly Val Ile Lys Pro Met Asp Thr Ala Asp Trp Lys Lys
    370                 375                 380

His Ala Leu Lys Phe Gly Thr Pro Gly Glu Ile Val Ala Gln Asp Met
```

385 390 395 400

Ile Glu Phe Gly Lys Tyr Ala Thr Asp Leu Val Asp Ala Asn Pro Asp
405 410 415

Asn Phe Arg Ile Phe Gly Pro Asp Glu Thr Lys Ser Asn Arg Leu Gln
420 425 430

Glu Val Phe Thr Arg Thr Ser Arg Gln Trp Leu Gly Arg Met Arg Pro
435 440 445

Glu Tyr Asp Glu Ala Leu Ser Pro Ala Gly Arg Val Ile Asp Ser Gln
450 455 460

Leu Ser Glu His Gln Ala Glu Gly Met Leu Glu Gly Tyr Val Leu Thr
465 470 475 480

Gly Arg His Gly Phe Phe Ala Ser Tyr Glu Ser Phe Leu Arg Val Val
485 490 495

Asp Ser Met Val Thr Gln His Phe Lys Trp Leu Arg Lys Cys Lys Thr
500 505 510

His Thr Thr Trp Arg Lys Asn Tyr Pro Ala Leu Asn Leu Ile Ala Thr
515 520 525

Ser Thr Val Phe Gln Gln Asp His Asn Gly Tyr Thr His Gln Asp Pro
530 535 540

Gly Ile Leu Thr His Leu Ala Glu Lys Thr Pro Glu Phe Ile Arg Glu
545 550 555 560

Tyr Leu Pro Ala Asp Thr Asn Ser Leu Leu Ala Val Met Asp Lys Ala
565 570 575

Phe Lys Ala Glu Asp Lys Val Asn Leu Ile Val Thr Ser Lys His Pro
580 585 590

Arg Pro Gln Phe Tyr Ser Ala Glu Glu Ala Glu Glu Leu Val Arg Glu
595 600 605

Gly Tyr Lys Val Ile Asp Trp Ala Ser Thr Val Ser Asn Asn Glu Glu
610 615 620

Pro Asp Val Val Phe Ala Ala Ala Gly Thr Glu Pro Asn Leu Glu Ala
625 630 635 640

Leu Ala Ala Val Ser Ile Leu His Lys Ala Phe Pro Glu Leu Lys Ile
645 650 655

Arg Phe Val Asn Val Val Asp Ile Leu Lys Leu Arg His Pro Ser Val
660 665 670

Asp Ala Arg Gly Leu Ser Asp Glu Glu Phe Asp Gln Val Phe Thr Thr
675 680 685

Asp Lys Pro Val Ile Phe Ala Phe His Gly Tyr Glu Gly Met Ile Arg
690 695 700

Asp Ile Phe Phe Asn Arg His Asn His Asn Leu Arg Val His Gly Tyr
705 710 715 720

Arg Glu Asn Gly Asp Ile Thr Thr Pro Phe Asp Met Arg Val Met Ser
725 730 735

Glu Leu Asp Arg Phe His Leu Ala Gln Asp Ala Ala Asn Ala Ala Leu
740 745 750

Gly Glu Asp Ala Ala Val Phe Ser Ala Lys Met Asp Glu Thr Val Ala
755 760 765

Tyr His Asn Ala Tyr Ile Arg Glu Asn Gly Asp Asp Ile Pro Glu Val
770 775 780

Gln Asn Trp Lys Trp Glu Asn Ile Asn Lys
785 790

<210> SEQ ID NO 35

<211> LENGTH: 791
<212> TYPE: PRT
<213> ORGANISM: Kingella oralis ATCC 51147

<400> SEQUENCE: 35

```
Met Gln Asn Thr Gln Phe Asp Thr Pro Glu Tyr Leu Ala Lys Val Asp
 1               5                  10                  15

Ala Trp Trp Arg Ala Ala Asn Tyr Ile Ser Ala Ala Gln Met Tyr Leu
            20                  25                  30

Lys Asp Asn Pro Leu Leu Lys Lys Pro Leu Thr Ala Asn Asp Val Lys
        35                  40                  45

Ala His Pro Ile Gly His Trp Gly Thr Val Pro Gly Gln Asn Phe Ile
    50                  55                  60

Tyr Ala His Leu Asn Arg Ala Ile Asn Lys Tyr Asp Val Asp Met Phe
65                  70                  75                  80

Tyr Ile Glu Gly Pro Gly His Gly Gly Gln Val Met Val Ser Asn Ser
                85                  90                  95

Tyr Leu Asp His Ser Tyr Thr Asp Ile Tyr Pro Glu Ile Thr Gln Asp
            100                 105                 110

Glu Ala Gly Leu Lys Lys Leu Cys Lys Ile Phe Ser Phe Pro Gly Gly
        115                 120                 125

Ile Ala Ser His Ala Ala Pro Glu Thr Pro Gly Ser Ile His Glu Gly
    130                 135                 140

Gly Glu Leu Gly Tyr Ala Leu Ser His Ala Phe Gly Ala Val Leu Asp
145                 150                 155                 160

Asn Pro Asn Ile Ile Ala Ala Ala Val Ile Gly Asp Gly Glu Ala Glu
                165                 170                 175

Thr Gly Pro Leu Cys Ala Gly Trp Phe Gly Asn Thr Phe Ile Asn Pro
            180                 185                 190

Val Asn Asp Gly Ala Val Leu Pro Ile Leu Tyr Leu Asn Gly Gly Lys
        195                 200                 205

Ile His Asn Pro Thr Ile Leu Ala Arg Lys Thr Asp Ala Glu Leu Thr
    210                 215                 220

Gln Tyr Phe Asn Gly Met Gly Trp Glu Pro Ile Phe Val Glu Val Ser
225                 230                 235                 240

Asp Pro Ala His Ser His Ala Ile Met Ala Gln Lys Leu Asp Glu Ala
                245                 250                 255

Val Glu Arg Ile Leu Ala Ile Trp Gln Asp Ala Arg Ser Arg Ser Ala
            260                 265                 270

Asn Asp Ala Thr Met Pro Arg Trp Pro Val Leu Val Ala Arg Ile Pro
        275                 280                 285

Lys Gly Trp Thr Gly Pro Lys Thr Trp Asn Gly Glu Pro Ile Glu Gly
    290                 295                 300

Gly Phe Arg Ala His Gln Val Pro Ile Pro Thr Asn Ser His Asp Met
305                 310                 315                 320

Ser Thr Ala Asp Ala Leu Glu Ala Trp Leu Arg Ser Tyr Arg Pro Glu
                325                 330                 335

Glu Leu Phe Asp Asp Asn Gly Arg Phe Leu Asp Lys Trp Arg Glu Ile
            340                 345                 350

Ser Pro Lys Gly Ala Lys Arg Met Ser Val His Pro Ile Thr Asn Gly
        355                 360                 365

Gly Val Ala Pro Lys Ala Leu Val Met Pro Asp Trp Thr Lys His Ala
    370                 375                 380

Leu Lys Ile Gly Thr Pro Gly Ser Gln Asp Ala Gln Asp Met Ile Glu
```

```
385                 390                 395                 400

Cys Gly Arg Leu Met Ala Asp Val Ile Thr Ala Asn Pro Asp Asn Phe
                405                 410                 415

Arg Ile Phe Gly Pro Asp Glu Thr Lys Ser Asn Arg Leu Asn Glu Val
            420                 425                 430

Phe Lys Val Thr Asn Arg Gln Trp Leu Gly Val Arg Asp Ala Ala Tyr
        435                 440                 445

Asp Glu Trp Ile Ala Pro Val Gly Arg Val Ile Asp Ser Gln Leu Ser
    450                 455                 460

Glu His Gln Ala Glu Gly Phe Leu Glu Gly Tyr Val Leu Thr Gly Arg
465                 470                 475                 480

His Gly Phe Phe Ala Ser Tyr Glu Ser Phe Leu Arg Val Val Asp Ser
                485                 490                 495

Met Ile Thr Gln His Phe Lys Trp Leu Arg Lys Cys Lys Thr His Ala
            500                 505                 510

Pro Trp Arg Lys Asp Tyr Pro Ser Leu Asn Leu Ile Ala Thr Ser Thr
        515                 520                 525

Val Phe Gln Gln Asp His Asn Gly Tyr Thr His Gln Asp Pro Gly Leu
    530                 535                 540

Leu Thr His Leu Ala Glu Lys Lys Pro Glu Phe Val Arg Glu Tyr Leu
545                 550                 555                 560

Pro Ala Asp Ala Asn Thr Leu Leu Ala Val Met Ser Glu Ala Leu Thr
                565                 570                 575

Ser Arg Asp Arg Ile Asn Leu Ile Val Ser Ser Lys His Leu Arg Pro
            580                 585                 590

Gln Phe Tyr Ser Ala Asp Glu Ala Lys Glu Leu Val Arg Glu Gly Tyr
        595                 600                 605

Lys Ile Ile Glu Trp Ala Ser Thr Cys His Asp Gly Glu Pro Asp Val
    610                 615                 620

Val Ile Ala Ala Ala Gly Thr Glu Pro Asn Met Glu Ala Leu Ala Ala
625                 630                 635                 640

Ile Asn Val Leu His Lys His Tyr Pro Glu Met Lys Ile Arg Phe Ile
                645                 650                 655

Asn Val Val Asp Ile Leu Lys Leu Arg His Pro Ser Ile Asp Pro Arg
            660                 665                 670

Gly Leu Ser Asp Glu Ala Phe Asp Ala Leu Phe Thr Arg Asp Lys Pro
        675                 680                 685

Val Val Phe Cys Phe His Gly Tyr Glu Asn Met Val Arg Asp Ile Phe
    690                 695                 700

Phe Pro Arg His Asn Arg Asn Val Arg Ile His Gly Tyr Arg Glu Asn
705                 710                 715                 720

Gly Asp Ile Thr Thr Pro Phe Asp Met Arg Val Leu Ser Glu Met Asp
                725                 730                 735

Arg Phe His Val Ala Lys Asp Ala Ala Gln Ala Val Tyr Gly Glu Lys
            740                 745                 750

Ala Ala Asp Phe Ala Asn Lys Met Asp Glu Thr Ile Gln Phe His Arg
        755                 760                 765

Ser Tyr Ile Arg Glu His Gly Lys Asp Ile Pro Glu Val Ala Glu Trp
    770                 775                 780

Lys Trp Gln Pro Leu Ala Lys
785                 790
```

<210> SEQ ID NO 36

<211> LENGTH: 792
<212> TYPE: PRT
<213> ORGANISM: Mycoplasma fermentans M64

<400> SEQUENCE: 36

```
Met Asn Lys Lys Glu Phe Asp Ser Lys Glu Tyr Leu Glu Lys Val Asp
 1               5                  10                  15

Ala Trp Trp Arg Ala Ala Asn Tyr Leu Ser Val Gly Gln Ile Tyr Leu
            20                  25                  30

Arg Asn Asn Pro Leu Leu Lys His Pro Leu Thr Ser Asp Asp Val Lys
        35                  40                  45

Val Tyr Pro Ile Gly His Trp Gly Thr Ile Ser Gly Gln Asn Phe Ala
    50                  55                  60

Tyr Ala His Leu Asn Arg Val Ile Asn Lys Tyr Asp Leu Asn Met Phe
65                  70                  75                  80

Tyr Ile Glu Gly Pro Gly His Gly Gly Gln Val Met Thr Ser Asn Ser
                85                  90                  95

Tyr Leu Asp Gly Ser Tyr Thr Glu Leu Phe Pro His Val Thr Gln Asp
            100                 105                 110

Glu Ala Gly Met Gln His Leu Phe Lys Tyr Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Ile Ser His Ala Thr Gly Ala Ile Leu Asp
145                 150                 155                 160

Asn Pro Asp Val Ile Ala Ala Thr Ile Val Gly Asp Gly Glu Ala Glu
                165                 170                 175

Thr Gly Pro Leu Ala Thr Ser Trp Phe Ser Asn Ser Phe Ile Asn Pro
            180                 185                 190

Val Asn Asp Gly Ala Val Leu Pro Ile Leu His Leu Asn Gly Gly Lys
        195                 200                 205

Ile Ser Asn Pro Thr Ile Leu Ser Arg Lys Ser Asn Glu Glu Leu Gln
    210                 215                 220

Gln Tyr Phe Arg Gly Met Gly Trp Glu Pro His Phe Val Glu Gly Asp
225                 230                 235                 240

Lys Pro Glu Val Met His Glu Leu Met Ala Lys Thr Leu Asp Ser Val
                245                 250                 255

Ile Glu Glu Ile Gln Ser Ile Gln Thr Lys Ala Arg Lys Lys Pro Ala
            260                 265                 270

Asp Lys Ala Lys Arg Pro Val Trp Pro Met Ile Val Leu Arg Thr Pro
        275                 280                 285

Lys Gly Trp Thr Gly Pro Lys Ser Trp Asn Lys Glu Ala Ile Glu Gly
    290                 295                 300

Ser Phe Arg Ala His Gln Val Pro Leu Pro Ile Asn Ala Glu Asn Met
305                 310                 315                 320

Glu His Ala Asp Ala Leu Glu Lys Trp Leu Arg Ser Tyr Arg Pro Glu
                325                 330                 335

Glu Leu Phe Asp Lys Lys Gly Lys Leu Val Lys Glu Ile Ala Ala Ile
            340                 345                 350

Ala Pro Lys Gly Lys Arg Arg Met Gly Met Asn Pro Ile Thr Asn Gly
        355                 360                 365

Gly Ile Asn Pro Lys Val Met Lys Leu Gly Asp Trp Arg Lys Phe Ala
    370                 375                 380

Leu His Phe Asp Arg Pro Gly Ser Val Val Ala Gln Asp Met Val Glu
```

```
385                 390                 395                 400

Leu Gly Thr Tyr Phe Ala Asp Leu Val Lys Arg Asn Pro Glu Asn Phe
                405                 410                 415

Arg Ile Phe Gly Pro Asp Glu Thr Lys Ser Asn Arg Leu Tyr Asn Leu
            420                 425                 430

Phe Lys Val Thr Asn Arg Gln Trp Met Glu Arg Ile Asp Ser Lys Leu
        435                 440                 445

Asp Glu Ala Leu Ser Pro Val Gly Arg Ile Ile Asp Ser Gln Leu Ser
    450                 455                 460

Glu His Gln Ala Gln Gly Phe Leu Glu Gly Tyr Val Leu Thr Gly Arg
465                 470                 475                 480

His Gly Ile Phe Ala Ser Tyr Glu Ser Phe Leu Arg Val Val Asp Ser
                485                 490                 495

Met Val Thr Gln His Met Lys Trp Leu Arg Lys Ala Lys Glu Ile Asn
            500                 505                 510

Trp Arg Lys Asp Tyr Pro Ser Leu Asn Ile Met Ala Thr Ser Thr Ala
        515                 520                 525

Phe Gln Gln Asp His Asn Gly Tyr Thr His Gln Asp Pro Gly Ile Ile
    530                 535                 540

Gly His Met Ala Asp Lys Arg Pro Glu Leu Ile Arg Glu Tyr Leu Pro
545                 550                 555                 560

Ala Asp Thr Asn Thr Leu Leu Ala Val Met Asp Lys Ala Phe Thr Glu
                565                 570                 575

Arg Asn Val Ile Asn Leu Ile Val Ser Ser Lys Gln Pro Arg His Gln
            580                 585                 590

Phe Tyr Ser Val Glu Glu Ala Glu Thr Leu Val Glu Lys Gly Leu Asp
        595                 600                 605

Ile Ile Asp Trp Ala Ser Thr Cys Ser Arg Asn Glu Thr Pro Asp Leu
    610                 615                 620

Val Val Val Ala Ser Gly Thr Glu Pro Asn Leu Glu Ala Leu Ala Thr
625                 630                 635                 640

Ile Ser Ile Leu Asn Lys Glu Tyr Pro Ser Met Lys Ile Arg Phe Val
                645                 650                 655

Asn Val Val Asp Leu Leu Lys Leu Arg His Pro Lys Ile Asp Pro Arg
            660                 665                 670

Gly Leu Ser Asp Glu Glu Phe Asp Glu Ile Phe Thr Lys Asp Lys Pro
        675                 680                 685

Val Leu Phe Ala Phe His Gly Phe Glu Gly Ile Leu Arg Asp Ile Phe
    690                 695                 700

Phe Asp Arg His Asn His Asn Leu Ile Ala His Gly Tyr Arg Glu Asn
705                 710                 715                 720

Gly Asp Ile Thr Thr Ser Phe Asp Ile Arg Gln Leu Ser His Met Asp
                725                 730                 735

Arg Phe His Met Ala Ser Asp Ala Ala Ala Ala Val Phe Gly Ser Ser
            740                 745                 750

Lys Ala Lys Glu Phe Met Asp Lys Met Glu Glu Thr Ile Gln Phe His
        755                 760                 765

Asn Lys Tyr Ile Arg Glu Val Gly Thr Asp Ile Pro Glu Val Lys Asn
    770                 775                 780

Trp Lys Trp Glu Gly Leu Ile Lys
785                 790
```

<210> SEQ ID NO 37

<211> LENGTH: 789
<212> TYPE: PRT
<213> ORGANISM: Granulicatella adiacens ATCC 49175

<400> SEQUENCE: 37

```
Met Thr Gln Phe Asp Thr Pro Glu Tyr Leu Ala Lys Val Asp Ala Trp
 1               5                  10                  15

Trp Arg Ala Ala Asn Tyr Ile Ser Val Ala Gln Met Tyr Leu Lys Asp
            20                  25                  30

Asn Pro Leu Leu Arg Arg Pro Ile Gln Lys Glu Asp Val Lys Leu His
        35                  40                  45

Pro Ile Gly His Trp Gly Thr Ile Ala Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Tyr Pro Gln Ile Thr Gln Asp Glu Ala
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ser Leu Ser His Ala Thr Gly Ala Val Leu Asp Asn Pro
145                 150                 155                 160

Asn Val Ile Ala Ala Ala Val Ile Gly Asp Gly Glu Ala Glu Thr Gly
                165                 170                 175

Pro Leu Ala Ala Gly Trp Phe Ser Asn Thr Phe Ile Asn Pro Val Asn
            180                 185                 190

Asp Gly Ala Val Leu Pro Ile Leu Tyr Leu Asn Gly Gly Lys Ile His
        195                 200                 205

Asn Pro Thr Ile Leu Ala Arg Arg Thr Asp Glu Glu Leu Thr Gln Phe
    210                 215                 220

Phe Asn Gly Leu Gly Trp Asp Pro Ile Phe Val Glu Gly Thr Asp Pro
225                 230                 235                 240

Glu Lys Val His Pro Leu Met Ala Ala Lys Leu Asp Glu Ala Ile Glu
                245                 250                 255

Lys Ile Gln Ala Ile Gln Lys Glu Ala Arg Ala Lys Ser Ala Glu Glu
            260                 265                 270

Ala Thr Met Pro His Trp Pro Val Leu Val Val Arg Thr Pro Lys Gly
        275                 280                 285

Trp Thr Gly Pro Lys Glu Trp Asn His Glu Pro Ile Glu Gly Gly Phe
    290                 295                 300

Arg Ala His Gln Val Pro Ile Pro Val Ser Gly Glu Ala Met Glu His
305                 310                 315                 320

Val Asp Ala Leu Val Asp Trp Leu Lys Ser Tyr Arg Pro Glu Glu Leu
                325                 330                 335

Phe Asp Glu Asn Gly Lys Leu Val Glu Glu Ile Ala Ala Ile Ser Pro
            340                 345                 350

Lys Gly Pro Arg Arg Met Ser Met Asn Pro Ile Thr Asn Ala Gly Val
        355                 360                 365

Val Lys Pro Met Glu Ile Thr Asp Trp Thr Lys His Ala Ile Asp Thr
    370                 375                 380

Ser Lys Pro Gly Ala Ile Gln Lys Gln Asp Met Ile Glu Phe Gly Lys
```

385 390 395 400

Phe Ala Ala Asp Leu Val Lys Ala Asn Pro Asp Asn Phe Arg Ile Phe
405 410 415

Gly Pro Asp Glu Thr Lys Ser Asn Arg Leu Asn Glu Val Phe Lys Ala
420 425 430

Thr Asn Arg Gln Trp Val Gly Arg Arg Asp Glu Ser Tyr Asp Glu Trp
435 440 445

Ile Ser Pro Val Gly Arg Val Ile Asp Ser Gln Leu Ser Glu His Gln
450 455 460

Ala Glu Gly Phe Leu Glu Gly Tyr Val Leu Thr Gly Arg His Gly Phe
465 470 475 480

Phe Ala Ser Tyr Glu Ser Phe Leu Arg Val Val Asp Ser Met Ile Thr
485 490 495

Gln His Phe Lys Trp Leu Arg Lys Ala Lys Thr His Ala Pro Trp Arg
500 505 510

Lys Asn Tyr Pro Ser Leu Asn Leu Ile Ala Thr Ser Thr Val Phe Gln
515 520 525

Gln Asp His Asn Gly Tyr Thr His Gln Asp Pro Gly Leu Leu Thr His
530 535 540

Leu Ala Glu Lys Lys Pro Glu Phe Val Arg Glu Tyr Leu Pro Ala Asp
545 550 555 560

Thr Asn Ser Leu Met Ala Val Met Ala Glu Ala Leu Ser Ser Glu Asp
565 570 575

Lys Ile Asn Leu Ile Val Ser Ser Lys His Pro Arg Pro Gln Phe Tyr
580 585 590

Ser Val Glu Glu Ala Lys Glu Leu Val Ser Glu Gly Tyr Lys Val Ile
595 600 605

Asp Trp Ala Ser Thr Val Lys Glu Gly Glu Glu Pro Asp Val Val Ile
610 615 620

Ala Ala Ala Gly Thr Glu Pro Asn Leu Glu Ala Leu Ala Gly Ile Ser
625 630 635 640

Ile Leu His Lys Gln Phe Pro Glu Leu Lys Ile Arg Phe Ile Asn Val
645 650 655

Val Asp Ile Leu Lys Leu Arg Ser Pro Lys Val Asp Pro Arg Gly Leu
660 665 670

Ser Asp Glu Glu Phe Asp Lys Leu Phe Thr Thr Asp Lys Pro Val Val
675 680 685

Phe Cys Phe His Gly Tyr Glu Gly Met Ile Arg Asp Leu Phe Phe Asp
690 695 700

Arg Asn Asn His Asn Val His Ile His Gly Tyr Arg Glu Asn Gly Asp
705 710 715 720

Ile Thr Thr Pro Phe Asp Met Arg Val Leu Ser Glu Met Asp Arg Phe
725 730 735

His Val Ala Lys Asp Ala Ala Val Ala Val Tyr Gly Glu Lys Ala Ser
740 745 750

Glu Phe Ala Ala Lys Met Asp Glu Thr Val Glu Phe His His Ser Tyr
755 760 765

Ile Arg Glu His Gly Glu Asp Ile Pro Glu Val Val Ser Trp Gln Trp
770 775 780

Glu Asn Val Asn Lys
785

<210> SEQ ID NO 38

-continued

<211> LENGTH: 796
<212> TYPE: PRT
<213> ORGANISM: Mycoplasma hominis ATCC 23114

<400> SEQUENCE: 38

```
Met Ile Ser Lys Ile Tyr Asp Asp Lys Lys Tyr Leu Glu Lys Met Asp
 1               5                  10                  15

Lys Trp Phe Arg Ala Ala Asn Tyr Leu Gly Val Cys Gln Met Tyr Leu
            20                  25                  30

Arg Asp Asn Pro Leu Leu Lys Lys Pro Leu Thr Ser Asn Asp Ile Lys
        35                  40                  45

Leu Tyr Pro Ile Gly His Trp Gly Thr Val Pro Gly Gln Asn Phe Ile
    50                  55                  60

Tyr Thr His Leu Asn Arg Val Ile Lys Lys Tyr Asp Leu Asn Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Ser Glu Ile Tyr Pro Glu Ile Ser Gln Asp
            100                 105                 110

Glu Ala Gly Leu Ala Lys Met Phe Lys Arg Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Ile Ser His Gly Thr Gly Ala Ile Leu Asp
145                 150                 155                 160

Asn Pro Asp Val Ile Cys Ala Ala Val Val Gly Asp Gly Glu Ala Glu
                165                 170                 175

Thr Gly Pro Leu Ala Thr Ser Trp Phe Ser Asn Ala Phe Ile Asn Pro
            180                 185                 190

Val Asn Asp Gly Ala Ile Leu Pro Ile Leu His Leu Asn Gly Gly Lys
        195                 200                 205

Ile Ser Asn Pro Thr Leu Leu Ser Arg Lys Pro Lys Glu Glu Ile Lys
    210                 215                 220

Lys Tyr Phe Glu Gly Leu Gly Trp Asn Pro Ile Phe Val Glu Trp Ser
225                 230                 235                 240

Glu Asp Lys Ser Asn Leu Asp Met His Glu Leu Met Ala Lys Ser Leu
                245                 250                 255

Asp Lys Ala Ile Glu Ser Ile Lys Glu Ile Gln Ala Glu Ala Arg Lys
            260                 265                 270

Lys Pro Ala Glu Glu Ala Thr Arg Pro Thr Trp Pro Met Ile Val Leu
        275                 280                 285

Arg Thr Pro Lys Gly Trp Thr Gly Pro Lys Gln Trp Asn Asn Glu Ala
    290                 295                 300

Ile Glu Gly Ser Phe Arg Ala His Gln Val Pro Ile Pro Val Ser Ala
305                 310                 315                 320

Phe Lys Met Glu Lys Ile Ala Asp Leu Glu Lys Trp Leu Lys Ser Tyr
                325                 330                 335

Lys Pro Glu Glu Leu Phe Asp Glu Asn Gly Thr Ile Ile Lys Glu Ile
            340                 345                 350

Arg Asp Leu Ala Pro Glu Gly Leu Lys Arg Met Ala Val Asn Pro Ile
        355                 360                 365

Thr Asn Gly Gly Ile Asp Ser Lys Pro Leu Lys Leu Gln Asp Trp Lys
    370                 375                 380

Lys Tyr Ala Leu Lys Ile Asp Tyr Pro Gly Glu Ile Lys Ala Gln Asp
```

```
385                 390                 395                 400

Met Ala Glu Met Ala Lys Phe Ala Ala Asp Ile Met Lys Asp Asn Pro
                405                 410                 415

Ser Ser Phe Arg Val Phe Gly Pro Asp Glu Thr Lys Ser Asn Arg Met
            420                 425                 430

Phe Ala Leu Phe Asn Val Thr Asn Arg Gln Trp Leu Glu Pro Val Ser
        435                 440                 445

Lys Lys Tyr Asp Glu Trp Ile Ser Pro Ala Gly Arg Ile Ile Asp Ser
    450                 455                 460

Gln Leu Ser Glu His Gln Cys Glu Gly Phe Leu Glu Gly Tyr Val Leu
465                 470                 475                 480

Thr Gly Arg His Gly Phe Phe Ala Ser Tyr Glu Ala Phe Leu Arg Val
                485                 490                 495

Val Asp Ser Met Leu Thr Gln His Met Lys Trp Ile Lys Lys Ala Ser
            500                 505                 510

Glu Leu Ser Trp Arg Lys Thr Tyr Pro Ser Leu Asn Ile Ile Ala Thr
        515                 520                 525

Ser Asn Ala Phe Gln Gln Asp His Asn Gly Tyr Thr His Gln Asp Pro
    530                 535                 540

Gly Leu Leu Gly His Leu Ala Asp Lys Arg Pro Glu Ile Ile Arg Glu
545                 550                 555                 560

Tyr Leu Pro Ala Asp Thr Asn Ser Leu Leu Ala Val Met Asn Lys Ala
                565                 570                 575

Leu Thr Glu Arg Asn Val Ile Asn Leu Ile Val Ala Ser Lys Gln Pro
            580                 585                 590

Arg Glu Gln Phe Phe Thr Val Glu Asp Ala Glu Glu Leu Leu Glu Lys
        595                 600                 605

Gly Tyr Lys Val Val Pro Trp Ala Ser Asn Ile Ser Glu Asn Glu Glu
    610                 615                 620

Pro Asp Ile Val Phe Ala Ser Ser Gly Val Glu Pro Asn Ile Glu Ser
625                 630                 635                 640

Leu Ala Ala Ile Ser Leu Ile Asn Gln Glu Tyr Pro His Leu Lys Ile
                645                 650                 655

Arg Tyr Val Tyr Val Leu Asp Leu Leu Lys Leu Arg Ser Arg Lys Ile
            660                 665                 670

Asp Pro Arg Gly Ile Ser Asp Glu Glu Phe Asp Lys Val Phe Thr Lys
        675                 680                 685

Asn Lys Pro Ile Ile Phe Ala Phe His Gly Phe Glu Gly Leu Leu Arg
    690                 695                 700

Asp Ile Phe Phe Thr Arg Ser Asn His Asn Leu Ile Ala His Gly Tyr
705                 710                 715                 720

Arg Glu Asn Gly Asp Ile Thr Thr Ser Phe Asp Ile Arg Gln Leu Ser
                725                 730                 735

Glu Met Asp Arg Tyr His Ile Ala Lys Asp Ala Ala Glu Ala Val Tyr
            740                 745                 750

Gly Lys Asp Ala Lys Ala Phe Met Asn Lys Leu Asp Gln Lys Leu Glu
        755                 760                 765

Tyr His Arg Asn Tyr Ile Asp Glu Tyr Gly Tyr Asp Met Pro Glu Val
    770                 775                 780

Val Glu Trp Lys Trp Lys Asn Ile Asn Lys Glu Asn
785                 790                 795
```

<210> SEQ ID NO 39

<211> LENGTH: 792
<212> TYPE: PRT
<213> ORGANISM: Mycoplasma crocodyli MP145

<400> SEQUENCE: 39

Met Lys Lys Thr Val Tyr Asp Thr Glu Leu Tyr Ile Glu Lys Leu Asp
1 5 10 15

Ala Trp Phe Arg Ala Ala Asn Tyr Leu Ser Val Gly Gln Met Tyr Leu
20 25 30

Arg Asn Asn Pro Leu Leu Arg Asn Lys Ile Thr Lys Asp Asp Val Lys
35 40 45

Val Tyr Pro Ile Gly His Trp Gly Thr Ile Pro Gly Gln Asn Phe Ala
50 55 60

Tyr Ala His Leu Asn Arg Val Ile Asn Lys Tyr Asp Leu Asn Met Phe
65 70 75 80

Tyr Ile Glu Gly Pro Gly His Gly Gly Gln Val Met Thr Ser Asn Ser
85 90 95

Tyr Leu Asp Gly Ser Tyr Thr Glu Leu Phe Pro His Val Thr Gln Asp
100 105 110

Leu Asp Gly Met Lys His Leu Phe Lys Tyr Phe Ser Phe Pro Gly Gly
115 120 125

Thr Ala Ser His Ala Ala Pro Glu Thr Pro Gly Ser Ile His Glu Gly
130 135 140

Gly Glu Leu Gly Tyr Ser Leu Ser His Ala Thr Gly Ala Ile Leu Asp
145 150 155 160

Asn Pro Asn Val Ile Ala Ala Thr Ile Val Gly Asp Gly Glu Ser Glu
165 170 175

Thr Gly Pro Leu Ala Ala Gly Trp Phe Ser Asn Ser Phe Ile Asn Pro
180 185 190

Val Asn Asp Gly Ala Val Leu Pro Ile Leu His Leu Asn Gly Gly Lys
195 200 205

Ile Ser Asn Pro Thr Ile Leu Cys Arg Lys Ser Asn Glu Glu Leu Thr
210 215 220

Asn Tyr Phe Leu Gly Met Gly Trp Glu Ala Ile Phe Val Glu Gly Glu
225 230 235 240

Asp Val Gln Lys Met His Lys Leu Met Ala Thr Lys Leu Asp Tyr Ala
245 250 255

Ile Glu Arg Ile Leu Ser Ile Gln Lys Glu Ala Arg Lys Gly Lys Ala
260 265 270

Glu Glu Ala Thr Arg Pro Leu Trp Pro Met Ile Val Leu Arg Thr Pro
275 280 285

Lys Gly Trp Thr Gly Pro Gln Lys Trp Asn Ser Asp Gln Ile Val Gly
290 295 300

Ser Phe Arg Ala His Gln Val Pro Ile Pro Val Asn Ser Glu Asn Met
305 310 315 320

Thr His Ile Asp Ala Leu Val Asp Trp Leu Lys Ser Tyr Asn Val Asp
325 330 335

Asn Leu Phe Asp Lys Lys Gly Lys Leu Val Pro Glu Ile Ala Glu Ile
340 345 350

Ala Pro Val Gly Asp Arg Arg Met Gly Met Asn Pro Val Thr Asn Gly
355 360 365

Gly Leu Asn Pro Arg Asn Leu Ala Leu Pro Asn Trp Gln Asp Phe Ala
370 375 380

Leu Asn Leu Glu Lys Pro Gly Ala Lys Ile Ala Gln Asp Met Val Glu

-continued

```
385                 390                 395                 400

Leu Gly Ser Tyr Phe Ala Lys Val Met Glu Met Asn Lys Asp Asn Phe
                405                 410                 415

Arg Leu Phe Gly Pro Asp Glu Thr Lys Ser Asn Arg Leu Phe Asn Val
            420                 425                 430

Phe Lys Val Thr Ser Arg Gln Trp Leu Glu Pro Ile Asn Pro Leu Phe
        435                 440                 445

Asp Glu Ala Leu Ser Pro Ala Gly Arg Val Ile Asp Ser Gln Leu Ser
    450                 455                 460

Glu His Gln Ala Glu Gly Phe Leu Glu Gly Tyr Val Leu Thr Gly Arg
465                 470                 475                 480

His Gly Val Phe Ala Ser Tyr Glu Ser Phe Leu Arg Val Val Asp Ser
                485                 490                 495

Met Leu Thr Gln His Met Lys Trp Leu Lys Lys Ala Asn Asp Val Ser
            500                 505                 510

Trp Arg Asn Asp Tyr Pro Ser Leu Asn Val Ile Ala Thr Ser Thr Ala
        515                 520                 525

Phe Gln Gln Asp His Asn Gly Tyr Thr His Gln Asp Pro Gly Leu Ile
    530                 535                 540

Gly His Leu Ala Asp Lys Thr Pro Glu Leu Ile Arg Gln Tyr Leu Pro
545                 550                 555                 560

Ala Asp Thr Asn Thr Leu Leu Ala Val Met Asp Lys Ser Leu Thr Glu
                565                 570                 575

Arg Asn Val Ile Asn His Ile Ile Ala Ser Lys Gln Pro Arg Glu Gln
            580                 585                 590

Phe Tyr Ser Ala Lys Glu Ala Ala Glu Leu Val Glu Lys Gly Leu Lys
        595                 600                 605

Val Ile Lys Trp Ala Ser Thr Val Glu Gly Asn Asp Glu Pro Asp Leu
    610                 615                 620

Val Val Ala Ala Ala Gly Thr Glu Pro Asn Leu Glu Ala Leu Ala Ala
625                 630                 635                 640

Ile Thr Ile Leu Asn Lys Glu Phe Pro Lys Leu Lys Ile Arg Phe Val
                645                 650                 655

Asn Val Val Asp Leu Met Lys Leu Arg His Pro Ser Ile Asp Pro Arg
            660                 665                 670

Gly Ile Thr Asp Lys Glu Phe Asp Lys Ile Phe Thr Lys Asp Lys Pro
        675                 680                 685

Val Leu Phe Ala Phe His Gly Tyr Glu Gly Ile Leu Arg Asp Ile Phe
    690                 695                 700

Phe Lys Arg Asn Asn His Asn Leu Ile Ala His Gly Tyr Arg Glu Asn
705                 710                 715                 720

Gly Asp Ile Thr Thr Ser Phe Asp Ile Arg Gln Leu Ser His Met Asp
                725                 730                 735

Arg Phe His Met Ala Ala Ser Ala Ala Val Ala Ala Leu Gly Lys Lys
            740                 745                 750

Ala Asn Ala Phe Glu Thr Lys Met Leu Glu Thr Ile Asp Phe His Thr
        755                 760                 765

Lys Tyr Ile Arg Glu Tyr Gly Thr Asp Ile Pro Glu Val Lys Glu Trp
    770                 775                 780

Lys Trp Asn Pro Leu Val Arg Lys
785                 790
```

<210> SEQ ID NO 40

<211> LENGTH: 789
<212> TYPE: PRT
<213> ORGANISM: Neisseria sp. oral taxon 014 str. F0314

<400> SEQUENCE: 40

Met Ser Ala Gln Tyr Asp Ser Ala Asp Tyr Leu Asn Lys Val Asp Ala
1               5                   10                  15

Trp Trp Arg Ala Ala Asn Tyr Ile Ser Val Ala Gln Met Tyr Leu Lys
            20                  25                  30

Asp Asn Pro Leu Leu Met Arg Pro Ile Gln Ala Ser Asp Val Lys Ala
        35                  40                  45

His Pro Ile Gly His Trp Gly Thr Ile Ala Gly Gln Asn Phe Ile Tyr
    50                  55                  60

Ala His Leu Asn Arg Ala Ile Asn Lys Tyr Asp Leu Asn Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Ser Glu Ile Tyr Pro Asn Ile Thr Gln Asp Glu
            100                 105                 110

Ala Gly Leu Lys Gln Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Val Gly Ala Val Leu Asp Asn
145                 150                 155                 160

Pro Asp Val Ile Ala Ala Thr Val Ile Gly Asp Gly Glu Ala Glu Thr
                165                 170                 175

Gly Pro Leu Ser Ala Gly Trp Phe Ser Asn Val Phe Ile Asn Pro Val
            180                 185                 190

Asn Asp Gly Ala Val Leu Pro Ile Leu Tyr Leu Asn Gly Gly Lys Ile
        195                 200                 205

His Asn Pro Thr Ile Leu Ala Arg Lys Ser Asp Glu Ser Leu Arg Leu
    210                 215                 220

Tyr Phe Glu Gly Leu Gly Trp Asp Pro Ile Phe Val Glu Ala Thr Asp
225                 230                 235                 240

Tyr Ala Thr Thr His Lys Val Met Ala Gln Lys Leu Asp Glu Ala Ile
                245                 250                 255

Glu Lys Ile Lys Ala Ile Gln Thr Lys Ala Arg Ala Gly Lys Ala Glu
            260                 265                 270

Glu Ala Val Met Pro Lys Trp Pro Val Leu Val Ala Arg Leu Pro Lys
        275                 280                 285

Gly Trp Thr Gly Pro Lys Val Trp Asn Gly Glu Pro Ile Glu Gly Gly
    290                 295                 300

Phe Arg Ala His Gln Val Pro Ile Pro Ala Ser Ser His Asp Met Ala
305                 310                 315                 320

Thr Val Asp Ser Leu Val Glu Trp Leu Lys Ser Tyr Arg Pro Glu Glu
                325                 330                 335

Leu Phe Asp Ala Asn Gly Thr Phe Lys Ala Glu Leu Arg Glu Ile Ser
            340                 345                 350

Pro Lys Gly Asp Arg Arg Met Ser Thr Asn Pro Ile Thr Asn Gly Gly
        355                 360                 365

Ile Asn Pro Arg Pro Leu Asn Thr Ala Asp Trp Lys Lys Phe Ala Leu
    370                 375                 380

Asp Asn Ser Asp Arg Gly Ser Ile Met Ala Gln Asp Met Ile Glu Phe

```
385                 390                 395                 400

Gly Lys Tyr Ala Ala Glu Leu Val Lys Ala Asn Pro Asp Asn Phe Arg
                405                 410                 415

Ile Phe Gly Pro Asp Glu Thr Lys Ser Asn Arg Met Asn Glu Val Phe
            420                 425                 430

Lys Val Thr Asn Arg Gln Trp Leu Glu Pro Ile Asp Lys Ala Tyr Asp
        435                 440                 445

Glu Trp Met Ser Pro Ala Gly Arg Val Ile Asp Ser Gln Leu Ser Glu
    450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ala Thr Gln His Phe Lys Trp Leu Arg Lys Cys Lys Thr His Ala Pro
            500                 505                 510

Trp Arg Lys Ser Tyr Pro Ser Leu Asn Leu Ile Ala Thr Ser Thr Val
        515                 520                 525

Phe Gln Gln Asp His Asn Gly Tyr Thr His Gln Asp Pro Gly Met Leu
    530                 535                 540

Thr His Leu Ala Glu Lys Lys Pro Glu Phe Ile Arg Glu Tyr Leu Pro
545                 550                 555                 560

Ala Asp Ala Asn Ser Leu Leu Ala Val Met Ser Glu Val Leu Ser Ser
                565                 570                 575

Lys Asp Lys Val Asn Leu Ile Val Ser Ser Lys His Pro Arg Pro Gln
            580                 585                 590

Phe Tyr Ser Ala Ala Glu Ala Glu Glu Leu Val Arg Glu Gly Tyr Lys
        595                 600                 605

Val Ile Asp Trp Ala Ser Thr Asp Lys Gly Gly Glu Pro Asp Val Val
    610                 615                 620

Ile Ala Ala Ala Ala Thr Glu Pro Asn Leu Glu Ala Leu Ala Ala Ile
625                 630                 635                 640

Thr Ile Leu Asn Lys Gln Phe Pro Glu Leu Lys Ile Arg Phe Ile Asn
                645                 650                 655

Val Val Asp Ile Leu Lys Leu Arg His Pro Lys Val Asp Pro Arg Gly
            660                 665                 670

Leu Thr Asp Glu Gln Phe Asp Ala Leu Phe Thr Lys Asp Lys Pro Val
        675                 680                 685

Ile Phe Cys Phe His Gly Tyr Glu Gly Met Val Arg Asp Ile Phe Phe
    690                 695                 700

Asp Arg His Asn His Asn Leu Arg Ile His Gly Tyr Arg Glu Asn Gly
705                 710                 715                 720

Asp Ile Thr Thr Pro Phe Asp Met Arg Val Leu Ser Glu Met Asp Arg
                725                 730                 735

Phe His Val Ala Lys Asp Ala Ala Leu Ala Val Tyr Gly Asp Lys Ala
            740                 745                 750

Gln Asp Phe Ala Lys Lys Met Asp Asp Thr Leu Ala Phe His His Ser
        755                 760                 765

Tyr Ile Arg Glu Asn Gly Glu Asp Ile Pro Glu Val Arg Asn Trp Lys
    770                 775                 780

Trp Glu Ala Leu Lys
785
```

<210> SEQ ID NO 41

-continued

<211> LENGTH: 788
<212> TYPE: PRT
<213> ORGANISM: Eremococcus coleocola ACS-139-V-Col8

<400> SEQUENCE: 41

```
Met Thr Val Asp Tyr Asn Ser Lys Glu Tyr Leu Thr Leu Val Asp Lys
 1               5                  10                  15

Trp Trp Arg Ala Ala Asn Tyr Leu Ser Val Gly Gln Met Phe Leu Arg
            20                  25                  30

Asp Asn Pro Leu Leu Gln Glu Glu Val Thr Ala Asp His Val Lys Leu
        35                  40                  45

Asn Pro Ile Gly His Trp Gly Thr Ile Gly Gly Gln Asn Phe Leu Tyr
    50                  55                  60

Ala His Leu Asn Arg Ile Ile Asn Lys Tyr Asn Val Asn Met Phe Tyr
65                  70                  75                  80

Ile Glu Gly Pro Gly His Gly Gly Gln Val Met Val Thr Asn Ser Tyr
                85                  90                  95

Leu Asp Gly Ser Tyr Thr Glu Arg Tyr Pro Glu Phe Thr Gln Asp Ile
            100                 105                 110

Ala Gly Met Lys Lys Leu Phe Lys Thr Phe Ser Phe Pro Gly Gly Ile
        115                 120                 125

Gly Ser His Ala Ala Pro Glu Thr Pro Gly Ser Met His Glu Gly Gly
    130                 135                 140

Glu Leu Gly Tyr Ala Leu Ser His Ala Thr Gly Ala Ile Leu Asp Asn
145                 150                 155                 160

Pro Asp Val Ile Ala Ala Thr Val Val Gly Asp Gly Glu Ala Glu Thr
                165                 170                 175

Gly Pro Leu Ala Ala Gly Trp Phe Ser Asn Val Phe Ile Asn Pro Val
            180                 185                 190

Ser Asp Gly Ala Val Leu Pro Ile Leu Tyr Leu Asn Gly Gly Lys Ile
        195                 200                 205

Ala Asn Pro Thr Ile Leu Ala Arg Lys Ser Asn Glu Asp Leu Thr Lys
    210                 215                 220

Tyr Phe Glu Gly Met Gly Trp Lys Pro Tyr Ile Val Glu Gly Thr Asp
225                 230                 235                 240

Pro Glu Gln Val His Pro Ile Met Ala Lys Val Leu Asp Glu Val Ile
                245                 250                 255

Glu Glu Ile Gln Ala Ile Gln Ala Glu Ala Arg Lys Gly Lys Ala Glu
            260                 265                 270

Asp Ala Lys Met Pro His Trp Pro Met Ile Leu Tyr Arg Thr Pro Lys
        275                 280                 285

Gly Trp Thr Gly Pro Glu Glu Val Glu Gly Lys Thr Ile Gln Gly Ser
    290                 295                 300

Phe Arg Ala His Gln Val Pro Ile Pro Val Ser Gly Arg Asn Met Glu
305                 310                 315                 320

Asp Ile Asp Leu Leu Ile Asn Trp Leu Lys Ser Tyr Gly Pro Glu Glu
                325                 330                 335

Leu Phe Thr Glu Asn Gly Glu Leu Val Asp Glu Leu Lys Glu Phe Ala
            340                 345                 350

Pro Lys Gly Asp His Arg Met Ala Met Asn Pro Leu Thr Asn Gly Gly
        355                 360                 365

Asn Pro Lys Pro Leu Asn Met Pro Asn Trp Lys Asp Tyr Ala Leu Glu
    370                 375                 380

Ile Gly Thr Pro Gly Ser Lys Asp Ala Gln Asp Met Ile Glu Phe Gly
```

-continued

```
385                 390                 395                 400

Gly Phe Ala Arg Asp Ile Val Lys Glu Asn Pro Glu Asn Phe Arg Ile
                405                 410                 415

Phe Gly Pro Asp Glu Thr Lys Ser Asn Arg Leu Asn Lys Val Phe Glu
            420                 425                 430

Val Thr Asn Arg Gln Trp Leu Glu Pro Ile Ser Glu Lys Phe Asp Glu
        435                 440                 445

Asn Met Ser Ala Ser Gly Arg Val Ile Asp Ser Gln Leu Ser Glu His
    450                 455                 460

Gln Asn Gln Gly Phe Leu Glu Ala Tyr Val Leu Thr Gly Arg His Gly
465                 470                 475                 480

Phe Phe Ala Ser Tyr Glu Ser Phe Phe Arg Thr Val Asp Ser Met Ile
                485                 490                 495

Thr Gln His Phe Lys Trp Ile Arg Lys Ser Ala Lys His Ser Trp Arg
            500                 505                 510

Lys Pro Tyr Gln Ser Leu Asn Leu Ile Ser Ala Ser Thr Val Phe Gln
        515                 520                 525

Gln Asp His Asn Gly Tyr Thr His Gln Asp Pro Gly Leu Leu Thr His
    530                 535                 540

Ile Gly Glu Lys His Gly Glu Tyr Met Arg Ala Tyr Leu Pro Ala Asp
545                 550                 555                 560

Thr Asn Ser Leu Leu Ala Val Met Asp Lys Ala Phe Arg Ser Glu Asn
                565                 570                 575

Val Ile Asn Tyr Val Val Thr Ser Lys His Pro Arg Pro Gln Phe Phe
            580                 585                 590

Thr Ala Asp Glu Ala Glu Glu Leu Val Asn Glu Gly Leu Lys Val Ile
        595                 600                 605

Asp Trp Ala Ser Thr Val Lys Asp Asn Glu Glu Pro Asp Val Val Ile
    610                 615                 620

Ala Ala Ala Gly Thr Glu Pro Asn Phe Glu Ala Ile Ala Ala Ile Ser
625                 630                 635                 640

Tyr Leu Val Lys Ala Phe Pro Glu Leu Lys Ile Arg Phe Val Asn Val
                645                 650                 655

Val Asp Leu Phe Arg Leu Arg Ser Pro Glu Ile Asp Pro Arg Gly Leu
            660                 665                 670

Ser Asp Asp Glu Phe Asp Ala Ile Phe Thr Lys Asp Lys Pro Val Phe
        675                 680                 685

Phe Ala Phe His Ser Tyr Glu Gly Met Leu Lys Asp Ile Phe Phe Thr
    690                 695                 700

Arg His Asn His Asn Leu Tyr Ala His Gly Tyr Arg Glu Asn Gly Glu
705                 710                 715                 720

Ile Thr Thr Pro Phe Asp Met Arg Val Leu Asn Glu Leu Asp Arg Phe
                725                 730                 735

His Leu Ser Ala His Val Ala Asp Val Val Tyr Gly Asp Lys Ala Arg
            740                 745                 750

Asp Tyr Val Ala Glu Met Lys Gly Lys Val Gln Glu His Arg Asp Tyr
        755                 760                 765

Val Glu Glu Tyr Gly Ala Asp Met Pro Glu Val Glu Asp Trp Lys Trp
    770                 775                 780

Glu Asp Ile Lys
785
```

<210> SEQ ID NO 42

<211> LENGTH: 789
<212> TYPE: PRT
<213> ORGANISM: Aerococcus urinae ACS-120-V-Col10a

<400> SEQUENCE: 42

Met Thr Asp Phe Asp Ser Lys Ala Tyr Leu Asp Lys Val Asp Ala Trp
1 5 10 15

Trp Arg Ala Ala Asn Tyr Leu Ser Val Gly Gln Met Tyr Leu Arg Asp
20 25 30

Asn Pro Leu Leu Asp Arg Glu Val Thr Ala Asp Asp Ile Lys Ile Thr
35 40 45

Pro Ile Gly His Trp Gly Thr Ile Ala Gly Gln Asn Phe Val Tyr Ala
50 55 60

His Leu Asn Arg Val Ile Asn Lys Tyr Asp Leu Asn Met Phe Tyr Ile
65 70 75 80

Glu Gly Pro Gly His Gly Gly Gln Val Met Gln Ala Asn Ala Tyr Leu
85 90 95

Asp Gly Thr Trp Thr Glu His Tyr Pro Glu Tyr Pro Gln Asn Lys Glu
100 105 110

Gly Met Gln Lys Phe Phe Lys Tyr Phe Ser Phe Pro Gly Gly Thr Gly
115 120 125

Ser His Ala Thr Ala Glu Ile Pro Gly Ser Ile His Glu Gly Gly Glu
130 135 140

Leu Gly Tyr Ser Leu Ser His Ala Thr Gly Ala Ile Leu Asp Asn Pro
145 150 155 160

Asp Val Ile Ala Ala Thr Val Ile Gly Asp Gly Glu Ser Glu Thr Gly
165 170 175

Pro Leu Ala Ala Ser Trp Leu Ser Asn Ser Phe Ile Asn Pro Val Thr
180 185 190

Asp Gly Ala Val Leu Pro Ile Leu Tyr Leu Asn Gly Gly Lys Ile Ala
195 200 205

Asn Pro Thr Ile Leu Glu Arg Lys Ser Asn Glu Asp Leu Ile Lys Tyr
210 215 220

Phe Gln Gly Leu Gly Trp Asp Pro Met Val Val Glu Gly Asn Asp Pro
225 230 235 240

Glu Lys Val His Pro Leu Met Ala Lys Thr Leu Asp Gln Ala Ile Glu
245 250 255

Lys Ile Lys Ser Ile Gln Gly Glu Ala Arg Lys Gly Ser Ala Asp Glu
260 265 270

Ala Thr Met Gly His Trp Pro Met Ile Leu Tyr Arg Thr Pro Lys Gly
275 280 285

Trp Thr Gly Pro Lys Ala Trp Glu Gly Asn Asp Ile Glu Gly Ser Phe
290 295 300

Arg Ala His Gln Val Pro Ile Pro Val Asn Ala Glu Asn Met Glu His
305 310 315 320

Val Asp Ala Leu Ile Asp Trp Leu Lys Ser Tyr Arg Pro Glu Glu Leu
325 330 335

Phe Thr Glu Glu Gly Gln Leu Arg Pro Glu Ile Ala Glu Ile Ala Pro
340 345 350

Lys Gly Asp Gln Arg Met Ala Ser Asn Pro Ile Thr Asp Gly Gly Ile
355 360 365

Asp Pro Lys Pro Leu Asp Leu Pro Asp Trp Arg Asp Tyr Ala Leu Asp
370 375 380

Phe Glu Thr Pro Gly Glu Arg Asp Ala Gln Asp Met Ile Glu Met Gly 385 390 395 400

Gly Tyr Ala Ala Gly Val Ile Glu Lys Asn Pro Asp Asn Phe Arg Ile
405 410 415

Phe Gly Pro Asp Glu Thr Lys Ser Asn Arg Leu Asn Lys Val Phe Asn
420 425 430

Val Thr Lys Arg Gln Trp Leu Glu Pro Ile Lys Asp Asn Tyr Asp Glu
435 440 445

Trp Met Ser Pro Ser Gly Arg Val Ile Asp Ser Gln Leu Ser Glu His
450 455 460

Gln Met Glu Gly Phe Leu Glu Ala Tyr Thr Leu Thr Gly Arg His Gly
465 470 475 480

Phe Phe Ala Ser Tyr Glu Ala Phe Ile Arg Thr Val Asp Ser Met Ile
485 490 495

Thr Gln His Phe Lys Trp Met Arg Glu Ala Ser Glu Tyr Lys Trp His
500 505 510

Lys Pro Tyr Gln Ser Leu Asn Leu Ile Ser Ser Ser Thr Ala Phe Gln
515 520 525

Gln Asp His Asn Gly Tyr Thr His Gln Asp Pro Gly Leu Leu Thr His
530 535 540

Leu Ala Glu Lys Lys Gly Glu Phe Val Arg Ala Tyr Leu Pro Ala Asp
545 550 555 560

Thr Asn Ser Leu Leu Ala Val Met Asp Lys Ala Leu Ser Ser Glu Asn
565 570 575

Val Ile Asn Tyr Ile Val Thr Ser Lys His Pro Arg Pro Gln Phe Phe
580 585 590

Ser Val Glu Glu Ala Glu Glu Phe Val Asp Lys Gly Tyr Lys Val Ile
595 600 605

Asp Trp Ala Ser Thr Val Glu Glu Gly Glu Glu Pro Asp Val Val Ile
610 615 620

Ala Ala Ser Gly Thr Glu Pro Thr Val Glu Thr Ile Ala Thr Ile Ser
625 630 635 640

Tyr Leu His Glu Ala Phe Pro Glu Leu Lys Ile Arg Tyr Val Asn Val
645 650 655

Val Asp Leu Tyr Arg Leu Arg His Pro Asn Ile Asp Pro Arg Gly Leu
660 665 670

Ser Asp Glu Glu Phe Asp Ala Val Phe Thr Lys Asp Lys Pro Val Phe
675 680 685

Phe Gly Phe His Ser Phe Glu Gly Leu Leu Lys Asp Ile Phe Phe Asp
690 695 700

Arg His Asn His Asn Leu Tyr Pro His Gly Tyr Arg Glu Glu Gly Ala
705 710 715 720

Ile Thr Thr Pro Phe Asp Met Arg Val Leu Asn Glu Leu Asp Arg Phe
725 730 735

His Phe Ala Ala His Val Ala Glu Val Val Tyr Gly Asp Lys Ala Gln
740 745 750

Asp Phe Ile Asp Gln Met Asn Ala Lys Val Glu Glu His Arg Ala Tyr
755 760 765

Ile Val Glu Tyr Gly Thr Asp Met Pro Glu Val Lys Glu Trp Lys Trp
770 775 780

Gln Pro Leu Glu Lys
785

<210> SEQ ID NO 43

<211> LENGTH: 792
<212> TYPE: PRT
<213> ORGANISM: Kingella kingae ATCC 23330

<400> SEQUENCE: 43

Met Thr Asn Lys Thr Gln Phe Asp Thr Pro Glu Tyr Leu Gly Lys Val
1               5                   10                  15

Asp Ala Trp Trp Arg Ala Ala Asn Tyr Ile Ser Val Ala Gln Met Tyr
            20                  25                  30

Leu Lys Asp Asn Pro Leu Leu Lys Thr Pro Leu Val Ala Asn Asp Val
        35                  40                  45

Lys Ala His Pro Ile Gly His Trp Gly Thr Val Pro Gly Gln Asn Phe
    50                  55                  60

Ile Tyr Ala His Leu Asn Arg Ala Ile Asn Lys Tyr Asp Val Asp Met
65                  70                  75                  80

Phe Tyr Ile Glu Gly Pro Gly His Gly Gly Gln Val Met Val Ser Asn
                85                  90                  95

Ser Tyr Leu Asp Gly Ser Tyr Thr Glu Ile Tyr Pro Asp Ile Thr Gln
            100                 105                 110

Asp Thr Ala Gly Leu Lys Lys Leu Cys Lys Ile Phe Ser Phe Pro Gly
        115                 120                 125

Gly Ile Ala Ser His Ala Ala Pro Glu Thr Pro Gly Ser Ile His Glu
    130                 135                 140

Gly Gly Glu Leu Gly Tyr Ala Leu Ser His Ala Phe Gly Ala Val Leu
145                 150                 155                 160

Asp Asn Pro Asn Val Ile Ala Ala Ala Val Ile Gly Asp Gly Glu Ala
                165                 170                 175

Glu Thr Gly Pro Leu Cys Ala Gly Trp Phe Gly Asn Thr Phe Ile Asn
            180                 185                 190

Pro Val Asn Asp Gly Ala Val Leu Pro Ile Leu Tyr Leu Asn Gly Gly
        195                 200                 205

Lys Ile His Asn Pro Thr Ile Leu Ala Arg Lys Thr Asp Glu Glu Leu
    210                 215                 220

Lys Gln Tyr Phe Asn Gly Met Gly Trp Glu Pro Ile Phe Val Asp Val
225                 230                 235                 240

Asn Asn Val Asp Asn Tyr His Glu Ile Met Ser Gln Lys Val Asp Glu
                245                 250                 255

Ala Val Glu His Ile Leu Ser Ile Trp Gln Thr Ala Arg Thr Gln Lys
            260                 265                 270

Ala Glu Asp Ala Thr Met Pro His Trp Pro Val Leu Val Ala Arg Ile
        275                 280                 285

Pro Lys Gly Trp Thr Gly Pro Lys Thr Trp His Gly Glu Pro Ile Glu
    290                 295                 300

Gly Gly Phe Arg Ala His Gln Val Pro Ile Pro Ala Ser Ser His Asp
305                 310                 315                 320

Met Glu Thr Ala Gly Glu Leu Glu Lys Trp Leu Arg Ser Tyr Arg Pro
                325                 330                 335

Glu Glu Leu Phe Asp Asp Asn Gly Cys Phe Leu Asp Lys Trp Arg Asp
            340                 345                 350

Ile Ser Pro Lys Gly Ala Lys Arg Met Ser Val His Pro Ile Thr Asn
        355                 360                 365

Gly Gly Ile Asn Pro Lys Ala Leu Val Met Pro Asp Trp Thr Gln His
    370                 375                 380

Ala Leu Glu Ile Gly Val Pro Gly Ser Gln Asp Ala Gln Asp Met Val

```
385                 390                 395                 400

Glu Cys Gly Arg Leu Met Ala Asp Val Val Thr Ala Asn Pro Asn Asn
                405                 410                 415

Phe Arg Ile Phe Gly Pro Asp Glu Thr Lys Ser Asn Arg Leu Asn Gln
            420                 425                 430

Val Phe Gln Val Thr Lys Arg Gln Trp Leu Gly Arg Arg Asp Glu Ala
        435                 440                 445

Tyr Asp Glu Trp Ile Ala Pro Val Gly Arg Val Ile Asp Ser Gln Leu
    450                 455                 460

Ser Glu His Gln Ala Glu Gly Phe Leu Glu Gly Tyr Val Leu Thr Gly
465                 470                 475                 480

Arg His Gly Phe Phe Ala Ser Tyr Glu Ser Phe Phe Arg Val Val Asp
                485                 490                 495

Ser Met Ile Thr Gln His Phe Lys Trp Leu Arg Lys Cys Lys Thr His
            500                 505                 510

Ala Ala Trp Arg Asn Asp Tyr Pro Ser Leu Asn Leu Ile Ala Thr Ser
        515                 520                 525

Thr Val Phe Gln Gln Asp His Asn Gly Tyr Thr His Gln Asp Pro Gly
    530                 535                 540

Leu Leu Thr His Leu Ala Glu Lys Lys Pro Glu Phe Val Arg Glu Tyr
545                 550                 555                 560

Leu Pro Ala Asp Ser Asn Thr Leu Met Ala Val Met Ser Glu Ala Leu
                565                 570                 575

Thr Ser Arg Asp Arg Ile Asn Leu Ile Val Ser Ser Lys His Leu Arg
            580                 585                 590

Pro Gln Phe Phe Asn Ala Glu Glu Ala Lys Glu Leu Val Arg Glu Gly
        595                 600                 605

Tyr Lys Val Ile Asp Trp Ala Ser Thr Cys His Asp Gly Glu Pro Asp
    610                 615                 620

Val Val Ile Ala Ala Ala Gly Thr Glu Pro Asn Met Glu Ala Leu Ala
625                 630                 635                 640

Ala Ile Ser Ile Leu His Lys Gln Phe Pro Glu Leu Lys Ile Arg Phe
                645                 650                 655

Ile Asn Val Val Asp Ile Leu Lys Leu Arg His Pro Ser Ile Asp Pro
            660                 665                 670

Arg Gly Leu Ser Asp Glu Gln Phe Asp Ala Leu Phe Thr Gln Glu Lys
        675                 680                 685

Pro Val Val Phe Cys Phe His Gly Tyr Glu Gly Met Ile Arg Asp Leu
    690                 695                 700

Phe Phe Pro Arg Ala Asn His Asn Val Arg Ile His Gly Tyr Arg Glu
705                 710                 715                 720

Asn Gly Asp Ile Thr Thr Pro Phe Asp Met Arg Val Leu Ser Glu Met
                725                 730                 735

Asp Arg Phe His Val Ala Lys Asp Ala Ala Gln Ala Val Tyr Gly Asp
            740                 745                 750

Lys Ala Ser Glu Phe Ala Lys Lys Met Gly Glu Thr Val Ala Phe His
        755                 760                 765

Arg Ser Tyr Ile Arg Glu His Gly Thr Asp Ile Pro Glu Val Ala Glu
    770                 775                 780

Trp Lys Trp Gln Pro Leu Ala Lys
785                 790

<210> SEQ ID NO 44
```

<211> LENGTH: 794
<212> TYPE: PRT
<213> ORGANISM: Streptococcus criceti HS-6

<400> SEQUENCE: 44

```
Met Asn Thr Asn Phe Asp Ser Ser Asp Tyr Leu Asn Lys Val Asp Ala
 1               5                  10                  15

Trp Trp Arg Ala Ala Asn Tyr Ile Ser Ala Ala Gln Met Tyr Leu Lys
            20                  25                  30

Asp Asn Pro Leu Leu Arg Arg Glu Val Ala Ala Glu Asp Leu Lys Ser
        35                  40                  45

His Pro Ile Gly His Trp Gly Thr Val Pro Gly Gln Asn Phe Ile Tyr
    50                  55                  60

Ala His Leu Leu Arg Ser Ile Asn Lys Tyr Asp Leu Asp Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Thr Glu Leu Asn Pro Gln Ile Ser Gln Thr Glu
            100                 105                 110

Glu Gly Leu Lys Gln Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Thr Gly Ala Val Leu Asp Asn
145                 150                 155                 160

Pro Asp Val Ile Ala Ala Thr Val Ile Gly Asp Gly Glu Ser Glu Thr
                165                 170                 175

Gly Pro Leu Met Ala Gly Trp Leu Ser Asn Thr Phe Ile Asn Pro Val
            180                 185                 190

Asn Asp Gly Ala Val Leu Pro Ile His Phe Leu Asn Gly Gly Lys Ile
        195                 200                 205

His Asn Pro Thr Ile Phe Glu Arg Lys Ser Asp Asp Glu Leu Lys Ala
    210                 215                 220

Phe Phe Thr Gly Leu Gly Trp Lys Pro Ile Phe Ala Asp Val Thr Ala
225                 230                 235                 240

Phe Ala Ser Asp His Ala Ala Ala His Lys Leu Phe Ala Ala Lys Leu
                245                 250                 255

Asp Glu Ala Ile Glu Glu Ile Arg Asn Ile Gln Ala Lys Ala Arg Lys
            260                 265                 270

Gly Ser Ala Asp Glu Ala Thr Met Pro Ala Trp Pro Val Ile Val Ala
        275                 280                 285

Arg Ile Pro Lys Gly Trp Thr Gly Pro Lys Ser Trp Lys Gly Thr Pro
    290                 295                 300

Ile Glu Gly Gly Trp Arg Ala His Gln Val Pro Ile Pro Val Asp Ser
305                 310                 315                 320

His His Met Glu His Val Asp Ala Leu Leu Asp Trp Leu Lys Ser Tyr
                325                 330                 335

Gln Pro Glu Glu Leu Phe Asp Ala Glu Gly His Leu Lys Ser Glu Val
            340                 345                 350

Ala Ala Leu Ser Pro Lys Gly Asn Arg Arg Met Ser Met Asn Pro Ile
        355                 360                 365

Thr Asn Ala Gly Val Ile Lys Pro Met Asp Thr Ala Asp Trp Lys Lys
    370                 375                 380

Arg Ala Phe Asp Ile Gln Thr Pro Gly Glu Ile Val Ala Gln Asp Met
```

```
385                 390                 395                 400

Ile Glu Phe Gly Lys Tyr Ala Ala Asp Leu Val Glu Ala Asn Pro Asp
                405                 410                 415

Asn Phe Arg Ile Phe Gly Pro Asp Glu Ser Lys Ser Asn Arg Leu Asn
            420                 425                 430

Glu Val Phe Thr Lys Thr Asn Arg Gln Trp Met Gly Arg Arg Asp Pro
        435                 440                 445

Ser Tyr Asp Glu Trp Leu Ser Pro Ala Gly Arg Val Ile Asp Ser Gln
    450                 455                 460

Leu Ser Glu His Gln Ala Glu Gly Phe Leu Glu Gly Tyr Val Leu Thr
465                 470                 475                 480

Gly Arg His Gly Phe Phe Ala Ser Tyr Glu Ser Phe Leu Arg Val Val
                485                 490                 495

Asp Thr Met Ile Thr Gln His Phe Lys Trp Leu Arg Lys Ser Lys Thr
            500                 505                 510

His Thr Thr Trp Arg Lys Asn Tyr Pro Ser Leu Asn Leu Ile Ala Thr
        515                 520                 525

Ser Thr Val Phe Gln Gln Asp His Asn Gly Tyr Thr His Gln Asp Pro
    530                 535                 540

Gly Val Leu Thr His Leu Ser Glu Lys Thr Pro Glu Tyr Ile Arg Glu
545                 550                 555                 560

Tyr Leu Pro Ala Asp Thr Asn Ser Leu Leu Ala Val Met Asp Lys Ala
                565                 570                 575

Phe Lys Asp Glu Asp Lys Ile Asn Leu Ile Val Thr Ser Lys His Pro
            580                 585                 590

Arg Pro Gln Phe Tyr Ser Val Glu Glu Ala Ser Glu Leu Val Glu Lys
        595                 600                 605

Gly Tyr Lys Val Ile Asp Trp Ala Ser Thr Val Gln Ala Asn Glu Glu
    610                 615                 620

Pro Asp Val Val Phe Ala Ala Ala Gly Thr Glu Pro Asn Leu Glu Ala
625                 630                 635                 640

Leu Ala Ala Ile Ser Ile Leu His Lys Thr Phe Pro Ser Leu Lys Ile
                645                 650                 655

Arg Phe Val Asn Val Val Asp Ile Leu Lys Leu Arg His Pro Asp Leu
            660                 665                 670

Asp Pro Arg Gly Leu Ser Asp Glu Glu Phe Asp Lys Val Phe Thr Lys
        675                 680                 685

Asp Lys Pro Val Ile Phe Ala Phe His Ala Tyr Glu Gly Met Ile Arg
    690                 695                 700

Asp Ile Phe Phe Arg Arg His Asn His Asn Leu His Val His Gly Tyr
705                 710                 715                 720

Arg Glu Asn Gly Asp Ile Thr Thr Pro Phe Asp Met Arg Val Met Ser
                725                 730                 735

Glu Leu Asp Arg Phe His Leu Ala Gln Asp Ala Ala Leu Thr Thr Leu
            740                 745                 750

Gly Glu Lys Ala Gln Ala Phe Ser Ala Lys Met Asp Glu Thr Val Ala
        755                 760                 765

Tyr His Lys Asp Tyr Ile Arg Glu His Gly Asp Asp Ile Pro Glu Val
    770                 775                 780

Gln Asn Trp Gln Trp Glu Asn Leu Asp Glu
785                 790
```

<210> SEQ ID NO 45

<211> LENGTH: 787
<212> TYPE: PRT
<213> ORGANISM: Streptococcus criceti HS-6

<400> SEQUENCE: 45

```
Met Thr Glu Phe Asp Ser Lys Asp Tyr Leu Ala Lys Val Asp Ala Trp
 1               5                  10                  15

Trp Arg Ala Ala Asn Tyr Ile Ser Val Ala Gln Met Tyr Leu Lys Asp
            20                  25                  30

Asn Pro Leu Leu Arg Arg Glu Val Ser Lys Glu Asp Val Lys Val His
        35                  40                  45

Pro Ile Gly His Trp Gly Thr Ile Ala Gly Gln Asn Phe Ile Tyr Ala
    50                  55                  60

His Leu Asn Arg Val Ile Asn Lys Phe Asp Leu Asn Met Phe Tyr Ile
65                  70                  75                  80

Glu Gly Pro Gly His Gly Gly Gln Val Met Val Ser Asn Ser Tyr Ile
                85                  90                  95

Asp Gly Ser Tyr Thr Glu Arg Tyr Pro Asn Ile Thr Gln Asp Glu Asp
            100                 105                 110

Gly Leu Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Ala Glu Thr Gly
                165                 170                 175

Pro Leu Asn Ala Gly Trp Phe Ser Asn Thr Phe Ile Asn Pro Val Asn
            180                 185                 190

Asp Gly Ala Val Leu Pro Ile Leu Tyr Leu Asn Gly Gly Lys Ile His
        195                 200                 205

Asn Pro Thr Ile Leu Ser Arg Lys Thr Asp Glu Glu Leu Thr His Leu
    210                 215                 220

Phe Gln Gly Leu Gly Trp Glu Pro Tyr Phe Val Glu Gly Asn Asp Pro
225                 230                 235                 240

Glu Val Ile His Ser Gln Met Ala Glu Thr Leu Asp Lys Val Ile Glu
                245                 250                 255

Lys Ile Lys Thr Ile Gln Thr Gln Ala Arg Gln Lys Pro Ala Glu Glu
            260                 265                 270

Ala Gln Gln Ala Gln Trp Pro Val Leu Ile Val Arg Thr Pro Lys Gly
        275                 280                 285

Trp Thr Gly Pro Lys Glu Trp Asn Gly Glu Pro Ile Glu Gly Gly Phe
    290                 295                 300

Arg Ala His Gln Val Pro Ile Pro Val Glu Ala Gly His Met Glu His
305                 310                 315                 320

Ile Asp Ala Leu Thr Asp Trp Leu Lys Ser Tyr Arg Pro Glu Glu Leu
                325                 330                 335

Phe Asp Glu Lys Gly Tyr Val Lys Glu Glu Ile Arg Val Ile Ser Pro
            340                 345                 350

Lys Gly Asn Arg Arg Met Ser Met Asn Pro Ile Thr Asn Ala Gly Ile
        355                 360                 365

Val Lys Lys Leu Asp Leu Ala Asp Trp Arg Lys His Ala Ile Asp Thr
    370                 375                 380

Ser Lys Pro Gly Ser Ile Met Lys Gln Asp Met Ile Glu Phe Gly Lys
```

```
385                 390                 395                 400

Tyr Ala Ala Asp Leu Val Lys Ala Asn Pro Asp Asn Phe Arg Ile Phe
                405                 410                 415

Gly Pro Asp Glu Thr Lys Ser Asn Arg Leu Asn Asn Val Phe Thr Ala
            420                 425                 430

Thr Asn Arg Gln Trp Leu Ala Pro Arg Asp Lys Ser Tyr Asp Glu Trp
        435                 440                 445

Ile Ser Pro Val Gly Arg Val Ile Asp Ser Gln Leu Ser Glu His Gln
    450                 455                 460

Ala Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Ile Thr
                485                 490                 495

Gln His Phe Lys Trp Leu Arg Lys Ser Lys Thr His Thr Asp Trp Arg
            500                 505                 510

Lys Asn Tyr Pro Ser Leu Asn Leu Ile Ala Thr Ser Thr Val Phe Gln
        515                 520                 525

Gln Asp His Asn Gly Tyr Thr His Gln Asp Pro Gly Leu Leu Thr His
    530                 535                 540

Leu Ala Glu Lys Thr Pro Glu Tyr Val Arg Glu Tyr Leu Pro Ala Asp
545                 550                 555                 560

Ser Asn Ser Leu Phe Ala Val Met Glu Tyr Ala Leu Ala Asp Glu Asp
                565                 570                 575

Lys Val Asn Val Ile Val Thr Ser Lys His Pro Arg Pro Gln Phe Tyr
            580                 585                 590

Ser Val Ala Glu Ala Gln Glu Leu Val Lys Glu Gly Tyr Lys Val Ile
        595                 600                 605

Asp Trp Ala Ser Asn Asp His Asp Gly Glu Pro Asp Ile Val Phe Ala
    610                 615                 620

Ala Ala Gly Thr Glu Pro Asn Leu Glu Val Leu Ala Gly Ile Ser Leu
625                 630                 635                 640

Leu His Lys Ala Phe Pro Glu Val Lys Ile Arg Phe Ile Asn Val Val
                645                 650                 655

Asp Ile Leu Lys Leu Arg Ser Pro Lys Val Asp Pro Arg Gly Leu Ser
            660                 665                 670

Asp Glu Ala Phe Asn Lys Leu Phe Thr Thr Asp Lys Pro Ile Val Phe
        675                 680                 685

Ala Tyr His Gly Tyr Glu Gly Gln Ile Arg Asp Leu Phe Phe Asn Arg
    690                 695                 700

Asp Asn His Lys Val Tyr Ile His Gly Tyr Arg Glu Asn Gly Asp Ile
705                 710                 715                 720

Thr Thr Pro Phe Asp Met Arg Val Met Ser Glu Met Asp Arg Phe His
                725                 730                 735

Ile Ala Lys Glu Ala Ala Gln Ala Val Leu Gly Asp Lys Ala Gln Gly
            740                 745                 750

Phe Ala Gln Glu Met Ala Asp Lys Leu Ala Tyr His Thr Ala Tyr Ile
        755                 760                 765

Arg Glu His Gly Asp Asp Ile Pro Glu Val Gln Asn Trp Gln Trp Glu
    770                 775                 780

Thr Ile Asp
785
```

<210> SEQ ID NO 46

-continued

<211> LENGTH: 794
<212> TYPE: PRT
<213> ORGANISM: Mycoplasma columbinum SF7

<400> SEQUENCE: 46

```
Met Ser Lys Thr Asn Phe Asp Ser Lys Lys Tyr Leu Asp Lys Ile His
1               5                   10                  15

Ala Trp Trp Arg Ala Ala Asn Tyr Leu Ser Val Gly Gln Met Tyr Leu
            20                  25                  30

Lys Asn Asn Pro Leu Leu Gln Glu Pro Leu Lys Asp Glu Asp Ile Lys
        35                  40                  45

Ile Tyr Pro Ile Gly His Trp Gly Thr Ile Pro Gly Gln Asn Leu Ile
    50                  55                  60

Tyr Ala His Leu Asn Arg Val Ile Asn Lys Tyr Asp Leu Asn Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Thr Glu Leu Phe Pro Glu Ile Thr Gln Asp
            100                 105                 110

Leu Ala Gly Leu Asn Lys Met Phe Lys Arg Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ala Leu Ser His Ala Thr Gly Ala Ile Leu Asp
145                 150                 155                 160

Asn Pro Asp Val Ile Ala Ala Thr Val Ile Gly Asp Gly Glu Ala Glu
                165                 170                 175

Thr Gly Pro Leu Met Ala Gly Trp Tyr Ser Ser Ser Phe Ile Asn Pro
            180                 185                 190

Val Asn Asp Gly Thr Val Leu Pro Ile Leu His Ile Asn Gly Gly Lys
        195                 200                 205

Ile Ser Asn Pro Thr Ile Leu Ala Arg Lys Thr Asp Lys Glu Ile Lys
    210                 215                 220

Gln Leu Leu Ala Gly Phe Gly Trp Glu Ala Ile Phe Val Glu Ala Asp
225                 230                 235                 240

Val Phe Arg Pro Glu Ala Ile His Leu Ser Met Ala Lys Ala Phe Asp
                245                 250                 255

Lys Ala Ile Glu Lys Ile Gln Arg Ile Gln Arg Glu Ala Arg Ala Asn
            260                 265                 270

Ser Ala Asn His Ala Lys Arg Pro Ile Trp Pro Ala Leu Val Val Arg
        275                 280                 285

Thr Pro Lys Gly Trp Thr Cys Pro His Lys Ile Asp Asp Lys Val Tyr
    290                 295                 300

Glu Gly Ser Phe Arg Ser His Gln Val Pro Leu Ala Val Ser Ser Glu
305                 310                 315                 320

Asn Thr Thr Lys Lys Val Asp Leu Val Asn Trp Leu Glu Ser Tyr Lys
                325                 330                 335

Pro Arg Glu Leu Phe Asn Gln Asp Gly Ser Phe Lys Ala His Tyr Ala
            340                 345                 350

Glu Ile Ala Pro Lys Gly Asn Lys Arg Met Ala Met Asn Pro Ile Thr
        355                 360                 365

Asn Gly Gly Ile Asn Pro Lys Asn Leu Asp Leu Pro Asn Trp Glu Gln
    370                 375                 380

Phe Ala Ile Asp Phe Asp Lys Pro Gly Ala Ile Lys Ala Gln Asp Met
```

```
385                 390                 395                 400

Val Ser Ala Gly Thr Trp Phe Ala Asp Val Ile Lys Arg Asn Pro Thr
                405                 410                 415

Asn Phe Arg Ile Phe Gly Pro Asp Glu Thr Lys Ser Asn Arg Leu Phe
            420                 425                 430

Asp Val Leu Lys Thr Thr Asn Arg Gln Trp Leu Glu Arg Val Asp Tyr
        435                 440                 445

Asp Leu Asp Glu Asn Ile Gly Pro Ala Gly Arg Val Ile Asp Ser Gln
    450                 455                 460

Leu Ser Glu His Gln Ala Glu Gly Phe Leu Glu Gly Tyr Val Leu Thr
465                 470                 475                 480

Gly Arg His Gly Met Phe Ala Ser Tyr Glu Ser Phe Leu Arg Val Val
                485                 490                 495

Asp Ser Met Leu Thr Gln His Met Lys Trp Val Ala Lys Ala Lys Lys
            500                 505                 510

Val His Trp Arg Asn Asp Tyr Pro Ser Leu Asn Val Ile Ala Thr Ser
        515                 520                 525

Thr Ala Phe Gln Gln Asp His Asn Gly Tyr Thr His Gln Asp Pro Gly
    530                 535                 540

Ile Leu Gly His Leu Ala Asp Lys Lys Pro Glu Leu Ile Arg Glu Tyr
545                 550                 555                 560

Leu Pro Ala Asp Ser Asn Thr Leu Leu Ala Val Leu Asp Lys Ala Phe
                565                 570                 575

Lys Glu Arg Asp Val Ile Asn Leu Ile Val Ala Ser Lys Gln Pro Arg
            580                 585                 590

Glu Gln Trp Phe Ser Pro Arg Glu Ala Asn Ile Leu Val Lys Asn Gly
        595                 600                 605

Leu Lys Val Ile Ser Trp Ala Ser Thr Cys Thr Leu Glu Glu Glu Pro
    610                 615                 620

Asp Leu Val Val Ala Ala Ala Gly Thr Glu Pro Thr Leu Glu Ala Leu
625                 630                 635                 640

Ala Ala Ile Ser Tyr Leu Asn Glu Lys Phe Pro Thr Leu Lys Ile Arg
                645                 650                 655

Phe Val Asn Val Val Asp Leu Leu Lys Leu Arg His Pro Ser Ile Asp
            660                 665                 670

Pro Arg Gly Leu Ser Asn Tyr Glu Phe Asp Ser Ile Phe Thr Lys Asp
        675                 680                 685

Lys Pro Ile Leu Phe Ala Phe His Gly Tyr Glu Ala Leu Ile Arg Asp
    690                 695                 700

Ile Phe Phe Leu Arg Asn Asn His Asn Leu His Ile His Gly Tyr Arg
705                 710                 715                 720

Glu Asn Gly Asp Ile Thr Thr Ser Phe Asp Ile Arg Leu Met Ser Glu
                725                 730                 735

Met Asp Arg Phe His Met Ala Gln Thr Ala Ala Lys Ala Val Leu Gly
            740                 745                 750

Tyr Asp Lys Ala Lys Ser Phe Val Asp Lys Met Gln Asp Lys Ile Asp
        755                 760                 765

Gln His Asn Ala Tyr Ile Lys Glu His Gly Ile Asp Met Asp Glu Val
    770                 775                 780

Arg Tyr Trp Thr Trp Lys Gly Leu Asn Lys
785                 790
```

<210> SEQ ID NO 47

<211> LENGTH: 797
<212> TYPE: PRT
<213> ORGANISM: Burkholderia phytofirmans PsJN

<400> SEQUENCE: 47

Met Ala Glu Ala Thr Ala His Pro Thr Pro Pro Gln Thr Leu Asp Ala
1 5 10 15

Asp Thr Leu Arg Asn Met Asp Arg Tyr Trp Arg Ala Cys Asn Tyr Leu
20 25 30

Ser Ala Gly Met Ile Tyr Leu Arg Asp Asn Pro Leu Leu Arg Glu Pro
35 40 45

Leu Lys Pro Glu His Ile Lys Asn Arg Leu Leu Gly His Trp Gly Ser
50 55 60

Asp Pro Gly Gln Ser Phe Leu Leu Val His Leu Asn Arg Leu Ile Lys
65 70 75 80

Lys Leu Asp Leu Asn Val Ile Tyr Val Ala Gly Pro Gly His Gly Ala
85 90 95

Pro Ala Thr Leu Ala Asn Cys Tyr Leu Glu Gly His Tyr Ser Glu Ile
100 105 110

Tyr Pro Asp Arg Ser Gln Asp Val Ala Gly Met Glu Arg Phe Phe Arg
115 120 125

Gln Phe Ser Phe Pro Gly Gly Ile Gly Ser His Cys Thr Pro Glu Thr
130 135 140

Pro Gly Ser Ile His Glu Gly Gly Glu Leu Gly Tyr Ser Leu Ser His
145 150 155 160

Gly Tyr Gly Ala Ala Phe Asp Asn Pro Asp Leu Ile Val Ala Val Met
165 170 175

Ile Gly Asp Gly Glu Ala Glu Thr Gly Pro Leu Ala Thr Ser Trp His
180 185 190

Ser Asn Lys Phe Leu Asn Pro Ile Arg Asp Gly Ala Val Leu Pro Val
195 200 205

Leu His Leu Asn Gly Tyr Lys Ile Ala Asn Pro Thr Ile Leu Ala Arg
210 215 220

Ile Pro Arg Glu Glu Leu Glu Ala Leu Leu Thr Gly Tyr Gly His Lys
225 230 235 240

Pro Tyr Phe Val Glu Gly Glu Asp Pro Ala Val Met His Gln Gln Met
245 250 255

Ala Ala Thr Leu Glu Gln Cys Ile Gly Glu Ile Arg Ala Ile Gln Gln
260 265 270

His Ala Arg Glu Ser Asn Asp Ala Ser Arg Pro Arg Trp Pro Met Ile
275 280 285

Val Leu Arg Ser Pro Lys Gly Trp Thr Gly Pro Lys Glu Val Asp Gly
290 295 300

His Lys Val Glu Gly Ser Trp Arg Ala His Gln Val Pro Val Leu Asp
305 310 315 320

Pro Ala Thr Asn Ser Lys Ser Leu Lys Leu Val Glu Asn Trp Leu Arg
325 330 335

Ser Tyr Glu Pro Glu Thr Leu Phe Asp Glu Ala Gly Arg Leu Val Lys
340 345 350

Glu Leu Arg Glu Leu Ala Pro Glu Gly Ala Arg Arg Ile Ser Ala Asn
355 360 365

Pro His Ala Asn Gly Gly Val Leu Cys Lys Thr Leu Ala Met Pro Pro
370 375 380

Phe Arg Asp Tyr Ala Val Ala Val Lys Lys Pro Ala Gly Ser Tyr Thr

-continued 385 390 395 400

Ser Pro Thr Glu Val Leu Gly Lys Phe Leu Arg Asp Val Met Arg Asn
405 410 415

Asn Met Thr Asn Phe Arg Val Phe Gly Pro Asp Glu Thr Ser Ser Asn
420 425 430

Lys Leu Thr Ala Ile Tyr Glu Ala Ser Glu Lys Thr Trp Leu Ala Gln
435 440 445

Thr Val Pro Ser Asp Ala Asp Gly Gly Glu Leu Ala Val Asp Gly Arg
450 455 460

Val Met Glu Met Leu Ser Glu His Thr Leu Glu Gly Trp Phe Glu Gly
465 470 475 480

Tyr Val Leu Thr Gly Arg His Gly Leu Phe Ala Thr Tyr Glu Ala Phe
485 490 495

Val His Val Ile Asp Ser Met Phe Asn Gln His Ala Lys Trp Leu Glu
500 505 510

Lys Ala Lys Arg Asp Leu Gly Trp Arg Gln Pro Val Pro Ser Ile Asn
515 520 525

Leu Leu Ile Thr Ser Leu Val Trp Arg Gln Asp His Asn Gly Phe Thr
530 535 540

His Gln Asp Pro Gly Phe Leu Asp Val Val Thr Asn Lys Ser Pro Asp
545 550 555 560

Val Val Arg Ile Tyr Leu Pro Pro Asp Ala Asn Cys Leu Leu Ser Val
565 570 575

Ala Asp His Cys Leu Arg Ser Arg Asp Tyr Val Asn Val Ile Val Ala
580 585 590

Asp Lys Gln Pro His Leu Gln Tyr Leu Asp Met Asp Ala Ala Val Thr
595 600 605

His Cys Thr Lys Gly Ile Gly Ile Trp Asp Trp Ala Ser Thr Asp Gln
610 615 620

Gly Val Glu Pro Asp Val Val Met Ala Cys Ala Gly Asp Ile Pro Thr
625 630 635 640

Met Glu Ala Leu Ala Ala Val Gln Ile Leu Lys Glu Gln Phe Ala Asp
645 650 655

Leu Lys Ile Arg Phe Val Asn Val Val Asp Leu Phe Arg Leu Met Pro
660 665 670

Glu His Ala His Pro His Gly Leu Ser Ser Arg Asp Phe Asp Ser Leu
675 680 685

Phe Thr Thr Asp Lys Pro Val Ile Phe Asn Phe His Ser Tyr Ala Ser
690 695 700

Leu Val His Lys Leu Thr Tyr Asn Arg Thr Asn His Asp Asn Leu His
705 710 715 720

Val His Gly Tyr His Glu Lys Gly Asn Ile Asn Thr Pro Leu Glu Leu
725 730 735

Ala Ile Ile Asn Gln Val Asp Arg Phe Ser Leu Ala Ile Asp Val Ile
740 745 750

Asp Arg Val Pro Arg Leu Arg Gly Val Gly Asp His Ala Lys Glu Trp
755 760 765

Leu Arg Gly Gln Ile Ile Glu His Leu Ala Tyr Ala His Ala Glu Gly
770 775 780

Ile Asp Lys Glu Glu Ile Arg Asn Trp Thr Trp Lys Gly
785 790 795

<210> SEQ ID NO 48

<211> LENGTH: 795
<212> TYPE: PRT
<213> ORGANISM: Lactobacillus buchneri NRRL B-30929

<400> SEQUENCE: 48

```
Met Thr Val Asp Tyr Asp Ser Lys Glu Tyr Leu Glu Leu Val Asp Lys
 1               5                  10                  15

Tyr Trp Arg Ala Ala Asn Tyr Leu Ser Val Gly Gln Leu Phe Leu Arg
            20                  25                  30

Asp Asn Pro Leu Leu Lys Arg Pro Leu Glu Ala Lys Asp Val Lys Val
        35                  40                  45

Lys Pro Ile Gly His Trp Gly Thr Ile Val Ser Gln Asn Leu Ile Tyr
    50                  55                  60

Ala Glu Leu Asn Arg Val Ile Asn Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Ser Asp Ile Tyr Pro Asn Ile Ser Gln Asp Glu
            100                 105                 110

Lys Gly Met Ala Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Leu Ser His Gly Thr Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

Thr Asp Gly Ala Val Leu Pro Ile Ile Asn Met Asn Gly Phe Lys Ile
        195                 200                 205

Ser Asn Pro Thr Ile Leu Ser Arg Met Ser Asp Glu Asp Leu Thr Ser
    210                 215                 220

Tyr Phe Lys Gly Met Gly Trp Asp Pro Tyr Phe Val Glu Ala Thr Ala
225                 230                 235                 240

Asp Thr Asp His Ala Lys Val Glu Glu Glu Phe Ala Lys Thr Leu Asp
                245                 250                 255

His Val Ile Glu Glu Ile Lys Ser Ile Gln Lys Asn Ala Arg Glu Asn
            260                 265                 270

Glu Thr Pro Asp Asn Val Lys Leu Pro Asn Trp Pro Met Ile Ile Phe
        275                 280                 285

Arg Ser Pro Lys Gly Trp Thr Gly Pro Lys Lys Asp Leu Asp Gly Asn
    290                 295                 300

Pro Ile Glu Gly Ser Phe Arg Ala His Gln Val Pro Ile Pro Val Ala
305                 310                 315                 320

Ala Gly Ser Met Glu His Lys Asp Leu Leu Asn Asp Trp Leu Lys Ser
                325                 330                 335

Tyr Lys Pro Glu Glu Leu Phe Asp Glu Asn Gly Thr Val Lys Pro Glu
            340                 345                 350

Ile Arg Ala Val Ala Pro Lys Gly Asp Lys Arg Met Ser Val Asn Pro
        355                 360                 365

Ile Thr Asn Gly Gly Ile Lys Pro Glu Pro Leu Lys Leu Pro Asp Val
    370                 375                 380

Arg Asn Phe Glu Val Lys Phe Asp Arg Gly Val Thr Gln Lys Gln Asp
```

```
385                 390                 395                 400

Met Ile Glu Trp Ser Asn Trp Leu Glu Lys Val Ala Glu Leu Asn Pro
                405                 410                 415

Thr Ser Phe Arg Gly Phe Gly Pro Asp Glu Thr Lys Ser Asn Arg Leu
            420                 425                 430

Tyr Ser Leu Leu Asp Asp Ser Lys Arg Gln Trp Met Glu Asp Ile His
        435                 440                 445

Glu Pro Phe Asp Glu Asp Leu Ser Asn His Gly Arg Val Ile Asp Ser
    450                 455                 460

Gln Leu Ser Glu His Gln Ala Glu Gly Trp Leu Glu Gly Tyr Val Leu
465                 470                 475                 480

Thr Gly Arg His Gly Phe Phe Ala Thr Tyr Glu Ser Phe Gly Arg Val
                485                 490                 495

Val Asp Ser Met Leu Thr Gln His Phe Lys Trp Leu Arg Lys Ala Ser
            500                 505                 510

Glu Gln Tyr Trp Arg Lys Gln Tyr Pro Ser Leu Asn Phe Val Asp Thr
        515                 520                 525

Ser Thr Val Phe Gln Gln Asp His Asn Gly Tyr Thr His Gln Asp Pro
    530                 535                 540

Gly Met Leu Thr His Leu Ala Glu Lys Lys Pro Glu Phe Ile Arg Glu
545                 550                 555                 560

Tyr Leu Pro Ala Asp Ala Asn Glu Leu Leu Ala Val Gly Asp Val Ala
                565                 570                 575

Phe Arg Thr Tyr Glu Lys Ile Asn Leu Ile Val Thr Ser Lys His Pro
            580                 585                 590

Arg Arg Gln Trp Tyr Thr Met Asp Glu Ala Gln Asn Leu Val Lys Asn
        595                 600                 605

Gly Leu Gly Tyr Ile Asp Trp Ala Ser Thr Asp Gln Gly Gln Glu Pro
    610                 615                 620

Asp Val Val Phe Ala Ala Ala Gly Ser Glu Pro Asn Leu Glu Ala Leu
625                 630                 635                 640

Ala Ala Ile Ser Ile Leu Asn Lys Glu Phe Pro Glu Met Lys Ile Arg
                645                 650                 655

Phe Ile Asn Val Val Asp Leu Leu Lys Leu Arg Ser Pro Lys Val Asp
            660                 665                 670

Pro Arg Gly Leu Ser Asp Glu Glu Phe Asp Asn Leu Phe Thr Thr Asp
        675                 680                 685

Lys Pro Val Ile Phe Ala Phe His Gly Phe Glu Asp Leu Ile Lys Asp
    690                 695                 700

Ile Phe Phe Asp Arg His Asn His Asn Leu His Val His Gly Tyr Arg
705                 710                 715                 720

Glu Asn Gly Asp Ile Thr Thr Pro Phe Asp Met Arg Val Leu Asn Gln
                725                 730                 735

Leu Asp Arg Phe Asp Leu Ala Lys Glu Ala Val Gln Asp Ile Pro Ala
            740                 745                 750

Tyr Thr Val Lys Gly Gly Tyr Phe Ile Gln Arg Met Asn Asp Met Val
        755                 760                 765

Asp Lys His Asn Ala Tyr Ile Arg Gln Glu Gly Thr Asp Leu Pro Glu
    770                 775                 780

Val Val Asp Trp Lys Trp Glu Gly Leu Lys Lys
785                 790                 795
```

<210> SEQ ID NO 49

<211> LENGTH: 826
<212> TYPE: PRT
<213> ORGANISM: Bifidobacterium gallicum DSM 20093

<400> SEQUENCE: 49

```
Met Thr Ser Pro Val Ile Gly Thr Pro Trp Gln Lys Leu Asn Arg Pro
 1               5                  10                  15

Val Ser Glu Glu Ala Ile Glu Gly Met Asp Lys Tyr Trp Arg Ala Ser
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys Tyr Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Tyr Pro Asn Ile Thr Lys Asp Glu Glu Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Val Ser Asp Glu Glu Leu His Asp Phe Phe Arg Gly Leu
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Asn Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Asn Trp Met Ala Ser Tyr Lys Pro Glu Glu Leu Phe Asp Asp
            340                 345                 350

Lys Gly Ala Ile Lys Asp Asp Val Val Asp Phe Met Pro Lys Gly Asp
        355                 360                 365

Leu Arg Ile Gly Ala Asn Pro Asn Ala Asn Gly Gly Val Ile Arg Glu
    370                 375                 380

Glu Leu Asp Leu Pro Ala Leu Glu Asn Tyr Glu Val Lys Glu Val Lys
```

385 390 395 400

Glu Phe Gly His Gly Trp Gly Gln Leu Glu Ala Thr Arg Lys Leu Gly
405 410 415

Glu Tyr Thr Arg Asp Ile Ile Lys Asn Asn Pro Asp Ser Phe Arg Ile
420 425 430

Phe Gly Pro Asp Glu Thr Ala Ser Asn Arg Leu Gln Ala Ser Tyr Glu
435 440 445

Val Thr Asn Lys Gln Trp Asp Asn Gly Tyr Leu Ser Lys Asp Leu Val
450 455 460

Asp Glu His Met Ala Val Thr Gly Gln Val Thr Glu Gln Leu Ser Glu
465 470 475 480

His Gln Cys Glu Gly Phe Leu Glu Ala Tyr Leu Leu Thr Gly Arg His
485 490 495

Gly Ile Trp Ser Ser Tyr Glu Ser Phe Val His Val Ile Asp Ser Met
500 505 510

Leu Asn Gln His Ala Lys Trp Leu Glu Ala Thr Val Arg Glu Ile Pro
515 520 525

Trp Arg Lys Pro Ile Ser Ser Met Asn Leu Leu Val Ser Ser His Val
530 535 540

Trp Arg Gln Asp His Asn Gly Phe Ser His Gln Asp Pro Gly Val Thr
545 550 555 560

Ser Val Leu Leu Asn Lys Thr Phe Asn Asn Asp His Val Ile Gly Leu
565 570 575

Tyr Phe Ala Thr Asp Ala Asn Val Leu Leu Ala Ile Ala Glu Lys Cys
580 585 590

Tyr Lys Ser Thr Asn Met Ile Asn Ala Ile Val Ala Gly Lys Gln Pro
595 600 605

Ala Ala Thr Trp Thr Thr Leu Asp Glu Ala Arg Glu Leu Val Ala Lys
610 615 620

Gly Ala Gly Glu Phe Glu Trp Ala Ser Asn Val Lys Thr Asn Asp Glu
625 630 635 640

Ala Glu Ile Val Leu Ala Ser Ala Gly Asp Val Pro Thr Gln Glu Leu
645 650 655

Met Ala Ala Ala Asp Arg Leu Asn Lys Leu Gly Val Lys Phe Lys Val
660 665 670

Val Asn Val Val Asp Leu Ile Lys Leu Gln Ser Ala Lys Glu Asn Asp
675 680 685

Gln Ala Leu Ser Asp Ala Glu Phe Ala Glu Leu Phe Thr Glu Asp Lys
690 695 700

Pro Val Leu Phe Ala Tyr His Ser Tyr Ala His Asp Val Arg Gly Leu
705 710 715 720

Ile Phe Asp Arg Pro Asn His Asp Asn Phe Asn Val Val Gly Tyr Lys
725 730 735

Glu Gln Gly Ser Thr Thr Thr Pro Tyr Asp Met Val Arg Val Asn Asp
740 745 750

Ile Asp Arg Tyr Glu Leu Thr Ala Thr Ala Leu Arg Met Ile Asp Ala
755 760 765

Asp Lys Tyr Ala Asp Glu Ile Lys Lys Leu Glu Asp Phe Arg Ile Glu
770 775 780

Ala Tyr Gln Phe Ala Val Asp Asn Gly Tyr Asp Ile Pro Asp Tyr Thr
785 790 795 800

Asp Trp Val Trp Pro Gly Val Lys Thr Asp Leu Pro Gly Ala Val Ser
805 810 815

```
Ala Thr Ala Ala Thr Ala Gly Asp Asn Glu
            820                 825


<210> SEQ ID NO 50
<211> LENGTH: 825
<212> TYPE: PRT
<213> ORGANISM: Bifidobacterium dentium Bd1

<400> SEQUENCE: 50

Met Thr Ser Pro Val Ile Gly Thr Pro Trp Lys Lys Leu Asn Ala Pro
 1               5                  10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Ala Gln Thr Asp Asp Met Thr Arg
        275                 280                 285

Pro Phe Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Pro Glu Val Thr Ala Phe Met Pro Thr Gly Glu
```

```
        355                 360                 365

Leu Arg Ile Gly Glu Asn Pro Asn Ala Asn Gly Gly Arg Ile Arg Glu
    370                 375                 380

Glu Leu Asn Leu Pro Ala Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
        435                 440                 445

Val Thr Asn Lys Gln Trp Asp Ala Gly Tyr Leu Ser Ala Gln Val Asp
    450                 455                 460

Glu His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asp Met Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Glu Trp Glu Trp Ala Ser Thr Ala Lys Ser Asn Asp Glu Ala
625                 630                 635                 640

Gln Ile Val Leu Ala Ser Ala Gly Asp Val Pro Ala Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Thr Lys Glu Asn Asp Glu
        675                 680                 685

Ala Ile Ser Asp Ala Asp Phe Ala Asp Leu Phe Thr Glu Asp Lys Pro
    690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Thr Pro Tyr Asp Met Val Arg Val Asn Asn Ile
            740                 745                 750

Asp Arg Tyr Glu Leu Val Ala Glu Ala Leu Arg Met Ile Asp Ala Asp
        755                 760                 765

Lys Tyr Ala Asp Lys Ile Asp Glu Leu Glu Ala Phe Arg Lys Glu Ala
    770                 775                 780
```

Phe Gln Phe Ala Val Asp Asn Gly Tyr Asp His Pro Asp Tyr Thr Asp
785 790 795 800

Trp Val Tyr Ser Gly Val Asn Thr Asn Lys Gln Gly Ala Val Ser Ala
805 810 815

Thr Ala Ala Thr Ala Gly Asp Asn Glu
820 825

<210> SEQ ID NO 51
<211> LENGTH: 825
<212> TYPE: PRT
<213> ORGANISM: Bifidobacterium bifidum IPLA 20015

<400> SEQUENCE: 51

Met Thr Ser Pro Val Ile Gly Thr Pro Trp Lys Lys Leu Asn Ala Pro
1 5 10 15

Val Ser Glu Glu Ala Leu Glu Gly Val Asp Lys Tyr Trp Arg Val Ala
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Phe Ile Ala Asp His Gly Gln Asn Thr Val Phe Ile Met Gly Pro Gly
85 90 95

His Gly Gly Pro Ala Gly Thr Ser Gln Ser Tyr Leu Asp Gly Thr Tyr
100 105 110

Thr Glu Thr Tyr Pro Asn Ile Thr Lys Asp Glu Ala Gly Leu Gln Lys
115 120 125

Phe Phe Arg Gln Phe Ser Tyr Pro Gly Gly Ile Pro Ser His Phe Ala
130 135 140

Pro Glu Thr Pro Gly Ser Ile His Glu Gly Gly Glu Leu Gly Tyr Ala
145 150 155 160

Leu Ser His Ala Tyr Gly Ala Ile Met Asp Asn Pro Ser Leu Phe Val
165 170 175

Pro Cys Ile Val Gly Asp Gly Glu Ala Glu Thr Gly Pro Leu Ala Thr
180 185 190

Gly Trp Gln Ser Asn Lys Leu Val Asn Pro Arg Thr Asp Gly Ile Val
195 200 205

Leu Pro Ile Leu His Leu Asn Gly Tyr Lys Ile Ala Asn Pro Thr Ile
210 215 220

Leu Ser Arg Ile Ser Asp Glu Glu Leu His Glu Phe Phe His Gly Met
225 230 235 240

Gly Tyr Glu Pro Tyr Glu Phe Val Ala Gly Phe Asp Asp Glu Asp His
245 250 255

Met Ser Ile His Arg Arg Phe Ala Glu Leu Phe Glu Ser Val Trp Asp
260 265 270

Glu Ile Cys Asp Ile Lys Ala Ala Ala Asn Thr Asp Asn Met His Arg
275 280 285

Pro Phe Tyr Pro Met Ile Ile Phe Arg Thr Pro Lys Gly Trp Thr Cys
290 295 300

Pro Lys Tyr Ile Asp Gly Lys Lys Thr Glu Gly Ser Trp Arg Ala His
305 310 315 320

Gln Val Pro Leu Ala Ser Ala Arg Asp Thr Glu Ala His Phe Glu Val

```
                325                 330                 335

Leu Lys Asn Trp Leu Glu Ser Tyr Lys Pro Glu Glu Leu Phe Asp Ala
            340                 345                 350

Asn Gly Ala Val Lys Asp Asp Val Leu Ala Phe Met Pro Lys Gly Glu
        355                 360                 365

Leu Arg Ile Gly Ala Asn Pro Asn Ala Asn Gly Gly Val Ile Arg Lys
    370                 375                 380

Asp Leu Val Leu Pro Ala Leu Glu Asp Tyr Glu Val Lys Glu Val Lys
385                 390                 395                 400

Glu Phe Gly His Gly Trp Gly Gln Leu Glu Ala Thr Arg Arg Leu Gly
                405                 410                 415

Val Tyr Thr Arg Asp Ile Ile Lys Asn Asn Met His Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Ala Lys Gly
    610                 615                 620

Ala Ala Ala Trp Asp Trp Ala Ser Thr Ala Lys Thr Asn Asp Glu Ala
625                 630                 635                 640

Gln Val Val Leu Ala Ala Ala Gly Asp Val Pro Thr Gln Glu Ile Met
                645                 650                 655

Ala Ala Ser Asp Lys Leu Lys Ala Leu Gly Ile Lys Phe Lys Val Val
            660                 665                 670

Asn Val Ala Asp Leu Leu Ser Leu Gln Ser Ala Lys Glu Asn Asp Glu
        675                 680                 685

Ala Leu Thr Asp Glu Glu Phe Ala Asp Ile Phe Thr Ala Asp Lys Pro
    690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Glu Leu
            740                 745                 750
```

```
Asp Arg Tyr Glu Leu Thr Ala Glu Ala Leu Arg Met Ile Asp Ala Asp
        755                 760                 765

Lys Tyr Ala Asp Glu Ile Gln Lys Leu Glu Asp Phe Arg Gln Glu Ala
    770                 775                 780

Phe Gln Phe Ala Val Asp Lys Gly Tyr Asp His Pro Asp Tyr Thr Asp
785                 790                 795                 800

Trp Val Tyr Ser Gly Val Lys Thr Asp Lys Lys Gly Ala Val Thr Ala
                805                 810                 815

Thr Ala Ala Thr Ala Gly Asp Asn Glu
            820                 825


<210> SEQ ID NO 52
<211> LENGTH: 2469
<212> TYPE: DNA
<213> ORGANISM: Mycobacterium gilvum Spyr1

<400> SEQUENCE: 52

atgaccaccg ccaccaccgc agaacgtcgt ccgctgagcg atcaggatgt tgatcgtctg     60

gatcgttggt ggcgtgcagc aaattatctg agcgttggtc agatttatct gctggataat    120

ccgctgctgc gtacaccgct gacccgtgaa gatgttaaac cgcgtctgct gggtcattgg    180

ggcaccacac cgggtctgaa ttttctgtat gcacatctga atcgtgcaat tgcccagcgt    240

cagcagagca ccatttatgt taccggtccg ggtcatggtg gtcctggtct ggttgcaaat    300

gcatatctgg atggcaccta tagcgaaatt tacagcgata ttacccagga tgatgaaggt    360

ctgcgtcgtc tgtttcgtca gtttagcttt ccgggtggta ttccgagcca tgttgcaccg    420

gaaactccgg gtagcattca tgaaggtggt gaactgggtt atgcactgag ccatgcatat    480

ggtgcagcat ttgataaccc ggacctgctg gttgccgcag ttgttggtga tggtgaagca    540

gaaacaggtc cgctggcaac cagctggcat agcaacaaat ttgtgaatgc agccaaagat    600

ggtgccgttc tgccgattct gcatctgaac ggctataaaa tcgcaaatcc gaccctgctg    660

gcacgcattc cgaccgatga actgcgtgca ctgatggttg gttatggtca tcatccgtat    720

tttttcgaag ttccggatga cgaaggcggt ccaggtgtgg atcatgcaga tgcccatcgt    780

cgttttgcac gtctgttaga tgatgttctg gatgaaattg ccgatatcaa aacccgtgca    840

cgcgaaggtg atgaaagccg tccggcatgg ccgatgattg tttttcgtac cccgaaaggt    900

tggacgggtc cggattatat tgatggcaaa aaaaccaccg gtagctggcg tgcccatcag    960

gttccgctgt caaatgcacg tgataccaaa gaacatctgg cagttctgag tgattggctg   1020

agcagctatc gtcctgatga gctgtttgat gccgatggtc gcctgctgcc ggaaattgca   1080

gaactggcac cgagcggtca gctgcgtatg agcgataatg cacatgcaaa tggcggtctg   1140

ctgctgaaag atctgcgtct gccggatttt cgtgaatatg cagttgatgt tccggcaccg   1200

ggtgcaaccg ttgccgaagc aacccgtgtt ctgggtcagt ggctgaccga agttattcgt   1260

ctgaatccgg ataactttcg catttttggt ccagatgaaa ccgcaagcaa tcgtctgcag   1320

gcagtttatg atgcaaccga taaacagtgg aacgccgaat tttttggtgc ggaagttgat   1380

gaacacctgg cacgtgcagg tcgtgttgtt gaaatgctga gtgaacatca gtgtcagggt   1440

tggctggaag gttacctgct gaccggtcgt catggtctgt ttaattgtta tgaagccttt   1500

atccacatcg tggatagcat gctgaaccag cacgcaaaat ggctgaaagt taccaatcat   1560

attccgtggc gtcgtcctat tgcaagcctg aattatcttc tgagcagtca tgtttggcgt   1620

caggatcata atggttttag tcatcaggat ccgggtttta ttgatcacgt tgtgaataaa   1680
```

agcgccaaag ttgtgcgtgt gtatctgcct ccggatgcca atacactgct gagtacctat 1740
gatcattgtc tgcgtagccg tcagtatgtt aatgttgttg ttagcggtaa acagccgagc 1800
ccgaactttc tgaccatgga acaggccgtt gcacattgta cccgtggcct gggtatttgg 1860
gaatgggcag gtagcgaaga actgggcaca gatccggatg tggttctggc aagtgccggt 1920
gatattccta ccctggaagc actggcagca gcagatattc tgcgccagca tctgcctgat 1980
ctgaaagtgc gttttgttaa cgttgtggat ctgatgcgcc tgcaggatag caccgaacat 2040
ccgcatggcc tgccagatcg tgattttgat atgattttta ccaccgatcg tccgatcatc 2100
tttgcctatc atggttatcc gtggctgatt catcgtctga cctatcgtcg tgccggtcat 2160
gataatctgc atgttcgtgg ttataaagaa gaaggtacaa ccaccacccc gttcgatatg 2220
gttatgctga atgatttaga tcgctatcac ctggtcatgg atgtgattga tcgtgtgccg 2280
agcctgggtt caacctgtgc agccttacgc cagcagatgg cagataaacg tattgcagct 2340
cgcgaatata cccgtgcgca tggcgaagat attccggaag ttaaagattg ggtttggcct 2400
gcagcacgtg aaagcggttt tggtacagcc ggtgcggatg gtgcgagcag caccggtggt 2460
gataatgaa 2469

<210> SEQ ID NO 53
<211> LENGTH: 2364
<212> TYPE: DNA
<213> ORGANISM: Shewanella baltica OS185

<400> SEQUENCE: 53
atgacccaga tccatgaaat taatgccctg aaaaaatacg tgcgtgccac caattttctg 60
gcaaccagcc agatttatct gaaacagaat gttctgcaca aacgtccgct ggcacatacc 120
gatatcaaac cgcgtctgct gggtcattgg ggcacctgtc cgggtattaa ctttgtttat 180
gcaaacatta accgcctgat cgtgaaacat aatcgcagct ttatctatct ggttggtccg 240
ggtcatggtt ttccggcagt tcaggcaaac ctgtttatgg aaggtagcct gagccatttt 300
tatccggaaa ccattccgta taatgaaacc ggcattgaag atatttgcaa aaaattcagc 360
gcagcctatg gttatccgag ccatgcaaat ccggaagcac cgggtcagat tctggaaggt 420
ggtgaactgg gttatagcct gtcagttggt tggggtgcag ttctggataa tccggatctg 480
attgcaaccg ttctgattgg tgatggtgaa gcagaaaccg gtcctctggc agcaagctgg 540
tatgccaatc gtctggtttc accggcaacc tcaggtgccg ttctgccgat tgttcatatt 600
aatggctata aaatcagcgg tccgacccgt atgggtcgta tgagccatga agaactggat 660
ctggaatttc gtggtctggg ctattttccg attattgtgg ataatgaact ggaagaggat 720
atttacgtgc agatgaccaa tgcaatggat accgcatatg ccatgattaa cgatattcag 780
cgtcgtgcac gtagcggtga agatgttgtt aaaccgaaat ggcctgttat tctgatgcgt 840
accgcaaaag gttggaccgg tgttagcgaa tacaaaggca aaaaacttga aggcaattgc 900
gaaagccatc aggtgattgt gaataaatgt gcaaccgata aaggtcatct ggatgcactg 960
gataactggc tggcaagcta tcattttcaa gaactgtatc agatgaacga caaaggcgaa 1020
ctgatttttg atgccgatat ctgcagcctg attccgccta aacagctggc atgtggtcgt 1080
cagcatctga cctatggtgg cgaagttgtt cgtgcactga ccaatccgga cctggaaaaa 1140
ctgagctatg gtccggaagt tccgcgtggt catcgtggtt atagtatgct gaaaatgggt 1200
gaatggatgc gtgatgcctt taaactgaat cgtgatcagc gtaatctgcg catttttttct 1260

```
ccggatgaaa cctatagcaa tcagctgcag gcagtttttg aagaaaccga tcgtgcatgg   1320
cagtggccga ttgaaagctg ggatgaggat atgagtcgtg aaggtcgtgt tattgaactg   1380
ctgagcgaaa atctgctgtt tggtatgctg catggttata ccgttaccgg tcgtcatggt   1440
atgtttccga cctatgaaag ctttagccag gttattagca gcatggccga tcagtattgc   1500
aaatatgtgt atgcaagcca gggtgtgcat tttcgtaaac cgctgccgag ctgtaatgtt   1560
gttctgagca gcctgctgga acgtcaggat cataatggtt attcacatca gaatccgagc   1620
tttctgggtg ccatgttaga aaaacatccg aaaattatca gcgcatatct gcctgcagat   1680
gcaaatagca ccctggttta taccgaacgt gcctatgcag atcgtgataa gctgaatatt   1740
ctggttgccg gaaaaaaaga actgccgcag tggctgagcc tggaagaagc acgtaaacag   1800
gcaaaagatg gtgttatggt ttgggatttt gccagtgatg aaaacccgga tattgtgctg   1860
gcaggttgtg gtgattatgt tacccaagaa tgtatggcca gcctggtgct gattcgtgaa   1920
ctgttaccgc gtgttaaaat tcgttttgtt agcgttaccg aactgagcag tgatggcctg   1980
ggtagccgta aattcaaaga aaaaccgtgg ctgatggatg aaattttcac ccaggataaa   2040
ggcgtggtgt ttaactatca tggctatccg aataccatca aaaagctgat cttcgactat   2100
aaaggcagcc gtcgttttcg cattaaaggc tatgaagaag aaggtagtac caccaccccg   2160
tttgatatgg gtgttcgtaa tggcaccagc cgctatcatc tggtgatcga tatggcatat   2220
aaactgtttc agcagggcgt gattgatgaa acaatgcatg tgagcattac caccgacatg   2280
ctgcagcgtc tggtggatca tcgtaattac attaaagcca atggtgtgga tccgatcgaa   2340
atcgaaaatt ggatttggac ccgt                                          2364
```

<210> SEQ ID NO 54
<211> LENGTH: 2385
<212> TYPE: DNA
<213> ORGANISM: Lactobacillus rhamnosus LMS2-1

<400> SEQUENCE: 54

```
atgagcatgg acaccaaagt gaaaaccgtt gattatagca gcaaagaata ttttgacaaa     60
atgaccgcat attggcgtgc agcaaattat gttagcgttg gtcagctgta tctgaaagat    120
aatccgctgc tggaacgtcc gctgaaaagc gaagatgtta aaccgcatcc gattggtcat    180
tggggcacca ttgcaggtca gaattttatc tatacccatc tgaatcgcgt gatcaacaaa    240
tatgatctga atatgttcta catcgaaggt ccgggtcatg gtggtcaggt tatggttagc    300
aatagctatc tggatggtag ctatagcgaa atttatccgc gtgttagcca ggataaagaa    360
ggtatgaaaa acctgtttac ccagtttagc tggcctggtg gtgttgcaag ccatgcaagc    420
gcacagacac cgggtagcat tcatgaaggt ggtgaactgg gttatgcact gagccatgcc    480
accggtgcaa ttctggataa cccggatgtt attgcagcag ttgttaccgg tgatggtgaa    540
accgaaaccg gtccgctggc agcaagctgg tttagtaata cctttattaa cccgattagc    600
gacggtgcca tcctgccgat tgttcatatg aatggcttta aaatcagcaa cccgaccatt    660
ctgagccgta aaagtgatga agatctgacc aaatatttcg aaggcatggg ttggaaaccg    720
tattttgttg aaggtgatga tccgaccaaa ctgaatccgg aaatggcaaa agttatggat    780
gcagccattg aagaaattaa agccatccag aaacatgccc gtgaaacagg tgataccacc    840
atgccgcatt ggcctgttat tatctttcgt agcccgaaag gttggacagg tccgaaaagc    900
tggaatggcg aaccgattga aggtagcttt cgtgcacatc agattccgat tccggttgat    960
gccgaagata tggaacatgc agatagcctg gcaggttggc tgaaatcata tcatccggaa   1020
```

gaactgtttg atgagaacgg taaactgatc cctgaactgg cagccctgcc tccgaaaggc 1080
gataaacgta tggcagccaa tccgattacc aatggtggcc tggatccgaa acctctggtt 1140
ctgccggatt atcgtaaata tgccctggat aataaagaac acggcaagca gattaaacag 1200
gacatgattg tttggagcga ttatctgcgt gatctgatta aactgaaccc gcataacttt 1260
cgtattttcg gtccggatga aaccatgagc aatcgtctgt atagcctgtt tgaagttacc 1320
aatcgtcagt ggctggaacc gatcaaagaa cctgcagatc agtatctggc accggcaggt 1380
cgtattattg atagccagct gagcgaacat cagagcgaag gttttaatga aggttatacc 1440
ctgaccggtc gtcatggtct gtttacaagc tatgaagcat ttctgcgtgt tgttgatagc 1500
atgctgaccc agcactttaa atggattcgt aaagcacatg aagaaccgtg gcataaagca 1560
tatccgagcc tgaatgttgt tagcaccagc accagttttc agcaggatca taatggttat 1620
acacatcagg atccgggtat tctgacccat atggcagaaa aaaaagcgga atatattcgc 1680
gagtatctgc cagcagatgc caatagcctg ctggcaatta gtccgaaact gtttagcagc 1740
cagaataccg ttaatgttct gatcaccagc aaacagcctc gtccgcagtt ttatagtatt 1800
gatgaagcca ccgttctggc aaatgcaggt ctgaaacgta ttgattgggc aagcaatgat 1860
gatggtgttg aaccggatgt ggtgattgca gccgcaggca ccgaaccgaa tatggaaagt 1920
ctggctgcaa ttaatctgct gcatgatgca tttccggatc tgaaaattcg ctttatcaat 1980
gtgctggatc tgctgaaact gcgttcaccg gaaattgatc ctcgtggtct gagtgatgca 2040
gaatttaaca gctatttcac caccgataaa ccgatcctgt ttgcctatca tggttttgaa 2100
ggtctgattc gcgatatttt ctttacccgt cagaatcgta acgtgctgat tcatggttat 2160
cgtgaagagg gtgatattac caccccgttt gatatgcgtg ttctgaatga actggatcgt 2220
tttcatctgg ccaaagatgt gattcagcat gttccggcat atgcggaaaa agcagcagca 2280
tttgttcaga aaatggatga taccctgcag tatcaccatg attttattcg tgcaaatggt 2340
gaggatattc cggaagttca agaatggacc tggaaaagca ttaaa 2385

<210> SEQ ID NO 55
<211> LENGTH: 2397
<212> TYPE: DNA
<213> ORGANISM: Lactobacillus crispatus ST1

<400> SEQUENCE: 55
atggccgtgg attatgatag caaagactat ctgaaaagcg tggatgcata ttggcgtgca 60
gcaaattatc tgagcgttgg tcagctgttt ctgatgaaaa atccgctgct gaaaacaccg 120
ctggttgcag aagatgttaa accgaaaccg attggtcatt ggggcaccat tgcaccgcag 180
aattttatct atgcacatct gaatcgtgtt ctgaaaaagt acgatctgaa tatgttctat 240
atcgaaggta gcggtcatgg tggtcaggtt atggttagca atagttatct ggatggtagc 300
tataccgaac gctatccgga aattacccag gatgagaaag gtatggcaaa actgtttaaa 360
cgctttagct ttccgggtgg tgttgcaagc catgcagcac cggaaacacc gggtagcatt 420
catgaaggtg gtgaactggg ttatagcctg agccatggca ccggtgcagt tctggataat 480
ccggatgtta ttgcagcagt tgaaattggt gatggtgaag cagaaaccgg tccgctggca 540
gcaagctggt ttagcgataa attcattaac ccgattaaag atggtgccgt tctgccgatt 600
ctgcagatca atggctttaa aatcagcaat ccgaccattg ttagccgtat gagcgatcaa 660
gaactgaccg aatattttcg tggtatgggt tgggatccgc attttgttag cgtttttaaa 720

```
ggtggtcgtt tcgatggcga aaaagatccg atgcaggttc acgaagaaat ggccaaaacc    780
atggatgaag tgatcgaaga gattaaggcc attcagaaac atgcgcgtga aaataatgat    840
gcaaccctgc cgcattggcc gatgattatc tttcagtgtc cgaaaggttg gacaggtccg    900
aaaaaagatt tagatggtaa tccgatcgaa aacagctttc gtgcacatca gattccgatt    960
ccggttgcac agggtgatat ggaacatgca gatatgctga cagattggct ggaaagctat   1020
aaaccggaag aactgttcaa tgaagatggc agcccgaaag aaattgttac cgaaaatacc   1080
gcaaaaggtg atcatcgtat ggccatgaat ccgattacca atggtggtat tgatccgaaa   1140
cgtctgaatc tgccggatta tcgtaaattt gccctgaaat ttgataaacc tggtagcgtt   1200
gaagcacagg atatggttga atgggcaaaa tatctggacg aagttgccaa actgaacccg   1260
accacctttc gcggttttgg tccggatgaa agcaaaagca atcgtctgtt tcagctgctg   1320
gatgatcaga aacgccagtg ggaacctgaa gttcatgaac cgaacgatga aaatctggca   1380
ccgagcggtc gtgttattga tagccagctg agcgaacatc aggatgaagg ttttctggaa   1440
ggttatgttc tgaccggtcg tcatggtttt tttgcaacct atgaagcatt tggtcgtgtg   1500
gtggatagca tgctgaccca gcatatgaaa tggctgcgta aagccaaaga acagtactgg   1560
cgtcacgatt atccgagcct gaattttgtt gcgaccagca ccgtttttca gcaggatcat   1620
aatggttata cccaccagga tccgggtatt ctgacccacc tgtatgaaaa aaatcgtccg   1680
gatctggtgc atgaatatct gccgagcgat accaataccc tgctggcagt tggtgataaa   1740
gcactgcagg atcgtgaatg tattaatgtt ctggttacca gcaaacagcc tcgtccgcag   1800
tggtttagta ttgaagaagc aaaaaaactg gtcgataaag gcctgggcta tattgattgg   1860
gcaagcacag ataaaggtgc aaaaccggat gtggtttttg ccagtaccga aacagaaccg   1920
acaattgaaa ccctggcagc cattgatatt ctgcataaga aatttccgga cctgaagatc   1980
cgttatatca atgttgttga cgtgatgaaa ctgatggatc cgaaggataa caaaaatggt   2040
ctgagcacgg aagaatttga tcgcctgttt ccgaaagatg ttccggttat ttttgcctgg   2100
catggctata aaagcatgat ggaaagtatt tggtttgccc gtaaacgcta taacgtgcat   2160
attcactgct atgaagaaaa cggtgatatt accaccccgt ttgatatgcg tgtgctgaat   2220
catctggatc gttttgatct ggcaaaagat gccgttgaaa gcatcgataa actgaaaggc   2280
aaaaacgccg attttatcag ccatatggat gacctgctgg aaaaacatca tcagtatatt   2340
cgcgataacg gcaaagatat gccggaagtt acagaatggc aatggtcagg cctgaaa      2397
```

<210> SEQ ID NO 56
<211> LENGTH: 2451
<212> TYPE: DNA
<213> ORGANISM: Leuconostoc citreum KM20

<400> SEQUENCE: 56

```
atggccgatt tcgacagcaa agagtatctg gaactggttg ataaatggtg gcgtgcaacc     60
aattatctga gcgcaggtat gatttttctg aaaagcaatc cgctgtttag cgttaccaat    120
accccgattc aggcagaaga tgttaaagtt aaaccgattg gtcattgggg caccattagc    180
ggtcagacct ttctgtatgc acatgcaaat cgtctgatca acaaatacga tctgaatatg    240
ttctatattg gcggtccggg tcatggtggt caggttatgg tgaccaatgc atatctggat    300
ggtgaatata ccgaagatta tccggaaatt acccaggatc tggaaggtat gagccgtctg    360
tttaaacgtt ttagctttcc gggtggtatt ggtagccata tgaccgcaca gacaccgggt    420
agcctgcatg aaggtggtga actgggttat agcctgagcc atgcatttgg tgcagttctg    480
```

gataatccgg atcagattgc atttgcagtt gttggtgatg gcgaagcaga aaccggtccg 540
agcatgacca gctggcatag caccaaattt ctgaatgcaa aaaatgatgg tgccgtgctg 600
ccgattctgg atctgaacgg ctttaaaatc agtaacccga ccatttttag ccgtatgtcc 660
gatgaagaaa tcaccaagtt ttttgaaggt ctgggctata gtccgcgttt tattgaaaac 720
gatgatatcc atgattacgc agcctatcat gaactggcag caaaagtgct ggatcaggca 780
attgaagata ttcaggccat tcagaaagat gcccgtgaaa atggtaaata tgaagatggt 840
acaattccgg catggcctgt tattattgca cgtctgccga aggttgggg tggtccgacc 900 catgatgagg atggtaatcc gattgaaaat agctttcgtg cacatcaggt tccgctgccg 960
ctggcacaga ataaactgga aaccctgagt cagtttgaag attggatgaa tagctacaaa 1020
ccggaagaac tgtttaatgc agatggcagc ctgaaagatg aactgaaagc aattgcaccg 1080
aaaggcgata aacgtatgag cgcaaacccg attgcaaatg gcggtcgtcg tcgtggtgaa 1140
gaagcaaccg atctgaccct gccggattgg cgtcagttta ccaatgatat aaccaatgaa 1200
aaccgtggtc acgaactgcc taaagttacc cagaatatgg atatgaccac cctgagcaat 1260
tacctggaag aagttgcaaa actgaatccg accagttttc gtgtttttgg tccggatgaa 1320
accatgagca atcgcctgtg gtcactgttc aataccacca atcgtcagtg gatggaagag 1380
gtgaaagaac cgaatgatca gtatgtgggt ccggaaggtc gtattattga tagccagctg 1440
agcgaacatc aggcggaagg ttggctggaa ggctataccc tgaccggtcg tgttggtatt 1500
tttgcaagct atgaaagctt tctgcgtgtt gttgatacca tggtgacaca gcactttaaa 1560
tggctgcgtc atgcaagcga acaggcatgg cgtaatgatt atcctagcct gaatctgatt 1620
gcaaccagca ccgcatttca gcaggatcat aatggttata cccatcagga tccgggtatg 1680
ctgacccatc tggcagagaa aaaaagcaac tttatccgtg aatatctgcc tgccgatggc 1740
aatagcctgc tggcagttca ggatcgtgca tttagcgaac gtcataaagt gaacctgatt 1800
atcgcaagca aacagcctcg tcagcagtgg tttaccgcag atgaagcaga tgagctggca 1860
aatgaaggcc tgaaaattat cgattgggca agtaccgcac cgagcggtga tgttgatatt 1920
acctttgcca gcagcggcac cgaaccgaca attgaaacgc tggcagccct gtggctgatt 1980
aatcaagcat ttccggaagt gaaattccgc tatgttaatg ttgtggaact gctgcgcctg 2040
cagaaaaaat cagaaagtca tatgaatgat gagcgcgaac tgagtgatgc agagtttaac 2100
aaatttttcc aggccgataa accggtgatc tttggttttc atgcatatga ggatctgatc 2160
gagagctttt ttttcgagcg taaattcaaa ggtgatgtgt atgtgcatgg ttatcgcgaa 2220
gatggcgata ttacaaccac ctatgatatg cgtgtttaca gcaaactgga tcgttttcat 2280
caggccaaag aagcagcaga aattctgtca gcaaatagca caattgacca ggcagcagcc 2340
gataccttta tcgaaaaaat ggatgcaacc ctggccaaac attttgaagt gacccgtaat 2400
gaaggtcgcg atattgaaga atttacggat tggaattgga gcgcactgaa a 2451

<210> SEQ ID NO 57
<211> LENGTH: 2385
<212> TYPE: DNA
<213> ORGANISM: Bradyrhizobium sp. S23321

<400> SEQUENCE: 57
atgaacaatc agcagcagag cgcactgagc cgtagcgatc tggatctgct ggatcgttat 60
tggcgtgcag caaattatct gagcgttggt cagatttacc tgctggacaa tccgctgctg 120

-continued

```
cgtgaaccgc tgcgtccgga acacattaaa ccgcgtctgc tgggtcattg gggcaccaca    180
ccgggtctga attttatcta tgcacatctg aatcgtgtta tccgtgcact ggacctgagc    240
gtgctgtatg tttgtggtcc gggtaatggt ggtcctggca tggttgcaaa tacctatctg    300
gaaggtagct atagcgaaat ctatccgaat attgcacgtg ataccgatgg tctgcgtaaa    360
ctgtttcgtc agtttagctt tccgggtggt attccgagcc atgcagcacc ggaaactccg    420
ggtagcattc atgaaggtgg tgaactgggt tatgcactgg ttcatgcata tggtgcagca    480
tttgataatc cggatctgat tgttgcatgt gttgttggtg atggtgaagc agaaaccggt    540
ccgctggcag caagctggca tagcaacaaa tttctgaatc cggttcatga tggtgccgtt    600
ctgccgattc tgcatctgaa cggctataaa atcgcaaatc cgaccgttct gggtcgtatg    660
cgtgatgaag aaattcgtga tttatttcgc ggttttggtc atgaacctct gtttgttgaa    720
ggtgatgatc cgaccctgat gcaccaggca atggcagatg cctttgatgt tgcatttgca    780
cgtattcgta gcatccagca gcatgcccgt gatggtcgta aagaaattga acgtccgcgt    840
tggccgatga ttgttctgcg tagcccgaaa ggttggacag gtccgaaaga agttgacggt    900
ctgaaagtgg aaggtttctg gcgtgcccat caggttccgg ttgcaggttg tcgtgaaaat    960
cctgcccatc tgaaaattct ggaagattgg atgcgtagct atgaaccgga aaaactgttc   1020
gatgcaagcg gtgcactgat tccggaactg caggccctgg ctccggaagg taatcgtcgt   1080
atgggtgcca atccgcatgc aaatggcggt ctgctgaaaa aagaactgaa actgccggat   1140
tttcgtagct ttgccctgga agttccgcag cctggtggtg ttaccggtga agccacacgc   1200
gaactgggca aattcctgcg tgacgttatt cgtctgaatg cagcagaacg taattttcgc   1260
attatgggtc cggatgaaac cgcaagcaat cgtctggatg ccgtttttga agaaaccgaa   1320
cgtgtttgga tggaaccgat tgaaccgtat gatgttcatc tggcacagga tggtcgcgtt   1380
atggaagtgc tgagcgaaca tctgtgtcag ggttggctgg aaggctatct gctgaccggt   1440
cgtcatggtt tttttagctg ttatgaagcc tttatccaca tcgtggatag catgtttaat   1500
cagcacgcaa aatggctgaa agttacccgt catctgccgt ggcgtcgtcc gattgcaagc   1560
ctgaattatc ttctgaccag ccatgtttgg cgtcaggatc ataatggttt tagtcatcag   1620
gatcctggtt ttgttgatct ggttgccaac aaaaaagcgg atattgtgcg tatctatttt   1680
ccgcctgatg ccaataccct gctgtggatt gcagatcatt gcctgcgtac ctataatcgc   1740
attaatgtta ttgtggcagg taaacagcct gcaccgcagt ggctgagcat gcaggatgca   1800
gcaacccatt gtgatgcagg tattggtatt tggagctggg ctggtaatga agatgcaaca   1860
ggcgaaccgc atgttgttat ggcatgtgcc ggtgatgtgc cgacactgga aaccctggca   1920
gccgttgacc tgctgcgcaa agcactgcct gatctgaaga ttcgtgttgt taatgttgta   1980
gatctgatga cactgcagcc taaagaacag catcctcatg gtctgagcga tcgcgatttt   2040
gatagtctgt ttaccagcga taaaccggtg atttttgcct atcatggtta tccgcacctg   2100
attcatcgtc tgacatataa tcgtaccaat catgcaggtc tgcatgtgcg tggttttatt   2160
gaagaaggta caaccaccac cccgtttgat atggttgttc tgaatgaact ggatcgctat   2220
cacctggcaa ttgaagccat tgaacgcgtt ccaggtctgg cagcgcgtgc cgcagcggtt   2280
aaacagcagt ttcgtgatgc cctgattgaa catagccatt atattcgtga acacggtgaa   2340
gatatgccgg aaatccgcga ttgggtttgg cctggtaaaa ccggt                  2385
```

<210> SEQ ID NO 58
<211> LENGTH: 2367

<212> TYPE: DNA
<213> ORGANISM: Brucella microti CCM 4915

<400> SEQUENCE: 58

```
atgcctgcaa aaggtccgct gacaccgcag cagctgagcc tgattaatcg ttattggcgt      60
gcagcaaatt atctgagcgt tggtcagatt tacctgatga aaaatccgct gctgcgtgaa     120
ccgctgcagc cggaacacat taaaccgcgt ctgctgggtc attggggcac cacaccgggt     180
ctgaatttta tctatgcaca tctgaatcgc attatccagc agcgtaatgc caatgtgatt     240
tatatctgtg gtccgggtca tggtggccct ggtatggttg caaataccta tctggaaggc     300
acctatagcg aaatttatcc ggcaattagc gaagatgaag caggtatgga acgtctgttt     360
cgtcagttta gctttccggg tggtattccg agccatgcag caccggaaac tccgggtagc     420
attcatgaag gtggtgaact gggttatgca ctggttcatg catatggtgc agcatttgat     480
aatccggatc tggttgttgc atgtgttgtt ggtgatggtg aagcagaaac cggtgcactg     540
gcaaccagct ggcatagcaa caaatttctg aatccggcac gtgatggcgc agttctgccg     600
attctgcatc tgaacggcta taaaatcgca aatccgaccg ttctggcacg tctgagtgat     660
gatgatctgg ataacctgtt tcgcggttat ggttatgaac cgtttttgt tgaaggtagc      720
gaaccggcag atatgcatca gaaaatggca gcaaccctgg ataccatttt tcagcgtatt     780
caggacatca aaaaaaacgc cgatgttcat agtccggaac gtccgcgttg gccgatgatt     840
attctgcgta gcccgaaagg ttggaccggt ccgaaaaccg ttgatggtct ggtggttgaa     900
aattactggc gtgcccatca ggttccggtt gccaattgtc gtgaaaatga tgcccatcgt     960
aaaatcctgg aagattggat gaaaagctat gatccgagcg acctgtttga tgagaaaggt    1020
gccctgaaac cggaactgcg tgccctggca ccgaaaggcg aagcccgtat gggtgccaat    1080
ccgcatgcga atggtggtct gctgcgcaaa gaactgcaca tgccggattt tcgccagtat    1140
gcagttaatg ttaccgaacc gggtgcaatt gaagcacaga gcaccaaaat tctgggtgat    1200
ttcctgcgtg atgtgatgaa actgaatgaa accgaaaaaa acttccgcat tttggtccg     1260
gatgaaacag caagcaatcg tctgggtagc gttctggaag cgaccaatcg tgtttggatg    1320
gccgaaacac tggatatgga tgatcacctg gcagcagatg gtcgtgttat ggaagttctg    1380
agcgaacatc tgtgtcaggg ttggctggaa ggttatctgc tgagcggtcg tcatggtttt    1440
tttagctgtt atgaagcctt catccacatc atcgatagca tgtttaatca gcatgcaaaa    1500
tggctgcagg ttgcacgcga actggaatgg cgtaaaccga ttagcagcct gaattacctg    1560
ctgaccagcc atgtttggcg tcaggatcat aatggtttta gtcatcagga tcctggtttt    1620
gtagatctgg tggcaaataa aagcgcagat attgtgcgtg tttattttcc gcctgatgcc    1680
aataccctgc tgtgggtggg tgatcattgc ctgaaaacct ggaatcgtgt gaatgttatt    1740
gttgcaggta aacagccaga accgcagtgg ctgaccatgg cggaagccga aaaacattgt    1800
gaagccggtc tgggcatttg ggaatgggca ggtacagaag atggcctgga accggatatt    1860
gttatggcat gtgccggtga tgttccgacc atggaaacgc tggcagccgt ggatttactg    1920
cgtcagagcc tgccgcatct gcgtattcgt gttgttaatg tggttgatct gatggttctg    1980
cagagtccgc atcagcatcc tcatggtatt agtgatgaag aatttgatcg tatgttcacc    2040
acaaatcgtc cggtgatttt tgcctatcat ggttatccgt atctgattca ccgtctggtt    2100
tataaacgta ccaatcacag caattttcac gtgcgtggtt ttattgaaca gggtacaacc    2160
accaccccgt ttgatatgac cgtgctgaat gagctggatc gttttcatct ggcaatggaa    2220
```

gcagttgaac gcctgccact gggtgaaagc gttgcaaaac cgctgattga taactttaca 2280
gaaaaactgg cactgcacaa agattatatt cgtcagcatg gcgaagatat gccggaaatt 2340
cgtgattgga aatggacctg gcctcgt 2367

<210> SEQ ID NO 59
<211> LENGTH: 2358
<212> TYPE: DNA
<213> ORGANISM: Lactobacillus salivarius ATCC 11741

<400> SEQUENCE: 59
atgaccgatt atagcagcca agaatacctg gataaactgg atgcatattg gcgtgcagca 60
aattatgtta gcgttggtca gctgtatctg aaagataatc cgctgctgcg tcgtccgctg 120
aaagcagaag atgttaaagt taaaccgatt ggtcattggg gcaccattgc aggtcagaat 180
tttatctatg cacatctgaa tcgcgtgatc aacaaatatg atctgaacat gttctatgtg 240
gaaggtccgg gtcatggtgg tcaggttatg gttagcaata gctatctgga tggtagctat 300
agcgaaatct atccggaaat tagccaggat gaacagggta tgaaacgtct gtttaaacgt 360
tttagctttc cgggtggtgt tgcaagccat gcagcaccgg aaacaccggg tagcattcat 420
gaaggtggtg aactgggtta tagcattagc catagcgtgg gtgcagttct ggataacccg 480
gatctgattg ttgcagcagt tgttggtgat ggtgaagcag aaaccggtcc gctggcagca 540
agctggcaga gcaataaatt cattaatccg attcatgatg gcgcagtgct gccgattctg 600
gatctgaatg gctttaaaat cagcaatccg accattctga gccgtgaaag tgatgaaacc 660
ctgaccaaat atttcgaagg tatgggttgg catccgatct ttgttgaagg tgatgatccg 720
aaattaatgc atccggcaat ggcaaaagca atggatgaag caattgaaga gattaaagcg 780
attcagaaaa acgcacgcga aaataacgat ccgagcctgc ctgcatggcc tgttattatc 840
tttcgtgcac cgaaaggttg gacaggtccg aaagaatggg atggcgaacc gatcgaaaaa 900
agctttcgcg cacatcagat tccgattccg gttgatcaga atgatatgca gcatgcagat 960
gcactggttg attggctgga aagctataaa ccggaagaac tgtttgatga aaacggcaaa 1020
ctgaaagccg aaattgcaga aattaccccg aaaggcgata aacgtatggc agccaatccg 1080
cataccaatc cgggtaaact gattcgcgaa gttatcaaac cggattttcg tgattttgca 1140
gttgatacca gcgttcctgg taaagaagtt gcacaggata tgaccgttct gggtaaatat 1200
ctggaaaaag tgctgagcga taaccgccat aattatcgtg tttttggtcc ggatgaaacg 1260
atgagcaatc gtctggcacc gatttttgat gttaccaaac gtcagtggct ggccgaaatc 1320
aaagaaccga atgatcagta tttagcaccg agcggtcagg tgattgatag ccagctgagt 1380
gaacatcagg cagaaggttt tctggaaggt tatgttctga ccggtcgtca tggttttttt 1440
gcaagctatg aaagttttct gcgtgtggtt gatagcatgc tgacccagca ctttaaatgg 1500
ctgcgtaaag caaccgaaca gccgtggcgt accagcattc cgagtctgaa tgttattgca 1560
accagcaccg tttttcagca ggatcataat ggttataccc atcaggatcc tggtattctg 1620
ggtcatctgg cagataaaaa acctgaatat atccgcgaat atctgcctgc cgatgcaaat 1680
agcctgctgg cagtttttga taaaaccatt aatgaccgcg acaaaattaa cctgattgtg 1740
gcaagcaaac atccgcgtca gcagttttat agcgcagcag aagcaaaaga actggtagat 1800
aaaggcctga aaattatcga ttgggcgagc accgataaaa atgccgaacc ggatgtggtt 1860
attgccgcag caggcaccga accgaacctg gaagcactgg cagcgattag cattctgcat 1920
gaaaaactgc cggatcttaa aatccgcttt attaacgttg tggacattct gaaactgcgt 1980

-continued agcccgaaag ttgatccgcg tggtctgagt gatgatgaat ttgatgccta tttcaccaaa 2040
gacaaaccgg tgatttttgc ctttcatggt tatgaaggtc tgctgcgcga tattttctat 2100
tatcgccata accataacgt ggcctttcac ggctatcgtg aaaatggtga tattaccacc 2160
ccgtttgata tgcgtgttct gtcacagatg gatcgttttg atctggttaa aagcgttgca 2220
ctgagtctgc ctgatgccga taaatatggc cagctggttg ccgaaatgga tgcaaaagtt 2280
gcaaaacatc atcagtatat ccgtgatgaa ggtacagatc tgccggaagt tgaaaattgg 2340
gaatggaaac cgctggat 2358

<210> SEQ ID NO 60
<211> LENGTH: 2400
<212> TYPE: DNA
<213> ORGANISM: Rhodococcus imtechensis RKJ300

<400> SEQUENCE: 60
atgaccgatg gtcgtcaggt tggtagccag gatagtgatg gtcattatag cgatagcgat 60
ctggatctgg acctgcgttg gtgggcagca gcaaattatc tgaccgttgc acagatttat 120
ctgcaggata atgcactgct gcgtgctccg ctgcgtccgg aacacattaa accgcgtctg 180
ctgggtcatt ggggcaccag tccgggtctg agcatgattt atgccctgct gaatcgtctg 240
attcgtcgta ccgataccga ttgtctgtat gttaccggtc ctggtcatgg tggtccggca 300
ctggttgcag caacctatct ggaaggcacc tatagcgaag tttatccggg tgttagccgt 360
gatgcagcag gtattcatcg tctgtgtcgt cagtttagca caccgggtgg tattccgagc 420
catgttagcg ttcagactcc gggtagcatt catgaaggtg gtgaactggg ttatgcactg 480
gcacatgcag ccggtgcagc atttgatcat ccgaatctgc tggttgcctg tgttattggt 540
gatggtgaag cagaaaccgg tccgctgagc ggtagctgga aactgcctgc atttctgaat 600
ccggaacgtg atggcgcagt tctgccgatt ctgcatgtta atggtgcaaa aattgcaggt 660
ccgaccgttt atggtcgtag ctcagatgca gatgttgaag cctttctggg tggtcagggt 720
tgggcaccga ccgtggtgag cggtgatgat ccgcgtcatg tttttccagc actgcatcgt 780
gcactgacag atgcacatgc cgcaattagt gatctgcagc gtgaagcacg tgcaggtcgt 840
cgtagcgcag caaaatggcc tgcaattgtt ctgcgtaccc cgaaaggttg gacaggtccg 900
cgtaccgttg atggtgttct ggttgaaggt acacatcgtg cccatcaggt tccgctgtca 960
ggtgttcgca ccgatgaagc acatctgcgt cagctggaag aatggatgcg tagctatggt 1020
ccgggtgagc tgtttgatag cagcggtgcc ctggttcctg atctggaacg tctggcaccg 1080
cagggtgata aacgtatggg tagcagcccg tatgcaaatg gtggccgtct gcgtgcagat 1140
ctgccggttc cgcctctgga aaaatatgcg ctggcaattg aaaaaccggg tacaaccctg 1200
catgaaacca cccgtgtgct gggtgaatta ctgcgtgatc tgtatgcagc caccgcaaca 1260
ccggatggtg gtggttattt tcgtctgttt tgtccggatg aaaccgcaag caatcgcctg 1320
ggtgcagttt ttgaagttac cgatcgttgt tggcagctgc cggtgaccga ttatgatgat 1380
ggtctgagtg cacgtggtcg tgttatggaa gttctgagcg aacatctgtg tgaaggttgg 1440
ctggaaggtt atctgctgag tggtcgccat ggtctgtttg caagctatga agcatttgca 1500
atggttagcg tgagcatgct ggttcagcat accaaatggc tgcagcatgc agttgatctg 1560
ccttggcgtg caccggttgc aagcctgaat gtgctgctga ccagcacctg ttggcgtaat 1620
gatcataatg gttttagtca tcagggtccg ggaatgattg atgcagttat tccgctggct 1680
ccggatgttg ttcgtatttg gctgccaccg gatagcaata ccctgctgtc aattgcagat 1740
cattgcctgc gtagcaccga tcatgtgaat ctgattgttg ttgataaaca gccgcatctg 1800
cagtatctga cactggccga agcccatgca cattgtgcag cgggtgccag cgtgtgggaa 1860
tgggcaggca ccgaaggtgc ggttggtgcg gatcctgatg ttgtgctggc agcggctggt 1920
gatgttccga cccaagaaat cctggcagcc gcacagctgc tgcgcgaaca tactccggat 1980
ctggttaccc gtgttgttaa tgttgtggat ctgatgggtc tgctgacgcc gaccgaacat 2040
ccgcatggtt ttgatgcacg tatgtttctg gatttgttta ccgcagatac ggatgtggtt 2100
tttgcctttc atggttatag ccgtgccgtt catgaactga ttcatggtcg ccctgcaccg 2160
gatcgttttc atgttcgcgg ttttagcgaa cagggtacga ccaccacccc gtttgatatg 2220
gttgttctga accgtatgag ccgttatcat ctggtgctgg aagcactgcg tcgcacccgt 2280
cgtgaacctg cgggtgcagg cgaactggca gatttttgtc tgcgccagtt agaacgccat 2340
ggcgaatatg ttgttgcaca cctggaagat atgccggaag ttcgtgattg gacctggtca 2400

<210> SEQ ID NO 61
<211> LENGTH: 2391
<212> TYPE: DNA
<213> ORGANISM: Burkholderia xenovorans LB400

<400> SEQUENCE: 61
atggcagaag caagcagccg tccgacccct ccgcaggttc tggatgcaga taccctgcgt 60
aatatggatc gttattggcg tgcatgtaat tatctgagcg caggtatgat ttatctgcgt 120
gataatccgc tgctgcgtga accgctgaaa ccggaacaca ttaaaaaccg tctgctgggt 180
cattggggta gcgatccggg tcagagcttt ctgctggtgc atctgaatcg tctgattcgt 240
aaactggatc tgaacgtgat ttatgttgca ggtcctggtc atggtgcacc ggcaaccctg 300
gcacattgtt atctggaagg tcattatagc gaaatttatc cggatcgtag cgaagatgaa 360
gccggtatgc agcgtttttt tcgtcagttt agctttccgg gtggtattgg tagccattgt 420
acaccggaaa caccgggtag cattcatgaa ggtggtgaac tgggttatag cctgagccat 480
ggttatggtg ccgcatttga taacccggat ctgattgtta ccgtgatgat tggtgatggt 540
gaagcagaaa ccggtccgct ggcaaccagc tggcatagca acaaatttct gaatccggtt 600
cgtgatggcg cagttctgcc ggttctgcac ctgaatggct ataaaatcgc aaatccgacc 660
attctggcac gtattccgcg tgaagaactg gaagcactgc tgaccggcta tggtcataaa 720
ccgtatttcg ttgaaggtga tgatccggca gttatgcatc agcagatggc agccaccctg 780
gaacagtgta ttggtgaaat tcgtgcaatt cagcagcatg cacgtgcaaa taatgatgca 840
acccgtccgc gttggccgat gattgttctg cgtagcccga aaggttggac aggtccgaaa 900
gaagttgacg gccataaagt ggaaggtagc tggcgtgccc atcaggttcc ggtgctggat 960
ccggttacca atggtaaaag cctgaaactg gttgaaaatt ggatgcgtag ctatgaaccg 1020
gaaagcctgt ttgatgaagc aggtcgtctg gttgaggaac tgcgcgaact ggcaccgaaa 1080
ggcgcacgtc gtattagcgc caatccgcat gcaaatggtg gtctgctgtg taaaaccctg 1140
gatatgcctg catttggtga ttatgcagtt gcagttaaaa aaccgggtgg cacctatacc 1200
agcccgaccg aagttctggg taaattcctg tgtgatgtta tgcgtcgcaa tatgaccaat 1260
tttcgtgttt ttggtccgga tgaaaccgca agcaataaac tgaccgcaat ttatgaagcc 1320
agcgaaaaaa cctggctggc ccagaccgaa ccgagtgatg ccgatggtgg cgatctggca 1380
gttgatggtc gtgttatgga aatgctgagc gaacatacac tggaaggctg gtttgaaggt 1440

-continued tatgttctga ccggtcgtca tggtctgttt gcaacctatg aagcatttgt gcatgtgatc 1500
gatagcatgt ttaatcagca cgcaaaatgg ctggaaaaag caaaacgtga tctgggttgg 1560
cgtcagccgg ttccgagcat taatctgctg attaccagcc tggtgtggcg tcaagatcat 1620
aatggtttta cacatcagga tcctggtttt ctggacgttg tgaccaataa atcaccggat 1680
gttgtgcgta tctatctgcc tccggatgcc aattgtctgc tgagtgttgc agatcattgc 1740
ctgcgtagtc gcgattatgt taatgttatt gttgccgata aacagccgca tctgcagtat 1800
ctggacatgg atgccgcagt tattcattgt accaaaggta ttggcatctg ggattgggca 1860
agcaccgatc agggtgttga acctgatgtt gttattgcaa gtgccggtga tattgccacc 1920
atggaagccc tggcagcagt tcagattctg aaagaacgtt ttgccgatct gaaaatccgt 1980
tttgtgaatg ttgttgacct gtttcgcctg atgccggaac atgcacatcc gcacggtctg 2040
agcaatcgtg attttgatag tctgtttacc gcaaccaaac cggtgatctt taactttcat 2100
agctatgcaa gcctggttca caaactgaca tataatcgta ccaaccatga taacctgcat 2160
gtgcatggct atcatgaaaa aggcaatatt aacacaccgc tggaactggc cattattaac 2220
caggttgatc gttttagcct ggcgattgat gtgattgatc gtgttccgaa actgcgtggt 2280
gtgggtgatc atgcaaaaga atggctgcgt ggccaggtta ttgaacatct ggcatatgca 2340
catgccgaag gcattgatcg cgaagaaatt cgcaattgga cctggaaagg t 2391

<210> SEQ ID NO 62
<211> LENGTH: 2361
<212> TYPE: DNA
<213> ORGANISM: Mycobacterium intracellulare ATCC 13950

<400> SEQUENCE: 62
atgacccatg caaccgcact gagtgatgat gaactggcac tgattgataa atactggcgt 60
gcagcaaatt atctgagcgt tggtcagatt tatctgctgg ataatccgct gctgaccgaa 120
ccgctgacca ttgatcatgt taaaccgcgt ctgctgggtc attggggcac cacaccgggt 180
ctgaatctgg tttatgcaca tctgaatcgt gttattcgtc atcgtgatgc cgatgttatt 240
tatgttaccg gtccgggtca tggtggtcct ggtctggttg caaatgcata tctggaaggc 300
acctatagcg aagtttatac cggtattgaa gaagataccg aaggtctgcg taaactgttt 360
cgtcagttta gctttccggg tggtattccg agccatgttg cagcacagac tccgggtagc 420
attcatgaag gtggtgaact gggttatgcc ctggttcatg catatggtgc agcactggat 480
aacccgtatc tggttgttgc atgtgttgtt ggtgatggtg aagcagaaac aggtccgctg 540
gcagcaagct ggcatagcaa caaatttctg aatccggtga ccgatggtgc cgttctgccg 600
attctggccc tgaatggcta taaaatcgca aatccgaccg ttctggcacg tattccgcat 660
gcagaactgg aaagcctgct gcgtggttat ggttatcgtc cgattaccgt tgccggtgat 720
gatccggcag atgttcatcg tcaactggca gctgccctgg atgatgcctt tgatgatatt 780
gcagcaattc agagcgcagc acgtggtggt aatggtgttg aacgtccggt ttggccgatg 840
attgttctgc gtaccccgaa aggttggacg ggtccgaaaa tggttgatgg caaaaaagtt 900
gaaggtacat ggcgtagcca tcaggttccg ttagcagcaa cccgtgataa tcctgaacat 960
cgtgcacagc tggaagaatg gctgcgtagc tatggtccag gcgaactgtt tgatgaaaat 1020
ggccgtctgc gtccggaact gcgtgcactg gcaccgagcg gtgatcgtcg tatgagcgca 1080
aacccgcatg ccaatggtgg actgctgctg cacgatctgg atctgccgga ttttcgtgat 1140
tatgcagttg cagtggaacg tcctgcagca gttacccatg aagccacccg tgttctgggt 1200
ggttttctgc gtgatgtgat tgcacgtaat aaagatcgtt ttcgcctgat gggtccggat 1260
gaaaccgcaa gcaatcgtct ggatgcagtt tatggtagca ccgataaagt ttggctgagc 1320
gaaattgaac cggatgatga gcatctggct ccggatggtc gtgtgatgga agttctgagt 1380
gaacatctgt gtcagggttg gctggaaggt tatttactga ccggtcgtca tggtctgttt 1440
aattgttatg aagcctttgt gcacatcgtg gatagcatgc tgaaccagca tgcaaaatgg 1500
ctggcaacca gccgtgaact gccgtggcgt cgtcctattg caagcctgaa ttacctgctg 1560
agcagccatg tgtggcgtca ggatcataat ggtgcaagtc atcaggatcc gggttttatt 1620
gatctggtgg ccaataaacg tccagaactg acccgtgtgt atctgccacc ggatggcaat 1680
accctgctgt ctgttgcaga tcattgtctg cgttcacgcg attacattaa tgttattgtt 1740
gcaggtaaac agccagccct ggcctatctg gatatggatg aagccgttgc acattgtacc 1800
cgtggcctgg gtatttggga atgggcaagc accgcaaccg atgatcctga tgttgtgctg 1860
gcatgtgcag gcgatattcc gaccctggaa accctggcag ccgcagatat tctgcgcagc 1920
gaactgcccg aactggccgt tcgtgttgtt aatgttgttg atctgatgcg tctgcagccg 1980
gatacagaac atccgcatgg cctgcctgat cgtgaatttg atgcactgtt tacaccggat 2040
cgtccggtga tttttgcata tcatggctat ccgtggctga tccatcgtct gacctatagt 2100
cgtaccaatc atgcacatat gcatgtgcgt ggctttaaag aacgtggtac aaccaccacc 2160
ccgtttgata tggtaatgct gaatgatctg gaccgttttc acttagttat ggatgttatc 2220
gatcgtgttg atggtctggc aagccgtgcc gcaatgctgc gtcagcgcat ggtggatgca 2280
cgtctggcag cgcgtatgta tacccgtgaa catggcgaag atgatccaaa aattagcggt 2340
tggacctggg gtccgagcga t 2361

<210> SEQ ID NO 63
<211> LENGTH: 2367
<212> TYPE: DNA
<213> ORGANISM: Nitrosomonas sp. Is79A3

<400> SEQUENCE: 63
atgaaaaaga ataccaagct gctgagtccg gaactgctgc acaaaatgga tgcatattgg 60
cgtgcagcaa attatctgag cgttggtcag atttatctgt atgataatcc gctgctgaaa 120
cagccgctga aactggcaca tatcaaaccg cgtctgctgg gtcattgggg caccacaccg 180
ggtctgaatt ttatctatgt tcatctgaac cgcattatca aagagcacga tctgaacgtt 240
atctatatta ccggtccggg tcatggtggt cctggtctgg ttgcaaatac ctatctggaa 300
ggcacctata gcgaagtgta tccgaatatt agccaggatg aagatggtat gcagcgtctg 360
ttcaaacagt ttagctttcc gggtggtatt ccgagccatg ttgcaccgga aactccgggt 420
agcattcatg aaggtggtga actgggttat agcctgagcc atgcatttgg tgcagcattt 480
gataaccctg gcctgctggt tgcctgtgtt gttggtgatg gtgaagcaga aacaggtccg 540
ctggcaacca gctggcatag caacaaattt ctgaatccgg ttcatgatgg tgcagttctg 600
ccgattctgc atctgaatgg ctataaaatc gcaggtccga ccgttctggc acgtattccg 660
tgtgatgaac tggaagcact gtttcgtggt tatggttata ccccgtattt tatcgaaggt 720
gatgatcctc tggaaatgca tcagcgtatg gcagcaaccc tggatgcagt tattgccaat 780
attcagagca ttcagcgtga tgcacgtacc catggtttta ccaaacgtcc gcattggccg 840
atgattattc tgcgtagccc gaaaggttgg acgggtccga aagttgttga tggtaaaccg 900
accgaaggta catttcgtag ccatcaggtt ccgatgggtg atatgagcca gcctggtcat 960
gttaaaattc tggaaaaatg gctgaaaagc tatcgtccgc aagaactgtt tgatgaaacc 1020
ggtaaactgc tggcagaact ggccgagctg gcaccgcagg gtgcacgtcg tatgggtgca 1080
aatccgcatg caaatggtgg tatgctgctg cgtgatctgc gtctgccgga ttttcgcgat 1140
tatgccgtta aagttgccaa tccgggtaca gttagcgcag aagcaacccg tacccagggt 1200
gaatttattc gtgatgttgt taaactgaac gccaccaact ttcgtgtttt tagtccggat 1260
gaaacggcaa gcaatcgttg gggtgccgtt tttgaagtta ccaatcgctg tagtaccgca 1320
gaaattgttc ctggtgatga ccatgtggct ccggatggtc gtgttatgga aatgttaagc 1380
gaacatcagt gtgaaggttg gctggaaggt tatctgctga ccggtcgtca tggctttttt 1440
agctgttatg aagcctttat ccacattatt gatagcatgt ttaaccagca tgccaagtgg 1500
ttaaaagtgg caaatgaaat tccgtggcgt cgtccgattg caagcctgaa ttacctgctg 1560
agcagccatg tgtggcgtca ggatcataat ggtttttcac atcaggatcc gggttttatt 1620
gatcatgtga tcaacaaaaa agccgaaatt attcgcatct atctgccacc ggatgccaat 1680
accctgctgt cagttaccga tcattgtctg cgttcacgta attatgtgaa tgttattgtt 1740
gcgggtaaac agcctcagcc gcagtggctg gatatggatg ccgcaattaa acattgtaca 1800
gccggtattg gtatttggga atgggccagc aatgatcagg gcgaagaacc ggatgttgtg 1860
atggcatgtg ccggtgatgc tccgaccatt gaaacactgg cagcagttga gctgctgtgg 1920
aaacattttc ctgaactgaa aattcgcgtg attaatgtgg ttgatctgat gagcctgcag 1980
ccacagagtg aacatcctca tggtctgagc gataaagatt ttgatggtct gtttaccaag 2040
gacaagccga ttatctttgc ctatcatggt tatccgtggc tgattcatcg tctgacctat 2100
cgtcgtacca atcatgataa cctgcatgtt cgcggttata aagaagaagg tacgaccagc 2160
accccgtttg atatggttgt aatgaatgat ctggatcgct ttcatctggt ggcagatgtg 2220
attgatcgtg ttccgcagct gggtagccgt gcagcctatg ttaaacaggc aattcgcgat 2280
aaactgatcg aacacaaaca gtacattaac cagtatggcg aagatatgcc ggaaattcgt 2340
aattggaaat ggaaaggtag cagcgtg 2367

<210> SEQ ID NO 64
<211> LENGTH: 2475
<212> TYPE: DNA
<213> ORGANISM: Schizosaccharomyces pombe 972h-

<400> SEQUENCE: 64
atggccaccc agaatgatat tccgaatagc acaccggaag atctggcaaa acaggttgaa 60
attgcagaaa aacatccgga tccgcctgca atgccgagcc gtctgccgga tagcctgaaa 120
accctggaag caaaaattga taccagcaaa attaccgatg aagaggttgc aaatgtgcat 180
cgttttcagc gtgcatgtga ttatctggca gcaagcctga tttttctgag caatggtctg 240
tataccggtg gtgatctgga agagaaagat atcaaaaccc gtctgctggg tcattggggc 300
acctgtccgg gtctgagcat tgtttatagc cattgcaatc gcatcatcaa caaatacgat 360
ctgaacatgc tgtttgttgt tggtcctggt catggtgcac cggcaattct gagcgcactg 420
ttcctggaag atagtctggg tccgttttat ccgcgttatc agtttaccaa agaaggcctg 480
aataacctga ttaacacctt tagcctgcct ggtggttttc cgagccatgt taatgccgaa 540
gttccgggtg caattcatga aggtggcgaa ctgggttatg cactgagcgt tagctatggt 600

```
gcagttctgg atcgtccgga tctgattgtt acctgtgttg tgggtgatgg tgaagcagaa     660

accggtccga ccgcaaccag ctggcatgca cataaatttc ttgatccggc agaaagcggt     720

gccgttattc cggttctgga actgaatggt tacaaaatta gcgaacgcac catttatggt     780

tgcatggatg atagcgaact gctgagcctg tttagcggtt ttggttatga agttgccatt     840

gtgaatgata caccggatca gaatcgtgtt atggcagcca ccatggattg ggcagttgaa     900

cgtattcatg atatccagca tcgtgcacgt gttaatcgcg aagaaattaa accgcgttgg     960

ccgatgatta ttctgcgtac cccgaaaggt aaaggttgtc cgaaatatct gaatggcaaa    1020

tttctggaag gcacctttcg tgcacatcag gttccgctga aactggcacg taccgatacc    1080

aatcagcgta atctgctgaa agattggctg aatagctata actgtcagga ttttctggat    1140

gaacatggtc tgccgaccaa aggtattacc gaacatctgc ctccgcgtga aaaacgtatg    1200

ggtcagcgtc atgaaaccta taatagttat ctgccactga aagtgccgga ctggaagaaa    1260

tatggtgtta aaaaaggtga aaccaccagt gcgaccagcg tggttggcca gtatctggac    1320

gagctgctgg ttaccaatga tagcaccctg cgcattttta gtccggatga actggaaagc    1380

aataaactgg atggtgccct gaaacatagc tatcgtacca tgcagaccga tccggaactg    1440

atggccaaac gtggtcgtgt taccgaagtg ctgagtgaac acctgtgtca gggttttatg    1500

cagggttata ccctgaccgg tcgtaccgcc atttttccgt catatgaagc atttatgacc    1560

atcgttgtta gcatgctggt tcagtatagc aaattcctga aatgggtctg ggaaacgggt    1620

tggcatggta aatttggtag tctgaattat gttaccagca gcacctgggc acgtcaagaa    1680

cataatggtt ttagccatca gagtccgcgt tttattacca ccatgctgag tctgaaaccg    1740

ggtgttagcc gtgtttattt tccgcctgat gcaaattgtt ttctggcaac cgttgcacgt    1800

tgtatgaaaa gcgaaaacac cattaatctg atggtcagca gtaaaaatcc gcagcctgca    1860

tatctgagcg tggaagaagc ggaacatcat tgtaaagccg gtgcaagcgt ttggaaattt    1920

gcaagcaccg ataatggtga aaatccggat gttgttattg ccggtgttgg caatgaaatc    1980

atgtttgaag ttgttaaagc agccgaaatg ctgcagaacg atatccctga actgcgtgtt    2040

cgtgtgatta atgtgaccga cctgatggtg ctgagcagtc tgcatccgca tggtatgaat    2100

cctgcagaat ttgattcact gtttacgaaa gatcgccacg tgcactttaa ctatcatggt    2160

tatgttatgg atctgaaggc actgctgttc gatcgtattc agggcacccg tgtgaccatg    2220

gaaggttatc gtgaagaagg tacaaccacc accccgttta atatgatgat gtgtaataat    2280

accagccgct atcatgttgc ccgtatggca ctgcagcatg ccctgcataa tccgaccgtt    2340

gcggttaatt gtaatatgct gtgtgcaaaa tatgcctgga aacttgaaga gatcgagaac    2400

tacatcatgg aaaacaaaga tgatcctccg gaaatttatg ccgcaccggt gtttaaaaac    2460

aaaaccagta ccctg                                                     2475
```

<210> SEQ ID NO 65
<211> LENGTH: 2388
<212> TYPE: DNA
<213> ORGANISM: Lactobacillus buchneri ATCC 11577

<400> SEQUENCE: 65

```
atgaccgtgg attacgatag caaagagtat ctggatctgc tggataaata ctggcgtgca      60

gcaaattatc tgagcgttgg tcagctgtat ctgcgtgata atccgctgct gaaacgtccg     120

ctgaaaagtg atgatgttaa aatcaaaccg attggtcatt ggggcaccat tgttagccag     180

aattttatct atgcacagct gaatcgtgcc atcaacaaat atgatctgaa tatgttctat     240
```

```
attgaaggca gcggtcatgg tggtcaggtt atggttagca atagctatct ggacggtagc    300
tatagcgata tttatccgaa tattagccag gacgaaaaag gcatgcagaa actgttcaaa    360
cagtttagct ttccgggtgg tgttgcaagc catgcagcac cggaaacacc gggtagcatt    420
catgaaggtg gtgaactggg ttatagcctg agccatggca ccggtgcaat tctggataac    480
ccggatgtta ttgcagcagt tgaaattggt gatggtgaaa gcgaaaccgg tccgctggca    540
gcaagctggt ttagcgataa attcattaat ccgattaccg atggtgcagt tctgccgatt    600
attaacatga acggtttcaa aattagcaat ccgaccattc tgagccgtat gagtgatgca    660
gatctgacgg attatttcaa aggtatgggt tgggaagccc attttgttga agcaaccgca    720
gataccgatc atgcaaaagt tgaagccgaa tttgcaaaaa ccctggatac cgtgattgag    780
aaaattaaga gcatccagaa aaacgcacgc gaaaatgaaa ctccggataa tgttaaactg    840
ccggtttggc cgatgattat ctttcgtagc ccgaaaggtt ggacaggtcc gaaaaaagat    900
ctggatggta acccgattga aggtagcttt cgtgcacatc aggttccgat tccggttgat    960
gcaaatgata tggaacatgc agatgaactg gttgactggc tgaaatcata taaaccggaa   1020
gaactgtttg atgaaaacgg caccctgaaa cctgaactgc gtgcactggc accgaaaggc   1080
gaacagcgta tgagcgtgaa tccgatcaca aatggtggta ttaaaccaga acctctgaaa   1140
ctgcctaatg tgcgtgattt tgaagtgaaa tttgataaac gtgggaccga gcagaaacag   1200
gatatgattg agtggtcaaa atggctggat gcagttgcaa aactgaaccc gaccaccttt   1260
cgtggttttg gtccggatga aaccaaaagc aatcgtctgt attcactgct ggacgatggt   1320
aaacgtcagt ggatggaaga tatccatgaa ccgtatgatg aggatctggc aaatcatggt   1380
cgtgttattg atagccagct gagcgaacat caggcagaag gttggctgga aggttatgtt   1440
ctgaccggtc gtcatggttt ttttgcaacc tatgaaagct ttggtcgcgt tgtggatagc   1500
atgctgaccc agcattttaa gtggctgcgt aaagcaagcg aacagtattg gcgtaaacag   1560
tatccgagcc tgaactttgt tgataccagc accgtttttc agcaggatca taatggttat   1620
acccatcagg atccgggtct gctgacacat ctggcggaaa aaaagccgga atttattcgt   1680
gaatatctgc ctgcagatgc caatgaactg ctggcagttg gtgatagcgc atttcgtaca   1740
tatgaaaaga ttaacctgat cgtgaccagc aaacatccgc gtcgccagtg gtatagtatg   1800
gatgaagcac agaatctggt gaaaaatggt ctgggctata tcgattgggc aagcaccgat   1860
cagggtcaag aaccggatgt ggtttttgca gccgcaggta gcgaaccgaa tctggaagcc   1920
ctggcagcca ttagtattct gaataaagaa ttcccggaac tgaagatccg ctttattaac   1980
gtggttgata tcctgaagct gaacagccct aaaaaggatc cgcgtggtct gtcagatgaa   2040
gaattcgata acctgtttac caccgacaaa ccggtgattt ttgcatggca tggctttgag   2100
gacatgatca aagacatctt ttttgatcgc cataaccaca acctgtatgt gcatggttat   2160
cgtgaaaatg gcgatattac caccccgttt gatatgcgtg ttctgaacga actggatcgt   2220
tttcatctgg cagcggatgc cattcgtcat attccggcat atgcagttaa aggtggctat   2280
tttatccagc gcatgaacaa catcgtggat aaacataatc gctatattcg cgaagttggt   2340
acggatctgc cggaagttac cagctggaat tgggaaccgc tgaacaaa                2388
```

<210> SEQ ID NO 66
<211> LENGTH: 2376
<212> TYPE: DNA
<213> ORGANISM: Streptomyces ghanaensis ATCC 14672

<400> SEQUENCE: 66

```
atgccggaag caccggatac ccgtaccgtt ctgagtgatg aagaactgcg taccctggat     60
gcacattggc gtgcagcaaa ttatctggca gcaggtcaga tttatctgct ggcaaatccg    120
ctgctgaccg aaccgctgcg tccggaacac attaaaccgc gtctgctggg tcattggggc    180
accagtccgg gtctgaatct ggtttatacc catctgaatc gtgttattgc aggtcgtggt    240
ctggatgccc tgtgtatttg ggtcctggt catggtggtc cgagcgttct ggccaatagc     300
tggctggaag gtagctatgg tgaaacctat ccggatgttg gtcgtgatgc agccggtatg    360
gaacgtctgt ttcgtcagtt tagctttccg ggtggtgtgc cgagccatgt tgcaccggaa    420
gttccgggta gcgttcatga aggtggtgaa ctgggttata gcctggcaca tgcatatggt    480
gcagcactgg atcatccggg actgctggtt gcatgcgtta ttggtgatgg tgaagcagaa    540
accggtccgc tggcagccag ctggcatagc aacaaatttc tggatccggt tcatgatggc    600
gcagttctgc cgattctgca tctgaacggc tataaaatcg ccaatccgac cgtgctggca    660
cgtctgcctg aagatgaact ggatagcctg ctgcgtggtt atggtcatga accgattcat    720
gttagcggtg atgatccggc agcagttcat cgtgcaatgg cccatgcaat ggatactgcc    780
ctggatcgta ttgccgaagt tcagcgtgcc gcacgtgaag atggtgttac cgaacgtgca    840
cgtacaccgg ttattgttct gcgcaccccg aaaggttgga ccggtcctgc ggaagttgat    900
ggtaaaccgg ttgaaggcac ctggcgtgcc catcaggttc ctctggcagg cgttcgtgat    960
aacccggaac atctgcgtca gctggaagca tggctgcgta gctatcgtcc tgaggaactg   1020
tttgatgatg ccggtcgtcc ggttgcagat gttctggcgt gtctgccaga aggtgatcgt   1080
cgtctgggta gcaccccgta tgcaaatggt ggcctgctgg tgcgcgaact gccgatgcct   1140
gcgctggatg attttgcagt tccggttgat aaaccgggta caaccctgca tgaacctacc   1200
cgtattctgg gtggtctgtt agaacgtatt atgcgtgata ccgcagatcg tcgcgatttt   1260
cgtctggttg gtccggatga aaccgcaagc aatcgtctgg aagccgttta tgatgcaagc   1320
ggtaaagcgt ggcaggcagg tacactggat gttgatgagc atctggatcg ccatggtcgt   1380
gtgatggaag ttctgagcga acacctgtgt cagggttggt tagaaggtta tttactgaca   1440
ggtcgtcatg gcctgtttag ctgttatgaa gcatttgtgc atatcgtgga tagcatggtt   1500
aaccagcata tcaaatggct gaaaaccagc cgtgaactgc catggcgtgc tccgattgca   1560
agcctgaatt acctgctgac aagccatgtg tggcgtcagg atcataatgg ttttagccat   1620
caggatccgg gttttgttga tcatgttctg aataaaagtc cggaagtggt tcgtgtgtat   1680
ctgcctccgg atgcaaatac cctgctgtca gttgccgatc atgcactgcg tagtcgtgat   1740
tatgttaatg ttgttgttgc cggtaaacag ccgtgttttg attggctgag cattgatgaa   1800
gcacgtgttc attgtgcacg tggtgcaggc atttgggaat gggcaggcac cgaaaatggc   1860
ggtgcacctg atgtggttct ggcatgtgcg ggtgatgttc cgacccaaga agtactggca   1920
gcggcacagc tgttacgtcg tcatctgccg gaactggcag ttcgtgttgt gaatgttgtg   1980
gatattgccc gtctgatgcc tcgtgaagaa catccgcatg gtatgacaga ttttgaatat   2040
gatggactgt tcaccgcaga caaaccggtg atttttgcct atcatggtta tccgtggctg   2100
attcaccgtc tggcctatcg tcgtaatggt catccgaatc tgcatgttcg tggttacaaa   2160
gaaagcggta cgaccaccac cccgtttgat atggttgttc gtaatgatct ggaccgttat   2220
cgcctggtaa tggatgttat tgatcgtgtt cctggtctgg ccgttcgcgc agcagccgtt   2280
cgtcagcgta tggcagatgc ccgtacccgt catcatgcat ggattcgtga acatggcacc   2340
```

gatttacctg aagttgcaga atggtcttgg aatgca 2376

<210> SEQ ID NO 67
<211> LENGTH: 2406
<212> TYPE: DNA
<213> ORGANISM: Cyanothece sp. PCC 8802

<400> SEQUENCE: 67
atggttgcaa caccggaacg tccgaccctg gaacagacac cgctgagcgc agaagaactg 60
cgtcagattc aggcatattg gcgtgcatgt aattatctgg cagtgggtat gatttatctg 120
cgtgataatc cgctgctgaa agatccgctg accgaagatc atgttaaaaa tcgtctgctg 180
ggtcattggg gtagcagtcc gggtctgagc tttatctata ttcatctgaa tcgcctgatc 240
aaaaaatacg gcctggatgt gatttatatg gcaggtcctg gtcatggtgc accgggtatt 300
ctgggtccgg tttatctgga aggcacctat agcgaaacct atccggataa aagcgaagat 360
gaagagggca tgaaaaaatt cttcaaacag tttagctttc cgggtggtat tggtagccat 420
tgtactccgg aaacaccggg ttcaattcat gaaggtggtg aactgggtta tagcctgagc 480
catgcatatg gtgcagcact ggataacccg gatctgattg ttgcagcagt tgttggtgat 540
ggtgaagcag aaaccggtcc gctggcaacc gcatggcata gcaataaatt cattaatccg 600
attcgtgatg gcgcagttct gccgattctg catctgaacg gctataaaat cgcaaatccg 660
accattctgg cacgtattag ccatgaggaa ctggaatacc tgtttaaagg ttatggctac 720
aaaccgtatt ttgtcgaagg tagcgatccg gaagttatgc atcagaaaat ggcagcaaca 780
ctggaaaccg caattgccga aattaaacat attcagcaag aggcacgtac cagcggtgtt 840
gcaaaacgtc ctatttggcc gatgattgtt ctgcgtagcc cgaaaggttg gacaggtccg 900
gcaagcgttg atggcaaaaa aacggaagat ttttggcgta gccatcaggt tccgctgagt 960
ggtatgcatg gtaatccggc acatattaaa gttctggaag attggctgaa aagctatacc 1020
cctgaagaac tttttgatga aaacggcacc ctgattccgg aactgaaaga actggcaccg 1080
accggtcatc atcgtatgag cgccaatccg catgccaatg gtggtctgct gcgtaaagat 1140
ctgaaaatgc cggattttcg taattatggt gttgaagttg ccaaaccggg tacagttgaa 1200
gtgggtaata ccgcactgct gggcaatttt ctgcgggatg ttatggccaa taatatgacc 1260
aattttcgtg tgtttggtcc ggatgaaacc gccagcaacc gtctgaatgc aatttatgaa 1320
atcagcaaaa aagtgtggat gggcgaaatt ctgccggaag atgcagatgg tacagaaatc 1380
accaccgatg gtcgtgttat ggaaatgctg agcgaacata ccctgcaggg ctggctggaa 1440
ggttatctgc tgaccggtcg ccatggtttt tttcatacct atgaagcatt tgcccatgtg 1500
gtggatagca tgtttaatca gcatgcaaaa tggctggaca tctgcaaaaa tgaagttccg 1560
tggcgtgcca gcgttagcag cctgaatatt ctgctgagca gcaccgtttg gcgtcaggat 1620
cataatggtt ttagtcatca ggatcctggt tatgttgatc tggttaccaa taaatcagcg 1680
gatgttgtgc gtgtttattt tcctccggat gcgaattgtc tgctgtcagt tgcaaatcat 1740
tgtctgaaat caaccgatta cgtgaacgtt attgttagcg ataagcagat ccatctgcag 1800
tatctgaata tggatcaggc catcaaacat tgcaccaaag gtattggcat ttgggattgg 1860
gcaagcaatg atgattgcgg tacggaaccg gatcatcctg atgttattat ggcaagctgt 1920
ggtgatgttg caaccaaaga agcactggca gccaccgcca ttctgcgcga agaatttccg 1980
gatttaaaag tgcgttttat caacgtggtt gacctgttca aactgcagag tgaaattgaa 2040
catcctcatg gtctgagtga tcgcgatttt gataaccttt tcaccaaaga caaaccgatc 2100
atctttaact ttcatggtta tccgtggctg atccacaaac tgacctatcg tcgtaccaat 2160
catcacaatc tgcatgttcg tggttataaa gagaaaggca atattaacac tccgctggaa 2220
ctggccatta acaatcagat tgatcgtttt aacctggtga tcgatgttat caatcgtgtt 2280
ccgaaactgg gtagcgcagc agcatatgtt tatgaacgta tgaaaaacgc catcatcgaa 2340
catcgtgcat atgcctatga acatggtatt gataagcccg agattaacaa ctggaaatgg 2400
cctcat 2406

<210> SEQ ID NO 68
<211> LENGTH: 2436
<212> TYPE: DNA
<213> ORGANISM: Neosartorya fischeri NRRL 181

<400> SEQUENCE: 68
atgaccagca aaggcgaaat tgaaagcctg agcgcatatg gtgttgcacg tagcaccatt 60
cagggtacac cgctgagcca ggatgaactg cgtaaaatgg atgcatattt tcgtgcaagc 120
atgtatctgt gtctgggtat gctgtatctg cgtgataatc cgctgctgaa agaaccgctg 180
aaagttgaac atctgaaagc acgtctgctg ggtcattggg gtagtgatgc cggtcagagc 240
tttacctgga ttcatatgaa ccgtctgatc aaaaaatacg atctggatgt gctgtttatt 300
agcggtccgg gtcatggtgc accgggtatt ctgtcacaga gctatctgga aggtgtttat 360
accgaagttt atccggaaaa aacccaggac gaaaaaggtc tgcagcgttt tttcaaacag 420
tttagctttc cgggtggtat tggtagccat gcaacaccgg aaacaccggg ttcaattcat 480
gaaggtggtg aactgggtta tagcattagt catgcatttg gcaccgtttt tgatcatccg 540
aatctgatta ccctgaccat ggttggtgat ggtgaagcag aaaccggtcc gctggcaacc 600
agctggcata gcaacaaatt tctgaatccg attacagatg gtgcagttct gccggttctg 660
catctgaatg gctataaaat caataacccg accattctgg cacgcattag ccatgaagaa 720
ctggaaatgc tgttaaaagg ttatggttgg accccgtatt ttgttgaagg tagcgatcgt 780
gaaagtatgc atcaggcaat ggcagcaacc ctggaacatt gtgttctgga aattaagaag 840
atccagaaac aggcacgcga aagcaataaa gcatttcgtc cgctgtggcc gatgattgtt 900
ctgcgtagcc cgaaaggttg gagcgcaccg cgtgaaattg atggtaaata cctggaaggc 960
ttttggcgtg cacatcagat tccgatcacc gatgttcaga gcaaaccgga acacttaaaa 1020
gtgctggaaa attggatgaa agcgtataag ccggaagagg tgtttgataa aaatggcacc 1080
ctgattccgg aactgaaaga gctggcaccg accggcacca gccgtatgag cgcaaatccg 1140
gtgggtaatg gtggtctgct gcgtcgtccg atggatctgc cggattttcg cgattatgca 1200
ctgaccgata ttgaaccggg tgttaccatt cgtccgagca tgagcaatat gagcaaatat 1260
ctgcgggatg ttgttgcccg taatatgacc acctttcgtg tttttggtcc ggatgaaacc 1320
gaatcaaata aactggccga aatctacaaa gccggtaaaa aggtttggat ggccgaatat 1380
ttcaaagaag atgaggacgg aggtaatctg gatatgcagg gtcgtgtgat ggaaattctg 1440
agcgaacata catgtgaagg ttggctggaa ggatatattc tgagtggtcg tcatggcatg 1500
ctgaatagtt atgagccgtt tattcatgtg atcgacagca tggttaatca gcattgcaaa 1560
tggattgaaa aatgcctggc agttgaatgg cgtgccaaag ttagcagcct gaatattctg 1620
ctgaccgcaa ccgtttggcg tcaggatcat aatggtttta cccatcagga tccgggtttt 1680
ctggacgttg ttgcaaataa aagtccggaa gttgtgcgta tttatctgcc tccggatggc 1740
aataccctgc tgagcaccat gaatcattgt tttcgtagcg tgaattacgt gaatgtgatt 1800
gtggcagata aacaagaaca tgtgcagttt ctgaacatgg aagaagcaat tgaacattgc 1860
accaaaggtg ttggtatttg ggattgggca agcaatgatc agggttgcga accggatgtg 1920
gttatggcaa gctgtggtga tgttgcaacc catgaagccc tggcagccac cgcactgctg 1980
cgcgaacatt taccgcagtt aaaagttcgt tttgttaatg tggttgacct gtttcgtctg 2040
attagcgata ttaatcatcc gcatggtatg ccggatcgtc agtggggtgc aatttttacc 2100
accgataaac cgatcatctt taactttcat agctatccgt ggctgattca tcgtctgacc 2160
tataaacgtc ctggtcagca taatctgcat gtgcgtggtt ataaagaaaa aggcaatatc 2220
gataccccgt ttgaactggc ggttcgtaat cagaccgatc gttatagcct ggccattgat 2280
gcaattgatc gtattccgag cctgggtaat accgcaagcg gtgttcgtga acgcctgatt 2340
aacctgcaac tggcagcgaa aaacaaagcc tttgatgatg gtattgatcc ggattatatt 2400
cgcaattgga cctgggatta tccgcgtaaa aaatgc 2436

<210> SEQ ID NO 69
<211> LENGTH: 2361
<212> TYPE: DNA
<213> ORGANISM: Enterococcus faecium TX1330

<400> SEQUENCE: 69
atggattata gcagcaaaga atattttgat aaaatgaccg catggtggcg tgcagcaaat 60
tatctgagcg ttggtcagat ttatctgaaa gataatccgc tgctgcgtcg taccctgaaa 120
ccggaagatg ttaaaaaaca cccgattggt cattggggca ccattccggg tcagaatttt 180
atctatgttc atctgaatcg cgtgatcaac aaatacgatc tgaacatgtt ttatatcgaa 240
ggtcctggtc atggtggtca ggttatggtt agcaatgcat atctggatgg tagctatacc 300
gaaatttatc cggaagttac cgaagatgaa acgggtatgc agaaactgtt taaacgtttt 360
agctttccgg gtggtattgc aagccatgca gcaccggaaa caccgggtag cattcatgaa 420
ggtggtgaac tgggttatag cctgagccat ggtgttggtg cagttctgga taatcctgaa 480
gttattagcg cagttgttat tggtgatggt gaagcagaaa ccggtccgct ggcaggtagc 540
tggtttagta atgtttttat caatccggtt accgatggtg cggtgctgcc gattctgcat 600
ctgaacggtg caaaaaattgc aaatccgacc attctggcac gtaaaagtga tggcgaactg 660
gccaattatt tcaatggtct gggttgggaa ccgtttttca ttgaaggtaa tgatccggaa 720
aaactgaatc cggtgatggc agaaaaaatg gatcaggcca ttgagaaaat caaaagcatt 780
cagaaagaag cccgtctgaa aaccgcagca gatgcaatga tgccgaaatg gcctgttctg 840
attgtgcgta ccccgaaagg ttggacaggt ccggaagaat gggatggtga gccgattgaa 900
ggcacctttc gtgcacatca ggttccgatt ccggttgatc aagaacatat ggatcatgca 960
gatgccctgc tgcgctggct gaaaagctat gaaccagaaa agctgtttga tgcacagggt 1020
cgtattctgg aagaaattcg tgaaattgca ccgaccggtg atcatcgtat ggcaaaaaat 1080
ccgattacaa atggtggtat ggatccgaaa ccgctgatta tgccggattg gaaacgttat 1140
accctgcagt ttgaaaaacc gggttcagtt accgcagaag atatgaccga actgggcaaa 1200
tttgttcgcg aaatcattga aaaaaacccg gaaaactttc gcatctttgg tccggatgaa 1260
accaaaagca atcgtctgaa tcaggtgttt aaaaccacca atcgtcagtg gatggaaaaa 1320
attgaaccgg aaaatgatga atggctgagc ccgagcggtc gtgttattga tagccagctg 1380
agcgaacatc aggatgaagg ttttttagaa ggttatgttc tgaccggtcg ccatggtttt 1440
tttgcaagtt atgaaagctt tctgcgtgtg gttgatagca tgctgaccca gcactttaaa 1500
tggatgcgta aaagccgtga tctgagctgg cgtaataact atccgagcct gaatctgatt 1560
gcaagtagca ccgtgtttca gcaggatcat aatggttata gtcaccagga tccgggtatt 1620
ctgacccatc tggccgaaaa aaaagcagaa tttattcgtg agtatctgcc tgccgatgca 1680
aatacactgc tggccgttat ggataaagca tttcgtagca gcgaaaagat caacctgatt 1740
atcagcagta aacatccgcg tgcacagttt tatagtgcag aagaagcagc cgttctggtt 1800
aatgaaggcc tgaaaattat cgattgggca agcaccgcaa aagaagaaga acctgaactg 1860
gtaattgcag cagcaggcac cgaaagtaat ctggaagcac tggcagcagt tactctgctg 1920
ctggaagagt ttccgaaact gaaaatccgc tttattaacg ttgtggacct gctgaaactg 1980
cgtcatccga gtcaggatcc tcgtggtctg agtgatgaag aatttgacaa atactttacc 2040
aaagataaac cgatcctgtt tgcctttcat ggctatgaaa cactgattcg caccatcttt 2100
tttgatcgcc ataatcatca tctgatgatt cacggctata aagagaatgg cgatattacc 2160
accccgtttg atatgcgtgt tgtgaatgaa ctggatcgtt atcatctggc aaaagatgca 2220
gccctgaaga ttaaaggtag ccaggccgaa gattttgcca aaaagatgga ccaaaaactg 2280
caagaacacc agaactatat ccgcgaaaat ggtattgatc tgccggaagt gctggactgg 2340
aaatggaaga atctggatca g 2361

<210> SEQ ID NO 70
<211> LENGTH: 2373
<212> TYPE: DNA
<213> ORGANISM: Listeria grayi DSM 20601

<400> SEQUENCE: 70
atgaccgatt atagcagccc gaactatctg gcaaaagttg atgcatggtg gcgtgcagca 60
gattttatca gcgttggtca gctgtatctg aaaggtaatc cgctgctgcg tcgtccgctg 120
gaaaaagaag atttaaaagt tcatccgatt ggtcattggg gcaccattag cggtcagaat 180
tttatctatg cacatctgaa tcgcgtgatc aacaaatatg atctgaatat gttctacatc 240
gaaggtccgg gtcatggtgg tcaggttatg gttagcaata gctatctgga tggtagctat 300
accgatacct atccgaccat tacccaggat gaagttggtc tgaccaaact gtataaacag 360
tttagctttc cgggtggtat tgcaagccat gcagcaccgg aaacaccggg tagcctgcat 420
gaaggtggtg aactgggtta tgcactgagc catgccaccg gtagcattct ggataatccg 480
gatgttattg cagcaaccgt tattggtgat ggtgaagcag aaaccggtcc gctgagcgca 540
ggttggttta gtaatacctt tattaacccg gttaatgatg gtgcagttct gccgattctg 600
tacctgaatg gtgcaaaaat tagcaatccg acaattctga gccgcaaaac cgataaagaa 660
ctgaccagct tttttcaggg tctgggttgg gatccgattt ttgttgaagg tgaagatcct 720
gccaaagtgc atccgctgat ggcagaaaaa ctggatcagg caattgaaaa aatcaaagcc 780
attcagaccg aagcacgtaa agaagccgca gataaagcaa ccatgccgac ctggcctgtt 840
attctgtttc gtaccccgaa aggttggaca ggtccgaaag aatggaataa tgaaccgatt 900
gaaggtagct ttcgtgcaca tcaggttccg attccggttg atcagcatca ttttgatcat 960
gttgatgccc tggaaaattg gctgcagagc tatcgtccgg aagaactgtt taccgaagaa 1020
ggtagtctga aagaagaaat caaaagcctg gcaccgaaaa atcgtatggc aaccaatccg 1080
attaccaatg gtggcattga tccgcagccg ctgcgtctgc cgagctggaa agattatgca 1140
gttgaaaccg caaacaaaga tgtgattacg caggatatga ttgagctggg tggttttgtt 1200
cgtgatatcg ttaaagaaaa cccggataac tttcgcattt ttggtccgga tgaaaccaaa 1260
agcaatcgcc tgaataaagt gtttgaagtg accaatcgtc agtggatgag caaagcagaa 1320
tttccgcgtg atgaatggct ggctccggca ggtcgtatta ttgatggcca gctgagcgaa 1380
catcaggcag aaggttttct ggaaggttat gttctgaccg gtcgtcatgg tttttttgca 1440
agctatgaaa gctttctgcg tgttgttgat agcatgctga cccagcactt taaatggctg 1500
cgtaaagcaa aagaacagac ctggcgtaat agttatccga gcctgaatgt gattgcaacc 1560
agcaccgttt ttcagcagga tcataatggt tatacccatc aggatccggg tgtgctgaca 1620
catctggccg aaaaaaaacc ggaatttatc cgtgaatatc tgcctgcaga taccaatagc 1680
ctgctggcag ttatgaatga agcatttcgt agcgaggaac tgattaatct gattgtgagc 1740
agcaaacatc cgcgtccgca gttttatagc gcagaagaag ctgaaattct ggttaaagat 1800
ggcctgaaaa tcattgattg ggcaagcacc gtgagcgaag ccgaagaacc ggatgtggtt 1860
attgccagtg caggtacaga accgaatctg gaagcactgg cagcagttac cctgctgaac 1920
gaagcctttc cgtcgctgaa aattcgcttt atcaacattg tggacattct gaaactgcgc 1980
catccggata tcgatccgcg tggcctgacc gatgaagaat ttgatcgtta tttcaccacg 2040
gacaaaccga tcatttttgc ctttcattca tatgaaggta tggtgcgcga tatctttttt 2100
aaccgccata atcacaacct gttcatccat ggttatcgcg aaaatggtga tattaccacc 2160
ccgtttgata tgcgtgttct gagtgaaatg gatcgttttc acctggccaa agatgcagcc 2220
gaagcagttt atggtgaaat tgcgaccagt tttgccgcag aaatggacgc cgttctgtca 2280
aaacatcatc actttattcg tgaaaacggc gaagatctgc cggaagttga gaattggaaa 2340
tggcaggcac tgaaaactga cctgctggaa gtg 2373

<210> SEQ ID NO 71
<211> LENGTH: 2364
<212> TYPE: DNA
<213> ORGANISM: Enterococcus casseliflavus EC30

<400> SEQUENCE: 71
atgaaaacca cctacgatac ccctgagtat taccagaaaa tgaatgcatg gtggcgtgca 60
gcaaattatc tgagcgttgg tcagatttat ctgaaagata atccgctgct gcgtcgtccg 120
attgaagaaa aagacctgaa agtgaatccg attggtcatt ggggcaccat tgcaggtcag 180
aattttatct atacccatct gaatcgcgtg atcaacaaat atgatctgaa tatgttctac 240
atcgaaggtc cgggtcatgg tggtcaggtt atggttgcaa atgcatatct ggatggtagc 300
tatagcgaaa tctatccgaa agcaacccag gatgaagcag gtatgaaaca cctgtttaaa 360
acctttagct ttccgggtgg tattgcaagc catgcagcac cggaaacacc gggtagcatt 420
catgaaggtg gtgaactggg ttatagcatt gcacatgcaa ccggtgcaat tctggataac 480
ccggatgtta ttgcagcagt tgttgttggt gatggtgaag cagaaaccgg tccgctggca 540
ggtagctggt ttagcaatac ctttattaac ccggttaacg atggtgccat tctgccgatt 600
ctgcatctga acggtgcaaa aattgcaaat ccgaccattc tggcacgtaa aagcgatcag 660
gatctgacca aatatttcga aggtatgggt tggaccccgt attttgttga aggtgatgat 720
ccggaagcag ttcatccgca gctggcacaa aaaatggatc aggcaattga gcagattcat 780
gcaattcagg cagaagcccg taaaggttca gccgaagagg cagcaatgcc gcattggcct 840
gttctgattg ttcgtacccc gaaaggttgg acaggtccga aagtttggga tggcgaaccg 900
atcgaaggcg gttttcgtgc acatcaggtt ccgattccgg ttaatgcaaa acatatggaa 960
catgttgatg cactgaccga ttggctgcag agctatcgtc cggaagaact gtttgatgaa 1020
aatggtcgta ttaaggccga aatccaagaa ctggcaccga aaggcgaaca gcgtatggca 1080
gttaacccga ttaccaatgg cggtattgat cctcagccgc tgcgtctgcc ggattggcag 1140
gcacatgcca ttgcaattga aactccgggt gaaaccaccg cacaggatat gatggttttt 1200
ggtaaatttg cccgtgatat tatcaaagag aacccggaca attttcgcat tttggtcct 1260 gatgaagcca aaagcaatcg tctgaatcat gtgtttgaag ttaccgatcg tcagtggctg 1320
gaaccgaaac atccggatta tgatgaatgg ctgagcagcg tgggtcgtgt tattgatagc 1380
cagctgagcg aacatcaggc cgaaggtttt ctggaaggtt atgttctgac cggtcgccat 1440 ggctttttg caagctatga aagctttctg cgtgttgtgg atagcatgat tacccagcac 1500
tttaaatggc tgcgtaaagc acatgatctg gattggcgta atccgtatcc gagcctgaat 1560
ctgattgcaa gtagcaccgt tttcagcag gatcataatg gttataccca ccaggatccg 1620
ggtattatga cccatattgc agaaaaaaaa gccgattttg tgcgtgttta tctgcctgca 1680
gatgcaaata gcctgatggc cgttatggcc gaaaccctgg caagcgaaga aaagattaat 1740
ctggttgtta gcagcaaaca tcctcgtccg cagttttata gcgcagatga agcgaaagtt 1800
ctggtgaaag atggtctgaa agttatcgat tgggcaagca ccgatgaagg tcaagaaccg 1860
gatattgtga ttgcagccgc aggtacagaa ccgaatctgg aagcactggc agccgttagc 1920
ctgctgattg aagcatttcc ggaactgaaa gtccgtttta tcaatgttgt tgacctgctg 1980
aaactgcgtc gccctgaagt tgatccgcgt ggtctgagcg acgaagcctt tgaagcctat 2040
tttaccaaag ataagccgat cgtgtttgcc tttcatggtt atgaaggcct gattcgcgat 2100
atcttttttg gccgtcgtaa tcagcagctg catattcatg gctatcgcga aaacggcgat 2160
attaccaccc cgtttgatat gcgtattctg tcagaactgg atcgttttca tctggcaaaa 2220
gatgcagcag aatgggttta tggtgaaaaa gccacagatt ttgcacagaa gatggcagat 2280
accgttgcat atcatcatga ttttatccgc gagaacggtt atgatattgc cgaagttgaa 2340
gaatgggaat ggaaaccgct gcgc 2364

<210> SEQ ID NO 72
<211> LENGTH: 2376
<212> TYPE: DNA
<213> ORGANISM: Mycoplasma alligatoris A21JP2

<400> SEQUENCE: 72
atgaaaaaga ataccttcga tacccaggac tatctggata aagttgatgc atggtttcgt 60
gcagcaaatt atctgagcgt tggtcagatg tatctgcgta ataatccgct gctgcgtagc 120
aaaattacca gtgatgatgt taaagtgtat ccgattggtc attggggcac cattccgggt 180
cagaattttg catatgcaca tctgaatcgc gtgatcaaca aatacaatct gaatatgttc 240
tacatcgaag gtcctggtca tggtggtcag gttatgacca gcaatagcta cctggatggt 300
agctataccg aactgtttcc gcatgtgacc caggatgttg caggtatgaa acacctgttt 360
aagtatttta gctttccggg tggcaccgca agccatgcag caccggaaac accgggtagc 420
attcatgaag gtggtgaact gggttatagc ctgagccatg ccaccggtgc aatcctggat 480
aatccgaatg ttattgcagc aaccattgtt ggtgatggtg aagcagaaac cggtccgctg 540
gcagcaagct ggtttagcaa tagttttatc aatccggtta atgatggtgc cgttctgccg 600
attctgcatc tgaacggtgg taaaattagc aatccgacca ttctgtgtcg caaaagcaat 660
aaagaactga ccgattattt tgccggtatg ggttgggaag cagtttttgt tgaaggtagt 720
gatgagaaag aaatgcacaa agttatggcc cagaaactgg attatgtgat cgaaaaaatt 780
cagagcattc agaacgaggc acgtaaaaaa ccggcaaatc aggcaacccg tccgatttgg 840
ccgatgatgg ttctgcgtac cccgaaaggt tggacaggtc cggatagctg gaataaagat 900
aaaattgtgg gtagctttcg tgcccatcag gttccgattc cggtgaatag cgcaaatatg 960
gaacatattg atgcactgct ggattggctg aaatcctata aagtggataa cctgttcgac 1020
aaaaatggca aactggttga tgaaattgca cagattgcac cgaaaggcga tcagcgtatg 1080
ggtatgaatc cgattaccaa tggtggcctg aacccgaaaa aactggtaat gcctcgttgg 1140
caggattttg cactgaaatt ttcaaaaccg ggtgagctgg ttaatcagga tatggttgag 1200
ctgggcacct attttgcaaa aatgatggaa ctgaacaagg acaactttcg tctgtttggt 1260
cctgatgaaa ccaaaagtaa tcgcctgtat aacgtgttca aagtgaccaa acgtcagtgg 1320
ctggaaccga ttagccctat tctggatgaa gcactgagtc cggaaggtcg tgttattgat 1380
agccagctga gcgaacatca ggcagaaggt tttctggaag gttatgttct gaccggtcgc 1440
catggtgttt ttgcaagcta tgaaagcttt ctgcgtgttg tggatagtat gctgacccag 1500
cacctgaaat ggctgaagaa agcaaaagat gttcattggc gtaatgatta tccgagcctg 1560
aatgtgattg cgaccagcac cgcatttcag caggatcata atggttatac acatcaggat 1620
ccgggtctga ttggccatct ggcagataaa actccggaaa ttattcgtca gtatctgcct 1680
gcagatacca ataccctgct ggcagttatg gataaaagcc tgaaagaacg caacgtgatt 1740
aaccatatca ttgcaagcaa acagcctcgc gaacagtttt atagcgaaca agaagcagca 1800
gaactggtag aaaaaggtct gaaagtaatt gattgggcaa gcaccaccaa aggtaatgaa 1860
gaaccggaac tggtggttgt tgcagcaggc accgaaccga atctggaagc cctggcagcc 1920
gtgacgattc tgaacaaaga gtatccgtca ctgaaaatcc gttttgtgaa tgtggttgat 1980
ctgatgaagc tgcgtcatcc gagtctggat ccgcgtggtc tgagcgataa agaatttgat 2040
gcaattttca ccagcaacaa gccgattgtg tttgcctttc atggttatga aggtattctg 2100
cgcgacatgt tttcaaacgc caataaccat aatctgatca cccatggcta tcgcgaaaat 2160
ggtgatatca caaccagctt tgatattcgc cagctgtcac atatggatcg ctttcatatt 2220
agcgcaagcg cagcaaaagc ggtgtatggt aataaagcac aagagttcga ggacaaaatg 2280
atccagacca ttgatttcca caccaaatat atccgtgaat atggcaccga tattcccgaa 2340
gttaaagaat ggaaatgggc agatctgacc cgtaaa 2376

<210> SEQ ID NO 73
<211> LENGTH: 2355
<212> TYPE: DNA
<213> ORGANISM: Carnobacterium sp. 17-4

<400> SEQUENCE: 73
atgaaaaact atgatagcaa agattatctg aaaaaagtgg acgcattttg gcgtgcagca 60
aattatctgt cagttggtca gctgtatctg cgtgataatc cgctgctgca gcgtccgctg 120
aaaagcaccg atgttaaagc acatccgatt ggtcattggg gcaccattag cggtcagaat 180
tttatctatg cacatctgaa tcgcgtgatc aacaaatatg atctgaatat gttctacatc 240
gaaggtccgg gtcatggtgg tcaggttatg attagcaatg catatctgga tggtagctat 300

```
accgaaatct atccggatat caccgaaaac aaagaaggca tgaagaaact gttcaagcag    360
tttagcagtc cgggtggtgt tgcaagccat gcagcaccgg aaacaccggg tagcattcat    420
gaaggtggtg aactgggtta tagcctgagc catgccaccg gtgcaattct ggataacccg    480
gatgttattg cagcaaccgt tattggtgat ggtgaagcag aaaccggtcc gctggcagca    540
ggttggttta gcaataattt cattaatccg gtgaatgatg gtgccgttct gccgattctg    600
tacctgaatg gtggtaaaat tagtaacccg accattctgg cacgtaaaag caatgaagat    660
ctgaagaaat atttcgaggg tatgggttgg aaaccgtatt ttgttgaagg caccgatccg    720
gaaaaagttc atccggttat ggcaaatacc ctggatgttg ttatcgaaga aattcgcagc    780
attcagaatg aagcccgtaa aggtaaagcc gaagatgttg aaatgccgca ttggcctgtg    840
atgattattc gtaccccgaa aggttggaca ggtccgaaag aatgggataa caaaaaaatc    900
gaaggcacgt ttcgtgcaca tcaggttccg attccggttg atgcagaaca tatggaatat    960
gtgaataaac tggtggactg gctgaaatca tatcgtccgg aagaactgtt taccgaaaat   1020
ggcaaactga tcgatgacct gaaagaactg acaccgaaag gcaataaacg tatggcaacc   1080
aatccgatta ccaatggtgg cattaatgca aaagcactga ttatcccgaa ttggaaacag   1140
catgcaattg ataccaccat tccgggtgca gttattgccc aggatatgga tgtttttggt   1200
gaacaggcac gtgatctgat tgttaaaaat ccgaacaact ttcgcatctt cggtccggat   1260
gaaaccaaaa gtaatcgcct ggataaaatc tttgaagtga ccaatcgtca gtggctggaa   1320
agcaaagaat taaccgatga atggcagagc agcgcaggtc gtgttattga tggccagctg   1380
agcgaacatc aggcagaagg ttttctggaa ggttatgttc tgaccggtcg tcatggtttt   1440
tttgcaagct atgaaagctt tctgcgtgtt gttgatagca tgctgaccca gcactttaaa   1500
tggctgcgta aagcaaccga tcagaaatgg cgtaataact atccgagcct gaatgtgatt   1560
gcaaccagca ccgtttttca gcaggatcat aatggttata cccatcagga tccgggtatt   1620
ctgacccatc tggcagaaaa aaaaccggaa tttatccgtg aatatctgcc tgcagatgca   1680
aatagtctga tggcagttat ggacaaaaca ctgcaagaag aacagctgat taacctgatc   1740
attagcagca aacatccgcg tccgcagttt tatagcgttg aagaagccga aattctggtt   1800
aaagatggcc tgaaaattat cgattgggcc agtaccgata atgatagcga accggatctg   1860
gttatcgcag cagccggtac agaaccgaac ctggaagcac tggcagccat gagcattctg   1920
cacaaagcat ttccggaact gaaaatccgc tttatcaaca ttgtggacat tctgaaactg   1980
cgtcacccgg atattgatag ccgtggtctg acagatgaaa aattcgatag ctatttcacc   2040
aaagagcagc cgattatctt tgcctttcat ggctttgaag gtctgattcg cgatatcttt   2100
tttaaccgcc ataaccataa tctgcgcatt cacggttatc gtgaaaatgg tgatattacc   2160
accccgtttg atatgcgtgt tctgaatgaa atggatcgtt ttcatctggc caaagatgcc   2220
gcaaaagccg tttatggtct gaaagccaac aaattcatgc aagagatgga aaacaccgtg   2280
aactttcatc atcagtatat tcgcgaaaac ggcattgata ttccggaagt gattaactgg   2340
aaatgggaaa aaatc                                                    2355
```

<210> SEQ ID NO 74
<211> LENGTH: 2397
<212> TYPE: DNA
<213> ORGANISM: Melissococcus plutonius ATCC 35311

<400> SEQUENCE: 74

```
atggaaaaag ataaatacag cagcaccgag tacctggaca aaattgataa atggtggcgt     60
```

-continued gcagcaaact atctgagcat tggtcagctg tatctgaaag ataatccgct gctgaaacgt 120
aaaattcgta gcgaggatgt taaatatcat ccgattggtc attggggcac cattgcaggt 180
cagaatttta tctatgcaca tctgaaccgc attatcaaca aatacgatct gaatatgttt 240
tatatcgagg gtccgggtca tggtggtcag gttatggtta gcaatagcta tctggatggt 300
agctataccg aaatttatcc ggcagttacc gaagatgaag caggtatgca gaaactgttt 360
aaacgtttta gctttccggg tggtgttagc agccatgccg caccggaaac accgggtagc 420
attcatgaag gtggtgaact gggttatagc ctgagccatg gtgttggtgc aattctggat 480
aacccggaag ttattagcgc agttgttatt ggtgatggtg aaagcgaaac cggtccgctg 540
gcgaccagct ggtttagtaa tacctttatt aacccggtta ccgatggtgc cgttctgccg 600
attctgcatc tgaatggtgc aaaaattgca aatccgacca ttctgggtcg taaaagcgat 660
aaagaactgg aacagtattt tcgtggtatg ggttggattc cgtattttgt ggaaggtaat 720
gatccgaatc agatgcatcc gctgatggca aaaaccctgg atcaggtgat tgaaaaaatc 780
cacagcattc aagaaaccgc acgtaaacag accgcagaaa cagcaagtat tcagaaatgg 840
cctctgattg ttctgcgtac cccgaaaggt tggacaggtc cgaaagaatg ggatggtaaa 900
ccgattgaag ttacctttcg tgcacatcag gttccgattc cgattgatca ggatcatatg 960
gaacatgttg atcagctggt gaattggctg aaaagctata aaccggaaga actgtttgat 1020
gaaacaggtc gtctgaatag cgaaattcgt gccattgcac cgatgaatga taaacgtatg 1080
gcaatgaatc cgattaccaa tggtggtatt aatccgaaac cgctgcagat gccggattgg 1140
cgtgaatttg atctgcatat tagcaaaccg ggtgagctgg ttgcacagga tatgctggaa 1200
tttggtaaaa tggttgcagc catcatcaaa aaaaacccgc agaactttct gatctttggt 1260
ccggatgaaa ccaaaagcaa tctgctgaat gatgcattta gcgttaccag ccgtcagtgg 1320
ctggaaccga tttatgaacc tcaggatgaa tggctggcac cgtcaggtcg tattattgat 1380
agccagctga gcgaacatca ggacgaaggt attctggaag gttatgttct gaccggtcgt 1440
catggttttt ttgcaagcta tgaagccttt attcgcatcg tggatagcat gattgcccag 1500
catatcaaat ggatgcgtaa agcaatggat ctgccgtggc gtaatggtta tagtagcctg 1560
aatctgattg caagcagtac cgcatttcag caggatcaca atggctatac ccaccaggat 1620
ccgggtatcc tgagtcatct ggcagaaaaa gaagcagatt ttatccacga atatgtgcct 1680
gcagatacca atagcctgct ggcagttatg gataaagttc tgaaaagtca gggcaaagtg 1740
aatctggtga ttagctcaaa acatccgcgt ccgcagtttt atagccctga agaagcacaa 1800
gaattagtta atcgtggcct gatggaaatt gattgggcaa gcaccgttgc agaaaatggc 1860
actccggaaa ttgtgattgt tgccgcaggc accgaaccga atatggaagc actggcagca 1920
attaatctga tcaatcagag ttttccgaaa ctgcagttcc gctttatcaa tgttgtggat 1980
ttactgaaac tgcgtcatcc tgcagttgat tcaagaggta ttagcgaagt ggaatataac 2040
cacctgttta ccgttgattc cccgattatc tttgtttgtc agggttattc aagcctgatt 2100
cgcagcctgt tctatgatcg taaaaatcgt ccggttagca tccatagcta ccaagaaaac 2160
ggtgccatta ccaccccgtt tgatatgcgt gttctgaata aaatcgatcg ttatcacctg 2220
gccaaagata ttgcactgac cgcatatggt agccgtggtg aagattttgc acgtgccatg 2280
gataccatcc tggaaaaaca caatcagtat attcgcgaaa cgggtaaaga tctgcctgaa 2340
gtgctgaatt ggaaatgggc tccgctgcat atctataacg aaaacattga acaggat 2397

<210> SEQ ID NO 75
<211> LENGTH: 2361
<212> TYPE: DNA
<213> ORGANISM: Tetragenococcus halophilus NBRC 12172

<400> SEQUENCE: 75
atgagcgtga acatcgacag caaagaatat ctggaacgta tgaatgcatg gtggcgtgca 60
gcaaactata ttagcgttgc acagattttt ctgcgtgata atccgctgct gcgtcgtccg 120
ctggaaaaag aagatatcaa aattaacccg attggtcatt ggggcaccat tagcggtcag 180
aattttatct atgttcatct gaaccgcgtg atcaacaaat atggtctgaa catgttttat 240
atcgaaggtc cgggtcatgg tggtcaggtt atggttagca atagctatat tgatggcagc 300
tatagcgaaa tctatccgga tgttacccag gatgaagcag gtctgaaaaa actgttcaaa 360
cagtttagct ttccgggtgg tatgggtagc catgcagcac cggaaacacc gggtagcatt 420
catgaaggtg gtgaactggg ttatagcatg agccatgccg ttggtgcagt tctggataat 480
cctgatgtta ttgcagcaac cgttattggt gatggtgaag cagaaaccgg tcctctggca 540
gcaagctgga tgagcaataa tttcattaat ccggtgaatg atggcgcagt gctgccgatt 600
ctgaatctga atggtgcaaa aattgcaaat ccgaccgttc tggcacgtaa aagcgataaa 660
gatctgcaga aatactttga aggtctgggt tggaaaccgt attttgtgga aggtgataac 720
ccggaaaaaa tgcatccgct gatggccgaa accctggatg cagttattaa cgaaattcag 780
agcattcaga aagaagcccg taaaggttca gccgaagatg tgaccatgcc gcattggcct 840
gttattgttt ttcgtacccc gaaaggttgg gaaggtccag aaaaatggga taatgagcag 900
attgcaggca cctttcgtgc acatcaggtt ccgattccga ttgatgcaag ccatatggaa 960
tatgcaaatg atctggcaaa atggctgaaa agctatcgtc cggaagaact gtttgatgaa 1020
aatggcacaa ttattgatgc gattaaagaa ctgagtccga aaggcgataa tcgcatgagt 1080
gttaatccga ttaccaatgg tggcctggat ccgaaagcac tgaatatgcc tgattggcat 1140
acccatgcag ttgataccag caaacgtggc accgataaag cacaggatat gagcgttctg 1200
ggtggtttta ttgccgatat tatggaaaac aacccgaaga actttcgcat ttttggtccg 1260
gatgaaacca aaagcaatcg cctgaataaa gtttttgatg tgacaaatcg tcagtgggtt 1320
gaacctcgtg aactgtcaga tgaatggcag agcgcagttg gtcgtgtgat cgatggtcag 1380
ctgagcgaac atcaggcaga aggttttctg gaaggctata ccctgaccgg tcgtcatggt 1440
ttttttgcaa gctatgaagc atttctgcgc attgttgata gcatgctgac ccagcacttt 1500
aaatggattc gtaaagccaa tgaaaaaagc tggcgcaaaa aatacccgag cctgaatgtg 1560
attagcagca gtaccgcatt tcagcaggat cataatggtt atacccatca ggatccgggt 1620
gtgattaccc atctggcaga aaaaaaaccg gaatatatcc gcgaatattt tccggcagat 1680
gcaaatagcc tgatggcggt tatggataaa gccctgaaag atgaaaacgt cattaacctg 1740
attacctcga gcaaacatcc gcgtccgcag ttttatagcg ttgaagaagc acaagaactg 1800
gtcgattatg gcgtgaaaaa aatcgattgg gcaagcaatg atcaggatag cgaaccggat 1860
attgtgtttg cagcagcagg tagtgaaccg aatctggaag cactggcagc gattagcatt 1920
ctgcatgaac agtttccgga aatgaaaatc cgctttatca atgttgtgga cctgctgaaa 1980
ctgcgtcatc cagatgttga tccgcgtggt ctgagtgatg aagcctttga tgagctgttt 2040
accacagata aaccggtgat ctttaacttt catggttatg aaggcctgat tcgcgatatc 2100 tttttttaccc gtcataatcg taatctgagc atccatggct atcgtgaaga tggtgatatt 2160
accaccccgt ttgatatgcg tgttaaaaat gaactggatc gctttcatct ggccaaagat 2220
gcagccaata ccatttatgc cgaaaaagca gccgatttca tccaagaaat ggacaaaacc 2280
ctgcagtatc accatgatta tattcgcgaa aacggtgatg atatcagcga agttcagaat 2340
tgggaatgga aagacctgaa a 2361

<210> SEQ ID NO 76
<211> LENGTH: 2379
<212> TYPE: DNA
<213> ORGANISM: Melissococcus plutonius DAT561

<400> SEQUENCE: 76
atgaccaaat atgatagcaa agaatatctg gccaaagtgg atgcattttg gcgtgcagca 60
aactatatta gcgttggtca gctgtatctg aaagataatc cgctgctgga tcgtccgatt 120
gaaaccaccg atgttaaagt tcatccgatt ggtcattggg gcaccattag cggtcagaat 180
tttatctatg cacatctgaa tcgcgtgatc aacaaatacg atctgaacat gttttatgtg 240
gaaggtccgg gtcatggtgg tcaggttatg gttagcaata gctatctgga tggtagctat 300
accgaaatct atccggaaat caccgaagat aaagagggtc tgaaaaaact gttcaaacag 360
tttagctttc cgggtggtat tgcaagccat gcagcaccgg aaactccggg tagcattcat 420
gaaggtggtg aactgggtta tagcattagc catgccaccg gtgcaattct ggataacccg 480
gatgttattg cagcaaccgt tgttggtgat ggtgaagcag aaaccggtcc gctgagcgca 540
ggttggtttg caaatacctt tattaacccg gttaacgatg gtgccattct gccgattctg 600
tacctgaatg gtggtaaaat tagcaatccg accattctgg aacgcaaaag tgatgaagaa 660
ctgaccaagt attttgaagg tatgggttgg aaaccgtatt ttgttgaagg caccgttccg 720
gataaagtgc atcctctgat ggcaaaaatc ctggatcata tcatcgaaga aatcaaagat 780
attcagaaag aagcccgtaa agacaaagcc gaaaatgcaa aaatgccgca ttggcctgtt 840
ctgattatgc gtaccccgaa aggttggaca ggtccgaaaa tttgggatga tgaaaaaatt 900
gagggcacct ttcgtgcaca tcaggttccg attccggttg atgcagaaca tatggaacat 960
attgatgcac tggttgattg gctgaaaagc tatcatccgg aagaactttt tgataaaaac 1020
ggcaccctga aaccggaact gaaagaactg gttccgaaag gcgatcgtcg tatggccaaa 1080
aacccgatta ccaatggtgg cctggatccg aaaccgctga aaatgaatgg ttgggaacag 1140
catgcaattg ataccagcac accgggtatg gttaccgcac aggatatgat tgtttttggc 1200
aattatgtcg aagatctgat caaagcaaac ccgaccaatt ttcgtatttt tggtccggat 1260
gaaaccaaaa gcaatcgcct gaataaagtg tttgatagca ccgatcgtca gtggatggaa 1320
ccgattagta atgcagatga atggcagagc agcgtgggtc gtgttattga tggccagctg 1380
agcgaacatc aggcagaagg ttttctggaa ggttatattc tgaccggtcg tcatggtttt 1440
tttgcaagct atgaaagctt tctgcgtgtt gtggatagca tgctgaccca gcactttaaa 1500
tggctgcgta aagcaaaaga acagagctgg cgtaaagagt atccggcact gaacattatt 1560
gcaaccagca ccgtttttca gcaggatcat aatggttata cccatcagga tccgggtatc 1620
ctgacccatc tggcagaaaa aaaagcagaa tatatccgtg aatacctgcc tgcagatgca 1680
aattgcctga tggccgttat ggataaagcc tttcaagaaa acgaagtgat taacctgatt 1740
gtgagcagta aacatccgcg tccgcagttt tatagcgtta ccgaagccaa agaattggtt 1800
gataaaggcg tgaaagtgat tgattgggca agcaatgatg aaggtcagac accggatatt 1860

```
gtgattgcag cgagcggcac cgaaccgaat ctggaagcac tggcagcaat taccctgctg   1920

aacaaagagt ttattgatct gaaaatccgc ttcgtgaacg tggtggatat cctgaaactg   1980

cgtcatccga gcattgatcc gcgtggtctg accgatgaag agtttgatgc aattttcacc   2040

aaggacaaac cgattgtgtt tgcctttcat ggctttgaag gcctgattcg cgatatcttt   2100

tttagccgta gcaatcatca gctgtttgtg catggttatc gtgaaaaagg tgatattacc   2160

accccgtttg atatgcgtgt tctgagtgaa atggatcgtt ttcacctggc aaaagatgtt   2220

gccgacaaag tgtataatga acaggcagcc gattttatga atcgcatgga tgaaattctg   2280

gcctttcacc atcagtatat tcgcaaaaac ggtatcgata ttccggaagt ggttaactgg   2340

aaatgggagg atctgcgcaa aaaaacgatt tgctttaat                          2379
```

<210> SEQ ID NO 77
<211> LENGTH: 2379
<212> TYPE: DNA
<213> ORGANISM: Mycoplasma arthritidis 158L3-1

<400> SEQUENCE: 77

```
atgaaaaaaa ccaattatga tagcaatgaa tatttcaatc tgattgataa atggtttcgc     60

gcagccaatt atctgagcgt tggtcagatt tatctgcgta ataatccgct gctgaaaacc    120

aaactggttg cagatgatgt taaaatctat ccgattggtc attggggcac cattccgggt    180

cagaatttta tctatgcaca tctgaatcgc gtgattaaca aatacgatct ggaaatgttc    240

tatatcgaag gtcctggtca tggtggtcag gtgatgatta gcaatagcta tctggatggt    300

agctataccg aaatttatcc ggaaatcacc gaagatgaag caggtctgaa aacgatgttt    360

aaacgtttta gctttccggg tggcaccgca agccatgcag caccggaaac tccgggtagc    420

attcatgaag gtggtgaact gggttatgca ctgagccatg ccaccggtgc aattctggat    480

aatccgaatg ttattgcagc aaccgttatt ggtgatggtg aagcagaaac cggtccgctg    540

gcagcaggtt ggtttagcaa ttcttttatc aatccggtta atgatggtgc cgttctgccg    600

attattcatc tgaacggtgc aaaaatttcc aacccgacca ttctgagccg taaaagcaat    660

caagaactgg aaaactattt tagcggtctg ggttgggaac cgctgtttgt tgaaggtgac    720

gatccgaaac tgatgcatcc gctgatggca aaaaaactgg atgaagccat tgagaagatt    780

cagatgattc aggcaagcgc acgtaaacat aaagcaagcg aagcaacccg tccggtttgg    840

ccgatgctga ttgttcgtac cccgaaaggt tggacaggtc ctaaagattg gaatggcgaa    900

gttgtggaag gtagctttcg tgcacatcag gttccgattc cggtgaatgc cctgaatatg    960

acccatatcg ataaactgga agcatggctg accagctatc atccggaaga actgtttgat   1020

aaaaacggca aaatcctgga agaaattcgt gccctggcac cgaaaggcct gaaacgtatg   1080

gcagttcatc cgattaccaa tggtggtatt aatccgcgta ccctgaaact gagcagctgg   1140

gaaaaatttg ccaccaaatt tgaaacccct ggccagatta aaggtcagga tatgatcgaa   1200

ctgggcaaat atttcgcaga aattatcacc ctgaacaagg ataactttcg catttttggt   1260

ccggatgaaa ccaaatccaa tcgtatgaat gccgtgttta atgtgaccaa acgtcagtgg   1320

ctggaaaaaa tcgcaccgac ctatgatgaa tggatgagtc cggaaggtcg tgttattgat   1380

agccagctga gcgaacatca ggcagaaggt tttctggaag gttatgttat taccggtcgc   1440

catggtgttt ttgcaagcta tgaagcattt ctgcgtgttg tggatagtat gctgacccag   1500

catatgaaat ggatgaagaa aagcctggaa ctgccgtggc gtaaagattt tccgagcctg   1560

aatgtgattg cgaccagcac cgcatttcag caggatcata atggttatac ccatcaggat   1620
```

ccgggtctgc tgggtcatct ggcagataaa cgtccggaac tgattcgtga atatctgcct 1680
gcagatacca attgcctgct ggcaaccatg gaaaaagcac tgaaagatcg taatgtgatc 1740
aacctgattg tggcaagcaa acagcctcgt gaacagtttt atagcgttga agaagccagc 1800
gaactggtac agaaaggcta taaaatcatt aattgggcca gcaacgtgag caaaaatgaa 1860
gaaccggatg ttgtgtttgc agcagccggt gttgaaccga atctggaagc tctggcagcc 1920
attagtattc tgaacaaaga attcccgaac ctgaaaatcc gttttgtgaa tgttctggat 1980
ctgctgaagc tgaaaagccc gaaacatgat ccgcgtggca ttagcgacga agaatttgat 2040
cagatcttca ccaaaaacaa accgatcatc tttgcctttc atggttatga aggcctgctg 2100
cgtgatatct tttttgatcg ccataaccat aacctgatca cccatggcta tcgtgaaaat 2160
ggcgatatca ccaccagttt tgatattcgt cagctgagtc atatggatcg ctttcatatt 2220
gcaaaagatg cagcaattgc agccctgggt aaagatggcg aaatgtttgc gaaaaaaatg 2280
gacagcaaac tgcaagaaca taccagttat gttcgcgagt atggctatga tctgccggaa 2340
gttgttaatt ggaaatggac caatctgaaa ccgattaaa 2379

<210> SEQ ID NO 78
<211> LENGTH: 2376
<212> TYPE: DNA
<213> ORGANISM: Streptococcus agalactiae NEM316

<400> SEQUENCE: 78
atgagcgagt tcgacaccaa aagctatctg gaaaaactgg atgcatggtg gcgtgcagca 60
aactatatta gcgcagcaca gatgtatctg aaagataatc cgctgctgcg tcgtgaactg 120
gttgaaaatg acctgaaagt tcatccgatt ggtcattggg gcaccgttcc gggtcagaat 180
tttatctatg cacatctgaa tcgtgccatc aacaaatatg atctggacat gttttatatc 240
gaaggtcctg gtcatggtgg tcaggttatg gttagcaata gttatctgga tggtagctat 300
accgaactga atccgaatat tgaacagacc gaagatggtt ttaaacagct gtgcaaaatc 360
tttagctttc cgggtggtat tgcaagccat gcagcaccgg aaacaccggg tagcattcat 420
gaaggtggcg aactgggtta tgcactgagc catgccaccg gtgcaattct ggataacccg 480
gatgttattg cagcaaccgt tattggtgat ggtgaaggcg aaaccggtcc gctgatggca 540
ggttggctga gcaatacctt tattaacccg gttaatgatg gtgcagttct gccgatcttt 600
tatctgaatg gcggtaaaat tcataatccg accatctttg aacgcaaaac cgatgaagaa 660
ctgtcccagt tttttgaagg tctgggttgg aaaccgattt ttgcagatgt tgttgaactg 720
agtgaagatc atgcagccgc acatgcactg tttgcagaaa aattagatca ggccatccaa 780
gagattaaaa ccattcagag cgaagcacgt cagaaaccgg cagaagaagc aattcaggca 840
aaatttccgg ttctggttgc acgtattccg aaaggttgga caggtccgaa agcatgggaa 900
ggcaccccga ttgaaggcgg ttttcgtgca catcaggttc cgattccggt tgatgcccat 960
catatggaac atgttgatag cctgctgagc tggctgcaga gctatcgtcc ggaagaatta 1020
tttgatgaaa gcggcaaaat cgtggatgaa attgcagcca ttagcccgaa aggcgatcgt 1080
cgtatgagca tgaacccgat taccaatgca ggtattgtta aagcaatgga taccgcagat 1140
tggaaaaaat tcgccctgga tattaatgtg ccaggccaga ttatggcaca ggatatgatt 1200
gaatttggca aatatgcagc ggatctggtg gatgcaaatc cggataattt tcgtattttt 1260
ggtccggatg aaacgaaaag caatcgtctg caagaagttt ttacccgtac cagccgtcag 1320

-continued

```
tggctgggtc gtcgtaaacc ggattatgat gaagcactga gtccggcagg tcgtgttatt   1380

gattcacagc tgagcgaaca tcaggcagaa ggttttctgg aaggttatgt tctgaccggt   1440

cgtcatggtt tttttgcaag ctatgaaagc tttctgcgtg ttgtggatag tatggttacc   1500

cagcacttta aatggctgcg taaaagcaaa acccatacca cctggcgtaa aaactatccg   1560

gcactgaatc tgattgccgc aagcaccgtt tttcagcagg atcataatgg ttatacccat   1620

caggatccgg gtattctgac ccatctggcc gaaaaaactc cggaatatat tcgtgaatat   1680

ctgcctgcag ataccaatag tctgctggca gttatggata aagcatttaa agccgaggac   1740

aagattaacc tgattgtgac cagcaaacat ccgcgtccgc agttttatag cattgcagaa   1800

gccgaagaac ttgttgccga aggctataaa gtgattgatt gggcaagcaa tgttagcctg   1860

aatcaagaac cggatgtggt ttttgccgca gcaggcacag aaccgaatct ggaagccctg   1920

gcagcaatta gcattctgca caaagccttt ccggaactga aaattcgttt tgtgaatgtg   1980

ctggacattc tgaaactgcg tcatccgagc caggatgcac gtggtctgag cgacgaagaa   2040

tttgataaag tgtttaccac cgataagccg gtgatctttg catttcattc ctacgaagat   2100

atgatccgcg atatcttttt tagccgtcat aatcacaatc tgcataccca tggttatcgc   2160

gaaaatggtg atattaccac cccgtttgat atgcgtgtta tgtcagaact ggatcgtttt   2220

catctggcgc aggatgccgc actggcaagc ctgggtaatg aagcccaggc atttagtgat   2280

gaaatgaatc agatggtggc ctatcacaaa gattatatcc gtgaacatgg tgatgatatt   2340

ccggaagttc agaattggaa atgggaaaac attaaa                             2376
```

```
<210> SEQ ID NO 79
<211> LENGTH: 2385
<212> TYPE: DNA
<213> ORGANISM: Mycoplasma agalactiae PG2

<400> SEQUENCE: 79

atgaaaaaaa gccatgattt tgatagcaaa gaatatctga atctggttga tgcatggtgg     60

cgtgcagcaa attatctgag cgttggtcag atgtatctgc gtaataatcc gctgctgaaa    120

attccgctga ccagcaatga tgttaaaatc tatccgattg gtcattgggg caccgttccg    180

ggtcagaatt ttatctatgc acatctgaac cgcattatca acaaatacga tctgaatatg    240

tttttatca gcggtcctgg tcatggtggt caggttattg caagcaatac ctatctggat    300

ggtagctata ccgaactgtt tccgcatgtt accaaagata ttaaaggtat gacccacctg    360

ttcaaatact ttagctttcc gggtggcacc gcaagccatg cagcaccgga atgtccgggt    420

agcattcatg aaggtggtga actgggttat agcctgagtc atgcagccgg tgcagttctg    480

gataatccgg atgttattgc cgcaaccgtt attggtgatg gtgaaagcga aaccggtccg    540

ctgagcgcag gttggtttat taacagcttt atcaatccgg caaatgatgg tgccgttctg    600

ccgattctgc atgttaatgg tggtaaaatt agcaacccga ccatttggag ccgtcgtagc    660

aatgaagaac tggttagcta ttttaccggt gccggttgga aaccgtttat tgttgaaggt    720

aatgagccgg aatatatgca tcatgaaatg gcaaaagcac tggatgcaag cgttgaactg    780

attaaacagt atcaggccga agcacgtaaa aatggtgcaa ataaagcaaa acgtccgcag    840

tggccgatga ttgttctgaa aagcccgaaa ggttggacag gtccgaaaga atggaatcat    900

gaagcaattg aaggttcctt tcgtgcacat caggttccgg ttccagttag cgcagaaaaa    960

atgcagcata ttgatgcact ggaaaattgg ctgcgtagct atcgtccgga agaacttttt   1020

gatgaaaatg cccagctgaa accggaaatt gcagcaattg caccgaaagg cgatcgtcgt   1080
```

atgggtaaaa acccgattgc aaatggtggc attaatccgc gtgcaattaa tgttggtgat 1140
tggaccaaat ttgccctgga tatcaaacag cctggcaaag ttattaatca ggatatggtt 1200
accctgggca gctatctggg cgaactgagc ctgctgaata aagataattt tcgtgtttgg 1260
ggtccggatg aacataaaag caatcgtctg tatgagatgt tcaaagttac cgatcgtcag 1320
tggctggatc gtatcgatga aaaatatgat gaatttctga gcagcgtggg tcgcattatt 1380
gatagccagc tgagcgaaca tcaggcagaa ggtatgctgg aaggttatgt tctgaccggt 1440
cgccatggtg tttttgcaag ctatgaaagc tttctgcgtg ttgtggatag catgctgacc 1500
caacatatga agtgggttaa aaaagcgctg gacattccgt ggcgtaatga ttatccgagc 1560
ctgaatgtga ttgcaaccag taatgcattt cagcaggatc ataatggtta tacccatcag 1620
gatcctggtc tgattggcca tctggcagat aaacgtccag aactgatccg tgaatattta 1680
ccggcagata ccaataccct gctggcaacc atggccaaag ccctgcagga tcgtaacgtg 1740
attaatctga ttatcagcag taaacagcca cgccatcagt tttttagtat tgaagaagca 1800
accgagctgg tcgaaaaagg cattaaaatc attgattggg ccagcaacat taagccgaac 1860
gaagaaccgg atctggtggt tgcagccagc ggtacagaaa gcaccattga aagcctggcc 1920
accattacct acctgcgtgc ccattttccg gaactgaaaa tccgttttgt taatgtgctg 1980
gatctgctga agctgcgtca tccgagtatt gatcctcgtg gtctgagcga tagcgaattt 2040
gatagtatct tcacgaaaga caaaccgatc ctgtttgcct ttcatggtta tgaagccatt 2100
ctgcgcgata tctttttcct gcgttcaaac cataacatta tcacccatgg ctatcgtgaa 2160
aatggcgata ttaccaccgc atttgatatt cgtctgctga gtgaaatgga tcgctttcat 2220
atgaccgcaa atgttgcaaa aaaactggca ccggttgttg gcgaaagcaa agcaaatgaa 2280
ctggtgaaac tgatggaaga taaaatcaaa gaacaccgtg cctatatcaa agagtatggc 2340
accgatctgc cggaagttaa agaatgggaa tggaccccgt ataaa 2385

<210> SEQ ID NO 80
<211> LENGTH: 2382
<212> TYPE: DNA
<213> ORGANISM: Streptococcus gordonii str. Challis substr. CH1

<400> SEQUENCE: 80
atgaccaccg actataacag caaagcctat ctggaaaaag ttgatgcatg gtggcgtgca 60
gcaaactata ttagcgcagc acagatgtat ctgaaagata atccgctgct gaaacgtgat 120
gttgttgcaa atgacctgaa agcacatccg attggtcatt ggggcaccgt tccgggtcag 180
aattttatct atgcacatct gaatcgcacc atcaacaaat atgatctgga catgttttat 240
atcgaaggtc ctggtcatgg tggtcaggtt atggttagca atagttatct ggatggtagc 300
tataccgaac tgaatccgaa tattccgcag aatgaagagg gttttaaaca cctgtgtaaa 360
atctttagct ttccgggtgg tattgcaagc catgcagcac cggaaacacc gggtagcatt 420
catgaaggtg gtgaactggg ttatgcactg agtcatgcag ccggtgcaat tctggataac 480
ccggatgtta ttgcagcaac cgttattggt gatggtgaag gcgaaaccgg tccgctgatg 540
gcaggttggc tgagcaatac ctttattaac ccggttaatg atggtgccat tctgccgatc 600
ttttatctga atggcggtaa aattcataat ccgaccatct ttgaacgcaa aaccgatgaa 660
gaactgaccc tgtttttga aggtctgggt tggaaaccga tttttgcaga tgttaccgca 720
attagcgaaa atcatgaagc agcacatgca ctgtttgcag ccaaactgga tgaagcaatt 780

-continued gaagagatca aaaaagttca ggcagaagca cgtaaaggta gcgcagaaga agcaacccag 840
gcaatttttc cggttctggt tgcacgtatt ccgaaaggtt ggacaggtcc gaaaagctgg 900
gaaggcaccc cgattgaagg cggttttcgt gcacatcagg ttccgattcc ggttgatgcc 960
catcatatgg aacatgttga cgcactgctg aattggctga aaagctatcg tccggaagaa 1020
ctttttgatg aaagcggtaa agttctgccg gaaattgccg caattggtcc taaaggtgat 1080
cgtcgtatgg caatgaaccc gattaccaat gccggtgtta ttaaacctat ggataccgca 1140
gattggaaaa aacacgcact gaaatttggc actccgggtg aaattgttgc acaggatatg 1200
atcgaattcg gtaaatatgc aaccgatctg gtggatgcaa atccggataa ttttcgtatt 1260
tttggtccgg acgaaaccaa aagtaatcgt ctgcaagaag tttttacccg taccagccgt 1320
cagtggctgg gtcgtatgcg tcctgaatat gatgaagccc tgagtccggc aggtcgtgtt 1380
attgatagcc agctgagcga acatcaggcc gaaggtatgc tggaaggtta tgttctgacc 1440
ggtcgtcatg gtttttttgc aagctatgaa agctttctgc gtgttgtgga tagcatggtt 1500
acccagcact ttaaatggct gcgtaaatgt aaaacccata ccacctggcg taaaaactat 1560
ccggcactga atctgattgc aaccagcacc gtttttcagc aggatcataa tggttatacc 1620
catcaggatc cgggtattct gacccatctg gcagaaaaaa ctccggaatt tatccgtgaa 1680
tatctgcctg cagataccaa tagcctgctg gcagttatgg ataaagcatt taaagccgag 1740
gataaggtga acctgattgt gaccagtaaa catccgcgtc cgcagtttta tagtgccgaa 1800
gaagcggagg aactggttcg tgaaggctat aaagtgattg attgggcaag caccgtgagc 1860
aacaacgaag aaccggatgt ggtttttgcc gcagcaggca cagaaccgaa tctggaagca 1920
ctggcagcag ttagcattct gcacaaagcc tttccggaac tgaaaattcg ttttgtgaat 1980
gtggtggaca ttctgaaact gcgtcatccg agcgttgatg cgcgtggtct gagcgacgaa 2040
gaatttgatc aggtgtttac caccgataaa ccggttatct ttgcctttca tggttatgaa 2100
ggcatgatcc gcgatatctt ttttaaccgc cataaccata atctgcgcgt tcatggctat 2160
cgtgaaaatg gtgatattac caccccgttt gatatgcgtg ttatgtcaga actggatcgt 2220
tttcatctgg cccaggatgc cgcaaatgca gccctgggtg aagatgcagc ggtttttagc 2280
gcaaaaatgg atgaaaccgt tgcatatcat aacgcctata ttcgcgaaaa tggggatgat 2340
attccggaag ttcagaattg gaaatgggaa aacattaaca aa 2382

<210> SEQ ID NO 81
<211> LENGTH: 2373
<212> TYPE: DNA
<213> ORGANISM: Kingella oralis ATCC 51147

<400> SEQUENCE: 81
atgcagaaca cccagtttga cacaccggaa tatctggcaa aagttgatgc atggtggcgt 60
gcagcaaact atattagcgc agcacagatg tatctgaaag ataatccgct gctgaaaaaa 120
ccgctgaccg caaatgatgt taaagcacat ccgattggtc attggggcac cgttccgggt 180
cagaatttta tctatgcaca tctgaatcgt gccatcaaca aatatgatgt ggacatgttt 240
tatatcgaag gtcctggtca tggtggtcag gttatggtta gcaatagcta tctggatcat 300
agctataccg atatctatcc ggaaattacc caggatgaag caggtctgaa aaagctgtgt 360
aaaatcttta gctttccggg tggtattgca agccatgcag caccggaaac accgggtagc 420
attcatgaag gtggtgaact gggttatgca ctgagccatg cctttggtgc agttctggat 480
aacccgaaca ttattgcagc agcagttatt ggtgatggtg aagcagaaac cggtccgctg 540
tgtgcaggtt ggtttggtaa tacctttatt aacccggtta atgatggtgc cgtgctgccg 600
attctgtacc tgaatggtgg taaaattcat aatccgacca ttctggcacg taaaaccgat 660
gccgaactga cccagtattt taacggtatg ggttgggaac cgatttttgt tgaagttagc 720
gatccggcac atagccatgc gattatggca cagaaactgg atgaggcagt tgaacgtatt 780
ctggccattt ggcaggatgc acgtagccgt agcgccaatg atgcaaccat gcctcgttgg 840
cctgttctgg ttgcccgtat tccgaaaggt tggacaggtc cgaaaacctg gaatggcgaa 900
ccgatcgaag gcggttttcg tgcacatcag gttccgattc cgaccaatag tcatgatatg 960
agcaccgcag atgcactgga agcatggctg cgtagctatc gtccggaaga actgtttgat 1020
gataatggtc gtttcctgga taaatggcgt gaaattagcc cgaaaggcgc aaaacgtatg 1080
agcgttcatc cgatcaccaa tggcggtgtt gcaccgaaag cactggttat gccggattgg 1140
accaaacatg ccctgaaaat tggcacccct ggtagccagg atgcccagga tatgattgaa 1200
tgtggtcgtc tgatggcaga tgttattacc gccaatccgg ataactttcg tatttttggt 1260
ccggatgaaa ccaaaagcaa tcgtctgaat gaagtgttca aagtgaccaa tcgtcagtgg 1320
ctgggtgttc gtgatgcagc ctatgatgaa tggattgcac cggttggtcg tgttattgat 1380
agccagctga gcgaacatca ggcagaaggt tttctggaag gttatgttct gaccggtcgt 1440
catggttttt ttgcaagcta tgaaagcttt ctgcgtgttg tggatagcat gattacacag 1500
cactttaagt ggctgcgcaa atgcaaaacc catgcaccgt ggcgtaaaga ttatccgagc 1560
ctgaatctga ttgcaaccag caccgttttt cagcaggatc ataatggtta tacccatcag 1620
gatccgggtc tgctgaccca tctggcagaa aaaaaacctg aatttgtgcg cgaatattta 1680
ccggcagatg ccaataccct gctggcagtt atgagcgaag cactgaccag ccgtgatcgt 1740
attaacctga ttgttagcag taaacatctg cgtccgcagt tttatagcgc agatgaagcc 1800
aaagaactgg ttcgtgaagg ctataaaatc attgaatggg caagcacctg tcatgacggt 1860
gaaccggatg ttgtgatcgc agcggcaggc accgaaccga atatggaagc cctggcagca 1920
attaatgttc tgcacaaaca ttacccggaa atgaaaatcc gctttatcaa cgtggtggat 1980
attctgaaac tgcgtcatcc gagcattgat ccgcgtggtc tgagtgatga agcgtttgat 2040
gccctgttta cccgtgataa accggttgtt ttttgctttc atggctatga gaatatggtg 2100
cgcgatatct tttttccgcg tcataatcgt aatgtgcgca tccatggtta tcgtgaaaat 2160
ggtgatatta ccaccccgtt tgatatgcgt gttctgtcag aaatggatcg ttttcatgtt 2220
gcaaaagatg ccgcacaggc agtttatggt gagaaagcag cagattttgc caacaaaatg 2280
gacgaaacca ttcagtttca tcgtagctac attcgcgaac atggtaaaga tattccggaa 2340
gttgcagaat ggaaatggca gccgctggcc aaa 2373

<210> SEQ ID NO 82
<211> LENGTH: 2376
<212> TYPE: DNA
<213> ORGANISM: Mycoplasma fermentans M64

<400> SEQUENCE: 82
atgaacaaaa aagaatttga tagcaaagaa tatctggaaa aggttgatgc atggtggcgt 60
gcagcaaatt atctgagcgt tggtcagatt tatctgcgta ataatccgct gctgaaacat 120
ccgctgacca gtgatgatgt taaagtttat ccgattggtc attggggcac cattagcggt 180
cagaattttg catatgcaca tctgaatcgc gtgatcaaca aatatgatct gaatatgttc 240

-continued

```
tacatcgaag gtccgggtca tggtggtcag gttatgacca gcaatagcta tctggatggt    300
agctataccg aactgtttcc gcatgttacc caggatgaag caggtatgca gcacctgttt    360
aaatacttta gctttccggg tggcaccgca agccatgccg caccggaaac accgggtagc    420
attcatgaag gtggtgaact gggttatagc attagccatg caaccggtgc aattctggat    480
aatccggatg ttattgcagc aaccattgtt ggtgatggtg aagcagaaac cggtccgctg    540
gcgaccagct ggtttagcaa tagtttttatc aatccggtta atgatggtgc cgttctgccg    600
attctgcatc tgaacggtgg taaaattagc aatccgacca ttctgagccg taaaagcaat    660
gaagaactgc agcagtattt tcgtggtatg ggttgggaac cgcattttgt tgaaggtgat    720
aaaccggaag taatgcatga actgatggca aaaaccctgg atagcgtgat tgaagaaatt    780
cagagcattc agaccaaagc ccgtaaaaaa ccggcagata aagcaaaacg tccggtttgg    840
ccgatgattg ttctgcgtac ccccgaaaggt tggacaggtc cgaaaagctg gaataaagaa    900
gcaattgaag gtagctttcg tgcacatcag gttccgctgc cgatcaatgc agaaaatatg    960
gaacatgcag atgccctgga aaaatggctg cgtagctatc gtccggaaga actttttgat   1020
aaaaaaggca aactggtgaa agagattgca gccattgcac ctaaaggtaa acgtcgtatg   1080
ggtatgaatc cgattaccaa tggtggcatt aatccgaaag ttatgaaact gggtgattgg   1140
cgtaaatttg ccctgcattt tgatcgtcct ggtagcgttg ttgcacagga tatggttgag   1200
ctgggcacct attttgcaga tctggttaaa cgcaatccgg aaaattttcg tatttttggt   1260
ccggacgaaa ccaaaagtaa tcgtctgtat aacctgttca aagtgaccaa tcgtcagtgg   1320
atggaacgca ttgatagtaa actggatgag gcactgagtc cggttggtcg tattattgat   1380
agccagctga gcgaacatca ggcacagggt tttctggaag gttatgttct gaccggtcgt   1440
catggcattt ttgcaagcta tgaaagcttt ctgcgtgttg tggatagcat ggtgacccag   1500
catatgaaat ggttacgtaa agccaaagaa atcaactggc gcaaagatta tccgtccctg   1560
aatattatgg caaccagcac cgcctttcag caggatcata atggttatac ccatcaggat   1620
ccgggtatta tcggtcatat ggcggataaa cgtccagaac tgattcgtga atacctgcct   1680
gcagatacca ataccctgct ggcagttatg gataaagcct ttaccgaacg caatgtgatt   1740
aatctgattg tgagcagcaa acagcctcgc catcagtttt atagcgttga agaagccgaa   1800
acgctggttg aaaaaggtct ggatattatc gattgggcaa gtacctgtag ccgtaatgaa   1860
actccggatc tggtggttgt tgccagcggc accgaaccga atctggaagc actggccacc   1920
atttctattc tgaacaaaga atacccgagc atgaaaatcc gttttgtgaa tgttgttgat   1980
ctgctgaagc tgcgtcatcc gaaaattgat ccgcgtggtc tgagtgatga agaattcgat   2040
gaaatcttta ccaaagataa gccggtgctg tttgcctttc atggttttga aggcattctg   2100
cgcgatattt tctttgatcg ccataaccat aacctgattg cacatggtta tcgcgaaaat   2160
ggtgatatca caaccagctt tgatattcgt cagctgtcac atatggatcg ttttcacatg   2220
gcaagtgatg cagcagcagc cgtttttggt agctcaaaag cgaaagaatt catggacaaa   2280
atggaagaaa ccattcagtt tcacaacaag tatattcgcg aagtgggcac cgatattccg   2340
gaagtgaaaa attggaaatg ggaaggcctg attaaa                             2376
```

<210> SEQ ID NO 83
<211> LENGTH: 2367
<212> TYPE: DNA
<213> ORGANISM: Granulicatella adiacens ATCC 49175

<400> SEQUENCE: 83
atgacccagt ttgacacacc ggaatatctg gcaaaagttg atgcatggtg gcgtgcagca 60
aactatatta gcgttgcaca gatgtatctg aaagataatc cgctgctgcg tcgtccgatt 120
cagaaagaag atgttaaact gcatccgatt ggtcattggg gcaccattgc aggtcagaat 180
tttatctatg cacatctgaa tcgtgccatc aacaaatatg atctggacat gttttatatc 240
gaaggtccgg gtcatggtgg tcaggttatg gttagcaata gctatctgga tggtagctat 300
accgaactgt atccgcagat tacccaggat gaagcaggtt ttaaacagct gtgcaaaatc 360
tttagctttc cgggtggtat tgcaagccat gcagcaccgg aaacaccggg tagcattcat 420
gaaggtggtg aactgggtta tagcctgagc catgccaccg gtgcagttct ggataacccg 480
aatgttattg cagcagcagt tattggtgat ggtgaagcag aaaccggtcc gctggcagca 540
ggttggttta gtaatacctt tattaacccg gttaatgatg gtgccgttct gccgattctg 600
tacctgaatg gcggtaaaat tcataatccg accattctgg cacgtcgtac cgatgaagaa 660
ctgacacagt tttttaacgg tctgggttgg gatccgattt ttgttgaagg caccgatccg 720
gaaaaagttc atccgctgat ggcagcaaaa ctggatgagg caattgaaaa aattcaggcc 780
atccagaaag aggcacgcgc aaaatcagcc gaagaggcaa ccatgccgca ttggcctgtt 840
ctggttgttc gtaccccgaa aggttggaca ggtccgaaag aatggaatca tgaaccgatt 900
gaaggcggtt ttcgtgcaca tcaggttccg attccggtta gcggtgaagc catggaacat 960
gttgatgccc tggttgattg gctgaaaagc tatcgtccgg aagaactttt tgatgaaaat 1020
ggcaaactgg tggaagaaat tgcagccatt agccctaaag gtccgcgtcg tatgagtatg 1080
aatccgatta ccaatgccgg tgttgttaaa ccgatggaaa ttaccgattg gaccaaacat 1140
gcaatcgata ccagcaaacc gggtgcaatt caaaaacagg atatgatcga attcggcaaa 1200
tttgcagccg atctggttaa agcaaatccg gataattttc gcattttcgg tccggatgaa 1260
accaaaagta atcgtctgaa cgaagtgttt aaagccacca atcgtcagtg ggttggtcgt 1320
cgtgatgaaa gctatgatga atggattagt ccggtgggtc gtgttattga tagccagctg 1380
agcgaacatc aggcagaagg ttttctggaa ggttatgttc tgaccggtcg tcatggtttt 1440
tttgccagct atgaaagttt tctgcgtgtt gtggatagca tgattacaca gcactttaaa 1500
tggctgcgta aagccaaaac ccatgcaccg tggcgtaaaa actatccgag cctgaatctg 1560
attgcaacca gcaccgtttt tcagcaggat cataatggtt atacccatca ggatccgggt 1620
ctgctgaccc atctggcaga aaaaaaaccg gaatttgtgc gtgaatattt accggcagat 1680
accaatagtc tgatggccgt tatggcagaa gcactgagca gcgaagataa aatcaacctg 1740
attgtgagca gtaaacatcc gcgtccgcag ttttatagcg ttgaagaagc aaaagaactg 1800
gtcagcgaag gctataaagt gattgattgg gcaagcaccg tgaaagaagg tgaagaaccg 1860
gacgttgtga tcgcagcagc cggtacagaa ccgaatctgg aagccctggc aggtattagc 1920
attctgcaca aacagtttcc ggaactgaaa atccgtttta tcaacgtggt ggatattctg 1980
aaactgcgtt caccgaaagt ggatccgcgt ggtctgagcg acgaagaatt tgataaactg 2040
tttaccaccg ataaaccggt ggtgttttgt tttcatggtt atgaaggtat gatccgcgac 2100
ctgttttttg atcgcaataa ccataacgtg catatccatg gctatcgcga aaatggtgat 2160
attaccaccc cgtttgatat gcgtgttctg agtgaaatgg atcgctttca tgttgcaaaa 2220
gatgcagccg ttgcagtgta tggtgaaaaa gcaagcgaat ttgccgctaa aatggacgaa 2280
accgttgaat ttcatcacag ctatattcgt gaacatggtg aggatattcc ggaagttgtt 2340
agctggcagt gggaaaatgt gaacaaa 2367

<210> SEQ ID NO 84
<211> LENGTH: 2388
<212> TYPE: DNA
<213> ORGANISM: Mycoplasma hominis ATCC 23114

<400> SEQUENCE: 84
atgattagca aaatctatga tgataaaaag tatctggaaa aaatggataa atggtttcgc 60
gcagcaaatt atctgggtgt ttgtcagatg tatctgcgtg ataatccgct gctgaaaaaa 120
ccgctgacca gcaatgatat caaactgtat ccgattggtc attggggcac cgttccgggt 180
cagaatttta tctataccca tctgaatcgc gtgatcaaga aatatgatct gaatatgttc 240
tacatcgaag gtcctggtca tggtggtcag gttatgatta gtaatagcta tctggatggc 300
agctatagcg aaatttatcc ggaaattagc caggatgaag caggtctggc caaaatgttt 360
aaacgtttta gctttccggg tggcaccgca agccatgcag caccggaaac accgggtagc 420
attcatgaag gtggtgaact gggttatagc attagccatg gcaccggtgc aattctggat 480
aacccggatg ttatttgtgc agcagttgtt ggtgatggtg aagcagaaac cggtccgctg 540
gcgaccagct ggtttagcaa tgcctttatt aacccggtta atgatggtgc cattctgccg 600
attctgcatc tgaacggtgg taaaattagc aatccgaccc tgctgagccg taaaccgaaa 660
gaagaaatca aaaaatactt tgaaggcctg ggctggaatc cgatttttgt tgaatggtca 720
gaagataaga gcaacctgga tatgcatgaa ctgatggcaa aaagcctgga taaagccatt 780
gaaagcatca aagaaattca ggcagaagca cgtaaaaaac ctgcagaaga agcaacccgt 840
ccgacctggc cgatgattgt tctgcgtacc ccgaaaggtt ggacaggtcc gaaacagtgg 900
aataatgaag caattgaagg tagctttcgt gcacatcagg ttccgattcc ggttagcgcc 960
tttaaaatgg aaaagattgc cgatcttgag aaatggctga aaagctacaa accggaagaa 1020
ctgtttgatg aaaatggcac gatcataaaa gaaatccgtg atctggctcc ggaaggtctg 1080
aaacgtatgg cagttaaccc gattaccaat ggtggtattg atagcaaacc tctgaaactg 1140
caggattgga aaaagtacgc actgaaaatt gattatccgg gtgaaattaa agcacaggat 1200
atggccgaaa tggccaaatt tgcagcagat atcatgaaag ataaccctag cagctttcgc 1260
gtttttggtc cggatgaaac caaaagcaat cgtatgtttg ccctgtttaa tgtgaccaat 1320
cgtcagtggc tggaaccggt tagtaagaaa tacgatgaat ggattagtcc ggcaggtcgc 1380
attattgatt cacagctgag cgaacatcag tgtgaaggtt ttctggaagg ttatgttctg 1440
accggtcgtc atggtttttt tgcaagctat gaagcatttc tgcgtgttgt ggatagcatg 1500
ctgacccaac atatgaaatg gatcaaaaag gcaagcgaac tgagctggcg taaaacctat 1560
ccgagcctga acattattgc aaccagtaat gcatttcagc aggatcataa tggttatacg 1620
catcaggatc cgggtctgct gggtcatctg gcagataaac gtccagaaat tatccgtgaa 1680
tatctgcctg cagataccaa tagcctgctg gcggttatga ataaagcact gaccgaacgt 1740
aatgtgatta atctgattgt tgcaagcaaa cagcctcgcg aacagttttt taccgttgaa 1800
gatgcagagg aactgctgga aaagggttat aaagttgttc cgtgggcaag caatattagc 1860
gaaaatgaag aaccggatat tgtgtttgcc agcagcggtg ttgaaccgaa tatcgaaagt 1920
ctggcagcaa ttagcctgat caatcaagaa tatcctcatc tgaaaatccg ctatgtgtat 1980
gtgctggatc tgctgaagct gcgtagtcgt aaaatcgatc cgcgtggtat tagtgatgaa 2040
gagtttgata aagtgtttac caaaaacaaa ccgattatct ttgcctttca tggctttgag 2100

```
ggactgctgc gcgatatttt ctttacccgt agcaaccata acctgattgc acatggttat   2160

cgtgaaaacg gtgatatcac aaccagcttt gatattcgtc agctgagtga gatggatcgt   2220

tatcatattg caaaagatgc tgccgaagcc gtgtatggta aagatgcaaa agcatttatg   2280

aacaaactgg atcagaaact ggaataccac cgcaactata tcgatgagta tggctatgat   2340

atgccggaag ttgtggaatg gaaatggaag aacatcaata aagaaaat                2388
```

<210> SEQ ID NO 85
<211> LENGTH: 2376
<212> TYPE: DNA
<213> ORGANISM: Mycoplasma crocodyli MP145

<400> SEQUENCE: 85

```
atgaaaaaaa ccgtgtatga taccgaactg tatattgaga aactggatgc atggtttcgt     60

gcagcaaatt atctgagcgt tggtcagatg tatctgcgta ataatccgct gctgcgtaac    120

aaaattacca aagatgatgt gaaagtgtat ccgattggtc attggggcac cattccgggt    180

cagaattttg catatgcaca tctgaatcgc gtgatcaaca aatatgatct gaatatgttc    240

tacatcgaag gtcctggtca tggtggtcag gttatgacca gcaatagcta tctggatggt    300

agctatacag aactgtttcc gcatgttacc caggatctgg acggtatgaa acacctgttt    360

aaatacttta gctttccggg tggcaccgca agccatgcag caccggaaac accgggtagc    420

attcatgaag gtggtgaact gggttatagc ctgagccatg ccaccggtgc aattctggat    480

aatccgaatg ttattgcagc aaccattgtt ggtgatggtg aaagcgaaac cggtccgctg    540

gcagcaggtt ggtttagcaa tagttttatc aatccggtta atgatggtgc cgttctgccg    600

attctgcatc tgaacggtgg taaaattagc aatccgacca ttctgtgtcg caaaagcaat    660

gaagaactga ccaactattt tctgggtatg ggttgggaag ccatttttgt tgaaggtgaa    720

gatgtgcaga aaatgcataa actgatggca accaaactgg actatgccat tgaacgtatt    780

ctgagcattc agaaagaagc ccgtaaaggt aaagcagaag aggccacccg tccgctgtgg    840

ccgatgattg ttctgcgtac ccccgaaaggt tggacaggtc cgcagaaatg gaatagcgat    900

cagattgtgg gtagctttcg tgcccatcag gttccgattc cggtgaatag tgaaaatatg    960

acccatattg atgccctggt tgattggctg aaaagctata atgttgataa cctgttcgat   1020

aaaaagggca aactggttcc ggaaattgcc gaaatcgcac cggtgggtga tcgtcgtatg   1080

ggtatgaatc cggtgaccaa tggtggcctg aatccgcgta atctggcact gccgaattgg   1140

caggattttg cactgaatct ggaaaaacct ggtgcaaaaa ttgcacagga tatggttgag   1200

ctgggttcct attttgcaaa agtgatggaa atgaataaag ataattttcg cctgttcggt   1260

ccggatgaaa ccaaaagtaa tcgtctgttt aacgtgttca aagttaccag ccgtcagtgg   1320

ctggaaccga ttaacccgct gtttgatgaa gcactgagtc cggcaggtcg tgttattgat   1380

agccagctga gcgaacatca ggcagaaggt tttctggaag gttatgttct gaccggtcgc   1440

catggtgttt ttgcaagcta tgaaagcttt ctgcgtgttg tggatagcat gctgacccag   1500

catatgaaat ggctgaagaa agcaaatgat gttagctggc gtaatgatta tccgagcctg   1560

aatgtgattg cgaccagcac cgcatttcag caggatcata atggttatac acatcaggat   1620

ccgggtctga ttggccatct ggcagataaa actccggaac tgattcgtca gtatctgcct   1680

gcagatacca ataccctgct ggcagttatg gataaaagcc tgaccgaacg taacgtgatt   1740

aaccatatca ttgcaagcaa acagcctcgc gaacagtttt atagcgcaaa agaagcagca   1800
```

gaactggttg aaaaaggtct gaaagtgatt aaatgggcaa gcaccgtgga aggtaatgat 1860
gaaccggatc tggttgttgc agcagcaggc accgaaccga acctggaagc cctggcagcc 1920
attacgattc tgaacaaaga atttccgaaa ctgaaaattc gcttcgtgaa tgtggttgac 1980
ctgatgaaac tgcgtcatcc gagcattgat ccgcgtggta ttaccgataa agaattcgac 2040
aaaatcttta cgaaagacaa gccggttctg tttgcctttc atggttatga aggtatcctg 2100
cgcgatatct tttcaaacg caataaccat aacctgatcg cacatggcta tcgtgaaaat 2160
ggtgatatca caaccagctt tgatattcgc cagctgtcac atatggatcg ttttcatatg 2220
gcagcaagcg cagcagttgc agcgctgggc aaaaaagcca atgcatttga aacaaaaatg 2280
ctggaaacca tcgattttca caccaaatat atccgcgaat acggcaccga tattccggaa 2340
gttaaagaat ggaagtggaa tcctctggtt cgcaaa 2376

<210> SEQ ID NO 86
<211> LENGTH: 2367
<212> TYPE: DNA
<213> ORGANISM: Neisseria sp. oral taxon 014 str. F0314

<400> SEQUENCE: 86
atgagcgcac agtatgatag cgcagattat ctgaataaag ttgatgcatg gtggcgtgca 60
gcaaactata ttagcgttgc acagatgtac ctgaaagata atccgctgct gatgcgtccg 120
attcaggcaa gtgatgttaa agcacatccg attggtcatt ggggcaccat tgcaggtcag 180
aattttatct atgcacatct gaatcgtgcc atcaacaaat atgatctgaa catgttctat 240
atcgaaggtc cgggtcatgg tggtcaggtt atggttagca atagctatct ggatggtagc 300
tatagcgaaa tctatccgaa tattacccag gatgaagcag gtctgaaaca gctgtgtaaa 360
atctttagct ttccgggtgg tattgcaagc catgcagcac cggaaacacc gggtagcatt 420
catgaaggtg gtgaactggg ttatgcactg agccatgccg ttggtgcagt tctggataac 480
ccggatgtta ttgcagcaac cgttattggt gatggtgaag cagaaaccgg tccgctgagc 540
gcaggttggt ttagcaatgt ttttatcaat ccggttaatg atggtgccgt gctgccgatt 600
ctgtatctga acggtggtaa aattcataac ccgaccattc tggcacgtaa aagtgatgaa 660
agcctgcgtc tgtattttga aggtctgggt tgggatccga tttttgttga agccaccgat 720
tatgcaacca cccataaagt tatggcacag aaactggatg aggccatcga aaaaatcaaa 780
gccattcaga ccaaagcacg tgcaggtaaa gccgaagagg cagttatgcc gaaatggcct 840
gttctggttg cacgtctgcc gaaaggttgg acaggtccga aagtgtggaa tggtgaaccg 900
attgaaggcg gttttcgtgc acatcaggtt cctattccgg caagcagcca tgatatggcc 960
accgttgata gcctggttga atggctgaaa agctatcgtc cggaagaact gtttgatgca 1020
aatggcacct ttaaagcaga actgcgtgaa attagcccga aaggcgatcg tcgtatgagc 1080
accaatccga ttaccaatgg tggcattaat ccgcgtcctc tgaataccgc agattggaaa 1140
aaattcgcac tggataatag cgatcgtggt agtattatgg cccaggatat gattgaattt 1200
ggcaaatatg cagccgaact ggttaaagcg aatccggata attttcgtat tttcggtccg 1260
gatgaaacca aaagcaatcg tatgaacgaa gtgttcaaag tgaccaatcg tcagtggctg 1320
gaaccgatcg ataaagcata tgatgaatgg atgagtccgg caggtcgtgt tattgatagt 1380
cagctgagcg aacatcaggc agaaggtttt ctggaaggtt atgttctgac cggtcgtcat 1440
ggtttttttg caagctatga aagctttctg cgtgttgtgg atagcatggc aacccagcac 1500
tttaaatggc tgcgtaaatg taaaacccat gcaccgtggc gtaaatcata tccgtcactg 1560
aatctgattg caaccagcac cgtttttcag caggatcata atggttatac ccatcaggat 1620
ccgggtatgc tgacccatct ggcagaaaaa aaaccggaat ttatccgtga atatctgcct 1680
gcagatgcca atagcctgct ggccgttatg agcgaagttc tgagcagcaa agataaagtg 1740
aacctgatcg ttagcagtaa acatcctcgt ccgcagtttt atagtgcagc agaagcggaa 1800
gaattagttc gtgaaggtta caaagttatc gattgggcaa gcaccgataa aggtggcgaa 1860
ccggatgtgg ttattgccgc agccgcaaca gaaccgaatc tggaagcact ggcagcaatt 1920
acaattctga acaaacagtt tccggaactg aaaatccgct ttattaacgt ggtggatatt 1980
ctgaaactgc gtcatcctaa agtggatccg cgtggtctga ccgatgaaca gttcgatgca 2040
ctgtttacca aagacaaacc ggtgattttt tgctttcatg gctatgaagg tatggtgcgc 2100
gatatctttt ttgatcgcca taaccataat ctgcgcatcc atggttatcg tgaaaatggt 2160
gatattacca ccccgtttga tatgcgtgtt ctgagtgaaa tggatcgttt tcatgttgca 2220
aaagatgcag ccctggcagt ttatggtgac aaagcacagg attttgccaa aaaaatggac 2280
gataccctgg catttcatca cagctatatt cgcgaaaatg gcgaagatat tccggaagtt 2340
cgtaattgga aatgggaagc cctgaaa 2367

<210> SEQ ID NO 87
<211> LENGTH: 2364
<212> TYPE: DNA
<213> ORGANISM: Eremococcus coleocola ACS-139-V-Col8

<400> SEQUENCE: 87
atgaccgtgg actacaacag caaagaatat ctgaccctgg ttgataaatg gtggcgtgca 60
gcaaattatc tgagcgttgg tcagatgttt ctgcgtgata atccgctgct gcaagaagag 120
gttaccgcag atcatgttaa actgaatccg attggtcatt ggggcaccat tggtggccag 180
aattttctgt atgcacatct gaatcgcatt atcaacaagt ataatgtgaa tatgttttat 240
atcgaaggcc ctggtcatgg tggtcaggtt atggttacca atagctatct ggatggtagc 300
tataccgaac gttatccgga atttacccag gatattgccg gtatgaaaaa actgtttaaa 360
accttcagct ttccgggtgg tattggtagc catgcagcac cggaaacacc gggtagcatg 420
catgaaggtg gtgaactggg ttatgcactg agccatgcca ccggtgcaat tctggataac 480
ccggatgtta ttgcagcaac cgttgttggt gatggtgaag cagaaaccgg tccgctggca 540
gcaggttggt ttagcaatgt ttttatcaat ccggtttcag atggtgcagt tctgccgatt 600
ctgtatctga atggtggtaa aattgcaaac ccgaccattc tggcacgtaa aagcaatgag 660
gatctgacca aatatttcga aggtatgggt tggaaaccgt atattgttga aggcaccgat 720
ccggaacagg ttcatccgat tatggcaaaa gttctggatg aagtgattga agaaattcag 780
gccattcagg cagaagcccg taaaggtaaa gccgaagatg caaaaatgcc gcattggccg 840
atgatcctgt atcgtacccc gaaaggttgg acaggtccgg aagaagttga aggtaaaaca 900
attcagggta gctttcgtgc acatcaggtt ccgattccgg ttagcggtcg taatatggaa 960
gatattgatc tgctgatcaa ctggctgaaa agctatggtc ctgaagaact gttcaccgaa 1020
aatggcgaac tggtagatga actgaaagaa tttgcaccga aaggcgatca tcgtatggca 1080
atgaacccgc tgaccaatgg cggtaatccg aaaccgctga atatgccgaa ttggaaagat 1140
tatgccctgg aaattggcac ccctggtagc aaagatgcac aggatatgat tgaatttggt 1200
ggttttgcgc gtgatatcgt gaaagaaaat ccggaaaact ttcgcatttt tggtccggat 1260

```
gaaaccaaaa gtaatcgcct gaataaagtg tttgaagtga ccaatcgtca gtggctggaa   1320

ccgattagcg aaaaatttga tgaaaacatg tcagcaagcg gtcgcgttat tgatagccag   1380

ctgagcgaac atcagaatca gggttttctg gaagcatatg ttctgaccgg tcgtcatggt   1440

ttttttgcaa gctatgaaag ctttttttcgt acggtggata gcatgattac ccagcacttt   1500

aaatggattc gcaaaagcgc aaaacatagc tggcgtaaac cttatcagag cctgaatctg   1560

attagcgcaa gcaccgtttt tcagcaggat cataatggtt atacccatca ggatccgggt   1620

ctgctgaccc atattggtga aaaacacggt gaatatatgc gtgcatatct gcctgcagat   1680

accaattcac tgctggcagt tatggataaa gcatttcgca gcgaaaacgt gattaactat   1740

gttgtgacca gcaaacatcc gcgtccgcag ttttttacag cagatgaagc cgaggaactg   1800

gttaatgaag gtctgaaagt tatcgattgg gccagtaccg ttaaagataa tgaagaaccg   1860

gatgtggtta ttgccgcagc cggtacagaa ccgaattttg aagcaattgc agcgatttcc   1920

tatctggtta aagcctttcc ggaactgaag attcgttttg ttaatgtggt tgacctgttt   1980

cgtctgcgta gtccggaaat tgatccgcgt ggtctgagtg atgatgaatt cgatgcaatc   2040

ttcaccaaag ataaaccggt gtttttttgcc tttcatagct acgaaggcat gctgaaagac   2100

atcttttttta cccgtcataa ccataatctg tacgcccatg gttatcgtga gaatggtgaa   2160

attaccaccc cgtttgatat gcgcgttctg aatgaactgg atcgttttca tctgagtgca   2220

catgttgcag atgttgtgta tggtgataaa gcccgtgatt atgttgccga aatgaaaggg   2280

aaagttcaag aacatcgtga ttacgtggaa gaatatggtg ccgatatgcc ggaagtagaa   2340

gattggaaat gggaggatat caaa                                          2364
```

<210> SEQ ID NO 88
<211> LENGTH: 2367
<212> TYPE: DNA
<213> ORGANISM: Aerococcus urinae ACS-120-V-Col10a

<400> SEQUENCE: 88

```
atgaccgact ttgacagcaa agcctatctg gataaagttg atgcatggtg gcgtgcagca     60

aattatctga gcgttggtca gatgtatctg cgtgataatc cgctgctgga tcgtgaagtt    120

accgcagatg atatcaaaat taccccgatt ggtcattggg gcaccattgc aggtcagaat    180

tttgtttatg cacatctgaa tcgcgtgatc aacaaatatg atctgaatat gttctacatc    240

gaaggtccgg gtcatggtgg tcaggttatg caggcaaatg catacctgga tggcacctgg    300

accgaacatt atccggaata tccgcagaat aaagaaggca tgcagaagtt cttcaaatat    360

ttcagctttc cgggtggcac cggtagccat gcaaccgcag aaattccggg tagcattcat    420

gaaggtggtg aactgggtta tagcctgagt catgccaccg gtgcaattct ggacaatccg    480

gatgttattg cagcaaccgt tattggtgat ggtgaaagcg aaaccggtcc gctggcagca    540

agctggctga gcaatagctt tattaacccg gttaccgatg gtgcagttct gccgattctg    600

tatctgaatg gtggtaaaat tgcaaacccg accattctgg aacgtaaaag caatgaagat    660

ctgattaaat actttcaggg tctgggttgg gatccgatgg ttgttgaagg taatgatccg    720

gaaaaagttc atccgctgat ggcaaaaacc ctggatcagg caattgaaaa aatcaaaagc    780

attcagggtg aagcccgtaa aggtagtgca gatgaagcaa ccatgggcca ttggccgatg    840

atcctgtatc gtaccccgaa aggttggaca ggtccgaaag catgggaagg caatgatatt    900

gaaggttcat ttcgtgcaca tcaggttccg attccggtta atgcagaaaa tatggaacat    960

gtggatgccc tgattgattg gctgaaaagc tatcgtccgg aagaactgtt taccgaagaa   1020
```

```
ggtcagctgc gtcctgaaat tgccgaaatt gcaccgaaag gcgatcagcg tatggcaagc   1080
aatccgatta cagatggtgg cattgatccg aaaccgctgg acctgccgga ttggcgtgat   1140
tatgcactgg attttgaaac accgggtgaa cgtgatgcac aggatatgat tgaaatgggt   1200
ggttatgccg caggcgttat cgaaaaaaat cctgataact ttcgcatctt cggtccggat   1260
gaaaccaaaa gtaatcgtct gaacaaagtg ttcaatgtga ccaaacgtca gtggctggaa   1320
ccgattaaag ataactatga tgaatggatg agcccgagcg gtcgtgttat tgatagccag   1380
ctgagcgaac atcagatgga aggttttctg gaagcatata ccctgaccgg tcgtcatggt   1440
tttttgcaa gctatgaagc atttattcgt accgtggata gcatgattac ccagcacttt   1500
aaatggatgc gcgaagcaag cgagtataaa tggcataaac cgtatcagag cctgaacctg   1560
attagcagca gcaccgcatt tcagcaggat cataatggtt atacccatca ggatccgggt   1620
ctgctgaccc atctggcaga aaaaaaaggt gaatttgtgc gtgcatatct gcctgcagat   1680
accaatagcc tgctggcagt tatggacaaa gcactgagca gcgaaaatgt gattaactat   1740
attgtgacca gcaaacatcc gcgtccgcag ttttttagcg ttgaagaagc agaagagttc   1800
gtcgataaag gctataaagt tatcgattgg gcaagcaccg tggaagaggg cgaagaaccg   1860
gatgtggtga ttgcagccag cggcaccgaa ccgaccgttg aaaccattgc caccattagc   1920
tatctgcatg aagcctttcc ggaactgaaa attcgttatg ttaatgtggt ggatctgtat   1980
cgcctgcgtc atccgaatat cgatccgcgt ggtctgagtg atgaagaatt tgatgccgtt   2040
ttcaccaaag ataaaccggt gtttttggc tttcatagct ttgaaggcct gctgaaagat   2100
atcttctttg atcgccataa ccataacctg tatccgcatg gttatcgtga ggaaggtgcc   2160
attaccaccc cgtttgatat gcgtgttctg aatgaactgg atcgctttca ttttgcagca   2220
catgttgccg aagttgtgta tggtgataaa gcccaggatt ttatcgatca gatgaatgcc   2280
aaagtggaag aacatcgtgc gtatattgtt gaatatggca ccgatatgcc ggaagtgaaa   2340
gaatggaaat ggcagccgct ggaaaaa                                        2367
```

<210> SEQ ID NO 89
<211> LENGTH: 2376
<212> TYPE: DNA
<213> ORGANISM: Kingella kingae ATCC 23330

<400> SEQUENCE: 89

```
atgaccaaca aaacccagtt cgacacaccg gaatatctgg gtaaagttga tgcatggtgg     60
cgtgcagcaa actatattag cgttgcacag atgtatctga aagataatcc gctgctgaaa    120
acaccgctgg ttgcaaatga tgttaaagca catccgattg gtcattgggg caccgttccg    180
ggtcagaatt ttatctatgc acatctgaat cgtgccatca acaaatatga tgtggacatg    240
ttttatatcg aaggtcctgg tcatggtggt caggttatgg ttagcaatag ctatctggat    300
ggtagctata ccgaaatcta tccggatatt acccaggata ccgcaggtct gaaaaaactg    360
tgtaaaatct ttagctttcc gggtggtatt gcaagccatg cagcaccgga aacaccgggt    420
agcattcatg aaggtggtga actgggttat gcactgagcc atgcctttgg tgcagttctg    480
gataacccga atgttattgc agcagcagtt attggtgatg gtgaagcaga aaccggtccg    540
ctgtgtgcag gttggtttgg taataccttt attaacccgg ttaatgatgg tgccgtgctg    600
ccgattctgt acctgaatgg tggtaaaatt cataatccga ccattctggc acgtaaaacc    660
gatgaagaac tgaaacagta ttttaacggt atgggttggg aaccgatttt tgtggatgtt    720
```

```
aacaacgtgg ataactatca cgaaattatg agccagaaag tggatgaagc cgttgaacat    780
attctgagca tttggcagac cgcacgtacc cagaaagccg aagatgcaac catgccgcat    840
tggcctgttc tggttgcccg tattccgaaa ggttggacag gtccgaaaac ctggcatggc    900
gaaccgatcg aaggcggttt tcgtgcacat caggttccga ttccggcaag cagccatgat    960
atggaaaccg caggcgaact ggaaaaatgg ctgcgtagct atcgtccgga agaacttttt   1020
gatgataatg gttgcttcct ggataagtgg cgtgatatta gcccgaaagg cgcaaaacgt   1080
atgagcgttc atccgatcac caatggtggc attaatccga aagcactggt tatgccggat   1140
tggacccagc atgcactgga aattggtgtt ccaggtagcc aggatgcaca ggatatggtt   1200
gaatgtggtc gtctgatggc agatgttgtt accgcaaatc cgaataactt tcgtattttt   1260
ggtccggacg aaaccaaaag caatcgtctg aatcaggttt ttcaggttac caaacgtcag   1320
tggctgggtc gccgtgatga agcatatgat gaatggattg caccggttgg tcgtgttatt   1380
gatagccagc tgagcgaaca tcaggcagaa ggtttttctgg aaggttatgt tctgaccggt  1440
cgtcatggtt tttttgcaag ctatgaaagc tttttttcgtg tggtggatag catgattacg  1500
cagcacttta aatggcttcg caaatgtaaa acccacgcag catggcgtaa tgattatccg   1560
agcctgaatc tgattgcaac cagcaccgtg tttcagcagg atcataatgg ctatacccat   1620
caggatccgg gtctgctgac ccatctggca gaaaaaaaac cggaatttgt gcgtgaatat   1680
ttaccggcag atagcaatac cctgatggcc gttatgagcg aagcactgac cagccgtgat   1740
cgtattaacc tgattgttag cagtaaacat ctgcgtccgc agtttttcaa tgcagaagaa   1800
gcaaaagaac tggttcgcga aggctataaa gtgattgatt gggcaagcac ctgtcatgac   1860
ggtgaaccgg atgttgtgat cgcagccgca ggcaccgaac cgaatatgga agccctggca   1920
gcaattagca ttctgcacaa acagtttccg gaactgaaga ttcgttttat caacgttgtg   1980
gatatcctga aactgcgtca tccgagcatt gatccgcgtg gtctgagtga tgaacagttt   2040
gatgcactgt ttacccaaga aaaacctgtg gtgttttgct ttcatggtta tgaaggtatg   2100
attcgcgacc tgttttttcc gcgtgcaaac cataatgttc gtattcatgg ctatcgcgaa   2160
aatggcgata ttacaacccc gtttgatatg cgtgttctgt cagaaatgga tcgttttcat   2220
gttgccaaag atgccgcaca ggcagtttat ggtgataaag caagcgaatt cgccaaaaaa   2280
atgggtgaaa ccgttgcatt tcatcgttcc tatattcgtg aacatggcac cgatattccg   2340
gaagttgcag aatggaaatg gcagccgctg gccaaa                             2376
```

<210> SEQ ID NO 90
<211> LENGTH: 2382
<212> TYPE: DNA
<213> ORGANISM: Streptococcus criceti HS-6

<400> SEQUENCE: 90

```
atgaatacca acttcgatag cagcgattac ctgaataaag ttgatgcatg gtggcgtgca     60
gcaaactata ttagcgcagc acagatgtat ctgaaagata atccgctgct gcgtcgtgaa    120
gttgcagcag aagatctgaa aagccatccg attggtcatt ggggcaccgt tccgggtcag    180
aattttatct atgcacatct gctgcgctcc atcaacaaat atgatctgga tatgttctat    240
atcgaaggtc ctggtcatgg tggtcaggtt atggttagca atagctatct ggatggtagc    300
tataccgaac tgaatccgca gattagccag accgaagagg gtctgaaaca gctgtgtaaa    360
atctttagct ttccgggtgg tattgcaagc catgcagcac cggaaacacc gggtagcatt    420
catgaaggtg gtgaactggg ttatgcactg agccatgcca ccggtgcagt tctggataac    480
```

```
ccggatgtta ttgcagcaac cgttattggt gatggtgaaa gcgaaaccgg tccgctgatg     540

gcaggttggc tgagcaatac ctttattaac ccggttaatg atggtgccgt tctgccgatt     600

cattttctga atggtggcaa aattcataat ccgaccatct ttgaacgtaa aagcgacgat     660

gaactgaaag cctttttttac cggtctgggt tggaaaccga tttttgcaga tgttaccgca     720

tttgcaagcg atcatgcagc cgcacataaa ctgtttgcag ccaaactgga tgaagccatt     780

gaagaaattc gtaacattca ggcaaaagcc cgtaaaggta gcgcagatga agcaaccatg     840

cctgcatggc ctgttattgt tgcacgtatt ccgaaaggtt ggacaggtcc gaaaagctgg     900

aaaggcaccc cgattgaagg cggttggcgt gcccatcagg ttccgattcc ggttgatagc     960

catcatatgg aacatgttga tgccctgctg gattggctga aaagttatca gccggaagaa    1020

ctgttcgatg cagaaggtca tctgaaatca gaagtggcag ccctgagccc gaaaggcaat    1080

cgtcgtatga gcatgaatcc gattaccaat gccggtgtta ttaaaccgat ggatacagcc    1140

gattggaaaa aacgtgcatt tgatattcag acccctggtg aaattgttgc ccaggatatg    1200

attgaatttg gcaaatatgc cgcagatctg gttgaagcaa atccggataa ttttcgtatt    1260

tttggtccgg atgaaagcaa aagcaatcgc ctgaatgaag tgtttaccaa aaccaatcgt    1320

cagtggatgg gtcgtcgtga tccgagctat gatgaatggc tgagtccggc aggtcgtgtt    1380

attgatagtc agctgagcga acatcaggcc gaaggttttc tggaaggtta tgttctgacc    1440

ggtcgtcatg gtttttttgc cagctatgaa agctttctgc gtgttgtgga taccatgatt    1500

acccagcact ttaaatggct gcgtaaaagt aaaacccata ccacctggcg taaaaactat    1560

ccgagcctga atctgattgc aaccagcacc gtttttcagc aggatcataa tggttataca    1620

catcaggatc cgggtgtgct gacccatctg agtgaaaaaa ctccggaata tatccgtgaa    1680

tatctgcctg cagataccaa tagcctgctg gcggttatgg ataaagcatt taaagatgag    1740

gacaaaatta acctgatcgt gaccagcaaa catccgcgtc cgcagtttta tagcgttgaa    1800

gaagcaagcg aactggtcga aaaaggctat aaagtgattg attgggcaag caccgtgcag    1860

gcaaatgaag aaccggatgt ggtttttgcc gcagcaggca cagaaccgaa tctggaagca    1920

ctggcagcaa ttagcattct gcacaaaacc tttccgagtc tgaaaattcg ttttgtgaac    1980

gtggtggata ttctgaaact gcgtcatccg gacctggatc cgcgtggtct gtctgatgaa    2040

gaatttgata aagtgttcac gaaagacaag ccggtgatct ttgcatttca tgcatatgaa    2100

ggtatgatcc gcgatatctt ttttcgtcgc cataaccata atctgcatgt gcatggttat    2160

cgcgaaaatg gtgatattac caccccgttt gatatgcgtg ttatgtcaga actggatcgt    2220

tttcatctgg cacaggatgc cgcactgacc accctgggtg aaaaagcaca ggcatttagc    2280

gcaaaaaatgg atgaaaccgt tgcctatcac aaagattata ttcgtgaaca tggggatgat    2340

attccggaag tgcagaattg gcagtgggaa aatctggacg aa                       2382
```

```
<210> SEQ ID NO 91
<211> LENGTH: 2361
<212> TYPE: DNA
<213> ORGANISM: Streptococcus criceti HS-6

<400> SEQUENCE: 91
```

```
atgaccgagt tcgacagcaa agattatctg gcaaaagttg atgcatggtg gcgtgcagca      60

aactatatta gcgttgcaca gatgtatctg aaagataatc cgctgctgcg tcgtgaagtt     120

agcaaagaag atgttaaagt tcatccgatt ggtcattggg gcaccattgc aggtcagaat     180
```

```
tttatctatg cacatctgaa tcgcgtgatc aacaaattcg atctgaacat gttttatatc    240
gaaggtccgg gtcatggtgg tcaggttatg gttagcaata gctatattga tggcagctat    300
accgaacgct atccgaatat tacccaggat gaagatggtc tgaaacagct gtgtaaaatc    360
tttagctttc cgggtggtat tgcaagccat gcagcaccgg aaacaccggg tagcattcat    420
gaaggtggtg aactgggtta tgcactgagc catgccaccg gtgcaattct ggataacccg    480
gatgttattg cagcaaccgt tattggtgat ggtgaagcag aaaccggtcc gctgaatgca    540
ggttggttta gtaatacctt tattaacccg gttaatgatg gtgcagttct gccgattctg    600
tacctgaatg gcggtaaaat tcataatccg accattctga gccgtaaaac cgatgaagaa    660
ctgacccacc tgtttcaggg tctgggttgg gaaccgtatt ttgttgaagg taatgatccg    720
gaagttatcc atagccagat ggccgaaacc ctggataaag ttatcgaaaa aatcaagacc    780
attcagaccc aggcacgtca gaaacctgca gaagaggcac agcaggcaca gtggcctgtt    840
ctgattgttc gtaccccgaa aggttggaca ggtccgaaag aatggaatgg tgaaccgatt    900
gaaggcggtt ttcgtgcaca tcaggttccg attccggttg aagcaggtca tatggaacat    960
atcgatgccc tgaccgattg gctgaaaagc tatcgtccgg aagaactttt tgatgagaaa   1020
ggctatgtga aagaagagat tcgcgttatt tcaccgaaag gcaatcgtcg tatgagcatg   1080
aatccgatta ccaatgccgg tattgtgaaa aaactggatc tggcagattg gcgtaaacat   1140
gcaattgata ccagcaaacc gggttccatt atgaaacagg atatgatcga attcggcaaa   1200
tatgcagcag atctggttaa agcaaatccg gataactttc gtattttcgg tccggatgaa   1260
accaaaagca atcgcctgaa taatgttttt accgcaacca atcgtcagtg gctggcaccg   1320
cgtgataaaa gttatgatga atggattagt ccggtgggtc gtgttattga tagtcagctg   1380
agcgaacatc aggcagaagg ttttctggaa ggttatgttc tgaccggtcg tcatggtttt   1440
tttgcaagct atgaaagctt tctgcgtgtt gtggatagca tgattacaca gcactttaaa   1500
tggctgcgta aaagcaaaac ccatacggat tggcgcaaaa actatccgag cctgaatctg   1560
attgcaacca gcaccgtttt tcagcaggat cataatggtt atacccatca ggatccgggt   1620
ctgctgaccc atctggcgga aaaaacccca gaatatgttc gtgaatatct gcctgcagat   1680
tccaatagcc tgtttgcagt tatggaatat gccctggcag acgaagataa agtgaatgtg   1740
attgtgacca gtaaacatcc gcgtccgcag ttttatagcg tggcagaagc acaagaactg   1800
gtaaaagaag gctacaaagt aattgattgg gccagcaatg atcatgatgg cgaaccggat   1860
attgtttttg cagccgcagg caccgaaccg aatctggaag ttctggcagg tattagcctg   1920
ctgcacaaag catttccaga agtgaaaatt cgctttatca acgtggtgga tattctgaaa   1980
ctgcgcagcc cgaaagtgga tccgcgtggt ctgagtgatg aagcatttaa caaactgttc   2040
accaccgata aaccgatcgt tttgcctat catggttatg aaggtcagat tcgtgacctg    2100
tttttttaacc gcgataacca caaagtgtat atccatggct atcgcgaaaa tggtgatatt   2160
accaccccgt ttgatatgcg tgttatgagc gaaatggatc gctttcatat tgcaaaagaa   2220
gcagcacagg ccgttctggg tgataaagca cagggttttg cccaagaaat ggcagataaa   2280
ctggcatatc ataccgccta tattcgtgaa catggtgatg atatcccgga agtgcagaat   2340
tggcagtggg aaaccattga t                                             2361
```

<210> SEQ ID NO 92
<211> LENGTH: 2382
<212> TYPE: DNA
<213> ORGANISM: Mycoplasma columbinum SF7

<400> SEQUENCE: 92
atgagcaaaa ccaattttga tagcaaaaaa tacctggata agatccatgc atggtggcgt 60
gcagcaaatt atctgagcgt tggtcagatg tatctgaaaa ataacccgct gctgcaagaa 120
ccgctgaaag atgaagatat caaaatctat ccgattggtc attggggcac cattccgggt 180
cagaatctga tttatgcaca tctgaatcgc gtgatcaaca aatatgatct gaatatgttc 240
tacatcgaag gtcctggtca tggtggtcag gttatgatta gcaatagcta tctggatggt 300
agctataccg aactgtttcc ggaaattacc caggatctgg caggtctgaa taaaatgttt 360
aaacgcttta gctttccggg tggcaccgca agccatgcag caccggaaac accgggtagc 420
attcatgaag gtggtgaact gggttatgca ctgagccatg ccaccggtgc aattctggat 480
aatccggatg ttattgcagc aaccgttatt ggtgatggtg aagcagaaac cggtccgctg 540
atggcaggtt ggtatagcag cagctttatt aacccggtta atgatggcac cgttctgccg 600
attctgcata ttaatggtgg taaaattagc aacccgacca ttctggcacg taaaaccgat 660
aaagaaatta aacagctgct ggcaggcttt ggttgggaag caatttttgt tgaagccgat 720
gtttttcgtc cggaagccat tcatctgagc atggcaaaag catttgataa agccatcgaa 780
aaaattcagc gtattcagcg cgaagcacgt gcaaatagcg caaatcatgc aaaacgtccg 840
atttggcctg cactggttgt tcgtaccccg aaaggttgga cctgtccgca taaaattgat 900
gataaagtgt atgaaggtag ctttcgtagc catcaggttc cgctggcagt tagcagcgaa 960
aataccacca aaaaagttga tctggtgaat tggctggaaa gctataaacc gcgtgaactg 1020
ttcaatcagg atggttcatt taaagcccat tatgccgaaa ttgcaccgaa aggcaataaa 1080
cgtatggcaa tgaatccgat taccaacggt ggtattaatc cgaaaaatct ggatctgccg 1140
aattgggaac agtttgccat tgatttcgat aaaccgggtg ccattaaagc acaggatatg 1200
gttagcgcag gcacctggtt tgcagatgtg attaaacgta atccgaccaa ctttcgtatc 1260
tttggtccgg atgaaaccaa aagcaatcgt ctgtttgatg tgctgaaaac caccaatcgt 1320
cagtggttag aacgtgttga ttatgacctg gatgaaaaca tcggtccggc aggtcgtgtt 1380
attgatagcc agctgagcga acatcaggca gaaggttttc tggaaggtta tgttctgacc 1440
ggtcgtcatg gtatgtttgc aagctatgaa agctttctgc gtgttgtgga tagcatgctg 1500
acccagcata tgaaatgggt tgcaaaagcg aaaaaagtgc attggcgtaa tgattatccg 1560
agcctgaatg tgattgcaac cagcaccgca tttcagcagg atcataatgg ttatacacat 1620
caggatccgg gtattctggg tcatctggcc gataaaaaac cggaactgat tcgtgaatat 1680
ctgcctgcag atagcaatac cctgctggcc gtgctggata aagcttttaa agaacgtgat 1740
gtcatcaacc tgattgtggc aagcaaacag cctcgtgaac agtggtttag cccacgtgaa 1800
gcaaatattc tggttaaaaa tgggctgaaa gttattagct gggcaagcac ctgtaccctg 1860
gaagaagaac cggatctggt tgtggcagca gcaggtacag aaccgacact ggaagcactg 1920
gcagcaatta gttatctgaa tgaaaaattc ccgaccctga aaatccgttt tgttaatgtt 1980
gtagacctgc tgaaactgcg tcatccgagc attgatccgc gtggtctgag caattatgaa 2040
ttcgatagca tctttaccaa ggacaaaccg atcctgtttg cctttcatgg ttatgaagcc 2100
ctgattcgcg atattttctt cctgcgcaat aaccataatc tgcacattca tggctatcgc 2160
gaaaatggtg atattaccac gagctttgat attcgtctga tgagcgaaat ggatcgtttt 2220
catatggcac agaccgcagc aaaagccgtt ctgggttacg ataaagcaaa aagcttcgtc 2280

```
gataaaatgc aggacaaaat cgatcagcat aatgcctaca tcaaagaaca tggcatcgat   2340

atggatgaag ttcgctattg gacatggaaa ggcctgaaca aa                      2382


<210> SEQ ID NO 93
<211> LENGTH: 787
<212> TYPE: PRT
<213> ORGANISM: Enterococcus gallinarum

<400> SEQUENCE: 93

Met Glu Thr Thr Phe Asp Thr Gln Glu Tyr Phe Asp Lys Met Asn Ala
 1               5                  10                  15

Trp Trp Arg Ala Ala Asn Tyr Leu Ser Val Gly Gln Ile Tyr Leu Lys
            20                  25                  30

Asp Asn Pro Leu Leu Arg Arg Pro Ile Glu Glu Lys Asp Leu Lys Val
        35                  40                  45

Asn Pro Ile Gly His Trp Gly Thr Ile Ala Gly Gln Asn Phe Ile Tyr
    50                  55                  60

Thr His Leu Asn Arg Val Ile Asn Lys Tyr Asp Leu Asn Met Phe Tyr
65                  70                  75                  80

Ile Glu Gly Pro Gly His Gly Gly Gln Val Met Val Ser Asn Ala Tyr
                85                  90                  95

Leu Asp Gly Ser Tyr Thr Glu Ile Tyr Pro Glu Val Thr Gln Asp Glu
            100                 105                 110

Ala Gly Met Gln His Leu Phe Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ala His Gly Thr Gly Ala Val Leu Asp Asn
145                 150                 155                 160

Pro Asp Val Ile Ala Ala Val Val Val Gly Asp Gly Glu Ala Glu Thr
                165                 170                 175

Gly Pro Leu Ala Gly Ser Trp Phe Ser Asn Thr Phe Ile Asn Pro Val
            180                 185                 190

Asn Asp Gly Ala Val Leu Pro Ile Leu His Leu Asn Gly Ala Lys Ile
        195                 200                 205

Ser Asn Pro Thr Ile Leu Ala Arg Lys Ser Asp Glu Asp Leu Thr Lys
    210                 215                 220

Tyr Phe Glu Gly Met Gly Trp Thr Pro Tyr Phe Val Glu Gly Asp Asp
225                 230                 235                 240

Pro Ala Thr Val His Pro Gln Met Ala Arg Ala Leu Asp Arg Ala Val
                245                 250                 255

Glu Gln Ile Lys Ala Ile Gln Thr Lys Ala Arg Gln Gly Lys Ala Asp
            260                 265                 270

Glu Ala Val Met Pro His Trp Pro Val Leu Ile Val Arg Thr Pro Lys
        275                 280                 285

Gly Trp Thr Gly Pro Lys Ile Trp Glu Gly Glu Pro Ile Glu Gly Gly
    290                 295                 300

Phe Arg Ala His Gln Val Pro Ile Pro Val Asn Ala His Gln Met Glu
305                 310                 315                 320

His Val Asp Ala Leu Ile Asp Trp Leu Lys Ser Tyr Lys Pro Glu Glu
                325                 330                 335

Leu Phe Asp Glu Ser Gly Arg Ile Lys Ala Glu Ile Gln Glu Leu Ala
            340                 345                 350

Pro Lys Gly Gln Gln Arg Met Ala Met Asn Pro Ile Thr Asn Gly Gly
```

```
        355                 360                 365

Ile Asp Pro Gln Pro Leu Lys Ile Thr Asp Trp Arg Gln His Ala Ile
    370                 375                 380

Asp Ile Gly Val Pro Gly Ser Thr Thr Ala Gln Asp Met Met Glu Phe
385                 390                 395                 400

Gly Lys Phe Ala Arg Asp Leu Ile Val Glu Asn Pro Thr Asn Phe Arg
                405                 410                 415

Ile Phe Gly Pro Asp Glu Ala Lys Ser Asn Arg Leu Asn His Val Phe
            420                 425                 430

Glu Val Thr Asn Arg Gln Trp Leu Glu Pro Lys Gln Pro Asn Tyr Asp
        435                 440                 445

Glu Trp Leu Ser Ala Thr Gly Arg Val Ile Asp Ser Gln Leu Ser Glu
    450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ile Thr Gln His Phe Lys Trp Thr Arg Lys Ser Lys Glu Leu Pro Trp
            500                 505                 510

Arg His Ala Tyr Pro Ser Leu Asn Leu Ile Ala Ser Ser Thr Val Phe
        515                 520                 525

Gln Gln Asp His Asn Gly Tyr Thr His Gln Asp Pro Gly Ile Met Thr
    530                 535                 540

His Ile Ala Glu Lys Lys Ala Glu Phe Val Arg Val Tyr Leu Pro Ala
545                 550                 555                 560

Asp Ala Asn Ser Leu Met Ala Val Met Ala Glu Thr Phe Gln Thr Glu
                565                 570                 575

Glu Gln Ile Asn Leu Ile Val Ser Ser Lys His Pro Arg Pro Gln Phe
            580                 585                 590

Tyr Thr Ala Glu Glu Ala Glu Ile Leu Val Lys Asp Gly Leu Lys Ile
        595                 600                 605

Ile Asp Trp Ala Ser Thr Asp Gln Gly Glu Pro Asp Leu Val Ile Ala
    610                 615                 620

Ala Ala Gly Thr Glu Pro Asn Leu Glu Ala Leu Ala Ala Val Ser Leu
625                 630                 635                 640

Leu Asn Glu Ala Phe Pro Glu Leu Lys Ile Arg Phe Ile Asn Val Val
                645                 650                 655

Asp Leu Leu Lys Ile Arg His Pro Asp Val Asp Pro Arg Gly Leu Thr
            660                 665                 670

Asp Glu Glu Phe Glu Ala Tyr Phe Thr Lys Asp Lys Pro Ile Ile Phe
        675                 680                 685

Ala Phe His Gly Tyr Glu Gly Leu Ile Arg Asp Ile Phe Phe Gly Arg
    690                 695                 700

Lys Asn Gln Arg Leu His Ile His Gly Tyr Arg Glu Asn Gly Asp Ile
705                 710                 715                 720

Thr Thr Pro Phe Asp Met Arg Ile Leu Ser Glu Leu Asp Arg Phe His
                725                 730                 735

Leu Ala Lys Asp Gly Ala Glu Trp Val Tyr Gly Glu Gln Ala Ala Asp
            740                 745                 750

Phe Ala Gln Arg Met Thr Glu Thr Val Ala Tyr His Tyr Asp Phe Ile
        755                 760                 765

Arg Glu Asn Gly Tyr Asp Ile Ala Glu Val Gln Asp Trp Gln Trp Lys
    770                 775                 780
```

```
Pro Leu Lys
785


<210> SEQ ID NO 94
<211> LENGTH: 796
<212> TYPE: PRT
<213> ORGANISM: Clostridium acetobutylicum

<400> SEQUENCE: 94

Met Gln Ser Ile Ile Gly Lys His Lys Asp Glu Gly Lys Ile Thr Pro
 1               5                  10                  15

Glu Tyr Leu Lys Lys Ile Asp Ala Tyr Trp Arg Ala Ala Asn Phe Ile
            20                  25                  30

Ser Val Gly Gln Leu Tyr Leu Leu Asp Asn Pro Leu Leu Arg Glu Pro
        35                  40                  45

Leu Lys Pro Glu His Leu Lys Arg Lys Val Val Gly His Trp Gly Thr
    50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95

Gln Val Met Val Ser Asn Ser Tyr Leu Asp Gly Thr Tyr Ser Glu Val
            100                 105                 110

Tyr Pro Asn Val Ser Arg Asp Leu Asn Gly Leu Lys Lys Leu Cys Lys
        115                 120                 125

Gln Phe Ser Phe Pro Gly Gly Ile Ser Ser His Met Ala Pro Glu Thr
    130                 135                 140

Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
    210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Thr Met His Lys Leu Met
                245                 250                 255

Ala Glu Thr Leu Asp Ile Val Thr Glu Glu Ile Leu Asn Ile Gln Lys
            260                 265                 270

Asn Ala Arg Glu Asn Asn Asp Cys Ser Arg Pro Lys Trp Pro Met Ile
        275                 280                 285

Val Leu Arg Thr Pro Lys Gly Trp Thr Gly Pro Lys Phe Val Asp Gly
    290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                325                 330                 335

Ser Tyr Lys Pro Glu Glu Leu Phe Asp Glu Asn Tyr Arg Leu Ile Pro
            340                 345                 350

Glu Leu Glu Glu Leu Thr Pro Lys Gly Asn Lys Arg Met Ala Ala Asn
```

```
        355                 360                 365

Leu His Ala Asn Gly Gly Leu Leu Leu Arg Glu Leu Arg Thr Pro Asp
    370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                405                 410                 415

Asn Glu Asp Thr Arg Asn Phe Arg Ile Phe Gly Pro Asp Glu Thr Met
            420                 425                 430

Ser Asn Arg Leu Trp Ala Val Phe Glu Gly Thr Lys Arg Gln Trp Leu
        435                 440                 445

Ser Glu Ile Lys Glu Pro Asn Asp Glu Phe Leu Ser Asn Asp Gly Arg
    450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                485                 490                 495

Phe Leu Arg Ile Val Asp Ser Met Ile Thr Gln His Gly Lys Trp Leu
            500                 505                 510

Lys Val Thr Ser Gln Leu Pro Trp Arg Lys Asp Ile Ala Ser Leu Asn
        515                 520                 525

Leu Ile Ala Thr Ser Asn Val Trp Gln Gln Asp His Asn Gly Tyr Thr
    530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
            580                 585                 590

Ser Lys His Pro Arg Gln Gln Trp Leu Thr Met Asp Gln Ala Val Lys
        595                 600                 605

His Val Glu Gln Gly Ile Ser Ile Trp Asp Trp Ala Ser Asn Asp Lys
    610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
            660                 665                 670

Glu Asn Glu His Pro His Gly Leu Ser Asp Lys Asp Tyr Asn Ala Leu
        675                 680                 685

Phe Thr Thr Asp Lys Pro Val Ile Phe Ala Phe His Gly Phe Ala His
    690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750

Asn Leu Pro Gln Leu Gly Asn Arg Gly Ala His Leu Val Gln Leu Met
        755                 760                 765

Asn Asp Lys Leu Val Glu His Asn Gln Tyr Ile Arg Glu Val Gly Glu
    770                 775                 780
```

Asp Leu Pro Glu Ile Thr Asn Trp Gln Trp His Val
785 790 795

<210> SEQ ID NO 95
<211> LENGTH: 2439
<212> TYPE: DNA
<213> ORGANISM: Listeria grayi

<400> SEQUENCE: 95
atggttaaag acattgtaat aattgatgcc ctccgtactc ccatcggtaa gtaccgcggt 60
cagctctcaa agatgacggc ggtggaattg ggaaccgcag ttacaaaggc tctgttcgag 120
aagaacgacc aggtcaaaga ccatgtagaa caagtcattt ttggcaacgt tttacaggca 180
gggaacggcc agaatcccgc ccgtcagatc gcccttaatt ctggcctgtc cgcagagata 240
ccggcttcga ctattaacca ggtgtgtggt tctggcctga aagcaataag catggcgcgc 300
caacagatcc tactcggaga agcggaagta atagtagcag gaggtatcga atccatgacg 360
aatgcgccga gtattacata ttataataaa gaagaagaca ccctctcaaa gcctgttcct 420
acgatgacct tcgatggtct gaccgacgcg tttagcggaa agattatggg tttaacagcc 480
gaaaatgttg ccgaacagta cggcgtatca cgtgaggccc aggacgcctt tgcgtatgga 540
tcgcagatga aagcagcaaa ggcccaagaa cagggcattt tcgcagctga aatactgcct 600
cttgaaatag gggacgaagt tattactcag gacgaggggg ttcgtcaaga gaccaccctc 660
gaaaaattaa gtctgcttcg gaccattttt aaagaagatg gtactgttac agcgggcaac 720
gcctcaacga tcaatgatgg cgcctcagcc gtgatcattg catcaaagga gtttgctgag 780
acaaaccaga ttccctacct tgcgatcgta catgatatta cagagatagg cattgatcca 840
tcaataatgg gcattgctcc cgtgagtgcg atcaataaac tgatcgatcg taaccaaatt 900
agcatggaag aaatcgatct ctttgaaatt aatgaggcat ttgcagcatc ctcggtggta 960
gttcaaaaag agttaagcat tcccgatgaa aagatcaata ttggcggttc cggtattgca 1020
ctaggccatc ctcttggcgc cacaggagcg cgcattgtaa ccaccctagc gcaccagttg 1080
aaacgtacac acggacgcta tggtattgcc tccctgtgca ttggcggtgg ccttggccta 1140
gcaatattaa tagaagtgcc tcaggaagat cagccggtta aaaaatttta tcaattggcc 1200
cgtgaggacc gtctggctag acttcaggag caagccgtga tcagcccagc tacaaaacat 1260
gtactggcag aaatgacact tcctgaagat attgccgaca atctgatcga aaatcaaata 1320
tctgaaatgg aaatccctct tggtgtggct ttgaatctga gggtcaatga taagagttat 1380
accatcccac tagcaactga ggaaccgagt gtaatcgctg cctgtaataa tggtgcaaaa 1440
atggcaaacc acctgggcgg ttttcagtca gaattaaaag atggtttcct gcgtgggcaa 1500
attgtactta tgaacgtcaa agaacccgca actatcgagc atacgatcac ggcagagaaa 1560
gcggcaattt ttcgtgccgc agcgcagtca catccatcga ttgtgaaacg aggtgggggt 1620
ctaaaagaga tagtagtgcg tacgttcgat gatgatccga cgttcctgtc tattgatctg 1680
atagttgata ctaaagacgc aatgggcgct aacatcatta acaccattct cgagggtgta 1740
gccggctttc tgagggaaat ccttaccgaa gaaattctgt tctctatttt atctaattac 1800
gcaaccgaat caattgtgac cgccagctgt cgcatacctt acgaagcact gagtaaaaaa 1860
ggtgatggta aacgaatcgc tgaaaaagtg gctgctgcat ctaaatttgc ccagttagat 1920
ccttatcgag ctgcaaccca caacaaaggt attatgaatg gtattgaggc cgtcgttttg 1980
gcctcaggaa atgacacacg ggcggtcgcg gcagccgcac atgcgtatgc ttcacgcgat 2040
cagcactatc ggggcttaag ccagtggcag gttgcagaag gcgcgttaca cggggagatc 2100
agtctaccac ttgcactcgg cagcgttggc ggtgcaattg aggtcttgcc taaagcgaag 2160
gcggcattcg aaatcatggg gatcacagag gcgaaggagc tggcagaagt cacagctgcg 2220
gtagggctgg cgcaaaacct ggcggcgtta agagcgcttg ttagtgaagg aatacagcaa 2280
ggtcacatgt cgctccaggc tcgctctctt gcattatcgg taggtgctac aggcaaggaa 2340
gttgaaatcc tggccgaaaa attacagggc tctcgtatga atcaggcgaa cgctcagacc 2400
atactcgcag agatcagatc gcaaaaagtt gaattgtga 2439

<210> SEQ ID NO 96
<211> LENGTH: 2442
<212> TYPE: DNA
<213> ORGANISM: Enterococcus faecium

<400> SEQUENCE: 96
atgaaagaag tggttatgat tgatgcggct cgcacaccca ttgggaaata cagaggtagt 60
cttagtcctt ttacagcggt ggagctgggg acactggtca cgaaagggct gctggataaa 120
acaaagctta agaaagacaa gatagaccaa gtgatattcg gcaatgtgct tcaggcagga 180
aacggacaaa acgttgcaag acaaatagcc ctgaacagtg gcttaccagt tgacgtgccg 240
gcgatgacta ttaacgaagt ttgcgggtcc ggaatgaaag cggtgatttt agcccgccag 300
ttaatacagt taggggaggc agagttggtc attgcagggg gtacggagtc aatgtcacaa 360
gcacccatgc tgaaacctta ccagtcagag accaacgaat acggagagcc gatatcatca 420
atggttaatg acgggctgac ggatgcgttt tccaatgctc acatgggtct tactgccgaa 480
aaggtggcga cccagttttc agtgtcgcgc gaggaacaag accggtacgc attgtccagc 540
caattgaaag cagcgcacgc ggttgaagcc ggggtgttct cagaagagat tattccggtt 600
aagattagcg acgaggatgt cttgagtgaa gacgaggcag taagaggcaa cagcactttg 660
gaaaaactgg gcaccttgcg gacggtgttt tctgaagagg gcacggttac cgctggcaat 720
gcttcaccgc tgaatgacgg cgctagtgtc gtgattcttg catcaaaaga atacgcggaa 780
aacaataatc tgccttacct ggcgacgata aaggaggttg cggaagttgg tatcgatcct 840
tctatcatgg gtattgcccc aataaaggcc attcaaaagt taacagatcg gtcgggcatg 900
aacctgtcca cgattgatct gttcgaaatt aatgaagcat tcgcggcatc tagcattgtt 960
gtttctcaag agctgcaatt ggacgaagaa aaagtgaata tctatggcgg ggcgatagct 1020
ttaggccatc caatcggcgc aagcggagcc cggatactga caaccttagc atacggcctc 1080
ctgcgtgagc aaaagcgtta tggtattgcg tcattatgta tcggcggtgg tcttggtctg 1140
gccgtgctgt tagaagctaa tatggagcag acccacaaag acgttcagaa gaaaaagttt 1200
taccagctta cccccctccga gcggagatcg cagcttatcg agaagaacgt tctgactcaa 1260
gaaacggcac ttattttcca ggagcagacg ttgtccgaag aactgtccga tcacatgatt 1320
gagaatcagg tctccgaagt ggaaattcca atgggaattg cacaaaattt tcagattaat 1380
ggcaagaaaa aatggattcc tatggcgact gaagaacctt cagtaatagc ggcagcatcg 1440
aacggcgcca aaatctgcgg gaacatttgc gcggaaacgc ctcagcggct tatgcgcggg 1500
cagattgtcc tgtctggcaa atcagaatat caagccgtga taaatgccgt gaatcatcgc 1560
aaagaagaac tgattctttg cgcaaacgag tcgtacccga gtattgttaa acgcggggga 1620
ggtgttcagg atatttctac gcgggagttt atgggttctt ttcacgcgta tttatcaatc 1680

```
gactttctgg tggacgtcaa ggacgcaatg ggggcaaaca tgatcaactc tattctcgaa   1740

agcgttgcaa ataaactgcg tgaatggttc ccggaagagg aaatactgtt ctccatcctg   1800

tcaaacttcg ctacggagtc cctggcatct gcatgttgcg agattccttt tgaaagactt   1860

ggtcgtaaca aagaaattgg tgaacagatc gccaagaaaa ttcaacaggc aggggaatat   1920

gctaagcttg acccttaccg cgcggcaacc cataacaagg ggattatgaa cggtatcgaa   1980

gccgtcgttg ccgcaacggg aaacgacaca cgggctgttt ccgcttctat tcacgcatac   2040

gccgcccgta atggcttgta ccaaggttta acggattggc agatcaaggg cgataaactg   2100

gttggtaaat taacagtccc actggctgtg gcgactgtcg gtggcgcgtc gaacatatta   2160

ccaaaagcca aagcttccct cgccatgctg gatattgatt ccgcaaaaga actggcccaa   2220

gtgatcgccg cggtaggttt agcacagaat ctggcggcgt tacgtgcatt agtgacagaa   2280

ggcattcaga aaggacacat gggcttgcaa gcacgttctt tagcgatttc gataggtgcc   2340

atcggtgagg agatagagca agtcgcgaaa aaactgcgtg aagctgaaaa aatgaatcag   2400

caaacggcaa tacagatttt agaaaaaatt cgcgagaaat ga                      2442
```

<210> SEQ ID NO 97
<211> LENGTH: 2448
<212> TYPE: DNA
<213> ORGANISM: Enterococcus gallinarum

<400> SEQUENCE: 97

```
atggaagaag tggtaattat agatgcacgt cggactccga ttggtaaata tcacgggtcg     60

ttgaagaagt tttcagcggt ggcgctgggg acggccgtgg ctaaagacat gttcgaacgc    120

aaccagaaaa tcaaagagga gatcgcgcag gtcataattg gtaatgtctt gcaggcagga    180

aatggccaga accccgcgcg gcaagttgct cttcaatcag ggttgtccgt tgacattccc    240

gcttctacaa ttaacgaggt ttgtgggtct ggtttgaaag ctatcttgat gggcatggaa    300

caaatccaac tcggcaaagc gcaagtagtg ctggcaggcg gcattgaatc aatgacaaat    360

gcgccaagcc tgtcccacta taacaaggcg gaggatacgt atagtgtccc agtgtcgagc    420

atgacactgg atggtctgac agacgcattt tctagtaaac ctatgggatt aacagcggaa    480

aacgtcgcac agcgctacgg tatctcccgt gaggcgcaag atcaattcgc atatcaatct    540

cagatgaaag cagcaaaagc gcaggcagaa aacaaattcg ctaaggaaat tgtgccactg    600

gcgggtgaaa ctaaaaccat cacagctgac gaagggatca gatcccaaac aacgatggag    660

aaactggcaa gtctcaaacc tgtttttaaa accgatggca ctgtaaccgc agggaatgct    720

agcaccatta atgacggggc cgcccttgtg ctgcttgcta gcaaaactta ctgcgaaact    780

aatgacatac cgtaccttgc gacaatcaaa gaaattgttg aagttggaat cgatccggag    840

attatgggca tctctccgat aaaagcgata caaacattgt tacaaaatca aaaagttagc    900

ctcgaagata ttggagtttt tgaaataaat gaagcctttg ccgcaagtag catagtggtt    960

gaatctgagt tgggattaga tccggctaaa gttaaccgtt atgggggtgg tatatcctta   1020

ggtcatgcaa ttggggcaac cggcgctcgc ctggccactt cactggtgta tcaaatgcag   1080

gagatacaag cacgttatgg tattgcgagc ctgtgcgttg gtggtggact tggactggca   1140

atgcttttag aacgtccaac tattgagaag gctaaaccga cagacaaaaa gttctatgaa   1200

ttgtcaccag ctgaacggtt gcaagagctg gaaaatcaac agaaaatcag ttctgaaact   1260

aaacagcagt tatctcagat gatgcttgcc gaggacactg caaaccattt gatagaaaat   1320

caaatatcag agattgaact cccaatgggc gtcgggatga acctgaaggt tgatgggaaa   1380
```

gcctatgttg tgccaatggc gacggaagag ccgtccgtca tcgcggccat gtctaatggt 1440
gccaaaatgg ccggcgaaat tcacactcag tcgaaagaac ggctgctcag aggtcagatt 1500
gttttcagcg cgaagaatcc gaatgaaatc gaacagagaa tagctgagaa ccaagctttg 1560
attttcgaac gtgccgaaca gtcctatcct tccattgtga aaagagaggg aggtctccgc 1620
cgcattgcac ttcgtcattt tcctgccgat tctcagcagg agtctgcgga ccagtccaca 1680
tttttatcag tggacctttt tgtagatgtg aaagacgcga tgggggcaaa tatcataaat 1740
gcaatacttg agggcgtcgc agccctgttt cgcgaatggt tccccaatga ggaaattctt 1800
ttttctattc tctcgaactt ggctacggag agcttagtca cggctgtttg tgaagtccca 1860
tttagtgcac ttagcaagag aggtggtgca acggtggccc agaaaattgt gcaggcgtcg 1920
ctcttcgcaa agacagaccc ataccgcgca gtgacccaca acaaagggat tatgaacggt 1980
gtagaggctg ttatgcttgc cacaggcaac gacacgcgcg cagtctcagc cgcttgtcat 2040
ggatacgcag cgcgcaccgg tagctatcag ggtctgacta actggacgat tgagtcggat 2100
cgcctggtag gcgagataac actgccgctg gccatcgcta cagttggagg cgctaccaaa 2160
gtgttgccca aagctcaagc ggcactggag attagtgatg ttcactcttc tcaagagctt 2220
gcagccttag cggcgtcagt aggtttagta caaaatctcg cggccctgcg cgcactggtt 2280
tccgaaggta tacaaaaagg gcacatgtcc atgcaagccc ggtctctcgc aatcgcggtc 2340
ggtgctgaaa aagccgagat cgagcaggtc gccgaaaagt tgcggcagaa cccgccaatg 2400
aatcagcagc aggcgctccg ttttcttggc gagatccgcg aacaatga 2448

<210> SEQ ID NO 98
<211> LENGTH: 2475
<212> TYPE: DNA
<213> ORGANISM: Enterococcus casseliflavus

<400> SEQUENCE: 98
atggaagaag ttgtcatcat tgacgcactg cgtactccaa taggaaagta ccacggttcg 60
ctgaaagatt acacagctgt tgaactgggg acagtagcag caaaggcgtt gctggcacga 120
aatcagcaag caaaagaaca catagcgcaa gttattattg gcaacgtcct gcaagccgga 180
agtgggcaga atccaggccg acaagtcagt ttacagtcag gattgtcttc tgatatcccc 240
gctagcacga tcaatgaagt gtgtggctcg ggtatgaaag cgattctgat gggtatggag 300
caaattcagc tgaacaaagc ctctgtggtc ttaacaggcg gaattgaaag catgaccaac 360
gcgccgctgt ttagttatta caacaaggct gaggatcaat attcggcgcc ggttagcaca 420
atgatgcacg atggtctaac agatgctttc agttccaaac caatgggctt aaccgcagag 480
accgtcgctg agagatatgg aattacgcgt aaggaacaag atgaatttgc ttatcactct 540
caaatgaagg cggccaaagc ccaggcggcg aaaaagtttg atcaggaaat tgtacccctg 600
acggaaaaat ccggaacggt tctccaggac gaaggcatca gagccgcgac aacagtcgag 660
aagctagctg agcttaaaac ggtgttcaaa aaagacggaa cagttacagc gggtaacgcc 720
tctacgataa atgatggcgc tgctatggta ttaatagcat caaaatctta ttgcgaagaa 780
caccagattc cttatctggc cgttataaag gagatcgttg aggtgggttt tgcccccgaa 840
ataatgggta tttcccccat taaggctata gacaccctgc tgaaaaatca agcactgacc 900
atagaggata taggaatatt tgagattaat gaagcctttg ctgcgagttc gattgtggta 960
gaacgcgagt tgggcctgga ccccaaaaaa gttaatcgct atggcggtgg tatatcactc 1020

```
ggccacgcaa ttggggcgac gggagctcgc attgcgacga ccgttgctta tcagctgaaa   1080

gatacccagg agcgctacgg tatagcttcc ttatgcgttg gtgggggtct tggattggcg   1140

atgcttctgg aaaacccatc ggccactgcc tcacaaacta attttgatga ggaatctgct   1200

tccgaaaaaa ctgagaagaa gaagttttat gcgctagctc ctaacgaacg cttagcgttt   1260

ttggaagccc aaggcgctat taccgctgct gaaaccctgg tcttccagga gatgacctta   1320

aacaaagaga cagccaatca cttaatcgaa aaccaaatca gcgaagttga aattccttta   1380

ggcgtgggcc tgaacttaca ggtgaatggg aaagcgtata atgttcctct ggccacggag   1440

gaaccgtccg ttatcgctgc gatgtcgaat ggcgccaaaa tggctggtcc tattacaaca   1500

acaagtcagg agaggctgtt acggggtcag attgtcttca tggacgtaca ggacccagaa   1560

gcaatattag cgaaagttga atccgagcaa gctaccattt tcgcggtggc aaatgaaaca   1620

tacccgtcta tcgtgaaaag aggaggaggt ctgcgtagag tcattggcag gaatttcagt   1680

ccggccgaaa gtgacttagc cacggcgtat gtatcaattg acctgatggt agatgttaag   1740

gatgcaatgg gtgctaatat catcaatagt atcctagaag gtgttgcgga attgtttaga   1800

aaatggttcc cagaagaaga aatcctgttc tcaattctct ccaatctcgc gacagaaagt   1860

ctggtaacgg cgacgtgctc agttccgttt gataaattgt ccaaaactgg gaatggtcga   1920

caagtagctg gtaaaatagt gcacgcggcg gactttgcta agatagatcc atacagagct   1980

gccacacaca ataaaggtat tatgaatggc gttgaagcgt taatcttagc caccggtaat   2040

gacacccgtg cggtgtcggc tgcatgccac ggttacgcgg cacgcaatgg gcgaatgcaa   2100

gggcttacct cttggacgat tatcgaagat cggctgatag gctctatcac attacctttg   2160

gctattgcga cagtgggggg tgccacaaaa atcttgccaa aagcacaggc cgccctggcg   2220

ctaactggcg ttgagacggc gtcggaactg gccagcctgg cggcgagtgt gggattagtt   2280

caaaatttgg ccgctttacg agcactagtg agcgagggca ttcagcaagg gcacatgagt   2340

atgcaagcta gatccctggc cattagcgta ggtgcgaaag gtactgaaat agagcaacta   2400

gctgcgaagc tgagggcagc gacgcaaatg aatcaggagc aggctcgtaa atttctgacc   2460

gaaataagaa attaa                                                    2475
```

<210> SEQ ID NO 99
<211> LENGTH: 1158
<212> TYPE: DNA
<213> ORGANISM: Listeria grayi

<400> SEQUENCE: 99

```
atgaccatga acgttggaat cgataaaatg tcattctttg ttccacctta ctttgtggac     60

atgactgatc tggcagtagc acgggatgtc gatcccaata agtttctgat tggtattggc    120

caggaccaga tggcagttaa tccgaaaacg caggatattg tgacatttgc cacaaatgct    180

gccaaaaaca tactgtcagc tgaggacctt gataaaattg atatggtcat agtcggcacc    240

gagagtggaa tcgatgaatc caaagcgagt gccgtagtgc ttcacaggtt gctcggtatc    300

cagaagtttg ctcgctcctt tgaaatcaaa gaagcctgtt atgggggtac cgcggcttta    360

cagttcgctg taaaccacat taggaatcat cctgaatcaa aggttcttgt agttgcatca    420

gatatcgcga aatacggcct ggcttctgga ggtgaaccaa cgcaaggtgc aggcgctgtg    480

gctatgctcg tctcaactga ccctaagatc attgctttca acgacgatag cctcgcgctt    540

acacaagata tctatgactt ctggcgacca gttggacatg actatcctat ggtcgacggg    600

cctcttagta cagagaccta catccagtca tttcagaccg tatggcagga atacacaaaa    660
```

cggtcgcagc atgcactggc agactttgct gcccttagct ttcatatccc gtatactaaa 720
atgggcaaaa aggcgctgct tgcaatcctt gaaggcgaat cagaggaggc tcagaaccgt 780
atactagcaa aatatgaaaa gagtatagcc tactccagaa aggcgggtaa cctgtatacc 840
ggtagcctgt atctaggact tatttcactt ctggaaaatg cagaagacct taaagctggt 900
gatttaatag gcctcttttc ttacggttcc ggtgctgttg cggagttttt ctcaggaagg 960
ctggttgagg actatcagga acagctactt aaaacaaaac atgccgaaca gctggcccat 1020
agaaagcaac tgacaatcga ggagtacgaa acgatgttct ccgatcgctt ggacgtggac 1080
aaagacgccg aatacgaaga cacattagct tatagcattt cgtcagtccg aaacaccgta 1140
cgtgagtaca ggagttga 1158

<210> SEQ ID NO 100
<211> LENGTH: 1155
<212> TYPE: DNA
<213> ORGANISM: Enterococcus faecium

<400> SEQUENCE: 100
atgaaaatcg gtattgaccg tctgtccttc ttcatcccga atttgtattt ggacatgact 60
gagctggcag aatcacgcgg ggatgatcca gctaaatatc atattggaat cggacaagat 120
cagatggcag tgaatcgcgc aaacgaggac atcataacac tgggtgcaaa cgctgcgagt 180
aagatcgtga cagagaaaga ccgcgagttg attgatatgg taatcgttgg cacggaatca 240
ggaattgacc actccaaagc aagcgccgtg attattcacc atctccttaa aattcagtcg 300
ttcgcccgtt ctttcgaggt aaaagaagct tgctatggcg gaactgctgc cctgcacatg 360
gcgaaggagt atgtcaaaaa tcatccggag cgtaaggtct tggtaattgc gtcagacatc 420
gcgcgttatg gtttggccag cggaggagaa gttactcaag gcgtgggggc cgtagccatg 480
atgattacac aaaacccccg gattctttcg attgaagacg atagtgtttt tctcacagag 540
gatatctatg atttctggcg gcctgattac tccgagttcc ctgtagtgga cgggcccctt 600
tcaaactcaa cgtatataga gagttttcag aaagtttgga accggcacaa ggaattgtcc 660
ggaagagggc tggaagatta tcaagctatt gcttttcaca taccctatac gaagatgggt 720
aagaaagcgc tccagagtgt tttagaccaa accgatgaag ataaccagga gcgcttaatg 780
gctagatatg aggagtctat tcgctatagc cggagaattg gtaacctgta cacaggcagc 840
ttgtaccttg gtcttacaag cttgttggaa aactctaaaa gtttacaacc gggagatcgg 900
atcggcctct tttcctatgg cagtggtgcg gtgtccgagt tctttaccgg gtatttagaa 960
gaaaattacc aagagtacct gttcgctcaa agccatcaag aaatgctgga tagccggact 1020
cggattacgg tcgatgaata cgagaccatc ttttcagaga ctctgccaga acatggtgaa 1080
tgcgccgaat atacgagcga cgtccccttt tctataacca agattgagaa cgacattcgt 1140
tattataaaa tctga 1155

<210> SEQ ID NO 101
<211> LENGTH: 1155
<212> TYPE: DNA
<213> ORGANISM: Enterococcus gallinarum

<400> SEQUENCE: 101
atgaacgtcg gcattgacaa aattaatttt ttcgttccac cgtattatct ggatatggtc 60
gacctggccc acgcacgcga agtggacccg aacaaattta caattggaat tggacaggat 120

```
cagatggctg tgagcaaaaa gacgcacgat atcgtaacat tcgcggctag tgccgcgaag    180
gaaattttag aacctgagga cttgcaagct atagacatgg ttatagttgg taccgaatcg    240
ggcattgacg agagcaaagc atccgcggtc gttttacatc gtttgttggg cgtacaacct    300
ttcgctcgca gttttgaaat taaagaagcc tgttacgggg caaccgcagg cattcagttt    360
gccaagactc atatacaagc gaacccggag agcaaggtcc tggtaattgc aagcgatata    420
gctcggtatg gtcttcggtc aggtggagag cccacacaag gcgcaggggc agttgctatg    480
cttctcacgg caaatcccag aatcctgacc ttcgaaaacg acaatctgat gttaacgcag    540
gatatttatg acttctggag accacttggt cacgcttacc ctatggtaga tggccacctt    600
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg ggctgatatc cttattggaa aacagttctc acctgtcggc gggcgaccgg    900
ataggattgt ttagttatgg gagtggcgct gtcagcgaat tttctccgg tcgtttagtg     960
gcaggctatg aaaatcaatt gaacaaagag gcgcataccc agctcctgga tcagcgtcag   1020
aagctttcca tcgaagagta tgaggcgatt tttacagatt ccttagaaat tgatcaggat   1080
gcagcgttct cggatgacct gccatattcc atccgcgaga taaaaaaacac gattcggtac  1140
tataaggaga gctga                                                    1155
```

<210> SEQ ID NO 102
<211> LENGTH: 1161
<212> TYPE: DNA
<213> ORGANISM: Enterococcus casseliflavus

<400> SEQUENCE: 102

```
atgaacgttg gaattgataa aatcaatttt ttcgttccgc cctatttcat tgatatggtg     60
gatctcgctc atgcaagaga agttgacccc aacaagttca ctataggaat aggccaagat    120
cagatggcag taaacaagaa aacgcaagat atcgtaacgt tcgcgatgca cgccgcgaag    180
gatattctga ctaaggaaga tttacaggcc atagatatgg taatagtggg gactgagtct    240
gggatcgacg agagcaaggc aagtgctgtc gtattgcatc ggcttttagg tattcagcct    300
tttgcgcgct cctttgaaat taaggaggca tgctatgggg ccactgccgg ccttcagttt    360
gcaaaagctc atgtgcaggc taatccccag agcaaggtcc tggtggtagc ttccgatata    420
gcacgctacg gactggcatc cggaggagaa ccgactcaag gtgtaggtgc tgtggcaatg    480
ttgatttccg ctgatccagc tatcttgcag ttagaaaatg ataatctcat gttgacccaa    540
gatatatacg atttttggcg cccggtcggg catcaatatc ctatggtaga cggccatctg    600
tctaatgccg tctatataga cagctttaaa caagtctggc aagcacattg cgagaaaaac    660
caacggactg ctaaagatta tgctgcattg tcgttccata ttccgtacac gaaaatgggt    720
aagaaagctc tgttagcggt ttttgcggag gaagatgaga cagaacaaaa gcggttaatg    780
gcacgttatg aagaatcaat tgtatacagt cgtcggactg gaaatctgta tactggctca    840
ctctatctgg gcctgatttc cttactggag aatagtagca gtttacaggc gaacgatcgc    900
ataggtctgt ttagctatgg ttcaggggcc gttgcggaat tttcagtgg cctcttggta     960
ccgggttacg agaaacaatt agcgcaagct gcccatcaag ctcttctgga cgaccggcaa   1020
aaactgacta tcgcagagta cgaagccatg tttaatgaaa ccattgatat tgatcaggac   1080
```

cagtcatttg aggatgactt actgtactcc atcagagaga tcaaaaacac tattcgctac 1140
tataacgagg agaatgaata a 1161

<210> SEQ ID NO 103
<211> LENGTH: 329
<212> TYPE: PRT
<213> ORGANISM: Streptomyces sp. CL190

<400> SEQUENCE: 103

Met Thr Asp Val Arg Phe Arg Ile Ile Gly Thr Gly Ala Tyr Val Pro
1 5 10 15

Glu Arg Ile Val Ser Asn Asp Glu Val Gly Ala Pro Ala Gly Val Asp
20 25 30

Asp Asp Trp Ile Thr Arg Lys Thr Gly Ile Arg Gln Arg Arg Trp Ala
35 40 45

Ala Asp Asp Gln Ala Thr Ser Asp Leu Ala Thr Ala Ala Gly Arg Ala
50 55 60

Ala Leu Lys Ala Ala Gly Ile Thr Pro Glu Gln Leu Thr Val Ile Ala
65 70 75 80

Val Ala Thr Ser Thr Pro Asp Arg Pro Gln Pro Pro Thr Ala Ala Tyr
85 90 95

Val Gln His His Leu Gly Ala Thr Gly Thr Ala Ala Phe Asp Val Asn
100 105 110

Ala Val Cys Ser Gly Thr Val Phe Ala Leu Ser Ser Val Ala Gly Thr
115 120 125

Leu Val Tyr Arg Gly Gly Tyr Ala Leu Val Ile Gly Ala Asp Leu Tyr
130 135 140

Ser Arg Ile Leu Asn Pro Ala Asp Arg Lys Thr Val Val Leu Phe Gly
145 150 155 160

Asp Gly Ala Gly Ala Met Val Leu Gly Pro Thr Ser Thr Gly Thr Gly
165 170 175

Pro Ile Val Arg Arg Val Ala Leu His Thr Phe Gly Gly Leu Thr Asp
180 185 190

Leu Ile Arg Val Pro Ala Gly Gly Ser Arg Gln Pro Leu Asp Thr Asp
195 200 205

Gly Leu Asp Ala Gly Leu Gln Tyr Phe Ala Met Asp Gly Arg Glu Val
210 215 220

Arg Arg Phe Val Thr Glu His Leu Pro Gln Leu Ile Lys Gly Phe Leu
225 230 235 240

His Glu Ala Gly Val Asp Ala Ala Asp Ile Ser His Phe Val Pro His
245 250 255

Gln Ala Asn Gly Val Met Leu Asp Glu Val Phe Gly Glu Leu His Leu
260 265 270

Pro Arg Ala Thr Met His Arg Thr Val Glu Thr Tyr Gly Asn Thr Gly
275 280 285

Ala Ala Ser Ile Pro Ile Thr Met Asp Ala Ala Val Arg Ala Gly Ser
290 295 300

Phe Arg Pro Gly Glu Leu Val Leu Leu Ala Gly Phe Gly Gly Gly Met
305 310 315 320

Ala Ala Ser Phe Ala Leu Ile Glu Trp
325

<210> SEQ ID NO 104
<211> LENGTH: 2466

<212> TYPE: DNA
<213> ORGANISM: Lactococcus lactis

<400> SEQUENCE: 104

```
atgaccgagt ataacagcga ggcctatctg aaaaaactgg ataaatggtg gcgtgcagca     60
acctatctgg gtgcaggtat gatttttctg aaagaaaatc cgctgtttag cgttaccggc    120
accccgatta aagcagaaaa tctgaaagcc aatccgattg gtcattgggg caccgttagc    180
ggtcagacct ttctgtatgc acatgcaaat cgtctgatca acaaatatga tcagaaaatg    240
ttttatatgg gtggtccggg tcatggtggt caggcaatgg ttgttccgag ctatctggat    300
ggtagctata ccgaagcata tccggaaatt acccaggatc tggaaggtat gagccgtctg    360
tttaaacgtt ttagctttcc gggtggtatt ggtagccata tgaccgcaca gacaccgggt    420
agcctgcatg aaggtggtga actgggttat gttctgagcc atgcaaccgg tgcaattctg    480
gatcagccgg aacaaattgc atttgcagtt gttggtgatg gtgaagccga aaccggtccg    540
ctgatgacca gctggcatag catcaaattt atcaacccga aaaacgatgg tgccattctg    600
ccgatcctgg atctgaatgg ctttaaaatc agcaatccga ccctgtttgc acgtaccagt    660
gatgttgata ttcgcaaatt tttcgaaggc ctgggctata gtccgcgtta tattgaaaat    720
gatgatattc acgactatat ggcctaccat aaactggcag cagaagtttt tgataaagcc    780
atcgaagata tccatcagat ccagaaagat gcccgtgaag ataatcgtta tcagaatggt    840
gaaattccgg catggccgat tgttattgca cgtctgccga aaggttgggg tggccctcgt    900
tataatgatt ggagcggtcc gaaatttgat ggtaaaggta tgccgattga acatagcttt    960
cgtgcacatc aggttccgct gccgctgagc agcaaaaata tgggcaccct gccggaattt   1020
gttaaatgga tgacctcata tcagcctgaa acactgttta atgcagatgg ttcactgaaa   1080
gaggaactgc gcgattttgc accgaaaggc gaaatgcgta tggcaagtaa tccggttacc   1140
aatggtggtg ttgatagcag caatctggtt ctgccggatt ggcaagaatt tgcaaacccg   1200
attagcgaaa ataatcgtgg taaactgctg ccggacacca atgataatat ggatatgaat   1260
gtgctgagca agtattttgc cgaaatcgtt aaactgaatc cgacacgttt tcgcctgttt   1320
ggtccggatg aaaccatgag caatcgtttt tgggaaatgt tcaaagtgac caatcgtcag   1380
tggatgcagg ttatcaaaaa tccgaacgat gaattcatta gtccggaagg tcgtattatt   1440
gatagccagc tgagcgaaca tcaggcagaa ggttggctgg aaggctatac cctgaccggt   1500
cgtaccggtg cctttgcaag ctatgaaagc tttctgcgtg ttgtggatag catgctgacc   1560
cagcatttca aatggattcg tcaggcagcc gaccagaaat ggcgtcatga ttatccgagc   1620
ctgaatgtta ttagcaccag caccgttttt cagcaggatc ataatggtta tacccatcag   1680
gatccgggta tgctgacaca tctggcagag aaaaaaagcg attttatccg tcagtatctg   1740
cctgccgatg gtaataccct gctggcagtg tttgatcgtg catttcagga tcgtagcaaa   1800
atcaatcata ttgtggcaag caaacagcct cgtcagcagt ggtttaccaa agaagaagcc   1860
gagaaactgg ccaccgatgg cattgcaacc attgattggg cgagcaccgc aaaagatggc   1920
gaagcagttg atctggtttt tgcaagtgcc ggtgcagaac cgaccattga aaccctggca   1980
gccctgcatc tggttaatga agtgtttccg caggcaaaat ttcgctatgt taatgttgtt   2040
gagctgggtc gtctgcagaa aaagaaaggt gcactgaatc aagaacgtga actgtccgat   2100
gaagaattcg agaaatattt cggtccgagc ggtacaccgg ttatttttgg ttttcatggt   2160
tatgaggatc tgattgaaag catcttttat cagcgtggtc atgatggcct gatcgttcat   2220
```

```
ggctatcgcg aagatggtga tattaccacc acctatgata tgcgtgttta tagcgaactg   2280

gatcgttttc atcaggccat tgatgcaatg caggtactgt atgtgaatcg caaagttaat   2340

cagggtctgg ccaaagcatt tatcgatcgt atgaaacgta ccctggtgaa acattttgaa   2400

gtgacccgta atgaaggcgt ggatattccg gattttaccg aatgggtttg gagcgatctg   2460

aagaaa                                                              2466


<210> SEQ ID NO 105
<211> LENGTH: 822
<212> TYPE: PRT
<213> ORGANISM: Lactococcus lactis

<400> SEQUENCE: 105

Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
            20                  25                  30

Asn Pro Leu Phe Ser Val Thr Gly Thr Pro Ile Lys Ala Glu Asn Leu
        35                  40                  45

Lys Ala Asn Pro Ile Gly His Trp Gly Thr Val Ser Gly Gln Thr Phe
    50                  55                  60

Leu Tyr Ala His Ala Asn Arg Leu Ile Asn Lys Tyr Asp Gln Lys Met
65                  70                  75                  80

Phe Tyr Met Gly Gly Pro Gly His Gly Gly Gln Ala Met Val Val Pro
                85                  90                  95

Ser Tyr Leu Asp Gly Ser Tyr Thr Glu Ala Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
    210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Gly Pro Arg Tyr Asn Asp Trp
    290                 295                 300

Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
```

-continued

```
                325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Glu Leu Arg Asp Phe Ala Pro
        355                 360                 365

Lys Gly Glu Met Arg Met Ala Ser Asn Pro Val Thr Asn Gly Gly Val
    370                 375                 380

Asp Ser Ser Asn Leu Val Leu Pro Asp Trp Gln Glu Phe Ala Asn Pro
385                 390                 395                 400

Ile Ser Glu Asn Asn Arg Gly Lys Leu Leu Pro Asp Thr Asn Asp Asn
                405                 410                 415

Met Asp Met Asn Val Leu Ser Lys Tyr Phe Ala Glu Ile Val Lys Leu
            420                 425                 430

Asn Pro Thr Arg Phe Arg Leu Phe Gly Pro Asp Glu Thr Met Ser Asn
        435                 440                 445

Arg Phe Trp Glu Met Phe Lys Val Thr Asn Arg Gln Trp Met Gln Val
    450                 455                 460

Ile Lys Asn Pro Asn Asp Glu Phe Ile Ser Pro Glu Gly Arg Ile Ile
465                 470                 475                 480

Asp Ser Gln Leu Ser Glu His Gln Ala Glu Gly Trp Leu Glu Gly Tyr
                485                 490                 495

Thr Leu Thr Gly Arg Thr Gly Ala Phe Ala Ser Tyr Glu Ser Phe Leu
            500                 505                 510

Arg Val Val Asp Ser Met Leu Thr Gln His Phe Lys Trp Ile Arg Gln
        515                 520                 525

Ala Ala Asp Gln Lys Trp Arg His Asp Tyr Pro Ser Leu Asn Val Ile
    530                 535                 540

Ser Thr Ser Thr Val Phe Gln Gln Asp His Asn Gly Tyr Thr His Gln
545                 550                 555                 560

Asp Pro Gly Met Leu Thr His Leu Ala Glu Lys Lys Ser Asp Phe Ile
                565                 570                 575

Arg Gln Tyr Leu Pro Ala Asp Gly Asn Thr Leu Leu Ala Val Phe Asp
            580                 585                 590

Arg Ala Phe Gln Asp Arg Ser Lys Ile Asn His Ile Val Ala Ser Lys
        595                 600                 605

Gln Pro Arg Gln Gln Trp Phe Thr Lys Glu Glu Ala Glu Lys Leu Ala
    610                 615                 620

Thr Asp Gly Ile Ala Thr Ile Asp Trp Ala Ser Thr Ala Lys Asp Gly
625                 630                 635                 640

Glu Ala Val Asp Leu Val Phe Ala Ser Ala Gly Ala Glu Pro Thr Ile
                645                 650                 655

Glu Thr Leu Ala Ala Leu His Leu Val Asn Glu Val Phe Pro Gln Ala
            660                 665                 670

Lys Phe Arg Tyr Val Asn Val Val Glu Leu Gly Arg Leu Gln Lys Lys
        675                 680                 685

Lys Gly Ala Leu Asn Gln Glu Arg Glu Leu Ser Asp Glu Glu Phe Glu
    690                 695                 700

Lys Tyr Phe Gly Pro Ser Gly Thr Pro Val Ile Phe Gly Phe His Gly
705                 710                 715                 720

Tyr Glu Asp Leu Ile Glu Ser Ile Phe Tyr Gln Arg Gly His Asp Gly
                725                 730                 735

Leu Ile Val His Gly Tyr Arg Glu Asp Gly Asp Ile Thr Thr Thr Tyr
            740                 745                 750
```

-continued

```
Asp Met Arg Val Tyr Ser Glu Leu Asp Arg Phe His Gln Ala Ile Asp
        755                 760                 765

Ala Met Gln Val Leu Tyr Val Asn Arg Lys Val Asn Gln Gly Leu Ala
    770                 775                 780

Lys Ala Phe Ile Asp Arg Met Lys Arg Thr Leu Val Lys His Phe Glu
785                 790                 795                 800

Val Thr Arg Asn Glu Gly Val Asp Ile Pro Asp Phe Thr Glu Trp Val
                805                 810                 815

Trp Ser Asp Leu Lys Lys
            820


<210> SEQ ID NO 106
<211> LENGTH: 125
<212> TYPE: DNA
<213> ORGANISM: Enterobacteria phage lambda

<400> SEQUENCE: 106

aattcatata aaaaacatac agataaccat ctgcggtgat aaattatctc tggcggtgtt      60

gacataaata ccactggcgg tgatactgag cacatcagca ggacgcactg accaccatga     120

aggtg                                                                 125


<210> SEQ ID NO 107
<211> LENGTH: 32
<212> TYPE: DNA
<213> ORGANISM: Artificial Sequence
<220> FEATURE:
<223> OTHER INFORMATION: Synthetic Construct

<400> SEQUENCE: 107

ctgtattcat gacgagtcct gttattggca cc                                    32


<210> SEQ ID NO 108
<211> LENGTH: 31
<212> TYPE: DNA
<213> ORGANISM: Artificial Sequence
<220> FEATURE:
<223> OTHER INFORMATION: Synthetic Construct

<400> SEQUENCE: 108

ctctatgaat tctcactcgt tgtcgccagc g                                     31


<210> SEQ ID NO 109
<211> LENGTH: 51
<212> TYPE: DNA
<213> ORGANISM: Artificial Sequence
<220> FEATURE:
<223> OTHER INFORMATION: Synthetic Construct

<400> SEQUENCE: 109

taaggaggaa taaaccatgc aaagtataat aggaaaacat aaggatgaag g               51


<210> SEQ ID NO 110
<211> LENGTH: 45
<212> TYPE: DNA
<213> ORGANISM: Artificial Sequence
<220> FEATURE:
<223> OTHER INFORMATION: Synthetic Construct

<400> SEQUENCE: 110

ttctagaaag cttcgttata catgccactg ccaattagtt atttc                      45
```

<210> SEQ ID NO 111
<211> LENGTH: 38
<212> TYPE: DNA
<213> ORGANISM: Artificial Sequence
<220> FEATURE:
<223> OTHER INFORMATION: Synthetic Construct

<400> SEQUENCE: 111
tgataacgaa taagagctcg agatctgcag ctggtacc 38

<210> SEQ ID NO 112
<211> LENGTH: 51
<212> TYPE: DNA
<213> ORGANISM: Artificial Sequence
<220> FEATURE:
<223> OTHER INFORMATION: Synthetic Construct

<400> SEQUENCE: 112
gactcgtcat ggtttattcc tccttattta atcgatacat taatatatac c 51

<210> SEQ ID NO 113
<211> LENGTH: 37
<212> TYPE: DNA
<213> ORGANISM: Artificial Sequence
<220> FEATURE:
<223> OTHER INFORMATION: Synthetic Construct

<400> SEQUENCE: 113
ggaataaacc atgacgagtc cagttattgg aacaccc 37

<210> SEQ ID NO 114
<211> LENGTH: 36
<212> TYPE: DNA
<213> ORGANISM: Artificial Sequence
<220> FEATURE:
<223> OTHER INFORMATION: Synthetic Construct

<400> SEQUENCE: 114
tctcgagctc ttattcgtta tcacccgcag tagcgg 36

<210> SEQ ID NO 115
<211> LENGTH: 38
<212> TYPE: DNA
<213> ORGANISM: Artificial Sequence
<220> FEATURE:
<223> OTHER INFORMATION: Synthetic Construct

<400> SEQUENCE: 115
cgacaacgag taagagctcg agatctgcag ctggtacc 38

<210> SEQ ID NO 116
<211> LENGTH: 51
<212> TYPE: DNA
<213> ORGANISM: Artificial Sequence
<220> FEATURE:
<223> OTHER INFORMATION: Synthetic Construct

<400> SEQUENCE: 116
gagaggtcat ggtttattcc tccttattta atcgatacat taatatatac c 51

<210> SEQ ID NO 117
<211> LENGTH: 36
<212> TYPE: DNA
<213> ORGANISM: Artificial Sequence
<220> FEATURE:
<223> OTHER INFORMATION: Synthetic Construct

<400> SEQUENCE: 117
ggaataaacc atgacctctc cagtaattgg cactcc 36

<210> SEQ ID NO 118
<211> LENGTH: 32
<212> TYPE: DNA
<213> ORGANISM: Artificial Sequence
<220> FEATURE:
<223> OTHER INFORMATION: Synthetic Construct

<400> SEQUENCE: 118
tctcgagctc ttactcgttg tcgcctgccg tg 32

<210> SEQ ID NO 119
<211> LENGTH: 38
<212> TYPE: DNA
<213> ORGANISM: Artificial Sequence
<220> FEATURE:
<223> OTHER INFORMATION: Synthetic Construct

<400> SEQUENCE: 119
cgataatgaa taagagctcg agatctgcag ctggtacc 38

<210> SEQ ID NO 120
<211> LENGTH: 51
<212> TYPE: DNA
<213> ORGANISM: Artificial Sequence
<220> FEATURE:
<223> OTHER INFORMATION: Synthetic Construct

<400> SEQUENCE: 120
gagaagtcat ggtttattcc tccttattta atcgatacat taatatatac c 51

<210> SEQ ID NO 121
<211> LENGTH: 36
<212> TYPE: DNA
<213> ORGANISM: Artificial Sequence
<220> FEATURE:
<223> OTHER INFORMATION: Synthetic Construct

<400> SEQUENCE: 121
ggaataaacc atgacttctc ccgtgattgg tactcc 36

<210> SEQ ID NO 122
<211> LENGTH: 34
<212> TYPE: DNA
<213> ORGANISM: Artificial Sequence
<220> FEATURE:
<223> OTHER INFORMATION: Synthetic Construct

<400> SEQUENCE: 122
tctcgagctc ttattcatta tcgcccgccg tagc 34

<210> SEQ ID NO 123
<211> LENGTH: 38
<212> TYPE: DNA
<213> ORGANISM: Artificial Sequence
<220> FEATURE:
<223> OTHER INFORMATION: Synthetic Construct

<400> SEQUENCE: 123
gctgaaaaaa taagagctcg agatctgcag ctggtacc 38

<210> SEQ ID NO 124
<211> LENGTH: 51

<212> TYPE: DNA
<213> ORGANISM: Artificial Sequence
<220> FEATURE:
<223> OTHER INFORMATION: Synthetic Construct

<400> SEQUENCE: 124
ccactgtcat ggtttattcc tccttattta atcgatacat taatatatac c 51

<210> SEQ ID NO 125
<211> LENGTH: 46
<212> TYPE: DNA
<213> ORGANISM: Artificial Sequence
<220> FEATURE:
<223> OTHER INFORMATION: Synthetic Construct

<400> SEQUENCE: 125
ggaataaacc atgacagtgg actatgactc aaaagagtac ttagag 46

<210> SEQ ID NO 126
<211> LENGTH: 36
<212> TYPE: DNA
<213> ORGANISM: Artificial Sequence
<220> FEATURE:
<223> OTHER INFORMATION: Synthetic Construct

<400> SEQUENCE: 126
tctcgagctc ttattttttc agcccttccc atttcc 36

<210> SEQ ID NO 127
<211> LENGTH: 38
<212> TYPE: DNA
<213> ORGANISM: Artificial Sequence
<220> FEATURE:
<223> OTHER INFORMATION: Synthetic Construct

<400> SEQUENCE: 127
ctggaaaggt taagagctcg agatctgcag ctggtacc 38

<210> SEQ ID NO 128
<211> LENGTH: 51
<212> TYPE: DNA
<213> ORGANISM: Artificial Sequence
<220> FEATURE:
<223> OTHER INFORMATION: Synthetic Construct

<400> SEQUENCE: 128
cttcagccat ggtttattcc tccttattta atcgatacat taatatatac c 51

<210> SEQ ID NO 129
<211> LENGTH: 32
<212> TYPE: DNA
<213> ORGANISM: Artificial Sequence
<220> FEATURE:
<223> OTHER INFORMATION: Synthetic Construct

<400> SEQUENCE: 129
ggaataaacc atggctgaag ccactgccca tc 32

<210> SEQ ID NO 130
<211> LENGTH: 39
<212> TYPE: DNA
<213> ORGANISM: Artificial Sequence
<220> FEATURE:
<223> OTHER INFORMATION: Synthetic Construct

<400> SEQUENCE: 130
tctcgagctc ttaacctttc caggtccaat tccggattt 39

<210> SEQ ID NO 131
<211> LENGTH: 38
<212> TYPE: DNA
<213> ORGANISM: Artificial Sequence
<220> FEATURE:
<223> OTHER INFORMATION: Synthetic Construct

<400> SEQUENCE: 131
atggcatgta taagagctcg agatctgcag ctggtacc 38

<210> SEQ ID NO 132
<211> LENGTH: 51
<212> TYPE: DNA
<213> ORGANISM: Artificial Sequence
<220> FEATURE:
<223> OTHER INFORMATION: Synthetic Construct

<400> SEQUENCE: 132
ttgattgcat ggtttattcc tccttattta atcgatacat taatatatac c 51

<210> SEQ ID NO 133
<211> LENGTH: 34
<212> TYPE: DNA
<213> ORGANISM: Artificial Sequence
<220> FEATURE:
<223> OTHER INFORMATION: Synthetic Construct

<400> SEQUENCE: 133
ggaataaacc atgcaatcaa tcatcggcaa acac 34

<210> SEQ ID NO 134
<211> LENGTH: 38
<212> TYPE: DNA
<213> ORGANISM: Artificial Sequence
<220> FEATURE:
<223> OTHER INFORMATION: Synthetic Construct

<400> SEQUENCE: 134
tctcgagctc ttatacatgc cattgccagt ttgtgatc 38

<210> SEQ ID NO 135
<211> LENGTH: 28
<212> TYPE: DNA
<213> ORGANISM: Artificial Sequence
<220> FEATURE:
<223> OTHER INFORMATION: Synthetic Construct

<400> SEQUENCE: 135
catgcgagca tgatccagag atttctga 28

<210> SEQ ID NO 136
<211> LENGTH: 28
<212> TYPE: DNA
<213> ORGANISM: Artificial Sequence
<220> FEATURE:
<223> OTHER INFORMATION: Synthetic Construct

<400> SEQUENCE: 136
gcttgtccgc aaacggacat atcaaggt 28

<210> SEQ ID NO 137
<211> LENGTH: 24
<212> TYPE: DNA
<213> ORGANISM: Artificial Sequence -continued

```
<220> FEATURE:
<223> OTHER INFORMATION: Synthetic Construct

<400> SEQUENCE: 137

cagctcccat gagcgaagcg gagt                                    24


<210> SEQ ID NO 138
<211> LENGTH: 24
<212> TYPE: DNA
<213> ORGANISM: Artificial Sequence
<220> FEATURE:
<223> OTHER INFORMATION: Synthetic Construct

<400> SEQUENCE: 138

gacgcgtcag cgtcgcatcc ggca                                    24


<210> SEQ ID NO 139
<211> LENGTH: 27
<212> TYPE: DNA
<213> ORGANISM: Artificial Sequence
<220> FEATURE:
<223> OTHER INFORMATION: Synthetic Construct

<400> SEQUENCE: 139

gctgcgatcg actgactatc gcaccga                                 27


<210> SEQ ID NO 140
<211> LENGTH: 27
<212> TYPE: DNA
<213> ORGANISM: Artificial Sequence
<220> FEATURE:
<223> OTHER INFORMATION: Synthetic Construct

<400> SEQUENCE: 140

cagacgcctg gcccacgttg tggatca                                 27


<210> SEQ ID NO 141
<211> LENGTH: 27
<212> TYPE: DNA
<213> ORGANISM: Artificial Sequence
<220> FEATURE:
<223> OTHER INFORMATION: Synthetic Construct


<400> SEQUENCE: 141

gcagcggacg ggcgagtaga ttgcgca                                 27


<210> SEQ ID NO 142
<211> LENGTH: 25
<212> TYPE: DNA
<213> ORGANISM: Artificial Sequence
<220> FEATURE:
<223> OTHER INFORMATION: Synthetic Construct

<400> SEQUENCE: 142

gtgatctaca acacgcctta tctat                                   25
```